US006992097B2

(12) United States Patent
Hauser et al.

(10) Patent No.: US 6,992,097 B2
(45) Date of Patent: Jan. 31, 2006

(54) GROWTH HORMONE SECRETAGOGUES

(75) Inventors: Kenneth Lee Hauser, Greencastle, IN (US); Jeffrey Alan Dodge, Indianapolis, IN (US); Mark Louis Heiman, Indianapolis, IN (US); Scott Alan Jones, Indianapolis, IN (US); Charles Arthur Alt, Greenwood, IN (US); Henry Uhlman Bryant, Indianapolis, IN (US); Jeffrey Daniel Cohen, Indianapolis, IN (US); James Densmore Copp, Greenwood, IN (US); Kennan Joseph Fahey, Indianapolis, IN (US); William Harlan Gritton, Zionsville, IN (US); Louis Nickolaus Jungheim, Indianapolis, IN (US); Joseph Henry Kennedy, Noblesville, IN (US); Charles Willis Lugar, III, McCordsville, IN (US); Brian Stephen Muehl, Indianapolis, IN (US); Alan David Palkowitz, Carmel, IN (US); Andrew Michael Ratz, Greenwood, IN (US); Gary Anthony Rhodes, Indianapolis, IN (US); Roger Lewis Robey, Greenwood, IN (US); David Edward Seyler, Greenfield, IN (US); Timothy Alan Shepherd, Indianapolis, IN (US); Kenneth Jeff Thrasher, Indianapolis, IN (US); William George Trankle, Southport, IN (US)

(73) Assignee: Eli Lilly and Company, Indianapolis, IN (US)

( * ) Notice: Subject to any disclaimer, the term of this patent is extended or adjusted under 35 U.S.C. 154(b) by 66 days.

(21) Appl. No.: 10/453,833

(22) Filed: Jun. 3, 2003

(65) Prior Publication Data

US 2004/0122234 A1 Jun. 24, 2004

Related U.S. Application Data

(62) Division of application No. 09/762,529, filed as application No. PCT/US99/03525 on Feb. 19, 1999, now Pat. No. 6,639,076.

(30) Foreign Application Priority Data

Aug. 18, 1998 (EP) .............................. 98306621
Aug. 18, 1998 (EP) .............................. 98306622

(51) Int. Cl.
*A61K 31/415* (2006.01)
*C07D 233/44* (2006.01)

(52) U.S. Cl. ................................ 514/398; 548/326.5
(58) Field of Classification Search ................. 514/398; 548/326.5
See application file for complete search history.

(56) References Cited

U.S. PATENT DOCUMENTS

| | | |
|---|---|---|
| 3,711,495 A | 1/1973 | Kulsa et al. |
| 3,984,426 A | 10/1976 | Winkelmann et al. |
| 5,206,235 A | 4/1993 | Fisher et al. |
| 5,242,903 A | 9/1993 | Bender et al. |
| 5,380,866 A | 1/1995 | Barnett et al. |
| 5,401,851 A | 3/1995 | Boyd et al. |
| 5,459,156 A | 10/1995 | Muller-Gliemann et al. |
| 5,492,916 A | 2/1996 | Marriello et al. |
| 5,492,920 A | 2/1996 | Chen et al. |
| 5,494,919 A | 2/1996 | Marriello et al. |
| 5,559,128 A | 9/1996 | Chakravarty et al. |
| 5,574,167 A | 11/1996 | Jaber |
| 5,578,593 A | 11/1996 | Chen et al. |
| 5,583,130 A | 12/1996 | Bochis et al. |
| 5,652,235 A | 7/1997 | Chen et al. |
| 5,661,161 A | 8/1997 | Anthony et al. |
| 5,663,146 A | 9/1997 | Bowers et al. |
| 5,663,171 A | 9/1997 | Chen et al. |
| 5,700,827 A | 12/1997 | Schnorrenberg et al. |
| 5,721,250 A | 2/1998 | Morriello et al. |
| 5,756,528 A | 5/1998 | Anthony et al. |

(Continued)

FOREIGN PATENT DOCUMENTS

| | | |
|---|---|---|
| EP | 0 662 481 B1 | 8/1993 |
| EP | 0 615977 A1 | 9/1994 |
| EP | 0 761219 A1 | 8/1996 |
| EP | 0 761 219 A | 3/1997 |
| EP | 0 761 220 A | 3/1997 |
| WO | WO 94/13696 A | 6/1994 |
| WO | WO 95/11029 A | 4/1995 |
| WO | WO 96/15148 A | 5/1996 |
| WO | WO 96/35713 A1 | 11/1996 |
| WO | WO 96/38471 A1 | 12/1996 |
| WO | WO 97/15573 A1 | 5/1997 |
| WO | WO 97/24369 A1 | 7/1997 |
| WO | WO 97/34604 A1 | 9/1997 |
| WO | WO 97/41878 A1 | 11/1997 |
| WO | WO 98/16527 A1 | 4/1998 |
| WO | WO 99 08697 A1 | 2/1999 |
| WO | WO 99/08699 A1 | 2/1999 |
| WO | PCT/US00/04274 | 2/2000 |
| WO | WO 00/49037 | 2/2000 |
| WO | WO 00/12047 A2 | 3/2000 |

OTHER PUBLICATIONS

Skamrov et al. "Specific protection . . ." CA 103:215 (1985).*

(Continued)

*Primary Examiner*—Celia Chang
(74) *Attorney, Agent, or Firm*—MaCharri Vorndran-Jones

(57) ABSTRACT

This invention relates to novel compounds which are useful in the modulation of endogenous growth hormone levels in a mammal. The invention further relates to novel intermediates for use in the synthesis of said compounds, as well as novel processes employed in these syntheses. Also included are methods of treating a mammal which include the administration of said compounds.

15 Claims, No Drawings

U.S. PATENT DOCUMENTS

| | | | |
|---|---|---|---|
| 5,773,441 A | 6/1998 | Hipskind et al. | |
| 5,798,337 A | 8/1998 | Somers et al. | |
| 5,830,855 A | 11/1998 | Takemoto | |
| 6,046,333 A | 4/2000 | Dorziotis et al. | |
| 6,217,341 B1 * | 4/2001 | Glick et al. | 439/66 |
| 6,329,342 B1 | 12/2001 | Kauffman et al. | |

OTHER PUBLICATIONS

Kim et al. "synthesis and antiinflammatory–analgesic . . ." CA 138:221510 (2002).*

U.S. Appl. No. 09/486,019, filed Aug. 19, 1998, Arthur et al. *Synthesis of 4–Nitroimidazoles with 1–Substituents Containing Acid, Ester or Phenol Functions, and Radiosensitizing Efficiency of Some of These Compounds*, Suwinski, et al., Arch. Pharm., vol. 325, pp. 317–324 (1992).

*Synthetic Approaches to the 'Azole' Peptide Mimetics*, Gordon, et al., Tetrahedron Letters, vol. 34, No. 12, pp. 1901–1904 (1993).

Chem. Abst. No. 130:209977, Kaufffman, et al., "Treatment of Congestive Heart Failure with Growth Hormone Secretagogues", Kauffman, et al. application of WO 99/08697, Aug. 19, 1998.

Chem. Abst. No. 130:182769, Dodge, et al;, *Preparation of Heterocyclic Peptide Derivatives as Growth Hormone Secretagogues*, application of WO 9908699, Aug. 19, 1998.

Chem. Abst. No. 119:261758, Uzunov, et al., *Some Aspects of the Enantiorecognition of Derivatized Primary Amines on a Pirkle–Type Chiral Stationary Phase Utilizing Tocainide and Mexiletine as Model Compounds*, (1993).

* cited by examiner

GROWTH HORMONE SECRETAGOGUES

This is a Divisional of prior application Ser. No. 09/762,529 filed on Apr. 17, 2001, now U.S. Pat. No. 6,639,076, which is a 371 of Application No. PCT/US99/53525, filed Feb. 19, 1999.

Growth hormone is a secretory protein of the pituitary gland of animals having wide ranging developmental effects on the organism. Artificial manipulation of growth hormone levels has been demonstrated to have significant therapeutic utility. Human growth hormone supplementation has been shown to be an effective treatment for growth hormone deficiencies and their related disease states in humans. Apart from this application, studies have uncovered new and significant properties of growth hormone which lend further importance to the ability to control growth hormone levels. For example, recent clinical studies indicate that growth hormone supplementation may be useful in combating the maladies of aging in humans. Elevated growth hormone levels in animals have been shown to result in increased lean muscle mass. One application of this latter observation could result in higher production of leaner meat products or in the production of larger and/or stronger animals.

While growth hormone is naturally produced by the pituitary gland, the secretion of growth hormone into the bloodstream is controlled by a second protein, Growth Hormone Releasing Factor (GRF). This hormone is also commonly known in the art as somatocrinin, Growth Hormone Releasing Hormone (GHRH), and Growth Releasing Hormone (GRH).

There are two ways to approach the problem of increasing circulating levels of growth hormone: (1) increase the level of human growth hormone in the organism directly or (2) increase the organism's natural tendency to produce growth hormone. The latter strategy may be achieved via supplementation with GRF. GRF has been demonstrated to increase the circulatory levels of growth hormone in vivo. (Rivier, et al., *Nature* (London), 300:276 (1982). The effect of GRF, including structural analogs thereof, on growth hormone production has been widely studied. A primary obstacle to the use of GRF as a direct supplement is its short lifespan in vivo. L. A. Frohman, et al., *Journal of Clinical Investigation*, 78:906 (1986). More potent and/or longer lasting GRF molecules are therefore desirable for the development of effective human therapeutic or animal husbandry agents.

The structure of GRF has been modified in numerous ways resulting in longer lasting and/or more potent GRF analogs. It has been demonstrated that the first 29 amino acids from the N-terminus are sufficient to retain full GRF activity. Speiss, et al., *Biochemistry*, 21:6037 (1982). One strategy has been the incorporation of novel D-amino acid residues in various regions of the GRF molecule. V. A. Lance, et al., *Biochemical and Biophysical Research Communications*, 119:265 (1984); D. H. Coy, et al., *Peptides*, 8(suppl. 1):49 (1986). Another strategy has modified the peptide backbone of GRF by the incorporation of peptide bond isosteres in the N-terminal region. D. Tourwe, *Janssen. Chim. Acta*, 3:3 (1985); S. J. Hocart, et al., *Journal of Medicinal Chemistry*, 33:1954–58 (1990). A series of very active analogs of GHRH is described in European Patent Publication 511,003, published Oct. 28, 1992.

In addition to the actions of GHRH there are various ways known to release growth hormone. For example, chemicals such as arginine, L-3,4-dihydroxyphenylalanine (L-DOPA), glucagon, vasopressin, and insulin-induced hypoglycemia, as well as activities such as sleep and exercise, indirectly cause growth hormone to be released from the pituitary by acting in some fashion on the hypothalamus, perhaps either to decrease somatostatin secretion or to increase the secretion of GHRH.

In cases where increased levels of growth hormone are desired, the problem has generally been solved by providing exogenous growth hormone or by administering GHRH, or a related peptidyl compounds which stimulates growth hormone production or release. In either instance the peptidyl nature of the compound has necessitated that it be administered by injection.

Other compounds have been developed which stimulate the release of endogenous growth hormone, such as analogous peptidyl compounds related to GHRH. These peptides, while considerably smaller than growth hormones are still susceptible to metabolic instability.

Administration of the hexapeptide growth hormone releasing peptide-6 (GHRP-6) results in the secretion of growth hormone in many species, including humans. This peptide is one of a series of synthetic peptides, the structures of which were based on the pentapeptide Metenkephalin. It has been shown that GHRP binds specifically to the pituitary, although the binding does not involve the opioid, GHRH, or the somatostatin-receptors.

In recent years significant efforts have been taken to develop nonpeptidyl analogs of this series of compounds. Such compounds, termed-growth hormone secretagogues, should be orally bioavailable, induce the production or release of growth hormone, and act in concert, or synergistically with GHRH.

Representative growth hormone secretagogues are disclosed in U.S. Pat. No. 3,239,345; U.S. Pat. No. 4,036,979, U.S. Pat. No. 4,411,890; U.S. Pat. No. 5,206,235; U.S. Pat. No. 5,248,841: U.S. Pat. No. 5,310,737; U.S. Pat. No. 5,310,017; European Patent Publication 144,230; European Patent Publication 513,974; Patent Cooperation Treaty Patent Publication WO 94/07486; Patent Cooperation Treaty Patent Publication WO 94/08583; Patent Cooperation Treaty Patent Publication WO 94/13696; U.S. Ser. No. 08/704,494, filed Aug. 20, 1996, U.S. Ser. No. 08/700,206, filed Aug. 20, 1996, and *Science*, 260:1640–1643 (1993).

U.S. Pat. No. 5,206,235, issued Apr. 27, 1993, describes a series of benzolactam compounds typified by the following structure.

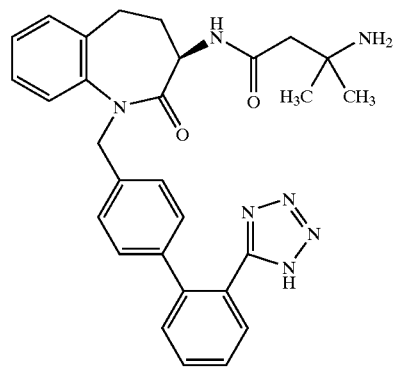

These compounds have demonstrated clinical activity in humans in raising the growth hormone secretory levels. B. J. Gertz, *Journal of Clinical Endocrinology and Metabolism*, 77:1393–1397 (1993).

Another group of growth hormone secretagogues is described in Patent Cooperation Treaty Patent Publication WO 94/13696, published Jun. 23, 1994. These compounds are typified by the following two structures.

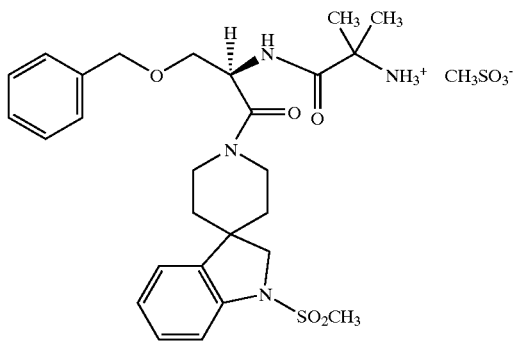

The present invention provides a series of compounds that have activity as growth hormone secretagogues. These compounds are non-peptidyl in nature and are, therefore, more metabolically stable than growth hormone, growth hormone releasing hormone, or analogs of either of these proteins. The compounds employed in the present invention are preferred for human pharmaceutical uses as well as veterinary uses, particularly in cattle, swine, sheep, poultry and fish.

The present invention relates to compounds of formula I

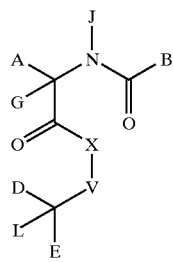

I wherein:
A is $C_1$–$C_6$alkyl, aryl, $C_1$–$C_6$alkylaryl, $C_1$–$C_6$alkyl(O)$C_1$–$C_6$alkylaryl, $C_1$–$C_6$alkyl(S)$C_1$–$C_6$alkylaryl, indolyl, indolinyl, thienyl, ($C_1$–$C_6$alkyl)thienyl, benzothienyl, benzofuranyl, naphthanyl, cyclohexyl, ($C_1$–$C_6$alkyl)indolyl, ($C_1$–$C_6$alkyl)benzothienyl, ($C_1$–$C_6$alkyl)naphthanyl, ($C_1$–$C_6$alkyl)benzofuranyl, and ($C_1$–$C_5$alkyl)cyclohexyl;

B is $NH_2$, $NHR_1$, $C_1$–$C_6$alkyl$NH_2$, $C_1$–$C_6$alkyl$NHR_1$, $C_1$–$C_6$alkylaryl$NH_2$, $C_1$–$C_6$alkylaryl$NHR_1$, $C_1$–$C_6$alkylcyclohexyl$NH_2$, $C_1$–$C_6$alkylcyclohexyl$NHR_1$, $R_1$-piperidin-3-yl($C_1$–$C_6$alkyl), $R_1$-piperidin-2-yl($C_1$–$C_6$alkyl), $R_1$-piperidin-4-yl($C_1$–$C_6$alkyl), $R_1$-quinoline-2-yl ($C_1$–$C_6$alkyl), $R_1$-(2,4-dihydroquinolin-2-yl($C_1$–$C_6$alkyl), $R_1$-isoquinolin-2-yl($C_1$–$C_6$alkyl), and $R_1$-(2,4-dihydroisoquinolin-2-yl($C_1$–$C_6$alkyl);

$R_1$ is hydrogen, $C_1$–$C_6$alkyl, $C_1$–$C_6$alkyl(OH), or $C_1$–$C_6$alkylidenyl(OH)$R_2$;

$R_2$ is $C_1$–$C_6$alkyl, $C_1$–$C_6$alkenyl, $C_1$–$C_6$alkyl(O)$C_1$–$C_6$alkyl, C(O)O—$C_1$–$C_6$alkyl, aryl, or $C_1$–$C_6$alkylaryl;

X is $C_1$–$C_6$alkylidenyl, O, S, NH, or N($C_1$–$C_6$alkyl);

V is selected from the group consisting of

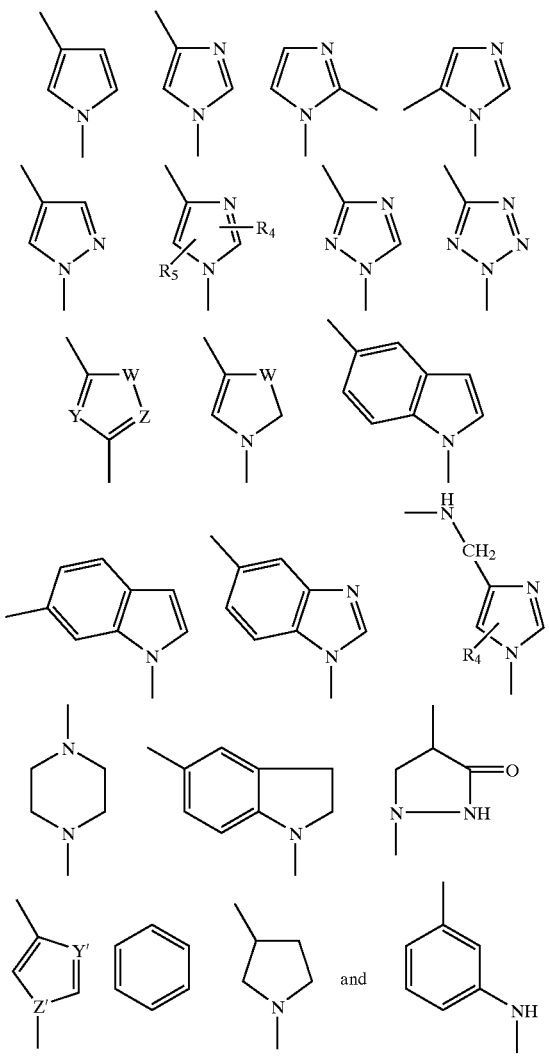

W is S, O, NH, or $CH_2$;
Y is N or CH;
Z is N or CH;
Y' is N or CH;
Z' is N or CH;
$R_4$ and $R_5$ are independently hydrogen, $C_1$–$C_6$alkyl, aryl, $C_1$–$C_6$alkylaryl, C(O)O($C_1$–$C_6$alkyl), C(O)N($C_1$–$C_6$alkyl)$_2$, or $C_1$–$C_6$alkylCOR$_7$;
$R_7$ is hydrogen, $C_1$–$C_6$alkyl, pyrrolidinyl, piperidinyl, homoproline, or proline;
D is hydrogen, $C_1$–$C_6$alkyl, $C_1$–$C_6$alkyl(O)(CO) $C_1$–$C_6$alkyl, $C_1$–$C_6$alkyl(O)(CO)N($C_3$–$C_6$alkyl)$_2$, $C_1$–$C_6$alkylaryl, C(O)$R_6$, $C_1$–$C_6$alkyl(O)$R_6$, $C_3$–$C_6$alkyl(OH), $C_1$–$C_6$alkylC(O)$R_6$, $C_1$–$C_6$alkyl$R_6$, aryl, (C₁–C₆alkyl)NHSO₂(C₁–C₆alkyl), (C₁–C₆alkyl)NHSO₂(aryl);

R₆ is H, C₁–C₆alkyl, aryl, naphthyl, C₁–C₆alkylaryl, acetyl, NH₂, NH(C₁–C₆alkyl), NH(C₁–C₆alkyl)O(C₁–C₆alkyl), NH(C₁–C₆alkyl)S(C₁–C₆alkyl), NH(C₁–C₆alkylidenyl)OCH₃, NH(C₁–C₆alkyl)aryl, NH(C₃–C₆cycloalkyl), NH(C₁–C₆alkyl)C(O)(C₁–C₆alkyl), NH(C₁–C₆alkyl)NH(C₁–C₆alkyl), NH(C₁–C₆alkyl)NH(C₁–C₆alkylaryl), NHSO₂(C₁–C₆alkylaryl), NH(C₁–C₆alkyl)C(O)O(C₁–C₆alkyl), NH(naphthyl), N(C₁–C₆alkyl)₂, N(C₁–C₆alkyl)(aryl), N(C₁–C₆alkyl)(C₁–C₆alkylaryl), O(C₁–C₆alkyl), O(aryl), O(C₁–C₆alkylaryl), piperidinyl, piperidinyl-C(O)NH(C₁–C₆alkyl), piperidinyl-C(O)NH(C₁–C₆alkylaryl), piperidinyl-C(O)N(C₁–C₆alkyl)₂, piperidinyl-C(O)N(C₁–C₆alkyl)(aryl), pyrrolidinyl, pyrrolidinyl C(O)NH(aryl)-, pyrrolidinyl C(O)NH(C₁–C₆alkyl)-, pyrrolidinyl C(O)NH(C₁–C₆alkyl)₂-, pyrrolidinyl C(O)NH(C₁–C₆alkylaryl), pyrrolidinyl C(O)NH(C₁–C₆alkyl)aryl-, pyrrolinyl, morpholino, hexamethyleneimino, heptamethyleneimino, quinolinyl, 2,4-dihydroquinolinyl, 1,2,3,4-tetrahydroquinolinyl, 2,4-dihydroisoquinolinyl, 1,2,3,4-tetrahydroisoquinolinyl, indolinyl, an amino acid selected from the group consisting of proline, homoproline, glycine, alanine, valine, leucine, isoleucine, tyrosine, tryptophan, phenylalanine, serine, threonine, asparagine, glutamic acid, aspartic acid, lysine, arginine, glutamine, histidine, cysteine, and methionine, or a nitrogen-containing heterocycle selected from the group consisting of

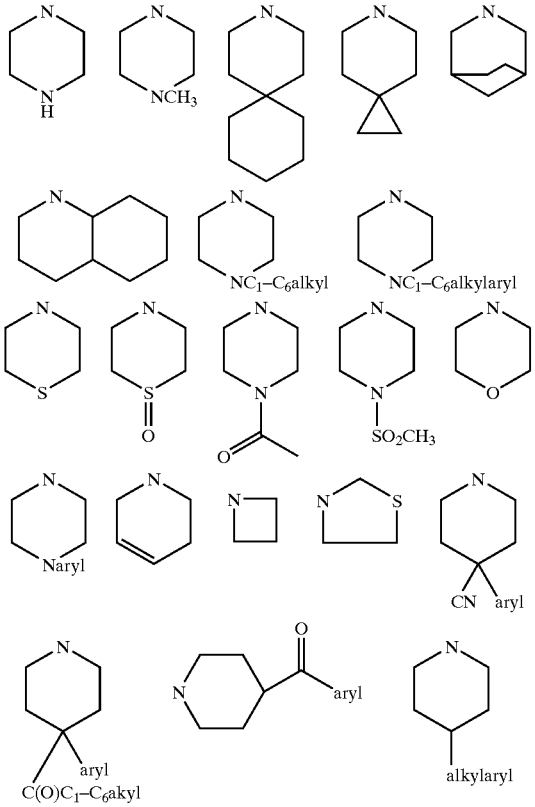

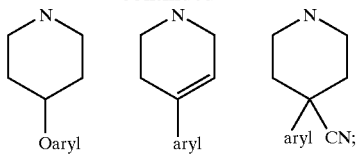

E is hydrogen, C₁–C₆alkyl, C(O)C₁–C₆alkyl, aryl, (aryl)C(O)NR₆, (aryl)(C₁–C₆alkyl)C(O)R₆, C₁–C₆alkylaryl, C(O)aryl, C₁–C₆alkylC(O)aryl, naphthyl, C₁–C₆alkylnaphthyl, C(O)naphthyl, C₁–C₆alkylC(O)naphthyl, heteroaryl, C₁–C₆alkylheteroaryl, C(O)heteroaryl, C₁–C₆alkylC(O)heteroaryl, indanyl, C₁–C₆alkylindanyl, C(O)indanyl, C₁–C₆alkylC(O)indanyl, cycloalkyl; or or D and E combine to form indanyl, fluorenyl, or cycloalkyl;

G is hydrogen, C₁–C₆alkyl, aryl, C₁–C₆alkylaryl, and C₁–C₆alkenyl;

J is hydrogen, C₁–C₆alkyl, aryl, and C₁–C₆alkylaryl;

L is hydrogen, C₁–C₆alkyl, C(O)OC₁–C₆alkyl, aryl, C₁–C₆alkylaryl, C(O)OC₁–C₆alkylaryl, C₁–C₆alkenyl, —F, and —CN, C₁–C₆alkyl-OH, C₁–C₆alkyl-O—C₁–C₆alkyl, C₁–C₆alkyl-C(O)R₆;

or a pharmaceutically acceptable salt or solvate thereof.

The present invention relates to compounds of formula I

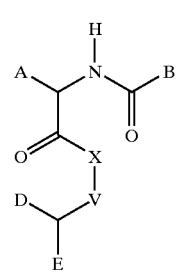

wherein:

A is C₁–C₆alkylaryl, C₁–C₆alkyl (O)C₁–C₆alkylaryl, (C₁–C₆alkyl)indol-3-yl, (C₁–C₆alkyl)benzothien-3-yl, (C₁–C₆alkyl)naphthan-2-yl, (C₁–C₆alkyl)benzofuran-3-yl, and (C₁–C₆alkyl)cyclohexyl;

B is C₁–C₆alkylNHR₁, C₁–C₆alkylarylNHR₁, C₁–C₆alkylcyclohexylNHR₁, R₁-piperidin-3-yl(C₁–C₆alkyl), R₁-piperidin-2-yl(C₁–C₆alkyl), R₁-piperidin-4-yl(C₁–C₆alkyl), R₁-quinolin-2-yl(C₁–C₆alkyl), R₁-(2,4-dihydroquinolin-2-yl(C₁–C₆alkyl), R₁-isoquinolin-2-yl(C₁–C₆alkyl), and R₁-(2,4-dihydroisoquinolin-2-yl (C₁–C₆alkyl);

R₁ is hydrogen, C₁–C₆alkyl, C₁–C₆alkyl(OH), or C₁–C₆alkylidenyl(OH)R₂;

R₂ is C₁–C₆alkyl, C₁–C₆alkenyl, C₁–C₆alkyl(O)C₁–C₆alkyl, C(O)O—C₁–C₆ alkyl, aryl, or C₁–C₆alkylaryl;

X is C₁–C₆alkylidenyl, O, S, NH, or N(C₁–C₆alkyl);

V is a nitrogen-containing heterocycle selected from the group consisting of

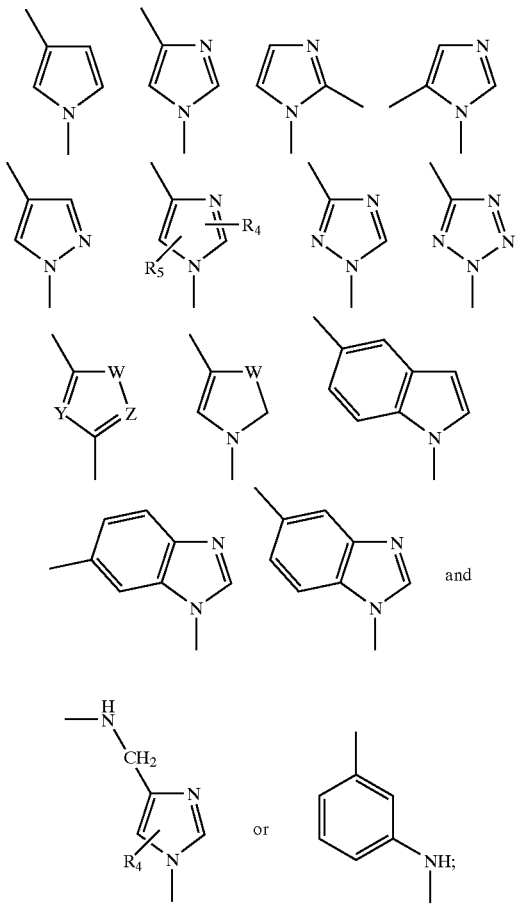

W is S, O, NH, or $CH_2$;
Y is N or CH;
Z is N or CH;
$R_4$ and $R_5$ are independently hydrogen, $C_1$–$C_6$alkyl, aryl, $C_1$–$C_6$alkylaryl, $C(O)O(C_1$–$C_6$alkyl), $C(O)N(C_1$–$C_6$alkyl)$_2$, or $C_1$–$C_6$alkylCOR$_7$;
$R_7$ is hydrogen, $C_1$–$C_6$alkyl, pyrrolidinyl, piperidinyl, homoproline, or proline;
D is $C(O)R_6$, $CH_2NHSO_2(C_1$–$C_6$alkyl), or $C_1$–$C_6$alkyl(OH);
$R_6$ is $NH_2$, $NH(C_1$–$C_6$alkyl), $NH(C_1$–$C_6$alkylidenyl)$OCH_3$, $NH(C_1$–$C_6$alkyl)aryl, $N(C_1$–$C_6$alkyl)$_2$, $N(C_1$–$C_6$alkyl)(aryl), $N(C_1$–$C_6$alkyl)($C_1$–$C_6$alkylaryl), $O(C_1$–$C_6$alkyl), piperidinyl or optionally substituted piperidinyl, pyrrolidinyl or optionally substituted pyrrolidinyl, pyrrolinyl or optionally substituted pyrrolinyl, morpholino, hexamethyleneimino, heptamethyleneimino, quinolinyl, 2,4-dihydroquinolinyl, isoquinolinyl, 2,4-dihydroisoquinolinyl, an amino acid selected from the group consisting of proline, homoproline, glycine, alanine, valine, leucine, isoleucine, tyrosine, tryptophan, phenylalanine, serine, threonine, asparagine, glutamic acid, aspartic acid, lysine, arginine, glutamine, histidine, cysteine, and methionine, or a nitrogen-containing heterocycle selected from the group consisting of

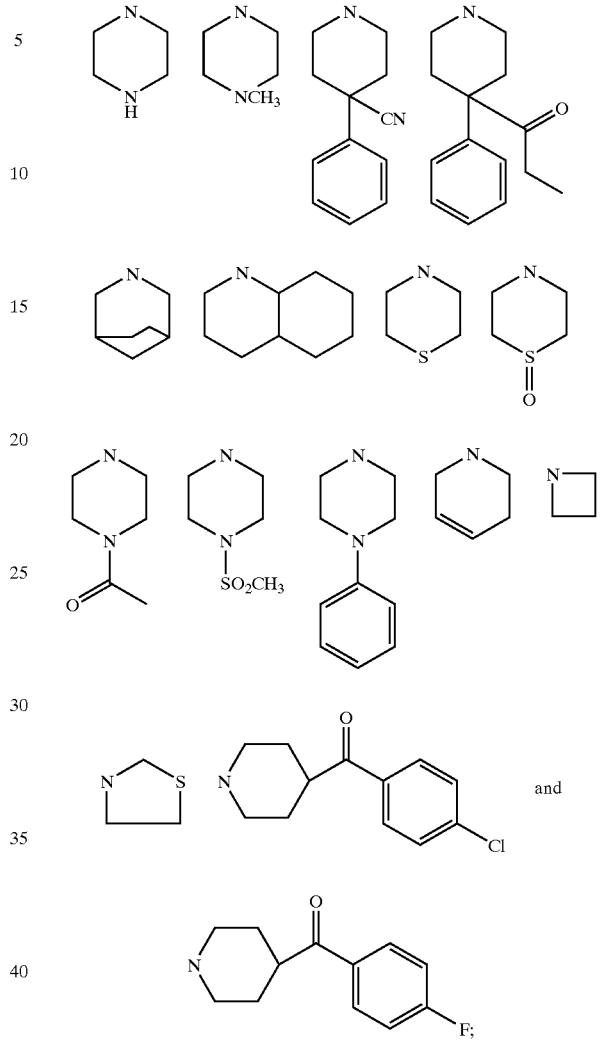

E is hydrogen, $C_1$–$C_6$alkyl, aryl $C_1$–$C_6$alkylaryl, naphthyl, or $C_1$–$C_6$alkylnaphthyl,
or a pharmaceutically acceptable salt or solvate thereof.

The present invention relates to compounds of Formula I, as follows:

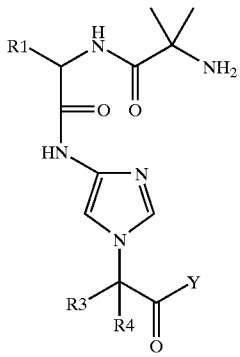

wherein R1 is $C_6H_3CH_2OCH_2$—, $C_6H_3(CH_2)_3$— or indol-3-ylmethyl; Y is pyrrolidin-1-yl, 4-$C_1$–$C_6$alkylpiperidin-1-yl or NR2R2; R2 are each independently a $C_1$ to $C_6$ alkyl; R3 is 2-napthyl or phenyl para-substituted by W; W is H, F, $CF_3$, $C_1$–$C_6$alkoxy or phenyl; and R4 is H or $CH_3$, or a pharmaceutically acceptable salt or solvate thereof.

The present invention further relates to pharmaceutical formulations containing compounds of formula I, alone or in combination with other growth hormone secretagogue compounds, and/or in combination with suitable bone-antiresorptive agents, and the use of said compounds and/or formulations at least for the increase in endogenous levels of growth hormone in a mammal.

The present invention yet further relates to methods for the treatment or prevention of a physiological condition which may be modulated by an increase in endogenous growth hormone, which method comprises administering to an animal in need of said treatment an effective amount of a compound of formula I.

The present invention additionally relates to compounds of formula IA:

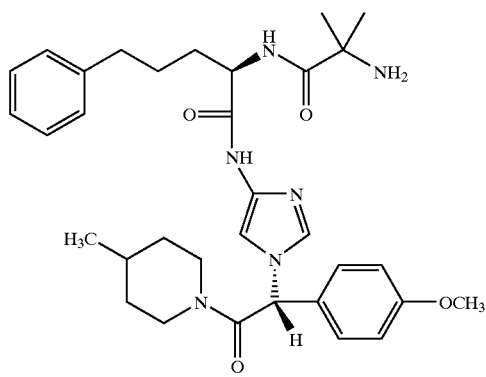

IA

The present invention still further relates to compounds of formula IB:

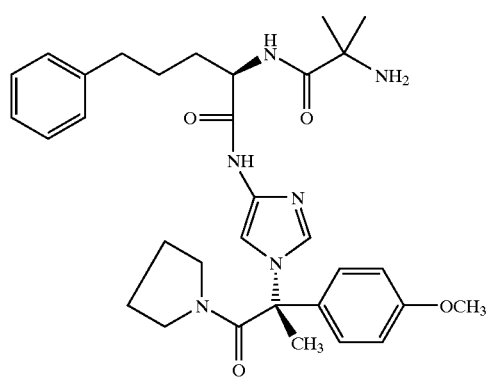

IB

The present invention additionally relates to compounds of formula Ia':

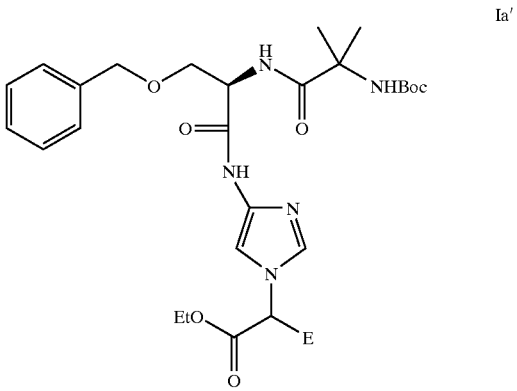

Ia' wherein E is as defined above.

Also provided are compounds of formula ZZ and ZZZ useful as chiral intermediates in the preparation of compounds of formula I:

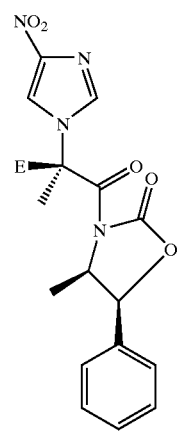

ZZ

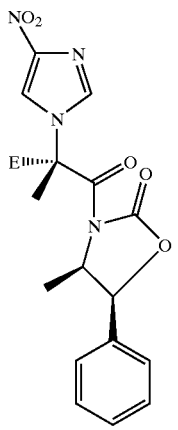

ZZZ wherein E is as defined above.

The present invention still further relates to processes for the preparation of compounds of formula I.

The terms and abbreviations used in the instant examples have their normal meanings unless otherwise designated. For example "° C" refers to degrees Celsius; "N" refers to normal or normality; "mmol" refers to millimole or millimoles; "g" refers to gram or grams; "ml" means milliliter or milliliters; "M" refers to molar or molarity; "MS" refers to mass spectrometry; "FDMS" refers to field desorption mass spectrometry; "UV" refers to ultraviolet spectroscopy; "IR" refers to infrared spectroscopy; and "NMR" refers to nuclear magnetic resonance spectroscopy.

As used herein, the term "$C_1$–$C_6$ alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl. The term "$C_1$–$C_6$ alkyl" includes within its definition the term "$C_1$–$C_4$ alkyl".

As used herein, the term "cycloalkyl" refers to cyclized chains of 1 to 6 carbon atoms and includes, but is not limited to, cyclopropyl, cyclobutyl, cyclopentyl, and cyclohexyl.

"Halo" represents chloro, fluoro, bromo or iodo.

"$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_4$ alkoxy".

"$C_2$–$C_6$ alkanoyl" represents a straight or branched alkyl chain having from one to five carbon atoms attached through a carbonyl moiety. Typical $C_2$–$C_6$ alkanoyl groups include ethanoyl (also referred to as acetyl), propanoyl, isopropanoyl, butanoyl, t-butanoyl, pentanoyl, hexanoyl, and the like.

"$C_1$–$C_6$ alkylidenyl" refers to a straight or branched, divalent, saturated aliphatic chain of one to six carbon atoms and includes, but is not limited to, methylenyl, ethylenyl, propylenyl, isopropylenyl, butylenyl, isobutylenyl, t-butylenyl, pentylenyl, isopentylenyl, hexylenyl, and the like.

The term "aryl" represents an aromatic ring or rings including phenyl, napthyl, biphenyl, and aromatic residues of 5 to 7-membered rings with 1 to 4 heteroatoms (a "heteroaryl"), all of which may be optionally substituted with one or more substituents, including $C_1$–$C_6$ alkyl, —O$C_1$–$C_6$ alkyl, —OCF$_3$, amide, NHamide, carboxamide, sulfonamide, NHsulfonamide, imide, hydroxy, carboxy, nitro, chloro, fluoro, tri(chloro or fluoro)methyl, cyano, and the like. The aromatic ring may be attached at any carbon atom or heteroatom which affords a stable structure. 3,4-methylenedioxyphenyl is included here.

The term "heterocycle" represents a stable 5- to 7-membered monocyclic or 7- to 10-membered bicyclic heterocyclic ring which is saturated or unsaturated and which consists of carbon atoms and from 1 to 4 heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached at any heteroatom or carbon atom which affords a stable structure, and may be optionally substituted with one or more substituents selected from the group consisting of $C_1$–$C_6$ alkyl, —O$C_1$–$C_6$ alkyl, hydroxy, nitro, chloro, fluoro, or tri(chloro or fluoro)methyl, and the like.

The term "carboxy-protecting group" as used herein refers to substituents of the carboxy group commonly employed to block or protect the carboxy functionality while reacting other functional groups on the compound. Examples of such protecting groups include methyl, ethyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylene-dioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4', 4"-trimethoxytrityl, 2-phenylprop-2-yl, trimethylsilyl, t-butyldimethylsilyl, phenacyl, 2,2,2-trichloroethyl, 2-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and the like. A preferred carboxy-protecting group for the practice of the present invention is methyl or ethyl. Further examples of these groups may be found in E. Haslam, supra, at Chapter 5, and T. W. Greene, et al., supra, at Chapter 5.

The term "amino-protecting group" as used herein refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl, and urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, n-butoxycarbonyl, (NBoc) t-butoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, fluorenylmethoxycarbonyl (FMOC), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl, and the like; benzoylmethylsulfonyl group, 2-nitrophenylsulfenyl, diphenylphosphine oxide and like amino-protecting groups.

The amino-protecting group employed is usually not critical so long as the derivatized amino group is stable to the condition of subsequent reactions on other positions of the intermediate molecule, and may be selectively removed at the appropriate point without disrupting the remainder of the molecule including any other amino-protecting groups. A preferred amino-protecting group for the practice of the present invention is t-butoxycarbonyl (NBoc). Further examples of groups referred to by the above terms are described by E. Haslam, *Protective Groups in Organic Chemistry*, (J. G. W. McOmie, ed., 1973), at Chapter 2; and T. W. Greene and P. G. M. Wuts, *Protective Groups in Organic Synthesis* (1991), at Chapter 7.

The term "leaving group" (Q) refers to a group of atoms that is displaced from a carbon atom by the attack of a nucleophile in a nucleophilic substitution reaction. Suitable leaving groups include bromo, chloro, and iodo, benzenesulfonyloxy, methanesulfonyloxy, and toluenesulfonyloxy. The term "leaving group" (Q) includes activating groups.

The term "activating group" as used herein refers a leaving group which, when taken with the carbonyl (—C=O) group to which it is attached, is more likely to take part in an acylation reaction than would be the case if the group were not present, as in the free acid. Such activating groups are well-known to those skilled in the art and may be, for example, succininidoxy, phthalimidoxy, benzotriazolyloxy, azido, or —O—CO—($C_4$-$C_7$ alkyl).

The compounds used in the method of the present invention may have one or more asymmetric centers. As a consequence of these chiral centers, the compounds of the present invention occur as racemates, mixtures of enantiomers and as individual enantiomers, as well as diastereomers and mixtures of diastereomers. All asymmetric forms, individual isomers and combinations thereof, are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in *Nomenclature of Organic Compounds: Principles and Practice*, (J. H. Fletcher, et al., eds., 1974) at pages 103–120.

In addition to the (R)-(S) system, the older D-L system is also used in this document to denote absolute configuration, especially with reference to amino acids. In this system, a Fischer projection formula is oriented so that the number 1 carbon of the main chain is at the top. The prefix "D" is used to represent the absolute configuration of the isomer in which the functional (determining) group is on the right side of the carbon atom at the chiral center and "L", that of the isomer in which it is on the left.

In order to preferentially prepare one optical isomer over its enantiomer, a number of routes are available. As an example, a mixture of enantiomers may be prepared, and then the two enantiomers may be separated. A commonly employed method for the resolution of the racemic mixture (or mixture of enantiomers) into the individual enantiomers is to first convert the enantiomers to diastereomers by way of forming a salt with an optically active acid or base. These diastereomers may then be separated using differential solubility, fractional crystallization, chromatography, or the like. Further details regarding resolution of enantiomeric mixtures may be found in J. Jacques, et al., *Enantiomers, Racemates, and Resolutions*, (1991).

Preferred compounds of the present invention are compounds of formula I wherein:

A is

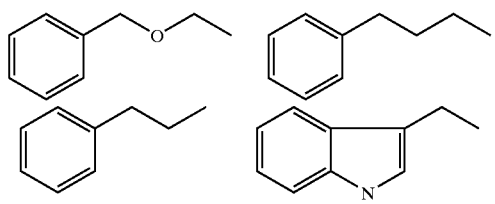

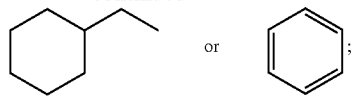

B is

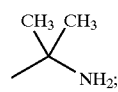

J is H;

G is H;

X is NH;

V is

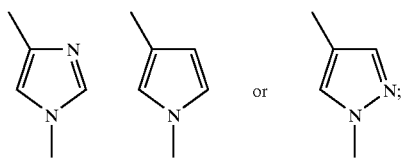

E is

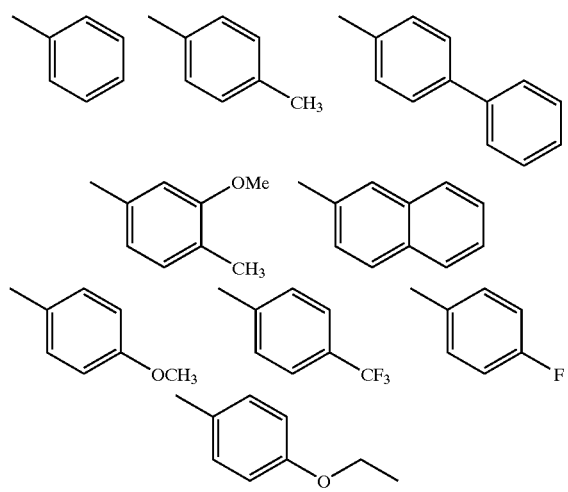

D is —C(O)$R_6$, where $R_6$ is 1-pyrrolidinyl, 1-piperidinyl, 4-methyl-1-piperidinyl, N,N-dimethyl,

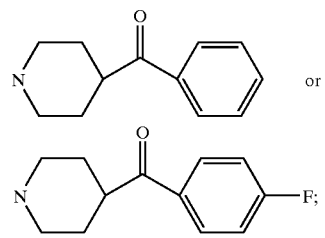

L is H or $CH_3$;

or a pharmaceutically acceptable salt or solvate thereof.

A preferred compound includes a compound of formula Id provided below:

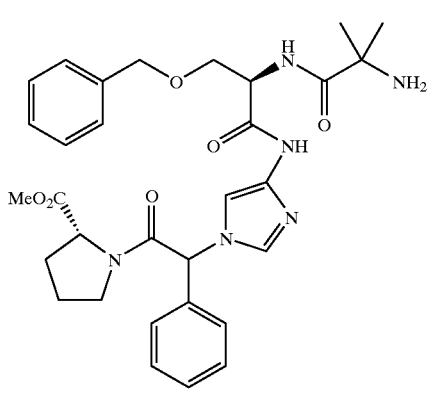

Id

Also preferred are compounds of formula IA and IB provided hereinabove.

During any of the following synthetic sequences it may be necessary or desirable to protect sensitive or reactive groups on any of the molecules concerned. This may be achieved by employing conventional protecting groups as described, supra.

The compounds of the present invention may be prepared by a number of routes, many of which are known to those of skill in the art. The particular order of steps to be employed in the synthesis of compounds of formula I is dependent upon the compound to be synthesized, the starting material employed, and the relative lability of the various substituted moieties. Examples of such synthetic routes may be found in Schemes I through IV provided below, as well as in the Examples.

One synthetic route to compounds of the present invention is provided in Scheme I below. The compounds of formula IV' and IV are commercially available, or may be prepared using techniques known in the art. A compound of formula IV may be prepared from a compound of formula IV' through an intermediate acid chloride prepared by standard methods using thionyl chloride or oxalyl chloride. Treatment of the resulting acid chloride with a bromine source, such as N-bromosuccinimide, followed by quenching of the acid chloride with ethanol, results in compounds of formula IV. It is to be understood that the bromine group on the compound of formula IV may in fact be any suitable leaving group (Q), as defined herein. This preparation is provided below in Scheme IA.

Scheme IA

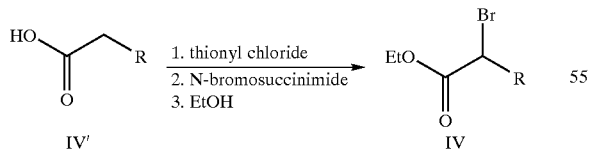

wherein R is representative of E as defined in a compound of formula I above.

The starting material further includes compounds of formula V, which are commercially available, or may be routinely synthesized using techniques readily known in the art. Compounds of formula IV may be coupled with a compound of formula V (4-nitroimidazole) by methods known in the art to generate a compound of formula IIb'.

Suitable agents to be employed in the coupling of these compounds include the treatment of a compound of formula IV with an organic or inorganic base, followed by reaction with the bromo compound of formula IV. Standard organic bases include trialkylamines, potassium hexamethyldisilazide, lithium hexamethyldisilazide, lithium diisopropylamide, potassium carbonate, and the like. Preferred for the practice of the present invention is sodium hydride or potassium carbonate in dimethylformamide. A compound of formula IIb' is then deprotected to provide a compound of formula IIb, using lithium hydroxide, although other deprotecting reagents may be employed in this reaction. Such deprotecting agents include standard saponification reagents such as sodium hydroxide, potassium hydroxide, and lithium hydroxide.

Substantially pure (R) enantiomers of compounds of formula IIb may also be synthesized by methods provided in U.S. Pat. No. 5,344,937 and 5,380,866, the disclosures of which are herein incorporated by reference.

A compound of formula IIb is then converted to the corresponding amide under appropriate conditions with a compound of formula VI to generate a compound of formula IIa. In general, amidation of primary or secondary amines of formula VI may be accomplished by a number of methods known in the art in which activation of the acid to form a better leaving group is the initial step. Suitable activating agents for this are also known in the art and include dicyclohexycarbodiimide (DCC), 1-(3-dimethylaminopropyl)-3-ethylcarbodiimide hydrochloride (EDC) with hydroxybenzotriazole (HOBT), oxalyl chloride, thionyl chloride, PyBOP® (benzotriazol-1-yloxytripyrrolidinephosphonium hexafluorophosphate), and the like. Preferred for the practice of the present invention is hydroxybenzotriazole (HOBT). The nitro group on the resulting compound of formula IIa may then be reduced to an amino group using any suitable means, employing a suitable reducing agent. Preferred for the practice of the present invention is a catalytic reduction employing hydrogen and 5% palladium on carbon. A compound of formula II is produced by this reduction reaction.

The preferred reaction temperature range employed in these reactions is between −40 and 150° C., and the most preferred range is between 10 and 40° C. These reactions may be conveniently carried out in situ, without isolation of the particular compound after its preparation.

Examples of these reactions are provided below in Scheme I.

Scheme I

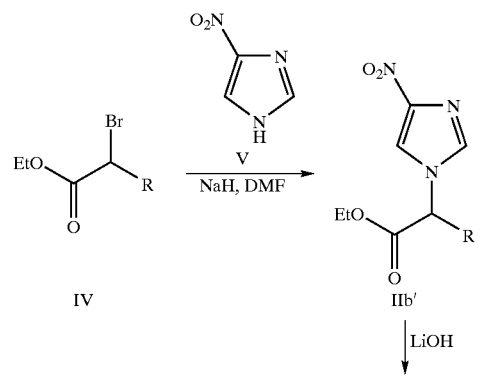

-continued

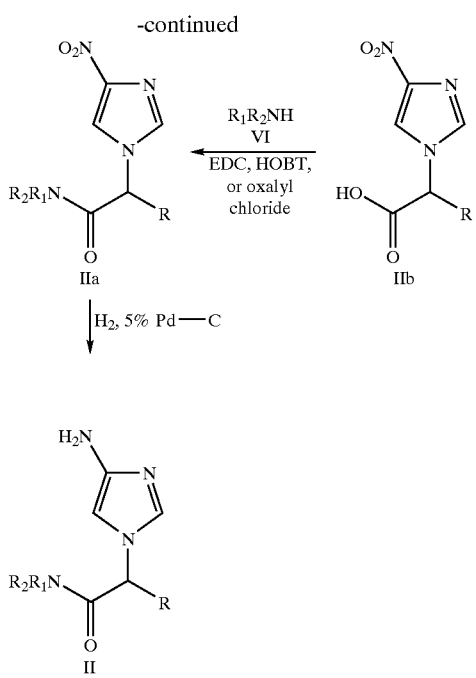

wherein R is representative of E as previously defined, and $R_2R_1N$ is $R_6$ as previously defined.

A second portion of the overall synthesis of compounds of formula I is provided in Scheme II below. Representative starting material for this synthesis is a compound of formula IIIb', which is a chemically-protected form of the amino acid O-serine. By chemically-protected it is meant that both the amino- and carboxy-functional groups have been suitably protected in order to facilitate further reactions with this molecule. Such protection reactions are known to those of skill in the art, and may be applied to other suitable starting materials. Intermediates of formula IIIb' are commercially available, or may be prepared by standard syntheses of amino acids. Such syntheses are well known to persons of ordinary skill in the art and are described, for example, in *Chemistry and Biochemistry of Amino Acids*, (G. C. Chapman ed., 1985). The protected amino group may be specifically deprotected using trifluoroacetic acid and methylene chloride to allow for further reactions with this amino functional group. This deprotection reaction results in a compound of formula IIIb.

A compound of formula IIIb may then be N-acylated with an amino-protected compound of formula X to produce a compound of formula IIIa'. Suitable activating agents for this N-acylation reaction are known in the art and include DCC, HOBT, EDC, and oxalyl chloride. Preferred for the practice of the present invention is HOBT. Compounds of formula X are commercially available, or are readily prepared from suitable available starting materials. The protected carboxy group on the compound of formula IIIa' is then selectively deprotected, typically using lithium hydroxide, to generate a compound of formula III. Compounds of formula III in which the starting material IIIb' is 2-Nboc-amino-pentanoic acid methyl ester may also be prepared by the route described in Scheme II.

A compound of formula III is then coupled with a compound prepared from the reduction of IIb' with hydrogen and a palladium catalyst employing a coupling reaction to generate a compound of formula Ia. Again, typical reagents for this N-acylation are known in the art, and include DCC and HOBT, which is the preferred method of coupling employed in the practice of the present invention. A compound of formula Ia is then selectively deprotected at the carboxy group, coupled at this site with a compound of formula VI, and then further deprotected at the amino group to generate a compound of formula Ia. Suitable agents for these deprotection and coupling reactions are discussed, intra, and are known in the art. Compounds of formula Ia are encompassed by formula I, and are pharmaceutically active.

The preferred reaction temperature range employed in these reactions is between −40 and 150° C., and the most preferred range is between 10 and 40° C. These reactions may be conveniently carried out in situ, without isolation of the particular compound after its preparation.

Alternatively, compounds of formula IIa can be coupled with compounds of formula III to provide intermediates which can be deprotected to give compounds of formula Ia.

Representative reactions are provided below in Scheme II.

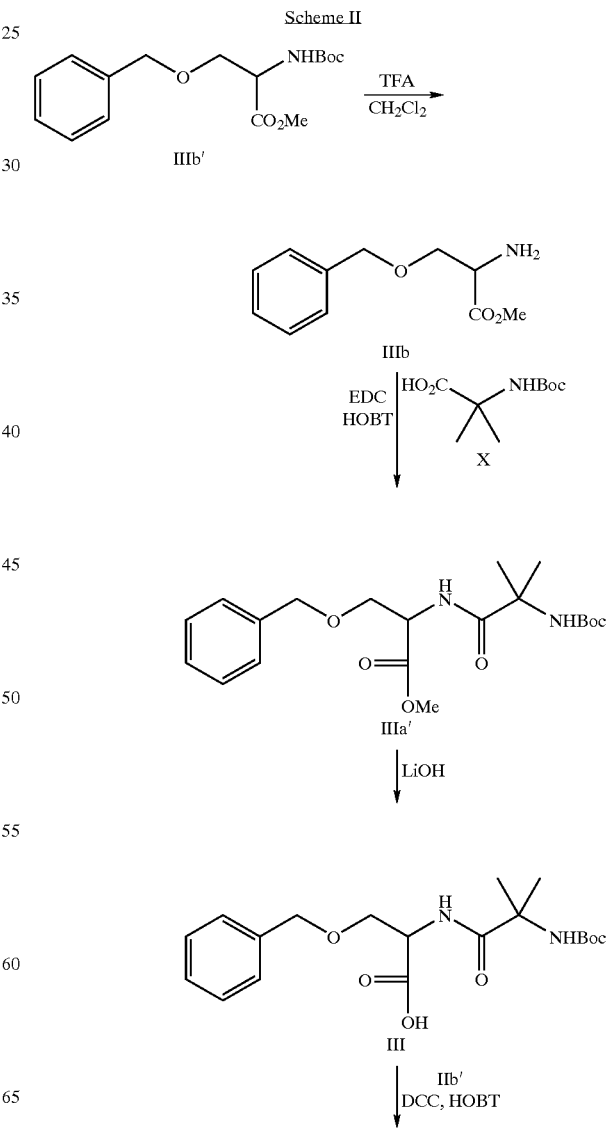

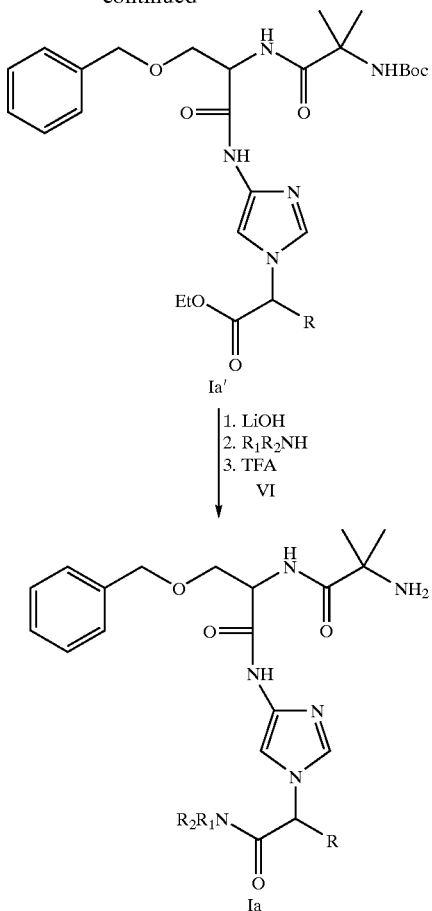
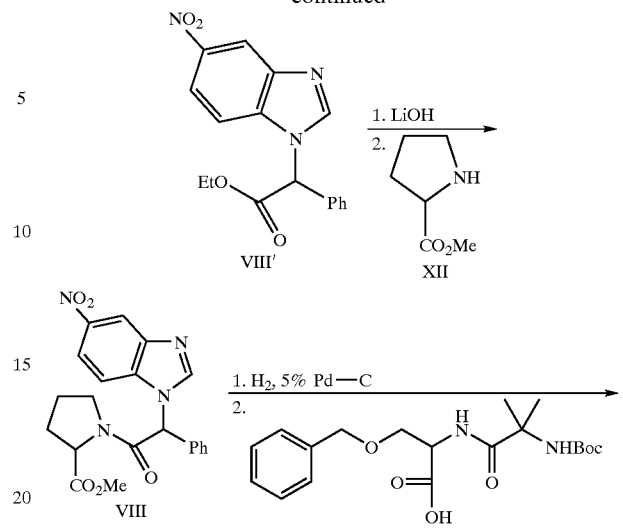
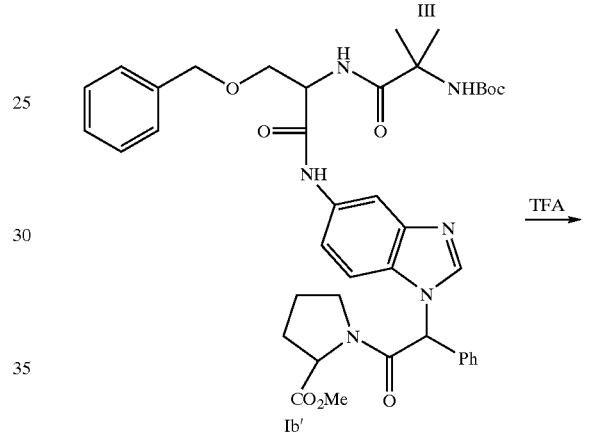

wherein R is E as previously defined, and $R_2R_1N$ is $R_6$ as previously defined.

An alternative synthetic scheme is provided in Scheme III below. A compound of formula VII (5-nitrobenzimidazole) is commercially available, or may be conveniently prepared using reactions known in the art. A compound of formula VII is coupled with a compound of formula IV in an alkylation reaction, using coupling agents as discussed, infra. A compound of formula VIII' is produced in which the carboxy functional group is protected. This protecting group is then removed as previously discussed, typically using lithium hydroxide, followed by coupling with a compound of formula XII. The nitro group on the resulting compound of formula VIII is then reduced, followed by coupling with a compound of formula III. The resulting compound of formula Ib' is then deprotected to provide a compound of formula Ib. Compounds of formula Ib are encompassed by formula I, and are pharmaceutically active. These reactions are provided below in Scheme III.

Scheme III

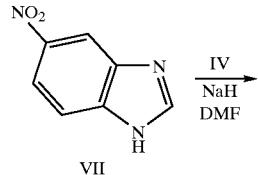

A still further representative synthesis of compounds of formula I is provided below in Scheme IV. Starting materials of formula IX (3-amino-nitrobenzene) are commercially available. Initially, a compound of formula IX is coupled with a compound of formula IV by means discussed previously. The resulting compound of formula XI' is then deprotected, followed by coupling with a compound of formula XII to provide a compound of formula XI. A compound of formula XI is then reduced and further coupled in an N-acylation reaction with a compound of formula III. The resulting compound of formula Ic' is then deprotected to result in a compound of formula Ic. Conditions for these reactions have been discussed previously. Compounds of formula Ic are encompassed by formula I, and are pharmaceutically active.

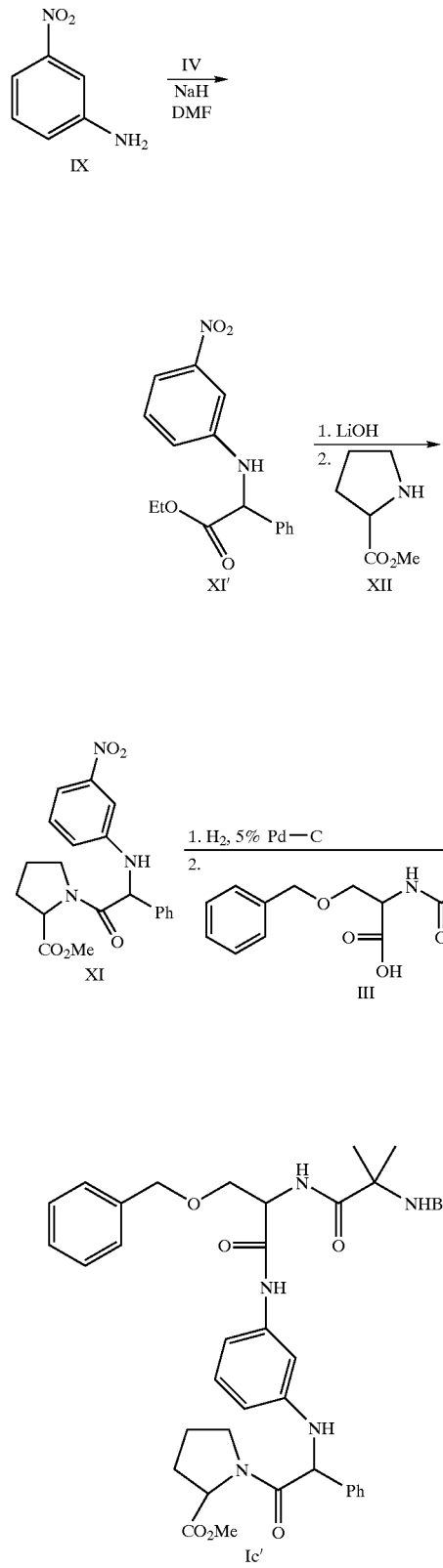

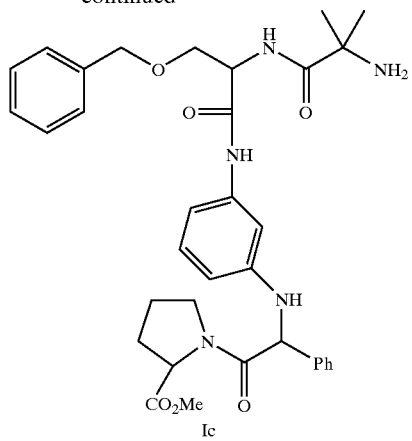

In addition to the Schemes described hereinabove, an enantiospecific protocol for the preparation of the compounds of formula I may be employed. Typically, a synthetic reaction design which maintains the chiral center present in the starting material in a desired orientation is chosen. The preferred reaction schemes are those that generally produce compounds in which greater than 95 percent of the product is the desired enantiomer. In Scheme V below, R-substituted phenyl is representative of the E substituents as provided in compounds of formula I above.

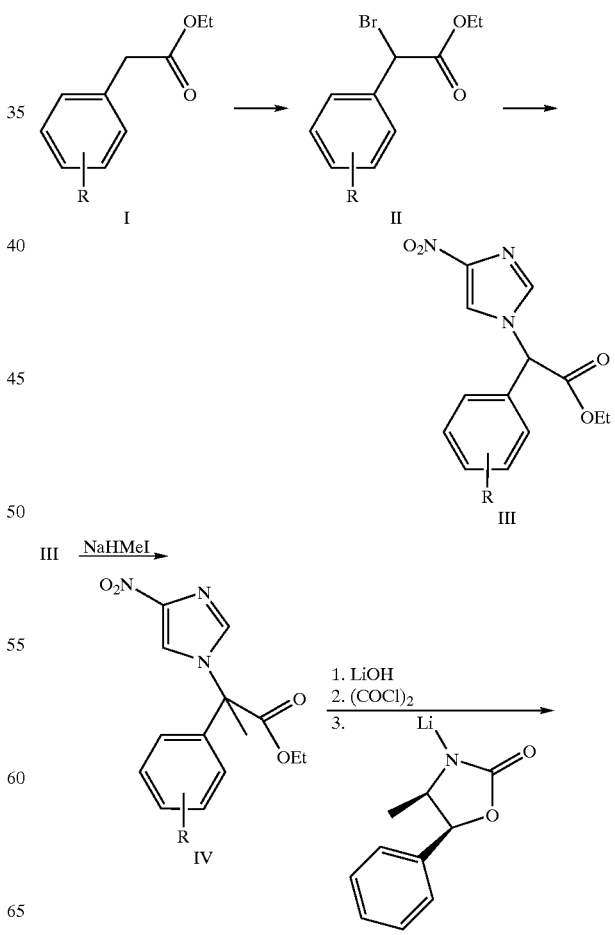

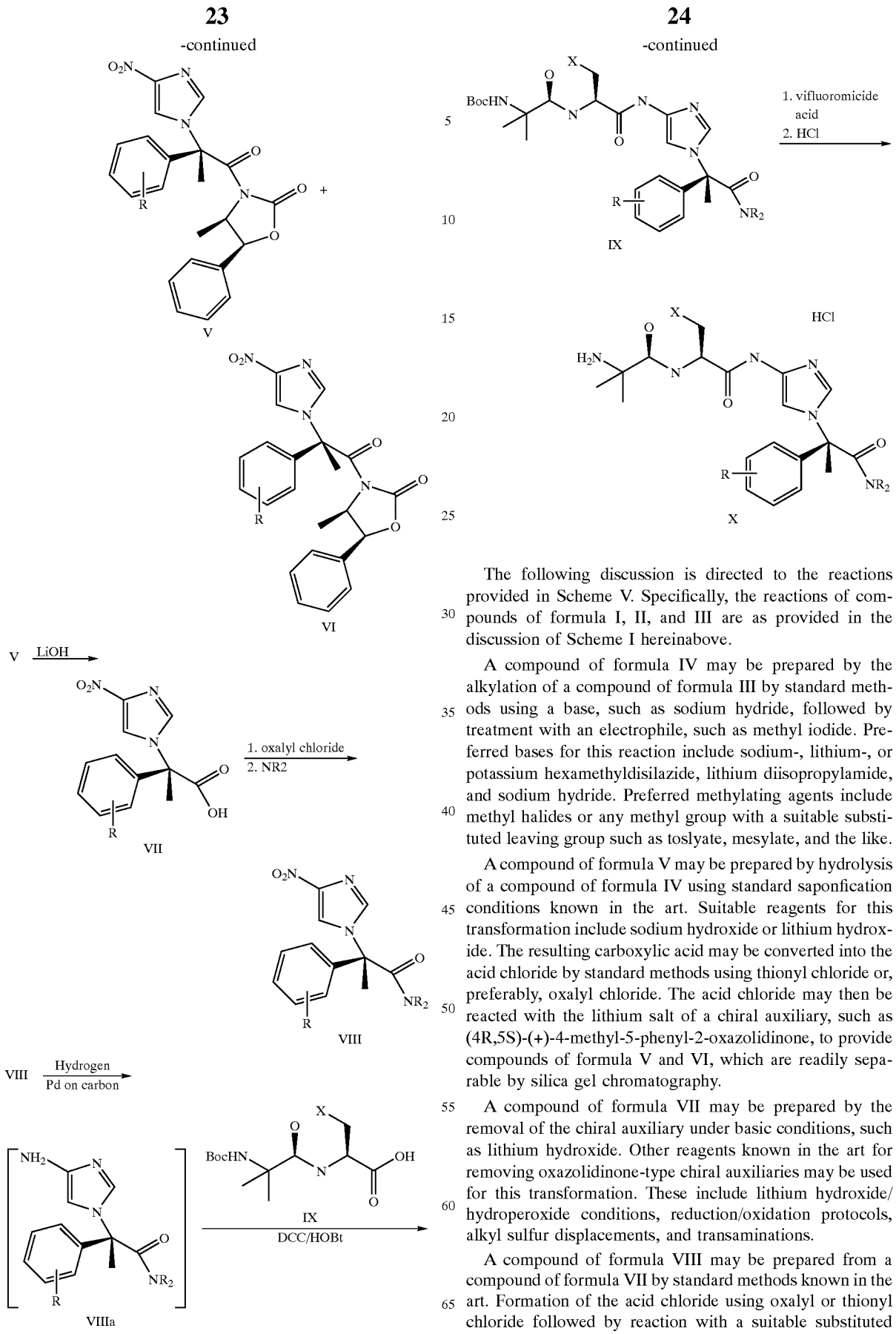

The following discussion is directed to the reactions provided in Scheme V. Specifically, the reactions of compounds of formula I, II, and III are as provided in the discussion of Scheme I hereinabove.

A compound of formula IV may be prepared by the alkylation of a compound of formula III by standard methods using a base, such as sodium hydride, followed by treatment with an electrophile, such as methyl iodide. Preferred bases for this reaction include sodium-, lithium-, or potassium hexamethyldisilazide, lithium diisopropylamide, and sodium hydride. Preferred methylating agents include methyl halides or any methyl group with a suitable substituted leaving group such as toslyate, mesylate, and the like.

A compound of formula V may be prepared by hydrolysis of a compound of formula IV using standard saponfication conditions known in the art. Suitable reagents for this transformation include sodium hydroxide or lithium hydroxide. The resulting carboxylic acid may be converted into the acid chloride by standard methods using thionyl chloride or, preferably, oxalyl chloride. The acid chloride may then be reacted with the lithium salt of a chiral auxiliary, such as (4R,5S)-(+)-4-methyl-5-phenyl-2-oxazolidinone, to provide compounds of formula V and VI, which are readily separable by silica gel chromatography.

A compound of formula VII may be prepared by the removal of the chiral auxiliary under basic conditions, such as lithium hydroxide. Other reagents known in the art for removing oxazolidinone-type chiral auxiliaries may be used for this transformation. These include lithium hydroxide/hydroperoxide conditions, reduction/oxidation protocols, alkyl sulfur displacements, and transaminations.

A compound of formula VIII may be prepared from a compound of formula VII by standard methods known in the art. Formation of the acid chloride using oxalyl or thionyl chloride followed by reaction with a suitable substituted amine (NR₂) provide compounds of formula VIII.

A compound of formula IX may be prepared by the reduction of a compound of formula VIII using hydrogen with palladium on carbon. Other methods known in the art which may be employed for the reduction of the nitro group include the use of tin(II)chloride, iron in an acidic solution, ferrous sulfate and aqueous alkali, activated alumina, and sodium sulfite. The resulting 4-amino imidazole compound of formula VIIa is then reacted directly with the appropriate dipeptide acid (a compound of formula IIX) under standard peptide coupling conditions involving formation of the active ester of the dipeptide followed by reaction with amine VIIa. Conditions suitable for amide formation include DCC, EDC, with HOBT. A compound of formula IIX may be prepared from the methyl ester of unnatural D-amino acids such as D-benzyloxyserine, D-tryptophan, and D-2-amino-5-phenyl-pentanoic acid and the like which are known in the art. Standard coupling protocols involving formation of the active ester of the amino acid using DCC/HOBt followed by reaction with N-Boc-aminoisobutyric acid provide dipeptide acids of formula IIX.

The Boc protecting group of a compound of formula IX may be removed under standard acidic conditions such as hydrochloric acid in acetic acid or ethyl acetate, trifluoroacetic acid, tetramethyliodosilane, aluminum chloride, sulfuric acid in dioxane, and methanesulfonic acid.

An additional method of preparing diastereomeric compounds of formula I involves the use of a chromatographic column which employs a chiral phase. An example of such a preparation may be found in Examples Part 6 as provided hereinbelow.

Preferred for the practice of the present invention are those compounds of formula I wherein the indicated stereochemistry is (R,R) at the two chiral centers. An example of this preferred stereochemistry is provided by compounds of formula IA and IB as provided hereinabove.

Two additional Schemes for providing chiral intermediates are provided hereinbelow as Schemes VA and VB. As described in Scheme VA, optically pure aryl glycine amino acids may be protected at the amino position by reaction with a suitable protecting group, such as Boc. Reaction of the Boc protected intermediate with a standard methylating agent, such as methyl iodide, may provide the corresponding phenolic methyl ether. The carboxamide may be prepared by coupling with an amine, such as dimethylamine, pyrrolidine, or 4-methyl piperidine, using standard coupling techniques. Preferred coupling agents for the invention are diethy cyanophosphorane (DECP), triethylamine and the amine at 0° C. The Boc protecting group may be removed under standard acidic conditions, with trifluoroacetic acid being preferred. The desired 4-nitroimidazole compounds can be prepared by reaction of the free amine with 1,4-dinitroimidazole to give optically pure compounds, as determined by chiral HPLC. Such chiral intermediates can be processed as described in Schemes I and II to provide diastereomerically pure products. For example, the chiral nitroimidazoles described in Scheme VA or VB may be reduced under standard conditions, such as hydrogenation with a palladium catalyst, to provide the corresponding chiral amino intermediate II. Such intermediates may be subsequently coupled with compounds of type III as previously described to provide a chiral intermediate which can be deprotected to give diastereomerically pure compounds of formula Ia.

Scheme VA

CHIRAL SYNTHESIS OF D-Phenylglycine Imidazole

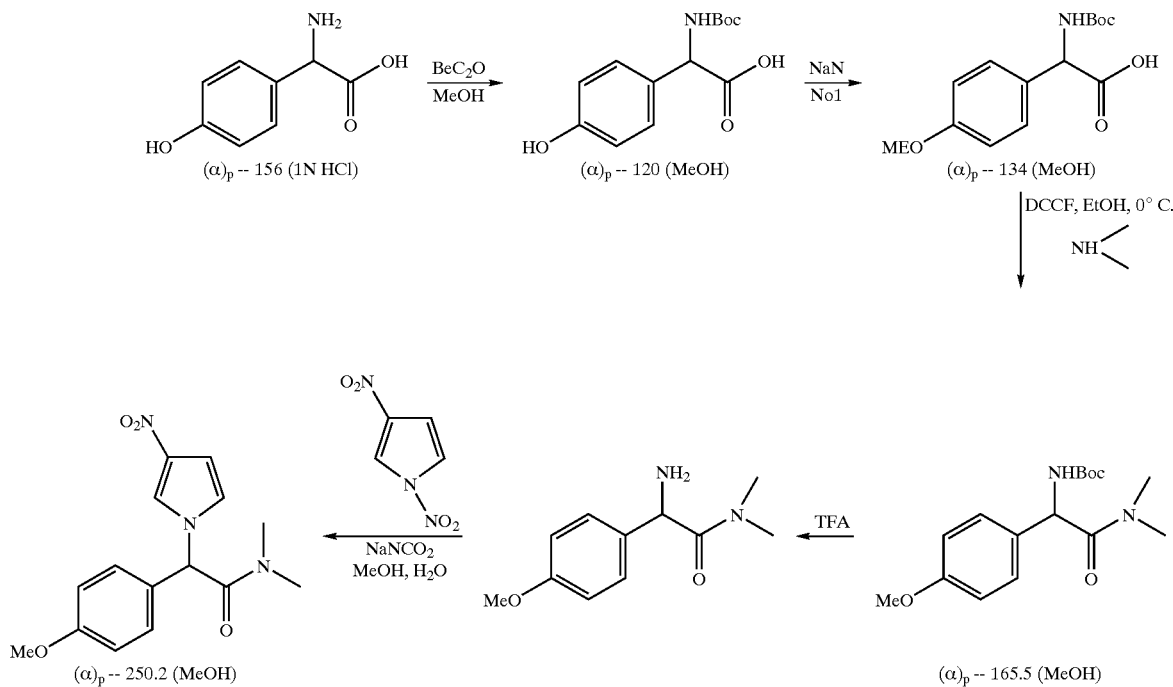

Scheme VB
Chiral Synthesis of L-Phenylglycine Imidazole
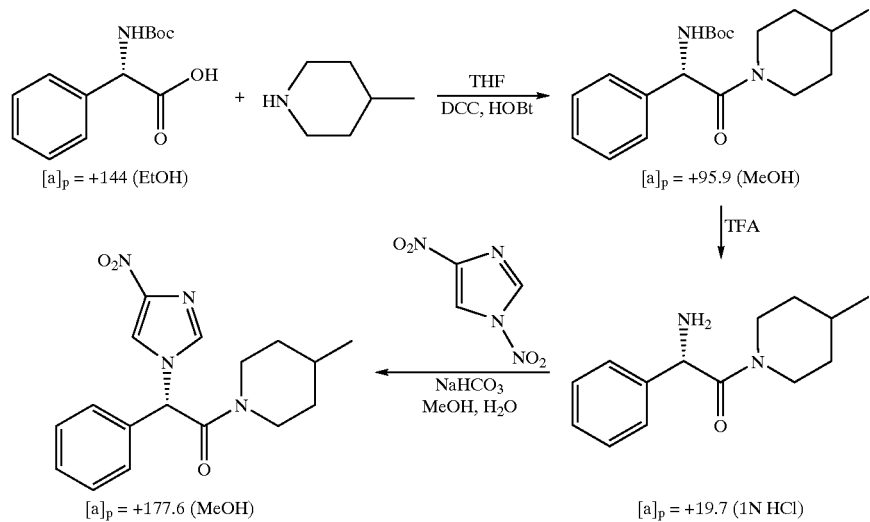
An additional approach and corresponding synthetic scheme for the preparation of compounds of the instant invention is provided below in Scheme VI:
Scheme VI
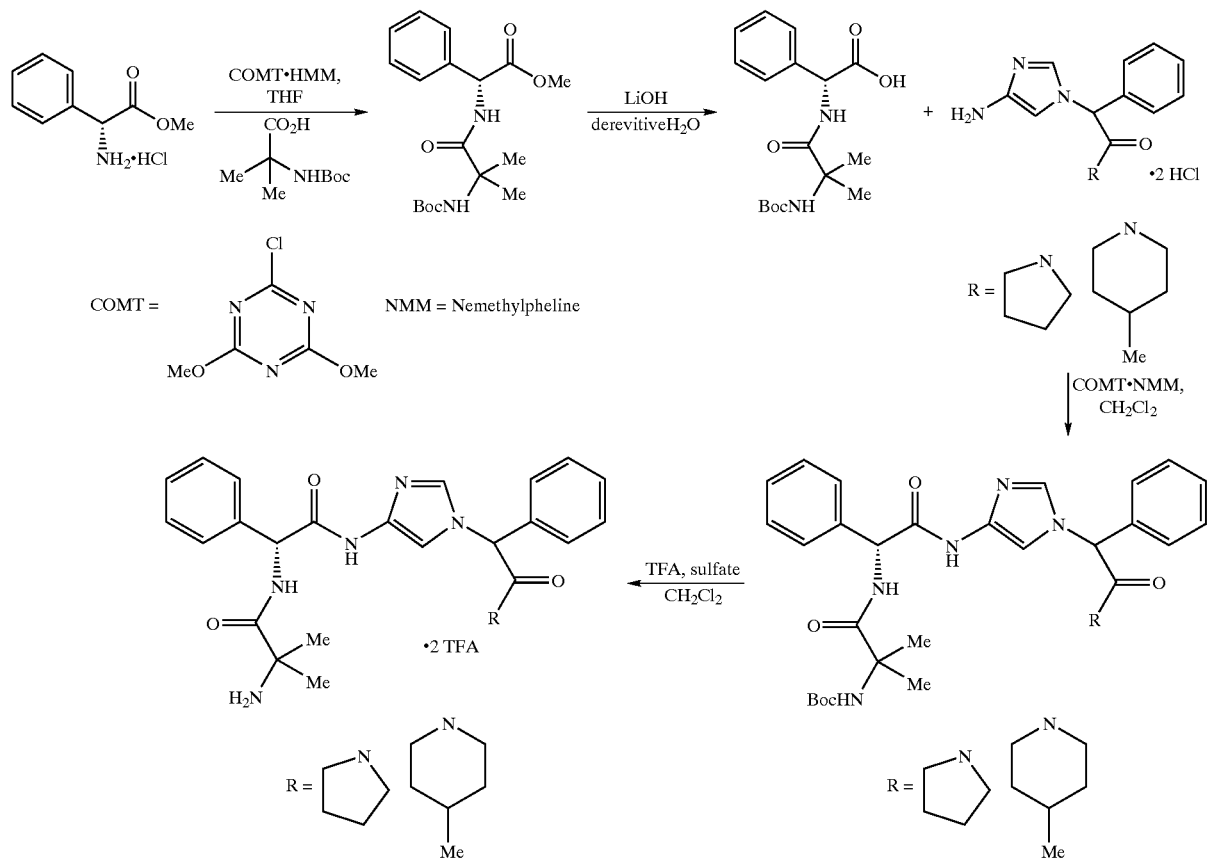

Pharmaceutically active compounds of formula I include at least compounds of formula IA, IB, Id, and Ia' as described herein.

Compounds of formula I may be conveniently screened for growth hormone secretagogue activity. A typical assay may employ pituitary cells established in culture, followed by a challenge with the various compounds of formula I, and the levels of growth hormone determined accordingly. Growth hormone levels may be calculated using various radioimmunoassay techniques known to those of skill in the art. Screening of compounds for growth hormone secretagogue activity may conveniently be scaled up for high throughput screening.

The invention further encompasses methods employing the pharmaceutically acceptable salts of the compounds defined by formula I. Although generally neutral, a compound of this invention can possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein refers to salts of the compounds of formula I which are substantially non-toxic to living organisms. Typical pharmaceutically acceptable salts include those salts prepared by reaction of the compounds of the present invention with a pharmaceutically acceptable mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, naphthalene-2-sulfonate, mandelate, mesylate, and the like. Preferred pharmaceutically acceptable acid addition salts are those formed with mineral acids such as hydrochloric acid and hydrobromic acid, and those formed with organic acids such as maleic acid and methanesulfonic acid.

Salts of amine groups may also comprise quaternary ammonium salts in which the amino nitrogen carries a suitable organic group such as an alkyl, alkenyl, alkynyl, or aralkyl moiety.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

This invention further encompasses methods employing pharmaceutically acceptable solvates of the compounds of Formula I. Many of the formula I compounds can combine with solvents such as water, methanol, ethanol and acetonitrile to form pharmaceutically acceptable solvates such as the corresponding hydrate, methanolate, ethanolate and acetonitrilate.

This invention also encompasses methods employing the pharmaceutically acceptable prodrugs of the compounds of formula I. A prodrug is a drug which has been chemically modified and may be biologically inactive at its site of action, but which may be degraded or modified by one or more enzymatic or other in vivo processes to the parent bioactive form. This prodrug should have a different pharmacokinetic profile than the parent, enabling easier absorption across the mucosal epithelium, better salt formation or solubility, or improved systemic stability (an increase in plasma half-life, for example).

Typically, such chemical modifications include:
1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form; or any combination of 1 to 3, supra. Conventional procedures for the selection and preparation of suitable prodrug derivatives are described, for example, in H, Bundgaard, *Design of Prodrugs*, (1985).

As used herein, the term "effective amount" means an amount of compound of the instant invention which is capable of inhibiting, alleviating, ameliorating, treating, or preventing further symptoms in mammals, including humans, which may be due to decreased levels of endogenous growth hormone.

By "pharmaceutically acceptable formulation" it is meant that the carrier, diluent, excipients and salt must be compatible with the active ingredient (a compound of formula I) of the formulation, and not be deleterious to the recipient thereof. Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms nay be: pills, tablets, powders, lozenges, syrups, aerosols, saches, cachets, elixirs, suspensions, emulsions, ointments, suppositories, sterile injectable solutions, or sterile packaged powders, and the like, depending on the type of excipient used.

Additionally, the compounds of this invention are well suited to formulation as-sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound required to treat, inhibit, or prevent the symptoms and/or disease of congestive heart failure in a mammal, including humans, according to this invention will depend upon the particular disease, symptoms, and severity. Dosage, routes of administration, and frequency of dosing is best decided by the attending physician. Generally, accepted and effective doses will be from 15 mg to 1000 mg, and more typically from 15 mg to 80 mg. Such dosages will be administered to a patient in need of treatment from one to three times each day or as often as needed for efficacy.

In addition, the growth hormone secretagogue compounds as disclosed herein may be administered to a patient in need of treatment in combination with other growth hormone secretagogues known in the art, and/or with a suitable bone anti-resorptive agent or agents for the prevention or treatment of osteoporosis and/or loss of muscle strength. Said suitable bone anti-resorptive agents include selective estrogen receptor modulators, bisphophonates, calcitonin, and hormone replacement therapeutic agents. Additionally, PTH may be administered in combination with said growth hormone secretagogues. Said combination therapy may be administered concomitantly or sequentially.

Suitable dosing ranges of compounds of formula I include 0.01 $\mu$g/kg/day to 60 mg/kg/day.

The present invention also relates to methods for the modulation of cardiac function which comprise the administration of a compound of Formula I.

The present invention further relates to methods for the treatment or prevention of congestive heart failure by administering, to an animal in need thereof, an effective amount of a compound of Formula I.

The present invention additionally relates to pharmaceutical formulations containing a growth hormone secretagogue alone or in combination with additional therapeutic agents useful for the treatment or prevention of congestive heart failure.

The use of growth hormone secretagogue compounds, for the modulation of cardiac function and for the treatment or prevention of congestive heart failure, are described in copending U.S. patent application Ser. No. 09/137,255, filed Aug. 19, 1998, titled "Treatment of Congestive Heart Failure With Growth Hormone Secretagogues", the teachings of which are incorporated herein in their entirety by reference.

The particular dosage of a compound required to treat, inhibit, or prevent the symptoms and/or disease of congestive heart failure in a mammal, including humans, according to this invention will depend upon the particular disease, symptoms, and severity. Dosage, routes of administration, and frequency of dosing is best decided by the attending physician. Generally, accepted and effective doses will be from 15 mg to 1000 mg, and more typically from 15 mg to 80 mg. Such dosages will be administered to a patient in need of treatment from one to three times each day or as often as needed for efficacy.

Representative pharmaceutical formulations containing compounds of formula I are provided below. The formulations which follow are given for purposes of illustration and are not intended to be limiting in any way. The total active ingredients in such formulations comprises from 0.1% to 99.9% by weight of the formulation. The term "active ingredient" means a compound of Formula I.

Formulation 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation 3

A dry powder inhaler formulation is prepared containing the following components:

| Ingredient | Weight % |
| --- | --- |
| Active Ingredient | 5 |
| Lactose | 95 |

The active mixture is mixed with the lactose and the mixture is added to a dry powder inhaling appliance.

Formulation 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation 5

Capsules, each containing 40 mg of medicament are made as follows:

| Ingredient | Quantity (mg/capsule) |
| --- | --- |
| Active ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation 6

Suppositories, each containing 25 mg of active ingredient are made as follows:

| Ingredient | Amount |
| --- | --- |
| Active Ingredient | 25 mg |
| Saturated fatty acid glycerides | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation 7

Suspensions, each containing 50 mg of medicament per 5.0 ml dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation 8

Capsules, each containing 15 mg of medicament, are made as follows:

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation 9

An intravenous formulation may be prepared as follows:

| Ingredient | Quantity |
| --- | --- |
| Active Ingredient | 250.0 mg |
| Isotonic saline | 1000 ml |

Formulation 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation 11

Sublingual or buccal tablets, each containing 10 mg of active ingredient, may be prepared as follows:

| Ingredient | Quantity Per Tablet |
| --- | --- |
| Active Ingredient | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C.

When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another formulation employed in the methods of the present invention employs transdermal delivery devices or patches. Such transdermal patches may be used to provide continuous or discontinuous infusion of the compounds of the present invention in controlled amounts. The construction and use of transdermal patches for the delivery of pharmaceutical agents is well known in the art. See, for example, U.S. Pat. No. 5,023,252, the disclosure of which is herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, the disclosure of which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The following Examples and Preparations are illustrative of the processes employed in the synthesis of the compounds of the present invention. As would be understood by persons skilled in the art, other synthetic schemes may be employed to prepare the compounds of the instant invention.

EXAMPLES PART 1

Preparation 1

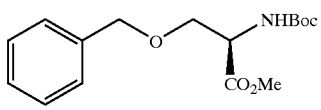

To a solution of boc-(OBz)-D-Ser-OH (25.0 g, 84.7 mmol) stirring in anhydrous N,N-dimethylformamide (500 mL) at room temperature was added sodium bicarbonate (14.2 g, 169 mmol) followed by methyl iodide (26.4 mL, 424 mmol). After 18 h, the reaction mixture was concentrated to approximately 100 mL. Ethyl acetate was added and the mixture washed with aqueous sodium bicarbonate and brine. The organic extract was dried and concentrated to give the desired compound (25 g, 96%) as a light yellow oil: $^1$H NMR (300 MHz, CDCl$_3$) d 1.45 (s, 9H), 3.70 (m, 1H), 3.75 (s, 3H), 3.85 (m, 1H), 4.50 (m, 3H), 7.30 (m, 5H); MS (FD) m/e 310; Anal. calc'd for $C_{16}H_{23}NO_5$: C, 62.12; H, 7.49; N, 4.53. Found: C, 62.31; H, 7.49; N, 4.43.

Preparation 2

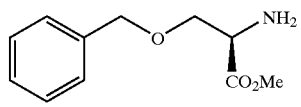

To a solution of a compound of Preparation 1 (5.0 g, 16 mmol) stirring in dichloromethane (25 mL) and anisole (1 mL) at 0° C. was added trifluoroacetic acid. After 4 h at room temperature, saturated sodium bicarbonate solution was added and the mixture extracted with ethyl acetate. The combined organic extracts were washed with brine, dried over sodium sufate, and concentrated. The crude product was used in the next step without further purification.

Preparation 3

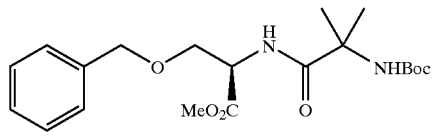

To a solution of a compound of Preparation 2 (65.4 mmol), boc-α-aminoisobutyric acid (13.2 g, 65.4 mmol), 1-hydroxybenzotriazole (8.8 g, 65.4 mmol), and N,N-diisopropylethylamine (22.8 mL, 130.7 mmol) stirring in dichloromethane (500 mL) at 0° C. was added 1-(3-dimethylaminopropyl)-3-ethylcarbodiimide (12.3 g, 71.9 mmol). After 18 h, ethyl acetate and saturated ammonium chloride were added and the mixture extracted with ammonium chloride, sodium bicarbonate, and brine. The organic extracts were dried over sodium sulfate and concentrated. Purification by silica gel chromatography (25% ethyl acetate/hexanes) yielded the desired compound (21.6 g, 83%) as a white solid: $^1$H NMR (300 MHz, CDCl$_3$) d 1.39 (s, 9H), 1.48 (s, 6H), 3.62 (dd, J=3.4, 9.1 Hz, 1H), 3.70 (s, 3H), 3.85 (dd, J=3.4, 9.1 Hz, 1H), 4.48 (dd, J=12.5, 22.7 Hz, 2H), 4.75 (m, 1H), 4.92 (s, 1H), 7.11 (d, J=8.6 Hz, 1H), 7.35 (m, 5H); MS (FD) m/e 395; Anal. calc'd for $C_{20}H_{30}N_2O_6$: C, 60.90; H, 7.67; N, 7.10. Found: C, 61.02; H, 7.78; N, 7.10.

Preparation 4

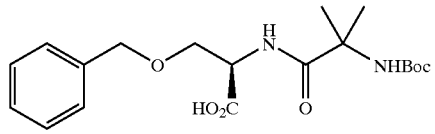

To a solution of a compound of Preparation 3 (5.30 g, 13.4) stirring in dioxane (100 mL)/water (50 mL) at room temperature was added lithium hydroxide (2.80 g, 67.3 mmol). After 18 h, water was added and the solution concentrated. The resulting mixture was extracted with diethyl ether. Sodium chloride was added to the aqueous layer and the pH adjusted to 3.5 with 1N HCl. The resulting mixture was extracted with ethyl acetate and the combined organic extracts dried over sodium sulfate then concentrated to yield the title compound (4.40 g, 66%) as a white foam: $^1$H NMR (300 MHz, CDCl$_3$) d 1.39 (s, 9H), 1.45 (s, 3H), 1.47 (s, 3H), 3.68 (m, 1H), 3.95 (m, 1H), 4.54 (s, 2H), 4.70 (m, 1H), 5.51 (bs, 1H), 7.18 (d, J=9.1 Hz, 1H), 7.25 (m, 5H), 9.90 (bs, 1H); MS (FD) m/e 381; Anal. calc'd for C₁₉H₂₈N₂O₆: C, 59.99; H, 7.42; N, 7.36. Found: C, 59.74; H, 7.26; N, 7.30.

Preparation 5

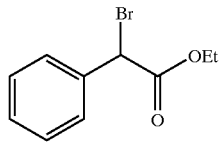

To a solution of α-bromophenylacetic acid (100 g, 466 mmol) stirring in absolute ethanol (500 mL) at room temperature was added p-toluenesulfonic acid monohydrate (10 g, 53 mmol). This solution was heated to reflux and, after 8 h, concentrated to dryness. The resulting residue was dissolved in ethyl acetate, washed with saturated aqueous sodium bicarbonate, brine, dried over sodium sulfate, filtered, and concentrated to yield 77 g (68%) of the desired product as an orange oil: ¹H-NMR is consistent with structure; MS (FD) 241.9, 243.9.

Preparation 6

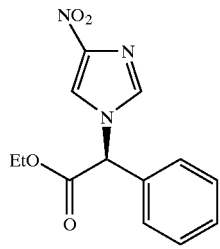

To a slurry of sodium hydride (13.6 g of a 60% dispersion in mineral oil, 341 mmol) stirring in N,N-dimethylformamide (240 mL) was carefully added 4'-nitroixidazole (38.6 g, 341 mmol) such that the temperature during the addition was maintained below 40° C. This resulting slurry was stirred for 1 h and then cooled to 5° C. To this mixture was slowly added BX8-MEZ-148 (76 g, 310 mmol) at a rate such that the reaction temperature was maintained below 20° C. After 4 h, the reaction was concentrated and subsequently extracted with ethyl acetate. The combined organic extracts were filtered, washed with water, brine, dried over sodium sulfate, filtered and concentrated. The resulting residue was purified by silica gel chromatography (methanol/chloroform gradient) to yield the 60.1 g (70%) of the desired product as a white solid: ¹H-NMR is consistent with structure; MS (FD) 275 (M+); Anal. Calc'd. for: C, 56.73; H, 4.73; N, 15.27. Found: C, 56.48; H, 4.78; N, 15.08.

Preparation 7

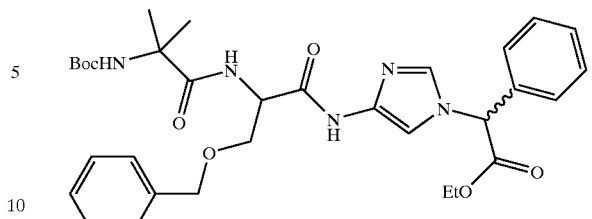

To a suspension of 5% Pd/C (0.85 g) and a compound of Preparation 6 (2.13 g, 7.21 mmol) stirring in dioxane (50 mL) at room temperature was added hydrogen (g) (35 psi) on a Parr apparatus. After 4 h, the mixture was purged with nitrogen, celite added, and the solution filtered through a pad of celite. To the resulting filtrate, under nitrogen atmosphere, was added a compound of Preparation 4 (2.74 g, 7.21 mmol), 1-hydroxybenzotriazole (0.97 g, 7.21 mmol), N,N-diisopropylethylamine (2.5 mL, 14.4 mmol), and 1-(3-dimethylaminopropyl)-3-ethylcarbodiimide (1.36 g, 7.93 mmol). After 18 hours, ethyl acetate was added and the mixture washed with saturated aqueous ammonium chloride, saturated aqueous sodium bicarbonate, and brine. The organic extract was dried over sodium sulfate and concentrated. Purification by silica gel chromatography (5% methanol/dichloromethane) yielded the title compound (1.25 g, 29%) as a yellow foam: ¹H NMR (300 MHz, CDCl₃) d 1.30 (t, J=6.9 Hz, 3H), 1.40 (s, 9H), 1.42 (s, 3H), 1.51 (s, 3H), 3.60 (dd, J=5.1, 9.7 Hz, 1H), 4.05 (m, 1H), 4.28 (m, 2H), 4.54 (dd, J=14.08, 26.3 Hz, 2H), 4.62 (m, 1H), 5.08 (bs, 1H), 5.82 (s, 1H), 7.12 (d, J=11.5 Hz, 1H), 7.35 (m, 12H), 9.75 (bs, 1H); MS (FD) m/e 607; Anal. calc'd for C₃₂H₄₁N₅O₇: C, 63.29; H, 6.80; N, 11.52. Found: C, 63.07; H, 6.81; N, 11.74.

Preparation 8

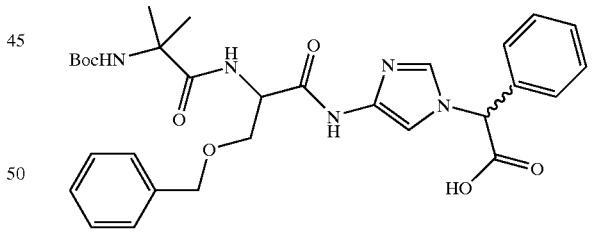

To a solution of a compound of Preparation 7 (5.3 g, 8.75) stirring in dioxane (50 mL)/water (25 mL) at room temperature was added lithium hydroxide (0.73 g, 17.50 mmol). After 20 min, water was added and the reaction concentrated to approximately 30 mL. The resulting mixture was extracted with diethyl ether and the aqueous layer saturated with sodium chloride then adjusted to pH 3.5 with 1N HCl. The mixture was extracted with ethyl acetate and the combined organic extracts dried over sodium sulfate and concentrated to yield the title compound (4.90 g, 97%) as a light orange foam: ¹H NMR (300 MHz, CDCl₃) d; MS (FD) m/e; Anal. calc'd for C,; H,; N,. Found: C,; H,; N,.

Preparation 9

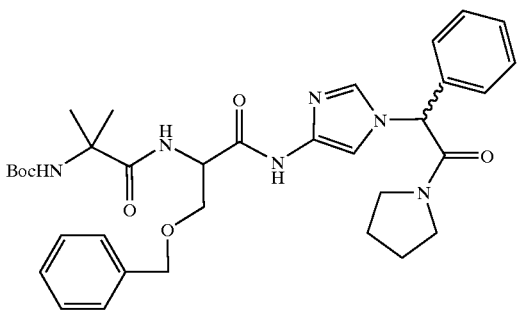

To a solution of a compound of Preparation 8 (2.09 g, 3.61 mmol), pyrrolidine (0.30 mL, 3.61 mmol), and 1-hydroxybenzotriazole (0.54 g, 3.97 mmol) stirring in anhydrous DMF (50 mL) at 0° C. was added 1,3-dicyclohexyl carbodiimide (0.82 g, 3.97 mmol). After 18 hours at room temperature, the reaction was concentrated, dissolved in dichloromethane, filtered, and concentrated. Purification by silica gel chromatography (5% methanol/dichloromethane) yielded the title compound (1.74 g, 76%) as a light orange solid: $^1$H NMR (300 MHz, CDCl$_3$) d 1.41 (s, 9H), 1.43 (s, 3H), 1.52 (s, 3H), 2.88 (m, 4H), 3.42 (m, 1H), 3.50 (m, 4H), 4.08 (m, 1H), 4.55 (dd, J=14.9, 27.4 Hz, 2H), 4.70 (m, 1H), 4.96 (d, J=4.0 Hz, 1H), 5.86 (s, 1H), 7.15 (d, J=6.9 Hz, 1H), 7.35 (m, 12H), 9.28 (bs, 1H); MS (FD) m/e 632; Anal. calc'd for C$_{34}$H$_{44}$N$_6$O$_6$: C, 64.54; H, 7.01; N, 13.28. Found: C, 63.48; H, 6.95; N, 12.19.

Example 1

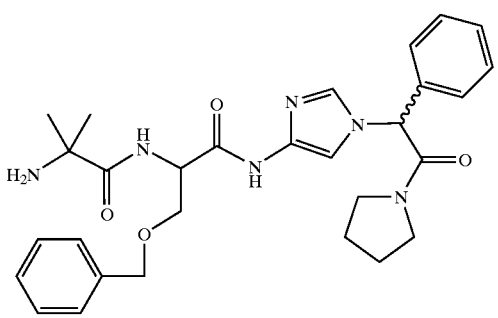

To a solution of a compound of Preparation 9 (1.00 g, 1.58 mol) and anisole (0.3 mL) stirring in anhydrous dichloromethane (12 mL) at 0° C. was added trifluoroacetic acid (3 mL) and the reaction mixture warmed to room temperature. After 4 h, the dichloromethane was removed in vacuo and excess diethyl ether added. After 20 min, the reaction mixture was filtered to yield the title compound (1.02 g, 85%) as a white solid: $^1$H NMR (300 MHz, CDCl$_3$) d 1.60 (s, 6H), 1.90 (m, 4H), 3.08 (m, 1H), 3.58 (m, 3H), 3.88 (m, 2H), 4.52 (m, 2H), 4.72 (m, 1H), 6.10 (m, 2H), 7.25 (m, 6H), 7.46 (m, 5H), 7.70 (m 1H), 6.00 (m, 1H), 8.40 (m, 1H), 11.15 (m, 1H); MS (FD) m/e 532 (M-2TFA); Anal. calc'd for C$_{33}$H$_{38}$F$_6$N$_6$O$_8$: C, 52.10; H, 5.03; H, 11.05. Found: C, 51.54; H, 5.25; N, 11.21.

Preparation 10

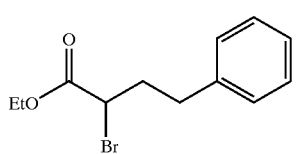

To a slurry of d,1-α-amino-4-phenylbutyric acid (20.0 g, 111 mmol) stirring in 3N sulfuric acid (200 mL) at 0° C. was added finely ground potassium bromide (48 g, 403 mmol). This slurry was cooled to −10° C., then a solution of sodium nitrite (11.0 g, 160 mmol in water (75 mL) was added dropwise. The resulting solution was stirred for 4 h while slowly warming to ambient temperature. The resulting precipitate was filtered to give 20.0 g of a yellow solid. To a solution of the yellow solid (18.8 g, 80 mmol) in absolute ethanol (400 mL) was added p-toluenesulfonic acid monohydrate (4.6 g, 24 mmol). This solution was refluxed for 4 h, filtered and concentrated. The resulting residue was purified by silica gel chromatography (ethyl acetate/hexanes gradient) to give 7.2 g (24%) of the desired product as a clear oil. $^1$H-NMR is consistent with structure; MS (FD) 269, 27.

Preparation 11

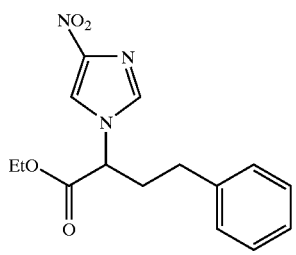

To a slurry of sodium hydride (1.0 g of a 60% dispersion in mineral oil, 24 mmol) stirring in N,N-dimethylformamide (200 mL) at ambient temperature was carefully added a solution of 4-nitroimidazole (5.7 g, 20 mmol). This mixture was cooled to 0° C. and a solution of a compound of Preparation 10 (15.2 g, 60 mmol) in N,N-dimethylformamide (10 mL) was added. After 16 h, the mixture was slowly warmed to ambient temperature, concentrated, and the resulting residue extracted with chloroform. The combined organic extracts were washed with water, brine, dried over sodium sulfate, filtered and concentrated. The resulting residue was purified by silica gel chromatography (chloroform) to give 5.0 g (82%) of the desired product as a clear oil. $^1$H-NMR is consistent with structure; MS (FD) 303 (M+); Anal. Calc'd for: C, 59.40; H, 5.65; N, 13.85. Found: C, 59.73; H, 5.71; N, 13.40.

Preparation 12

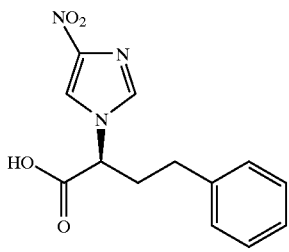

To a solution of a compound of Preparation 11 (4.24 g, 14 mmol) stirring in tetrahydrofuran (30 mL) and ethanol (30 mL) at room temperature was added 2NaOH (35 mL, 70 mmol). After 1 h, this mixture was treated with 5N HCl until pH=2.5. Ethyl acetate (30 mL) and water (30 mL) were added and the resulting solution was extracted with ethyl acetate. The combined organic extracts were washed with brine, dried over sodium sulfate, filtered and concentrated to give 3.8 g (98%) of the desired product as a yellow oil: $^1$H-NMR is consistent with structure; MS (FD) 276 (M+).

Preparation 13

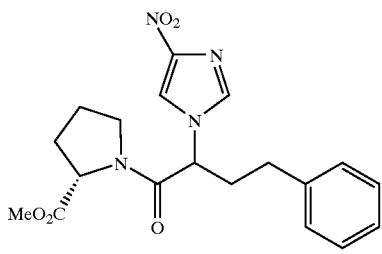

To a solution of a compound of Preparation 12 (3.8 g, 14 mmol), 1-proline methylester (1.8 g, 14 mmol) and 1-hydroxybenzotriazole hydrate (2.1 g, 15 mmol) stirring in N,N-dimethylformamide (150 mL) at room temperature was added 1,3-dicyclohexylcarbodiimide (3.2 g, 15.4 mmol). After 16 h, the mixture was concentrated and the resulting residue partitioned between ethyl acetate and water. The combined organic extracts were washed with water, brine, dried over sodium sulfate, and concentrated. The resulting orange oil was purified by silica gel chromatography (methanol/chloroform gradients) to give 3.8 g (70%) of the desired product as a yellow oil: $^1$H-NMR is consistent with structure; MS (FD) 386.2 (M+).

Preparation 14

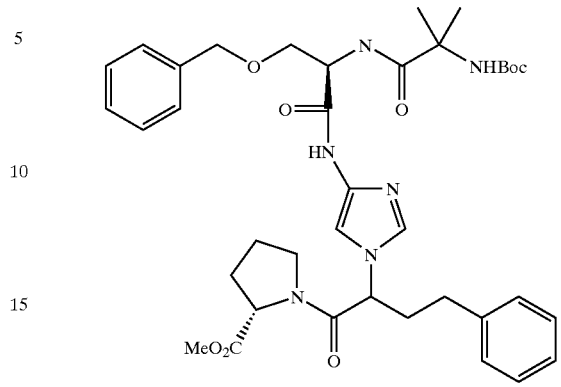

To a slurry of 10% Pd/C in dioxane (10 mL) was added a solution of a compound of Preparation 13 (2.4 g, 6.2 mmol) in dioxane (100 mL). The mixture was then treated with hydrogen gas (40 psi) on a Parr apparatus. After 5 h, an amount of 10% Pd/C (0.5 g) in dioxane (10 mL) was added. The mixture was hydrogenated for 4 h then carefully filtered through celite. To the resulting filtrate was added a compound of Preparation 4 (2.4 g, 6.2 mmol), 1-hydroxybenzotriazole hydrate (0.92 g, 6.8 mmol), followed by 1,3-dicyclohexylcarbodiimide (1.4 g, 6.8 mmol). After 16 h, the reaction was concentrated and the resulting residue extracted with ethyl acetate. The combined organic extracts were washed with saturated aqueous sodium bicarbonate, brine, dried over sodium sulfate, filtered, and concentrated. Purification silica gel chromatography (methanol/chloroform gradient) gave 2.2 g (50%) of the desired product as a tan foam: $^1$H-NMR is consistent with structure; MS (FD) 718.7 (M+); Anal Calc'd for; C, 63.49; H, 7.01; N, 11.69. Found: C, 63.30; H, 6.91; N, 11.84.

Example 2

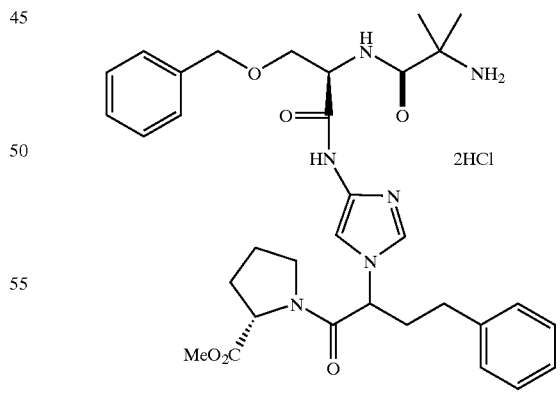

To a solution of a compound of Preparation 14 (2.1 g, 3.0 mmol) stirring in dichloromethane (25 mL) was added trifluoroacetic acid (8 mL, 104 mmol). After one h, water (25 mL) was added and the solution was quenched carefully with sodium carbonate, then extracted with chloroform. The combined organic extracts were washed with brine, dried over sodium sulfate, filtered and concentrated. To a solution of the resulting residue in diethyl ether (40 mL) was added a saturated solution of HCl in diethyl ether (40 mL). The resulting slurry was concentrated to dryness to yield 1.6 g (80%) of the desired product as a tan foam: $^1$H-NMR is consistent with structure; MS (FD) 618.3 (M+); Anal. Calc'd. for: C, 57.31; H, 6.41; N, 12.15. Found: C, 57.52; H, 6.19; N, 12.04. IR (KBr) 2954, 1743, 1656, 1559, 1496, 1453 cm$^{-1}$.

Preparation 15

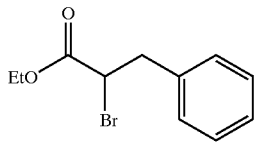

Reaction of d,1-α-phenylalanine (20.0 g, 120 mmol), potassium bromide (48 g, 400 mmol), sodium nitrite (11.0 g, 160 mmol), water (75 mL), 3N sulfuric acid (200 mL), p-toluenesulfonic acid monohydrate (5.7 g, 30 mmol) and absolute ethanol (500 mL) according to Preparation 10 gave 18.0 g (70%) of the desired product as a colorless oil: $^1$H-NMR is consistent with structure; MS (FD) 256, 258.

Preparation 16

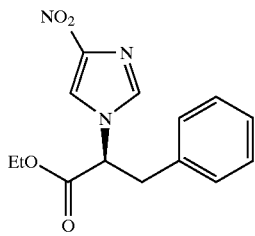

Reaction of a compound of Preparation 15 (15.22 g, 60 mmol), sodium hydride (2.84 g of a 60% dispersion in mineral oil, 72 mmol), 4-nitroimidazole (8.1 g, 72-mmol) in N,N-dimethylformamide (400 mL) according to Preparation 11 gave 9.5 g (55%) of the desired product as a yellow foam: $^1$H-NMR is consistent with structure; MS (FD) 289.1 (M+); Anal. Calc'd. for: C, 50.13; H, 5.23; N, 14.53. Found: C, 58.40; H, 5.17; N, 14.24.

Preparation 17

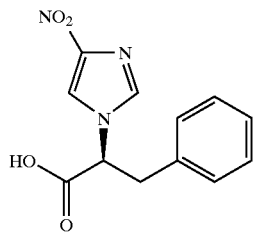

Reaction of a compound of Preparation 16 (3.3 g, 12.0 mmol), 2N NaOH (30 mL, 60 mmol) in ethyl acetate (30 mL)/ethanol (30 mL) according Preparation 12 gave 2.85 g (90%) of the desired product as a white solid: $^1$H-NMR is consistent with structure; MS (FM) 262 (M+): Anal. Calc'd. for: C, 55.17; H, 4.24; N, 16.09. Found: C, 55.14; H, 4.24; N, 15.94.

Preparation 18

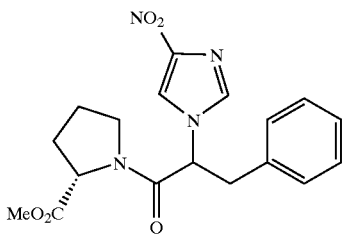

Reaction of a compound of Preparation 17 (2.8 g, 11.0 mmol), 1-proline methylester (1.4 g, 11.0 mmol), 1-hydroxybenzotriazole hydrate (1.63 g, 12.1 mmol), and 1,3-dicyclohexylcarbodiimide (2.5 g, 12.1 mmol) in N,N-dimethylformamide (150 mL) according to Preparation 13 gave 3.2 g (70.4%) of the desired product as a white solid: $^1$H-NMR is consistent with structure; MS (FD) 372 (M+).

Preparation 19

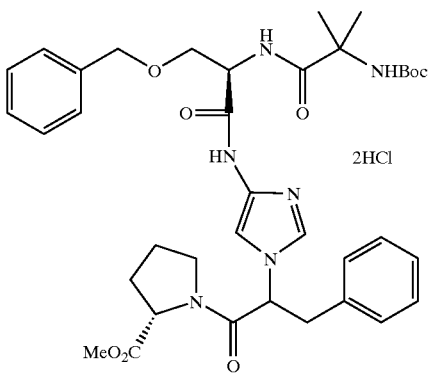

Reaction of a compound of Preparation 18 (0.6 g, 1.6 mmol), 5% Pd/C (0.66 g) in ethyl acetate (50 mL), ethanol (50 mL) and dichloromethane (4 mL), a compound of Preparation 4 (0.46 g, 1.2 mmol), 1-hydroxybenzotriazole hydrate (0.18 g, 1.3 mmol) and 1,3-dicyclohexylcarbodiimide (0.27 g, 1.3 mmol) in N,N-dimethylformamide (100 mL) according to Preparation 14 gave 0.29 g (34%) of the desired product as a tan foam: $^1$H-NMR is consistent with structure; MS (FD) 704.5 (M+).

Example 3

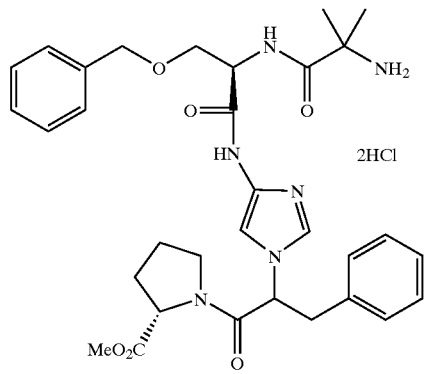

Reaction of a compound of Preparation 19 (0.23 g, 0.33 mmol), trifluoroacetic acid (4.0 mL, 24 mmol) in dichloromethane (12 mL), followed by treatment with HCl/ethyl acetate solution (40 mL), according to Example 2 gave 0.17 g (77%) of the desired product as a white foam: ¹H-NMR is consistent with structure; MS (FD) 604 (M+); Anal. Calc'd for: C, 56.72; H, 6.25; N, 12.40. Found: C, 56.53; H, 6.31; N, 12.19. IR (KBr) 2931.09, 1743.64, 1653.48, 1533.67, 1453.73 (cm⁻¹).

Preparation 20

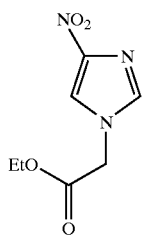

Reaction of ethylbromoacetate (4.9 mL, 44 mmol), 4-nitroimidazole (5.00 g, 44 mmol) and potassium carbonate (12.2 g, 88 mmol) at ambient temperature in N,N-dimethylformamide (50 mL) according to Preparation 3 from Examples Part 2A gave 7.77 g (88%) of the desired product as an orange solid: ¹H-NMR was consistent with structure; MS (FD) 199 (M+); Anal. Calc'd for: C, 42.21; H, 4.55; N, 21.10. Found: C, 42.51; H, 4.66; N, 21.24.

Preparation 21

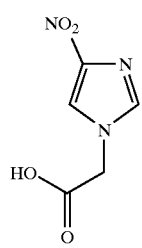

Reaction of a compound of Preparation 20 (2.00 g, 10.0 mmol) and 2N NaOH (30 mL, 60 mmol) in tetrahydrofuran (5 mL) and ethanol (5 mL) according Preparation 12 gave 1.3 g (76%) of the desired product as a tan solid which is carried on without further purification.

Preparation 22

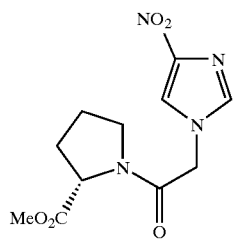

Reaction of a compound of Preparation 21 (1.20 g, 7.0 mmol), 1-proline methylester hydrochloride (1.27 g, 8.4 mmol), 1-hydroxybenzotriazole hydrate (1.04 g, 8.4 mmol), triethylamine (1.95 mL, 14.0 mmol) and 1,3-dicyclohexylcarbodiimide (1.6 g, 8.4 mmol) in N,N-dimethylformamide according to Preparation 13 gave 0.6 g (30%) of the desired compound as a tan semi-solid: ¹H-NMR is consistent with structure; MS (FD) 282 (M+).

Preparation 23

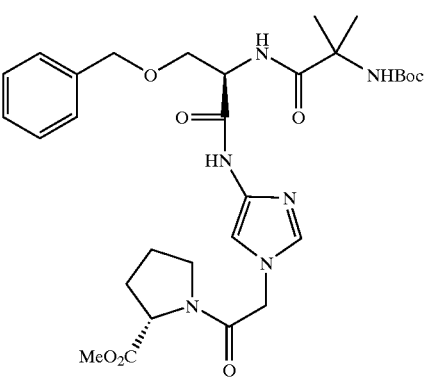

Hydrogenation of a compound of Preparation 22 (0.47 mg, 1.7 mmol) and 5% Pd—C (0.15 g) in ethyl acetate (20 mL)/ethanol (20 mL) followed by treatment with 1-hydroxybenzotriazole hydrate (225 mg, 1.7 mmol), 1,3-dicyclohexylcarbodiimide (340 mg, 1.7 mmol) and 368979 (633 mg, 1.7 mmol) according to Preparation 14 gave 0.45 g (39%) of the desired product: ¹H-NMR is consistent with structure; MS (FD) 614 (M+).

Example 4

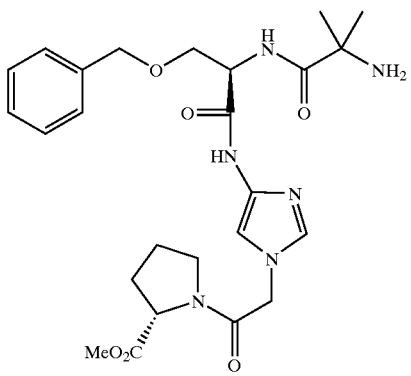

Reaction of a compound of Preparation 23 (0.40 g, 0.65 mmol) and trifluoroacetic acid (5 mL, 64 mmol) in dichloromethane (20 mL) according to Example 2 gave 0.22 g (67%) of the desired product as an off-white solid: ¹H-NMR is consistent with structure; MS (FD) 514 (M+); Anal. Calc'd for: C, 58.35; H, 6.66; N, 16.33. Found: C, 58.25; H, 6.40; N, 16.16.

Preparation 24

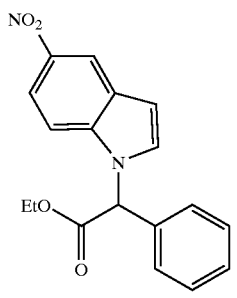

Reaction of 5-nitroindole (3.0 g, 18.5 mmol), α-bromophenylacetic acid ethylester (4.5 g, 18.5 mmol), and sodium hydride (0.8 g, 20 mmol, 60% dispersion in mineral oil) in N,N-dimethylformamide (75 mL) according to Preparation 1 gave 3.9 g (65%) of the desired product: $^1$H-NMR is consistent with structure; MS (FD) 324 M+; Anal. Calc'd for: C, 66.66; H, 4.97; N, 8.64. Found: C, 66.80; H, 5.11; N, 8.81.

Preparation 25

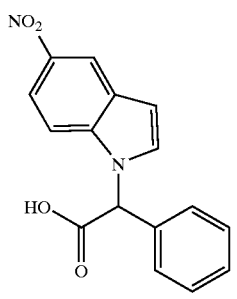

Reaction of a compound of Preparation 24 (2.0 g, 6.2 mmol) and 2N NaOH (50 mL, 100 mmol) in tetrahydrofuran (10 mL)/ethanol (8 mL) according to Preparation 12 gave 1.4 g (76%) of the desired product as a yellow solid: $^1$H-NMR is consistent with structure; MS (FD) 296 (M+); Anal. Calc'd for: C, 64.86; H, 4.08; N, 9.45. Found: C, 64.60; H, 4.14; N, 9.29.

Preparation 26

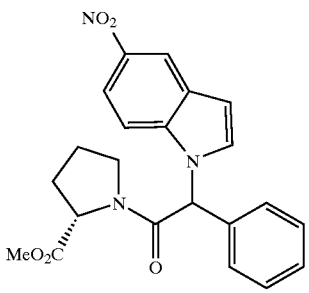

Reaction of a compound of Preparation 25 (1.0 g, 5.7 mmol), 1-hydroxybenzotriazolehydrate (0.85 g, 6.3 mmol), 1-proline methylester hydrochloride (1.03 g, 6.3 mmol), triethylamine (1.6 mL, 11.4 mmol) and 1,3-dicyclohexylcarbodiimide (1.3 g, 6.3 mmol) in N,N-dimethylformamide (25 mL) according to Preparation 13 gave 1.35 g (58%) of the desired product as yellow solid: $^1$H-NMR is consistent with structure; MS (FD) 407 (M+); Anal. Calc'd for: C, 64.86; H, 5.20; N, 10.31. Found: C, 65.20; H, 5.50; N, 10.10.

Preparation 27

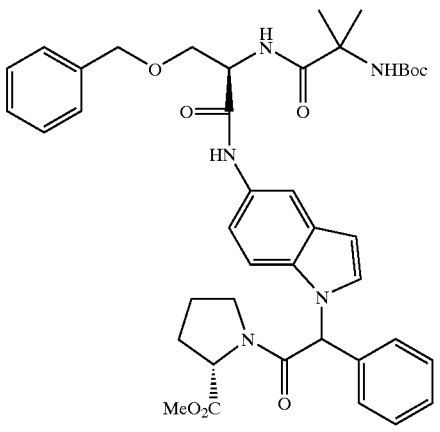

Hydrogenation of a compound of Preparation 26 (0.41 g, 1.0 mmol) with 5% Pd—C (0.08 g) in ethanol (25 mL)/ethyl acetate (25 mL) followed by treatment with 1-hydroxybenzotriazole hydrate (0.15 g, 1.1 mmol), 1,3-dicyclohexylcarbodiimide (0.23 g, 1.1 mmol) and 368979 (0.42 g, 1.1 mmol) according to Preparation 14 gave 0.38 g (51%) of the desired product: $^1$H-NMR is consistent with structure; MS (FD) 739.7 (M+)

Example 5

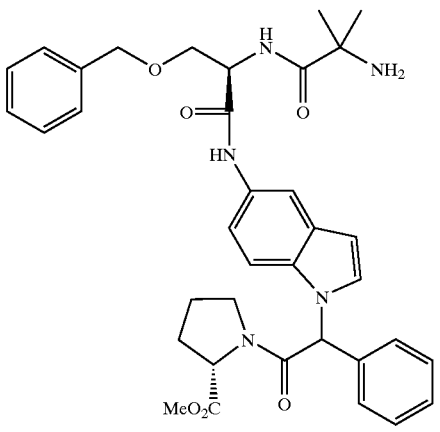

Reaction of a compound of Preparation 27 (0.38 g, 0.51 mmol) and trifluoroacetic acid (2 mL, 26 mmol) in dichloromethane (10 mL) according to Example 2 gave 0.125 g (38%) of the desired product: $^1$H-NMR is consistent with structure; MS (FD) 639 (M+); Anal. Calc'd for 1H$_2$O: C, 65.74; H, 6.59; N, 10.65. Found: C, 65.75; H, 6.42; N, 10.98.

Preparation 28

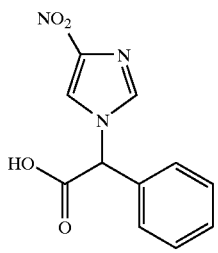

To a solution of a compound of Preparation 6 (27 g, 98 mmol) stirring in tetrahydrofuran (60 mL) and absolute ethanol (60 mL) at ambient temperature was added 2N NaOH (250 mL, 500 mmol). After 3.5 h, the mixture was washed with diethyl ether and the organic extract subsequently washed with water. The combined aqueous extracts were acidified and the resulting mixture extracted with ethyl acetate. The combined organic extracts were washed once with brine, dried over sodium sulfate, filtered, and concentrated to give 24.2 q (75%) of the desired product as a tan solid: $^1$H-NMR was consistent with structure; MS (FD) 246.9 (M+); Anal. Calc'd for: C, 53.44; H, 3.67; N, 17.00. Found: C, 53.71; H, 3.67; N, 16.83. mp=218–221° C.

Preparation 29

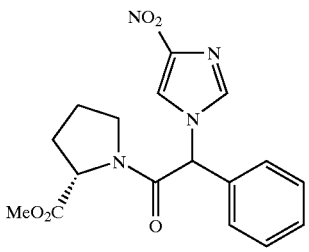

To a slurry of a compound of Preparation 28 (8.15 g, 33 mmol) stirring in dichloromethane (100 mL) was added oxalyl chloride (11.5 mL, 130 mmol) and N,N-dimethylformamide (2 drops). After 90 min at ambient temperature, the mixture was concentrated and the residue was dissolved in dichloromethane (40 mL). The resulting solution was added a N,N-diisopropylethylamine (6.5 mL, 360 mmol) and 1-prolinemethylester (3.9 g, 20 mmol) in dichloromethane (4 ml). After 2 h at ambient temperature, the mixture was extracted with ethyl acetate and the combined organic extracts washed with water, brine, dried over sodium sulfate, filtered, and concentrated. The resulting residue was purified by silica gel chromatography (ethyl acetate/hexanes) to give 10.7 g (71%) of the desired product as tan foam: $^1$H-NMR is consistent with structure; Anal. Calc'd for: C, 56.98; H, 5.06; N, 15.63. Found: C, 56.75; H, 5.14; N, 15.44. Mp, 103–111° C.

Preparation 30

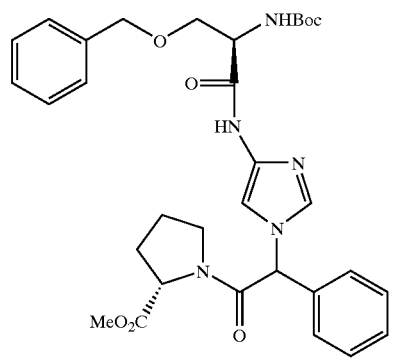

To a slurry of 5% Pd/C (0.28 g) in ethyl acetate (30 mL) was added a solution of a compound of Preparation 29 (1.0 g, 2.8 mmol) in ethanol (100 mL). The mixture was hydrogenated at 40 psi on a Parr apparatus. After 25 min, additional 5% Pd/C (0.5 g) was added and the mixture subsequently hydrogenated for 45 min, then filtered through celite and concentrated. To a slurry of the resulting residue in N,N-dimethylformamide (100 mL) was added boc-d-benzyloxyserine (0.62 g, 2.1 mmol), 1-hydroxybenzotriazole hydrate (0.31 g, 2.3 mmol) followed by 1,3-dicyclohexylcarbodiimide (0.48 g, 2.3 mmol). After 48 h, the mixture was filtered and concentrated and the residue purified by radial chromatography (silica gel, methanol/chloroform gradient). The resulting product was dissolved in ethyl acetate and washed with water, dried over sodium sulfate, filtered, and concentrated to give 0.5 g (30%) of the desired product as a tan foam: $^1$H-NMR is consistent with structure; MS (FD) 605 (M+).

Preparation 31

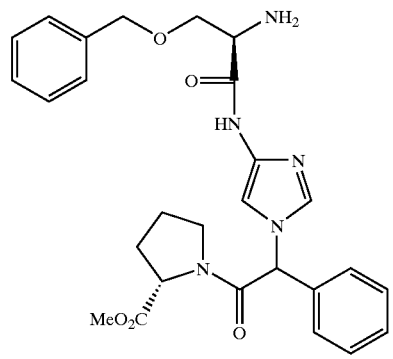

To a solution of a compound of Preparation 30 (3.1 g, 5.1 mmol) stirring in methanol (200 mL) at room temperature was added 5N HCl (51.0 mmol). After 16 h, the residue was partitioned between ethyl acetate and water and extracted with ethyl acetate. The combined organic extracts were washed with brine, dried over sodium sulfate, filtered and concentrated to give 2.1 g (81%) of the desired compound as a tan foam: $^1$H-NMR is consistent with structure; MS (FD) 506 (M+): Anal. Calc'd; for: C, 64.14; H, 6.18; N, 13.85. Found: C, 63.92, H, 6.18; N, 13.56.

Preparation 32

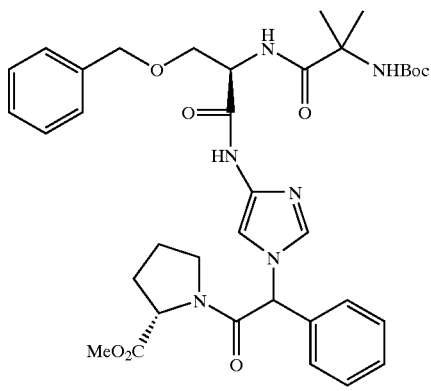

To a solution of a compound of Preparation 31 (2.1 g, 4.2 mmol) stirring in N,N-dimethylformamide (200 mL) was added Boc-α-aminoisobutyric acid (0.85 g, 4.2 mmol), 1-hydroxybenzotriazole hydrate (0.62 g, 4.6 mmol). After 16 h, mixture was concentrated to dryness and the resulting residue extracted with ethyl acetate. The combined organic extracts were washed with water, brine, dried over sodium sulfate, filtered, and concentrated. Purification by silica gel chromatography (methanol/chloroform) gave 2.3 g (80%) of the desired product as a tan foam: $^1$H-NMR is consistent with structure; MS (FD) 690 (M+).

Example 6

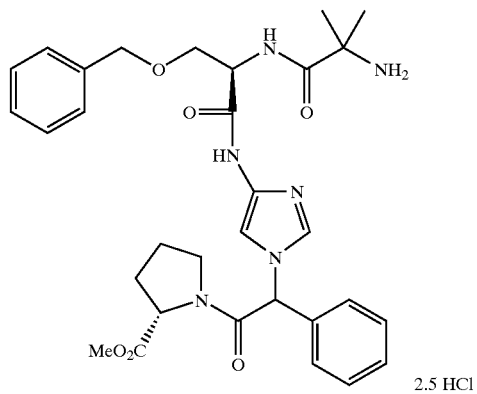

2.5 HCl

To a solution of the compound of Preparation 32 (1.75 g, 2.5 mmol) stirring in dichloromethane (190 mL) was added trifluoroacetic acid (63 mL, 780 mmol). After 1 h, the mixture was poured carefully into saturated aqueous sodium bicarbonate and extracted with ethyl acetate. The combined organic extracts were washed with brine, dried over sodium sulfate, filtered, and concentrated. The residue was dissolved in ethyl acetate (250 mL) and subsequently treated with a saturated solution of HCl in ethyl acetate (100 mL). The resulting mixture was concentrated to dryness, triturated with diethyl ether, and filtered to give 0.6 g (38%) of the desired product as a tan solid: $^1$H-NMR is consistent with structure; MS (FD) 590 (M+); Anal. Calc'd for: C, 54.60; H, 5.92; N, 12.33. Found: C, 54.47; H, 5.72; N, 12.16. IR (KBr) 3164, 3030, 2978, 2952, 2878, 1743, 1664, 1531, 1456, 1436, 1498, 1197, 1179 cm$^{-1}$.

Preparation 33

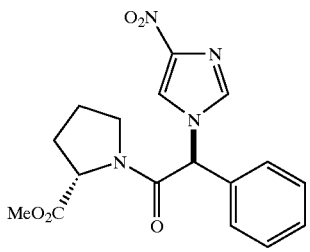

The optically enriched S-isomer was isolated by selective crystallization (ethyl acetate/hexanes) of a compound of Preparation 29 to give 1.3 g of the desired isomer: $^1$H-NMR is consistent with structure; MS (FD) 358 (M+); Anal. Calc'd for: C, 56.98; H, 5.06; N, 15.63. Found: C, 57.22; H, 4.87; N, 15.34. mp=114–118° C.

Preparation 34

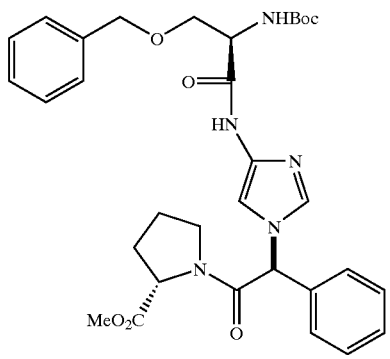

Hydrogenation of a compound of Preparation 29 (1.0 g, 2.8 mmol) and 5% Pd/C (0.756 g) in absolute ethanol (20 mL)/ethyl acetate (20 mL), followed by treatment of the resulting mixture with boc-d-benzyloxyserine (0.83 g, 2.8 mmol), 1-hydroxybenzotriazole hydrate (0.42 g, 3.4 mmol) and 1,3-dicyclohexylcarbodiimide (0.64 g, 3.1 mmol according to Preparation 1 gave 0.69 g (41%) of the desired product as a crystalline solid. Purification by silica gel chromatography (methanol/chloroform) followed by re-crystallization from ethyl acetate: $^1$H-NMR is consistent with structure; MS (FD) 605 (M+); Anal. Calc'd. for: C, 63.46; H, 6.49; N, 11.56. Found: C, 63.61; H, 6.31; N, 11.38; mp=184–186° C.

Preparation 35

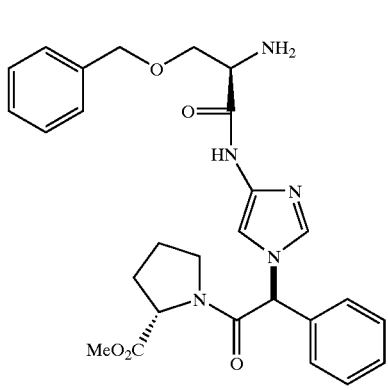

Reaction of a compound of Preparation 34 (0.61 g, 1.0 mmol) and trifluoroacetic acid (1.7 mL, 22 mmol) in dichloromethane (40 mL) according to Preparation 1 gave 0.5 g (100%) of the desired product as a foam: $^1$H-NMR is consistent with structure; MS (FD) 506 (M+); mp=55–60° C.

Preparation 36

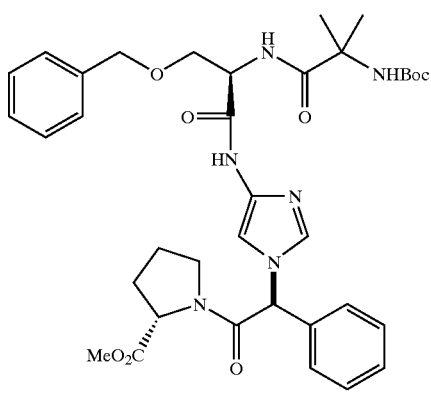

Reaction of a compound of Preparation 35 (0.5 g, 1 mmol), 1-hydroxybenzotriazole hydrate (0.15 g, 1.1 mmol) and 1,3-dicyclohexylcarbodiimide (0.23 g, 1.1 mmol) in N,N-dimethylformamide (15 mL) according to Preparation 32 gave 0.69 g (100%) of the desired product as a foam: $^1$H-NMR is consistent with structure; MS (FD) 690.2 (M+); mp=81–84° C.

Example 7

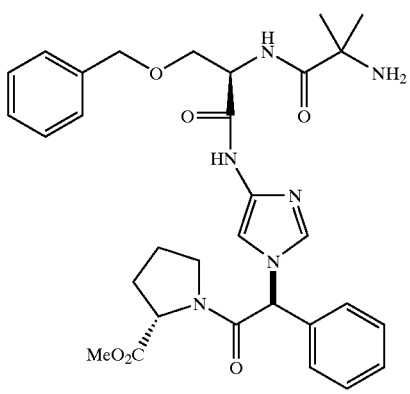

Reaction of a compound of Preparation 36 (0.595 g, 0.95 mmol) and trifluoroacetic acid (0.7 mL, 9.0 mmol) in dichloromethane (25 mL) according to Preparation 1 gave 0.37 g (75%) of the desired product as a solid: $^1$H-NMR was consistent with structure; MS (FD) 590 (M+); Anal. Calc'd for: C, 63.04; H, 6.48; N, 14.23. Found: C, 62.98; H, 6.59; N, 14.01. Mp, 156–159° C.

Preparation 37

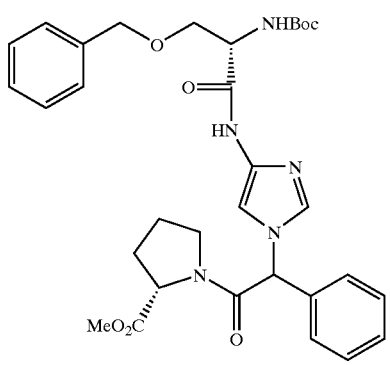

Reaction of a compound of Preparation 29 (2.63 g, 8.0 mmol), boc-1-benzyloxyserine (2.4 g, 8.0 mmol), 1-hydroxybenzotriazole hydrate (1.2 g, 8.8 mmol), 1,3-dicyclohexylcarbodiimide (1.8 g, 8.8 mmol) in N,N-dimethylformamide (250 mL) gave 2.4 g (50%) of the desired product as tan foam: $^1$H-NMR is consistent with structure; MS (FD) 605 (M+).

Preparation 38

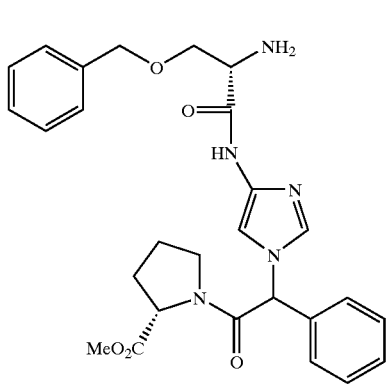

Reaction of a compound of Preparation 37 (2.3 g, 3.8 mmol), trifluoroacetic acid (35 mL, 45 mmol) in dichloromethane (90 mL) gave 1.4 g (74%) of the desired product as a tan foam: ¹H-NMR is consistent with structure; MS (FD) 506 (M+).

Preparation 39

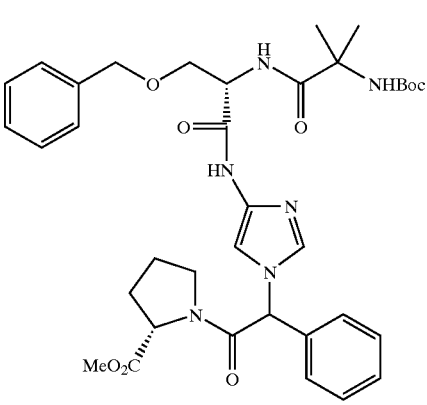

Reaction of a compound of Preparation 38 (1.1 g, 2.2 mmol), boc-α-aminoisobutyric acid (0.45 g, 2.2 mmol), 1-hydroxybenzotriazole hydrate (0.33 g, 2.4 mmol) and 1,3-dicyclohexylcarbodiimide (0.5 g, 2.4 mmol) in N,N-dimethylformamide (100 mL) gave 0.84 g (55%) of the desired product as a tan foam: ¹H-NMR is consistent with structure; MS (FD) 690 (M+).

Example 8

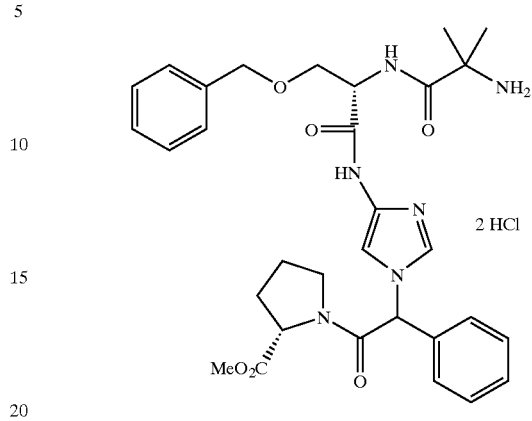

Reaction of a compound of Preparation 39 (0.7 g, 1.0 mmol), trifluoroacetic acid (25 mL, 320 mmol) in dichloromethane, and followed by dissolution in ethyl acetate (100 mL) and treatment with ethyl acetate saturated with HCl (100 mL) yielded 0.29 g (44%) of the desired compound as a white solid: ¹H-NMR is consistent with structure; MS (FD) 590 (M+); Anal. Calc'd for: C, 56.11; H, 6.08; N, 12.66. Found: C, 56.16; H, 5.92; N, 12.56. IR (KBr) 3163.75, 3031.15, 2952.46, 2876.38, 1745.07, 1664.94, 1530.69, 1497.79, 1453.37, 1435.81, 1197.21, 1177.62, 1094.93, 747.95, 701.04 cm$^{-1}$.

Preparation 40

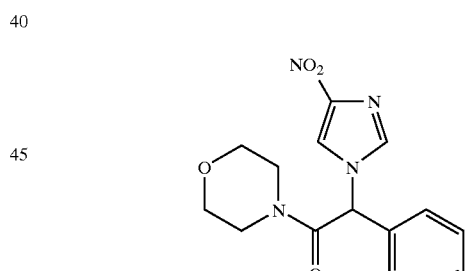

To a solution of a compound of Preparation 28 (1.0 g, 4.0 mmol), morpholine (0.35 mL, 4.0 mmol), 1-hydroxybenzotriazole hydrate (0.6 g, 4.4 mmol) stirring in N,N-dimethylformamide (50 mL) at room temperature was added 1,3-dicyclohexylcarbodiimide (0.9 g, 4.4 mmol). After 16 h, the mixture was concentrated, and the residue extracted with ethyl acetate. The combined organic extracts were filtered, washed with saturated aqueous sodium bicarbonate, water, brine, dried over sodium sulfate, filtered, and concentrated. The resulting residue was purified by silica gel chromatography (methanol/chloroform) to give 0.75 g (60%) of the desired product as a white foam: ¹H-NMR is consistent with structure; MS (FD) 316 (M+).

Preparation 41

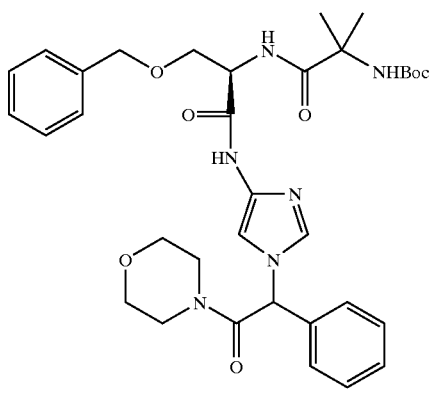

To a slurry of 5% Pd/C (0.18 g) in ethyl acetate (5 mL) was carefully added a solution of a compound of Preparation 40 (0.67 g, 2.0 mmol) in ethyl acetate (25 mL)/ethanol (25 mL). The resulting slurry was treated with hydrogen gas at 40 psi on a Parr apparatus. After 1 h, a slurry of 5% Pd/C (0.18 g) in ethyl acetate (10 mL) was added to this mixture, followed by hydrogenation at 40 psi. After 1 h, the mixture was filtered through celite and concentrated. To the residue stirring in N,N-dimethylformamide (100 mL) was added a compound of Preparation 4 (0.53 g, 1.4) and 1-hydroxybenzotriazole hydrate (0.21 g, 1.54 mmol followed by 1,3-dicyclohexylcarbodiimide (0.32 g, 1.54 mmol). After 16 h at room temperature, the solution was concentrated and extracted with ethyl acetate. The combined organic extracts were washed with water, brine, dried over sodium sulfate, filtered, and concentrated. The resulting residue was purified by silica gel chromatography (methanol/chloroform) to yield 0.27 g (30%) of the desired product as a tan foam: $^1$H-NMR is consistent with structure; MS (FD) 448 (M+).

Example 9

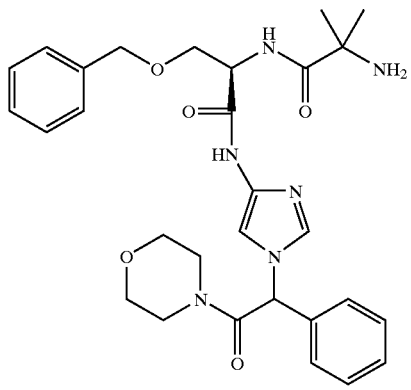

To a solution of a compound of Preparation 41 (0.27 g, 0.42 mmol) stirring in dichloromethane (12 mL) at room temperature was added trifluoroacetic acid (4 ml, 51 mmol). After 1.5 h, water (40 mL) was added and the reaction mixture quenched carefully with solid sodium bicarbonate. The resulting mixture was extracted with ethyl acetate and the combined organic extracts washed with brine, dried over sodium sulfate, filtered and concentrated. The concentrate was dissolved in ethyl acetate (40 mL) and subsequently treated with a saturated solution of HCl in ethyl acetate (40 mL). After 15 min, the mixture was concentrated to give 0.14 g (54%) of the desired product as a white solid: $^1$H-NMR is consistent with structure; MS (FD) 548 (M+); Anal. Calc'd. for: C, 56.04; H, 6.16; N, 13.52. Found: C, 55.78; H, 6.11; N, 13.27; IR (KBr) 2927, 2858.9, 1659.3, 1542.2, 1114.4 cm$^{-1}$.

Preparation 42

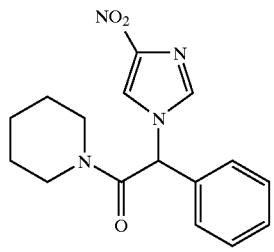

Reaction of a compound of Preparation 28 (1.0 g, 4.0 mmol), piperidine (0.4 mL, 4.0 mmol), 1-hydroxybenzotriazole hydrate (0.6 g, 4.4 mmol) and 1,3-dicyclohexylcarbodiimide (0.9 g, 4.4 mmol) in N,N-dimethylformamide (50 mL) gave 0.95 g (75%) of the desired product as a tan foam: $^1$H-NMR is consistent with structure; MS (FD) 314 (M+).

Preparation 43

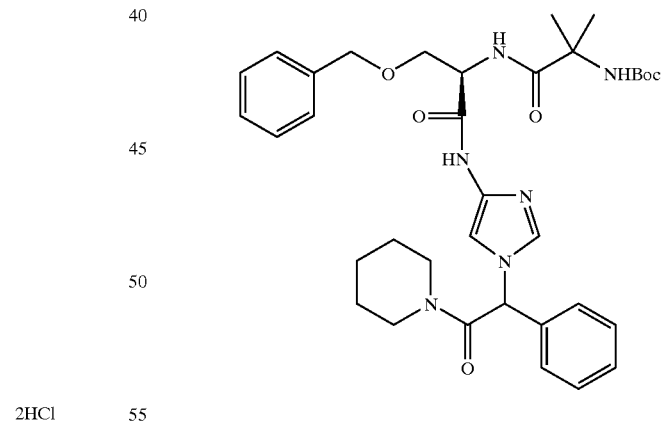

Hydrogenation of a compound of Preparation 42 (0.91 g, 2.9 mmol) in ethyl acetate (50 mL)/ethanol (50 mL), 5% Pd/C (0.36 g) in ethyl acetate (5 mL) followed by reaction with a compound of Preparation 4 (0.95 g, 2.5 mmol), 1-hydroxybenzotriazole hydrate (0.37 g, 2.75 mmol), and 1,3-dicyclohexylcarbodiimide (0.57 g, 2.75 mmol) gave 0.43 g (25%) of the desired product as a tan foam: $^1$H-NMR is consistent with structure; MS (FD) 646 (M+).

Example 10

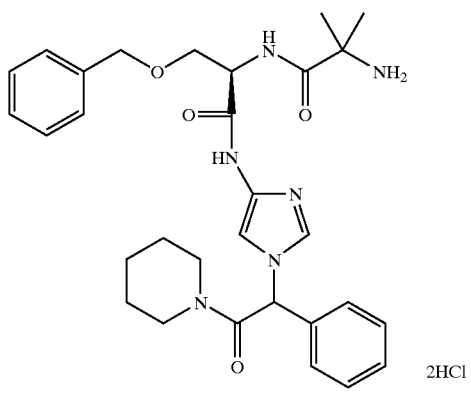

2HCl

Reaction of a compound of Preparation 43 (0.38 g, 0.59 mmol) and trifluoroacetic acid (4 mL, 51 mmol) in dichloromethane (12 mL) followed by acidification with HCl gave 0.03 g (8.3%) of the desired product as a tan solid:

$^1$H-NMR is consistent with structure; MS. (FD) 546 (M+); IR (KBr) 3141, 2937, 2859, 1642, 1534, 1453, 1444 cm$^{-1}$.

Preparation 44

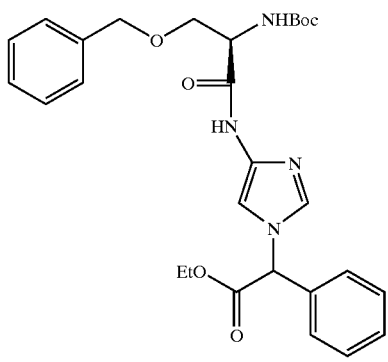

To a slurry of 5% Pd/C (1.0 g) in ethyl acetate (25 mL) was added a solution of a compound of Preparation 6 (8.25 g, 30 mmol) in ethyl acetate (25 mL)/absolute ethanol (25 mL). The slurry was hydrogenated at 40 psi on a Parr apparatus. After 75 min, a slurry of 5% Pd/C (0.7 g) in ethyl acetate (25 mL) was added to the reaction mixture. After hydrogenation at 40 psi for 1.5 h, the mixture was filtered through celite and concentrated. The concentrate was dissolved in N,N-dimethylformamide (500 mL) and boc-d-benzyloxyserine (9.0 g, 30.8 mmol), 1-hydroxybenzotriazole hydrate (4.5 g, 33 mmol) and 1,3-dicyclohexylcarbodiimide (6.8 g, 33 mmol) added. After 16 h at ambient temperature, the mixture was concentrated and the residue extracted with ethyl acetate. The combined organic extracts were washed with water, brine, dried over sodium sulfate, filtered, and concentrated. Purification by silica gel chromatography (methanol/chloroform) gave 8.33 g (53%) of the desired product as a tan solid: $^1$H-NMR is consistent with structure; MS (FD) 522 (M+); Anal. Calc'd. for: C, 64.35; H, 6.56; N, 10.72. Found: C, 64.59; H, 6.83; N, 10.77.

Preparation 45

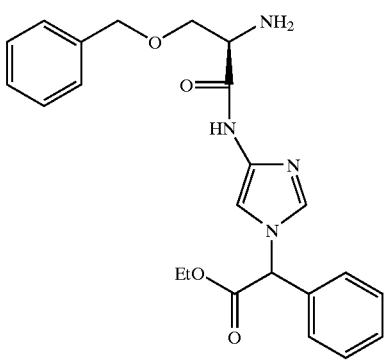

To a solution of a compound of Preparation 44 (8.1 g, 15.5 mmol) stirring at room temperature in dichloromethane (75 mL) was added trifluoroacetic acid (25 mL, 320 mmol). After 50 min, the mixture was carefully poured into a saturated aqueous solution of sodium bicarbonate and extracted with ethyl acetate. The combined organic extracts were washed with brine, dried over sodium sulfate, filtered and concentrated to give 6.5 g (99%) of the desired product as a tan solid. $^1$H-NMR is consistent with structure; MS (FD) 422 (M+).

Preparation 46

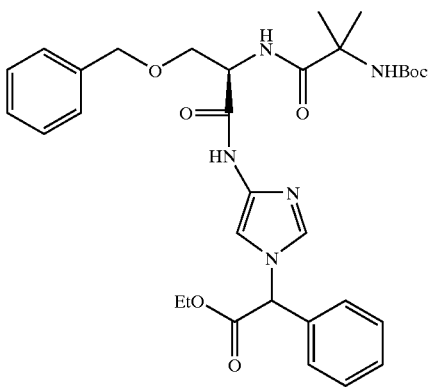

To a solution of a compound of Preparation 45 (6.5 g, 15.0 mmol), boc-α-aminoisobutyric acid (3.05 g, 15.0 mmol), 1-hydroxybenzotriazole hydrate (2.23 g, 16.5 mmol) stirring in N,N-dimethylformamide (400 mL) at room temperature was added 1,3-dicyclohexylcarbodiimide (3.4 g, 16.5 mmol). After 16 h, the mixture was concentrated and the resulting residue extracted with ethyl acetate. The combined organic extracts were washed with water, brine, dried over sodium sulfate, filtered, and concentrated. Purification by silica gel chromatography (methanol/chloroform) gave 6.39 g (70%) of the desired product as a tan foam: $^1$H-NMR is consistent with structure; MS (FD) 607 (M+). Anal. Calc'd. for: C, 63.25; H, 6.80; N, 11.52. Found: C, 63.36; H, 6.92; N, 11.59.

Preparation 47

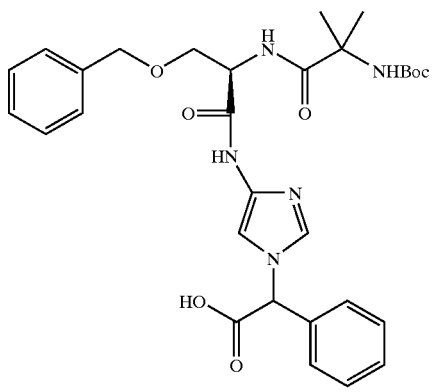

To a solution of a compound of Preparation 46 (6.04 g, 9.9 mmol) stirring in absolute ethanol (50 mL)/tetrahydrofuran (50 mL) at room temperature was added 1N NaOH (50 mL, 49.5 mmol). After 30 min, the mixture was acidified with 1N HCl and extracted with ethyl acetate. The combined organic extracts were washed with brine, dried over sodium sulfate, filtered, and concentrated to give 5.4 g (94%) of the desired product as a tan foam: $^1$H-NMR is consistent with structure; MS (FD) 590 (M+); Anal. Calc'd. for: C, 62.16; H, 6.43; N, 12.08. Found: C, 61.86; H, 6.29; N, 12.06.

Preparation 48

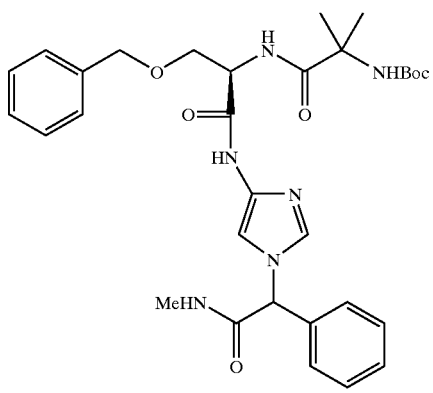

To a solution of a compound of Preparation 47 (0.7 g, 1.2 mmol), N-methylamine hydrochloride (0.08 g, 1.2 mmol), triethylamine (0.5 min, 3.6 mmol), and 1-hydroxybenzotriazole hydrate (0.18 g, 1.32 mmol) stirring in N,N-dimethylformamide (50 mL) at room temperature was added 1,3-dicyclohexylcarbodiimide (0.27 g, 1.32 mmol). After 16 h, the mixture was concentrated and the resulting residue extracted with ethyl acetate. The combined organic extracts were washed with water, brine, dried over sodium sulfate, filtered, and concentrated. Purification by silica gel chromatography (methanol/chloroform) gave 0.25 g (35%) of the desired product as a white solid: $^1$H-NMR is consistent with structure; MS (FD) 592.4 (M+); Anal. Calc'd for 0.32 mmol hydrate: C, 62.21; H, 6.76; N, 14.04. Found: C, 62.17; H, 6.74; N, 14.19.

Example 11

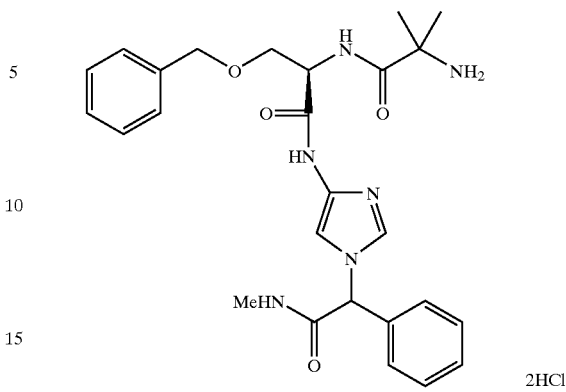

To a slurry of a compound of Preparation 48 (0.2 g, 0.34 mmol) stirring in dichloromethane (12 mL) at room temperature was added trifluoroacetic acid (4 mL, 52 mmol). After 2 h, additional trifluoroacetic acid (4 mL, 52 mmol) was added and the reaction was heated to reflux. After 7 h, the mixture was cooled to room temperature, water (40 mL) added, followed excess solid sodium bicarbonate. The mixture was extracted with ethyl acetate and the combined organic extracts washed with brine, dried over sodium sulfate, filtered and concentrate. The resulting crude product was dissolved in ethyl acetate (40 mL) and a saturated solution of HCl in diethyl ether was added (40 mL). After 15 min, this slurry was concentrated to give 0.13 g (68%) of the desired product as a white solid: $^1$H-NMR is consistent with structure; MS (FD) 492 (M+); Anal. Calc'd for: C, 55.22; H, 6.06; N, 14.86. Found: 55.33; H, 6.28; N, 13.24; IR (KBr) 3224, 3061, 3032, 2962, 2936, 2873, 1678, 1636, 1538, 1498, 1454, 1101 cm$^{-1}$.

Preparation 49

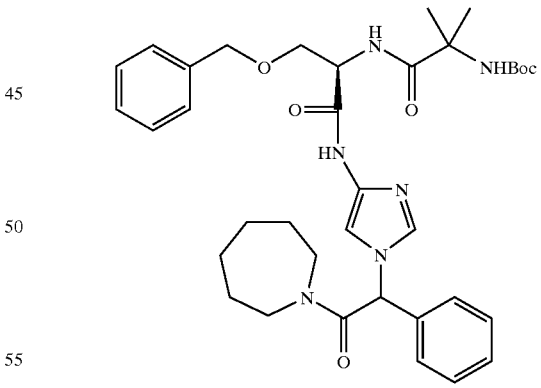

Reaction of a compound of Preparation 47 (1.00 g, 580 mmol), hexamethyleneimine, (0.2 mL, 1.7 mmol), 1-hydroxybenzotriazole hydrate (0.25 g, 1.9 mmol) and 1,3-dicyclohexylcarbodiimide (0.4 g, 1.9 mmol) in N,N-dimethylformamide (50 ml) as described in Preparation 4 gave 0.76 g (68%) of the desired product as a tan foam: $^1$H-NMR is consistent with structure; MS (FD) 660.2 (M+); Anal. Calc'd for: C, 65.43; H, 7.32; N, 12.02. Found: C, 65.92; H, 7.86; N, 11.71.

Example 12

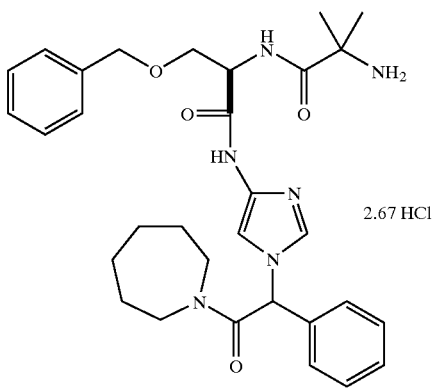

2.67 HCl

Reaction of a compound of Preparation 49 (0.67 g, 1.0 mmol) and trifluoroacetic acid (4 mL, 52 mmol) in dichloromethane (12 mL) for 1 h at ambient temperature, followed by acidification with HCl in ethyl acetate, according to Preparation 4 gave 0.3 g (48%) of the desired product as a white solid: $^1$H-NMR is consistent with structure; MS (FD) 560.4 (M); Anal. Calc'd for: C, 58.77; H, 6.56; N, 12.01. Found: C, 56.48; H, 6.41; N, 12.06.

Preparation 50

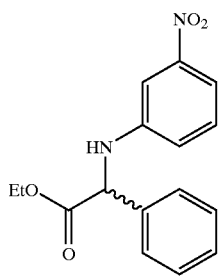

To a solution of m-nitroaniline (1.0 g, 7.24 mmol) stirred in anhydrous N,N-dimethylformamide (40 mL) at room temperature was added a solution of a compound of Preparation 5 (2.11 g, 8.69 mmol) in anhydrous N,N-dimethylformamide (10 mL). After 2.5 h, the reaction mixture was diluted with $H_2O$ (70 mL) and extracted with ethyl acetate. The combined organic extracts were washed with brine, dried ($Na_2SO_4$), and concentrated to give a yellow oil. Purification by radial chromatography (silica gel, 10%–75% ethyl acetate/hexanes) provided 1.65 g (76%) of the product (1:1 mixture of diastereomers) as an orange solid. $^1$H NMR (300 MHz, CDCl$_3$) d 7.47–7.53 (m, 3H), 7.33–7.41 (m, 4H), 7.20–7.25 (app. t, 1H, J=8.1 Hz), 6.81–6.85 (dd, 1H, J=8.0 Hz; 2.1 Hz), 5.10 (s, 1H), 4.12–4.26 (m, 2H), 1.20–1.25 (t, 3H, J=7.1 Hz); $^{13}$C NMR (75.5 MHz, CDCl$_3$) d 171.0, 149.2, 146.5, 136.4, 129.6, 128.9, 128.5, 127.0, 119.1, 112.5, 107.2, 62.1, 60.3, 13.9; FD+ MS for $C16H_{16}N_2O_4$=300; Anal. calcd. for $C_{16}H_{16}N_2O_4$: C, 63.99; H, 5.37; N, 9.33; Found: C, 64.77; H, 5.26; N, 9.17.

Preparation 51

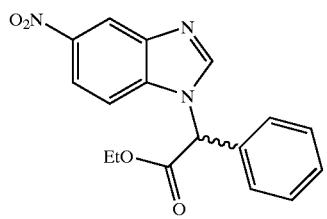

To a slurry of sodium hydride (0.15 g of a 60% dispersion in mineral oil, 3.86 mmol) stirring in N,N-dimethylformamide (30 mL) at room temperature, was added a solution of 6-nitrobenzimidazole (0.60 g, 3.68 mmol) in N,N-dimethylformamide (10 mL). After 10 min, a solution of α-bromophenylacetic acid ethylester in N,N-dimethylformamide (10 mL) was added and the solution stirred for 4 h at room temperature, quenched with water, and extracted with ethyl acetate. The combined organic extracts were washed with water, brine, dried (Na$_2$SO$_4$) and concentrated. Purification by silica gel chromatography (25%–75% ethyl acetate/hexanes) gave 0.580 g (50%) of the product (mixture of diastereomers) as a yellow oil: $^1$H NMR (300 MHz, CDCl$_3$) d 8.72–8.73 (d, 1H, J=2.1 Hz), 8.22–8.27 (dd, 1H, J=9.2 Hz; 2.1 Hz), 8.15 (s, 1H), 7.44–7.50 (app. t, 3H, J=6.9 Hz), 7.34–7.41 (m, 3H), 6.19 (s, 1H), 4.26–4.39 (m, 2H), 1.27–1.33 (t, 3H, J=6.9 Hz): FD+ MS for $C_{17}H_{15}N_3O_4$=325; Anal. calcd. for $C_{17}H_{15}N_3O_4$: C, 62.76; H, 4.65; N, 12.92; Found: C, 62.89; H, 4.92; N, 12.92.

Preparation 52

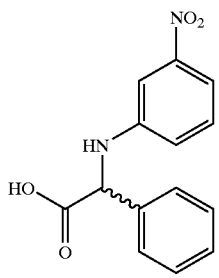

To a solution of a compound of Preparation 50 (0.81 g, 2.73 mmol) stirring in dioxane-(30 mL) at room temperature was added LiOH.H$_2$O (0.57 g, 13.6 mmol) and H$_2$O (15 mL). After 45 min, the mixture was concentrated to a volume of approximately 20 mL. The resulting aqueous solution was diluted with H$_2$O (75 mL) and extracted with diethyl ether. The aqueous layer was acidified with 1N HCl and extracted with ethyl acetate. The combined organic extracts were washed with brine, dried (Na$_2$SO$_4$) and concentrated to give 0.71 g (95%) of the product (1:1 mixture of diastereomers) as a yellow solid: $^1$H NMR (300 MHz, CDCl$_3$) δ 7.48–7.55 (m, 3H), 7.35–7.43 (m, 4H), 7.21–7.27 (app. t, 1H, J=8.1 Hz), 6.81–6.85 (dd, 1H, J=8.2 Hz; 2.0 Hz), 5.16 (s, 1H); FD+ MS for $C_{14}H_{12}N_2O_4$=272; Anal. calcd. for $C_{14}H_{12}N_2O_4$: C, 61.76; H, 4.44; N, 10.29; Found: C, 62.15; H, 4.52; N, 9.63.

Preparation 53

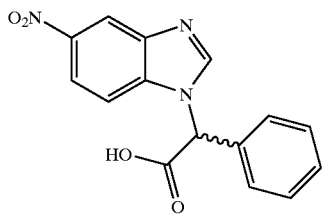

To a solution of a compound of Preparation 51 (0.48 g, 1.48 mmol) stirring in dioxane (20 mL) at room temperature was added LiOH.H$_2$O (0.31 g, 7.38 mmol) and H$_2$O (10 mL). After 45 min, the reaction mixture was concentrated to a volume of approximately 15 mL. The resulting aqueous solution was diluted with H$_2$O (75 mL) and extracted with diethyl ether. The aqueous layer was acidified with 1N HCl and extracted with ethyl acetate. The combined organic extracts were washed with brine, dried (Na$_2$SO$_4$) and concentrated to give 0.450 g (>95%) of the product (1:1 mixture of diastereomers) as a light yellow solid: $^1$H NMR (300 MHz, DMSO) δ 8.63 (s, 1H), 8.56–8.57 (d, 1H, J=2.1 Hz), 8.14–8.20 (dd, 1H, J=9.2 Hz; 2.1 Hz), 7.82–7.86 (d, 1H, J=9.2 Hz), 7.52–7.58 (m, 2H), 7.38–7.49 (m, 3H), 6.88 (s, 1H); FD+ MS for C$_{15}$H$_{11}$N$_3$O$_4$=297; Anal. calcd. for C$_{15}$H$_{11}$N$_3$O$_4$; C, 60.61; H, 3.73; N, 14.14; Found: C, 59.59; H, 4.16; N, 12.76.

Preparation 54

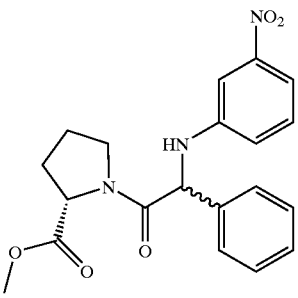

To a solution of a compound of Preparation 52 (0.75 g, 2.78 mL), L-proline methyl ester hydrochloride (0.46 g, 2.78 mmol), 1-hydroxybenzotriazole hydrate (0.38 g, 2.78 mmol) and N,N-diisopropylethylamine (1.26 g, 9.72 mmol) in anhydrous 1,2-dichlormethane (30 mL) stirring at room temperature, was added 1-(3-dimethylaminopropyl)-3-ethylcarbodiimide (0.585 g, 3.05 mmol). After 18 h, the reaction mixture was diluted with H$_2$O (50 mL) extracted with ethyl acetate. The combined organic extracts were washed with 10% citric acid, sat'd aqueous sodium bicarbonate, water, brine, dried (Na$_2$SO$_4$) and concentrated. Purification by radial chromatography (silica gel, 40%–75% ethyl acetate/hexanes) gave 0.56 g (53%) of the product (1:1 mixture of diastereomers) as a yellow solid: $^1$H NMR (300 MHz, CDCl$_3$) δ 7.43–7.50 (m, 3H), 7.27–7.43 (m, 4H), 7.13–7.20 (app. t, 1H, J=7.5 Hz), 6.83–6.91 (t, 1H, J=5.8 Hz), 5.14 (s, 1H), 4.52–4.58 (m, 0.5H), 4.41–4.47 (m, 0.5H), 3.89–3.97 (m, 1H), 3.71 (s, 1.5H), 3.62 (s, 1.5H), 3.23–3.36 (m, 1H), 1.82–2.24 (m, 5H); $^{13}$C NMR (75.5 MHz, CDCl$_3$) d 172.2, 171.7, 168.7, 168.5, 149.0, 146.9, 146.5, 136.4, 135.9, 129.5, 129.4, 129.0, 128.8, 128.5, 128.2, 128.0, 127.8, 119.9, 119.6, 112.2, 112.0, 106.5, 106.5, 59.5, 59.4, 59.3, 59.3, 52.2, 52.0, 46.7, 46.7, 28.7, 28.6, 24.9, 24.5; FD+ MS for C$_{20}$H$_{21}$N$_3$O$_5$=383; Anal. calcd. for C$_{20}$H$_{21}$N$_3$O$_5$: C, 62.65; H, 5.52; N, 10.96; Found: C, 61.93; H, 5.62; N, 10.46.

Preparation 55

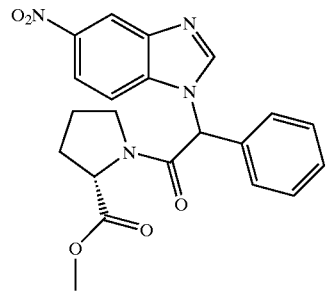

To a solution of a compound of Preparation 53 (0.43 g, 1.46 mmol), L-proline methyl ester hydrochloride (0.24 g, 1.46 mmol), 1-hydroxybenzotriazole hydrate (0.20 g, 1.46 mmol) and N,N-diisopropylethylamine (0.66 g, 5.10 mmol) stirring in anhydrous 1,2-dichloromethane (30 mL) at room temperature was added 1-(3-dimethylaminopropyl)-3-ethylcarbodiimide (0.31 g, 1.60 mmol). After 18 h, the reaction mixture was quenched with H$_2$O (50 mL) and extracted with ethyl acetate. The combined organic extracts were washed with 10% citric acid, saturated aqueous sodium bicarbonate, H$_2$O, brine, dried (Na$_2$SO$_4$) and concentrated. Purification by radial chromatography (silica gel, 50% ethyl acetate/hexanes to 100% ethyl acetate gradient) gave 0.25 g (42%) of the a single diastereomer as a white foam solid: $^1$H NMR (300 MHz, CDCl$_3$) d 8.75–8.76 (s, 1H, J=2.1 Hz), 8.28–8.32 (dd, 1H, J=8.9 Hz; 2.1 Hz), 7.91 (s, 1H), 7.45–7.58 (m, 6H), 6.26 (s, 1H), 4.65–4.70 (m, 1H), 3.83–3.92 (m, 1H), 3.78 (s, 3H), 3.30–3.39 (m, 1H), 1.95–2.30 (m, 5H); FD+ MS for C$_{21}$H$_{20}$N$_4$O$_5$=408; Anal. calcd. for C$_{21}$H$_{20}$N$_4$O$_5$: C, 61.76; H, 4.94; N, 13.72; Found: C, 61.24; H, 5.16; N, 13.10.

Preparation 56

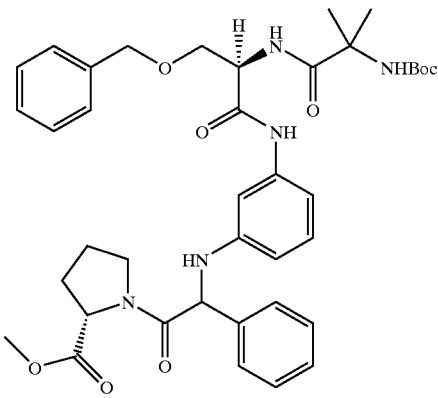

To a slurry of 5% Pd/C (0.07 g) in ethanol (30 mL) was added a solution of a compound of Preparation 54 (0.15 g, 0.39 mmol) in ethyl acetate (30 mL). The mixture was treated with hydrogen gas (32 psi) at room temperature for 4 h on a Parr apparatus then carefully filtered through celite. The resulting filtrate was evaporated to provide an off-white solid foam which was dissolved in N,N-dimethylformamide (30 mL). To this solution was added a compound of Preparation 4 (0.16 g, 0.41 mmol), 1-hydroxybenzotriazole hydrate (0.06 g, 0.41 mmol) and 1,3-dicyclohexylcarbodiimide (0.09 g, 0.45 mmol). This solution was stirred overnight at room temperature and subsequently diluted with water (50 mL) then extracted with ethyl acetate. The combined organic extracts were washed with water, brine, dried ($Na_2SO_4$) and evaporated to provide a tan foam. Purification by radial chromatography (silica gel, 50% ethyl acetate/hexanes to 100% ethyl acetate gradient) yielded 0.23 g (82%) of the product (mixture of diastereomers) as an off-white solid foam. $^1H$ NMR (300 MHz, $CDCl_3$) d 8.83–8.91 (m, 1H), 7.44–7.51 (m, 2H), 7.20–7.36 (m, 8H), 6.88–7.06 (m, 3H), 6.32–6.38 (app. t, 1H, J=6.9 Hz), 5.28 (s, 1H), 5.12–5.19 (m, 1H), 4.88–4.91 (br. s, 1H), 4.48–4.60 (m, 3H), 4.17–4.24 (m, 1H), 3.64–3.72 (app. q, 2H, J=8.0 Hz), 3.62 (s, 3H), 3.39–3.52 (m, 1H), 3.28–3.39 (m, 1H), 1.81–2.15 (m, 5H), 1.53–1.57 (app. d, 3H, J=7.9 Hz), 1.38 (s, 3H), 1.39 (s, 9H); FD+ MS for $C_{39}H_{49}N_5O_8$=716; Anal. calcd. for $C_{39}H_{49}N_5O_8$: C, 65.44; H, 6.90; N, 9.78; Found: C, 65.23; H, 7.43; N, 10.34.

Preparation 57

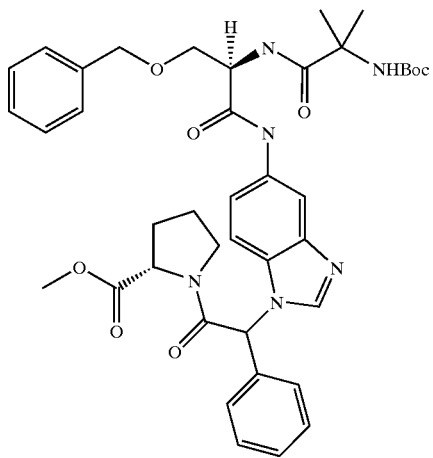

To a slurry of 5% Pd/C (0.042 g) in ethanol (30 mL) was added a solution of a compound of Preparation 55 (0.08 g, 0.20 mmol) in ethyl acetate (30 mL). The mixture was treated with hydrogen gas (32 psi) at room temperature for 4 h (Parr apparatus) then carefully filtered through celite. The resulting filtrate was evaporated to provide a white solid foam which was dissolved in N,N-dimethylformamide (20 mL). To this solution was added a compound of Preparation 4 (0.08 g, 0.20 mmol), 1-hydroxybenzotriazole hydrate (0.03 g, 0.22 mmol) and 1,3-dicyclohexylcarbodiimide (0.05 g, 0.22 mmol). This solution was stirred overnight at room temperature and subsequently diluted with water (50 mL) then extracted with ethyl acetate. The combined organic extracts were washed with water and brine, dried ($Na_2SO_4$) and concentrated. Purification by radial chromatography (silica gel, 75% ethyl acetate/hexanes to 100% ethyl acetate gradient) yielded 0.10 g (66%) of the product (one diastereomer) as an off-white solid foam: $^1H$ NMR was consistent with structure;

FD+ MS for $C_{40}H_{48}N_6O_8$=740.

Example 13

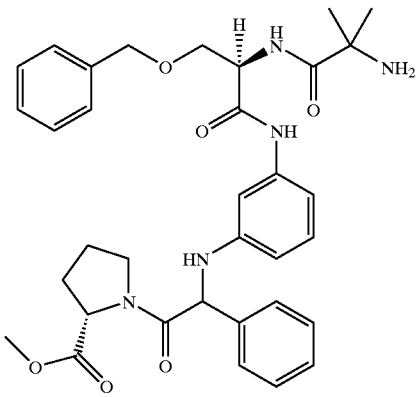

To a solution of a compound of Preparation 56 (0.17 g, 0.24 mmol) and anisole (0.03 g, 0.26 mL) stirring in anhydrous dichloromethane (5 mL) at 0° C. was added trifluoroacetic acid (1 mL). After 4 h, the reaction mixture was quenched carefully with saturated aqueous sodium bicarbonate extracted with ethyl acetate. The combined organic extracts were washed with sat'd aqueous sodium bicarbonate, water, brine, dried ($NaS_2O_4$) and evaporated to yield the desired product (1:1 mixture of diastereomers) as an off-white foam: 0.100 g (67%). $^1H$ NMR was consistent with structure; FD+ MS for $C_{34}H_{41}N_5O_6$=615; Anal. calcd for $C_{34}H_{41}N_5O_6$: C, 66.32; H, 6.71; N, 11.37; Found: C, 65.83; H, 6.50, N, 6.50.

Example 14

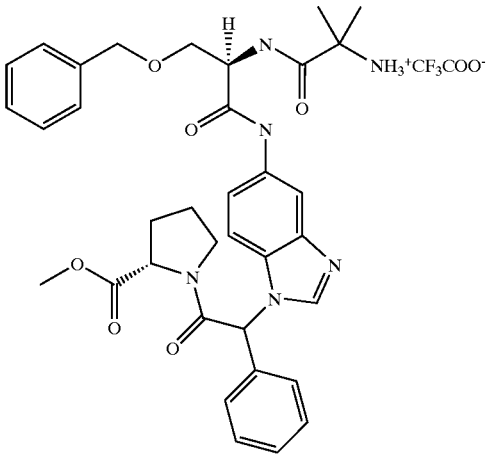

To a solution of Preparation 57 (0.080 g, 0.11 mmol) and anisole (0.0123 g, 0.114 mmol) stirring in anhydrous dichloromethane (5 mL) at 0° C. was added trifluoroacetic acid (1 mmol). After 4 h, the mixture was quenched carefully with saturated sodium bicarbonate and extracted with ethyl acetate. The combined organic extracts were washed with saturated aqueous sodium bicarbonate, water, brine, dried ($NaS_2O_4$) and concentrated to yield foam 0.09 g (95%) of the desired product (one diastereomer) as an off-white solid: $^1H$ NMR was consistent with structure; FD+ MS for $C_{35}H_{40}N_6O_6 \cdot 2CF_3COOH$=640 (M-2$CF_3COOH$); Anal. calcd. for $C_{39}H_{42}N_6O_{10}F_6$: C, 53.92; H, 4.87; N, 9.67; Found: C, 51.86; H, 4.74; N, 9.54.

EXAMPLES PART 2A

Preparation 1a

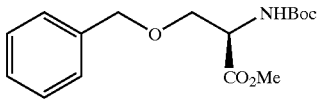

tert-Butyloxycarbonyl-O-benzyl-D-serine methyl ester.

To a solution of t-butyloxycarbonyl-O-benzyl-D-serine (25.0 g, 84.7 mmol) stirring in dimethylformamide (500 mL) at room temperature was added sodium bicarbonate (14.2 g, 169 mmol) followed by methyl iodide (26.4 mL, 424 mmol). After 18 h, the reaction mixture was concentrated to approximately 100 mL. Ethyl acetate was added and the mixture washed with aqueous sodium bicarbonate and brine. The organic extract was dried and concentrated to give the desired compound (25 g, 96%) as a light yellow oil: $^1$H NMR (300 MHz, CDCl$_3$) d 1.45 (s, 9H), 3.70 (m, 1H), 3.75 (s, 3H), 3.85 (m, 1H), 4.50 (m, 3H), 7.30 (m, 5H); MS (FD) m/e 310; Anal. calc'd for C$_{16}$H$_{23}$NO$_5$: C, 62.12; H, 7.49; N, 4.53. Found: C, 62.31; H, 7.49; N, 4.43.

Preparation 1b

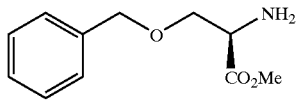

O-benzyl-D-serine methyl ester.

To a solution of tert-butyloxycarbonyl-O-benzyl-D-serine methyl ester (BF8-EZ0-275) (5.0 g, 16 mmol) stirring in dichloromethane (40 mL) and anisole (1 ml) at 0° C. was added trifluoroacetic acid (10 mL). After 4 h at room temperature, a saturated aqueous solution of sodium bicarbonate was added and the resulting mixture extracted with ethyl acetate. The combined organic extracts were washed with brine, dried over sodium sufate, and concentrated. The crude product was used in the next step without further purification.

Preparation 1c

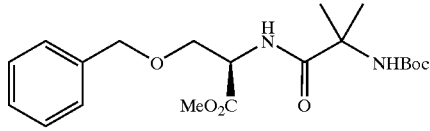

To a solution of O-benzyl-D-serine methyl ester (the product of Preparation 1b) (65.4 mmol), boc-a-aminoisobutyric acid (13.2 g, 65.4 mmol), 1-hydroxybenzotriazole (8.8 g, 65.4 mmol), and N,N-diisopropylethylamine (22.8 mL, 130.7 mmol) stirring in dichloromethane (500 mL) at 0° C. was added 1-(3-dimethylaminopropyl)-3-ethylcarbodiimide (12.3 g, 71.9 mmol). After 18 h, ethyl acetate and ammonium chloride (saturated aqueous solution) were added and the resulting mixture extracted with aqueous ammonium chloride, aqueous sodium bicarbonate, and brine. The organic extracts were dried over sodium sulfate and concentrated. Purification by flash chromatography (25% ethyl acetate/hexanes) yielded the desired compound (21.6 g, 83%) as a white solid: $^1$H NMR (300 MHz, CDCl$_3$) d 1.39 (s, 9H), 1.48 (s, 6H), 3.62 (dd, J=3.4, 9.1 Hz, 1H), 3.70 (s, 3H), 3.85 (dd, J=3.4, 9.1 Hz, 1H), 4.48 (dd, J=12.5, 22.7 Hz, 2H), 4.75 (m, 1H), 4.92 (s, 1H), 7.11 (d, J=8.6 Hz, 1H), 7.35 (m, 5H); MS (FD) m/e 395; Anal. calc'd for C$_{20}$H$_{30}$N$_2$O$_6$: C, 60.90; H, 7.67; N, 7.10. Found: C, 61.02; H, 7.78; N, 7.10.

Preparation 1d

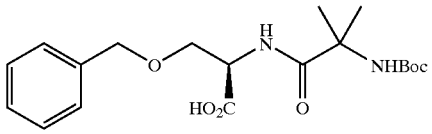

To a solution of the product of Preparation 1c (5.30 g, 13.4) stirring in dioxane (100 mL)/water (50 mL) at room temperature was added lithium hydroxide (2.80 g, 67.3 mmol). After 18 h, water was added and the solution concentrated. The resulting mixture was extracted with diethyl ether. Brine was added to the aqueous layer and the pH adjusted to 3.5 with 1N HCl. The resulting mixture was extracted with ethyl acetate and the combined organic extracts dried over sodium sulfate then concentrated to yield the title compound (4.40 g, 86%) as a white foam: $^1$H NMR (300 MHz, CDCl$_3$) d 1.39 (s, 9H), 1.45 (s, 3H), 1.47 (s, 3H), 3.68 (m, 1H), 3.95 (m, 1H), 4.54 (s, 2H), 4.70 (m, 1H), 5.51 (bs, 1H), 7.18 (d, J=9.1 Hz, 1H), 7.25 (m, 5H), 9.90 (bs, 1H); MS (FD) m/e 381; Anal. calc'd for C$_{19}$H$_{28}$N$_2$O$_6$: C, 59.99; H, 7.42; N, 7.36. Found: C, 59.74; H, 7.26; N, 7.30.

Preparation 1e

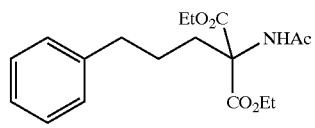

A solution of sodium ethoxide was generated by the addition of sodium metal (52.89 grams, 2.3007 mol) over 3 hours to ethanol (1500 mL). To the sodium ethoxide solution at ambient temperature was added a solution of diethylacetamidomalonate (499.75 grams, 2.3007 mol) dissolved in ethanol (225 mL). The reaction mixture was stirred for 1.5 hours at ambient temperature. 1-bromo-3-phenylpropane (458.07 grams, 2.3007 mol) was added over 15 minutes and the reaction mixture was refluxed until complete as determined by hplc (16 hours). The reaction mixture was concentrated to dryness and the residue partitioned between ethyl acetate (1×1500 mL and 2×500 mL) and water (1500 mL). The ethyl acetate layers were combined, washed with saturated sodium chloride solution (4×500 mL), dried using sodium sulfate, and concentrated to give 752.1 grams (98%), of the desired compound as a light yellow solid. A 1.0 gram sample was recrystallized from hexane:ethyl acetate (19.1, v:v) to give a mp 84–86° C. $^1$H nmr (CDCl$_3$): δ 1.18–1.23 (t, 6H), 1.37–1.50 (m, 2H), 2.02 (s, 3H), 2.34–2.41 (m, 2H), 2.58–2.62 (t, 2H), 4.16–4.24 (q, 4H), 6.76 (s, broad, 1H), 7.11–7.28 (m, 5H). $^{13}$C nmr (CDCl$_3$): δ 13.95, 23.03–25.67, 31.85, 35.45, 62.46, 66.49, 125.40, 125.90, 128.27, 128.35, 141.77, 168.11, 168.94. MS (FIA) m/z 336.3([M+H]$^+$). IR (KBr, cm$^{-1}$) 1645.98 (amide), 1744.76 (C=O). Anal. Calcd. for C$_{18}$H$_{25}$NO$_3$: C, 64.46; H, 7.51; N, 4.17. Found: C, 64.60; H, 7.37; N, 4.39.

Preparation 1f

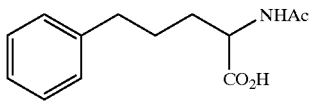

(DL)-N-Acetyl-2-amino-5-phenylpentanoic Acid. A slurry consisting of the product of Preparation 1e (249.15 grams, 0.7428 mol) and 2.5 N sodium hydroxide solution was heated at 100° C. for three hours. The reaction mixture was cooled to 30° C. and the pH adjusted to 5.0 using concentrated hydrochloric acid. The solution was heated to 100° C. and the pH was held at 5.0 using concentrated hydrochloric acid as needed until the reaction was complete as determined by hplc. The solution was filtered while hot through diatomaceous earth. The filtrate was cooled to 5–10° C. and the pH adjusted to 1.0 using concentrated hydrochloric acid. The resulting slurry was stirred for 1 hour at 5° C., filtered, and dried in vacuum at 50° C. to give 160.34 grams (92%) of (DL)-N-acetyl-2-amino-5-phenylpentanoic acid as a white powder, mp 145–148° C. $^1$H nmr (DMSO-d$_6$): δ 1.60–1.71 (m, 4H), 1.86 (s, 3H), 2.56–2.59 (m, 2H), 4.19–4.23 (m, 1H), 7.16–7.30 (m, 5H), 8.14 (d, 1H). $^{13}$C nmr (DMSO-d$_6$): δ 23.17, 28.25, 31.55, 35.51, 52.55, 126.60, 129.14, 142.64, 170.25, 174.65. MS (FIA) m/z 236.2 (M$^+$). IR (KBr, cm$^{-1}$) 1609.17 (amide), 1741.12 (C=O). Anal. Calcd. for C$_{13}$H$_{17}$NO$_3$: C, 66.36; H, 7.28; N, 5.95. Found: C, 66.41; H, 7.15; N, 5.96.

Preparation 1g

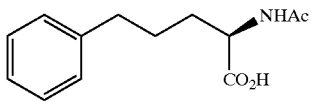

(D)-N-Acetyl-2-amino-5-phenylpentanoic Acid. A solution consisting of (DL)-N-acetyl-2-amino-5-phenylpentanoic acid (438.0 grams, 1.862 mmol), cobalt chloride (1.10 grams), 2N potassium hydroxide solution (931 mL, 1.862 mol), and water (8000 mL) was adjusted to a pH of 8.0 by the addition of 2N potassium hydroxide solution. To the reaction mixture was added Acylase I (*aspergillus melleus*, 39.42 grams) and vigorously stirred for 24 hours at 40° C. while maintaining a pH of 8.0 by addition of 2N potassium hydroxide. The resulting slurry was filtered. The filtrate was adjusted to a pH of 2.0 giving a thick slurry. The product was isolated by filtration, washed with hexane (2000 mL) and dried in vacuum at 50° C. to give 188.52 grams (43%) of (D)-N-acetyl-2-amino-5-phenylpentanoic acid. $^1$H nmr (DMSO-d$_6$): δ 1.59–1.74 (m, 4H), 1.86 (s, 3H), 2.57–2.60 (m, 2H), 4.22–4.26 (m, 1H), 7.16–7.30 (m, 5H), 8.02 (d, 1H), 12.39 (s, broad, 1H). $^{13}$C nmr (DMSO-d$_6$): δ 23.18, 28.13, 31.66, 35.54, 52.58, 126.56, 129.10, 142.67, 170.12, 174.48. MS (FIA) m/z 236.1 (M$^+$). IR (KBr, cm$^{-1}$) 1625.08 (amide), 1700.24 (C=O). Anal. Calcd. for C$_{13}$H$_{17}$NO$_3$: C, 66.36; H, 7.28; N, 5.95. Found: C, 66.49; H, 7.00; N, 6.03.

Preparation 1h

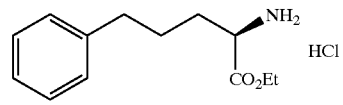

(D)-2-Amino-5-phenylpentanoic Acid, Ethyl Ester Hydrochloride. A solution consisting of (D)-N-acetyl-2-amino-5-phenylpentanoic acid (188.8 grams, 0.8024 mol), ethanol (535 mL), and concentrated hydrochloric acid (268 mL, 3.21 mol) was warmed to 85° C. and monitored by hplc. The reaction was determined to be incomplete by hplc at 14.5 hours and additional concentrated hydrochloric acid (50 mL) was added. The reaction was determined to be complete by hplc after 22.5 hours. Water was azeotropically distilled from the reaction by continuous addition and distillation of 8000 mL of ethanol. The ethanol was azeotropically distilled from the reaction by the continuous addition and distillation of ethyl acetate (2000 mL). Upon cooling the solution to 0° C. the product crystallized. The solution containing the product was stirred for 1 hour at 0° C., filtered, and the cake dried in vacuum at 40° C. to give 199.0 grams (96%) of 2-amino-5-phenylpentanoic acid, ethyl ester hydrochloride, mp 117–121° C. $^1$H nmr (DMSO-d$_6$): δ 1.15–1.21 (t, 3H), 150–189 (m, 4H), 2.48–2.67 (m, 2H), 3.92–3.98 (t, 1H), 4.08–4.25 (m, 2H), 7.12–7.29 (m, 5H), 8.76 (s, broad, 3H). $^{13}$C nmr (DMSO-d$_6$): δ 13.90, 25.97, 29.52, 34.41, 51.71, 61.56, 124.91, 125.81, 128.24, 141.27, 169.35. MS (FIA) m/z 222.3 (M$^{30}$). IR (KBr, cm$^{-1}$) 1741.14 (C=O). [α]$^{20}$$_D$=−11.17 (c=30.62 mg/3 mL, MeOH). Anal. Calcd. for C$_{13}$H$_{20}$NO$_2$Cl: C, 60.58; H, 7.82; N, 5.43. Found: C, 60.45; H, 7.67; N, 5.55.

Preparation 1i

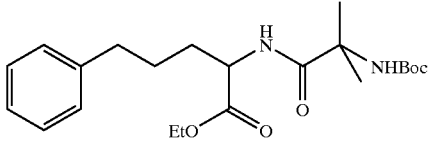

A slurry consisting of N-t-BOC-α-aminoisobutyric acid (90.64 grams, 0.446 mmol), 2-chloro-4,6-dimethoxy-1,3,5-triazine (75.90 grams, 0.425 mmol), N-methyl morpholine (88.13 grams, 0.871 mmol), and diethyl ether (1000 mL) was stirred at ambient temperature until complete as determined by hplc (3 hours). The D-2-amino-5-phenylpentanoic acid, ethyl ester hydrochloride (109.55 grams, 0.425 mmol) was added and the reaction mixture stirred for 16 hours at ambient temperature. The reaction mixture was partitioned between 10% citric acid solution (1000 mL) and ethyl acetate (3×500 mL). The organic phase was washed with 10% citric acid solution (3×500 mL), saturated sodium bicarbonate solution (3×500 mL), water (1×500 mL), dried using sodium sulfate, and concentrated to dryness. The residue was recrystallized from hexane (3000 ml) to give 155.11 grams of the desired compound: mp 97–99° C. $^1$H nmr (CDCl$_3$): δ 1.25–1.28 (t, 3H), 1.43 (s, 9H), 1.48 (s, 3H), 1.50 (s, 3H), 1.70–1.73 (m, 3H), 1.87–1.93 (m, 1H), 2.62–2.67 (m, 2H), 4.16–4.21 (m, 2H), 4.57–4.62 (m, 1H), 4.95 (s, 1H), 6.96 (s, broad, 1H), 7.16–7.19 (m, 3H), 7.26–7.33 (m, 2H). $^{13}$C nmr (CDCl$_3$): δ 14.53, 26.32, 27.17, 28.67, 32.47, 35.73, 52.54, 57.17, 61.62, 126.21, 128.69, 128.79, 142.12, 154.99, 172.81, 174.69. MS (FIA) m/z 407.5 ([M+H]⁺). IR (KBr, cm⁻¹) 1652.75, 1685.52 (amides), 1741.73 (C=O). [α]$^{20}_D$=-7.83 (c=10.22 mg/1 mL, MeOH). UV (0.1% trifluoroacetic acid in water:acetonitrile) $\lambda_{max}$ 215.6 nm. Anal. Calcd. for $C_{22}H_{34}N_2O_5$: C, 65.00; H, 8.43; N, 6.89. Found: C, 65.23; H, 8.34; N, 6.94.

Preparation 1j

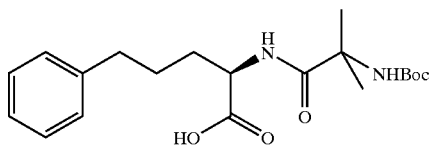

A solution consisting of the product of Preparation 1i (152.53 grams, 0.3752 mol) and tetrahydrofuran (884 mL) was cooled to 5° C. A solution consisting of lithium hydroxide (26.96 grams, 1.126 mol) and water (1419 mL) was added to the reaction dropwise over 10 minutes maintaining a temperature of 5–10° C. Ethanol (183 mL) was added and the reaction stirred at 5–10° C. until complete as determined by hplc (2 hours). The pH of the reaction mixture was adjusted to 2.0 using 6 N hydrochloric acid solution while maintaining 5–10° C. The product was extracted from solution with ethyl acetate (3×500 mL). The ethyl acetate extracts were combined, dried using sodium sulfate, and concentrated to dryness to give 141.51 grams (100%) of The desired compound: ¹H nmr (DMSO-d₆): δ 1.32–1.37 (m, 15H), 1.57–1.75 (m, 4H), 2.51–2.58 (m, 2H), 4.23–4.27 (m, 1H), 6.85 (s, broad, 1H), 7.15–7.28 (m, 5H), 7.42 (d, 1H), 12.5 (s, broad, 1H). ¹³C nmr (DMSO-d₆): δ 26.31, 27.85, 29.00, 31.86, 35.60, 52.53, 56.60, 78.95, 126.52, 129.05, 129.10, 142.69, 155.06, 174.40, 175.17. MS (FIA) m/z 379.5 ([M+H]⁺). IR (KBr, cm⁻¹) 1641.98, 1692.22 (amides), 1719.72 (C=O). [α]$^{20}_D$=5.73 (c=10.48 mg/1 mL, MeOH). Anal. Calcd. for $C_{20}H_{30}N_2O_5$: C, 63.47; H, 7.99; N, 7.40. Found: C, 63.25; H, 7.84; N, 7.46.

Preparation 1L

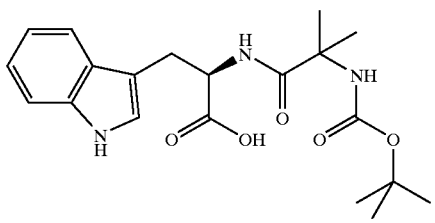

N-Methyl morpholine (4.79 mL, 2 eq, 47.3 mm) was added to a stirred slurry of N-Boc-α-aminoisobutyric acid (4.43 g, 21.7 mm, 1 eq) and 3.89 g (21.7 mm, 1.0 eq) of 2-chloro-(4,6)-dimethoxy-1,3,5-triazine (CDMT) in 100 mL of diethyl ether. After stirring the reaction mixture at ambient temperature for 1.5 hours, D-tryptophan ester hydrochloride was added. After stirring overnight, the reaction mixture was quenched by the addition of 150 mL of 10% aqueous citric acid solution. The layers were separated and the ether layer was washed with 50 mL of saturated sodium bicarbonate solution and 50 mL of water. Lithium hydroxide (2.43 g, 5 eq) was dissolved in 100 ml of water and the solution was added to the diethyl ether solution and stirred vigorously for 4 hours at room temperature. The layers were separated and the pH of the aqueous layers was adjusted to 5.6 with 1M HCl. The pH was then adjusted to 3.95 with 10% citric acid solution and the aqueous layer was extracted with 100 mL of ethyl acetate. The ethyl acetate layers were washed with brine, dried over magnesium sulfate and filtered. The volatiles were removed under vacuum to give 82% yield of the desired product as a white foam. ¹H-NMR consistent with structure.

Preparation 2A

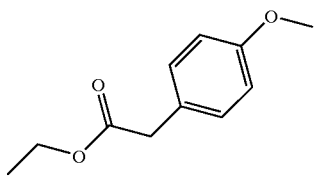

To a solution of 4-methoxyphenylacetic acid (98 g, 590 mmol) in absolute ethanol (300 mL) was added of p-toluenesulfonic acid (20 g, 105 mmol). The reaction mixture was heated to reflux and maintained at that temperature for 5 h then cooled to room temperature and concentrated to dryness. The resulting oil was purified by flash chromatography (silica gel, 20% ethyl acetate/hexanes) to give 102 g (89%) of the desired product as a colorless oil: ¹H-NMR (d, DMSO) 1.17 (t, J=8.7 Hz, 3H), 3.56 (s, 2H), 3.73 (s, 3H), 4.05 (q, J=7.2 Hz, 2H), 6.87 (d, J=8.7 Hz, 2H), 7.17 (d, 8.7 Hz, 2H); MS (ion spray) 195.3 (M+1); Anal. Calc'd for $C_{11}H_{14}O_3$: C, 68.02; H, 7.27. Found: C, 67.95, 7.17.

Preparation 2B

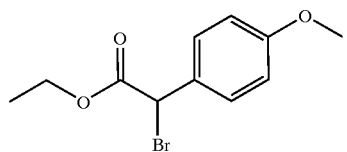

To a solution of the product of Preparation 2A (40 g, 200 mmol) in carbon tetrachloride (500 mL) was added N-bromosuccinimide (37 g, 206 mmol) and hydrobromic acid (4 drops of 48% aqueous solution). The resulting mixture was heated to reflux and maintained at that temperature for 5 h then cooled to room temperature, filtered, and concentrated. The resulting oil was purified by flash chromatography (silica gel, chloroform) to give 51.1 g (94%) of the desired product as a colorless oil: ¹H-NMR (d, DMSO) 1.19 (t, J=8.4 Hz, 3H), 3.77 (s, 3H), 4.18 (m, 2H), 5.88 (s, 1H), 6.95 (d, J=8.4 Hz, 2H), 7.50 (d, J=8.4 Hz, 2H); MS (FD) 272, 274 (M+); Anal. Calc'd for $C_{11}H_{13}BrO_3$: C, 48.37; H, 4.80. Found: C, 48.52, 4.77.

Preparation 3

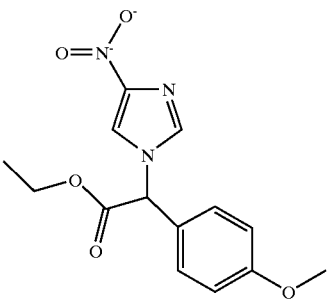

To a solution of the product of Preparation 2B (49.5 g, 181 mmol) stirring in dimethylformamide (500 mL) at room temperature was added 4-nitroimidazole (20.5 g, 181 mmol) and potassium carbonate (75 g, 543 mmol). After 16 h, the reaction was filtered and concentrated. The resulting oil was partitioned between ethyl acetate and water and extracted with ethyl acetate. The combined organic extracts were washed with brine, dried over sodium sulfate, filtered and concentrated. The resulting oil was purified by flash chromatography (silica gel, 30–70% ethyl acetates/hexanes gradient) to yield 33.6 g (61%) of the desired product as an orange oil that solidifies upon standing: $^1$H-NMR (d, DMSO) 1.17 (t, J=7.2 Hz, 3H), 3.78 (s, 3H), 4.25 (q, J=7.2 Hz, 2H), 6.57 (s, 1H), 7.02 (d, J=8.7 Hz, 2H), 7.46 (d, J=8.7 Hz, 2H), 7.92 (s, 1H), 8.38 (s, 1H); MS (ion spray) 306 (M+1); Anal. Calc'd for $C_{14}H_{15}N_3O_3$: C, 55.08; H, 4.95; N, 13.76. Found: C, 54.93; H, 4.89; N, 13.82.

Preparation 4

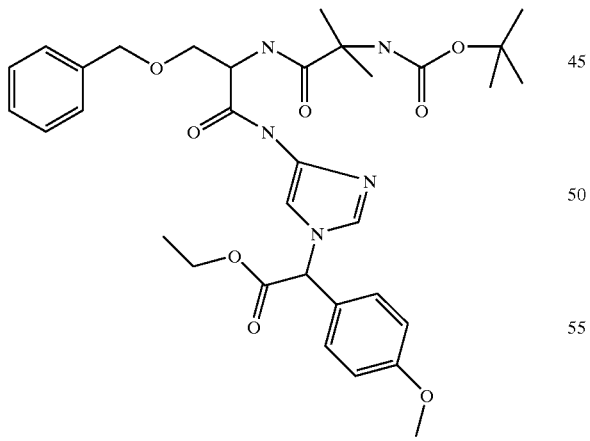

To a slurry of 10% palladium on carbon (6.0 g) in tetrahydrofuran (30 mL) was added a slurry of the product of Preparation 3 (8.4 g, 27.5 mmol) in tetrahydrofuran (30 mL). The reaction mixture placed under a hydrogen atmosphere (40 mm Hg) using a Parr apparatus until the reduction was complete then filtered through celite. To the resulting solution stirring at room temperature was added the product of Preparation 1d (10.5 g, 27.5 mmol), 1-hydroxybenzotriazole (4.1 g, 30.3 mmol) and 1-(3-dimethylaminopropyl)-3-ethylcarbodiimide (6.3 g, 30.3 mmol). After 16 h, the reaction mixture was concentrated and the resulting oil was slurried in ethyl acetate and filtered. The solution was diluted with water and then extracted with ethyl acetate. The combined organic extracts were washed with brine, dried over sodium sulfate, filtered and concentrated. The resultant crude material was purified by flash chromatography (silica gel, 3% methanol/chloroform) to give 14.4 g (83%) of the desired product as a tan foam: $^1$H-NMR (d, DMSO) 1.78 (t, J=7.2 Hz, 3H), 1.27–1.32 (m, 15H), 3.60 (m, 1H), 3.67 (m, 1H), 3.76 (s, 3H), 4.20 (d, J=7.2 Hz, 2H), 4.44 (d, J=3.0 Hz, 2H), 4.57 (s, 10H), 6.35 (s, 1H), 6.97 (d, J=7.2 Hz, 2H), 7.20–7.35 (m, 10H), 7.40 (m, 1H), 7.52 (s, 1H); MS (ion spray) 638 (M+1); Anal. Calc'd for $C_{33}H_{43}N_5O_9$: C, 62.15; H, 6.80; N, 10.98. Found: C, 62.41; H, 6.85; N, 11.09.

Preparation 5

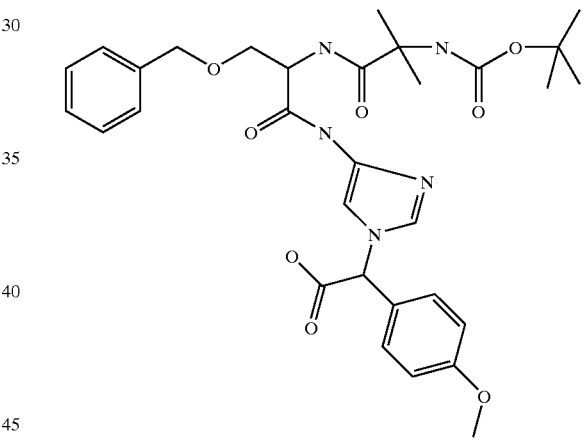

To a solution of the product of Preparation 4 (14.4 g, 23 mmol) stirring in dioxane (150 mL) at room temperature was added a solution of of lithium hydroxide (0.65 g, 27.6 mmol) in water (75 mL). After 20 min, the reaction mixture was acidified to pH=2.9 with 1 N hydrochloric acid. To the resulting solution was added water and ethyl acetate the mixture was extracted with ethyl acetate. The combined organic extracts were washed with brine, dried over sodium sulfate and concentrated to yield 13.0 g (93%) of the desired product as a yellow foam: $^1$H NMR (d, DMSO) 1.25–1.40 (m, 15H), 3.65–3.70 (m, 2H), 3.76 (s, 3H), 4.44 (d, J=3.4 Hz, 2H), 4.57 (m, 1H), 6.20 (s, 1H), 6.97 (d, J=3.4 Hz, 2H), 7.15–7.35 (m, 10H), 7.42 (m, 1H), 7.53 (s, 1H), 10.2 (s, 1H); MS (ion spray) 610.7 (M+1); Anal. Calc'd for $C_{31}H_{39}N_5O_8$: C, 61.07; H, 6.45; H, 11.49. Found: C, 60.90; H, 6.43; N, 11.32.

Preparation 6

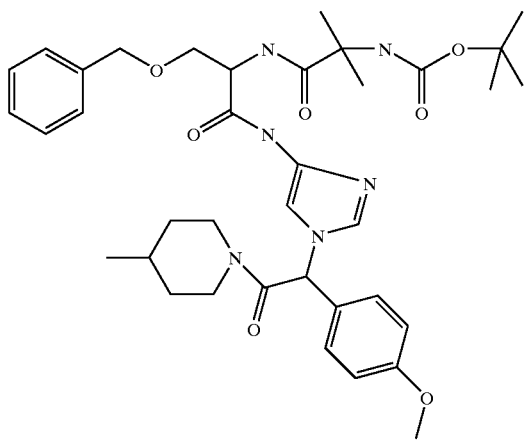

To a solution of the product of Preparation 5 (8.0 g, 13.0 mmol) stirring in dimethylformamide (150 mL) at room temperature was added 4-methylpiperidine (1.6 mL, 13.0 mmol), 1-hydroxybenzotriazole (2.0 g, 14.3 mmol) and 1-(3-dimethylaminopropyl)-3-ethylcarbodiimide (3.0 g, 14.3 mmol). After 16 h, the reaction mixture was filtered and concentrated. The resulting material was partitioned between ethyl acetate and water and extracted with ethyl acetate. The combined organic extracts were washed with brine, dried over sodium sulfate, filtered and concentrated to dryness. The resulting crude material was purified by flash chromatography (silica gel, 3% methanol/chloroform) to yield 7.65 g (85%) of the desired product as a yellow foam: $^1$H-NMR (d, DMSO) 0.2 (m, 1H), 0.50 (d, J=6.0 Hz, 1.5H), 0.80 (d, J=6.0 Hz, 1.5H), 1.05 (m, 1H), 1.22–1.45 (m, 15H), 1.50–1.65 (m, 4H), 2.65 (m, 1H), 3.00 (m, 1H), 3.55 (m, 1H), 3.65 (m, 1H), 3.75 (s, 3H), 4.37 (m, 1H), 4.40–4.50 (m 2H), 4.60 (m, 1H), 6.62 (d, J=13 Hz, 1H), 6.98 (t, J=9.4 Hz, 2H), 7.10–7.45 (m, 11H), 10.15 (br s, 1H); MS (ion spray) 691.3 (M+1); Anal. Calc'd for $C_{37}H_{50}N_6O_7 \cdot 0.6H_2O$: C, 63.34; H, 7.35; N, 11.98. Found: C, 63.25; H, 7.03; 11.87.

Examples 1 and 2

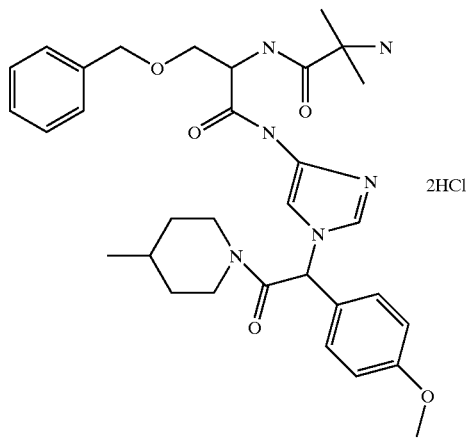

2HCl

To a solution of the product of Preparation 6 (7.26 g, 10.5 mmol) stirring in dichloromethane (25 mL) at room temperature was added trifluoroacetic acid (10 mL). After 4 h, the reaction mixture was poured into a saturated solution of sodium bicarbonate extracted with chloroform. The combined organic extracts were washed with brine, dried over sodium sulfate, filtered and concentrated to yield 6.12 g (99%) of the free base as a tan foam. The diastereomeric material (3.0 g) was chromatographed on an 8×15 cm Prochrom column packed with Kromasil CHI-DMP chiral phase using an eluent mixture of 3A alcohol (13% by v), dimethylethylamine (0.2% by v) in heptane at a flow rate of 250 mL/min to provide the individual diastereomers in pure form:

Example 1

Isomer 1

To a solution of the purified isomer in ethyl acetate was added a saturated solution of hydrochloric acid in diethyl ether. The resulting slurry was concentrated to dryness to yield 1.1 g (37%) of the desired product as a white solid: $^1$H NMR (d, DMSO) 0.50 (d, J=6.0 Hz, 1.5H), 0.80 (d, J=6.0 Hz, 1.5H), 1.16 (m, 1H), 1.35 (m, 1H), 1.50–1.70 (m, 8H), 2.60–2.70 (m, 2H), 3.03 (m, 1H), 3.65–3.80 (m, 6H), 4.40 (m, 1H), 4.53 (s, 2H), 4.75 (m, 1H), 6.90–7.08 (m, 3H), 7.25–7.45 (m, 9H), 8.20–8.40 (m, 4H), 8.61 (d, J=7.5 Hz, 1H), 11.15 (br s, 1H); $t_R$=7.93 min; MS (ion spray) 591.6 (M+1); Anal. Calc'd for $C_{32}H_{42}N_6O_3 \cdot 2HCl$: C, 57.92; H, 6.69; N, 12.66. Found: C, 57.72; H, 6.47; N, 12.42.

Example 2

Isomer 2

To a solution of the purified isomer in ethyl acetate was added a saturated solution of hydrochloric acid in diethyl ether. The resulting slurry was concentrated to yield 0.98 g (33%) of the desired product as a white solid: $^1$H NMR (d, DMSO) 0.50 (d, J=6.0 Hz, 1.5H), 0.80 (d, J=6.0 Hz, 1.5H), 1.16 (m, 1H), 1.35 (m, 1H), 1.50–1.70 (m, 8H), 2.60–2.70 (m, 2H), 3.03 (m, 1H), 3.65–3.80 (m, 6H), 4.40 (m, 1H), 4.53 (s, 2H), 4.75 (m, 1H), 6.90–7.08 (m, 3H), 7.25–7.45 (m, 9H), 8.20–8.40 (m, 4H), 8.61 (d, J=7.5 Hz, 1H), 11.15 (br s, 1H); $t_R$=11.78 min; MS (ion spray) 591.6 (M+1); Anal. Calc'd for $C_{32}H_{42}N_6O_3 \cdot 2HCl$: C, 57.29; H, 6.64; N, 12.53. Found: C, 57.23; H, 6.29; N, 12.57.

Preparation 7

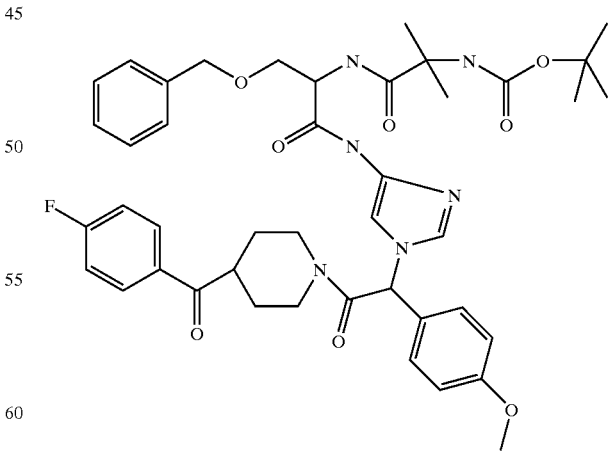

Reaction of the product of Preparation 5 (0.6 g, 1.0 mmol), 4-(4-fluorobenzoyl)piperidine hydrochloride (0.24 g, 1.0 mmol), triethylamine (0.15 ml, 1.1 mmol), 1-hydroxybenzotriazole (0.16 g, 1.1 mmol), and 1-(3- dimethylaminopropyl)-3-ethylcarbodiimide 10.23 g, 1.1 mmol) in dimethylformamide (40 mL) as described in Preparation 6 gave 0.58 g (73%) of the desired product as a tan foam: $^{1}$H-NMR (d, DMSO) 1.20–1.40 (m, 18H), 1.40–1.90 (m, 3H), 2.83 (m, 1H), 3.55–3.73 (m, 3H), 3.75 (s, 3H), 3.85 (m, 1H), 4.45 (d, J=3.8 Hz, 2H), 4.60 (m, 1H), 6.65 (d, J=10.93 Hz, 1H), 6.95–7.05 (m, 2H), 7.10–7.20 (m, 2H), 7.20–7.50 (m, 11H), 8.00–8.10 (m, 2H), 10.15 (br s, 1H); MS (FD) 798.7 (M+); Anal. Calc'd for $C_{43}H_{51}FN_6O_8$: C, 64.65; H, 6.43; N, 10.53. Found: C, 64.38; H, 6.48; N, 10.61.

Examples 3 and 4

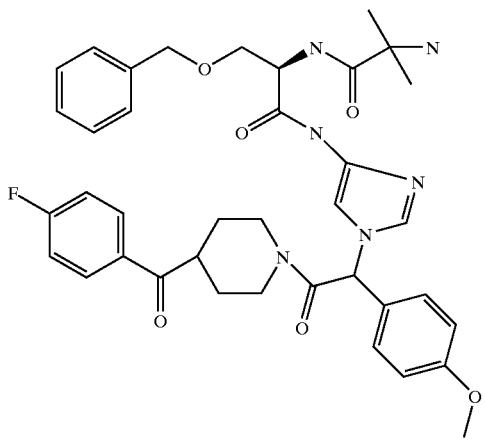

Reaction of the product of Preparation 7 (0.53 g, 0.66 mmol) and trifluoroacetic acid (2 mL) in dichloromethane (6 mL) as described in Example 1 gave 0.34 g (74%) of the desired mixture of diastereomers as a tan foam. This material (0.11 g) was purified by HPLC (8×15 cm Prochrom column packed with Kromasil® CHI-DMP chiral phase, eluent mixture of 3A alcohol and dimethylethylamine in heptane) to provide the individual diastereomers which were converted to their respective hydrochloride salts as described in Example 1.

Example 3

Isomer 1

$^{1}$H-NMR (d, DMSO) 1.15–1.20 (m, 6H), 1.20–1.60 (m, 3H), 1.70 (m, 1H), 2.90 (m, 1H), 3.55–3.70 (m, 4H), 3.75 (s, 3H), 3.85 (m, 1H), 4.40 (m, 1H), 4.40–4.55 (m, 2H), 4.60 (m, 1H), 6.65 (d, J=11 Hz, 1H), 7.00–7.05 (m 2H), 7.20 (m, 1H), 7.20–7.40 (m, 13H), 8.00–8.10 (m, 2H), 10.40 (br s, 1H); $t_R$=6.4 min; MS (ion spray) 699.7 (M+1); Anal. Calc'd for $C_{38}H_{43}FN_4O_6$: C, 65.31; H, 6.20; N, 12.03. Found: C, 65.08; H, 6.18; N, 11.87.

Example 4

Isomer 2

$^{1}$H-NMR (d, DMSO) 1.15–1.20 (m, 6H) 1.20–1.60 (m, 3H), 1.70 (m, 1H), 2.90 (m, 1H), 3.55–3.70 (m, 4H), 3.75 (s, 3H), 3.85 (m, 1H), 4.40 (m, 1H), 4.40–4.55 (m, 2H), 4.60 (m, 1H), 6.65 (d, J=11 Hz, 1H), 7.00–7.05 (m 2H), 7.20 (m, 1H), 7.20–7.40 (m, 13H), 8.00–8.10 (m, 2H), 10.40 (br s, 1H); $t_R$=8.0 min; MS (high res) calc'd for $C_{38}H_{44}FN_6O_6$: 699.3306. Found: 699.3313.

Preparation 8

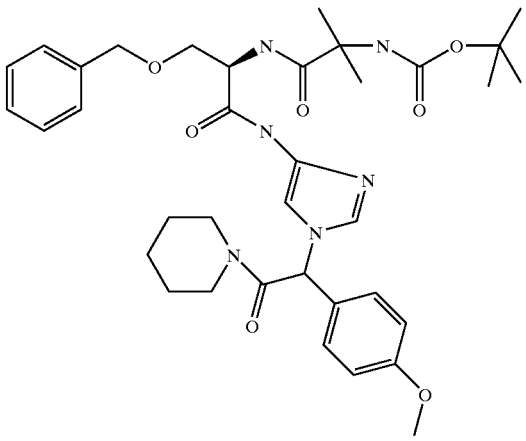

Reaction of the product of Preparation 5 (1.0 g, 1.7 mmol), piperidine (0.17 mL, 1.7 mmol), 1-hydroxybenzotriazole (0.25 g, 1.9 mmol), 1-(3-dimethylaminopropyl)-3-ethylcarbodiimide (0.4 g, 1.9 mmol), and dimethylformamide (15 mL) as described in Preparation 6 gave 0.7 g (60%) of the desired product as a tan foam: $^{1}$H-NMR (d, DMSO) 0.97 (m, 1H), 1.25–1.40 (m, 15H), 1.40–1.55 (m, 7H), 3.30–3.45 (m, 2H), 3.60 (m, 1H), 3.67 (m, 1H), 3.75 (s, 3H), 4.45 (d, J=3.4 Hz, 2H), 4.57 (m, 1H), 6.62 (s, 1H), 6.98 (d, J=8.7 Hz, 2H), 7.13 (m, 1H), 7.25–7.45 (m, 10H), 10.15 (br s, 1H); MS (ion spray) 677.5 (M+1); Anal. Calc'd for $C_{36}H_{48}N_6O_7$: C, 63.89; H, 7.15; N, 12.42. Found: C, 63.97; H, 6.99; N, 12.44.

Example 5

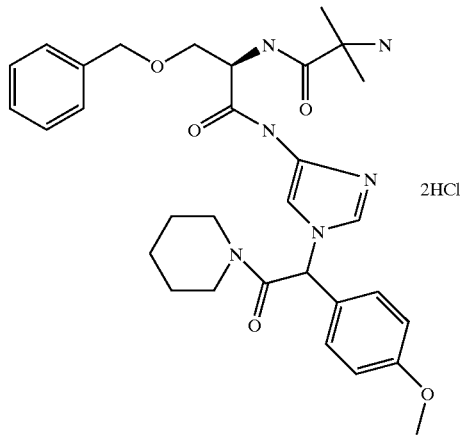

Reaction of the product of Preparation 8 (0.68 g, 1.0 mmol) and trifluoroacetic acid (2 mL) in dichloromethane (6 mL) as described in Example 1 gave 0.6 g (93%) of the desired product as a white solid: $^{1}$H-NMR (d, DMSO) 0.95 (m, 1H), 1.30–1.60 (m, 11H), 3.20–3.40 (m, 3H), 3.60–3.75 (m, 3H), 3.78 (s, 3H), 4.50–4.55 (m, 2H), 4.75 (m, 1H), 6.80 (s, 1H), 7.05 (d, J=9.0 Hz, 2H), 7.25–7.35 (m, 7H), 7.37 (d, J=8.7 Hz, 2H), 8.10 (m, 1H), 8.20–8.30 (m, 3H), 8.58 (d, J=7.6 Hz, 1H), 11.00 (br s, 1H); MS (ion spray) 577.4 (M+1); Anal. Calc'd for $C_{31}H_{40}N_6O_5 \cdot 2.2HCl$: C, 56.68; H, 6.48; N, 12.79. Found: C, 56.70; H, 6.64; N, 12.37.

Preparation 9

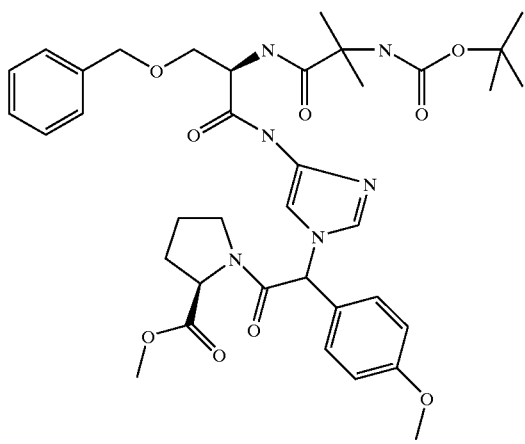

Reaction of the product of Preparation 5 (1.42 g, 2.3 mmol), d-proline methyl ester (0.3 g, 2.3 mmol), 1-hydroxybenzotriazole (0.35 g, 2.5 mmol), and 1-(3-dimethylaminopropyl)-3-ethylcarbodiimide (0.53 g, 2.5 mmol) in tetrahydrofuran (15 mL) as described in Preparation 6 gave 0.99 g (60%) of the desired product as a white foam: $^1$H-NMR (d, DMSO) 1.25–1.40 (m, 11H), 1.75–1.90 (m, 2H), 2.40 (m, 1H), 3.30 (m, 1H), 3.60–3.80 (m, 7H), 4.40 (m, 1H), 4.45–4.50 (m, 2H), 4.57 (m, 1H), 6.50 (m, 1H), 6.95–7.05 (m, 2H), 7.10–7.40 (m, 11H), 10.20 (br s, 1H); MS (ion spray) 721.3 (M+1); Anal. Calc'd for $C_{37}H_{48}N_6O_9$: C, 61.65; H, 6.71; N, 11.66. Found: C, 61.42; H, 6.43; N, 11.65.

Example 6

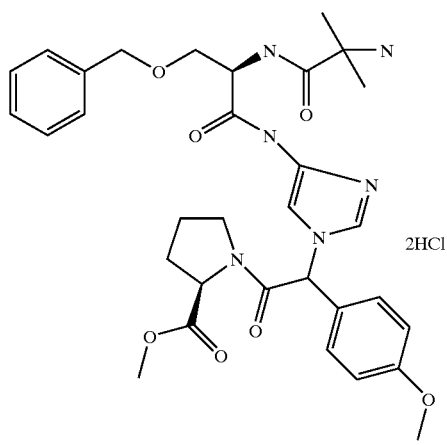

Reaction of the product of preparation 9 (0.87 g, 1.2 mmol) and trifluoroacetic acid (2 mL) in dichloromethane (6 mL) as described in Example 1 gave 0.58 g (70%) of the desired product: $^1$H-NMR (d, DMSO) 1.40–1.60 (m, 6H), 1.75–1.95 (m, 3H), 2.20 (m, 1H), 2.95 (m, 1H), 3.60–3.80 (m, 9H), 4.40 (m, 1H), 4.50–4.55 (m, 2H), 4.75 (m, 1H), 6.70 (s, 1H), 7.00 (t, J=8.7 Hz, 2H), 7.40–7.45 (m, 9H), 8.05 (m, 1H), 8.20–8.30 (m, 3H), 8.55 (m, 1H), 10.95 (m, 1H); MS (ion spray) 621.5 (M+1); Anal. Calc'd for $C_{32}H_{40}N_6O_7 \cdot 2.3HCl$: C, 54.55; H, 6.05; N, 11.93. Found: C, 54.46; H, 5.81; N, 11.79.

Preparation 10

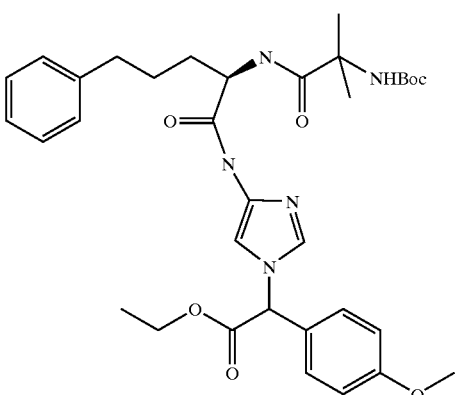

To a suspension of 5% palladium on carbon (1.75 g) and tetrahydrofuran (120 mL) was added the product of Preparation 3 (3.51 g, 11.5 mmol). The reaction mixture was placed under a hydrogen atmosphere (40 mm Hg) on a Parr apparatus for 2 h then filtered through celite. The filtrate was subsequently added to a solution of the product of Preparation 1j (4.33 g, 11.5 mmol), 1-(3-dimethylaminopropyl)-3-ethylcarbodiimide (2.60 g, 12.6 mmol) and 1-hydroxybenzotriazole (1.72 g, 12.6 mmol) stirring in tetrahydrofuran (50 mL) at 0° C. After 16 h at room temperature, the reaction mixture was concentrated. The resulting residue was dissolved in ethyl acetate, filtered and the resulting filtrate concentrated. The crude residue was purified by flash chromatography (silica gel, 90% ethyl acete/hexanes to 10% methanol/ethyl acetate gradient) to give 4.5 g (62%) the desired product as a light orange foam: $^1$H NMR consistent with structure; MS (IS) m/e 636 (M+1). Anal. ($C_{34}H_{45}N_5O_7$) C, H, N.

Preparation 11

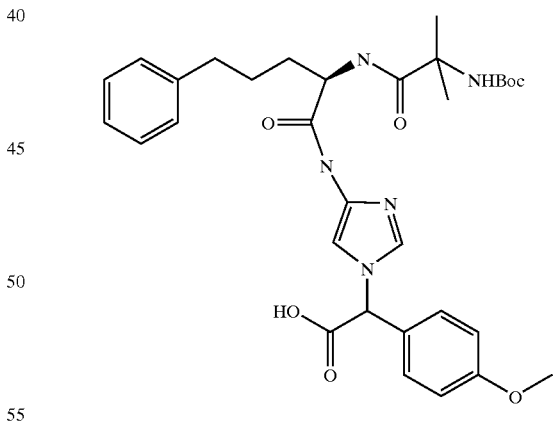

To a solution of the product of Preparation 10 (2.01 g, 1.59 mmol) stirring in tetrahydrofuran (30 mL) and water (15 mL) at room temperature was added lithium hydroxide (0.26 g, 6.30 mmol). After 25 min, the reaction mixture was concentrated and the resulting residue was diluted with water and extracted with diethyl ether. The aqueous extracts were acidified to pH 2–3 with 1N hydrochloric acid and then extracted with ethyl acetate. The combined organic extracts were washed with brine, dried with sodium sulfate and concentrated to provide 0.96 g (99%) of the desired compound as a light tan foam that was used without further purification: ¹H NMR consistent with structure; MS (IS) m/e 608 (M+1). Anal. (C$_{32}$H$_{41}$N$_5$O$_7$) C: calcd, 63.25; found, 62.68, H, N.

Preparation 12

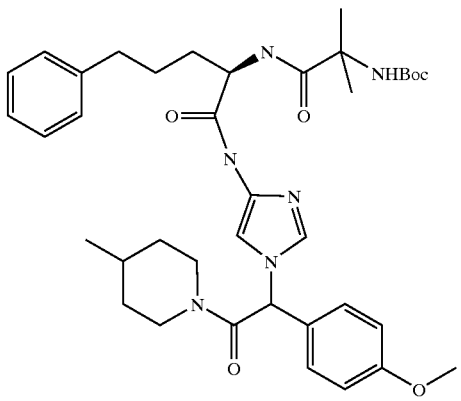

To a solution of the product of Preparation 11 (0.93 g, 1.53 mmol) stirring in dichloromethane (25 mL) at room temperature was added N-methylmorpholine (0.20 mL, 1.83 mmol) and of 2-chloro-(4,6)-dimethoxy-1,3,5-triazine (0.35 g, 1.99 mmol). After 1 h, 4-methylpiperidine (0.20 mL, 1.68 mmol) was added and the resulting mixture was stirred room temperature for 2 h at which time 2-chloro(4,6)-dimethoxy-1,3,5-triazine (0.10 g, 0.70 mmol) was added. After 1 h, the reaction mixture was concentrated and the resulting residue purified by flash chromatography (silica gel, ethyl acetate/methanol gradient) to give the desired compound as a light yellow solid foam (0.875 g, 83%): ¹H NMR consistent with structure; MS (IS) m/e 689 (M+1). Anal. (C$_{38}$H$_{52}$N$_6$O$_4$) C, H, N.

Example 7

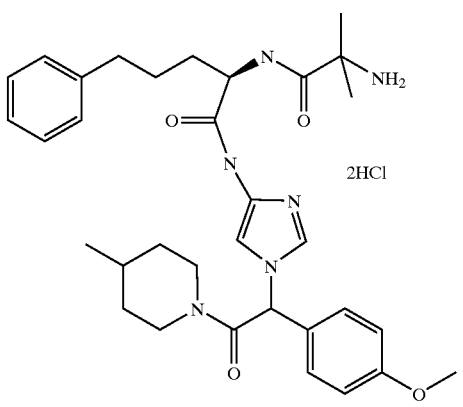

To a solution of the product of Preparation 12 (0.77 g, 1.12 mmol) and anisole (0.13 mL, 1.13 mmol) stirring in dichloromethane (20 mL) at 0 C was added trifluoroacetic acid. After 3–4 h, the reaction mixture was warmed to room temperature and then quenched by pouring over cold saturated aqueous sodium bicarbonate. The organic layer was collected and the aqueous layer was extracted twice with dichloromethane. The combined organic extracts were washed with aqueous sodium bicarbonate, water, brine, then dried over sodium sulfate and concentrated. The resulting material was purified by flash chromatography (silica gel, 5% methanol/95% ethyl acetate gradient to 5% triethylamine/10% methanol/85% ethyl acetate) to provide 0.63 g (95%) of the desired mixture of diastereomers as an off-white solid foam. The mixture (190 mg) was resolved by chiral HPLC [Kromasil packing material, 15% 3A alcohol/85% heptane (w/0.2% dimethylamine)] to provide the two desired diastereomers. To a solution of diastereomer 2 (65 mg) (retention time=9.00 min) stirring in ethyl acetate (5 mL) was added saturated solution of hydrochloric acid in diethyl ether. The resulting white precipitate was collected by vacuum filtration and rinsed with diethyl ether to provide the desired compound (60 mg) as a white amorphous solid: ¹H NMR consistent with structure; MS (IS) m/e 589 (M+1). Anal. (C$_{33}$H$_{44}$N$_6$O$_4$.2HCl) C, H, N.

Preparation 13

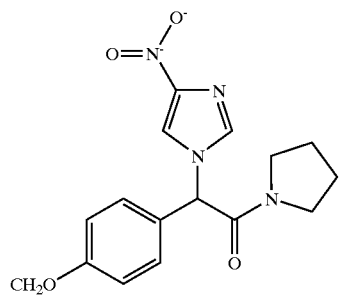

To a solution of Preparation 3 (3.00 g, 9.84 mmol) stirring in tetrahydrofuran (10 mL) and ethanol (5 mL) was added to sodium hydroxide (20 mL of a 5 N aqueous solution). The resulting mixture was stirred at ambient temperature until hydrolysis was complete and subsequently acidified to pH 2.0 with aqueous hydrochloric acid. The reaction mixture was extracted with ethyl acetate, dried over sodium sulfate, and concentrated. The resulting carboxylic acid was combined with pyrrolidine (0.710 g, 10 mmol), 1-hydroxybenzotriazole hydrate (1.35 g, 10 mmol) and 1,3-dicyclohexylcarbodiimide (2.06 g, 10.0 mmol) stirring in tetrahydrofuran (100 mL) at room temperature. After 18 h, the mixture was concentrated, the residue slurried in ethyl acetate then filtered and concentrated. Purification by flash chromatography (silica gel, chloroform/methanol) provided afford 2.74 g (84%) of the desired product: MS: (M+H)$^+$ 331.2; ¹H NMR (300 MHz, DMSO-d$_6$) δ 8.19 (d, 1H, J=1.51 Hz), 7.80 (d, 1H, J=1.51 Hz), 7.45 (d, 2H, J=8.67 Hz), 7.02 (d, 2H, J=8.67 Hz), 6.58 (s, 1H), 3.77 (s, 3H), 3.75–3.60 (m, 1H) 3.45–3.30 (m, 2H), 2.90–2.75 (m, 1H) 1.95–1.60 (m, 4H); Anal. Calcd. for C$_{16}$H$_{18}$N$_4$O$_4$: C, 58.18; H, 5.49; N, 16.96. Found: C, 58.44; H, 5.45; N, 16.87.

Preparation 14

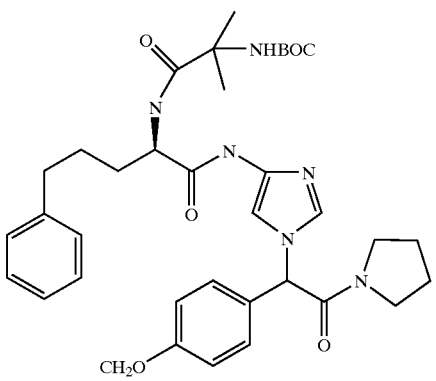

The product of Preparation 13 (1.13 g, 3.42 mmol) was added to a mixture of 10% palladium/carbon (0.65 g) and palladium/black (0.15 g) in tetrahydrofuran (40 mL) and the mixture shaken under hydrogen (38 psi) in a Parr apparatus. After reduction was complete, the reaction mixture was filtrated through celite and the filtrate immediately combined with 1,3-dicyclohexylcarbodiimide (0.71 g, 3.45 mmol), 1-hydroxybenzotriazole (0.46 g, 3.40 mmol), the product of Preparation 1j (1.30 g, 3.44 mmol) and additional tetrahydrofuran (60 mL). After stirring overnight at ambient temperature, the mixture was concentrated and the residue slurried in ethyl acetate then filtered. The filtrate was concentrated and the residue purified by flash chromatography (silica gel, chloroform/methanol) which afforded 1.50 g (66%) of the desired product which was used without further purification.

Example 8

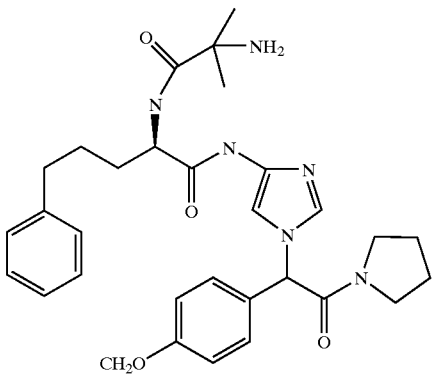

To a solution of the product of Preparation 14 (1.45 g, 2.20 mmol) in dichloromethane (30 mL) was added trifluoroacetic acid (10 mL). After 2 h, the mixture was concentrated and the residue treated with excess aqueous sodium bicarbonate and extracted. The combined organic extracts were concentrated and the resulting residue was purified by flash chromatography (silica gel, chloroform/methanol) to provide 0.68 g of the desired product as a yellow solid: MS: (M+H)$^+$ 561.3. $^1$H NMR was consistent with product. Anal. Calcd. for $C_{31}H_{40}N_6O_4 \cdot 0.2CHCl3$: C, 64.11; H, 6.93; N, 14.38. Found: C, 64.19; H, 7.19; N, 14.50. The isomeric mixture (1.72 g) was separated as previously described in Example 7 to provide 0.64 g of isomer 1 ($t_R$=7.50 min) and 0.49 g of isomer 2 ($t_R$=10.15 min). Isomer 2 (486 mg, 0.87 mmol) was dissolved in a minimal amount of ethyl acetate and treated with an excess of saturated hydrochloric acid in ethyl acetate. Concentration and subsequent evaporation from diethyl ether allowed for recovery of 580 mg of an off-white solid: MS: (M+H)$^+$ 561.3, 562.4. $^1$H NMR was consistent with product. Anal. Calcd. for $C_{31}H_{40}N_6O_4 \cdot 3.0$ HCl: C, 55.57; H, 6.47; N, 12.54. Found: C, 56.40; H, 6.43; N, 12.20.

Preparation 15

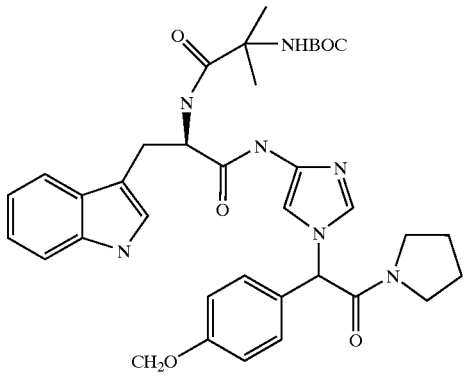

The product of Preparation 13 (0.85 g, 2.57 mmol) was combined with 10% palladium/carbon (0.50 g) and palladium/black (0.15 g) in tetrahydrofuran (40 mL) and the mixture shaken under a hydrogen atmosphere (38 psi) in a Parr apparatus. After reduction was complete, the catalyst was removed by filtration through celite and the amine/tetrahydrofuran solution was immediately combined with 1,3-dicyclohexylcarbodiimide (0.53 g, 2.57 mmol), 1-hydroxybenzotriazole (0.35 g, 2.57 mmol), the product of Preparation 1L (1.00 g, 2.57 mmol) and additional tetrahydrofuran (60 mL). After stirring overnight at ambient temperature, the mixture was concentrated and the residue slurried in ethyl acetate and filtered. The filtrate was concentrated and the residue purified by flash chromatography (silica gel, chloroform/methanol) which gave 1.62 g of the desired product which was used without further purification.

Example 9

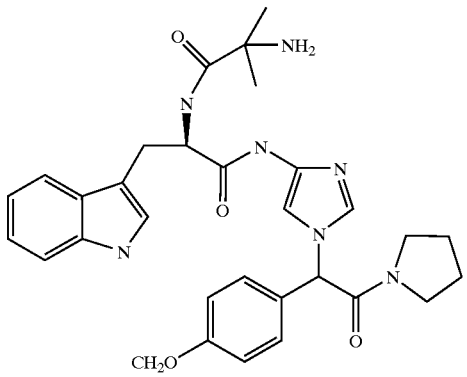

The compound of Preparation 15 (1.57 g, 2.34 mmol) was dissolved in dichloromethane (25 mL) and trifluoroacetic acid (10 mL) added. The resulting mixture was stirred at ambient temperature for 2.5 h, concentrated, and the residue treated with excess aqueous sodium bicarbonate. The aqueous mixture was extracted with ethyl acetate and the combined organic extracts concentrated and dried. The residue was chromatographed over silica gel (chloroform/methanol) to provide 0.71 g (53%) of the desired product: MS: (M+H)+ 572.5. ¹NMR was consistent with product. Anal. Calcd. for $C_{31}H_{37}N_7O_4 \cdot 0.35$ CHCl$_3$: C, 61.38; H, 6.14; N, 15.98. Found: C, 61.36; H, 6.11; N, 16.08. The isomeric mixture (2.16 g) was separated as previously described in Example 7 to provide 1.10 g of isomer 1 ($t_R$=10.34 min) and 0.80 g of isomer 2 ($t_R$=13.70 min). The product derived from isomer 2 (0.80 g, 1.40 mmol) was dissolved in a minimal amount of ethyl acetate and the resulting solution treated with an excess of hydrochloric acid in ethyl acetate. The solution was then concentrated to provide 0.88 g (82%) of the desired product as an off white solid: MS: (M+H)+ 572.3, 573.4. ¹H NMR was consistent with product. Anal. Calcd. For $C_{31}H_{37}N_7O_4 \cdot 3.0HCl$: C, 54.67; H, 5.92; N, 14.40. Found: C, 54.25; H, 5.89; N, 13.35.

Preparation 16

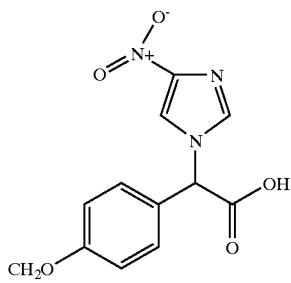

To a solution of the product of Preparation 3—411159— (5.75 g, 18.9 mmol) stirring at room temperature in tetrahydrofuran (10 mL) was added sodium hydroxide (25 mL of a 5 N aqueous solution) along with water (15 mL) and ethanol (10 mL). After hydrolysis was complete, the mixture was acidified to pH 2.0 with aqueous hydrochloric acid and extracted. The combined organic extracts were dried, filtered, and concentrated to give the desired product in quantitative yield as a tan solid: ¹H NMR (300 MHz, DMSO-d$_6$) δ 14.05–13.60 (bs, 1H), 8.34 (s, 1H) 7.90 (s, 1H), 7.45 (d, 2H, J=8.67 Hz), 7.00 (d, 2H, J=8.67 Hz), 6.42 (s, 1H), 3.77 (s, 3H). FDMS: 277 (M)+ Anal. Calcd. for $C_{12}H_{11}N_3O_5 \cdot 0.67H_2O$: C, 49.82; H, 4.30; N, 14.52. Found: C, 50.05; H, 4.01; N, 14.12.

Preparation 17

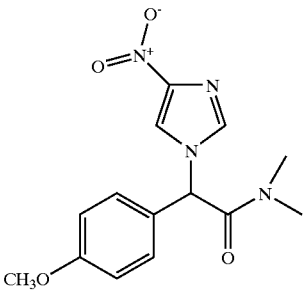

The compound of Preparation 16 (2.50 g, 9.0 mmol) was combined with aqueous dimethylamine (40%, 1.15 mL, 9.0 mmol), 1-hydroxy-benzotriazole hydrate (1.22 g, 9.0 mmol) and 1,3-dicyclohexylcarbodiimide (1.86 g, 9.0 mmol) in tetrahydrofuran (60 mL) and the mixture stirred at ambient temperature. After 18 h, the mixture was concentrated and the residue slurried in ethyl acetate and filtered. The filtrate was concentrated and the resulting residue purified by flash chromatography (silica gel, chloroform/methanol) to afford 1.83 g (67%) of the desired product: ¹H NMR (300 MHz, DMSO-d$_6$) δ 8.14 (s, 1H) 7.76 (s, 1H), 7.42 (d, 2H, J=8.67 Hz), 7.00 (d, 2H, J=8.67 Hz), 6.78 (s, 1H), 3.77 (s, 3H), 2.91 (2, 3H), 2.85 (s, 3H). ESMS: (M+H)+ 305.2.

Preparation 18

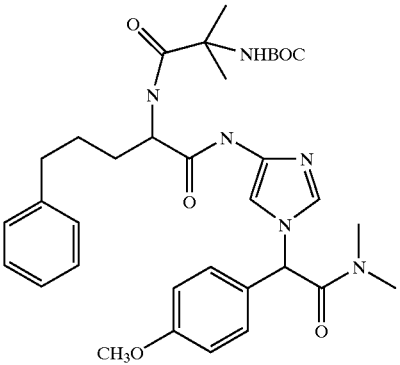

The compound of Preparation 17 (1.26 g, 4.14 mmol) was combined with 10% palladium/carbon (0.70 g) and palladium/black (0.15 g) in tetrahydrofuran (40 mL) and the mixture shaken under a hydrogen atmosphere (38 psi) in a Parr apparatus. After reduction was complete, the catalyst was removed by filtration through celite and the solution was immediately combined with 1,3-dicyclohexylcarbodiimide (0.82 g, mmol), 1-hydroxybenzotriazole mono-hydrate (0.54 g, 4.0 mmol), the product of Preparation 1j, (1.50 g, 3.97 mmol), and additional tetrahydrofuran (60 mL). After stirring overnight at ambient temperature, the mixture was concentrated and the resulting residue slurried in ethyl acetate and filtered. The filtrate was concentrated and the residue purified by silica gel chromatography (chloroform/methanol) which provided 1.50 g (57%) of the desired product. MS: (M+H)+ 635.6. ¹H NMR was consistent with product. Anal. Calcd. for $C_{34}H_{46}N_6O_6$: C, 64.33; H, 7.30; N, 13.24. Found: C, 64.09; H, 7.09; N, 13.01.

Example 10

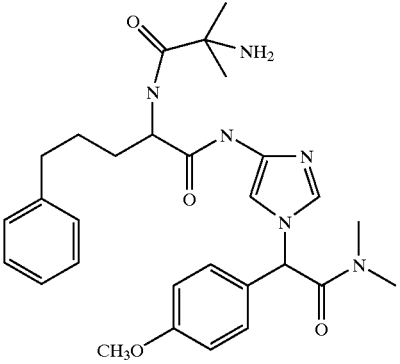

To a solution of the compound of preparation 18 (1.45 g, 2.29 mmol) stirring in dichloromethane (50 mL) at room temperature was added trifluoroacetic acid (15 mL). After 3 h, the reaction mixture was concentrated and the residue treated with excess aqueous sodium bicarbonate. The mixture was extracted with ethyl acetate and the combined organic extracts were dried over sodium sulfate and concentrated. The residue was purified by flash chromatography (silica gel, chloroform/methanol) to give 0.73 g (60%) if the desired product as a yellow solid: (60%. ESMS: $(M+H)^+$ 535.4. $^1$H NMR was consistent with product. Anal. Calcd. for $C_{29}H_{38}N_6O_4 \cdot 0.05$ $CHCl_3$: C, 64.54; H, 7.09; N, 15.54. Found: C, 64.28; H, 6.70; N, 15.35. The diastereomeric mixture (2.35 g) was resolved by HPLC (8×15 cm Prochrom column packed with Kromasil CHI-DMP chiral phase using an eluent mixture of 3A alcohol and dimethylethylamine in heptane to provide the individual diastereomers in pure form (isomer 1, $t_R$=7.84 min), isomer 2 (1.03 g, $t_R$=10.27 min). To a solution of isomer 2 (1.03 g, 1.93 mmol) in ethyl acetate was added a saturated solution of hydrochloric acid in ethyl acetate. The resulting solution was concentrated, treated with diethyl ether and concentrated to provide 1.23 g of the desired product as an off white solid: ESMS: $(M+H)^+$ 535.3, 536.4. $^1$H NMR was consistent with product. Anal. Calcd. for $C_{29}H_{38}N_6O_4 \cdot 3.0HCl$: C, 54.08; H, 6.42; N, 13.05. Found: C, 54.12; H, 6.38; N, 12.06.

Preparation 19

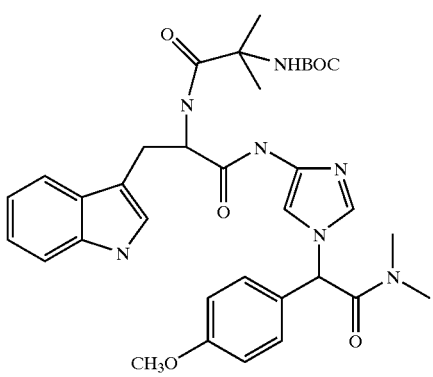

The compound of preparation 17 (0.73 g, 2.38 mmol) was combined with 10% palladium/carbon (0.50 g) and palladium/black (0.10 g) in tetrahydrofuran (40 mL) and the mixture shaken under hydrogen (38 psi) in a Parr apparatus. After reduction was complete, the catalyst was removed by filtration through celite and the resulting solution was immediately combined with dicyclohexylcarbodiimide (0.49 g, 2.38 mmol), 1-hydroxybenzotriazole mono-hydrate (0.32 g, 2.37 mmol), the product of Preparation 1L (0.93 g, 2.39 mmol) and additional tetrahydrofuran (60 mL). After stirring overnight at ambient temperature, the mixture was concentrated and the residue slurried in ethyl acetate and filtered. The filtrate was concentrated and the residue purified by silica gel chromatography (chloroform/methanol) to provide 0.76 g (50%) of the desired product as an off white solid which was used without further purification.

Example 11

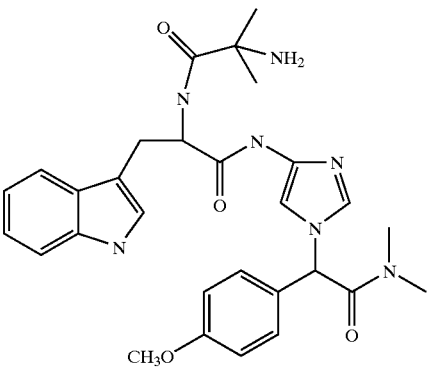

To a solution of the compound of preparation 19 (0.74 g, 1.15 mmol) stirring at room temperature in dichloromethane (30 mL) was added trifluoroacetic acid (10 mL). After 2 h, the mixture was concentrated and the residue treated with excess aqueous sodium bicarbonate. The resulting mixture was extracted with ethyl acetate and the combined organic extracts were concentrated. The residue was purified by flash chromatography (silica gel, chloroform/methanol) to provide 0.23 g (37%) of the desired product: ESMS: $(M+H)^+$ 546.6. $^1$H NMR was consistent with product. Anal. Calcd. for $C_{29}H_{35}N_7O_4 \cdot 0.25$ CHCl3: C, 61.05; H, 6.17; N, 17.04. Found: C, 61.41; H, 6.32; N, 16.52. The isomeric mixture (2.00 g) was separated as described in Example 10 to provide 0.73 g of isomer 1 ($t_R$=9.85 min) and 0.82 g of isomer 2 ($t_R$=12.87 min). To a solution of isomer 2 (0.82 g, 1.50 mmol) stirring in ethyl acetate and methanol was added a saturated solution of hydrochloric acid in ethyl acetate. The resulting mixture was concentrated to provide 0.84 g of the desired product: ESMS: $(M+H)^+$ 546.2, 547.3. $^1$H NMR was consistent with product. Anal. Calcd. for $C_{29}H_{35}N_7O_4 \cdot 3.0$ HCl: C, 53.18; H, 5.85; N, 14.97. Found: C, 53.73; H, 6.03; N, 14.04.

Preparation 20

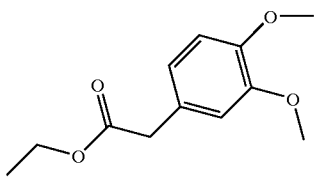

Reaction of (3,4-dimethoxyphenyl) acetic acid (30.0 g, 153 mmol) and p-toluenesulfonic acid (6.5 g, 33.8 mmol) in absolute ethanol (200 mL) according to Preparation 1 gave 31.6 g (92%) of the desired product as a yellow oil: $^1$H-NMR is consistent with structure; MS (ion spray) 225 (M+1); Anal. Calc'd for $C_{12}H_{16}O_4$: C, 64.27; H, 7.19. Found: C, 64.08; H, 7.07.

Preparation 21

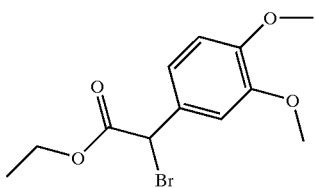

Reaction of the compound of Preparation 20 (1.5 g, 6.7 mmol), N-bromosuccinimide (1.3 g, 7.4 mmol), 2,2'-azobis(2-methylpropionitrile) (0.2 g) in carbon tetrachloride (30 mL) as described in Preparation 2 provided 2.03 g (100%) of the desired product as a clear oil: $^1$H-NMR is consistent with structure; Anal. Calc'd for $C_{12}H_{15}BrO_4$: C, 47.54; H, 4.99. Found: C, 47.64; H, 5.17.

Preparation 22

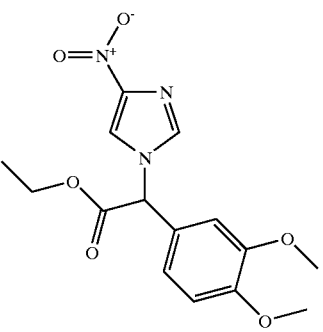

Reaction of the product of Preparation 21 (13.3 g, 44 mmol), 4-nitroimidazole (5.0 g, 44 mmol) and sodium hydride (2.1 g, 53 mmol) in tetrahydrofuran (400 mL) as described in Preparation 3 provided 22.6 g (85%) of the desired product as a tan oil. $^1$H-NMR is consistent with structure; MS (ion spray) 334.1 (M−1); Anal. Calc'd for $C_{15}H_{17}N_3O_6 \cdot 0.1CHCl3$: C, 52.23; H, 4.96; N, 12.10. Found: C, 52.55; H, 4.81; N, 11.85.

Preparation 23

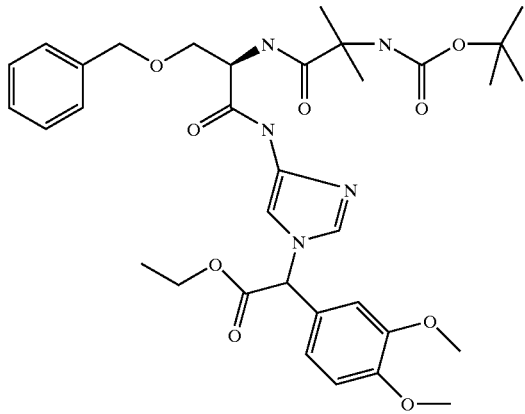

Hydrogenation of the compound of Preparation 22 (2.1 g, 6.3 mmol) with 10% palladium on carbon (1.5 g) in tetrahydrofuran (100 mL) followed by reaction with the product of Preparation 1d (2.4 g, 6.3mmol), 1-hydroxybenzotriazole (0.97 g, 6.9 mmol), 1-(3-dimethylaminopropyl)-3-ethylcarbodiimide (1.43 g, 6.9 mmol) as described in Preparation 4 gave 2.08 g (49%) of the desired product as a red foam: $^1$H-NMR is consistent with structure; MS (ion spray) 668.4 (M+1).

Preparation 24

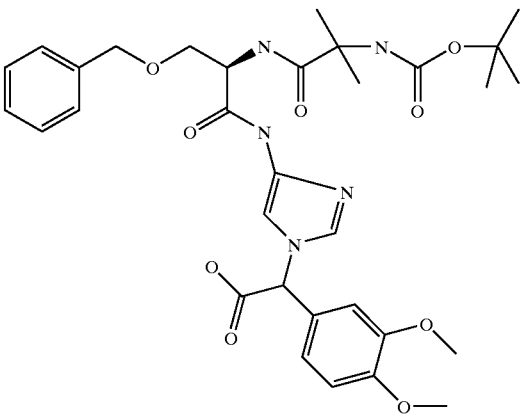

Reaction of the product of Preparation 23 (426814) (1.93 g, 2.9 mmol) and lithium hydroxide (0.08 g, 3.5 mmol) in dioxane (50 mL) and water (25 mL) as described in Preparation 5 provided 1.68 g (91%) of the desired product as a tan foam: $^1$H-NMR is consistent with structure; MS (ion spray) 640.3 (M+1); Anal. Calc'd for $C_{32}H_{41}N_5O_9$: C, 60.08; H, 6.46; N, 10.95. Found: C, 60.31; H, 6.75; N, 10.65.

Preparation 25

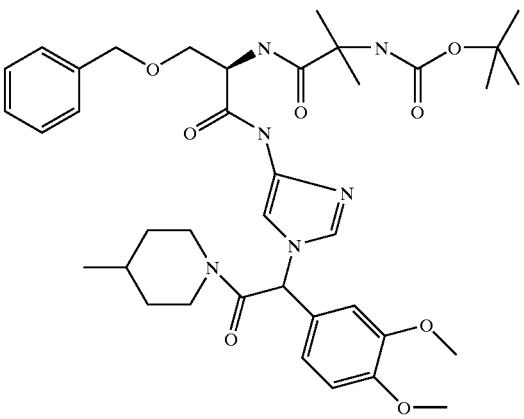

Reaction of the product of Preparation 25 (426815) (0.8 g, 1.3 mmol), 4-methylpiperidine (0.16 mL, 1.3 mmol), 1-hydroxybenzotriazole (0.2 g, 1.43 mmol) and 1-(3-dimethylaminopropyl)-3-ethylcarbodiimide (0.3 g, 1.43 mmol) in dimethylformamide (20 mL) as described in Preparation 6 provided 0.56 g (60%) of the desired product as a tan foam: $^1$H-NMR is consistent with structure; MS (ion spray) 721.5 (M+1); Anal. Calc'd for $C_{38}H_{52}N_6O_8$: C, 63.31; H, 7.27; N, 11.66. Found: C, 63.18; H, 7.30; N, 11.60.

Example 12

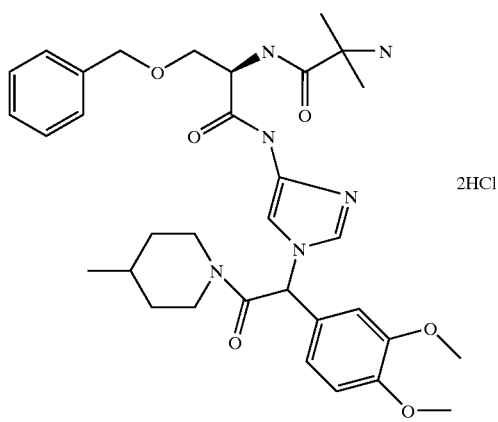

2HCl

Reaction of the compound of Preparation 25 (0.5 g, 0.7 mmol and trifluoroacetic acid (2 mL) in dichloromethane (6 mL) as described in Example 1 gave 0.4 g (83%) of the desired mixture of isomers as a white solid: $^1$H-NMR is consistent with structure; MS (ion spray) 621.6 (M+1); Anal. Calc'd for $C_{33}H_{44}N_6O_6$.2.3-hydrochloric acid: C, 56.25; H, 6.62; N, 11.93. Found: C, 56.39; H, 6.33; N, 11.83.

Preparation 26

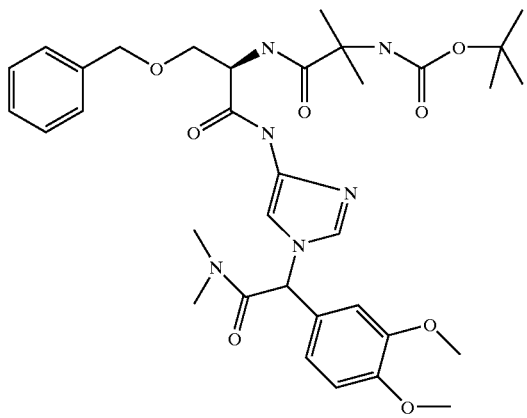

Reaction of the the product of Preparation 24 (0.8 g, 1.3 mmol), dimethylamine hydrochloride (0.11 g, 1.3 mmol), triethylamine (0.2 mL, 1.43 mmol), 1-hydroxybenzotriazole (0.2 g, 1.43 mmol) and 1-(3-dimethylaminopropyl)-3-ethylcarbodiimide (0.3 g, 1.43 mmol) in dimethylformamide (20 mL) as described in Preparation 6 gave 0.3 g (35%) of the desired product as a tan foam: $^1$H-NMR is consistent with structure; MS (ion spray) 667.4 (M+1); Anal. Calc'd for $C_{34}H_{46}N_6O_8$: C, 61.25; H, 6.95; N, 12.60. Found: C, 60.83; H, 6.48; N, 12.45.

Example 13

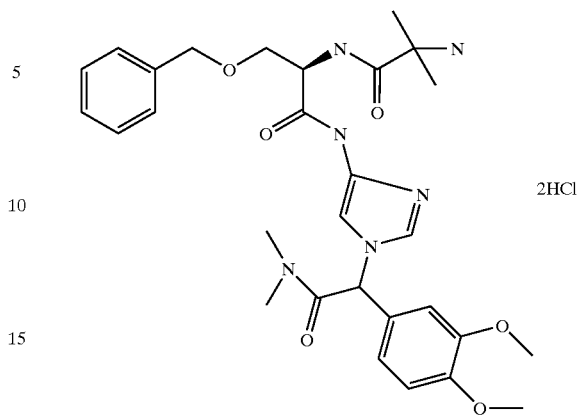

2HCl

Reaction of the product of Preparation 26 (0.28 g, 0.42 mmol) and trifluoroacetic acid (2 mL) in dichloromethane (6 mL) as described in Example 1 gave 0.21 g (78%) of the desired mixture of isomers as a white solid: 1H-NMR is consistent with structure; MS (high res) calc'd for $C_{29}H_{39}N_6O_6$: 567.2931. Found: 567.2938. Anal. Calc'd for $C_{29}H_{38}N_6O_6$.2hydrochloric acid: C, 54.46; H, 6.30; N, 13.14. Found: C, 54.67; H, 6.08; N, 13.00.

Preparation 27

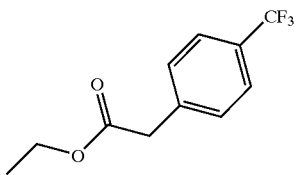

Reaction of 4-trifluoromethylphenyl acetic acid (15.0 g, 73.4 mmol) and p-toluenesulfonic acid (2.8 g, 14.7 mmol) in absolute ethanol (100 mL) as described in Preparation 1 gave 16.3 g (95%) of the desired product as colorless oil: $^1$H-NMR (d, DMSO) 1.18 (t, J=7.0 Hz, 3H), 3.80 (s, 2H), 4.10 (q, J=7.0 Hz, 2H), 7.49 (d, J=7.9 Hz, 2H), 7.69 (d, J=7.9 Hz, 2H); MS (FD) 232 (M+); Anal. Calc'd for $C_{13}H_{11}F_3O_2$: C, 56.90; H, 4.77. Found: C, 56.81; H, 4.85.

Preparation 28

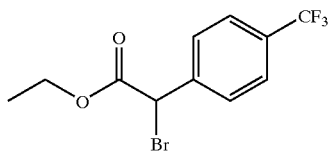

Reaction of the product of Preparation of 27 (15.8 g, 68.0 mmol), N-bromosuccinimide (12.5 g, 70 mmol) and 48% HBr (3 drops) in carbon tetrachloride (80 mL) as described in Preparation 2 gave 19.8 g (94%) of the desired product as a colorless oil: $^1$H-NMR (d, DMSO) 1.19 (t, J=7.2 Hz, 3H), 4.15–4.25 (m, 2H), 6.07 (s, 1H), 7.78 (s, 4H); MS (FD) 309, 311 (M+); Anal. Calc'd for $C_{11}H_{10}BrF_3O_2$: C, 42.47; H, 3.24. Found: C, 42.38; H, 3.13.

Preparation 29

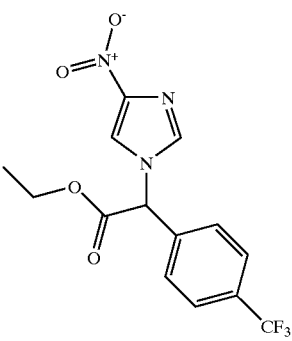

Reaction of the product Or Preparation 28 (51.8 g, 167 mmol), 4-nitroimidazole (18.8 g, 167 mmol), and potassium carbonate (51 g, 368 mmol) in N,N-dimethylformamide (600 mL) as described Preparation 3 gave 21.7 g (38%) of the desired product as a viscous orange oil: $^1$H-NMR (d, DMSO) 1.19 (t, J=7.2 Hz, 3H), 4.26 (q, J=7.2 Hz, 2H), 6.80 (s, 1H), 7.76 (d, J=8.3 Hz, 2H), 7.83 (d, J=8.3 Hz, 2H), 8.01 (s, 1H), 8.51 (s, 1H); MS (ion spray) 344 (M+1); Anal. Calc'd for $C_{14}H_{12}F_3O_4$: C, 48.99; H, 3.52; N, 12.24. Found: C, 49.03; H, 3.74; N, 11.96.

Preparation 30

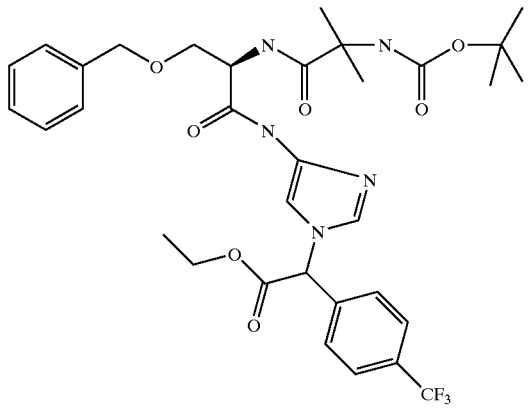

Hydrogenation of the product of Preparation 29 (8.5 g, 24.8 mmol) with 10% palladium on carbon (6.0 g) in tetrahydrofuran (70 mL) followed by coupling with the product of Preparation 1d (9.5 g, 24.8 mmol), 1-hydroxybenzotriazole (3.7 g, 27.3 mmol) and 1-(3-dimethylaminopropyl)-3-ethylcarbodiimide (5.6 g, 27.3 mmol) as described in Preparation 4 gave 12.8 g (77%) of the desired product as a tan foam: $^1$H-NMR (d, DMSO) 1.17 (t, J=7.2 Hz, 3H), 1.25–1.35 (m, 15H), 3.60 (m, 1H), 3.70 (m, 1H), 4.27 (q, J=7.2 Hz, 2H), 4.44 (d, J=2.6 Hz, 2H), 4.60 (m, 1H), 6.63 (s, 1H), 7.23–7.30 (m, 7H), 7.45 (m, 1H), 7.58–7.65 (m, 3H), 7.81 (d, J=8.3 Hz, 2H), 10.25 (br s, 1H); MS (ion spray) 676.5 (M+1); Anal. Calc'd for $C_{33}H_{40}F_3N_5O_7$: C, 58.66; H, 5.97; N, 10.36. Found: C, 58.58; H, 6.17; N, 10.27.

Preparation 31

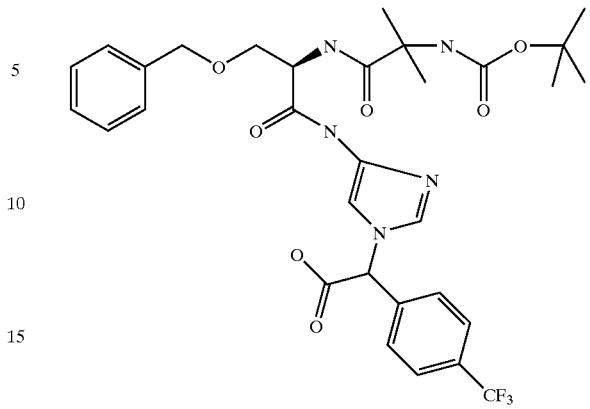

Reaction of the product of Preparation 30 (12.3 g, 18.2 mmol) and lithium hydroxide (0.52 g, 21.8 mmol) in dioxane (100 mL) and water (75 mL) as described in Preparation 5 gave 11.8 g (100%) of the desired product as tan foam: $^1$H-NMR (d, DMSO) 1.20–1.35 (m, 15H), 3.60 (m, 1H), 3.65 (m, 1H), 4.45 (d, J=2.6 Hz, 2H), 4.60 (m, 1H), 6.46 (s, 1H), 7.15 (m, 1H), 7.20–7.35 (m, 6H), 7.42 (m, 1H), 7.57–7.65 (m, 3H), 7.79 (d, J=8.3 Hz, 2H), 10.25 (br s, 1H); MS (ion spray) 648.9 (M+1); Anal. Calc'd for $C_{31}H_{36}F_3N_5O_7$: C, 57.41; H, 5.60; N, 10.81. Found: C, 57.31; H, 5.59; N, 10.53.

Preparation 32

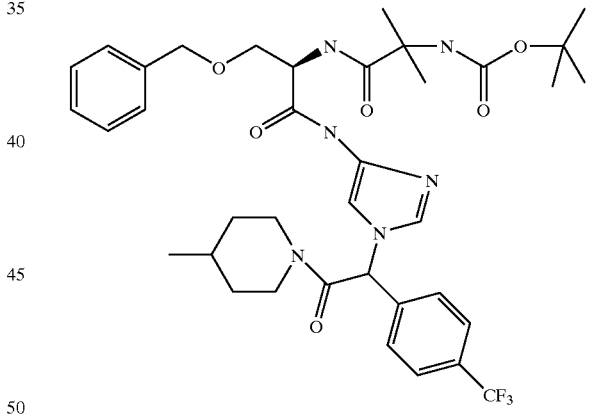

Reaction of the product of Preparation 31 (8.0 g, 12.3 mmol), 4-methylpiperidine (1.5 mL, 12.3 mmol), 1-hydroxybenzotriazole (1.83 g, 13.5 mmol) and 1-(3-dimethylaminopropyl)-3-ethylcarbodiimide (2.8 g, 13.5 mmol) in N,N-dimethylformamide (150 mL) as described in Preparation 6 gave 7.33 g (81%) of the desired product as a tan foam: $^1$H-NMR (d, DMSO) 0.78 (d, J=6.0 Hz, 1.5H), 0.84 (d, J=6.0 Hz, 1.5H), 0.95 (m, 1H), 1.25–1.35 (m, 16H), 1.50–1.70 (m, 4H), 2.65 (m, 1H), 3.60 (m, 1H), 3.67 (m, 1H), 3.80 (m, 1H), 4.35–4.50 (m, 3H), 4.60 (m, 1H), 6.88 (d, J=9.8 Hz, 1H), 7.20–7.30 (m, 7H), 7.45 (m, 1H), 7.48–7.55 (m, 2H), 7.60 (m, 1H), 7.75–7.85 (m, 2H), 10.25 (br s, 1H); MS (ion spray) 729 (M+1); Anal. Calc'd for $C_{37}H_{47}F_3N_6O_6$: C, 60.98; H, 6.50; N, 11.53. Found: C, 61.24; H, 6.44; N, 11.77.

Examples 14 and 15

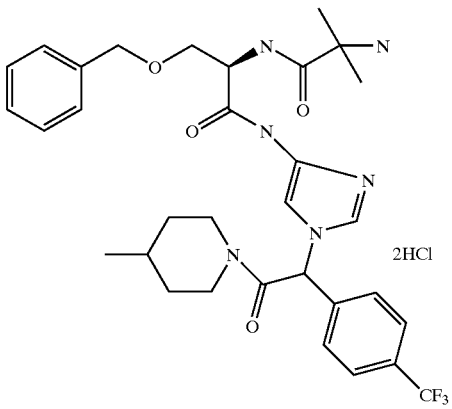

Reaction of the product of Preparation 32 (7.0 g, 10.0 mmol) and trifluoroacetic acid (10 mL) in dichloromethane (25 mL) as described in Example 1 gave 5.62 g (93%) of the desired product (3.0 g) as a tan foam which was purified by HPLC (8×15 cm Prochrom column packed with Kromasil CHI-DMP chiral phase with an eluent mixture of 3A alcohol and dimethylethylamine in heptane) to give 1.5 g (45%) of isomer 1 and 1.1 g (30%) of isomer 2.

Example 14

Isomer 1

$^1$H-NMR (d, DMSO) 0.25 (m, 1H), 0.76 (d, J=6.4 Hz, 1.5H), 0.86 (d, J=6.4 Hz, 1.5H), 1.00 (m, 1H), 1.45–1.70 (m, 8H), 2.65–2.75 (m, 2H), 3.15 (m, 1H), 3.65–3.80 (m, 3H), 4.40 (m, 1H), 4.51 (s, 2H), 4.75 (m, 2H), 7.10 (d, J=12.8 Hz, 1H), 7.20–7.40 (m, 6H), 7.58 (d, J=8.0 Hz, 1H), 7.67 (d, J=8.0 Hz, 1H), 7.90–7.80 (m, 2H), 8.10 (br s, 1H), 8.20–8.35 (m, 3H), 8.55 (d, J=7.5 Hz, 1H), 10.95 (br s, 1H); $t_R$=8.23 min; MS (ion spray) 629.3 (M+1); Anal. Calc.d for $C_{32}H_{39}F_3N_6O_4 \cdot 2HCl$: C, 54.78; H, 5.89; N, 11.98. Found: C, 54.85; H, 5.71; N, 11.70.

Example 15

Isomer 2

$^1$H-NMR (d, DMSO) 0.25 (m, 1H), 0.76 (d, J=6.4 Hz, 1.5H), 0.86 (d, J=6.4 Hz, 1.5H), 1.00 (m, 1H), 1.45–1.70 (m, 8H), 2.65–2.75 (m, 2H), 3.15 (m, 1H), 3.65–3.80 (m, 3H), 4.40 (m, 1H), 4.51 (s, 2H), 4.75 (m, 2H), 7.10 (d, J=12.8 Hz, 1H), 7.20–7.40 (m, 6H), 7.58 (d, J=8.0 Hz, 1H), 7.67 (d, J=8.0 Hz, 1H), 7.80–7.90 (m, 2H), 8.10 (br s, 1H), 8.20–8.35 (m, 3H), 8.55 (d, J=7.5 Hz, 1H), 10.95 (br s, 1H); $t_R$=10.77 min; MS (ion spray) 629.3 (M+1); Anal. Calc.d for $C_{32}H_{39}F_3N_6O_4 \cdot 2.2HCl$: C, 54.22; H, 5.86; N, 11.85. Found: C, 54.15; H, 5.84; N, 11.64.

Preparation 33

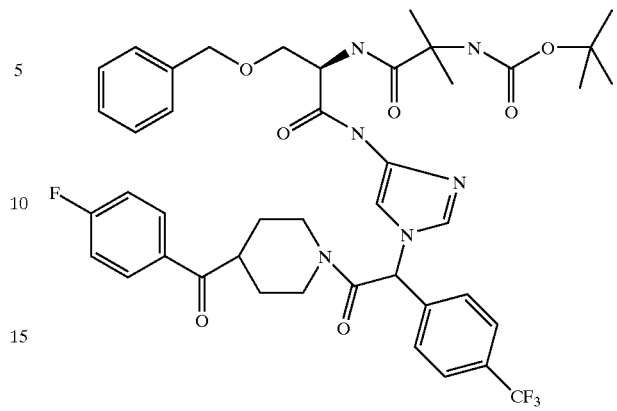

Reaction of the product of Preparation 31 (0.6 g, 0.93 mmol), 4-(4-fluorobenzoyl)piperidine hydrochloride (0.23 g, 0.93 mmol), triethylamine (0.15 mL, 10.2-mol), 1-hydroxybenzotriazole (0.14 g, 1.02 mmol) and 1-(3-dimethylaminopropyl)-3-ethylcarbodiimide (0.21 g, 1.02 mmol) in dimethylformamide (30 mL) as described in Preparation 6 provided in 0.35 g (45%) of the desired product as a yellow foam: $^1$H-NMR (d, DMSO) 1.25–1.35 (m, 15H), 1.40–1.50 (m, 2H), 1.75 (m, 1H), 1.85 (m, 1H), 2.85–3.00 (m, 2H), 3.55–3.75 (m, 3H), 3.90 (m, 1H), 4.40–4.50 (m, 3H), 4.60 (m, 1H), 6.90 (m, 1H), 7.25–7.40 (m, 12H), 7.50–7.60 (m, 3H), 8.03–8.10 (m, 2H), 10.20 (br s, 1H); MS (ion spray) 837.4 (M+1); Anal. Calc'd for $C_{43}H_{48}F_4N_6O_7$: C, 61.71; H, 5.78, N, 10.04. Found: C, 61.53, H, 5.98; N, 9.95.

Example 16

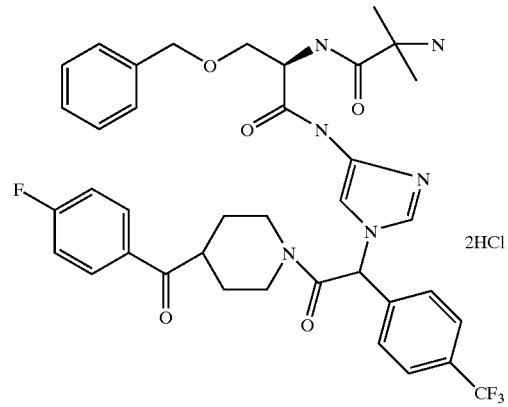

Reaction of the product of Preparation 33 (0.34 g, 0.4 mmol) and trifluoroacetic acid (2 mL) in dichloromethane (6 mL) as described in Example 1 gave 0.2 g (63%) of the desired product as a yellow solid: $^1$H-NMR (d, DMSO) 1.45–1.65 (m, 6H), 1.75 (m, 1H), 1.85 (m, 1H), 2.85–3.05 (m, 2H), 3.25 (m, 1H), 3.60–4.00 (m, 7H), 4.40–4.55 (m, 3H), 4.75 (m, 1H), 7.05 (d, J=10.6 Hz, 1H), 7.25–7.40 (m, 8H), 7.55–7.70 (m, 2H), 7.75–7.85 (m, 2H), 8.00–8.10 (m, 2H), 8.15–8.25 (m, 3H), 8.50 (d, J=7.2 Hz, 1H), 10.75 (br s, 1H); MS (ion spray) 737.0 (M+1): Anal. Calc'd for $C_{38}H_{40}F_4N_6O_5 \cdot 2.4HCl$: C, 55.37; H, 5.18; N, 10.20. Found: C, 55.39; H, 5.45; N, 10.07.

Preparation 34

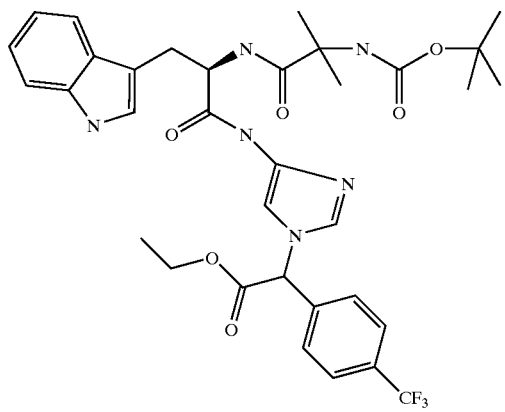

Hydrogenation of the product of Preparation 29 (1.75 g, 5.1 mmol) with 10% palladium on carbon (1.4 g) in tetrahydrofuran (60 mL) followed by reaction with the product of Preparation 1L (2.0 g, 5.1 mmol), 1-hydroxybenzotriazole (0.76 g, 5.6 mmol) and 1-(3-dimethylaminopropyl)-3-ethylcarbodiimide (1.16 g, 5.6 mmol) as described in Preparation 4 gave 2.51 g (72%) of the desired product as a tan foam: $^1$H-NMR (d, DMSO) 1.15–1.35 (m, 18H), 3.05–3.15 (m, 2H), 4.25 (m, 2H), 4.65 (br s, 1H), 6.62 (s, 1H), 6.85 (m, 1H), 6.95–7.08 (m, 2H), 7.20–7.30 (m, 2H), 7.40–7.55 (m, 2H), 7.55–7.65 (m, 3H), 7.82 (d, J=8.3 Hz, 2H), 10.20 (br s, 1H), 10.75 (br s, 1H); MS (ion spray) 685 (M+1); Anal. Calc'd for $C_{34}H_{39}F_3N_6O_6 \cdot 1H_2O$: C, 58.11; H, 5.88; N, 11.96. Found: C, 58.15; H, 5.59; N, 11.92.

Preparation 35

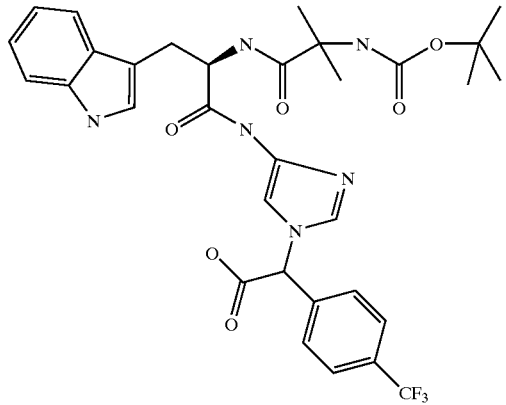

Reaction of the product of Preparation 34 (2.2 g, 3.2 mmol) and lithium hydroxide (0.1 g, 3.9 mmol) in dioxane (50 mL) and water (25 mL) as described in Preparation 5 gave 2.1 g (100%) of the desired product as a tan foam: $^1$H-NMR (d, DMSO), 1.15–1.35 (m, 15H), 3.05–3.15 (m, 2H), 4.65 (br s, 1H), 6.97 (s, 1H), 6.90 (m, 1H), 6.98–7.10 (m, 2H), 7.20–7.30 (m, 2H), 7.40–7.55 (m, 2H), 7.57–7.64 (m, 3H), 7.80 (d, J=8.3 Hz, 2H), 10.20 (br s, 1H), 10.75 (br s, 1H), 13.90 (br s, 1H); MS (ion spray) 657.4 (M+1); Anal. Calc'd for $C_{32}H_{35}F_3N_6O_6$: C, 58.53; H, 5.37; N, 12.80. Found: C, 59.28; H, 5.17; N, 12.65.

Preparation 36

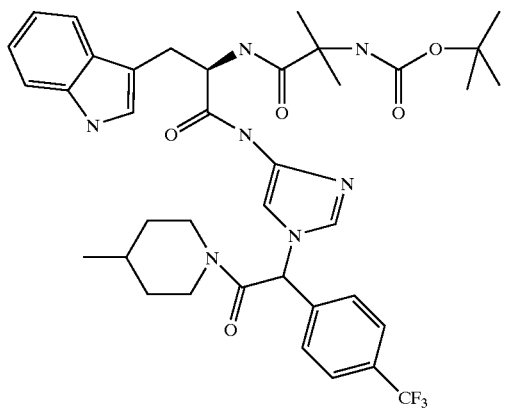

Reaction of the product of Preparation 35 (0.7 g, 1.1 mmol), 4-methylpiperidine (0.13 mL, 1.1 mmol), 1-hydroxybenzotriazole (0.17 g, 1.2 mmol) and 1-(3-dimethylaminopropyl)-3-ethylcarbodiimide (0.26 g, 1.2 mmol) in N,N-dimethylformamide (30 mL) as described in Preparation 6 provided 0.47 g (58%) of the desired product as a tan foam: $^1$H-NMR (d, DMSO) 0.78 (d, J=6.4 Hz, 1.5H), 0.86 (d, J=6.3 Hz, 1.5H), 1.15–1.35 (m, 18H), 1.50–1.70 (m, 3H), 2.60–2.70 (m, 2H), 3.00–3.15 (m, 2H), 3.30 (m, 1H), 4.40 (m, 1H), 4.65 (m, 1H), 6.85–6.95 (m, 2H), 7.00–7.10 (s, 2H), 7.17–7.30 (m, 2H), 7.40–7.60 (m, 4H), 7.75–7.85 (m, 2H), 10.20 (br s, 1H), 10.75 (br s, 1H); MS (ion spray) 738.5 (M+1); Anal. Calc'd for $C_{38}H_{46}F_3N_7O_5 \cdot 1H_2O$: C, 60.39; H, 6.40; N, 12.97. Found: C, 160.18; H, 6.21; N, 12.99.

Examples 17 and 18

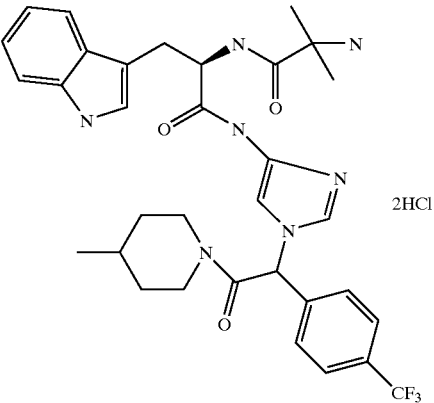

Reaction of the product of Preparation 36 (4.8 g, 6.5 mmol) and trifluoroacetic acid (16 mL) in dichloromethane (40 mL) as described in Example 1 gave 2.0 g (44%) of the desired mixture as a tan foam. Purification by HPLC (8×15 cm Prochrom column packed with Kromasil CHI-DMP chiral phase with an eluent mixture of 3A alcohol (13% by v), dimethylethylamine (0.2% by v) in heptane at a flow rate of 250 mL/min) gave 0.5 g (12%) of isomer 1 and 0.4 g (9%) of isomer 2.

Example 17

Isomer 1

$^1$H-NMR (d, DMSO) 0.77 (d, J=6.5 Hz, 1.5H), 0.87 (d, J=6.0 Hz, 1.5H), 1.00 (m, 1H), 1.32 (s, 3H), 1.50 (s, 3H), 1.50–1.70 (m, 2H), 2.72 (m, 1H), 3.00–3.30 (m, 4H), 3.75 (m, 1H), 4.05–4.33 (m, 3H), 4.20 (m, 1H), 4.78 (m, 1H), 6.94 (m, 3H), 7.20 (s, 1H), 7.30–7.40 (m, 2H), 7.55–7.70 (m, 2H), 7.75–8.00 (m, 4H), 8.05–8.15 (m, 2H), 8.50 (m, 1H), 10.86 (s, 1H), 11.05 (s, 1H); $t_R$=6.01 min; MS (ion spray) 638.2 (M+1).

Example 18

Isomer 2

$^1$H-NMR (d, DMSO) 0.77 (d, J=6.5 Hz, 1.5H), 0.87 (d, J=6.0 Hz, 1.5H), 1.00 (m, 1H), 1.32 (s, 3H), 1.50 (s, 3H), 1.50–1.70 (m, 2H), 2.72 (m, 1H), 3.00–3.30 (m, 4H), 3.75 (m, 1H), 4.05–4.33 (m, 3H), 4.20 (m, 1H), 4.78 (m, 1H), 6.94 (m, 3H), 7.20 (s, 1H), 7.30–7.40 (m, 2H), 7.55–7.70 (m, 2H), 7.75–8.00 (m, 4H), 8.05–8.15 (m, 2H), 8.50 (m, 1H), 10.86 (s, 1H), 11.05 (s, 1H); $t_R$=7.5 min; MS (ion spray) 638.2 (M+1).

Preparation 37

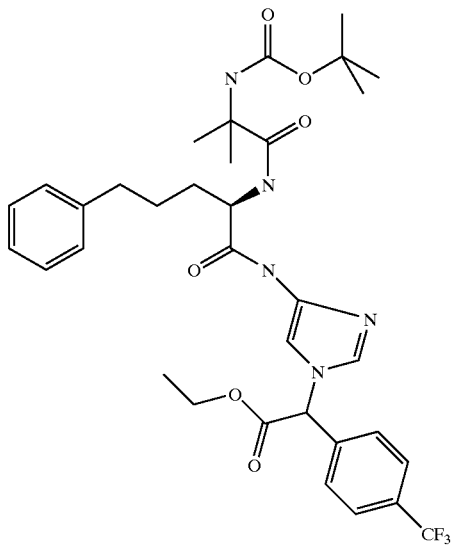

A mixture of the product of Preparation 29 (11.1 g, 32.3 mmol) and 5% palladium on carbon (1.7 g) in tetrahydrofuran (100 mL) was hydrogenated at 60 psi at room temperature using a Parr apparatus. After 1.5 h, the resulting brown solution was filtered through celite and concentrated to give 8.8 g (87%) crude oil which was used without purification. To a mixture of the amine stirring at 0° C. in tetrahydrofuran (20 mL) was added the product of Preparation 1j (10.6 g, 28.1 mmol) in tetrahydrofuran (30 mL). To this mixture was added 1-hydroxy-7-azobenzotriazole (4.0 g, 29.5 mmol) and 1,3-dicyclohexylcarbodiimide (6.1 g, 29.5 mmol). The solution was allowed to warm to room temperature and the resulting mixture filtered after 3 days. The filtrate was concentrated and subsequently purified by flash chromatography (silica gel, 3.5% methanol/ dichloromethane) to provide 12.1 g (64%) of the desired product as an orange solid: $^1$H-NMR (d, DMSO) 1.15 (t, J=7 Hz, 3H), 1.18–1.32 (m, 15H), 1.35–1.70 (m, 4H), 3.23 (1,2H), 4.19 (q, J=7 Hz, 2H), 4.31 (m, 1H), 6.58 (s, 1H), 7.00 (br s, 1H), 7.05–7.22 (m, 6H), 7.41 (m, 1H), 7.52–7.58 (m, 3H), 7.75 (d, J=8 Hz, 2H), 10.19 (br s, 1H); MS (ion spray) 674.7 (M+1); Anal. Calc'd for $C_{34}H_{42}F_3N_5O_6$: C, 60.61; H, 6.28; N, 10.39. Found: C, 60.44; H, 6.48; N, 10.36.

Preparation 38

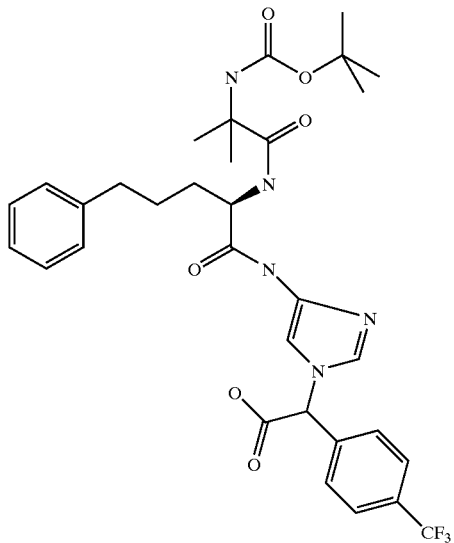

To a solution of the product of Preparation 37 (12.0 g, 17.8 mmol) stirring in dioxane (20 ml) and water (20 ml) at room temperature was added lithium hydroxide (0.84 g, 35.6 mmol). After 90 min with intermittent sonication, the reaction was poured into a solution of sodium bisulfate (12 g/50 mL $H_2O$) and brine (20 mL) then extracted with ethyl acetate. The combined organic extracts were dried over sodium sulfate, filtered, and concentrated to provide 11.5 g (100%) of the desired product as a tan solid: $^1$H-NMR (d, DMSO) 1.17–1.31 (m, 15H), 1.40–1.70 (m, 4H), 2.45 (m, 2H), 4.33 (m, 1H), 6.40 (s, 1H), 7.00 (m, 1H), 7.05–7.23 (s, 6H), 7.40 (m, 1H), 7.55–7.71 (m, 3H), 7.76 (d, J=8 Hz, 2H), 10.25 (br s, 1H); MS (ion spray) 646.6 (M+1); Anal. Calc'd for $C_{32}H_{38}F_3N_5O_6 \cdot 0.7H_2O$: C, 58.39; H, 6.03; N, 10.64. Found: C, 58.52; H, 6.01; N, 9.87*.

Preparation 39

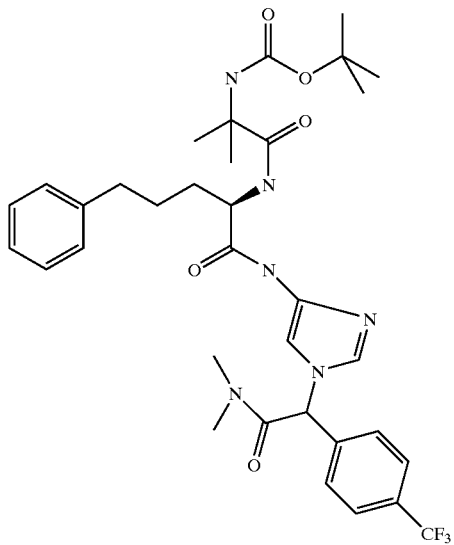

To a solution of the product of Preparation 38 (6.0 g, 9.3 mmol) stirring at 0° C. in dimethylformamide was added dimethylamine hydrochloride (0.76 g, 9.3 mmol), diethylcyanophosphonate (1.41 mL, 9.3 mmol), and triethylamine (1.29 mL, 9.3 mmol). After 30 min, a second equivalent of dimethylamine hydrochloride, DECP and triethylamine were added. After 30 min, the reaction mixture was diluted with ethyl acetate (300 mL) and washed with aqueous sodium bisulfate and brine. The organic extract was dried over sodium sulfate, filtered, and concentrated. The resulting crude material was purified by radial chromatography (silica gel, 4% methanol in dichloromethane) to give 4.7 g (75%) of the desired product as a tan foam: $^1$H-NMR (d, CDCl$_3$) 1.25 (s, 9H), 1.42 (s, 6H), 1.60–1.80 (m, 4H), 1.90 (br s, 1H), 2.57 (m, 2H), 2.98 (s, 6H), 4.48 (m, 1H), 7.05–7.21 (m, 6H), 7.50 (m, 1H), 7.62–7.76 (m, 5H), 8.93 (br s, 1H), 10.93 (br s, 1H); MS (ion spray) 673.7 (M+1).

Examples 19 and 20

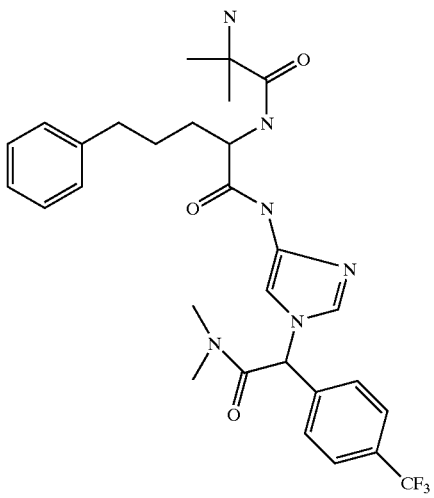

To the product of Preparation 39 (4.7 g, 7.0 mmol) was stirred at room temperature in a saturated solution of hydrochloric acid in glacial acetic acid (30 mL). After 90 min, the mixture was concentrated. The resulting material diluted with ethyl acetate and extracted with aqueous sodium bicarbonate. The organic extract was dried over sodium sulfate, filtered, and concentrated to give 3.7 g (93%) of an orange solid. MS (ion spray) 573.4 (M+1). The diastereomers (3.4 g) were separated by chiral chromatography using a Kromasil-CHI normal phase column to provide 1.40 g (41%) of isomer 1 and 1.26 g (37%) of isomer 2. The individual isomers were dissolved in a saturated solution of hydrochloric acid in glacial acetic acid (4 mL) and subsequently concentrated to provide the desired products as tan solids:

Example 19

Isomer 1

$^1$H-NMR (d, DMSO) 1.41 (s, 3H), 1.42 (s, 3H), 1.51–1.73 (m, 4H), 2.53 (m, 2H), 2.82 (s, 3H), 2.84 (s, 3H), 4.39 (m, 1H), 6.91 (s, 1H), 7.10 (m, 3H), 7.18–7.29 (m, 3H), 7.55 (d, J=8 Hz, 2H), 7.78 (d, J=8 Hz, 2H), 7.91 (hr s, 1H), 8.15 (hr s, 3H), 8.38 (d, J=7.5 Hz, 1H), 10.78 (br s, 1H); MS (ion spray) 573.4 (M+1); Anal. Calc.d for C$_{29}$H$_{35}$F$_3$N$_6$O$_3$.2.3HCl: C, 53.06; H, 5.73; N, 12.80. Found: C, 52.90; H, 5.66; N, 12.70.

Example 20

Isomer 2

$^1$H-NMR (d, DMSO) 1.42 (s, 6H), 1.51–1.73 (m, 4H), 2.53 (m, 2H), 2.82 (s, 3H), 2.84 (s, 3H), 4.39 (m, 1H), 6.91 (s, 1H), 7.10 (m, 3H), 7.18–7.29 (m, 3H), 7.55 (d, J=8 Hz, 2H), 7.78 (d, J=8 Hz, 2H), 7.91 (br s, 1H), 8.15 (br s, 3H), 8.38 (d, J=7.5 Hz, 1H), 10.78 (br s, 1H); MS (ion spray) 573.4 (M+1); Anal. Calc.d for C$_{29}$H$_{35}$F$_3$N$_6$O$_3$.2HCl: C, 53.96; H, 5.78; N, 13.02. Found: C, 53.84; H, 5.71; N, 12.93.

Preparation 40

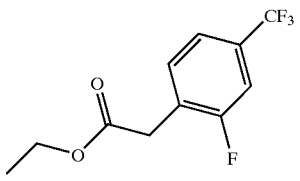

Reaction of (2-fluoro-4-trifluoromethyl)phenylacetic acid (20.0 g, 90 mmol) and p-toluenesulfonic acid (5.0, 26 mmol) in absolute ethanol (200 mL) as described in Preparation 1 provided 22.5 g (100%) of the desired product an a colorless oil: $^1$H-NMR is consistent with structure; MS (FD) 250 (M+); Anal Calc'd for C$_{11}$H$_{10}$F$_4$O$_2$: C, 52.81; H, 4.03. Found: C, 52.94; H, 3.94.

Preparation 41

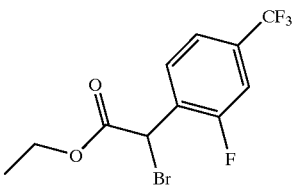

Reaction of the product of Preparation 40 (16.8 g, 67 mmol), N-bromosuccinimide (12.3 g, 69 mmol) and 48% HBr (3 drops) in carbon tetrachloride (170 mL) as described in Preparation 2 gave 22.05 g (100%) of the desired product as a colorless oil: $^1$H-NMR is consistent with structure; MS (FD) 328, 330 (M+); Anal. Calc'd for C$_{11}$H$_9$BrF$_4$O$_2$: C, 40.15; H, 2.76. Found: C, 40.00; H, 2.77.

Preparation 42

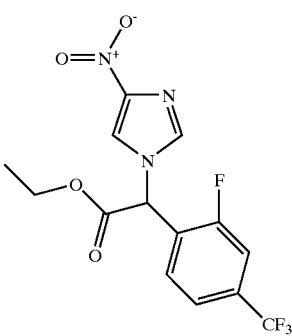

Reaction of the product of Preparation 41 (21.4 g, 65 mmol), 4-nitroimidazole (8.8 g, 78 mmol) and potassium carbonate (26.8 g, 195 mmol) in dimethylformamide (300 mL) as described in Preparation 3 gave 3.75 g (16%) of the desired product as a tan oil; $^1$H-NMR is consistent with structure; MS (ion spray) 362.2 (M+1); Anal. Calc'd for C$_{14}$H$_{11}$F$_4$N$_3$O$_4$: C, 46.55; H, 3.07; N, 11.63. Found: C, 47.13; H, 3.49; N, 11.37.

Preparation 43

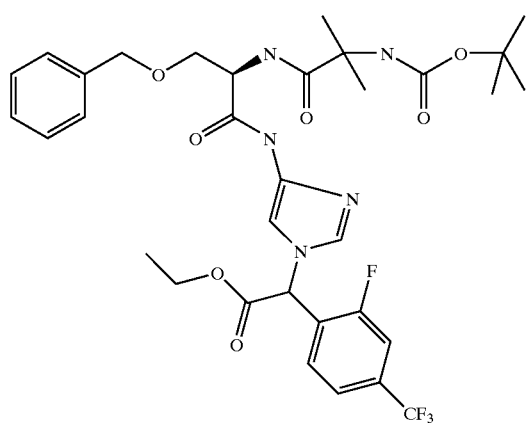

Reduction of the product of Preparation 42 (2.88 g, 8.0 mmol) with 10% palladium on carbon (1.45 g) in tetrahydrofuran (60 mL) followed by coupling with the product of Preparation 1d gave (3.0 g, 8.0 mmol), 1-hydroxybenzotriazole (1.2 g, 8.8 mmol) and 1-(3-dimethylaminopropyl)-3-ethylcarbodiimide (8.8 mmol) as described in Preparation 4 gave 2.85 g (51%) of the desired product as a tan foam: $^1$H-NMR is consistent with structure; MS (ion spray) 694.4 (M+1); Anal. Calc'd for $C_{33}H_{39}F_4N_5O_7$: C, 57.14; H, 5.67; N, 10.10. Found: C, 57.28; H, 5.59; N, 10.09.

Preparation 44

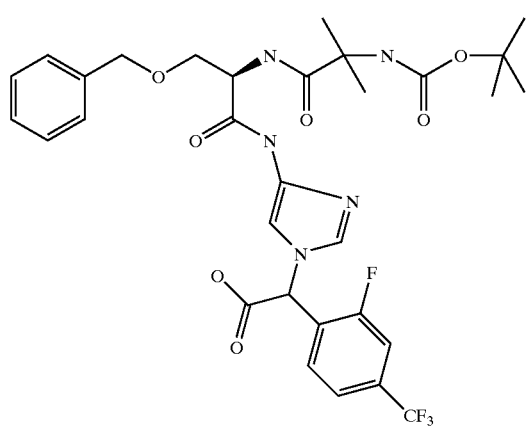

Reaction of the product of Preparation 43 (2.64 g, 3.8 mmol) and lithium hydroxide (0.11 g, 4.6 mmol) in dioxane (50 mL) and water (25 mL) as described in Preparation 5 gave 2.53 g (100%) of the desired product as a tan foam. $^1$H-NMR is consistent with structure; MS (ion spray) 664.4 (M+1).

Preparation 45

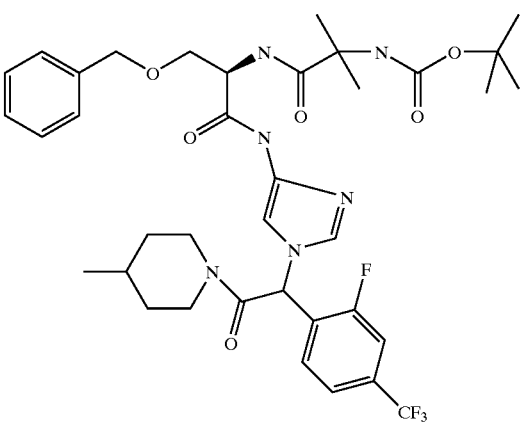

Reaction of the product of Preparation 44 (0.8 g, 1.2 mmol), 4-methylpiperidine (0.14 mL, 1.2 mmol), 1-hydroxybenzotriazole (0.18 g, 1.32 mmol) and 1-(3-dimethylaminopropyl)-3-ethylcarbodiimide (0.27 g, 1.32 mmol) in dimethylformamide (40 mL) as described in Preparation 6 gave 0.63 g (70%) of the desired product as a yellow foam: $^1$H-NMR is consistent with structure; MS (ion spray) 747.4 (M+1).

Example 21

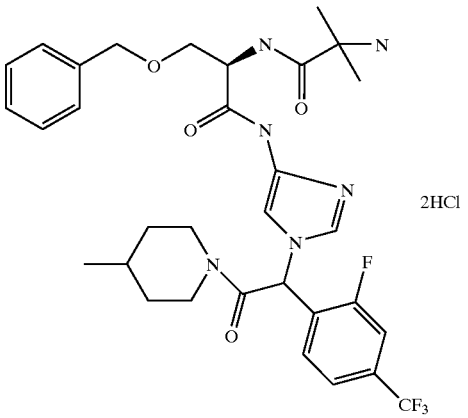

Reaction of the product of Preparation 46 (0.54 g, 0.72 mmol) and trifluoroacetic acid (2 mL) in dichloromethane (6 mL) as described in Example 1 gave 0.4 g (77%) of the desired mixture of isomers as a white solid. $^1$H-NMR is consistent with structure; MS (ion spray) 647.6 (M+1); Anal. Calc'd for $C_{32}H_{38}F_4N_6O_4 \cdot 2HCl$: C, 53.41; H, 5.60; N, 11.68. Found: C, 53.34; H, 5.84; N, 11.65.

Preparation 46

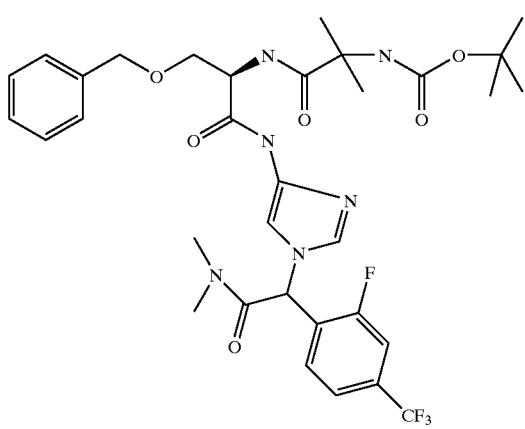

Reaction of the product of Preparation 44 (0.8 g, 1.2 mmol), dimethylamine hydrochloride (0.1 g, 1.2 mmol) triethylamine (0.19 mL, 1.3 mmol), 1-hydroxybenzotriazole (0.18 g, 1.3 mmol) and 1-(3-dimethylaminopropyl)-3-ethylcarbodiimide (0.27 g, 1.3 mol) in dimethylformamide (40 mL) as described in Preparation 6 gave 0.48 g (58%) of the desired product: $^1$H-NMR is consistent with structure; MS (ion spray) 693.4 (M+1); Anal. Calc'd for $C_{33}H_{40}F_4N_6O_6$: C, 57.22; H, 5.82; N, 12.13. Found: C, 57.48; H, 5.74; N, 12.02.

Example 22

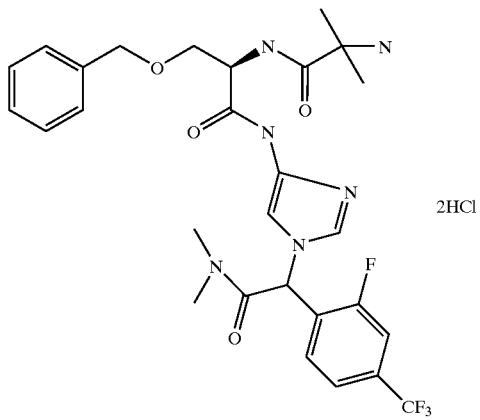

Reaction of the product of Preparation 46 (0.43 g, 0.62 mmol) and trifluoroacetic acid (2 mL) in dichloromethane (6 mL) as described in Example 1 gave 0.25 g (60%) of the desired product as a mixture of diastereoisomers. $^1$H-NMR is consistent with structure; MS (ion spray) 593.9 (M+1); Anal. Calc'd for $C_{28}H_{32}F_4N_6O_4$·2-hydrochloric acid: C, 50.53; H, 5.15; N, 12.62. Found: C, 50.25; H, 5.20; N, 12.35.

Preparation 47

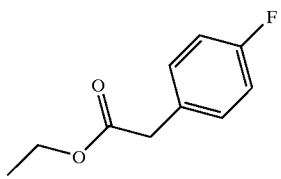

Reaction of 4-fluorophenylacetic acid (15.0 g, 97.0 mmol), p-toluenesulfonic acid (2.0 g, 10.5 mmol) and absolute ethanol (100 mL) as described in Preparation 1 gave 15.4 g (87%) of the desired product as a colorless oil: $^1$H-NMR (d, DMSO) 1.17 (t, J=7.2 Hz, 3H), 3.66 (s, 2H), 4.06 (q, J=7.2 Hz, 2H), 7.10–7.20 (m, 2H), 7.25–7.35 (m, 2H); MS (FD) 182 (M+); Anal. Calc'd for $C_{10}H_{11}FO_2$: C, 65.92; H, 6.09. Found: C, 65.67; H, 5.96.

Preparation 48

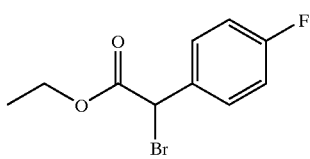

Reaction of the product of Preparation 47 (14.9 g, 82 mmol), N-bromosuccinimide (14.9 g, 84.5 mmol) and 48% HBr (4 drops) in carbon tetrachloride (80 mL) as described in Preparation 2 gave 18.3 g (85%) of the desired product as a colorless oil: $^1$H-NMR (d, DMSO) 1.19 (t, J=7.2 Hz, 3H), 4.15–4.25 (m, 2H), 5.95 (s, 1H), 7.15–7.30 (m, 2H), 7.56–7.70 (m, 2H); MS (FD) 260, 262 (M+); Anal. Calc'd for $C_{10}H_{10}BrFO_2$: C, 46.00; H, 3.96. Found: C, 46.10; H, 3.95.

Preparation 49

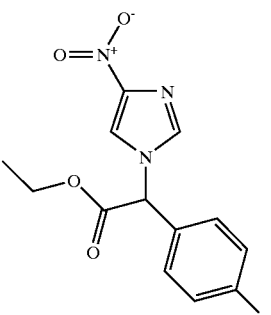

Reaction of the product of Preparation 48 (68 g, 260 mmol), 4-nitroimidazole (35.0 g, 312 mmol) and potassium carbonate (108 g, 780 mmol) in dimethylformamide (300 mL) as described in Preparation 3 gave 39.8 g (52%) of the desired product as an orange oil: $^1$H-NMR (d, DMSO) 1.83 (t, J=7.2 Hz, 3H), 4.25 (q, J=7.2 Hz, 2H), 6.66 (s, 1H), 7.25–7.35 (m, 2H), 7.55–7.65 (m, 2H), 7.95 (d, 1.13 Hz, 1H), 8.44 (d, J=1.5 Hz, 1H); MS (ion spray) 294.2 (M+1); Anal. Calc'd for $C_{13}H_{12}FN_3O_4$: C, 53.24; H, 4.12; N, 14.33. Found: C, 53.51; H, 4.07; N, 14.42.

Preparation 50

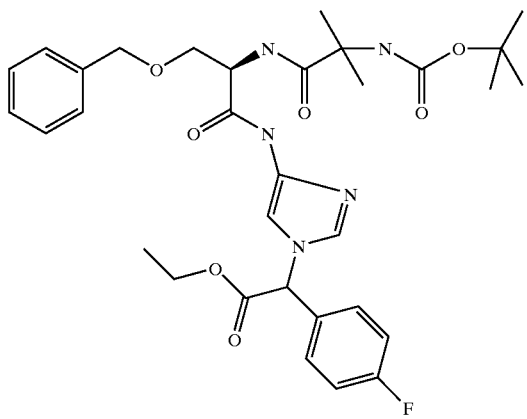

Reduction of the product of Preparation 49 (8.9 g, 30.3 mmol) with 10% palladium on carbon (6.0 g) in tetrahydrofuran (120 mL) followed by coupling with the product of Preparation 1d (11.4 g, 30 mmol), 1-hydroxybenzotriazole (4.5 g, 33 mmol) and 1-(3-dimethylaminopropyl)-3-ethylcarbodiimide (6.8 g, 33 mmol) as described in Preparation 4 gave 10.8 g (58%) of the desired product as a tan foam: $^1$H-NMR (d, DMSO) 1.18 (t, J=7.2 Hz, 3H), 1.25–1.35 (m, 15H), 3.60 (m, 1H), 3.70 (m, 1H), 4.25 (q, J=7.2 Hz, 2H), 4.44 (d, J=2.6 Hz, 2H), 4.60 (m, 1H), 6.47 (s, 1H), 7.20–7.40 (m, 9H), 7.40–7.50 (m, 3H), 7.56 (s, 1H), 10.25 (br s, 1H); MS (ion spray) 626.1 (M+1); Anal. Calc'd for $C_{32}H_{40}FN_5O_7$: C, 61.43; H, 6.44; N, 11.19. Found: C, 61.63; H, 6.42; N, 11.26.

Preparation 51

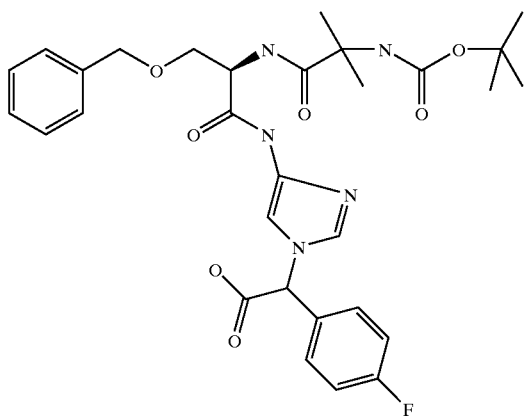

Reaction of the product of Preparation 50 (10.5 g, 17.0 mmol) and lithium hydroxide (0.48 g, 20.4 mmol) in dioxane (200 mL) and water (100 mL) as described in Preparation 5 gave 10.1 g (100%) of the desired product as a tan foam: 1H-NMR (d, DMSO) 1.25–1.40 (m, 15H), 3.35 (br s, 1H), 3.60 (m, 1H), 3.70 (m, 1H), 4.44 (d, J=2.6 Hz, 2H), 4.60 (m, 1H), 6.33 (s, 1H), 7.20–7.35 (m, 9H), 7.40–7.50 (m, 3H), 7.56 (s, 1H), 10.20 (br s, 1H); MS (ion spray) 598.5 (M+1); Anal. Calc'd for $C_{30}H_{36}FN_5O_7$: C, 60.29; H, 6.07; N, 11.72. Found: C, 60.38; H, 6.29; N, 11.49.

Preparation 52

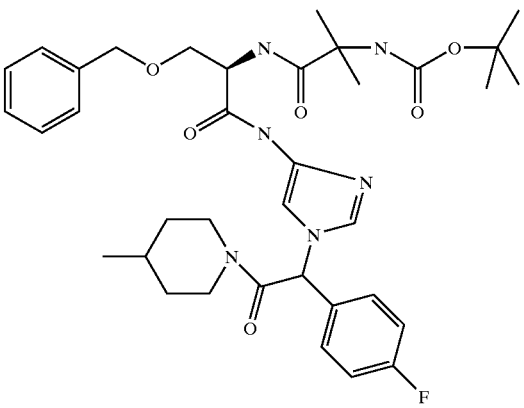

Reaction of product of Preparation 51 (9.2 g, 15.4 mmol), 4-methylpiperidine (1.83 mL, 15.4 mmol), 1-hydroxybenzotriazole (2.3 g, 17 mmol) and 1-(3-dimethylaminopropyl)-3-ethylcarbodiimide (3.5 g, 17 mmol) in dimethylformamide (100 mL) as described in Preparation 6 gave 9.7 g (93%) of the desired product as a tan foam: $^1$H-NMR (d, DMSO) 0.76 (d, J=6.1 Hz, 1.5H), 0.86 (d, J=6.1 Hz, 1.5H), 1.00 (m, 1H), 1.20–1.40 (m, 15H), 1.45–1.70 (m, 3H), 2.55–2.70 (m, 2H), 3.05 (m, 1H), 3.60 (m, 1H), 3.65–3.75 (m, 2H), 4.40 (m, 1H), 4.44 (d, J=2.6 Hz, 2H), 4.60 (m, 1H), 6.73 (d, J=11.3 Hz, 1H), 7.15–7.35 (m, 9H), 7.35–7.50 (m, 4H), 10.20 (br s, 1H). MS (ion spray) 679.6 (M+1); Anal. Calc'd for $C_{36}H_{47}FN_6O_6$: C, 63.70; H, 6.98; N, 12.38. Found: C, 63.44; H, 6.86; N, 12.22.

Examples 23 and 24

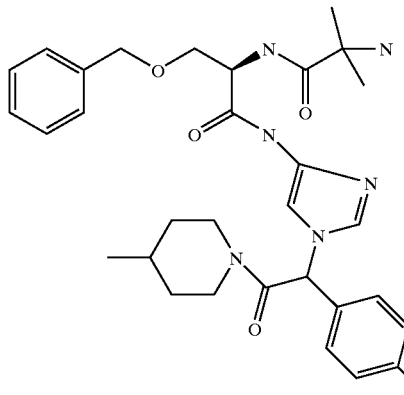

Reaction of the product of Preparation 52 (9.7 g, 14.3 mmol) with trifluoroacetic acid (16 mL) in dichloromethane (40 mL) as described in Example 1 gave 6.8 g (73%) of the desired product as a mixture of diastereoisomers. The mixture (3.2 g) was purified by HPLC (8×15 cm Prochrom column packed with Kromasil CHI-DMP chiral phase with an eluent mixture of 3A alcohol and dimethylethylamine in heptane) to give 0.8 g (24%) of isomer 1 and 0.9 g (26%) of isomer 2 as white solids:

Example 23

Isomer 1

$^1$H-NMR (d, DMSO) 0.75 (d, J=6.4 Hz, 1.5H), 0.88 (d, J=6.4 Hz, 1.5H), 1.10 (m, 1H), 1.35 (m, 1H), 1.45–1.70 (m,

8H), 2.60–2.75 (m, 2H), 3.15 (m, 1H), 3.65–3.85 (m, 3H), 4.35 (m, 1H), 4.52 (s, 2H), 4.75 (m, 1H), 6.95 (d, J=11.3 Hz, 1H), 7.20–7.49 (m, 9H), 7.45 (m, 1H), 7.52 (m, 1H), 8.05 (br s, 1H), 8.25 (m, 3H), 8.56 (m, 1H), 10.95 (br s, 1H); $t_R$=6.73 min; MS (ion spray) 579.4 (M+1); Anal. Calc'd for $C_{31}H_{39}FN_6O_4 \cdot 2HCl \cdot 0.2CHCl_3$: C, 56.29; H, 6.24; N, 12.67. Found: C, 56.47; H, 6.17; N, 12.24.

Example 24

Isomer 2

$^1$H-NMR (d, DMSO) 0.75 (d, J=6.4 Hz, 1.5H), 0.88 (d, J=6.4 Hz, 1.5H), 1.10 (m, 1H), 1.35 (m, 1H), 1.45–1.70 (m, 8H), 2.60–2.75 (m, 2H), 3.15 (m, 1H), 3.65–3.85 (m, 3H), 4.35 (m, 1H), 4.52 (s, 2H), 4.75 (m, 1H), 6.95 (d, J=11.3 Hz, 1H), 7.20–7.49 (m, 9H), 7.45 (m, 1H), 7.52 (m, 1H), 8.05 (br s, 1H), 8.25 (m, 3H), 8.56 (m, 1H), 10.95 (br s, 1H); $t_R$=9.09 min; MS (ion spray) 579.4 (M+1); Anal. Calc'd for $C_{31}H_{39}FN_6O_4 \cdot 2HCl$: C, 57.14; H, 6.34; N, 12.90. Found: C, 57.17; H, 6.18; N, 12.79.

Preparation 53

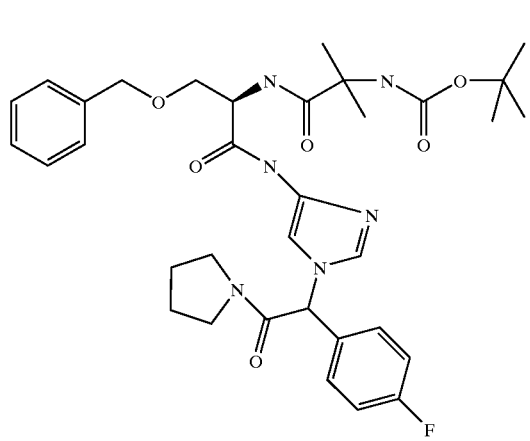

Reaction of the product of Preparation 51 (0.6 g, 1.0 mmol), pyrrolidine (0.08 mL, 1.0 mmol), 1-hydroxybenzotriazole (0.15 g, 1.1 mmol) and 1-(3-dimethylaminopropyl)-3-ethylcarbodiimide (0.23 g, 1.1 mmol) in dimethylformamide (20 mL) as described in Preparation 6 gave 0.27 g (41%) of the desired product as a white foam: $^1$H-NMR is consistent with structure; MS (FD) 650.5 (M+); Anal. Calc'd for $C_{34}H_{43}FN_6O_6 \cdot 0.6H_2O$: C, 61.73; H, 6.73; N, 12.70. Found: C, 61.98; H, 6.43; N, 12.66.

Example 25

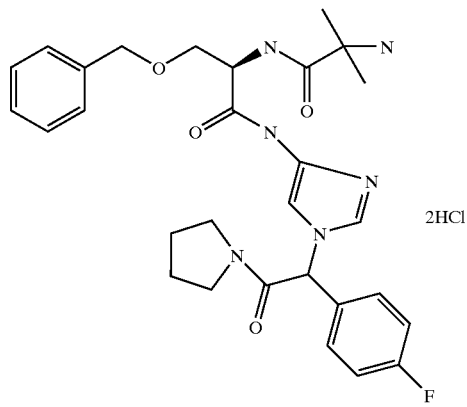

Reaction of the product of Preparation 53 (0.2 g, 0.3 mmol) and trifluoroacetic acid (4 mL) in dichloromethane (6 mL) as described in Example 1 gave 0.16 g (84%) of the desired mixture of isomers as a yellow solid: $^1$H-NMR is consistent with structure. MS (high res) calc'd for $C_{29}H_{36}FN_6O_4$: 551.2782. Found: 551.2790.

Preparation 54

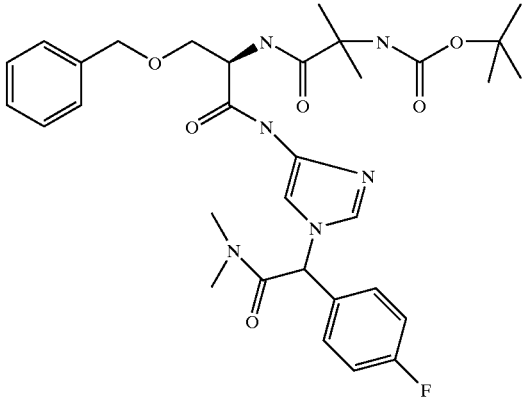

Reaction of the product of Preparation 51 (1.0 g, 1.7 mmol), dimethylamine hydrochloride (0.14 g, 1.7 mmol), triethylamine (0.26 mL, 1.9 mmol), 1-hydroxybenzotriazole (0.26 g, 1.9 mmol) and 1-(3-dimethylaminopropyl)-3-ethylcarbodiimide (0.4 g, 1.9 mmol) in dimethylformamide (30 mL) as described in Preparation 6 gave 0.55 g (52%) of the desired product as a tan foam: $^1$H-NMR is consistent with structure; MS (ion spray) 625.4 (M+1); Anal. Calc'd for $C_{32}H_{41}FN_6O_6$: C, 61.53; H, 6.61; N, 13.45. Found: C, 61.22; H, 6.33; N, 13.44.

Example 26

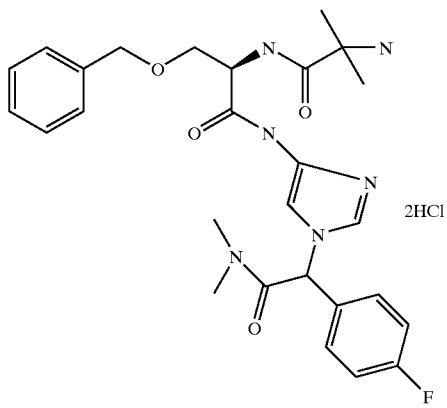

Reaction of the product of Preparation 54 (0.54 g, 0.86 mmol) and trifluoroacetic acid (2 mL), dichloromethane (6 mL) as described in Example 1 gave 0.4 g (77%) of the desired product as a mixture of isomers: $^1$H-NMR is consistent with structure. MS (ion spray) 525.4 (M+1); Anal. Calc'd for $C_{27}H_{33}FN_6O_6 \cdot 2HCl$: C, 54.27; H, 5.90; N, 14.06. Found: C, 53.11; H, 5.70; N, 13.58.

Example 27

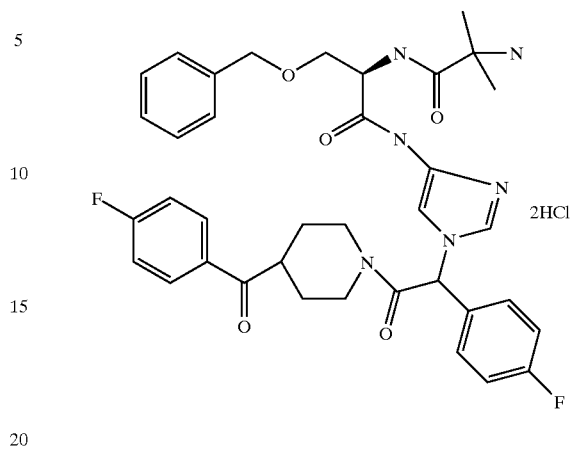

Reaction of the product of Preparation 55 (0.4 g, 0.5 mmol) with trifluoroacetic acid (2 mL) in dichloromethane (6 mL) as described in Example 1 gave 0.32 g (82%) of the desired product as a yellow foam: $^1$H-NMR is consistent with structure. MS (high res) calc'd for $C_{37}H_{41}F_2N_6O_5$: 687.3106. Found: 687.3103. Anal. Calc'd for $C_{37}H_{40}F_2N_6O_5 \cdot 2.4HCl$: C, 57.40; H, 5.52; N, 10.85. Found: C, 57.56; H, 5.53; N, 10.50.

Preparation 55

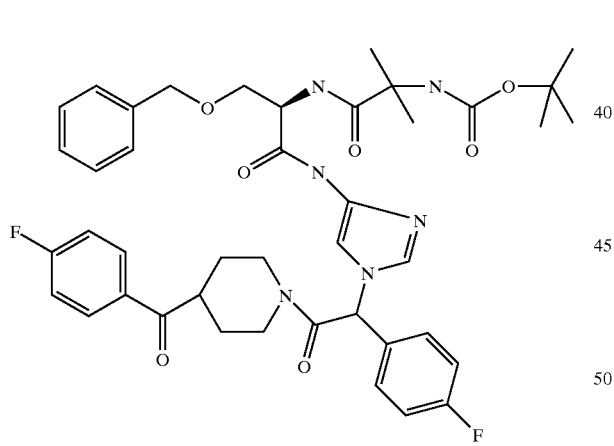

Reaction of the product of Preparation 51 (0.6 g, 1.0 mmol), 4-(4-fluorobenzoyl)piperidine hydrochloride (0.25 g, 1.0 mmol), triethylamine (0.16 mL, 1.1 mmol), 1-hydroxybenzotriazole (0.15 g, 1.1 mmol) and 1-(3-dimethylaminopropyl)-3-ethylcarbodiimide (0.23 g, 1.1 mmol) in dimethylformamide (40 mL) as described Preparation 6 gave 0.42 g (53%) of the desired product as a tan foam: $^1$H-NMR is consistent with structure; MS (ion spray) 787.4 (M+); Anal. Calc'd for $C_{42}H_{48}F_2N_6O_7$: C, 63.83; H, 6.17; N, 10.63. Found: C, 63.95; H, 5.90; N, 10.44.

Preparation 56

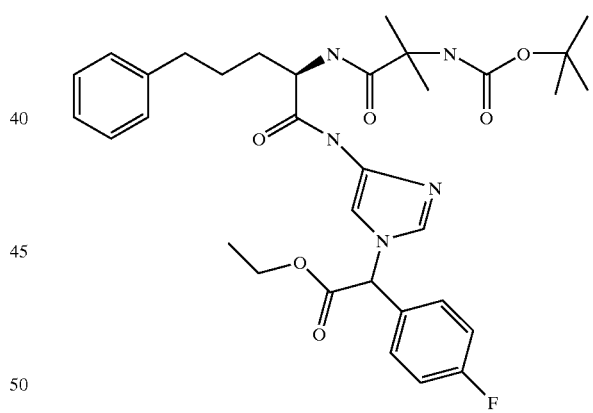

Reduction of the product of Preparation 4 (4.8 g, 16.0 mmol) with 10% palladium on carbon (5.0 g) and tetrahydrofuran (160 mL) followed by coupling with the product of Preparation 1j (6.0 g, 16.0 mmol), 1-hydroxybenzotriazole (2.4 g, 17.6 mmol) and 1-(3-dimethylaminopropyl)-3-ethylcarbodiimide (3.6 g, 17.6 mmol) as described in Preparation 4 gave 15.4 g (77%) of the desired product as a tan foam: $^1$H-NMR (d, DMSO) 1.17 (t, J=7.2 Hz, 3H), 1.23–1.45 (m, 15H), 1.45–1.57 (m, 6H), 7.16 (g, J=6.8 Hz, 2H), 4.40 (m, 1H), 6.45 is, 1H), 7.05 (m, 1H), 7.10–7.30 (m, 8H), 7.40–7.48 (m, 3H), 7.54 (s, 1H), 10.20 (br s, 1H); MS (ion spray) 624.4 (M+1); Anal. Calc'd for $C_{33}H_{42}FN_5O_6$: C, 63.55; H, 6.79; N, 11.23. Found: C, 63.83; H, 6.78; N, 11.38.

Preparation 57

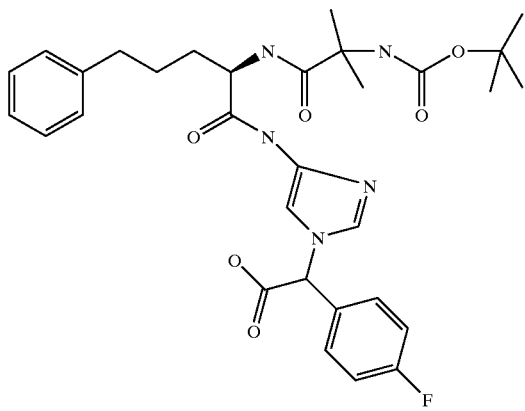

Reaction of the product of Preparation 56 (14.8 g, 24.0 mmol) with lithium hydroxide (0.66 g, 29.0 mmol in dioxane (200 mL) and water (100 mL) as in described in Preparation 5 gave 14.3 g (100%) of the desired product as a tan foam: $^1$H-NMR (d, DMSO) 1.25–1.40 (m, 15H), 1.50–1.75 (m, 6H), 4.40 (s, 1H), 6.60 (s, 1H), 7.05 (s, 1H), 7.10–7.30 (m, 8H), 7.40–7.50 (m, 3H), 7.55 (s, 1H), 10.2 (br s, 1H), 13.63 (br s, 1H); MS (ion spray) 596.5 (M+1); Anal. Calc'd for $C_{31}H_{38}FN_5O_6 \cdot 0.1$dioxane: C, 62.39; H, 6.47; N, 11.59. Found: C, 62.16; H, 6.56; N, 11.28.

Preparation 58

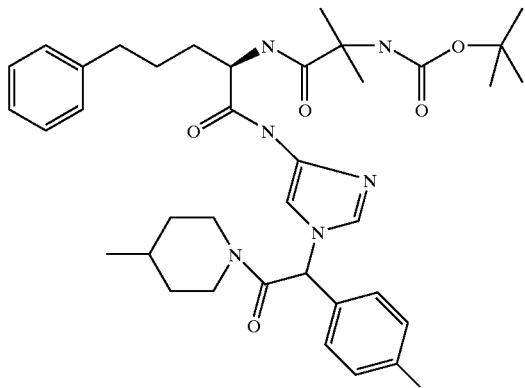

Reaction of the product of Preparation 57 (13.3 g, 23.1 mmol), 4-methylpiperidine (3 mL, 23.1 ml), 1-hydroxybenzotriazole (3.4 g, 25.4 mmol) and 1-(3-dimethylaminopropyl)-3-ethylcarbodiimide (5.2 g, 25.4 mmol) in dimethylformamide (100 mL) as described in Preparation 6 gave 14.4 g (93%) of the desired product as a tan foam: $^1$H-NMR (d, DMSO) 0.76 (d, J=6.4 Hz, 1.5H), 0.86 (d, J=4.9 Hz, 1.5H), 1.00 (m, 1H), 1.25–1.45 (m, 17H), 1.45–1.75 (m, 8H), 2.60–2.80 (m, 2H), 3.75 (m, 1H), 4.30–4.45 (m, 2H), 6.71 (d J=11.7 Hz, 1H), 7.05 (m, 1H), 7.10–7.30 (m, 9H), 7.30–7.45 (m, 3H), 10.15 (m, 1H); MS (ion spray) 677.5 (M+1); Anal. Calc'd for $C_{37}H_{49}FN_6O_5$: C, 65.66; H, 7.30; N, 12.42. Found: C, 65.78; H, 7.19; N, 12.44.

Examples 28 and 29

Reaction of the product of Preparation 58 (13.8 g, 20.4 mmol) with trifluoroacetic acid (16 mL) in dichloromethane (40 mL) as described in Example 1 gave 10.5 g (89%) of the desired mixture as a tan foam. The mixture (4.0 g) was purified by HPLC (8×15 cm Prochrom column packed with Kromasil CHI-DMP chiral phase with an eluent mixture of 3A alcohol and dimethylethylamine in heptane) to give 1.5 g (38%) of isomer 1 and 0.77 g (20%) of isomer 2 as white solids:

Example 28

Isomer 1

$^1$H-NMR (d, DMSO) 0.75 (t, J=6.4 Hz, 1.5H), 0.87 (t, J=6.0 Hz, 1.5H), 1.15 (m, 1H), 1.35 (m, 1H), 1.45–1.80 (m, 12H), 2.55–2.75 (m, 3H), 3.05 (m, 1H), 3.65–3.75 (m, 2H), 4.30–4.50 (m, 2H), 6.94 (d, J=12 Hz, 1H), 7.10–7.20 (m, 2H), 7.20–7.40 (m, 7H), 7.45 (m, 1H), 7.55 (m, 1H), 8.08 (m, 1H), 8.15–8.30 (m, 3H), 8.44 (t, J=7.2 Hz, 1H), 10.90 (br s, 1H); $t_R$=6.62 min; MS (ion spray) 578.3 (M+1); Anal. Calc'd for $C_{32}H_{41}FN_6O_3 \cdot 2.3$HCl: C, 58.81; H, 6.61; N, 12.72. Found: C, 57.91; H, 6.55; N, 12.72.

Example 29

Isomer 2

$^1$H-NMR (d, DMSO) 0.75 (t, J=6.4 Hz, 1.5H), 0.87 (t, J=6.0 Hz, 1.5H), 1.15 (m, 1H), 1.35 (m, 1H), 1.45–1.80 (m, 12H), 2.55–2.75 (m, 3H), 3.05 (m, 1H), 3.65–3.75 (m, 2H), 4.30–4.50 (m, 2H), 6.94 (d, J=12 Hz, 1H), 7.10–7.20 (m, 2H), 7.20–7.40 (m, 7H), 7.45 (m, 1H), 7.55 (m, 1H), 8.08 (m, 1H), 8.15–8.30 (m, 3H), 8.44 (t, J=7.2 Hz, 1H), 10.90 (br s, 1H); $t_R$=8.95 min; MS (ion spray) 578.3 (M+1); Anal. Calc'd for $C_{32}H_{41}FN_6O_3 \cdot 2.3$HCl: C, 58.81; H, 6.61; N, 12.72. Found: C, 58.05; H, 6.64; N, 12.43.

Preparation 59

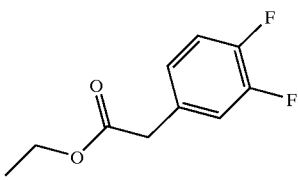

Reaction of 3,4-difluorophenylacetic acid (25.0 g, 145 mmol) with p-toluenesulfonic acid (9.5 g, 49.5 mmol) in absolute ethanol (150 mL) as described in Preparation 1 gave 28.7 g (99%) of the desired product as a colorless oil: $^1$H-NMR is consistent with structure; MS (FD) 201 (M+).

Preparation 60

Reaction of the product of Preparation 59 (10.0 g, 50.0 mmol, N-bromosuccinimide (9.17 g, 51.5 mmol) and 48% HBr (4 drops) in carbon tetrachloride (40 mL) as in Preparation 2 gave 12.0 g (86%) of the desired product as a colorless oil which was used without further purification: 3H-NMR is consistent with structure; MS (ion spray) 278, 280 (M+1).

Preparation 61

Reaction of the product of Preparation 60 (10.5 g, 38 mmol), 4-nitroimidazole (5.2 g, 45.6 mmol) and potassium carbonate (15.1 g, 114 mmol) in dimethylformamide (400 mL) as described in Preparation 3 gave 4.54 g (39%) of the desired product as an orange oil: $^1$H-NMR is consistent with structure; MS (ion spray) 312.0 (M+1); Anal. Calc'd for $C_{13}H_{11}F_2N_3O_4 \cdot 0.2H_2O$: C, 49.59; H, 3.65; N, 13.35. Found: C, 49.58; H, 3.62; N, 13.09.

Preparation 62

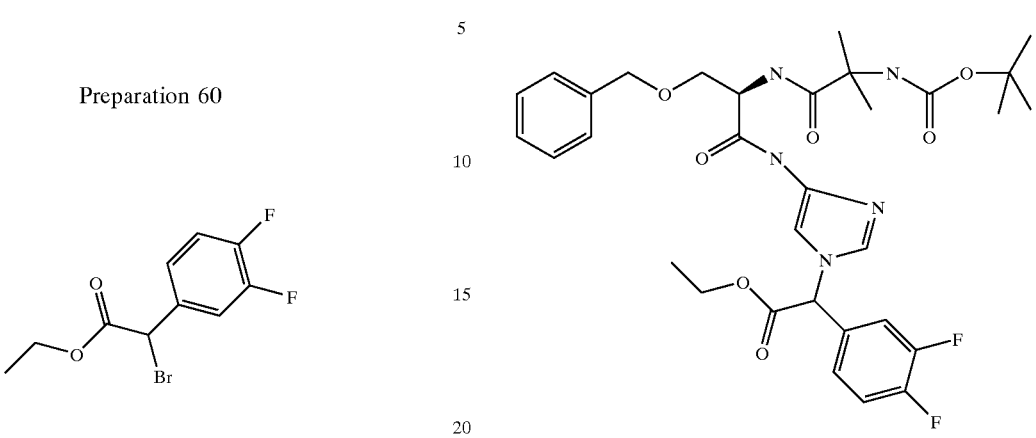

Reduction of the product of Preparation 61 (1.35 g, 4.3 mmol) with 10% palladium on carbon (0.8 g) in tetrahydrofuran (40 mL) followed by coupling with the product of Preparation 1d (1.64 g, 4.3 mmol), 1-hydroxybenzotriazole (0.7 g, 4.7 mmol) and 1-(3-dimethylaminopropyl)-3-ethylcarbodiimide (1.04 g, 4.7 mmol) as described in Preparation 4 gave 1.9 g (69%) of the desired product as a tan foam: $^1$H-NMR is consistent with structure; MS (ion spray) 644 (M+1); Anal. Calc'd for $C_{32}H_{39}F_2N_5O_7$: C, 59.71; H, 6.11; N, 10.80. Found: C, 59.72; H, 6.04; N, 10.63.

Preparation 63

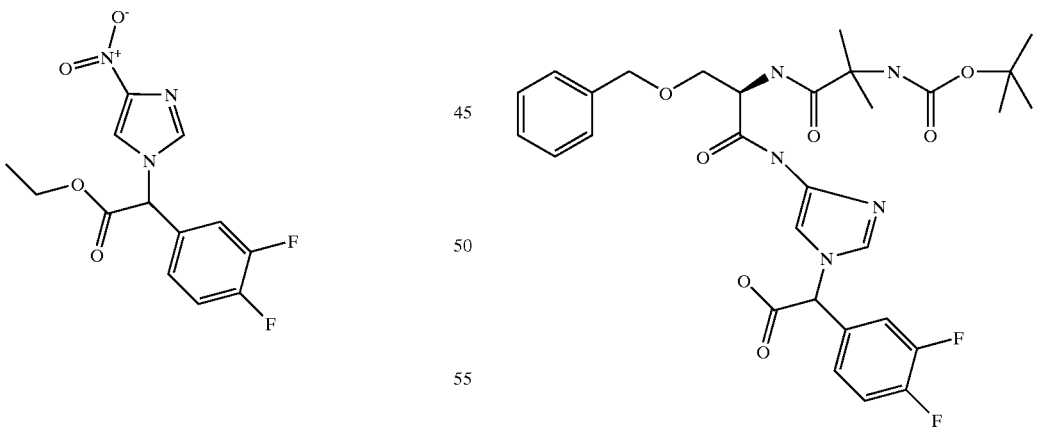

Reaction of the product of preparation 62 (1.9 g, 3.0 mmol) with lithium hydroxide (0.09 g, 3.6 mmol) in dioxane (50 mL) and water (25 mL) as described in Preparation 5 gave 1.6 g (87%) of the desired product as a tan foam: $^1$H-NMR is consistent with structure; MS (ion spray) 616.4 (M+1).

Preparation 64

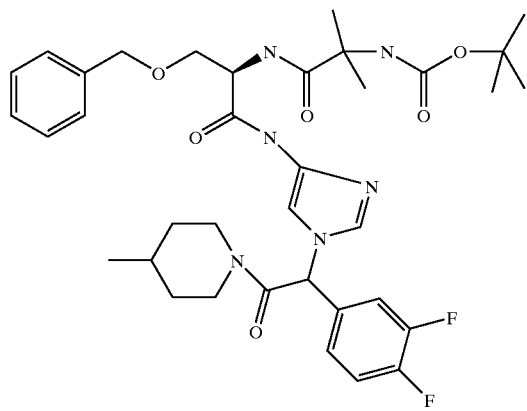

Reaction of the product of Preparation 63 (0.5 g, 0.8 mmol), 4-methylpiperidine (0.1 mL, 0.8 mol), 1-hydroxybenzotriazole (0.12 g, 0.88 mmol) and 1-(3-dimethylaminopropyl)-3-ethylcarbodiimide (0.18 g, 0.88 mmol) in dimethylformamide (40 mL) as described in Preparation 6 gave 0.3 g (54%) of the desired product as a white foam: $^1$H-NMR is consistent with structure; MS (ion spray) 697 (M+1); Anal. Calc'd for $C_{36}H_{46}F_2N_6O_6$; C, 62.06; H, 6.65; N, 12.06. Found: C, 61.82; H, 6.57; N, 11.96.

Preparation 65

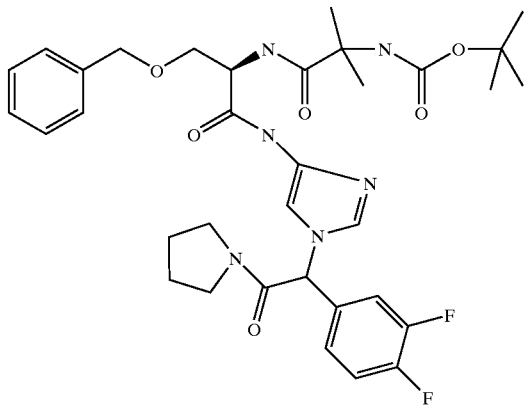

Reaction of the product of Preparation 63 (0.5 g, 0.8 mmol), pyrrolidine (0.07 mL, 0.8 mmol), 1-hydroxybenzotriazole (0.12 mL, 0.88 mmol) and 1-(3-dimethylaminopropyl)-3-ethylcarbodiimide (0.18 g, 0.88 mmol) in dimethylformamide (40 mL) as described in Preparation 6 gave 0.25 g (42%) of the desired product as a tan foam: $^1$H-NMR is consistent with structure. MS (ion spray) 669.4 (M+1); Anal. Calc'd for $C_{34}H_{42}F_2N_6O_5 \cdot 0.7H_2O$: C, 59.94; H, 6.42; N, 12.33. Found: C, 59.96; H, 6.28; N, 11.97.

Example 30

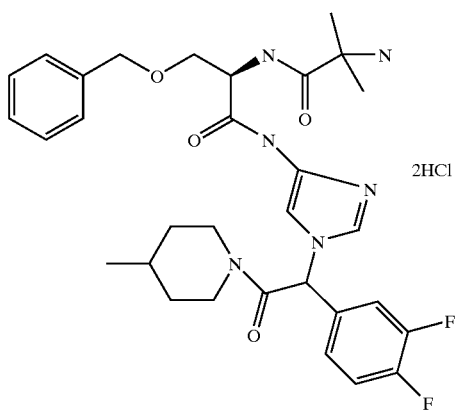

Reaction of the product of Preparation 64 (0.22 g, 0.3 mmol) and trifluoroacetic acid (2 mL) in dichloromethane (6 mL) as described in Example 1 gave 0.2 g (100%) of the desired mixture of isomers as a yellow foam: $^1$H-NMR in consistent with structure; MS (ion spray) 597.5 (M+1); Anal. Calc'd for $C_{31}H_{38}F_2N_6O_4 \cdot 2.2HCl$; C, 55.01; H, 5.99; N, 12.42. Found: C, 55.16; H, 5.96; N, 12.20.

Example 31

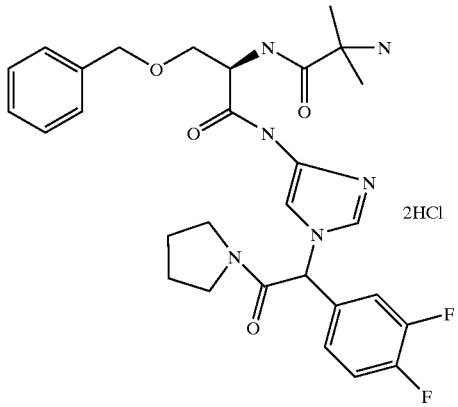

Reaction of the product of Preparation 65 (0.2 g, 0.3 mmol) and trifluoroacetic acid (2 mL) in dichloromethane (6 mL) as described in Example 1 gave 0.14 g (74%) of the desired product as a yellow foam: $^1$H-NMR is consistent with structure; MS (ion spray) 569.4 (M+1); Anal. Calc'd for $C_{29}H_{34}F_2N_6O_4 \cdot 2.2HCl$: C, 53.68; H, 5.62; N, 12.95. Found: C, 53.83; H, 5.57; N, 12.37.

Preparation 66

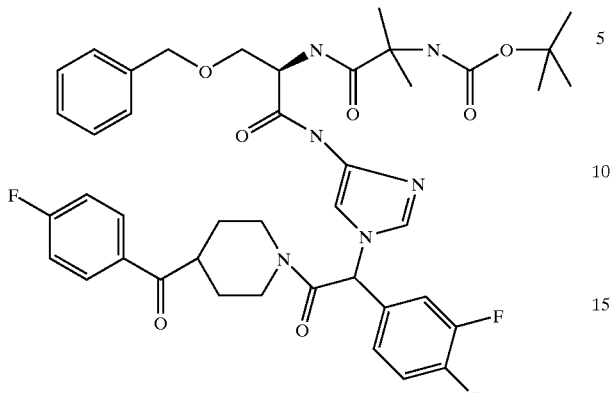

Reaction of the product of preparation 63 (0.5 g, 0.8 mmol), 4-(4-fluorobenzoyl)piperidine hydrochloride (0.2 g, 0.8 mmol), triethylamine (0.13 mL, 0.88 mmol), 1-hydroxybenzotriazole (0.12 g, 0.88 mmol) and 1-(3-dimethylaminopropyl)-3-ethylcarbodiimide (0.18 g, 0.88 mmol) in dimethylformamide (40 mL) as described in Preparation 5 gave 0.14 g (22%) of the desired product as a white foam: $^1$H-NMR is consistent with structure; MS (ion spray) 805.6 (M+1); Anal. Calc'd for $C_{42}H_{47}F_3N_6O_7$: C, 62.68; H, 5.89; N, 10.44. Found: C, 62.45; H, 5.82; N, 10.40.

Example 32

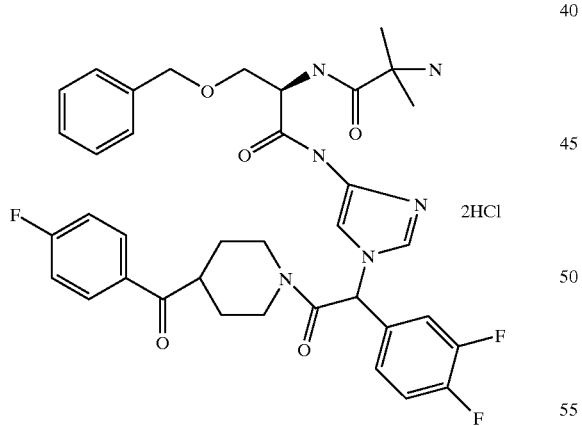

Reaction of the product of Preparation 66 (0.14 g, 0.17 mmol) and trifluoroacetic acid (2 mL) in dichloromethane (6 mL) as described in Example 1 gave 0.1 g (77%) of the desired mixture of isomers as a yellow solid: $^1$H-NMR is consistent with structure; MS (ion spray) 705.5 (M+1); Anal. Calc'd for $C_{37}H_{39}F_3N_6O_5 \cdot 2.1HCl$: C, 56.88; H, 5.30; N, 10.76. Found: C, 56.64; H, 5.31; N, 10.30.

Preparation 67

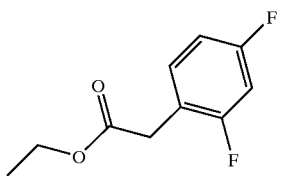

Reaction of 2,4-difluorophenylacetic acid (20 g, 116 mmol) and p-toluenesulfonic acid (6.0 g, 31 mmol) in absolute ethanol (150 mL) as described in Preparation 1 gave 22.1 g (95%) of the desired product as a colorless oil which solidifies upon setting: $^1$H-NMR is consistent with structure; MS (FD) 200 (M+).

Preparation 68

Reaction of the product of Preparation 67 (21.4 g, 100 mmol), N-bromosuccinimide (19.6 g, 103 mmol) and 48% HBr (6 drops) in carbon tetrachloride (100 mL) as described in Preparation 2 gave 27.9 g (100%) of the desired product as a colorless oil: $^1$H-NMR is consistent with structure; MS (FD) 278, 280 (M+); Anal. Calc'd for $C_{10}H_9BrF_2O_2$: C, 43.04; H, 3.25. Found: C, 42.92; H, 3.15.

Preparation 69

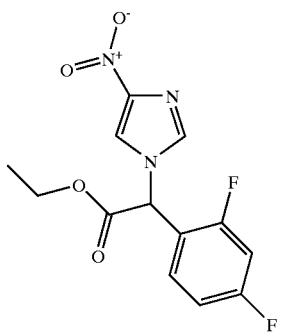

Reaction of the product of Preparation 68 (26.9 g, 96 mmol), 4-nitroimidazole (13.0 g, 115 mmol) and potassium carbonate (40 g, 288 mmol) in dimethylformamide (150 mL) as described in Preparation 3 gave 14.3 g (48%) of the desired product as an orange oil: $^1$H-NMR is consistent with structure; MS (ion spray) 312 (M+1); Anal. Calc'd for $C_{13}H_{11}F_2N_3O_4$: C, 50.17; H, 3.56; N, 13.50. Found: C, 49.90; H, 3.56; N, 13.26.

Preparation 70

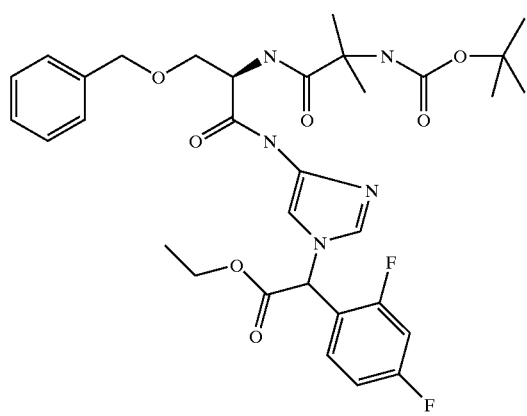

Reduction of the product of preparation 69 (1.35 g, 4.3 mmol) with 10% palladium on carbon (0.8 g) in tetrahydrofuran (40 mL) followed by coupling with the product of Preparation 1d (1.64 g, 4.3 mmol), 1-hydroxybenzotriazole (0.7 g, 4.7 mmol) and 1-(3-dimethylaminopropyl)-3-ethylcarbodiimide (1.04 g, 4.7 mmol) as described in Preparation 4 gave 1.52 g (55%) of the desired product as a tan foam: $^1$H-NMR is consistent with structure; MS (ion spray) 644.5 (M+1); Anal. Calc'd for $C_{32}H_{39}F_2N_5O_7$: C, 59.71; H, 6.11; N, 10.88. Found: C, 59.43; H, 5.97; N, 10.91.

Preparation 71

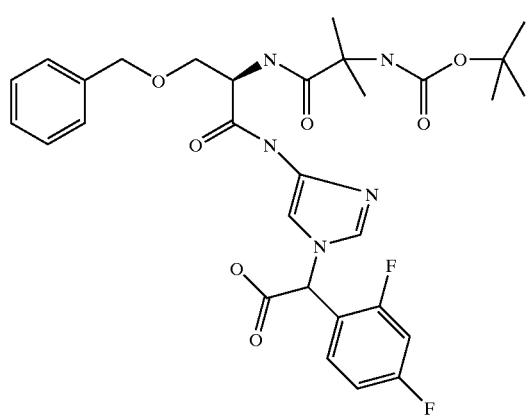

Reaction of the product of preparation 70 (1.42 g, 2.2 mmol) with lithium hydroxide (0.07 g, 2.64 mmol) in dioxane (50 mL) and water (25 mL) as described in Preparation 5 gave 1.35 g (100%) of the desired product as a tan foam: $^1$H-NMR is consistent with structure; MS (ion spray) 616.3 (M+1); Anal. Calc'd for $C_{30}H_{35}F_2N_5O_7$: C, 58.33; H, 5.73; N, 11.38. Found: C, 57.71; H, 5.86; N, 10.80.

Preparation 72

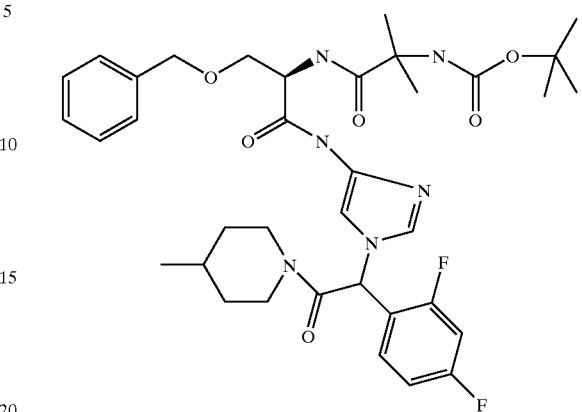

Reaction of the product of Preparation 71 (0.6 g, 1.0 mmol), 4-methylpiperidine (0.12 mL, 1.0 mmol), 1-hydroxybenzotriazole (0.15 g, 1.1 mmol) and 1-(3-dimethylaminopropyl)-3-ethylcarbodiimide (0.23 g, 1.1 mmol) in dimethylformamide (30 mL) as described in Preparation 6 gave 0.66 g (94%) of the desired product as a tan foam: $^1$H-NMR is consistent with structure; MS (FD) 696 (M+); Anal. Calc'd for $C_{36}H_{46}F_2N_6O_6$: C, 62.05; H, 6.65; N, 12.06. Found: C, 62.21; H, 6.48; N, 12.17.

Example 33

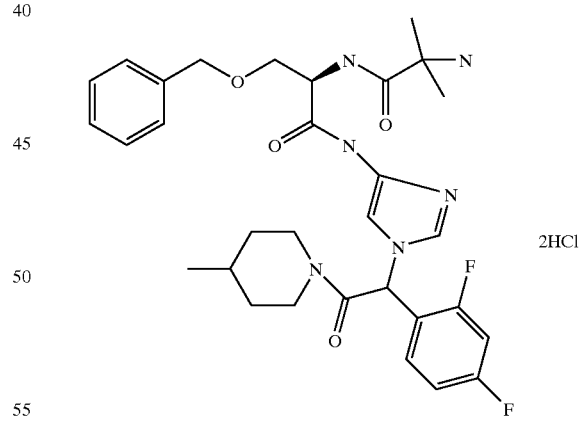

Reaction of the product of Preparation 72 (0.51 g, 0.73 mmol) and trifluoroacetic acid (2 mL) in dichloromethane (6 mL) as in described in Example 1 gave 0.25 g (51%) of the desired product as tan foam: $^1$H-NMR is consistent with structure; MS (ion spray) 597.5 (M+1); Anal. Calc'd for $C_{31}H_{38}F_2N_6O_4 \cdot 2.2HCl$: C, 55.01; H, 5.99; H, 12.42. Found: C, 56.92; H, 5.98; N, 12.36.

Preparation 73

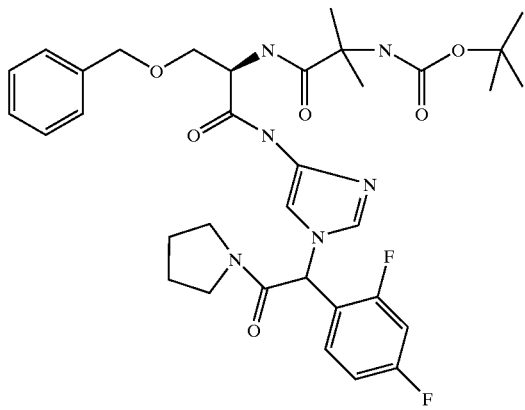

Reaction of the product of Preparation 71 (0.6 g, 1.0 mmol), pyrrolidine (0.8 mL, 1.0 mmol), 1-hydroxybenzotriazole (0.15 g, 1.1 mmol) and 1-(3-dimethylaminopropyl)-3-ethylcarbodiimide (0.23 g, 1.1 mmol); dimethylformamide (30 mL) as described in Preparation 6 gave 0.4 g (58%) of the desired product as a white foam: $^1$H-NMR is consistent with structure; MS (ion spray) 669.5 (M+1); Anal. Calc'd for $C_{32}H_{42}F_2N_6O_6$: C, 61.07; H, 6.33; N, 12.57. Found: C, 60.84; H, 6.31; N, 12.32.

Example 34

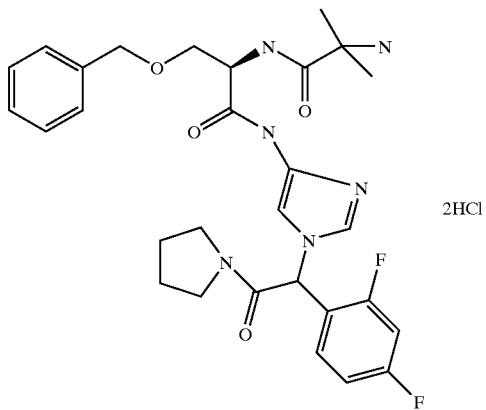

Reaction of the product of Preparation 73 (0.3 g, 0.45 mmol) and trifluoroacetic acid (2 mL) in dichloromethane (6 mL) as described in Example 1 gave 0.21 g (70%) of the desired product as a white foam: $^1$H-NMR is consistent with structure: MS (ion spray) 569.4 (M+1); Anal. Calc'd for $C_{29}H_{34}F_2N_6O_4 \cdot 2.3HCl$: C, 53.38; H, 5.61; N, 12.88. Found: C, 53.59; H, 5.58; N, 12.42.

Preparation 74

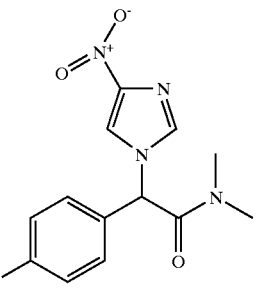

To a solution of the compound of Preparation 49 (17.0 g. 58.0 mmol) stirring at room temperature was added to sodium hydroxide (125 mL of a 2N aqueous solution) along with tetrahydrofuran (10 mL) and ethanol (10 mL). After hydrolysis was complete, the mixture was cooled in an bath and acidified to pH 2.75 with aqueous hydrochloric acid and extracted with ethyl acetate. The combined organic extracts were washed with water, dried over sodium sulfate and concentrated to provide 15.0 g (99%) of the desired carboxylic acid. The crude material was combined with aqueous N,N-dimethyl amine (40%, 9.0 mL, 71.8 mmol), 1-hydroxybenzotriazole hydrate (7.64 g, 56.6 mmol) and 1,3-dicyclohexylcarbodiimide (11.7 g, 56.6 mmol) in tetrahydrofuran (150 mL). After 18 h, the mixture was concentrated and the residue slurried in ethyl acetate, filtered, and the filtrate concentrated. Purification of the concentrate by flash chromatography (silica gel, chloroform/methanol) provided 10.2 g (62%) of the desired product: ESMS: $(M+H)^+$ 293.1. $^1$H NMR (300 MHz, (DMSO-$d_6$) δ 8.21 (d, 1H, J=1.51 Hz) 7.80 (d, 1H, J=1.13 Hz), 7.60–7.50 (m, 2H), 7.38–7.25 (m, 2H), 6.88 (s, 1H), 2.92 (s, 3H), 2.86 (s, 3H). Anal. Calcd. for $C_{13}H_{13}N_4O_3$: C, 53.43; H, 4.48; N, 19.17. Found: C, 53.43; H, 4.71; N, 19.07.

Preparation 75

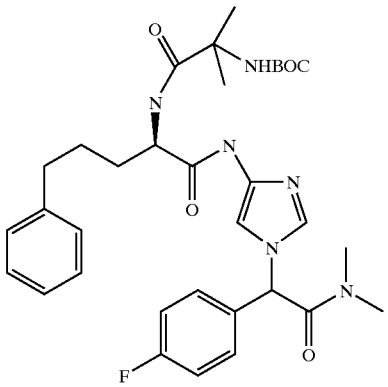

The product of Preparation 74 (2.0 g (6.85 mmol) was combined with 10% palladium/carbon (1.80 g) and palladium/black (0.20 g) in tetrahydrofuran (75 mL) and the mixture shaken under a hydrogen atmosphere (38 psi) in a Parr apparatus. After reduction was complete, the catalyst was removed by filtration through celite and the resulting solution was immediately added to a solution of 1,3-dicyclohexylcarbodiimide (1.51 g, 7.3 mmol), 1-hydroxybenzotriazole (1.0 g, 7.3 mmol), the product of Preparation 1j (2.77 g, 7.3 mmol) in tetrahydrofuran (50 mL) at room temperature. After 16 h, the mixture was concentrated and the residue slurried in ethyl acetate them filtered. The filtrate was concentrated and resulting crude product purified by flash chromatography (silica gel chloroform/methanol) which afforded 3.47 g (81%) of the desired product: ESMS: (M+H)+ 623.5, 624.6. $^1$H NMR was consistent with product. Anal. Calcd. for $C_{33}H_{43}N_6O_4F$, 0.02 CHCl3: C, 63.44; H, 6.94; N, 13.44. Found: C, 63.04; H; 7.41; N, 11.93.

Example 35

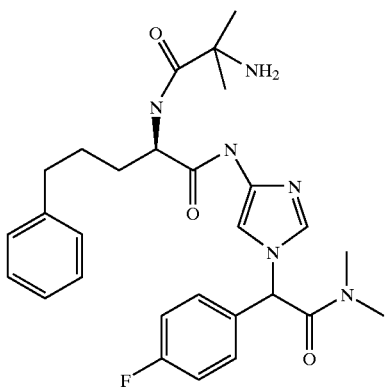

To a solution of the product of Preparation 75 (1.45 g, 2.29 mmol) stirring at room temperature in dichlormethane (50 mL) was added trifluoroacetic acid (15 mL). After 3 hours, the mixture was concentrated and the material treated with excess aqueous sodium bicarbonate. The aqueous mixture was extracted with ethyl acetate and the combined organic extracts concentrate. The resulting residue purified by flash chromatography (silica gel, chloroform/methanol) to provide 1.55 g of the desired product: ESMS: (M+H)+ 523.3. The isomeric mixture (3.44 g) was separated as previously described in Example 7 to provide 0.98 g of pure isomer 1 ($t_R$=7.94 min) and 0.81 g of isomer 2 ($t_R$=10.57 min). For isomer 2, 0.80 g (1.53 mmol) was dissolved in ethyl acetate/methanol and treated with a saturated solution of hydrochloric acid in diethyl ether. The resulting mixture was concentrated to provide 0.90 g (92%) of the desired product as a light tan solid: ESMS: (M+H)+ 523.4, 524.5. $^1$H NMR was consistent with product. Anal. Calcd. for $C_{28}H_{35}N_6O_3F$.3.25HCl: C, 52.46; H, 6.01; N, 13.11. Found: C, 52.49; H, 6.23; N, 11.80.

Preparation 75

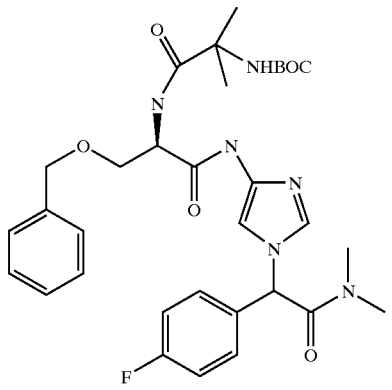

The product of Preparation 74 (2.00 g, 6.85 mmol) was combined with 10% palladium/carbon (1.80 g) and palladium/black (0.20 g) in tetrahydrofuran 75 mL) and the mixture shaken under hydrogen atmosphere (39 psi) in a Parr apparatus. After reduction was complete, the catalyst was removed by filtration through celite and the amine/tetrahydrofuran solution was immediately combined with 1,3-dicyclohexylcarbodiimide (1.41 g, 6.85 mmol), 1-hydroxybenzotriazole mono-hydrate (0.93 g, 6.85 mmol) the product of Preparation 1j (2.60 g, 6.84 mmol) and additional tetrahydrofuran (75 mL). After stirring overnight at the ambient temperature, the mixture was concentrated and the residue slurried in ethyl acetate. The filtrate was concentrated and the residue purified by flash chromatography (silica gel, chloroform/methanol) to provide 3.65 g (85%) of the desired product as a tan solid: ESMS: (M+H)+ 625.4. $^1$H NMR was consistent with product. Anal. Calcd for $C_{32}H_{41}N_6O_6$.0.03 chloroform: C, 61.17; H, 6.60; N, 13.34. Found: C, 61.25; H, 6.90; N, 12.69.

Example 36

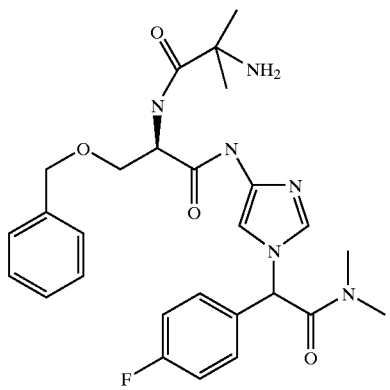

To a solution of the product of Preparation 75 (3.30 g), 5.3 mmol) stirring in dichloromethane (30 mL) at room temperature was added trifluoroacetic acid (10 m). After 3 h, the mixture was concentrated and the residue treated with excess aqueous sodium bicarbonate. The resulting mixture was extracted with ethyl acetate and the combined organic extracts were washed with 1N aqueous sodium hydroxide, dried over sodium sulfate, and concentrated. The residue was purified by flash chromatography (silica gel, chloroform/methanol) to provide 1.40 g (51%) of the desired product as a light tan solid: ESMS: (M+H)+, 525.3. ¹H NMR was consistent with product. Anal. Calcd. for $C_{27}H_{33}N_6O_4F \cdot 1.3$ methanol: C, 60.03; H, 6.80; N, 14.84. Found: C, 60.19; H, 6.81; N, 14.56. The isomeric mixture (3.20 g) was separated as previously described in Example 7 to give 1.57 g of isomer 1 ($t_R$=7.57 min) and 0.88 g of isomer 2 ($t_R$=10.43 min). For isomer 2, 0.88 g (1.68 mmol) was dissolved in ethyl acetate and treated with a saturated solution of hydrochloric acid in diethyl ether. The resulting mixture was concentrated, washed with diethyl ether to give 0.97 g of the desired product: ESMS: (M+H)+ 525.4, 526.7. ¹H NMR was consistent with product. Anal. Calcd. for $C_{25}H_{33}N_6O_4F \cdot 2.75HCl$: C, 51.73; H, 6.07; N, 13.41. Found: C, 51.62; H, 5.74; N, 13.34.

Preparation 76

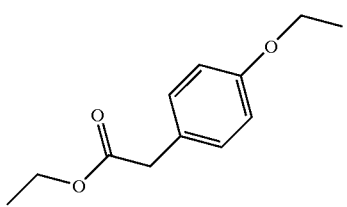

Reaction of 4-ethoxyphenylacetic acid (23.5 g, 130 mmol) and p-toluenesulfonic acid (4.0 g, 21 mmol) in absolute ethanol (150 mL) as described in Preparation 1 gave 23.2 g (86%) of the desired product as a colorless oil: ¹H-NMR (d, DMSO) 1.17 (t, J=7.2 Hz, 3H), 1.31 (t, J=7.2 Hz, 3H), 3.56 (s, 2H), 3.99 (q, J=7.2 Hz, 2H), 4.05 (q, J=7.2 Hz, 2H), 6.85 (d, J=8.7 Hz, 2H), 7.14 (d. J=8.7 Hz, 2H); MS (ion spray) 209 (M+1); Anal. Calc'd for $C_{12}H_{16}O_3$: C, 69.21; H, 7.74. Found: C, 68.91; H, 7.55.

Preparation 77

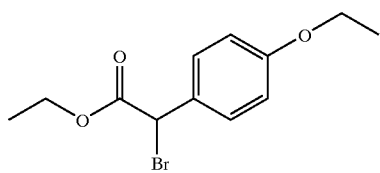

To a solution of the product of Preparation 76 (53 g, 255 mmol) stirring in carbon tetrachloride (600 mL) at room temperature was added 46.6 g (262 mmol) of N-bromosuccinimide and 3.0 g (18.3 mmol) of 2,2'-azobis(2-methylpropionitrile). The resulting reaction mixture was heated to reflux. After 3.5 h, the solution was cooled to room temperature, filtered and concentrated. The resulting oil was chromatographed on silica gel using chloroform as eluent to afford 70.9 g (97%) of the desired product as a colorless oil: ¹H-NMR (d, DMSO) 1.17 (t, J=7.2 Hz, 3H), 1.25–1.35 (m, 3H), 4.00–4.10 (m, 2H), 4.13–4.25 (m, 2H), 5.86 (s, 1H), 6.92 (d, J=8.7 Hz, 2H), 7.47 (d, J=9.0 Hz, 2H); MS (FD) 287, 289 (M+).

Preparation 78

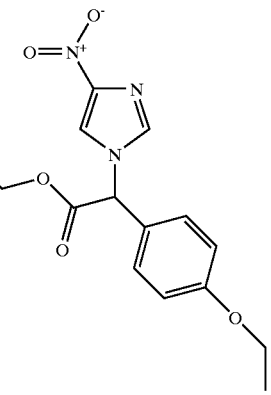

Reaction of the product of Preparation 77 (11.4 g, 40 mmol), 4-nitroimidazole (4.5 g, 40 mmol) and potassium carbonate (16.6 g, 120 mmol) in dimethylformamide (100 mL) as described in Preparation 3 gave 5.47 g (43%) of the desired product as a yellow oil: ¹H-NMR (d, DMSO) 1.18 (t, J=7.2 Hz, 3H), 1.29 (t, J=7.2 Hz, 3H), 4.03 (q, J=7.2 Hz, 2H), 4.23 (q, J=7.2 Hz, 2H), 6.54 (s, 1H), 6.70 (d, J=8.7 Hz, 2H), 7.42 (d, J=8.7 Hz, 2H), 7.90 (s, 1H), 8.34 (s, 1H); MS (ion spray) 320.2 (M+1); Anal. Calc'd for $C_{15}H_{17}N_3O_5$: C, 56.42; H, 5.37; N, 13.16. Found: C, 56.29; H, 5.17; N, 13.15.

Preparation 79

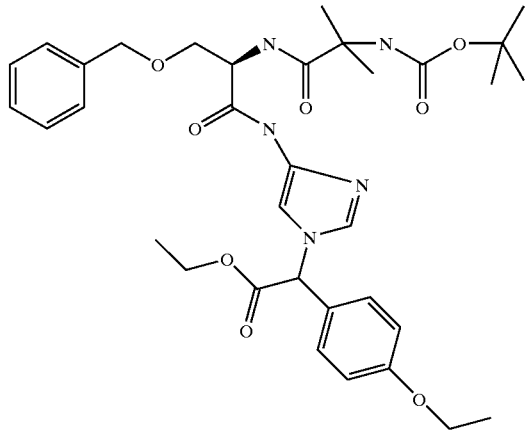

Reduction of the product of Preparation 78 (9.6 g, 30 mmol) with 10% palladium on carbon (7.0 g) in tetrahydrofuran (100 mL) followed by coupling with the product of Preparation 1d (11.5 g, 30 mmol), 1-hydroxybenzotriazole (4.5 g, 33 mmol) and 1-(3-dimethylaminopropyl)-3-ethylcarbodiimide (6.8 g, 33 mmol) as described in Preparation 4 gave 9.9 g (50%) of the desired product as a tan foam: ¹H-NMR (d, DMSO) 1.17 (t, J=7.2 Hz, 3H), 1.25–1.40 (m, 18H), 3.58 (m, 1H), 3.70 (m, 1H), 4.02 (q, J=7.2 Hz, 2H), 4.20 (q, J=7.2 Hz, 2H), 4.44 (d, J=3.4 Hz, 2H), 4.60 (m, 1H), 6.33 (s, 1H), 6.95 (d, J=8.7 Hz, 2H), 7.15–7.35 (m, 9H), 7.43 (m, 1H), 7.51 (m, 1H), 10.2 (br s, 1H); MS (ion spray) 652.4 (M+1); Anal. Calc'd for $C_{34}H_{45}N_5O_8$: C, 62.66; H, 6.96; N, 10.74. Found: C, 62.92; H, 7.00; N, 10.98.

Preparation 80

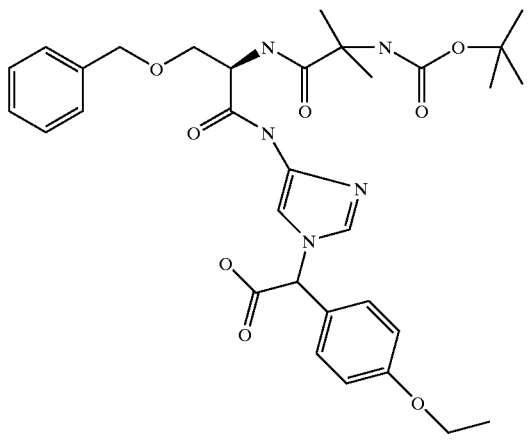

Reaction of the product of Preparation 80 (9.7 g, 15.0 mmol) and lithium hydroxide (0.42 g, 18.0 mmol) in dioxane (200 mL) and water (100 mL) as described in Preparation 5 gave 9.4 g (100%) of the desired product as a tan foam: ¹H-NMR (d, DMSO) 1.25–1.40 (m, 18H), 3.60 (m, 1H), 3.68 (m, 1H), 4.02 (q, J=7.2 Hz, 2H), 4.44 (d. J=3.0 Hz, 2H), 4.60 (m, 1H), 6.19 (m, 1H), 6.95 (d, J=8.7 Hz, 2H), 7.28–7.35 (m, 9H), 7.40 (m, 1H), 7.51 (s, 1H), 10.2 (br s, 1H), 13.5 (br s, 1H); MS (ion spray) 624.5 (M+1); Anal. Calc'd for $C_{43}H_{41}N_5O_8$: C, 61.62; H, 6.63; N, 11.23. Found: C, 61.58; H, 6.92; N, 10.99.

Preparation 81

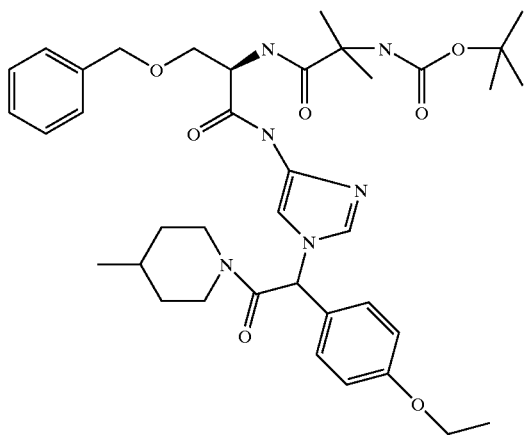

Reaction of the product of Preparation 80 (7.43 g, 12.0 mmol), 4-methylpiperidine (1.42 mL, 12.0 mmol), 1-hydroxybenzotriazole (1.78 g, 13.2 mmol) and 1-(3-dimethylaminopropyl)-3-ethylcarbodiimide (2.72 g, 13.2 mmol) in dimethylformamide (100 mL) as described in Preparation 6 gave 6.4 g (76%) of the desired product as a tan foam: ¹H-NMR (d, DMSO) 0.74 (d, J=6.4 Hz, 1.5 H), 0.87 (d, J=6.0 Hz, 1.5H), 1.05 (m, 1H), 1.25–1.40 (m, 18H), 1.50–1.70 (m, 3H), 2.55–2.70 (m, 2H), 3.00 (m, 1H), 3.57 (m, 1H), 3.65–3.85 (m, 2H), 4.00–4.20 (m, 2H), 4.38 (m, 1H), 4.44 (d, J=3.4 Hz, 2H), 4.60 (m, 1H), 6.61 (d, J=12.0 Hz, 1H), 6.95–7.00 (m, 2H), 7.15–7.20 (m, 2H), 7.20–7.45 (m, 9H), 10.15 (br s, 1H); MS (ion spray) 705.5 (M+1); Anal. Calc'd for $C_{38}H_{52}N_6O_7$: C, 64.75; H, 7.44; N, 11.92. Found: C, 64.59; H, 7.21; N, 11.87.

Examples 37 and 38

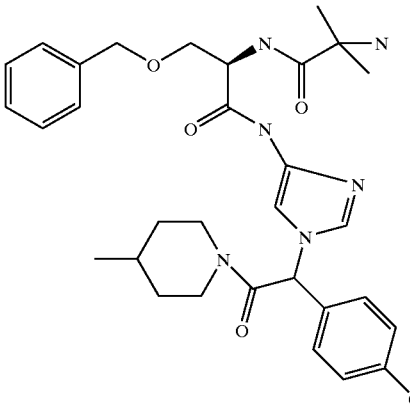

Reaction of the product of Preparation 81 (6.4, 9.1 mmol) and trifluoroacetic acid (10 mL) in dichloromethane (25 mL) as described in Example 1 gave 4.71 g (77%) of the desired mixture of diastereomers as a tan foam. Resolution of the diastereomers (2.4 g) by HPLC (Kromsil CHI-DMP chiral stationary phase, 3A alcohol/dimethylethylamine/heptane) provided 200 mg (8%) of isomer 1 and 0.8 g (31%) of isomer 2, both isolated as white solids after acidification with hydrochloric acid as described in Example 7:

Example 37

Isomer 1

¹H-NMR (d, DMSO) 0.74 (d. J=6.4 Hz, 1.5H), 0.88 (d, J=6.0 Hz, 1.5H), 1.20 (m, 1H), 1.31 (t, J=6.8 Hz, 3H), 1.45–1.70 (m, 8H), 2.60–2.70 (m, 2H), 3.05 (m, 1H), 3.65–3.80 (m, 3H), 4.00–4.20 (m, 3H), 4.37 (m, 1H), 4.52 (s, 2H), 4.75 (m, 1H), 6.80 (d, J=13.2 Hz, 1H), 6.95–7.05 (m, 2H), 7.25–7.40 (m, 9H), 7.92 (br s, 1H), 8.20–8.30 (m, 3H), 8.53 (d, J=7.2 Hz, 1H), 10.9 (br s, 1H); $t_R$=9.17 min; MS (ion spray) 605 (M+1); Anal. Calc'd for $C_{33}H_{44}N_6O_5 \cdot 2HCl \cdot 0.1$ $CHCl_3$: C, 58.45; H, 6.74; N, 12.74. Found: C, 58.64; H, 6.77; N, 12.36.

Example 38

Isomer 2

¹H-NMR (d. DMSO) 0.74 (d. J=6.4 Hz, 1.5H), 0.88 (d, J=6.0 Hz, 1.5H), 1.20 (m, 1H), 1.31 (t, J=6.8 Hz, 3H), 1.45–1.70 (m, 8H), 2.60–2.70 (m, 2H), 3.05 (m, 1H), 3.65–3.80 (m, 3H), 4.00–4.20 (m, 3H). 4.37 (m, 1H), 4.52 (s, 2H), 4.75 (m, 1H), 6.80 (d, J=13.2 Hz, 1H), 6.95–7.05 (m, 2H), 7.25–7.40 (m, 9H), 7.92 (br s, 1H), 8.20–8.30 (m, 3H), 8.53 (d, J=7.2 Hz, 1H), 10.9 (br a, 1H); $t_R$=12.68 min; MS (ion spray) 605 (M+1); Anal. Calc'd for $C_{33}H_{44}N_6O_5 \cdot HCl$: C, 59.35; H, 6.85; N, 12.96. Found: C, 59.62; H, 7.01; N, 12.71.

Preparation 82

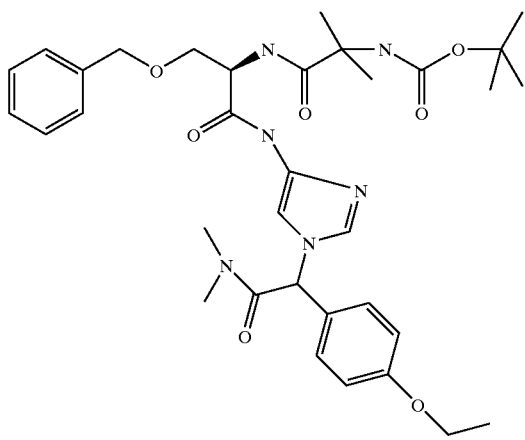

Reaction of the product of Preparation 80 (0.9 g, 1.5 mmol), dimethylamine hydrochloride (0.13 g, 1.5 mmol), triethylamine (0.23 mL, 1.65 mmol), 1-hydroxybenzotriazole (0.23 g, 1.65 mmol) and 1-(3-dimethylaminopropyl)-3-ethylcarbodiimide (0.34 g, 1.65 mmol) in dimethylformamide (50 mL) as described in Preparation 6 gave 0.46 g (47%) of the desired product as a tan foam: $^1$H-NMR (d, DMSO) 1.25–1.35 (m, 18H), 2.90 (m, 6H), 3.57 (m, 1H), 3.67 (m, 1H), 4.03 (q, J=7.2 Hz, 2H), 4.43–4.47 (m, 2H), 4.57 (m, 1H), 6.55 (m, 1H), 6.97 (d, J=8.7 Hz, 2H), 7.15–7.45 (m, 11H), 10.16 (br s, 1H); MS (ion spray) 651.4 (M+1); Anal. Calc'd for $C_{34}H_{46}N_6O_7$: C, 62.75; H, 7.13; N, 12.91. Found: C, 62.55; H, 6.84; N, 12.84.

Examples 39 and 40

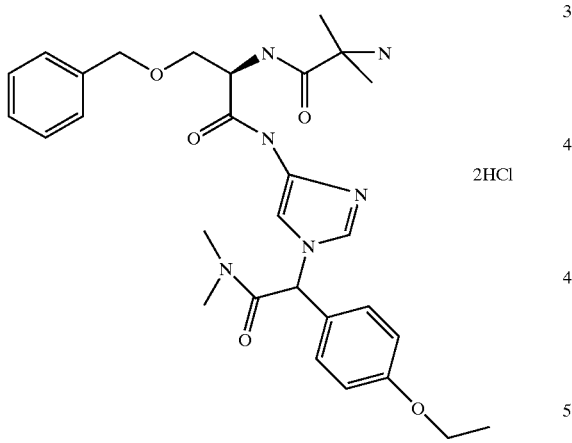

2HCl

Reaction of the product of Preparation 82 (0.44 g, 0.68 mmol) and trifluoroacetic acid (2 mL) in dichloromethane (6 mL) as described in Example 1 gave 0.19 g (45%) of the desired product as a tan foam. Resolution of the diastereomers (90 mg, 0.14 mmol) by HPLC (Kromsil CHI-DMP chiral stationary phase, 3A alcohol/dimethylethylamine/heptane) provided 50 mg (50%) of isomer 1 and 27 mg (27%) of isomer 2, both isolated as white solids after acidification with hydrochloric acid as described in Example 7:

Example 39

Isomer 1

$^1$H-NMR (d, DMSO) 1.32 (t, J=6.8 Hz, 3H), 1.50 (s, 6H), 2.86 (s, 3H), 2.90 (s, 3H), 3.70-3.80 (m, 2H), 4.03 (q, J=7.2 Hz, 2H), 4.52 (s, 2H). 4.75 (m, 1H), 6.76 (s, 1H), 7.00 (d, J=8.7 Hz, 2H), 7.25–7.40 (m, 9H), 8.06 (m, 1H), 8.20–8.30 (m, 3H), 8.52–8.60 (m, 1H), 11.00 (br s, 1H); $t_R$=7.70 mn; MS (high res) calc'd for $C_{29}H_{39}N_6O_5$: 551.2982. Found: 551.2987. Anal. Calc'd for $C_{29}H_{38}N_6O_5 \cdot 2.3HCl \cdot 0.3$ethyl acetate: C, 54.88; H, 6.51; N, 12.72. Found: C, 54.70; H, 6.49; N, 12.43.

Example 40

Isomer 2

$^1$H-NMR (d, DMSO) 1.32 (t, J=6.8 Hz, 3H), 1.50 (s, 6H), 2.86 (s, 3H), 2.90 (s, 3H), 3.70–3.80 (m, 2H), 4.03 (q, J=7.2 Hz, 2H), 4.52 (s, 2H), 4.75 (m, 1H), 6.76 (s, 1H), 7.00 (d, J=8.7 Hz, 2H), 7.25–7.40 (m, 9H), 8.06 (m, 1H), 8.20–8.30 (m, 3H), 8.52–8.60 (m, 1H), 11.00 (br s, 1H); $t_R$=9.09 min; MS (high res) calc'd for $C_{29}H_{39}N_6O_5$: 551.2982. Found: 551.2976. Anal. Calc'd for $C_{29}H_{39}N_6O_5 \cdot 2.HCl \cdot 0.3$ ethyl acetate: C, 55.18; H, 6.53; N, 12.79. Found: C, 55.01; H, 6.33; N, 12.54.

Preparation 83

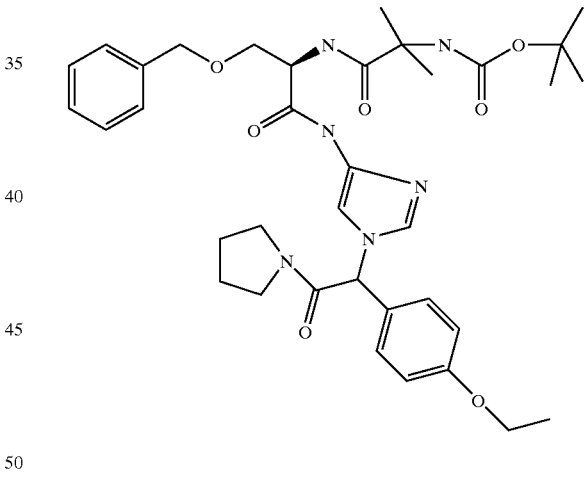

Reaction of the product of Preparation 80 (0.9 g, 1.5 mmol), pyrrolidine (0.13 mL, 1.5 mmol), 1-hydroxybenzotriazole (0.23 g, 1.65 mmol) and 1-(3-dimethylaminopropyl)-3-ethylcarbodiimide (0.34 g, 1.65 mmol) in dimethylformamide (40 mL) as described in Preparation 6 gave 0.7 g (74%) of the desired product as a tan foam: $^1$H-NMR (d, DMSO) 1.25–1.40 (m, 18H), 1.70–1.90 (m, 4H), 2.95 (m, 1H), 3.30–3.40 (m, 2H), 3.55–3.70 (m, 3H), 4.03 (q, J=7.2 Hz, 2H), 4.44 (d, J=3.4 Hz, 2H), 4.57 (m, 1H), 6.34 (s, 1H), 6.97 (d, J=8.7 Hz, 2H), 7.20–7.35 (m, 9H), 7.40–7.45 (m, 2H), 10.15 (br s, 1H); MS (ion spray) 677.6 (M+1); Anal. Calc'd for $C_{36}H_{48}N_6O_7 \cdot 0.2H_2O$: C, 63.55; H, 7.17; N, 12.35. Found: C, 63.32; H, 6.96; N, 12.24.

Example 41

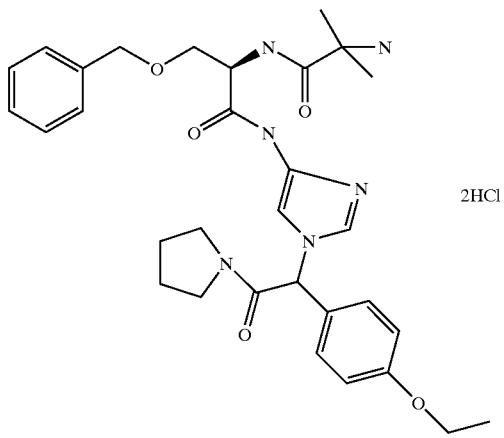

2HCl

Reaction of the product of Preparation 83 (0.59 g, 0.9 mmol) and trifluoroacetic acid (2 mL) in dichloromethane (6 mL) as described in Example 1 gave 0.36 g (64%) of the desired product as a mixture of isomers: $^1$H-NMR (d, DMSO) 1.32 (t, J=6.8 Hz, 3H), 1.45–1.60 (m, 6H), 1.65–1.90 (m, 4H), 2.90 (m, 1H), 3.25–3.45 (m, 2H), 3.65–3.75 (m, 3H), 4.02 (q, J=6.8 Hz, 2H), 4.45–4.55 (m, 2H), 4.70–4.80 (m, 1H), 6.54 (s, 1H), 6.98 (d, J=8.7 Hz, 2H), 7.20–7.40 (m, 9H), 8.05 (m, 1H), 8.20–8.30 (m, 3H), 8.54 (d, J=7.2 Hz, 1H), 10.95 (br s, 1H); MS (high res) calc'd for $C_{31}H_{41}N_6O_5$: 577.3138. Found: 577.3132. Anal. Calc'd for $C_{31}H_{40}N_6O_5 \cdot 2HCl$: C, 57.32; H, 6.52; N, 12.94. Found: C, 57.46; H, 6.59; N, 12.91.

Preparation 84

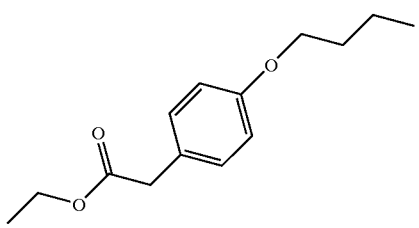

Reaction of 4-butyloxyphenylacetic acid (10.0 g, 48 mmol) and p-toluenesulfonic acid (2.5 g, 13 mmol) in absolute ethanol (100 mL) as described in Preparation 1 gave 11.04 g (98%) of the desired product as a colorless oil: $^1$H-NMR (d, DMSO) 0.94 (t, J=7.4 Hz, 3H), 1.18 (t, J=7.0 Hz, 3H), 1.40–1.50 (m, 2H), 1.60–1.80 (m, 2H), 3.57 (s, 2H), 3.93 (q, J=6.5 Hz, 2H), 4.08 (g, J=7.3 Hz, 2H), 6.86 (d, J=8.4 Hz, 2H), 7.15 (d, J=8.4 Hz, 2H); MS (ion spray) 237 (M+1); Anal. Calc'd for $C_{14}H_{20}O_3$: C, 71.16; H, 8.53. Found: C, 71.33; H, 8.55.

Preparation 85

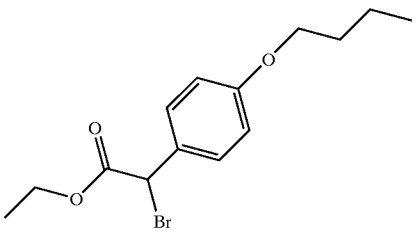

To a solution of the product of Preparation 84, 6.0 g (25 mmol) in 100 mL of carbon tetrachloride was added 4.7 g (25.8 mmol) of N-bromosuccinimide and 0.6 g of 2,2'-azobis(2-methylpropionitrile). The reaction mixture was heated to reflux. After 3.5 h, the mixture was cooled to room temperature, filtered and concentrated. The resulting oil was purified by flash chromatography (silica gel, 3% methanol/chloroform) to proved 6.9 g (88%) of the desired product as a colorless oil: $^1$H-NMR (d, DMSO) 0.93 (t, J=7.35H, 3H), 1.20 (t, J=7.2 Hz, 3H), 1.40–1.50 (m, 2H), 1.60–1.80 (m, 2H), 3.95–4.05 (m, 2H), 4.10–4.15 (m, 2H), 5.87 (s, 1H), 6.93 (d, J=8.7 Hz, 2H), 7.45 (d, J=8.7 Hz, 2H); MS (FD) 314, 316 (M+); Anal. Calc'd for $C_{14}H_{19}BrO_3 \cdot 0.5CHCl_3$: C, 52.54; H, 5.98. Found: C, 52.35; H, 5.84.

Preparation 86

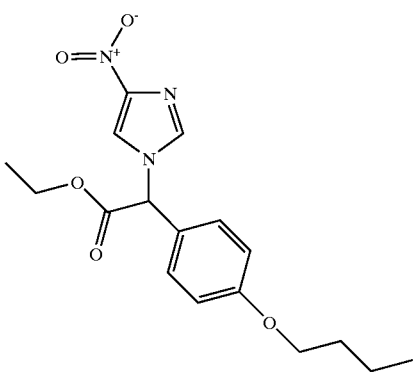

Reaction of the product of Preparation 85 (5.82 g, 19.0 mmol), 4-nitroimidazole (2.1 g, 19.0 mmol) and potassium carbonate (8.0 g, 57 mmol) in dimethylformamide (150 mL) as described in Preparation 3 gave 3.5 g (53%) of the desired product as a yellow oil: $^1$H-NMR (d, DMSO) 0.93 (t, J=7.3 Hz, 3H), 1.19 (t, J=7.0 Hz, 3H), 1.35–1.50 (m, 2H), 1.60–1.80 (m, 2H), 3.92–4.04 (m, 2H), 4.20–4.30 (m, 2H), 6.56 (s, 1H), 6.99 (d. J=8.6 Hz, 2H), 7.44 (d, J=8.6 Hz, 2H), 7.92 (s, 1H), 8.37 (s, 1H); MS (ion spray) 348.3 (M+1); Anal. Calc'd for $C_{27}H_{22}N_3O_5$: C, 58.78; H, 6.09; N, 12.10. Found: C, 59.08; H, 6.21; N, 12.19.

Preparation 87

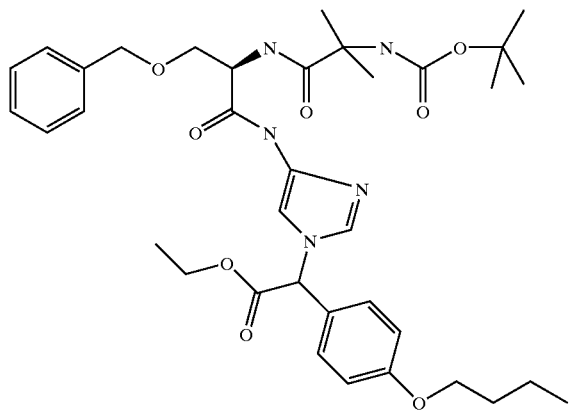

Reduction of the product of Preparation 86 (1.5 g, 4.3 mmol) with 10% palladium on carbon (0.8 g) in tetrahydrofuran (40 mL) followed by coupling with the product of Preparation 1d (1.64 g, 4.3=mmol), 1-hydroxybenzotriazole (0.7 g, 4.7 mmol) and 1-(3-dimethylaminopropyl)-3-ethylcarbodiimide (1.04 g, 4.7 mmol) as described in Preparation 4 gave 1.1 g (38%) of the desired product as a tan foam: $^1$H-NMR d, DMSO) 0.92 (t, J=7.5 Hz, 3H), 1.18 (t, J=7.2 Hz, 3H), 1.25–1.40 (m, 15H), 1.40–1.50 (m, 2H), 1.60–1.75 (m, 2H), 3.60 (m, 1H), 3.70 (m, 1H), 3.95–4.00 (m, 2H), 4.20–4.25 (m, 2H). 4.45–4.48 (m, 2H), 4.57 (m, 1H), 6.35 (s, 1H), 6.97 (t, J=9.0 Hz, 2H), 7.15–7.35 (m, 9H), 7.40 (m, 1H), 7.50 (s, 1H), 10.20 (br s, 1H); MS (ion spray) 680.5 (M+1); Anal. Calc'd for $C_{36}H_{49}N_5O_8$: C, 63.61; H, 7.27; N, 10.30. Found: C, 63.53; H, 6.99; N, 10.54.

Preparation 88

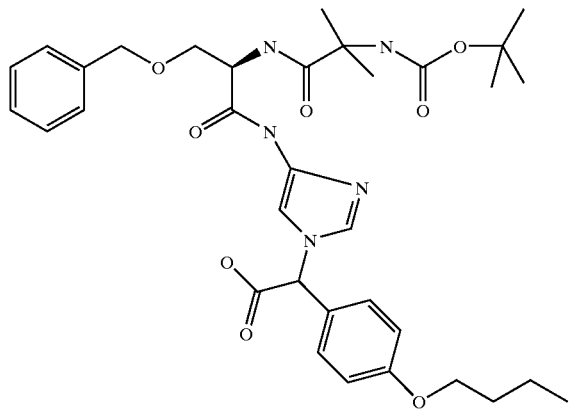

Reaction of the product of Preparation 87 (1.1 g, 1.6 mmol) and lithium hydroxide (0.5 g, 1.92 mmol) in dioxane (50 mL) and water 125 mL) as described in Preparation 5 gave 1.04 g (100%) of the desired product as a ton foam: $^1$H-NMR (d, DMSO) 0.95 (t, J=7.5 Hz, 3H), 1.25–1.35 (m, 15H), 1.35–1.50 (m, 2H), 1.65–1.75 (m, 21H), 3.57 (m, 1H), 3.65 (m, 1H), 3.95 (t, J=6.4 Hz, 2H), 4.57 (m, 1H), 6.19 (d, J=1.5 Hz, 2H), 6.20 (s, 1H), 6.96 (d, J=8.7 Hz, 2H), 7.10–7.35 (m, 9H), 7.40 (m, in), 7.50 (s, 1H), 10.20 (br s, 1H), 13.45 (br s, 1H); MS (ion spray) 652.5 (M+1); Anal. Calc'd for $C_{32}H_{45}N_5O_8$: C, 62.66; H, 6.96; N, 10.75. Found: C, 62.45; H, 7.07; N, 10.72.

Preparation 89

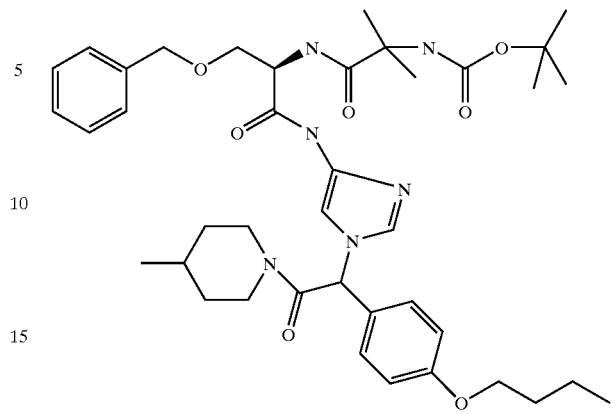

Reaction of the product of Preparation 88 (1.0 g, 1.6 mmol), 4-methylpiperidine (0.19 mL, 1.6 mmol), 1-hydroxybenzotriazole (0.24 g, 1.8 mmol) and 1-(3-dimethylaminopropyl)-3-ethylcarbodiimide (0.35 g, 1.8 mmol) in dimethylformamide (60 mL) as described in Preparation 6 gave 0.57 g (48%) of the desired product as a tan foam: $^1$H-NMR (d, DMSO) 0.75 (d. J=6.0 Hz, 1H), 0.85–0.95 (m, 6H), 1.25–1.40 (m, 15H), 1.40–1.75 (m, 7H), 2.55–2.75 (m, 2H), 3.00 (m, 1H), 3.55 (m, 1H), 3.60–3.85 (m, 2H), 3.95–4.00 (m, 2H), 4.60 (m, 1H), 4.85–4.98 (m, 3H), 6.97 (d, J=8.7 Hz, 1H), 6.90–7.00 (m, 2H), 7.15 (m, 1H), 7.20–7.45 (m, 10H), 10.15 (br s, 1H); MS (ion spray) 733.5 (M+1); Anal. Calc'd for $C_{40}H_{56}N_6O_7$: C, 65.55; H, 7.70; N, 11.47. Found: C, 65.44; H, 7.49; N, 11.59.

Examples 42 and 43

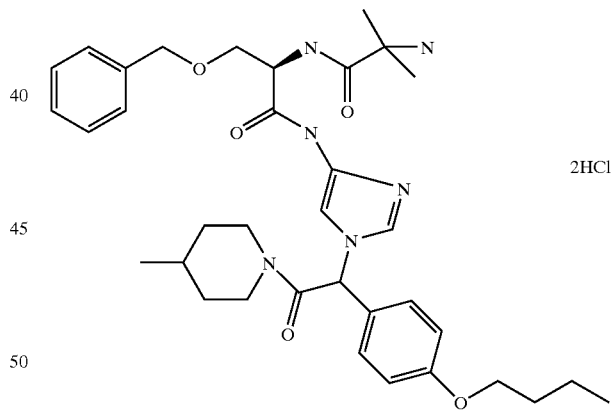

2HCl

Reaction of the product of Preparation 89 (0.55 g, 0.75 mmol) and trifluoroacetic acid (2 mL) in dichloromethane (6 mL) as described in Example 1 gave 0.4 g (75%1 of the desired product as a mixture diastereomers. This material was resolved by H (Kromsil CHI-DMP chiral stationary phase, 3A alcohol/dimethylethylamine/heptane) to provide the desired diastereomers, both isolated as white solids after acidification with hydrochloric acid as described Example 7:

Example 42

Isomer 1

$^1$H-NMR (d, DMSO) 0.75 (d, J=6.4 Hz, 1H), 0.85–1.00 (m, 5H), 1.25–1.40 (m, 2H), 1.40–1.50 (m, 2H), 1.50–1.60

(m, 6H), 1.60–1.75 (m, 4H), 2.60–2.70 (m, 2H), 3.00 (m, 1H), 3.60–3.75 (m, 3H), 3.95–4.00 (m, 2H), 4.52 (s, 2H), 4.75 (m, 1H), 4.88 (m, 1H), 6.89 (d, J=14 Hz, 1H), 7.00–7.05 (m, 2H), 7.20–7.40 (m, 9H), 8.10 (m, 1H), 8.20–8.30 (m, 3H), 8.60 (m, 1H), 11.02 (br s, 1H); $t_R$=5.90 min; MS (high res) calc'd for $C_{35}H_{49}N_6O_5$: 633.3764. Found: 633.3768. Anal. Calc'd for $C_{35}H_{49}N_6O_5 \cdot 2.3HCl$: C, 58.66; H, 7.07; N, 11.73. Found: C, 58.59; H, 6.99; N, 11.46.

Example 43

Isomer 2

$^1$H-NMR (d, DMSO) 0.75 (d, J=6.4 Hz, 1H), 0.85–1.00 (m, 5H), 1.25–1.40 (m, 2H), 1.40–1.50 (m, 2H), 1.50–1.60 (m, 6H), 1.60–1.75 (m, 4H), 2.60–2.70 (m, 2H), 3.00 (m, 1H), 3.60–3.75 (m, 3H), 3.95–4.00 (m, 2H), 4.52 (s, 2H), 4.75 (m, 1H), 4.88 (m, 1H), 6.89 (d, J=14 Hz, 1H), 7.00–7.05 (m, 2H), 7.20–7.40 (m, 9H), 8.10 (m, 1H), 8.20–8.30 (m, 3H), 8.60 (m, 1H), 11.02 (br s, 1H); $t_R$=7.47 min; MS (high res) calc'd for $C_{35}H_{49}N_6O_5$: 633.3764. Found: 633.3762. Anal. Calc'd for $C_{35}H_{49}N_6O_5 \cdot HCl$: C, 59.57; H, 7.14; N, 11.91. Found: C, 59.74; H, 7.30; N, 11.72.

Preparation 90

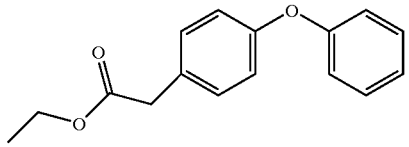

Reaction of 4-phenoxyphenylacetic acid (25.0 g, 110 mmol) and p-toluenesulfonic acid (5.0 g, 26 mmol) in absolute ethanol (150 mL) as in described in Preparation 1 gave 27.6 g (98%) of the desired product as a yellow oil: $^1$H-NMR (d, DMSO) 1.18 (t, J=7.2 Hz, 3H), 3.64 (s, 2H), 4.08 (q, J=7.2 Hz, 2H), 6.90–7.00 (m, 4H), 7.13 (t, J=7.5 Hz, 1H), 7.23 (d, J=8.7 Hz, 2H), 7.40 (t, J=5.7 Hz, 2H); MS (ion spray) 257.2 (M+1); Anal. Calc'd for $C_{15}H_{16}O_3$: C, 74.98; H, 6.29. Found: C, 74.88; H, 6.31.

Preparation 91

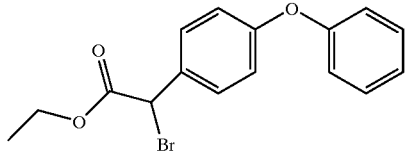

Reaction of the product of Preparation 90 (10.0 g, 39.0 mmol), N-bromosuccinimide (7.2 g, 40.2 mmol) and 48% HBr (4 drops) in carbon tetrachloride (40 mL) as described in Preparation 2 gave 11.9 g (92%) of the desired product as a colorless oil: $^1$H-NMR (d, DMSO) 1.21 (t, J=7.3 Hz, 3H), 4.15–4.30 (m, 2H), 5.94 Cs, 1H), 6.95–7.15 (m, 4H), 7.20 (m, 1H), 7.40–7.50 (m, 2H), 7.52–7.70 (m, 2H); MS (FD) 334, 336 (M+); Anal. Calc'd for $C_{16}H_{15}BrO_3 \cdot 0.05CHCl3$: C, 56.51; H, 4.45. Found: C, 56.85; H, 4.27.

Preparation 92

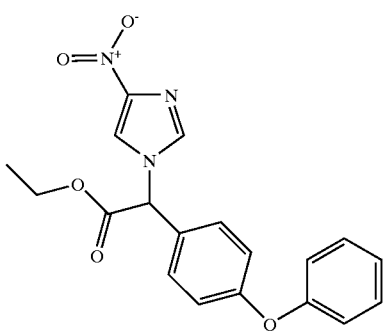

Reaction of the product of Preparation 91 (10.9 g, 33.0 mmol), 4-nitroimidazole (4.5 g, 39.6 mmol) and potassium carbonate (13.4 g, 99.0 mmol) in dimethylformamide (150 mL) as described in Preparation 3 gave 5.92 g (49%) of the desired product as a yellow oil: $^1$H-NMR (d, DMSO) 1.17 (t, J=6.8 Hz, 3H), 4.25 (g, J=7.2 Hz, 2H), 6.60 (s, 1H), 7.00–7.10 (m, 4H), 7.17 (t, J=7.2 Hz, 1H), 7.43 (t, J=6.0 Hz, 2H), 7.53 (d, J=6.8 Hz, 2H), 7.94 (s, 1H), 8.41 (s, 1H); MS (ion spray) 368.2 (M+1); Anal. Calc'd for $C_{19}H_{17}N_3O_5 \cdot 0.15CHCl3$: C, 59.30; H, 4.49; N, 10.91. Found: C, 59.55; H, 4.73; N, 10.97.

Preparation 93

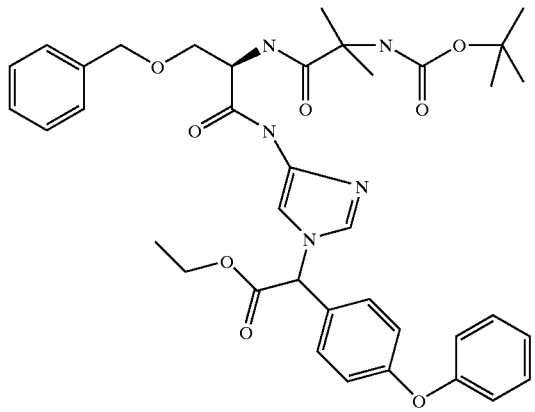

Reaction of the product of Preparation 92 (1.58 (4.3 mmol) with 10% palladium on carbon (0.8 g) in tetrahydrofuran (70 mL) followed by coupling with the product of Preparation 1d (1.64 g, 4.3 mmol), 1-hydroxybenzotriazole (0.7 g, 4.7 mmol) and 1-(3-dimethylaminopropyl)-3-ethylcarbodiimide (1.04 g, 4.7 mmol) as described in Preparation 4 gave 1.92 g (62%) of the desired product as a tan foam: $^1$H-NMR (d, DMSO) 1.20 (t, J=7.2 Hz, 3H), 1.25–1.35 (m, 15H), 3.57 (m, 1H), 3.70 (m, 1H), 4.25 (q. J=7.2 Hz, 2H), 4.45–4.47 (m, 2H), 4.60 (m, 1H), 6.43 (s, 1H), 7.00–7.10 (m, 4H), 7.20 (m, 1H), 7.25–7.35 (m, 6H), 7.35–7.45 (m, 6H), 7.55 (s, 1H), 10.20 (br s, 1H); MS (ion spray) 700.7 (M+1); Anal. Calc'd for $C_{38}H_{45}N_5O_8$: C, 65.22; H, 6.48; N, 10.01. Found: C, 65.12; H, 6.43; N, 9.87.

Preparation 94

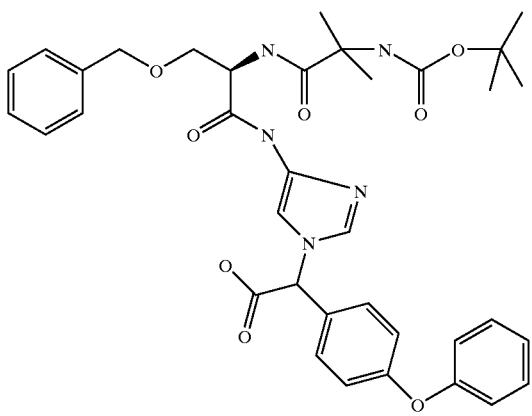

Reaction of the product of Preparation 93 (1.72 g, 2.5 mmol) and lithium hydroxide (0.07 g, 3.0 mmol) in dioxane (50 mL) and water (25 mL) as described in Preparation 5 gave 1.68 g (100%) of the desired product as a tan foam: $^1$H-NMR (d, DMSO) 1.25–1.40 (m, 15H), 3.60 (m, 1H), 3.70 (m, 1H), 4.45–4.50 (m, 2H), 4.57 (m, 1H), 6.25 (s, 1H), 7.00–7.07 (m, 4H), 7.15–7.35 (m, 8H), 7.35–7.45 (m, 5H), 7.55 (s, 1H), 10.20 (br s, 1H), 13.55 (br s, 1H); MS (ion spray) 672.6 (M+1; Anal. Calc'd for $C_{36}H_{41}N_5O_8$: C, 64.37; H, 6.15; N, 10.43. Found: C, 64.56; H, 6.37; N, 10.23.

Preparation 95

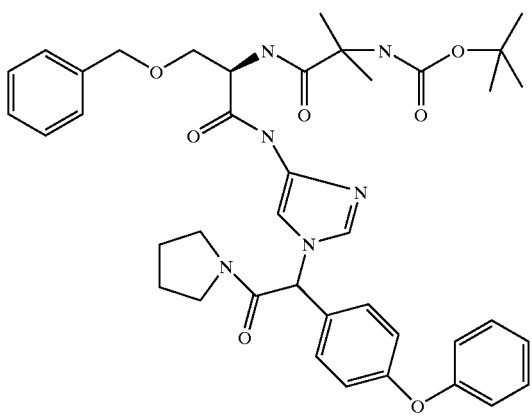

Reaction of the product of Preparation 94 (0.45 g, 0.67 mmol), pyrrolidine (0.07 mL, 0.67 mmol), 1-hydroxybenzotriazole (0.1 g, 0.74 mmol) and 1-(3-dimethylaminopropyl)-3-ethylcarbodiimide (0.15 g, 0.74 mmol) in dimethylformamide (30 mL) as described in Preparation 6 gave 0.22 g (45%) of the desired product as a white foam: $^1$H-NMR (d, DMSO) 1.20–1.40 (m, 15H), 1.65–1.90 (m, 4H), 3.05 (m, 1H), 3.25–3.45 (m, 2H), 3.55–3.75 (m, 3H), 4.45–4.50 (m, 2H), 4.60 (m, 1H), 6.43 (s, 1H), 7.05 (t, J=8.7 Hz, 3H), 7.20 (m, 1H), 7.25–7.30 (m, 7H), 7.35–7.50 (m, 7H), 10.20 (br s, 1H); MS (ion spray) 725.7 (M+1); Anal. Calc'd for $C_{40}H_{48}N_6O_7$: C, 66.28; H, 6.68; N, 11.59 Found: C, 66.42; H, 6.68; N, 11.59.

Example 44

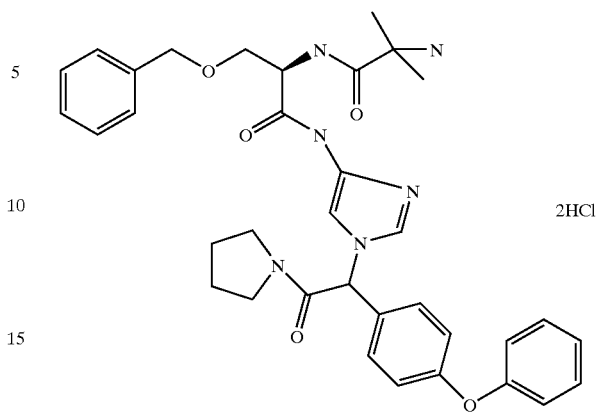

Reaction of the product of Preparation 95 (0.22 g, 0.3 mmol) and trifluoroacetic acid (2 mL) in dichloromethane (6 mL) as described in ale 1 gave 0.2 g (100%) of the desired mixture of isomers: $^1$H-NMR (d, DMSO) 1.45–1.55 (m, 6H), 1.70–1.90 (m, 4H), 2.95 (m, 1H), 3.25–3.45 (m, 2H), 3.50–3.90 (m, 3H), 4.45–4.55 (m, 2H), 4.75 (m, 1H), 6.60 (m, 1H), 7.00 (m, 3H), 7.20 (m, 1H), 7.25–7.50 (m, 12H), 7.98 (m, 1H), 8.15–8.30 (m, 3H), 8.52 (t, J=7.6 Hz, 1H), 10.88 (br s, 1H); MS (ion spray) 625.4 (M+1); Anal. Calc'd for $C_{35}H_{40}N_6O_5 \cdot 2HCl$; C, 60.26; H, 6.07; N, 12.05. Found: C, 60.02; H, 6.01; N, 11.81.

Preparation 96

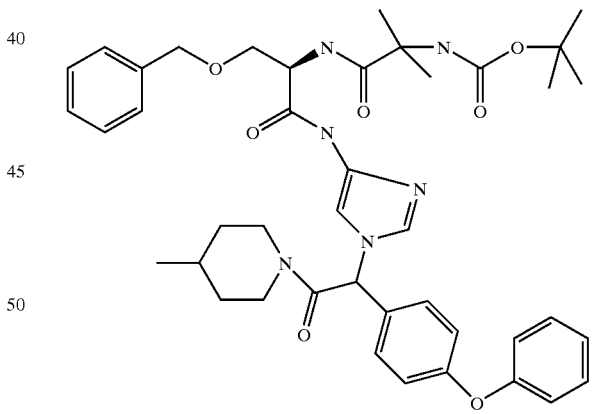

Reaction of the product of Preparation 94 (0.6 g, 0.9 mmol), 4-methylpiperidine (0.1 mL, 0.9 mmol), 1-hydroxybenzotriazole (0.14 g, 1.0 mmol) and 1-(3-dimethylaminopropyl)-3-ethylcarbodiimide (0.2 g, 1.0 mmol) in dimethylformamide (30 mL) as described in Preparation 6 gave 0.4 g (59%) of the desired product as a white foam: $^1$H-NMR is consistent with structure; MS (ion spray) 753.5 (M+1); Anal Calc'd for $C_{42}H_{52}N_6O_7$: C, 67.00; H, 6.96; N, 11.16. Found: C, 66.73; H, 6.91; N, 11.04.

Example 45

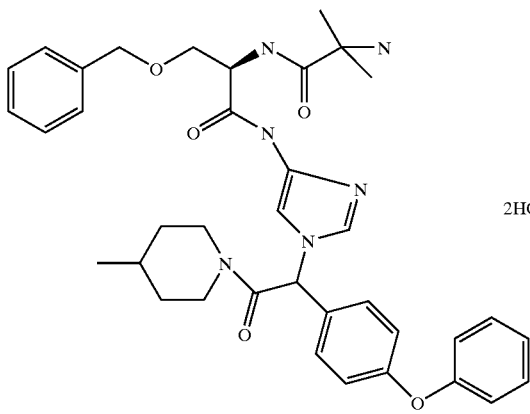

2HCl

Reaction of the product of Preparation 96 (10.34 g, 0.45 mmol) and trifluoroacetic acid (2 mL) in dichloromethane (6 mL) as described in Example 1 gave 0.27 g (83%) of the desired mixture of isomers as a white solid: $^1$H-NMR is consistent with structure; MS (high res) calc'd for $C_{37}H_{45}N_6O_5$: 653.3451. Found: 653.3446.

Preparation 97

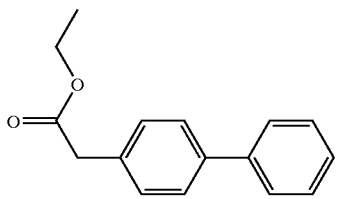

Reaction of biphenylacetic acid (25.2 g, 119 mmol) and p-toluenesulfonic acid (3.3 g, 17 mmol) in absolute ethanol (250 mL) as described in Preparation 1 gave 25.4 g (89%) of the desired product as a yellow oil: $^1$H-NMR is consistent with structure; MS (FD) 240.1 (M+); Anal. Calc'd for $C_{16}H_{16}O_2$: C, 79.97; H, 6.71. Found: C, 79.75; H, 6.59.

Preparation 98

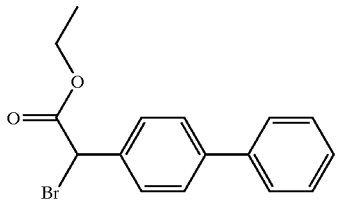

Reaction of the product of Preparation 97 (18.0 g, 75.0 mmol), N-bromosuccinimide (13.7 g, 77.25 mL) and 48% HBr (4 drops) in carbon tetrachloride (80 mL) as described in Preparation 2 gave 22.56 g (94%) of the desired product as a yellow oil: $^1$H-NMR is consistent with structure; MS (FD) 318, 320 (M+); Anal. Calc'd for $C_{16}H_{15}BrO_2 \cdot 0.05$Chydrochloric acid$_3$: C, 60.21; H, 4.74. Found: C, 59.50; H, 4.75.

Preparation 99

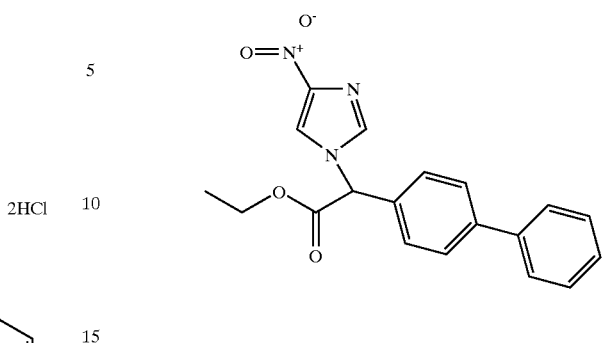

To a slurry of sodium hydride (2.42 g, 60.5 mmol) stirring in dimethylformamide (200 mL) at room temperature was added 4-nitroimidazole (6.9 g, 60.5 mmol). After 10 min, the product of Preparation 98 (17.62 g, 55.0 mmol) was added. After 16 h, the reaction mixture was concentrated and the residue was slurried in ethyl acetate then filtered. The resulting oil was partitioned between ethyl acetate and water then extracted with ethyl acetate. The combined organic extracts were washed with brine, dried over sodium sulfate, filtered and concentrated. The resulting oil was absorbed onto silica gel and purified by flash chromatography (silica gel, 30–50% ethyl acetate/hexanes) to yield 12.0 g (62%) of the desired product as a yellow viscous oil: $^1$H-NMR is consistent with structure; MS (FD) 351 (M+).

Preparation 100

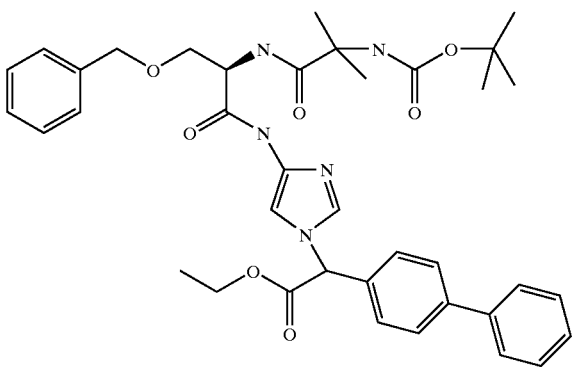

Reduction of the product of Preparation 99 (2–0 g, 5.8 mmol) under a hydrogen atmosphere with 10% palladium on carbon (0.8 g) and tetrahydrofuran (70 mL) followed by coupling with the product of Preparation 1d (2.2 g, 5.8 mmol), 1-hydroxybenzotriazole (0.86 g, 6.4 mmol) and 1-(3-dimethylaminopropyl)-3-ethylcarbodiimide (1.3 g, 6.4 mmol) as described in Preparation 4 gave 0.7 g (18%) of the desired product as a tan foam: $^1$H-NMR is consistent with structure; MS (FD) 683 (M+); Anal. Calc'd for $C_{38}H_{45}N_5O_7$: C, 66.75; H, 6.63; N, 10.34. Found: C, 66.79; H, 6.48; N, 10.32.

Preparation 101

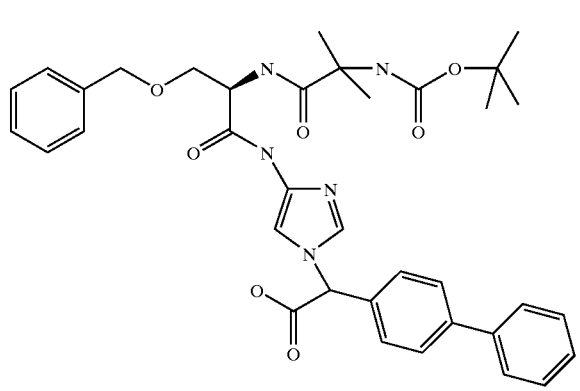

Reaction of the product of Preparation 100 (0.7 g, 1.0 mmol) and lithium hydroxide (0.03 g, 1.2 mmol) in dioxane (20 mL) and water (10 mL) as described in Preparation 5 gave 0.66 g (100%) of the desired product as a tan foam: $^1$H-NMR is consistent with structure; MS (FD) 656 (M+); Anal. Calc'd for $C_{36}H_{41}N_5O_7$: C, 65.94; H, 6.30; N, 10.68. Found: C, 65.90; H, 6.37; N, 10.42.

Preparation 102

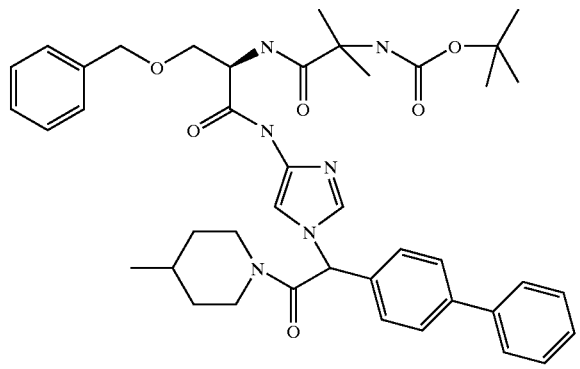

Reaction of the product of Preparation 101 (0.7 g, 1.1 mmol) with 4-methylpiperidine (0.13 mL, 1.1 mmol), 1-hydroxybenzotriazole (0.17 g, 1.2 mmol) and 1-(3-dimethylaminopropyl)-3-ethylcarbodiimide (0.25 g, 1.2 mmol) in dimethylformamide (40 mL) as described in Preparation 6 gave 0.52 g (65%) of the desired product as a tan foam: $^1$H-NMR is consistent with structure; MS (FD) 728.4 (M+); Anal. Calc'd for $C_{37}H_{47}F_3N_6O_6$: C, 60.98; H, 6.50; N, 11.53. Found: C, 61.18; H, 6.35; N, 11.44.

Examples 46 and 47

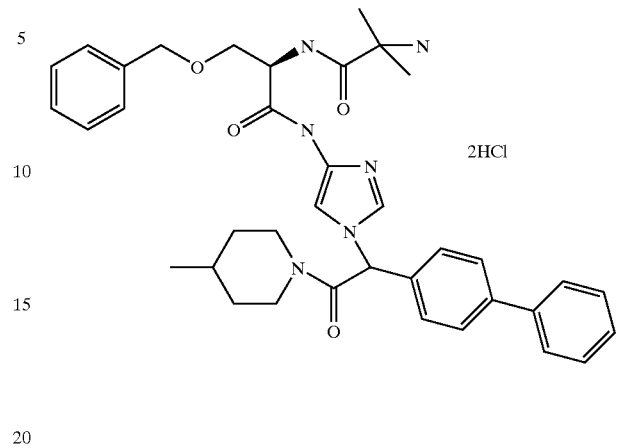

Reaction of the product of Preparation 102 (0.36 g, 0.49 mmol) and trifluoroacetic acid (4 mL) in dichloromethane (12 mL) as described in Example 1 gave 0.3 g (88%) of the desired mixture of isomers. Resolution of the diastereomers (4 g, 3.6 mmol) by HPLC (Kromsil CHI-DMP chiral stationary phase, 3A alcohol/dimethylethylamine/heptane eluant) provided provided 0.5 (16%) of isomer 1 and 0.5 mg (12%) of isomer 2, both isolated as white solids after formation of their respective hydrochloride salts as described in Example 7:

Example 46

Isomer 1

$^1$H-NMR is consistent with structure; $t_R$=6.9 min; MS (ion spray) 637.4 (M+1); Anal. Calc'd for $C_{37}H_{44}N_6O_4 \cdot 2.5HCl$: C, 61.05; H, 6.44; N, 11.54. Found: C, 60.89; H, 6.53; N, 11.25.

Example 47

Isomer 2

$^1$H-NMR is consistent with structure; $t_R$=9.2 min; MS (ion spray) 637.4 (M+1); Anal. Calc'd for $C_{37}H_{44}N_6O_4 \cdot 2.6HCl$: C, 60.75; H, 6.42; N, 11.49. Found: C, 60.67; H, 6.63; N, 11.18.

Preparation 103

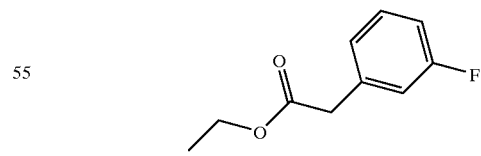

Reaction of 3-fluorophenylacetic acid (15.0 g, 97.0 mmol) and p-toluenesulfonic acid (3.0 g, 16 mmol) in absolute ethanol as described in Preparation 1 gave 16.5 g (94%) of the desired product as a colorless oil; 1H-NMR is consistent with structure; MS (FD) 182 (M+); Anal. Calc'd for $C_{10}H_{11}FO_2$: C, 65.92; H, 6.09. Found: C, 64.94; H, 5.99.

Preparation 104

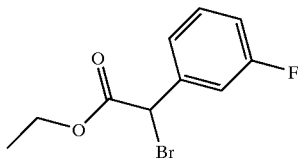

Reaction of the product of Preparation 103 (15.0 g, 82 mmol), N-bromosuccinimide (15.0 g, 84.5 mmol) and 48% HBr (4 drops) in carbon tetrachloride 180 mL) as described in Preparation 2 gave 19.2 g (90%) of the desired product as a colorless oil: $^1$H-NMR is consistent with structure; MS (FD) 259, 261 (M+); Anal. Calc'd for $C_{10}H_{10}BrFO_2$: C, 46.00; H, 3.86. Found: C, 45.71; H, 3.90.

Preparation 105

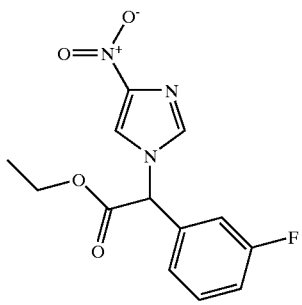

Reaction of the product of Preparation 104 (15.0 g, 58.0 mmol), 4-nitroimidazole (7.8 g, 63.8 mmol) and sodium hydride ((2.8 g, 63.8 mmol) in dimethylformamide (200 mL) as in described in Preparation 3 gave 11.13 g (65%) of the desired product as a yellow oil: $^1$H-NMR is consistent with structure; MS (FD) 293 (M+); Anal. Calc'd for $C_{13}H_{12}FN_3O_4$: C, 53.24; H, 4.12; N, 14.33. Found: C, 53.12; H, 4.22; N, 14.47.

Preparation 106

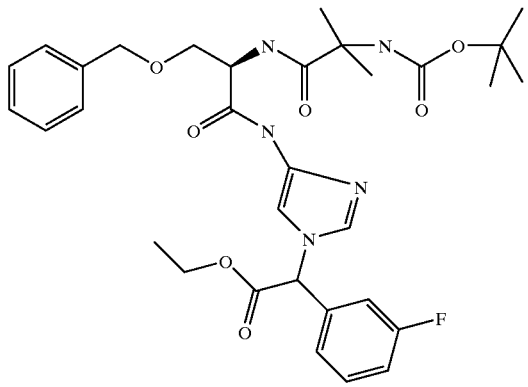

Reaction of the product of Preparation 105 (1.7 g, 5.8 mmol) with 10% palladium on carbon (0.7 g) in tetrahydrofuran (40 mL) under a hydrogen atmosphere followed by coupling with the product of Preparation 1d (2.2 g, 5.8 mmol), 1-hydroxybenzotriazole (0.86 g, 6.4 mmol) and 1-(3-dimethylaminopropyl)-3-ethylcarbodiimide (1.3 g, 6.4 mmol) as described in Preparation 4 gave 2.05 g (60%) of the desired product as a yellow foam: $^1$H-NMR is consistent with structure; MS (FD) 625 (M+); Anal. Calc'd for $C_{32}H_{40}FN_5O_7$: C, 61.43; H, 6.44; N, 11.19. Found: C, 61.28; H, 6.64; N, 11.32.

Preparation 106

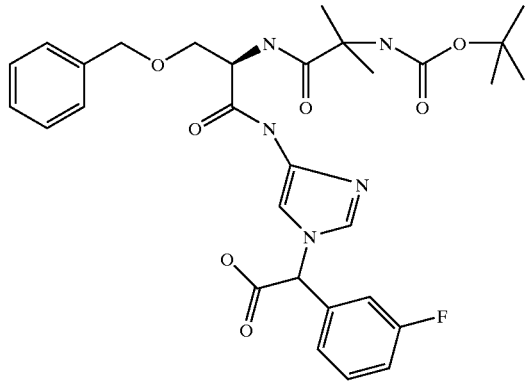

Reaction of the product of Preparation 104 (0.12 g, 3.2 mmol) and lithium hydroxide (0.09 g, 3.84 mmol) in dioxane (40 mL) and water (20 mL) as described in Preparation 5 gave 1.91 g (100%) of the desired product as a tan foam: $^1$H-NMR is consistent with structure; MS (FD) 598 (M+); Anal. Calc'd for $C_{30}H_{36}FN_5O_7$: C, 60.29; H, 6.07; N, 11.72. Found: C, 60.21; H, 6.41; N, 11.06.

Preparation 107

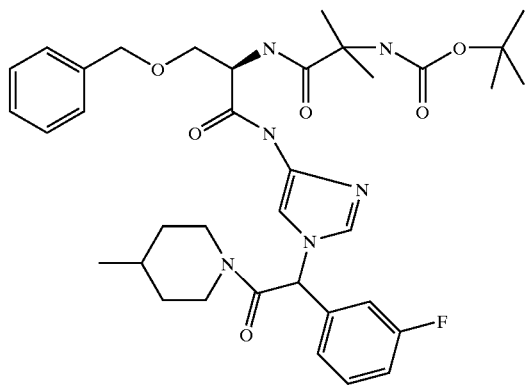

Reaction of the product of Preparation 106 (0.7 g, 1.2 mmol), 4-methylpiperidine (0.14 mL, 1.2 mmol), 1-hydroxybenzotriazole (0.18 g, 1.3 mmol) and 1-(3-dimethylaminopropyl)-3-ethylcarbodiimide (0.27 g, 1.3 mmol) in dimethylformamide (100 mL) as described in Preparation 6 gave 0.52 g (64%) of the desired product as a white solid: $^1$H-NMR is consistent with structure; MS (FD) 678 (M+); Anal. Calc'd for $C_{36}H_{47}FN_6O_6$: C, 63.70; H, 6.98; N, 12.38. Found: C, 63.62; H, 7.10; N, 12.31.

Example 48

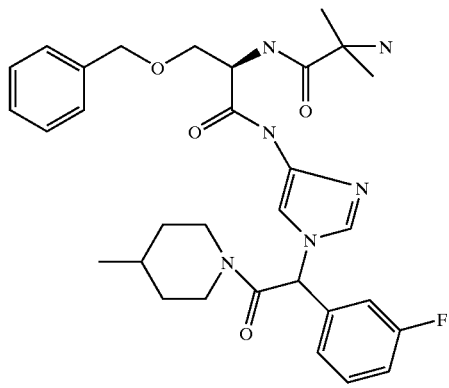

Reaction of the product of Preparation 107 (0.51 g, 0.75 mmol) and trifluoroacetic acid (2 mL) in dichloromethane (6 mL) as described in Example 1 gave 0.24 g (49%) of the desired mixture of isomers as a yellow solid: $^1$H-NMR is consistent with structure; MS (FD) 578 (M+); Anal. Calc'd for $C_{31}H_{39}FN_6O_4 \cdot 2.7HCl$: C, 54.99; H, 6.21; N, 12.41. Found: C, 54.97; H, 6.23; N, 12.40.

Preparation 108

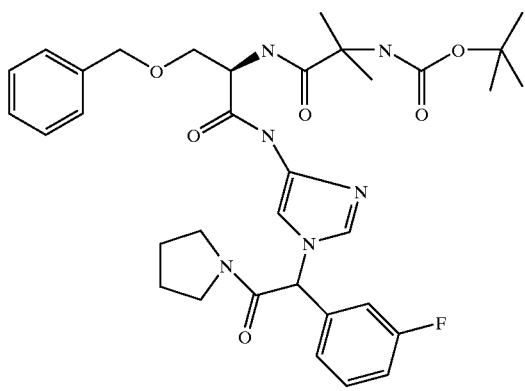

Reaction of the product of Preparation 106 (0.7 g, 1.2 mmol), pyrrolidine (0.1 mL, 1.2 mmol), 1-hydroxybenzotriazole (0.18 g, 1.3 mmol) and 1-(3-dimethylaminopropyl)-3-ethylcarbodiimide (0.27 g, 1.3 mmol) in dimethylformamide (40 mL) as described in Preparation 6 gave 0.54 g (69%) of the desired product as a yellow foam: $^1$H-NMR is consistent with structure; MS (FD) 650 (M+); Anal. Calc'd for $C_{34}H_{43}FN_6O_6 \cdot 0.2CHCl3$: C, 60.89; H, 6.45; N, 12.46. Found: C, 60.91; H, 6.39; N, 12.36.

Example 49

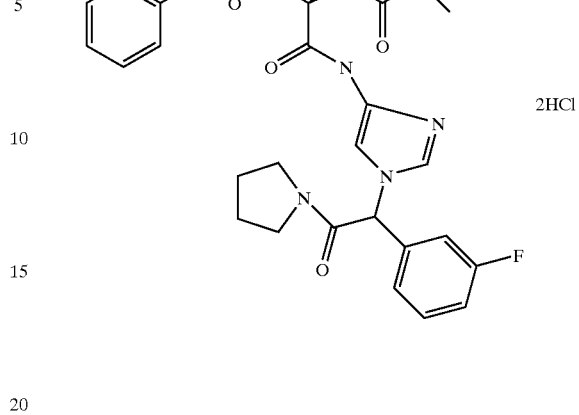

Reaction of the product of Preparation 108 (0.4 g, 0.6 mmol) and trifluoroacetic acid (2 mL) in dichloromethane (6 mL) as described in ale 1 gave 0.3 g (79%) of the desired mixture of isomers as a yellow solid: $^1$H-NMR is consistent with structure; MS (FD) 550 (M+); Anal. Calc'd for $C_{29}H_{35}FN_6O_4 \cdot 2.2HCl$: C, 55.21; B. 5.94; N, 13.32. Found: C, 55.07; H, 5.91; N, 12.53.

Preparation 109

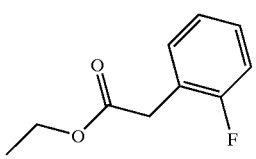

Reaction of 2-fluorophenylacetic acid (15.0 g, 97.0 mmol) and p-toluenesulfonic acid (2.8 g, 14.5 mmol) in absolute ethanol (100 mL) as described in Preparation 1 gave 17.0 g (96%) of the desired product as a colorless oil: $^1$H-NMR is consistent with structure; MS (FD) 182 (M+).

Preparation 110

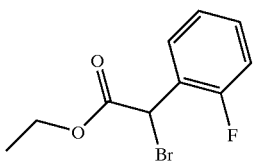

Reaction of the product of Preparation 109 (15.0 g, 82 mmol), N-bromosuccinimide (15.0 g, 84.5 mmol) and 48% HBr (3 drops) in carbon tetrachloride (80 mL) as described in Preparation 2 gave 21 g (98%) of the desired product as a colorless oil: $^1$H-NMR is consistent with structure; MS (FD) 260 (M+).

Preparation 111

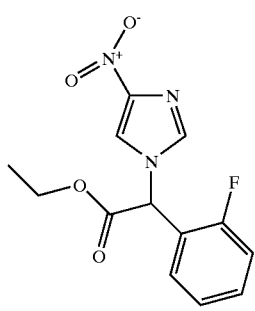

Reaction of the product of Preparation 110 (15.0 g, 58 mmol), 4-nitroimidazole (7.8 g, 63.8 mmol) and sodium hydride (2.8 g, 63.8 mmol) in dimethylformamide (200 mL) as described in Preparation 3 gave 11.36 g (67%) of the desired product as a white solid: $^1$H-NMR is consistent with structure; MS (FD) 293.1 (M+); Anal. Calc'd for $C_{13}H_{12}FN_3O_4$: C, 53.24; H, 4.12; N, 14.33. Found: C, 53.54; H, 4.18; N, 14.11.

Preparation 112

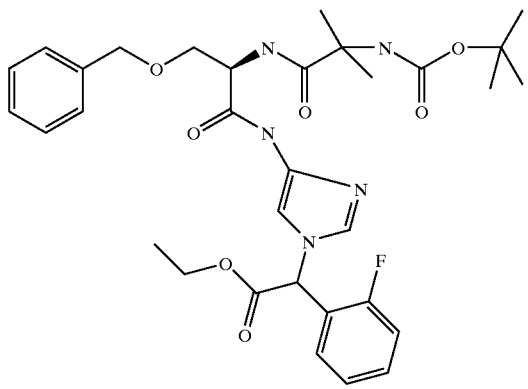

Reaction of the product of Preparation 111 (1.7 g, 5.8 mmol) with 10% palladium on carbon (0.7 g) in tetrahydrofuran (50 mL) under a hydrogen atmosphere followed by coupling with the product of Preparation 1d (2.2 g, 5.68 mmol), 1-hydroxybenzotriazole (0.86 g, 6.4 mmol) and 1-(3-dimethylaminopropyl)-3-ethylcarbodiimide (1.3 g, 6.4 mmol) as described in Preparation 4 gave 2.4 g (67%) of the desired product as a tan foam: $^1$H-NMR is consistent with structure; MS (FD) 625 (M+); Anal. Calc'd for $C_{32}H_{40}FN_5O_7$: C, 61.43; H, 6.44; N, 11.19. Found: C, 61.51; H, 6.50; N, 11.34.

Preparation 113

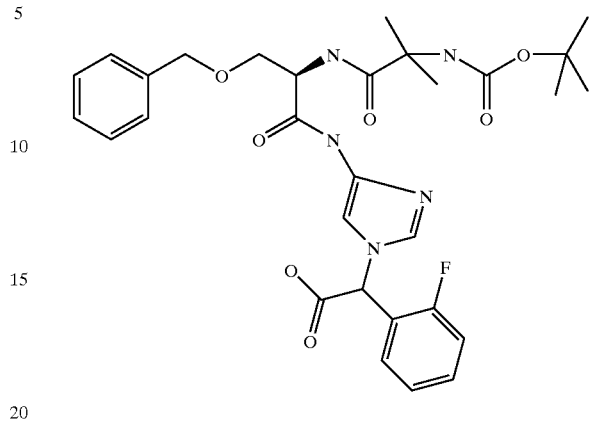

Reaction of the product of Preparation 112 (2.35 g, 3.8 mmol) and lithium hydroxide (0.1 g, 4.6 mmol) in dioxane (40 mL) and water (20 mL) as described in Preparation 5 gave 2.27 g (100%) of the desired product as a tan foam: $^1$H-NMR is consistent with structure; MS (FD) 598 (M+); Anal. Calc'd for $C_{30}H_{36}FN_5O_7$: C, 60.29; H, 6.07; H, 11.72. Found: C, 60.08; H, 6.28; N, 11.42.

Preparation 114

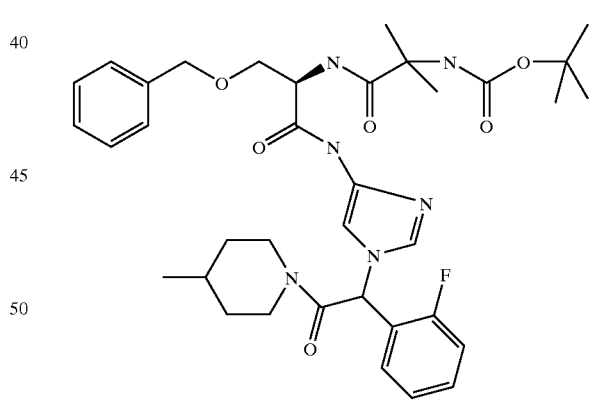

Reaction of the product of Preparation 113 (0.7 g, 1.2 mmol), 4-methylpiperidine (0.14 mL, 1.2 mmol), 1-hydroxybenzotriazole (0.18 g, 1.3 mmol) and 1-(3-dimethylaminopropyl)-3-ethylcarbodiimide (0.27 g, 1.3 mmol) in dimethylformamide (100 mL) as described in Preparation 6 gave 0.56 g (69%) of the desired product as a tan foam: $^1$H-NMR is consistent with structure; MS (FD) 678.2 (M+); Anal. Calc'd for $C_{36}H_{47}FN_6O_6$: C, 63.70; H, 6.98; N, 12.38. Found: C, 63.44; H, 7.05; N, 12.10.

Example 50

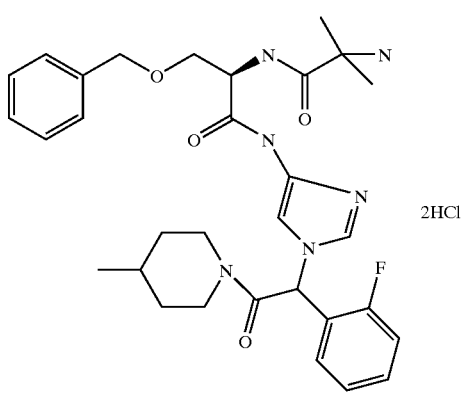

2HCl

Reaction of the product of Preparation 114 (0.53 g, 0.78 mmol) and trifluoroacetic acid (4 mL) in dichloromethane (12 mL) as described in Example 1 gave 0.38 g (75%) of the desired mixture of isomers as a yellow solid: $^1$H-NMR is consistent with structure; MS (FD) 578 (M+); Anal. Calc'd for $C_{31}H_{39}FN_6O_4 \cdot 2HCl$: C, 56.51; H, 6.30; N, 12.75. Found: C, 56.45; H, 6.10; N, 12.43.

Preparation 115

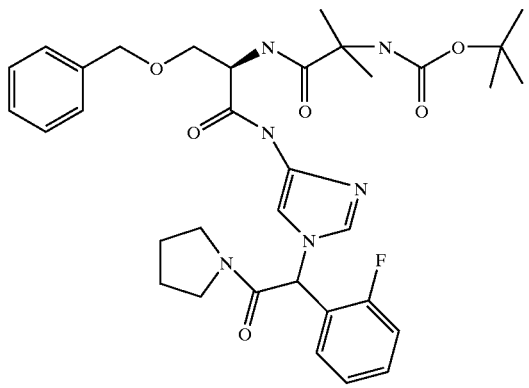

Reaction of the product of Preparation 113 (0.7 g, 1.2 mmol), pyrrolidine (0.1 mL, 1.2 mmol), 1-hydroxybenzotriazole (0.18 g, 1.3 mmol) and 1-(3-dimethylaminopropyl)-3-ethylcarbodiimide (0.27 g, 1.3 mmol) in dimethylformamide (100 mL) as described in Preparation 6 gave 0.6 g (77%) of the desired product as a tan foam. $^1$H-NMR is consistent with structure; MS (FD) 650 (M+); Anal. Calc'd for $C_{34}H_{43}FN_6O_6$: C, 62.75; H, 6.66; N, 12.91. Found: C, 62.53; H, 6.58; N, 12.71.

Example 51

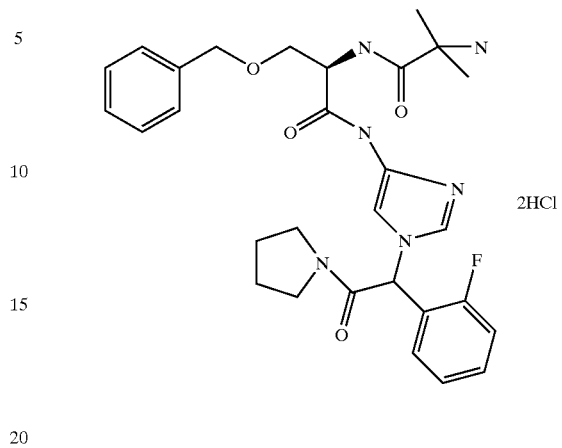

2HCl

Reaction of the product of Preparation 115 (0.46 g, 0.7 mmol) and trifluoroacetic acid (4 mL) indichloromethane (12 mL) as described in Example 1 gave 0.44 g (100%) of the desired mixture of isomers as a white foam: $^1$H-NMR is consistent with structure. MS (high res) calc'd for $C_{29}H_{36}FN_6O_4$: 551.2782. Found: C, 551.2779. Anal. Calc'd for $C_{29}H_{35}FN_6O_4 \cdot 2HCl$: C, 55.86; H, 5.98; N, 13.48. Found: C, 56.09; H, 5.91; N, 13.44.

Preparation 116

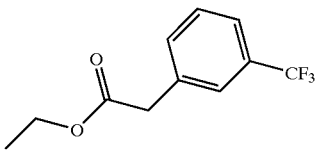

Reaction of 3-trifluoromethylphenylacetic acid (15.0 g, 73.4 mmol) and p-toluenesulfonic acid (3 g, 15.6 mmol) in Absolute ethanol (200 mL) as described in Preparation 1 gave 15.6 g (93%) of the desired product as a colorless oil: $^1$H-NMR is consistent with structure; MS (FD) 232 (M+); Anal. Calc'd for $C_{11}H_{11}F_3O_2$: C, 56.90; H, 4.77. Found: C, 56.93; H, 4.65.

Preparation 117

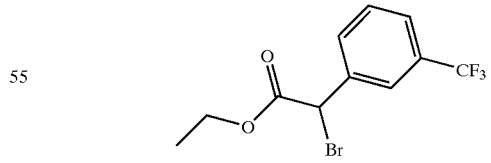

Reaction of the product of Preparation 116 (10.0 g, 44.0 mmol), N-bromosuccinimide (8.0 g, 45.3 mmol) and 48% HBr (4 drops) in carbon tetrachloride (70 mL), as described in Preparation 2 gave 11.2 g (82%) of the desired product as a colorless oil: $^1$H-NMR is consistent with structure; MS (FD) 264 (M+); Anal. Calc'd for $C_{11}H_{10}BrF_3O_2$: C, 42.47; H, 3.24. Found: C, 42.37; H, 3.26.

Preparation 118

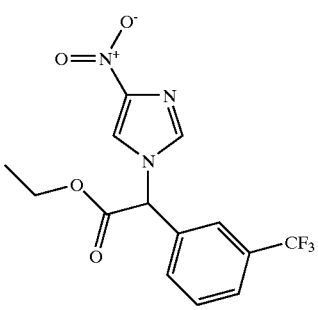

Reaction of the product of Preparation 117 (11.2 g, 36.0 mmol), 4-nitroimidazole (4.9 g, 43.2 mmol) and sodium hydride (1.7 g, 43.2 mmol) in dimethylformamide (180 mL) as described in Preparation 3 gave 6.22 g (50%) of the desired product as a yellow oil: $^1$H-NMR is consistent with structure; MS (FD) 343.1 (M+); Anal. Calc'd for $C_{14}H_{12}F_3N_3O_4$: C, 48.99; H, 3.52; N, 12.24. Found: C, 48.74; H, 3.63; N, 12.06.

Preparation 119

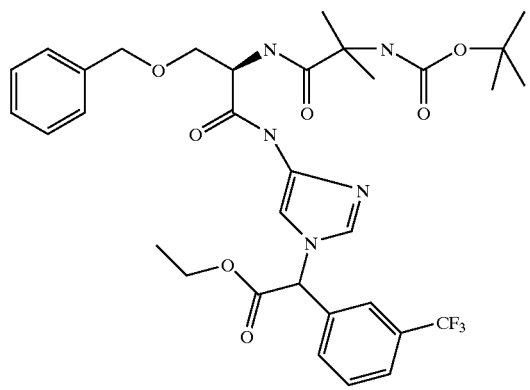

Reaction of the product of Preparation 118 (2.0 g, 5.8 mmol) with 10% palladium on carbon (0.6 g) in tetrahydrofuran (80 mL) under an atmosphere of hydrogen followed by coupling with the product of Preparation 1d (2.2 g, 5.8 mmol), 1-hydroxybenzotriazole (0.86 g, 6.4 mmol) and 1-(3-dimethylaminopropyl)-3-ethylcarbodiimide (1.3 g, 6.4 mmol) as described in Preparation 4 gave 1.82 g (47%) of the desired product as a tan foam: $^1$H-NMR is consistent with structure; MS (FD) 675.4 (M+); Anal. Calc'd for $C_{33}H_{40}F_3N_5O_7$: C, 58.66; H, 5.97; N, 10.36. Found: C, 58.67; H, 5.87; N, 10.51.

Preparation 120

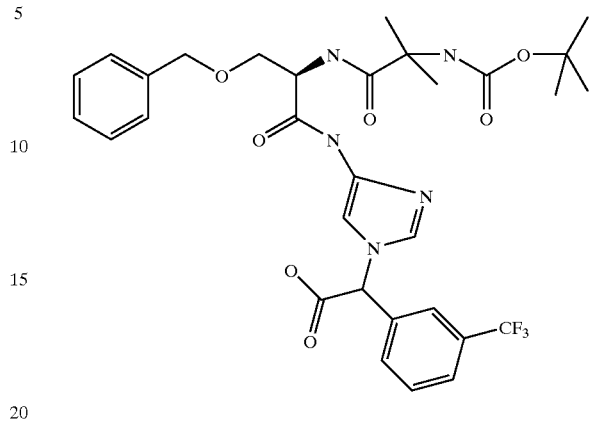

Reaction of the product of Preparation 120 (1.67 g, 2.5 mmol) and lithium hydroxide (0.07 g, 2.8 mmol) in dioxane (40 mL) and water (20 mL) as described in Preparation 5 gave 1.60 g (99%) of the desired product as a yellow foam: $^1$H-NMR is consistent with structure; MS (FD) 648 (M+); Anal. Calc'd for $C_{31}H_{36}F_3N_5O_7$: C, 57.49; H, 5.60; N, 10.81. Found: C, 57.52; H, 5.62; N, 10.75.

Preparation 121

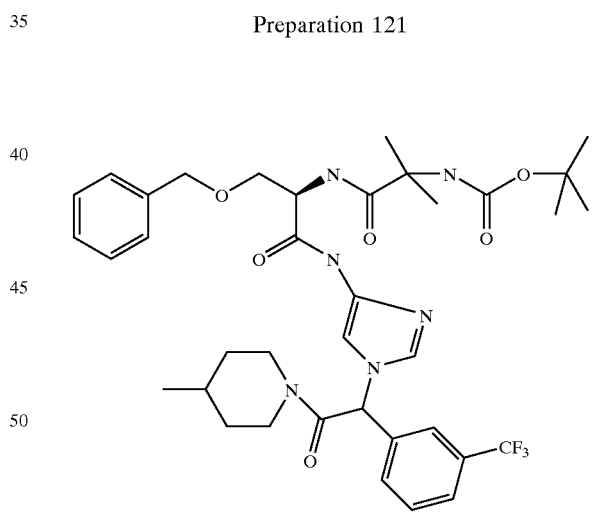

Reaction of the product of Preparation 120 (0.6 g, 0.93 hydroxybenzotriazole (0.13 g, 1.02 mmol) and 1-(3-mmol), 4-methylpiperidine (0.11 mL, 0.93 mmol), 1-dimethylaminopropyl)-3-ethylcarbodiimide (0.12 g, 1.02 mmol) in dimethylformamide (40 mL) as described in Preparation 6 gave 0.55 g (81%) of the desired product as a tan foam: $^1$H-NMR is consistent with structure; MS (FD) 728.9 (M+); Anal. Calc'd for $C_{37}H_{47}F_3N_6O_4$: C, 60.96; H, 6.50; N, 11.53. Found: C, 60.81; H, 6.57; N, 11.69.

Example 52

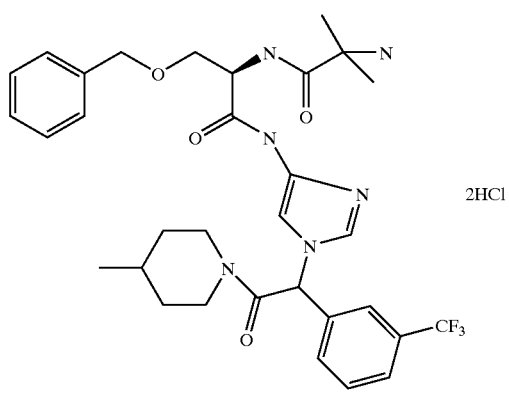

2HCl

Reaction of the product of Preparation 121 (0.5 g, 0.68 mmol) and trifluoroacetic acid (2 mL) in dichloromethane (6 mL) as described in Example 1 gave 0.33 g (69%) of the desired mixture of isomers as a yellow solid: $^1$H-NMR is consistent with structure; MS (ion spray) 628.8 (M+1); Anal. Calc'd for $C_{32}H_{39}F_3N_6O_4 \cdot 2.3HCl$: C, 53.94; H, 5.84; N, 11,79. Found: C, 53.89; H, 5.92; N, 11.65.

Preparation 122

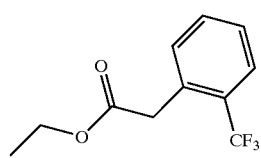

Reaction of 3-trifluoromethylphenylacetic acid (15.0 g, 73.4 mmol) and p-toluenesulfonic acid (2.8 g, 14.5 mmol) in absolute ethanol (200 mL) as described in Preparation 1 gave 16.11 g (94%) of the desired product as a colorless oil: $^1$H-NMR is consistent with structure; MS (FD) 232 (M+). Anal. Calc'd for $C_{11}H_{11}F_3O_2$: C, 56.90; H, 4.77. Found: C, 56.64; H, 4.90.

Preparation 123

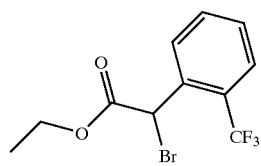

Reaction of the product of Preparation 122 (15.0 g, 65 mmol), N-bromosuccinimide (11.9 g, 67.0 mmol) and 48% HBr (4 drops) in carbon tetrachloride (80 mL) as described in Preparation 2 gave 17.1 g (85%) of the desired product as a colorless oil: $^1$H-NMR is consistent with structure; MS (FD) 311, 313 (M+).

Preparation 124

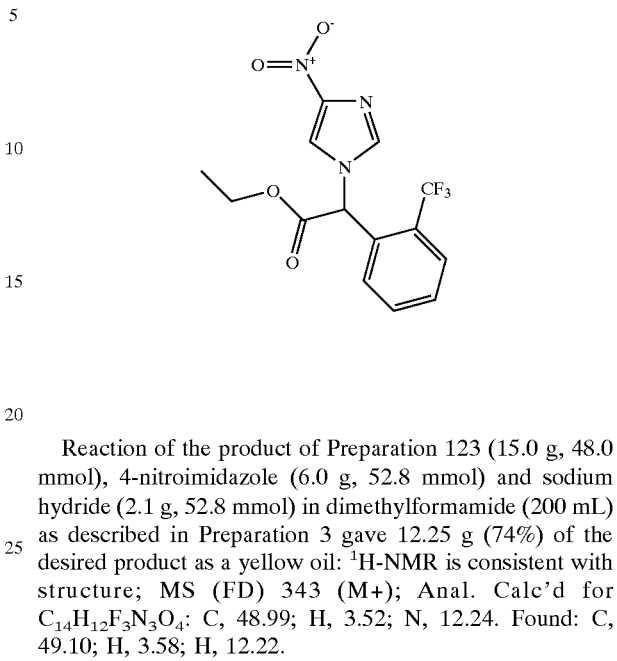

Reaction of the product of Preparation 123 (15.0 g, 48.0 mmol), 4-nitroimidazole (6.0 g, 52.8 mmol) and sodium hydride (2.1 g, 52.8 mmol) in dimethylformamide (200 mL) as described in Preparation 3 gave 12.25 g (74%) of the desired product as a yellow oil: $^1$H-NMR is consistent with structure; MS (FD) 343 (M+); Anal. Calc'd for $C_{14}H_{12}F_3N_3O_4$: C, 48.99; H, 3.52; N, 12.24. Found: C, 49.10; H, 3.58; H, 12.22.

Preparation 125

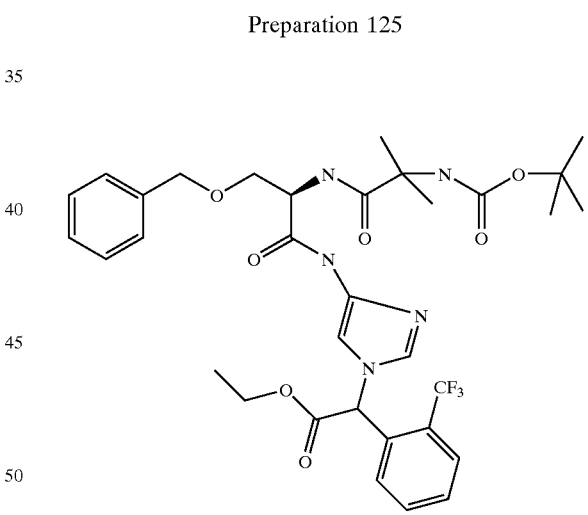

Reaction of the product of Preparation 124 (2.0 g, 5.8 mmol) with 10% palladium on carbon (1.0 g) in tetrahydrofuran (60 mL) under a hydrogen atmosphere followed by coupling with the product of Preparation 1d (2.2 g, 5.8 mmol), 1-hydroxybenzotriazole (0.86 g, 6.4 mmol) and 1-(3-dimethylaminopropyl)-3-ethylcarbodiimide (1.3 g, 6.4 mmol) as described in Preparation 4 gave 3.16 g (93%) of the desired product as a tan foam: $^1$H-NMR is consistent with structure; MS (FD) 675.4 (M+); Anal. Calc'd for $C_{33}H_{40}F_3N_5O_7$: C, 58.66; H, 5.97; N, 10.36. Found: C, 58.81; H, 6.04; N, 10.12.

Preparation 126

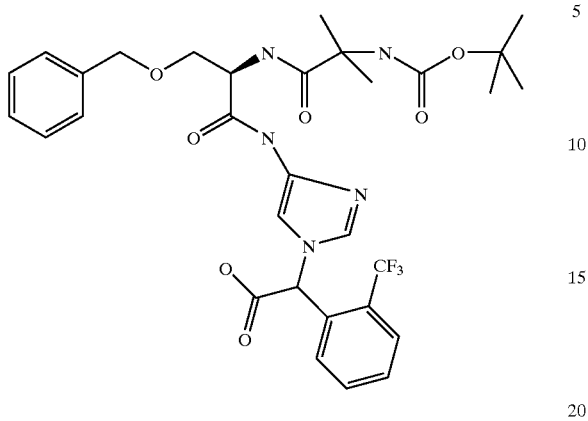

Reaction of the product of Preparation 125 (2.78 g, 4.1 mmol) with lithium hydroxide (0.12 g, 4.9 mmol) in dioxane (40 mL) and water (20 mL) as described in Preparation 5 gave 2.6 g (98%) of the desired product as a yellow foam: $^1$H-NMR is consistent with structure; MS (FD) 648.2 (M+); Anal. Calc'd for $C_{31}H_{36}F_3N_6O_7$: C, 57.49; H, 5.60; N, 10.81. Found: C, 58.06; H, 6.14; N, 10.27.

Example 53

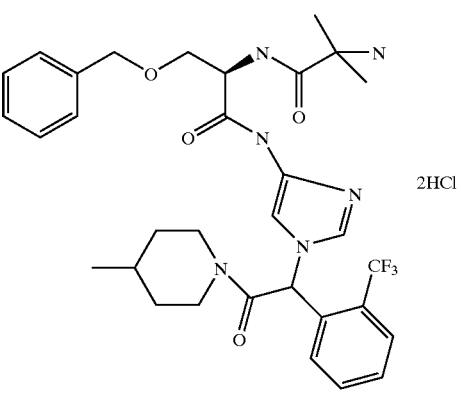

Reaction of the product of Preparation 127 (0.3 g, 0.41 mmol) and trifluoroacetic acid (2 mL) in dichloromethane (6 mL) as described in Example 1 gave 0.28 g (97%) of the desired mixture of isomers as a white solid: $^1$H-NMR is consistent with structure; MS (FD) 628 (M+); Anal. Calc'd for $C_{32}H_{39}F_3N_6O_4 \cdot 2.2HCl$: C, 54.22; H, 5.86; N, 11.85. Found: C, 54.33; H, 5.84; N, 11.56.

Preparation 127

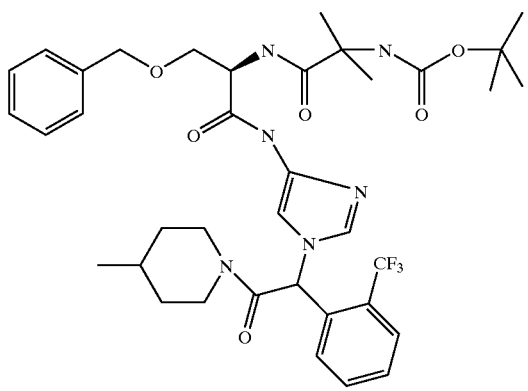

Reaction of the product of Preparation 126 (0.7 g, 1.1 mmol), 4-methylpiperidine (0.13 mL, 1.1 mmol), 1-hydroxybenzotriazole (0.17 g, 1.2 mmol) and 1-(3-dimethylaminopropyl)-3-ethylcarbodiimide (0.25 g, 1.2 mmol) in dimethylformamide (30 mL) as described in Preparation 6 gave 0.32 g (40%) of the desired product as a tan foam: $^1$H-NMR is consistent with structure; MS (FD) 728 (M+); Anal. Calc'd for $C_{37}H_{47}F_3N_6O_6$: C, 60.98; H, 6.50; N, 11.53. Found: C, 60.76; H, 6.59; N, 11.36.

Preparation 128

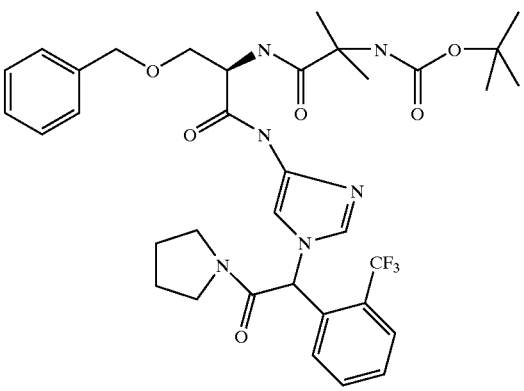

Reaction of the product of Preparation 126 (0.5 g, 0.77 mmol), pyrrolidine (0.07 mL, 0.77 mmol), 1-hydroxybenzotriazole (0.12 g, 0.85 mmol) and 1-(3-dimethylaminopropyl)-3-ethylcarbodiimide (0.18 g, 0.85 mmol) in dimethylformamide 130 mL) as described in Preparation 6 gave 0.2 g (37%) of the desired product as a tan solid: $^1$H-NMR is consistent with structure; MS (FD) 700 (M+); Anal. Calc'd for $C_{35}H_{43}F_3N_6O_6 \cdot 0.4H_2O$: C, 59.38; H, 6.24; N, 11.87. Found: C, 59.17; H, 6.24; N, 11.87.

Example 54

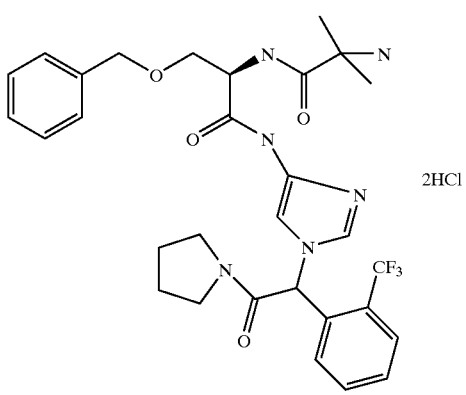

Reaction of the product of Preparation 128 (0.2 g, 0.29 mmol) and trifluoroacetic acid (2 mL) in dichloromethane (6 mL) as described in Example 1 gave 0.18 g (100%) of the desired mixture of isomers as a white solid: $^1$H-NMR is consistent with structure; MS (FD) 600 (M+).

Example 55

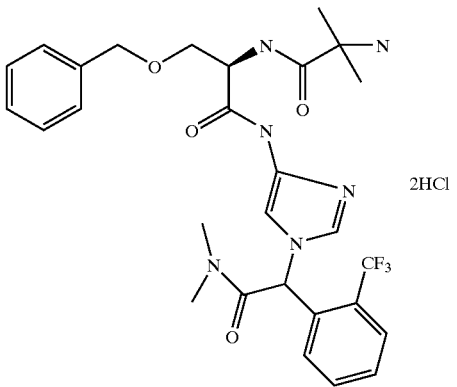

Reaction of the product of Preparation 129 (0.42 g, 0.62 mmol) and trifluoroacetic acid (2 mL) in dichloromethane (6 mL) as described in Example 1 gave 0.3 g (75%) of the desired mixture of isomers as a yellow solid: $^1$H-NMR is consistent with structure; MS (FD) 574 (M+); Anal. Calc'd for $C_{28}H_{33}F_3N_6O_4 \cdot 2.8HCl$: C, 48.70; H, 5.33; N, 12.42. Found: C, 49.84; H, 5.27; N, 12.09.

Preparation 129

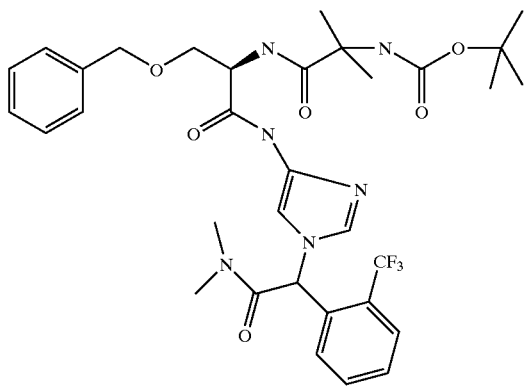

Reaction of the product of preparation 126 (0.75 g, 1.2 mmol), dimethylamine hydrochloride (0.1 g, 1.2 mmol), triethylamine (0.19 g, 1.3 mmol), 1-hydroxybenzotriazole (0.18 g, 1.3 mmol) and 1-(3-dimethylaminopropyl)-3-ethylcarbodiimide (0.27 g, 1.3-mmol) in dimethylformamide (40 mL) as described in Preparation 6 gave 0.49 g (60%) of the desired product as a tan foam: $^1$H-NMR is consistent with structure; MS (FD) 675 (M+); Anal. Calc'd for $C_{33}H_{41}F_3N_6O_6$: C, 58.75; H, 6.13; N, 12.46. Found: C, 58.69; H, 6.12; N, 12.28.

Preparation 130

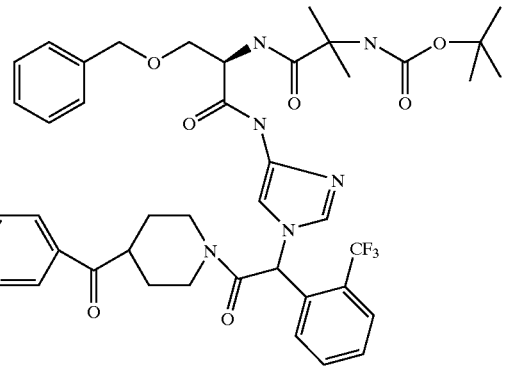

Reaction of the product of Preparation 126 (0.5 g, 0.77 mmol), 4-(4-fluorobenzoyl)piperidine hydrochloride (0.19 g, 0.77 mmol), triethylamine (0.12 mL, 0.85 mmol), 1-hydroxybenzotriazole (0.12 g, 0.85 mmol) and 1-(3-dimethylaminopropyl)-3-ethylcarbodiimide (0.18 g, 0.85 mmol) in dimethylformamide (40 mL) as described in Preparation 6 gave 0.45 g (69%) of the desired product as a yellow foam: $^1$H-NMR is consistent with structure; MS (FD) 836.8 (M+); Anal. Calc'd for $C_{43}H_{48}F_4N_6O_7 \cdot 0.4H_2O$: C, 61.19; H, 5.83; N, 9.96. Found: C, 60.92; H, 5.56; N, 10.09.

Example 56

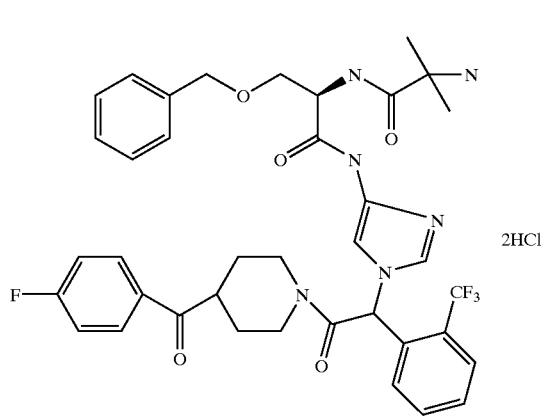

2HCl

Reaction of the product of Preparation 130 (0.4 g, 0.48 mmol) and trifluoroacetic acid (2 mL) in dichloromethane (6 mL) as described in Example 1 gave 0.26 g (67%) of the desired mixture of isomers as a white solid. $^1$H-NMR is consistent with structure; MS (FD) 736.7 (M+); Anal. Calc'd for $C_{39}H_{40}F_4N_6O_5 \cdot 2.1HCl$: C, 56.12; H, 5.22; N, 10.33. Found: C, 56.08; H, 5.46; N, 10.38.

Preparation 131

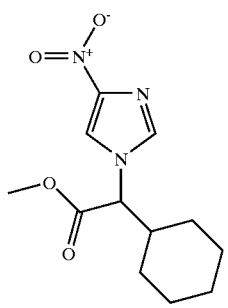

Reaction of alpha-bromocyclohexylacetic acid (5.0 g, 21.0 mmol), 4-nitroimidiazole (2.6 g, 23.1 mmol) and sodium hydride (0.93 g, 23.1 mmol) in dimethylformamide (45 mL) as described in Preparation 3 gave 1.9 g (34%) of the desired product as a clear oil: $^1$H-NMR is consistent with structure; MS (ion spray) 268 (M+1); Anal. Calc'd for $C_{12}H_{17}N_3O_4$: C, 53.92; H, 6.41; N, 15.72. Found: C, 53.63; H, 6.33; N, 15.77.

Preparation 132

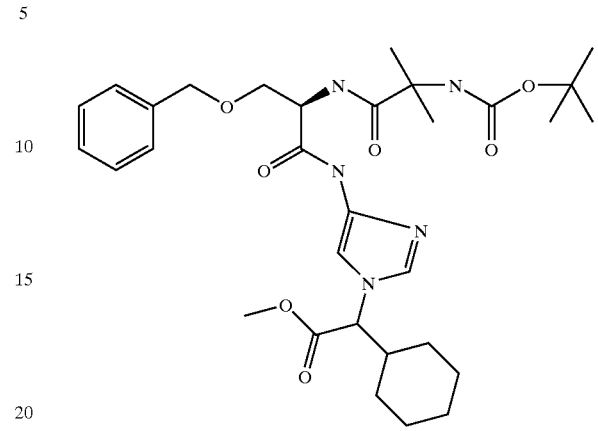

Reaction of the product of Preparation 131 (1.4 g, 5.2 mmol) with 10% palladium on carbon (0.8 g) in tetrahydrofuran (60 mL) under a hydrogen atmosphere followed by coupling with the product of Preparation 1d (2.0 g, 5.2 mmol), 1-hydroxybenzotriazole (0.8 g, 5.7 mmol) and 1-(3-dimethylaminopropyl)-3-ethylcarbodiimide (1.2 g, 5.7 mmol) as described in Preparation 4 gave 2.09 g (65%) of the desired product as a tan foam. $^1$H-NMR is consistent with structure; MS (ion spray) 600.4 (M+1); Anal. Calc'd for $C_{31}H_{45}N_5O_7$: C, 62.08; H, 7.56; N, 11.68. Found: C, 62.04; H, 7.53; N, 11.74.

Preparation 133

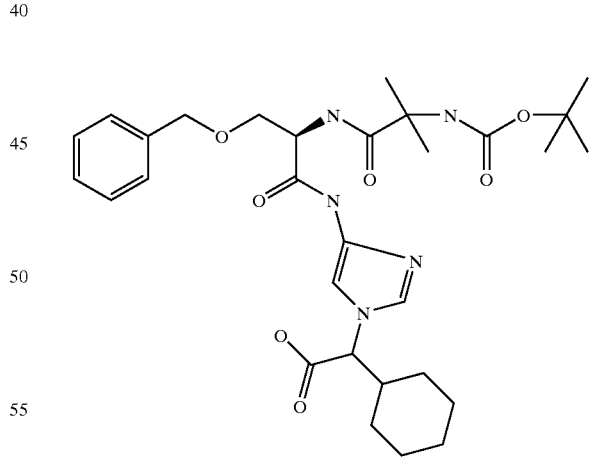

Reaction of the product of Preparation 132 (2.0 g, 3.3 mmol) with lithium hydroxide (0.1 g, 4.0 mmol) in dioxane (50 mL) and water (25 mL) as described in Preparation 5 gave 1.9 g (99%) of the desired product as a tan foam: 1H-NMR is consistent with structure; MS (ion spray) 586.4 (M+1); Anal. Calc'd for $C_{30}H_{43}N_5O_7$: C, 61.52; H, 7.40; N, 11.96. Found: C, 61.41; H, 7.42; N, 11.82.

Preparation 134

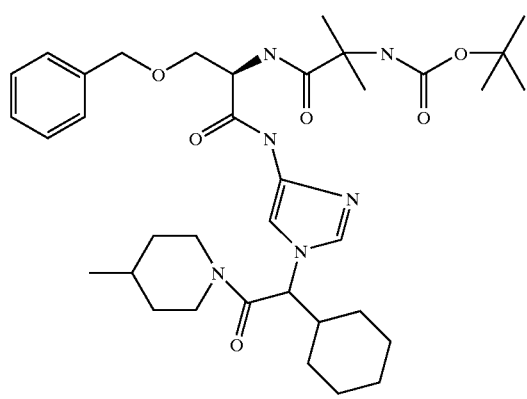

Reaction of the product of Preparation 133 (0.8 g, 1.4 mmol), 4-methylpiperidine (0.17 mL, 1.4 mmol), 1-hydroxybenzotriazole (0.21 g, 1.54 mmol), and 1-(3-dimethylaminopropyl)-3-ethylcarbodiimide (0.32 g., 1.54 mmol) in dimethylformamide (30 mL) as described in Preparation 6 gave 0.92 g (99%) of the desired product as a tan foam: $^1$H-NMR is consistent with structure; MS (ion spray) 667.5 (M+1); Anal. Calc'd for $C_{36}H_{34}N_4O_6$: C, 64.84; H, 8.16; N, 12.60. Found: C, 64.55; H, 7.73, N, 12.26.

Preparation 135

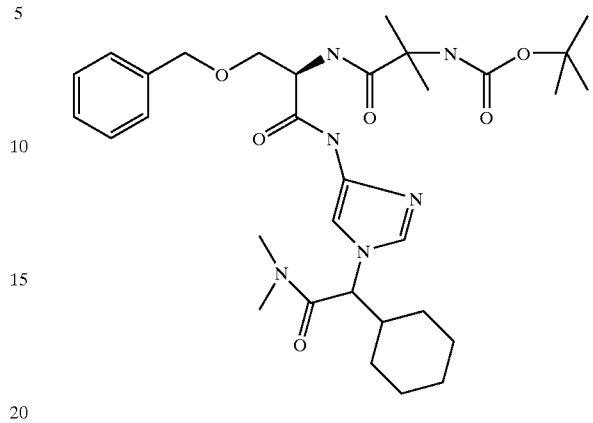

Reaction of the product of Preparation 133 (0.8 g, 1.4 mmol), dimethylamine hydrochloride (0.12 g, 1.4 mmol), triethylamine (0.22 mL, 1.54 mmol), 1-hydroxybenzotriazole (0.21 g, 1.54 mmol) and 1-(3-dimethylaminopropyl)-3-ethylcarbodiimide (0.32 g, 1.54 mmol) in dimethylformamide (30 mL) as described in Preparation 6 gave 0.86 g (100%) of the desired product as a tan foam: $^1$H-NMR is consistent with structure; MS (ion spray) 613.4 (M+1); Anal. Calc'd for $C_{32}H_{48}N_6O_6$: C, 62.72; H, 7.90; N, 13.72. Found: C, 62.44; H, 7.64; N, 13.57.

Example 57

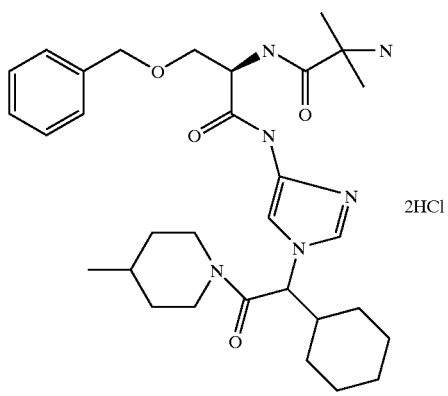

2HCl

Reaction of the product of Preparation 134 (0.7 g, 1.0 mmol) and trifluoroacetic acid (2 mL), in dichloromethane (6 mL) as described in Example 1 gave 0.43 g (64%) of the desired mixture of isomers as a tan solid: $^1$H-NMR is consistent with structure; MS (ion spray) 567.6 (M+1); Anal. Calc'd for $C_{31}H_{46}N_6O_4 \cdot 2HCl$: C, 58.21; H, 7.56; N, 13.14. Found: C, 58.36; H, 7.33; N, 13.19.

Example 58

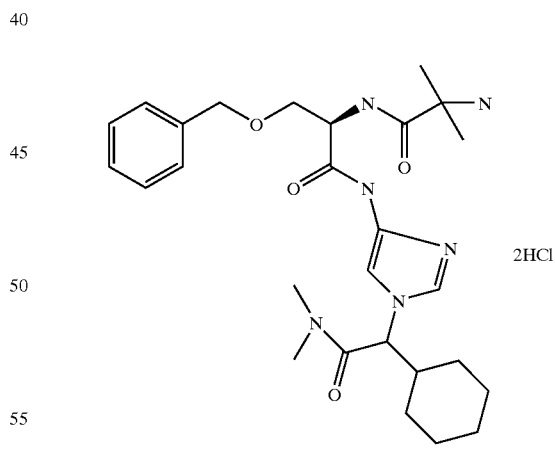

2HCl

Reaction of the product of Preparation 135 (0.7 g, 1.0 mmol) and trifluoroacetic acid (2 mL) in dichloromethane (6 mL) as described in Example 1 gave 0.43 g (64%) of the desired mixture of isomers as a tan solid: $^1$H-NMR is consistent with structure; MS (ion spray) 567.6 (M+1); Anal. Calc'd for $C_{32}H_{46}N_6O_4 \cdot 2HCl$: C, 58.21; H, 7.56; N, 13.14. Found: C, 58.36; H, 7.33; N, 13.19.

Preparation 136

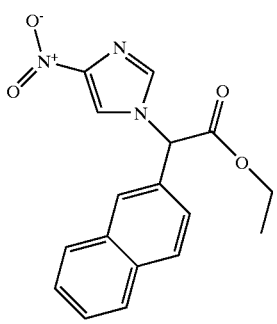

To a suspension of 2-naphthyl acetic acid (49.37 g, 265.0 mmol) in carbon tetrachloride (55 mL) was added and thionyl chloride (80 mL). The mixture was heated to reflux for 20 minutes then cooled to ambient temperature. Carbon tetrachloride (125 mL), N-bromosuccinimide (56.60 g, 318.0 mmol) and hydrobromic acid (48% aq., 0.5 mL) were added. The mixture was heated to reflux for 30 min, cooled to ambient temperature, filtered, and concentrated. The resulting material was dissolved in dichloromethane (200 mL) and excess ethanol (100 mL) was added dropwise. After 1 h, the reaction was concentrated and the resulting crude material was purified by flash chromatography (silica gel, 30% ethyl acetate/hexane) to yield a tan solid. This crude material was dissolved dimethylformamide (200 mL) and 4-nitroimidazole (29.78 g, 263.5 mmol) and potassium carbonate (72.70 g, 526.8 mmol) were added. After 16 h, the reaction was concentrated to 100 mL. Ethyl acetate and water were added and the mixture washed with sodium bicarbonate and brine. The organic layer was dried over sodium sulfate and concentrated. The crude material was was purified by flash chromatography (silica, 30% ethyl acetate/hexane) to yield 40.2 g (47%) of the desired product as a brown foam $^1$H NMR (300 MHz, CDCl$_3$)—consistent with structure; Anal. calcd. for $C_{17}H_{15}N_3O_4$; 62.76 C, 4.65 H, 12.92 N; found 60.54 C, 4.35 H, 12.04 N; ISMS (M+)—326.

Preparation 137

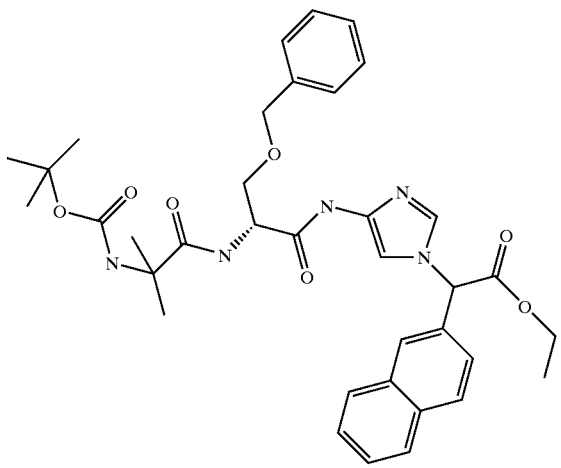

Reaction of the product of Preparation 136 (4.80 g, 14.77 mmol) with 5% palladium on carbon (2.5 g) in tetrahydrofuran (100 mL) under a hydrogen atmosphere followed by coupling with the product of Preparation 1d (5.61 g, 14.77 mmol), EDCI (2–79 g, 16.25 mmol), 1-hydroxybenzotriazole (2.00 g, 14.77 mmol), and N-methylmorpholine (1.6 mL, 14.77 mmol) as described in Preparation 4 gave (6.04 g, 62%) of the desired product as a light orange foam: $^1$H NMR (300 MHz, CDCl$_3$)—consistent with structure; Anal. calcd. for $C_{36}H_{43}N_5O_7$; 65.74 C, 6.59 H, 10.65 N; found 64.02 C, 6.09 H, 10.13 N; ISMS (M+)—658.

Preparation 138

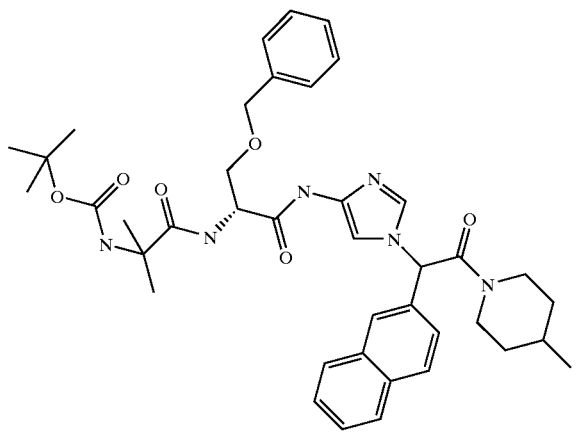

A solution of lithium hydroxide (0.38 g, 9.16 mmol) in water (50 mL) was added to a solution of the product of Preparation 137 (6.04 g, 9.16 mmol) in tetrahydrofuran (100 mL). After 30 min. water was added and the mixture washed with diethyl ether. The aqueous layer was adjusted to pH=3.0 with sodium bisulfate, saturated with sodium chloride, and washed with ethyl acetate. The combined organic extracts were dried over sodium sulfate, and concentrated. To the resulting crude material stirring at room temperature in dimethylformamide (50 mL) was added 1-(3-dimethylaminopropyl)-3-ethylcarbodiimide (2.08 g, 10.01 mmol), 1-hydroxybenzotriazole (1.24 g, 9.16 mmol) and 4-methylpiperidine (1.1 mL, 9.16 mmol). After 18 h, the reaction was quenched with saturated bicarbonate, and washed with ethyl acetate. The combined organic extracts were washed with brine, dried over sodium sulfate, and concentrated. The crude material was purified by flash chromatography (silica gel, 5% methanol/dichloromethane) to yield 4.9 g (75%) of the desired product as a pale yellow foam: $^1$H NMR (300 MHz, CDCl$_3$)—consistent with structure; Anal. calcd. for $C_{40}H_{50}N_6O_6$; 67.58 C, 7.09 H, 11.82 N; found 65.60 C, 7.09 H, 11.50 N; ISMS (M+)—711.

Examples 59 and 60

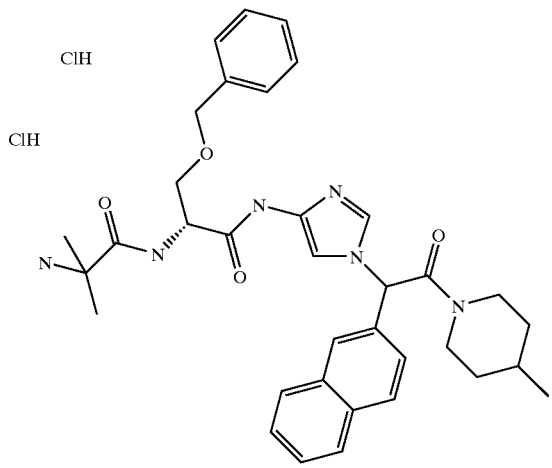

To a solution of of the product of Preparation 138 (4.90 g, 6.89 mmol) stirring at room temperature in dichloromethane (40 mL) and anisole (1.0 mL) was added to trifluoroacetic acid (10 mL). After 3 hours, the reaction was quenched with saturated sodium bicarbonate and extracted with ethyl acetate. The combined organic extracts were washed with brine, dried over sodium sulfate and concentrated. The resulting crude material was purified by flash chromatography. (silica gel, 5% methanol/dichloromethane) to give the product as a mixture of diastereomers. This material was resolved by HPLC (Kromsil CHI-DMP chiral stationary phase, 3A alcohol/dimethylethylamine/heptane eluant) to provide the free amine of the desired products. The individual diastereomers were dissolved in ethyl acetate and treated with a saturated solution of hydrochloric acid in diethyl ether. The resulting precipiate was filtered to yield the desired products (426779–0.64 g, 14%) (426780–0.43 g, 9%) as tan solids:

Example 59

$^1$H NMR (300 MHz, CDCl$_3$)—consistent with structure; Anal. calcd. for $C_{35}H_{44}N_6O_4Cl_2$; 61.49 C, 6.49 H, 12.29 N; found 60.28 C, 6.38 H, 11.74 N; ISMS (M+)—611.

Example 60

$^1$H NMR (300 MHz, CDCl$_3$)—consistent with structure; Anal. calcd. for $C_{35}H_{44}N_6O_4Cl_2$; 61.49 C, 6.49 H, 12.29 N; found 47.81 C, 5.29 H, 9.83 N; ISMS (M+)—611.

Preparation 139

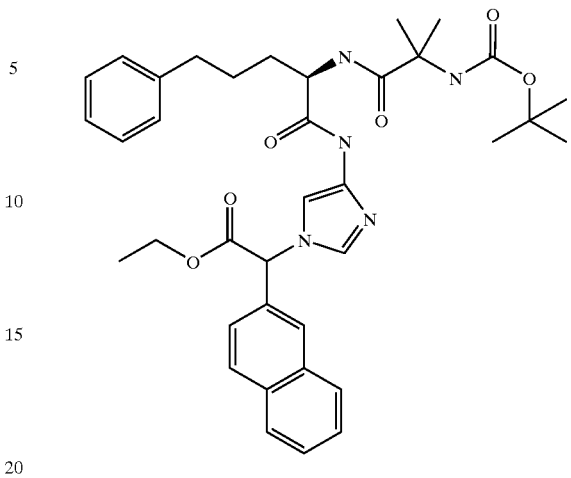

Reaction of the product of Preparation 136 (1.31 g, 4.02 mmol) with 10% palladium on carbon (0.5 g) in tetrahydrofuran (50 mL) under a hydrogen atmosphere followed by coupling with the product of Preparation 1j (1.52 g, 4.02 mmol), 1-hydroxybenzotriazole (0.68 g, 4.42 mmol), and 1-(3-dimethylaminopropyl)-3-ethylcarbodiimide (0.91 g, 4.42 mmol) as described in Preparation 4 to give 1.06 g (38%) of the title compound as a tan solid: $^1$H NMR (d$^6$-DMSO, d): 1.22 (m, 18H), 1.50 (m, 4H), 2.55 (m, 2H), 4.26 (q, J=9.0 Hz, 2H), 4.37 (bs, 1H), 5.75 (s, 1H), 6.60 (s, 1H), 7.02 (bs, 1H), 7.16 (m, 3H), 7.22 (m, 3H), 7.43 (m, 1H), 7.50 (d. J=9.3 Hz, 2H), 7.60 (m, 2H), 7.97 (m, 3H), 10.21 (m, 1H). Ion spray MS (M$^+$+1): 656.

Preparation 140

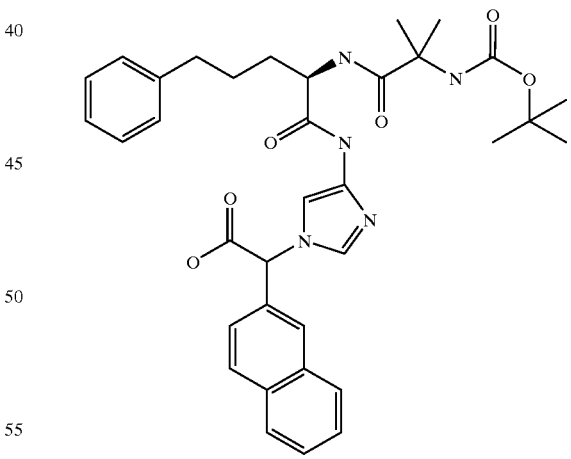

Reaction of the product of Preparation 139 (1.06 g, 1.62 mmol) with lithium hydroxide 75 mg, 1.78 mmol) in dioxane (30 mL) and water (15 mL) as described in Preparation 5 gave 1.01 g (100%) of the title compound as a golden yellow solid: $^1$H NMR (d$^6$-DMSO, d): 1.20 (m, 15H), 1.50 (m, 4H), 2.55 (m, 2H), 4.38 (bs, 1H), 6.58 (s, 1H). 7.02 (bs, 1H), 7.17 (m, 3H), 7.25 (m, 3H), 7.35 (m, 1H), 7.50 (m, 2H), 7.58 (m, 2H), 7.98 (m, 3H), 8.09 (m, 1H), 10.36 (bs, 1H). Ion spray MS (M$^+$+1): 628.

Preparation 141

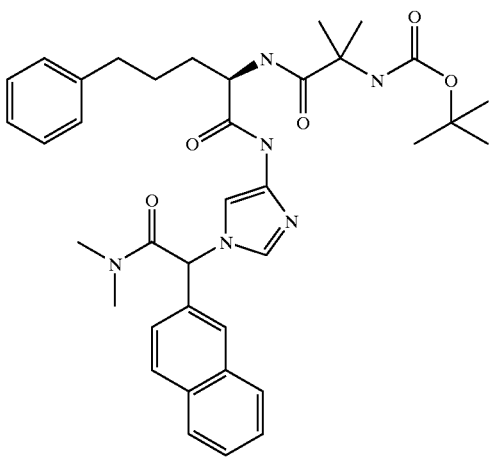

To a solution of the product of Preparation 140 (500 mg, 0.80 mmol) dimethylamine-hydrochloric acid (72 mg, 0.88 mmol), triethylamine (0.12 mL, 0.88 mmol), 1-hydroxybenzotriazole (134 mg, 0.88 mmol) and 1-(3-dimethylaminopropyl)-3-ethylcarbodiimide (18 mg, 0.88 mmol) in dimethylformamide (20 mL) as described in Preparation 6 gave 342 mg (66%) of the title compound as a white solid: $^1$H NMR (d$^6$-DMSO, d): 1.27 (m, 15H), 1.57 (m, 4H), 2.55 (m, 2H), 2.90 (s, 3H), 2.95 (s, 3H), 4.38 (bs, 1H), 6.80 (s, 1H), 7.02 (bs, 1H), 7.15 (m, 3H), 7.22 (m, 3H), 7.35 (m, 1H), 7.47 (m, 2H), 7.57 (m, 2H), 7.88 (s, 1H), 7.98 (m, 3H), 10.15 (bs, 1H). Ion spray MS (M$^+$+1): 655. Anal. (C$_{37}$H$_{46}$N$_6$O$_5$): H, N; C: calcd 67.87; found 66.19.

Example 61

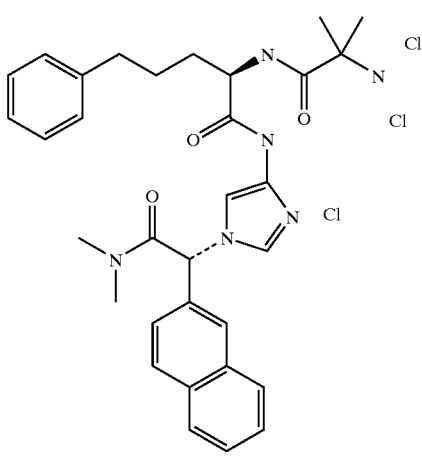

Reaction of the product of Preparation 141 (333 mg, 0.51 mmol) with trifluoroacetic acid (5 mL) in dichloromethane (17 mL) as described in Example 1 gave 52 mg (65%) of a tan solid which was purified by HPLC (Kromasil CHI-DMP chiral stationary phase, 3A alcohol/dimethylethylamine/heptane eluant) to give the free amine which was acidied with hydrochloric acid to provide the desired product: $^1$H NMR (d$^6$-DMSO, d): 1.21 (m, 6H), 1.57 (m, 4H), 2.54 (m, 2H), 2.90 (s, 3H), 2.95 (s, 3H), 4.41 (bs, 1H), 6.82 (s, 1H), 7.02 (bs, 1H), 7.14 (m, 3H), 7.24 (m, 3H), 7.48 (m, 2H), 7.57 (m, 2H), 7.87 (s, 1H), 7.97 (m, 3H), 8.12 (bs, 1H), 10.40 (s, 1H). FAB+ exact MS (M$^+$+1): 555.3084 calcd, 555.3079 found Anal. (C$_{32}$H$_{41}$N$_6$O$_3$Cl$_3$): C, H, N.

Preparation 142

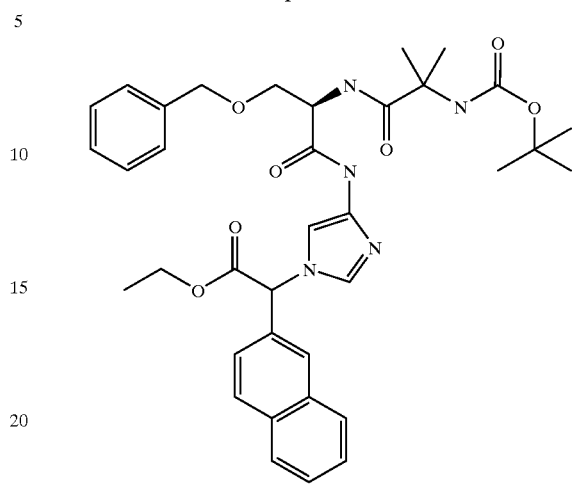

Reaction of the product of Preparation 136 (8.7 g, 27 mmol) with 10% palladium on carbon (4.0 g) under a hydrogen atmosphere followed by coupling with the product of Preparation 1d (10.14 g, 26.7 mmol), 1-hydroxybenzotriazole (4.49 g, 29.3 mmol), and 1-(3-dimethylaminopropyl)-3-ethylcarbodiimide (6.05 g, 29.3 mmol) as described in Preparation 4 gave 5.4 g (31%) of the title compound as a tan solid: $^1$H NMR (d$^6$-DMSO, d): 1.26 (t, J=7.4 Hz, 3H), 1.40 (s, 9H), 1.55 (m, 6H), 3.55 (m, 1H), 4.02 (s, 1H), 4.25 (m, 2H), 4.50 (dd, J=10.0 Hz, 2H), 4.86 (s, 1H), 5.92 (s, 1H), 7.02 (d, J=7.0 Hz, 1H), 7.22 (m, 8H), 7.33 (m, 3H), 7.41 (s, 1H), 7.49 (m, 1H), 7.80 (m, 2H), 9.22 (bs, 1H). Ion spray MS (M$^+$+1): 658. Anal. (C$_{36}$H$_{43}$N$_5$O$_7$): C, H, N.

Preparation 143

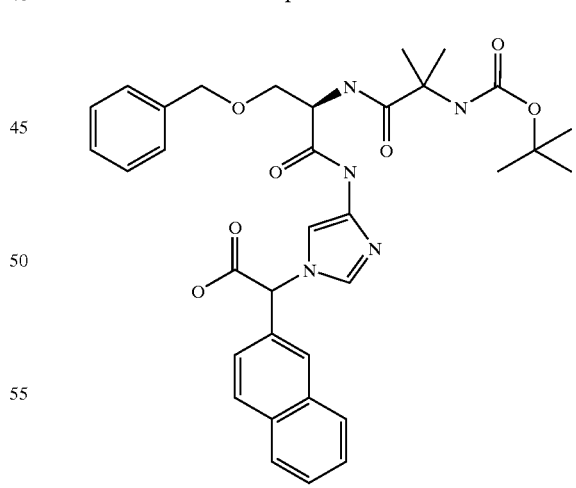

Reaction of the product of Preparation 142 (5.39 g, 8.19 mmol) with lithium hydroxide (361 mg, 8.60 mmol) in dioxane (120 mL) and water (75 mL) as described in Preparation 5 gave 4.92 g (95%) of the title compound as a golden yellow solid: $^1$H NMR (d$^6$-DMSO, d): 1.28 (m, 15H), 3.57 (m, 1H), 3.66 (m, 1H), 4.43 (s, 2H), 4.48 (d, J=5.3 Hz, 1H), 4.56 (bs, 1H), 5.75 (bs, 1H), 7.13 (bs, 1H), 7.26 (m, 6H), 7.31 (d, J=6.0 Hz, 2H), 7.40 (m, 1H), 7.45 (m, 2H), 7.65 (s, 1H), 7.83 (m, 3H), 10.10 (bs, 1H). Ion spray MS (M$^+$+1): 630.

Preparation 144

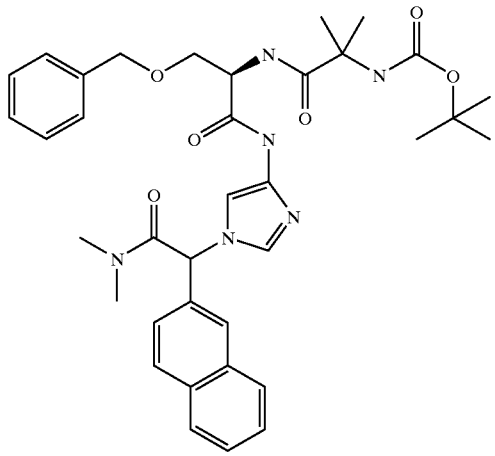

Reaction of the product of Preparation 143 (4.88 g, 7.75 mmol), dimethylamine (4.2 mL, 8.53 mmol, 2.0M in tetrahydrofuran), 1-hydroxy-7-azabenzotriazole (1.16 g, 8.53 mmol) and 1-(3-dimethylaminopropyl)-3-ethylcarbodiimide (1.76 g, 8.53 mmol) in tetrahydrofuran (120 mL) as described in Preparation 6 gave 2.06 g (40%) of the title compound as a yellow foam: 4$^1$H NMR (d$_6$DMSO, d): 1.28 (m, 15H), 2.92 (s, 3H), 2.95 (s, 3H), 3.60 (m, 1H), 4.43(d. J=4.5 Hz), 4.57 (bs, 1H), 6.83 (s, 1H), 7.24 (m, 8H), 7.39 (m, 1H), 7.50 (m, 1H), 7.56 (m, 2H), 7.88 (s, 1H), 7.96 (m, 3H). Ion spray MS (M$^+$+1): 657 Anal. ($C_{36}H_{44}N_6O_4$): H, N; C: calcd 65.84; found 63.70.

Example 62

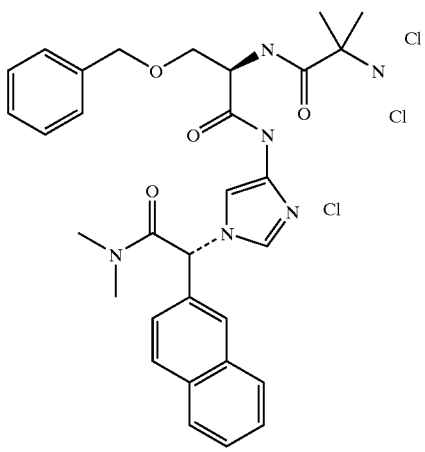

To a solution of glacial acetic acid saturated with dry hydrochloric acid (50 mL, ~3N in hydrochloric acid) stirring at room temperature was added the product of Preparation 144 (1.87 g, 2.85 mmol). After 2 h, the solution was concentrated, washed with aqueous sodium bicarbonate solution, dried over magnesium sulfate and concentrated. The resulting crude material was purified by HPLC (Column) to give 0.5 g of the desired isomer which was dissolved in ethyl acetate and added dropwise to a stirred solution of anhydrous diethyl ether saturated with hydrochloric acid. The resulting white precipitate was collected by filtration and dried to give 474 mg (79%) white solid: $^1$H NMR (d$^6$-DMSO, d): 1.47 (m, 6H), 2.90 (s, 3H), 2.95 (s, 3H), 3.65 (dd, J=9 Hz, 2H), 4.49 (d, J=7.9 Hz, 2H), 4.73 (m, 1H), 6.93 (s, 1H), 7.18 (s, 1H), 7.26 (m, 6H), 7.49 (d, J=8.7 Hz, In), 7.60 (m, 2H), 7.84 (d, J=10.5 Hz, 1H), 7.98 (m, 3H), 8.14 (d, J=9.4 Hz, 2H), 8.45 (d, J=6.8 Hz, 1H), 10.74 (bs, 1H). FAB+ exact MS (M$^+$+1): 557.2876 calculated, 557.2873 found Anal. ($C_{31}H_{39}N_6O_4Cl_3$): H, N; C: calcd, 56.01; found, 56.72.

EXAMPLES PART 2B

Preparation 145

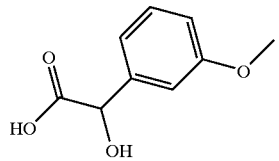

To a solution of m-anisaldehyde, 27.2 g (200 mmol) and benzyltriethylammonium chloride, 2.46 g (10.8 mmol) stirring in chloroform (32 mL) at 56° C. was added sodium hydroxide (50 mL of 50% aqueous solution) dropwise over a period of 2 h keeping the temperature between 54° C. and 58° C. After 1 h, the solution was cooled, then poured into an ice/water mixture. The resulting mixture was washed with ether. The aqueous layers were acidified with 6 N sulfuric acid, then extracted with ether. The organic extracts were washed with brine, dried over sodium sulfate, filtered, and concentrated to yield 36.4 g of an oil which was used without purification.

Preparation 146

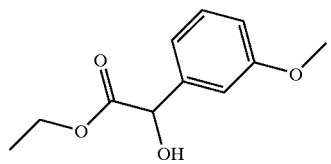

To a solution of the compound of Preparation 145 (36.4 g, 200 mmol) stirring in absolute ethanol (200 mL) was slowly added a solution of concentrated sulfuric acid (20 mL). The resulting mixture was heated to reflux for 5 h then cooled to ambient temperature, poured into an ice/water mixture, and extracted with ether. The combined organic extracts were washed with saturated sodium bicarbonate and brine then dried over sodium sulfate and concentrated. The resulting material was purified by flash chromatography (silica gel, 15% ethyl acetate/hexanes) to give 13.6 g (33% over the two steps) of the desired product an oil: $^1$H-NMR is consistent with structure.

Preparation 147

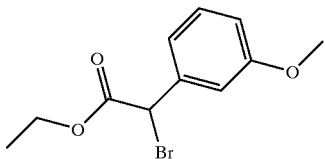

To a solution of the product of Preparation 146 (4.0 g, 19 mmol) stirring in chloroform (50 mL) at 0° C. was added phosphorus tribromide (2.1 mL, 21 mmol). The reaction mixture was a to ambient temperature and stirred for 5 h, then poured into an ice/water mixture and extracted with chloroform. The combined organic extracts were washed with brine, dried over sodium sulfate, filtered and concentrated. The residue was purified by flash chromatography (silica gel, chloroform) to yield 3.9 g (75%) of the desired product as an oil: $^1$H-NMR is consistent with structure; MS (FD) 272, 274 (M+).

Preparation 148

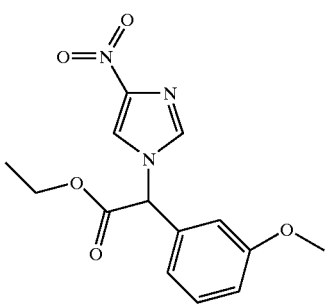

To a slurry of sodium hydride (0.86 g, 20 mmol) stirring in dimethylformamide (30 mL) at room temperature was added 4-nitroimidazole (2.26 g, 20 mmol). The reaction was cooled to 0° C. and 3.9 g (19 mmol) of the product of Preparation 147 was added. After 16 g, the mixture was slowly warming to ambient temperature. The reaction was poured into an ice/water mixture and extracted with ethyl acetate. The combined organic extracts were washed with water, brine, dried over sodium sulfate, and concentrated. The residue was purified by flash chromatography (silica gel, 40% ethyl acetate/hexanes) to yield 0.87 g (15%) of the desired product: $^1$H-NMR is consistent with structure; MS (ion spray) 306 (M+1); Anal. Calc'd for $C_{14}H_{15}N_3O_5$: C, 55.08; H, 4.95; N, 13.76. Found: C, 55.63; H, 4.99; N, 12.98.

Preparation 149

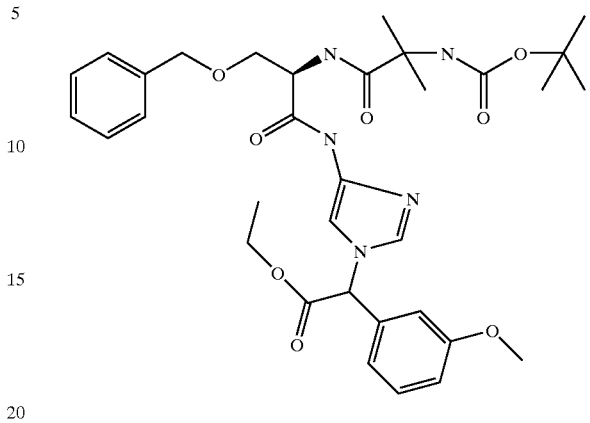

To a slurry of 10% palladium on carbon (2.26 g, 20 mmol) in tetrahydrofuran was added a solution of the product of Preparation 148 (1.21 g, 3.96 mmol) in tetrahydrofuran (20 mL). The mixture was reacted under a hydrogen atmosphere (40 psi) on a Parr apparatus for 3 h and subsequently filtered through celite. To this solution was added of the product of Preparation 1d (1.5 g, 3.96 mmol), 1-hydroxybenzotriazole (0.59 g, 4.35 mmol) and 1-(3-dimethylaminopropyl)-3-ethylcarbodiimide (0.9 g, 4.35 mmol). After 16 h, the reaction mixture was filtered and concentrated. The resulting residue was purified by flash chromatography (silica gel, chloroform to 1% methanol/chloroform gradient) to yield 2.24 g (89%) of the desired product: $^1$H-NMR is consistent with structure; MS (ion spray) 638.4 (M+1); Anal. Calc'd for $C_{33}H_{43}N_5O_8$: C, 62.15; H, 6.80; N, 10.98. Found: C, 61.47; H, 6.41; N, 11.09.

Preparation 150

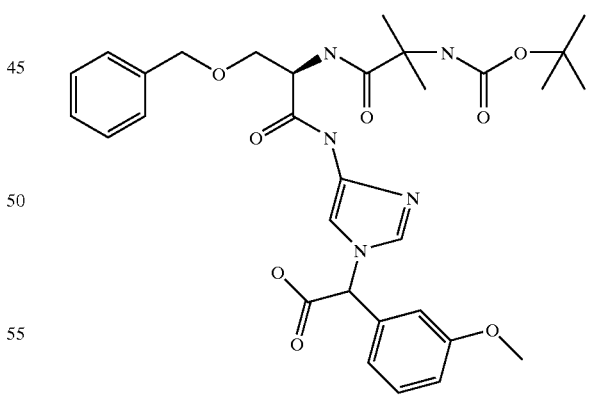

To a solution of the product of Preparation 149 (2.19 g, 3.4 mmol) stirring in dioxane (50 mL) at room temperature was added a solution of lithium hydroxide (0.1 g, 4.08 mmol) in water (35 mL). After 15 min, the reaction was acidified to pH=3.0 with 1 N hydrochloric acid and extracted with ethyl acetate. The combined organic extracts were washed with brine, dried over sodium sulfate, filtered and concentrated to yield 2.0 g (95%) of the desired product as a tan foam: ¹H-NMR is consistent with structure; MS (ion spray) 610 (M+1); Anal. Calc'd for $C_{31}H_{39}N_5O_8$·1.2-dioxane: C, 60.10; H, 6.85; N, 9.79. Found: C, 59.78; H, 6.58; N, 10.14.

Preparation 151

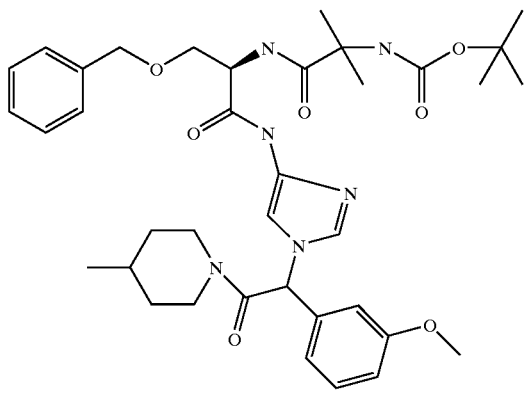

To a solution of the product of Preparation 150 (0.6 g, 1.0 mmol) was added of 4-methylpiperidine (0.12 mL, 1.0 mmol), 1-hydroxybenzotriazole (0.15 g, 1.1 mmol) and 1-(3-dimethylaminopropyl)-3-ethylcarbodiimide (0.23 g, 1.1 mmol). After 16 h. the reaction mixture was concentrated, slurried in ethyl acetate and filtered. Water was added and the mixture was extracted with ethyl acetate. The combined organic extracts were washed with brine, dried over sodium sulfate, filtered and concentrated. The residue was purified by flash chromatography (silica gel, 4% methanol/chloroform) to yield 0.46 g (67%) of the desired product as a white foam: ¹H-NMR is consistent with structure; MS (ion spray) 691.3 (M+1); Anal. Calc'd for $C_{37}H_{50}N_6O_7$: C, 64.33; H, 7.29; N, 12.16. Found: C, 64.07; H, 7.29; N, 12.34.

Examples 63 and 64

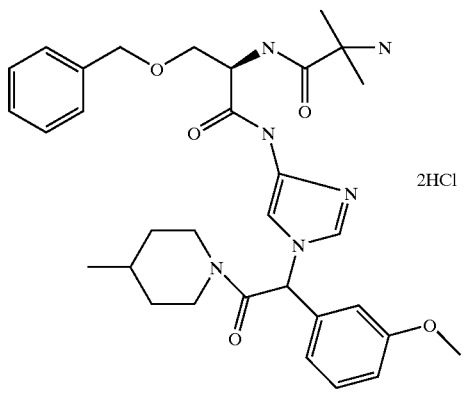

To a solution of the product of Preparation 151 (0.37 g, 0.53 mmol) stirring in dichloromethane (6 mL) at room temperature was added trifluoroacetic acid (2 mL). After 1 h, the reaction mixture was poured into a solution of saturated sodium bicarbonate. The mixture was extracted with chloroform. The combined organic extracts were washed with brine, dried over sodium sulfate, filtered, and concentrated. The residue was dissolved in ethyl acetate and this solution was acidified with a saturated solution of hydrochloric acid in ether. The resulting slurry was concentrated to yield 0.3 g (86%) of the desired product: ¹H-NMR is consistent with structure; MS (ion spray) 591.6 (M+1); Anal. Calc'd for $C_{32}H_{42}N_6O_5$·2.2HCl: C, 57.29; H, 6.64; N, 12.53. Found: C, 57.18; H, 6.54; N, 12.23. 0.14 g (0.2 mmol) of the free base was sent for chiral separation. Resolution of the diastereomers by HPLC gave two products:

Example 63

Isomer 1

To the solution of the purified isomer in ethyl acetate was added a saturated solution of hydrochloric acid in ether. The resulting slurry was concentrated to yield 0.04 g (28%) of the desired isomer as a white solid: ¹H-NMR is consistent with structure; $t_R$=6.92 min; MS (high res) Calc'd for $C_{32}H_{43}N_6O_5$: 591.3295. Found: 591.3299. Anal. Calc'd for $C_{32}H_{43}N_6O_5$·2.2HCl: C, 57.29; H, 6.64; N, 12.53. Found: C, 57.29; H, 6.25; N, 12.37.

Example 64

Isomer 2

To the solution of the purified isomer in ethyl acetate was added a saturated solution of hydrochloric acid in ether. The resulting slurry was concentrated to yield 0.03 g (21%) of the desired isomer as a tan foam: ¹H-NMR is consistent with structure; $t_R$=9.64 min; MS (high res) Calc'd for $C_{32}H_{43}N_6O_5$: 591.3295. Found: 591.3288.

Preparation 152

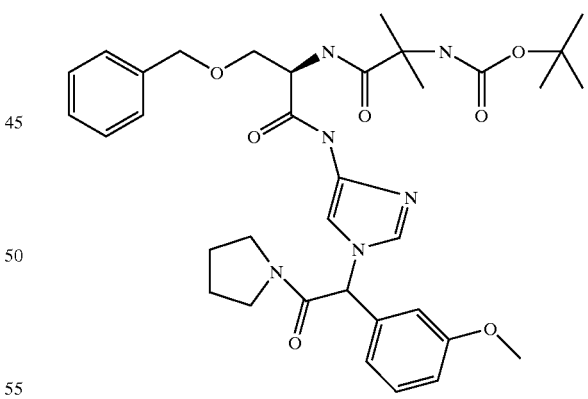

To a solution of the product of Preparation 150 (0.6 g, 1.0 mmol), pyrrolidine (0.8 mL, 1.0 mmol), 1-hydroxybenzotriazole (0.15 g, 1.1 mmol), 1-(3-dimethylaminopropyl)-3-ethylcarbodiimide (0.23 g, 1.1 mmol), in dimethylformamide (20 mL) as described in Preparation 150 gave 0.42 g (64%) of the desired product as a white foam: ¹H-NMR is consistent with structure; MS (ion spray) 663.4 (M+1); Anal. Calc'd for $C_{35}H_{46}N_6O_7$: C, 63.43; H, 7.00; N, 12.68. Found: C, 63.39; H, 6.97; N, 12.58.

Example 65

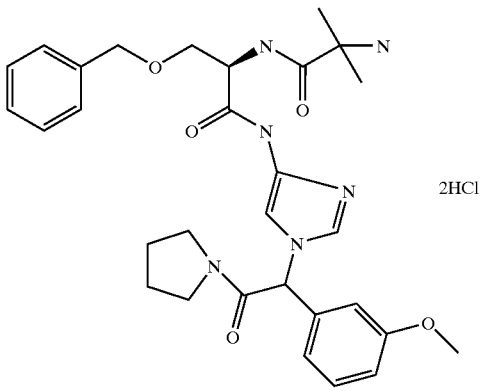

2HCl

To a solution of the product of Preparation 152 (0.35 g, 0.53 mmol) and trifluoroacetic acid (2 mL) in dichloromethane (6 mL) as in described in Example 63 gave 0.23 g (68%) of the desired product as a white solid: ¹H-NMR is consistent with structure; MS (ion spray) 563.5 (M+1); Anal. Calc'd for $C_{30}H_{38}N_6O_5 \cdot 2.3HCl$: C, 55.73; H, 6.28; N, 13.00. Found: C, 55.97; H, 6.18; N, 12.87.

Preparation 153

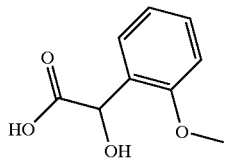

To a solution of 2-anisaldehyde (13.5 g, 100 mmol), benzyltriethylammonium chloride (1.23 g, 5 mmol), chloroform (16 mL) and 50% sodium hydroxide (25 mL) as described Preparation 145 gave 15.0 g of the desired product as an oil which was carried without further purification.

Preparation 154

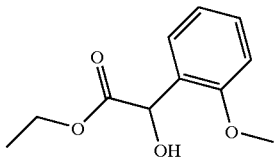

To a solution of the product of Preparation (15.04 g, 83 mmol), concentrated sulfuric acid (10 mL) and absolute ethanol (100 mL) as described in Preparation 146 gave 8.1 g (38% over the two steps) of the desired product as an oil: ¹H-NMR is consistent with structure; MS (FD) 210 (M+).

Preparation 155

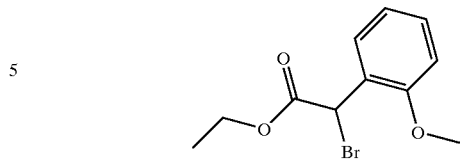

To a solution of the product of Preparation (4.0 g, 19 mmol), phosphorus tribromide (2.05 mL, 20 mmol) and chloroform (50 mL) as described in Preparation 147 gave 4.9 g (95%) of the desired product: ¹H-NMR is consistent with structure; MS (FD) 272, 274 (M+).

Preparation 156

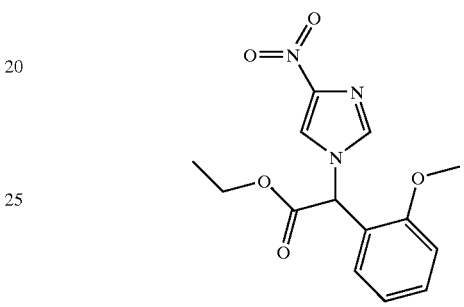

Reaction of the product of Preparation 155 (5.18 g, 19.0 mmol), 4-nitroimidazole (2.37 g, 20.9 mmol) and sodium hydride (0.84 g, 20.9 mmol) in dimethylformamide (50 mL) as described in Preparation 148 gave 5.8 g (100%) of the desired product as a colorless oil which solidifies upon standing: ¹H-NMR is consistent with structure; MS (FD) 305 (M+); Anal. Calc'd for $C_{14}H_{15}N_3O_5$: C, 55.08; H, 4.95; N, 13.76. Found: C, 54.87; H, 4.96; N, 13.47.

Preparation 157

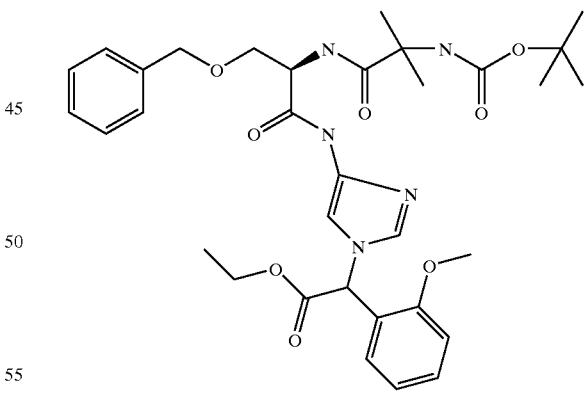

Reduction of the product of Preparation 156 (1.8 g, 5.8 mmol), 10% palladium on carbon (0.9 g) in tetrahydrofuran (80 mL) followed by coupling with the product of Preparation 1d (2.2 g, 5.8 mmol), 1-hydroxybenzotriazole (0.86 g, 6.4 mmol), and 1-(3-dimethylaminopropyl)-3-ethylcarbodiimide (1.3 g, 6.4 mmol), as described in Preparation 149 gave 2.0 g (54%) of the desired compound as a tan foam: ¹H-NMR is consistent with structure; MS (FD) 637 (M+); Anal. Calc'd for $C_{33}H_{43}N_5O_8 \cdot 0.2H2O$: C, 61.80; H, 6.82; N, 10.92. Found: C, 61.65; H, 6.93; N, 11.12.

Preparation 158

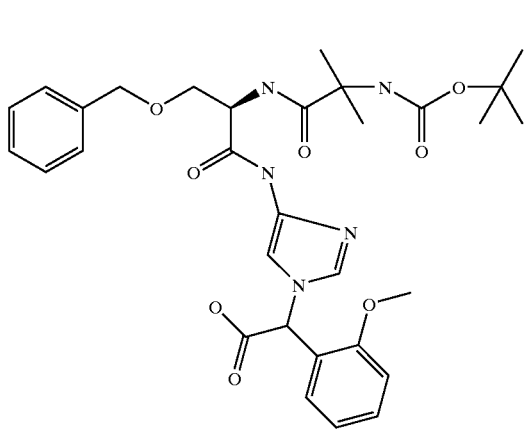

Reaction of the product of Preparation 157 (1.95 g, 3.0 mmol) and lithium hydroxide (0.09 g, 3.6 mmol) in dioxane (40 mL) and water (20 mL) as described in Preparation 150 gave 1.72 g (94%) of the desired product as a white foam: $^1$H-NMR is consistent with structure; MS (FD) 610 (M+).

Example 66

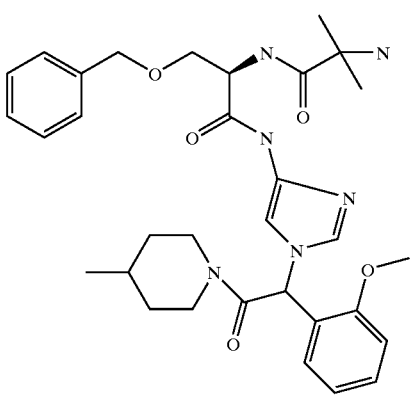

Reaction of the product of Preparation 159 (0.4 g; 0.58 mmol) and trifluoroacetic acid (2 mL) in dichloromethane (6 mL) as described in Example 63 gave 0.3 g (79%) of the desired product as a white solid: $^1$H-NMR is consistent with structure; MS (high res) Calc'd for $C_{32}H_{43}N_6O_5$: 591.3295. Found: 591.3298. Anal. Calc'd for $C_{32}H_{42}N_6O_5 \cdot 2HCl$: C, 57.92; B. 6.68; N, 12.66. Found: C, 57.27; H, 6.24; N, 11.82.

Preparation 159

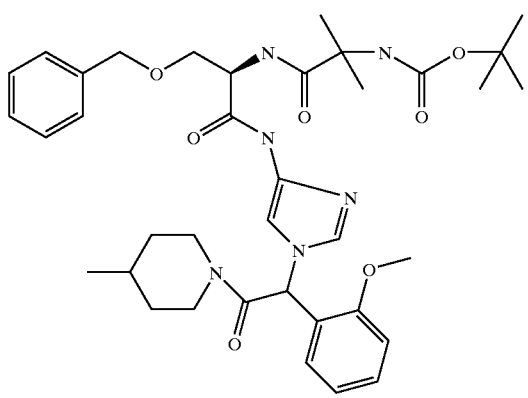

Reaction of the product of Preparation 158 (0.5 g, 0.82 mmol), 4-methylpiperidine (0.1 mL, 0.82 mmol), 1-hydroxybenzotriazole (0.12 g, 0.9 mmol), and 1-(3-dimethylaminopropyl)-3-ethylcarbodiimide (0.19 g, 0.9 mmol) in dimethylformamide (40 mL) as described in Preparation 151 gave 0.45 g (80%) of the desired product as a tan foam: $^1$H-NMR is consistent with structure; MS (FD) 690 (M+); Anal. Calc'd for $C_{37}H_{50}N_6O_7$: C, 64.33; H, 7.30; N, 12.16. Found: C, 64.32; H, 7.21; H, 11.97.

Preparation 160

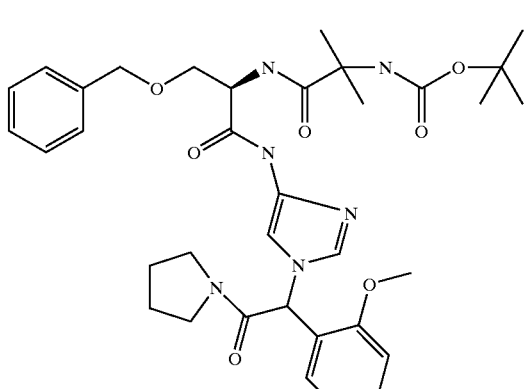

Reaction of the product of Preparation 158 (0.5 g, 0.82 mmol), pyrrolidine (0.07 mL), 1-hydroxybenzotriazole (0.12 g 0.9 mmol) and 1-(3-dimethylaminopropyl)-3-ethylcarbodiimide (0.19 g, 0.9 mmol) in dimethylformamide (40 mL as described in Preparation 151 gave 0.35 g (65%) of the desired product as a tan foam: $^1$H-NMR is consistent with structure; MS (FD) 662 (M+); Anal. Calc'd for $C_{35}H_{46}N_6O_7$: C, 63.43; H, 7.00; N, 12.68. Found: C, 63.26; H, 6.94; N, 12.43.

Example 67

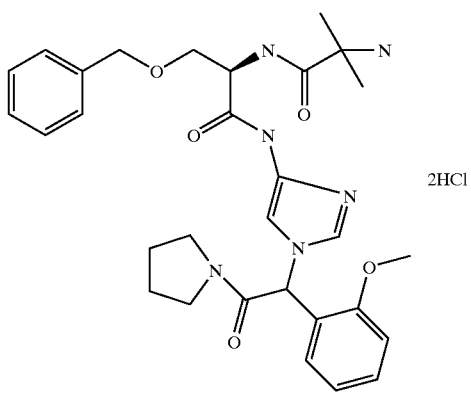

2HCl

Reaction of the product of Preparation 160 (0.3 g, 0.4 mmol) and trifluoroacetic acid (2 mL) in dichloromethane (6 mL) as described in Example 63 gave 0.24 g (96%) of the desired product as a white solid: $^1$H-NMR is consistent with structure; MS (high res) Calc'd for $C_{30}H_{39}N_6O_5$: 563.2982. Found: 563.2989. Anal. Calc'd for $C_{30}H_{38}N_6O_5 \cdot 2.4HCl$: C, 55.42; H, 6.26; N, 12.93. Found: C, 55.51; H, 6.10; N, 12.30.

Preparation 161

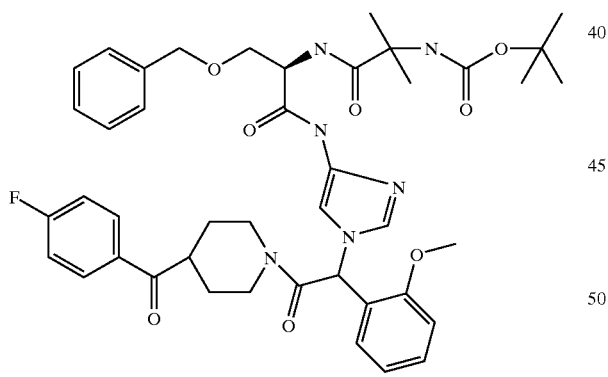

Reaction of the product of Preparation 158 (0.5 g, 0.82 mmol), 4-(4-fluorobenzoyl)piperidine hydrochloride (0.2 g, 0.82 mmol), triethylamine (0.13 mL, 0.9 mmol), 1-hydroxybenzotriazole (0.12 g, 0.9 mmol) and 1-(3-dimethylaminopropyl)-3-ethylcarbodiimide (0.19 g, 0.9 mmol) in dimethylformamide (40 mL) as described in Preparation 151 gave 0.41 g (62%) of the desired product as a white foam: $^1$H-NMR is consistent with structure; MS (FD) 799 (M+); Anal. Calc'd for $C_{43}H_{51}FN_6O_8$: C, 64.65; H, 6.43; N, 10.52. Found: C, 64.44; H, 6.56; N, 10.53.

Example 68

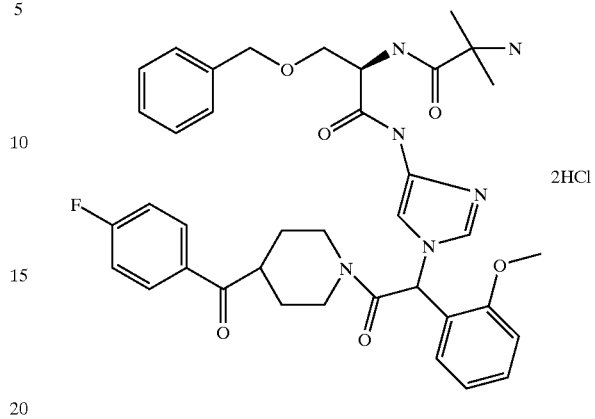

2HCl

Reaction of the product of Preparation 161 (0.36 g, 0.45 mmol) and trifluoroacetic acid (2 mL) in dichloromethane (6 mL) as described in Example 63 gave 0.26 g (74%) of the desired product as a white solid: $^1$H-NMR is consistent with structure; MS (FD) 699 (M+); Anal. Calc'd for $C_{38}H_{43}FN_6O_6 \cdot 2HCl$: C, 59.14; H, 5.88; N, 10.89: Found: C, 59.36; H, 5.99; N, 10.80.

Preparation 162

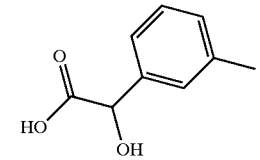

Reaction of 3-tolylbenzaldehyde (12 g, 100 mmol), benzyltriethylammonium chloride (1.23 g, 5 mmol), chloroform (16 mL) and 50% sodium hydroxide (25 mL) as described in Preparation 145 gave 16.2 g of an oil which was used without purification.

Preparation 163

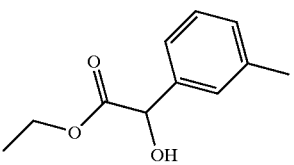

Reaction of the product of Preparation 162 (16.2 g, 98 mmol), conc. sulfuric acid (10 mL) and absolute ethanol (100 mL) an described in Preparation 146 gave 10.8 g (52% over the two steps) of the desired product as an oil: $^1$H-NMR is consistent with structure; MS (FD) 194 (M+).

Preparation 164

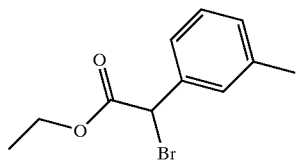

Reaction of the product of Preparation 163 (4.85 g, 25 mmol), phosphorus tribromide (2.65 mL, 27.5 mmol) and chloroform (50 mL) as described in Preparation 147 gave 3.71 g (58%) of the desired product as an oil: 1H-NMR is consistent with structure; MS (FD) 256 (M+).

Preparation 164

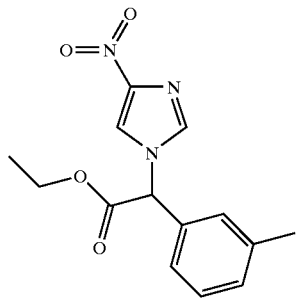

Reaction of the product of Preparation 164 (3.7 g, 14.4 mmol), 4-nitroimidazole (1.8 g, 15.9 mmol) and sodium hydride (0.64 g, 15.9 ml) in dimethylformamide (30 mL) as described in Preparation 148 gave 3.2 g (77%) of the desired product as an oil: $^1$H-NMR is consistent with structure; MS (FD) 289 (M+); Anal. Calc'd for $C_{14}H_{15}N_3O_4$: C, 58.13; H, 5.23; N, 14.52. Found: C, 58.18; H, 5.53; N, 14.89.

Preparation 165

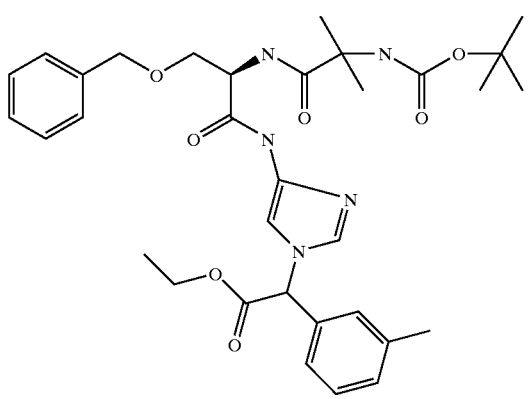

Reduction of the product of Preparation 164 (1.15 g, 4.0 mmol), 5% palladium on carbon (0.57 g) in tetrahydrofuran (30 mL) followed by coupling with the product of Preparation 1d (1.5 g, 4.0 mmol), 1-hydroxybenzotriazole (0.6 g, 4.4 mmol) and 1-(3-dimethylaminopropyl)-3-ethylcarbodiimide (0.9 g, 4.4 mmol) as described in Preparation 149 gave 2.24 g (90%) of the desired product: $^1$H-NMR is consistent with structure; MS (FD) 621 (M+); Anal. Calc'd for $C_{33}H_{43}N_5O_7$: C, 63.75; H, 6.97; N, 11.26. Found: C, 63.69; H, 7.06; N, 11.27.

Preparation 166

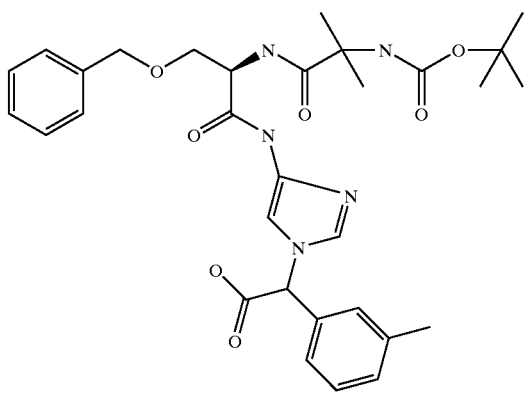

Reaction of the product of Preparation 165 (2.0 g, 3.3 mmol) with lithium hydroxide (0.088 g, 3.64 mmol) in dioxane (20 mL) and water (10 mL) as described in Preparation 150 gave 1.95 g (100%) of the desired product: $^1$H-NMR is consistent with structure; MS (FD) 594 (M+); Anal. Calc'd for $C_{3}H_{39}N_5O_7 \cdot 1H_2O$: C, 61.59; H, 6.93; N, 10.38. Found: C, 61.26; H, 6.86; N, 10.77.

Preparation 167

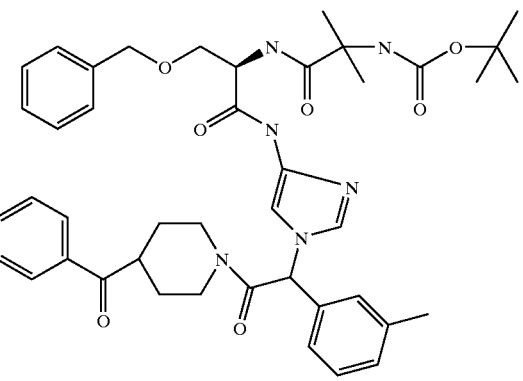

Reaction of the product of Preparation 166 (0.6 g, 1.0 mmol), (0.7 g, 4-(4-fluorobenzoyl)piperidine hydrochloride (0.24 g, 1.0 mmol), triethylamine (0.1 g, 1.0 mmol), 1-hydroxybenzotriazole (0.15 g, 1.1 mmol) and 1-(3-dimethylaminopropyl)-3-ethylcarbodiimide (0.23 g, 1.1 mmol), in dimethylformamide (13 mL) as described in Preparation 151 gave 0.7 g (90%) of the desired product: $^1$H-NMR is consistent with structure; MS (FD) 782 (M+); Anal. Calc'd for $C_{43}H_{51}FN_6O_7$: C, 65.97; H, 6.57; N, 10.73. Found: C, 66.01; H, 6.54; N, 10.52.

Examples 69 and 70

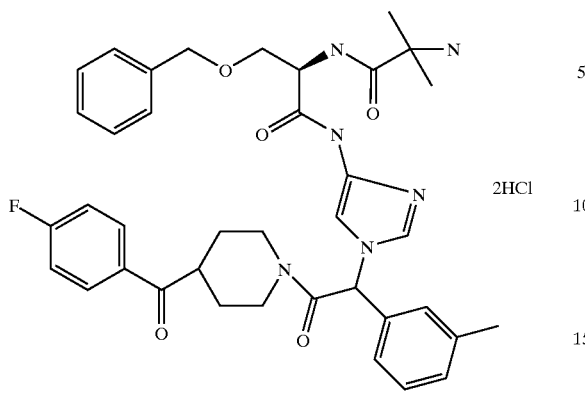

Reaction of the product of Preparation 167 (0.47 g, 0.6 mmol) with trifluoroacetic acid (4 mL) in dichloromethane (12 mL) as described Example 63 gave 0.44 g (98%) of the desired product as a foam: $^1$H-NMR is consistent with structure; MS (ion spray) 682.2 (M+1); Anal. Calc'd for $C_{38}H_{43}FN_6O_5 \cdot 2.55HCl$: C, 59.22; H, 5.94; N, 10.90. Found: C, 58.84; H, 5.94; N, 10.73. Resolution of the diastereomers (0.25 g, 0.37 mmol) by chiral HPLC gave the individual isomers:

Example 69

Isomer 1

0.069 g (27%) of the desired isomer as the free base. $^1$H-NMR is consistent with structure; $t_R$=5.2 min; MS (ion spray) 683.4 (M+1).

Example 70

Isomer 2

0.065 g (26%) of the desired isomer as the free base. $^1$H-NMR is consistent with structure; $t_R$=6.5 min; MS (ion spray) 683.4 (M+1); Anal. Calc'd for $C_{38}H_{43}FN_6O_5 \cdot 0.1H_2O$: C, 63.48; H, 6.17; N, 11.68. Found: C, 63.07; H, 6.07; N, 11.39.

Preparation 168

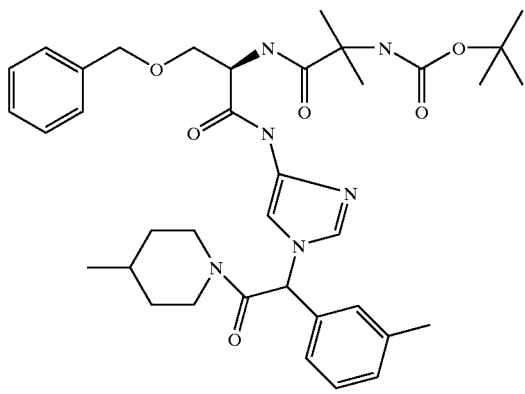

Reaction of the product of Preparation 166 (0.59 g, 1.0 mmol), 4-methylpiperidine (0.099 g, 1.0 mmol), 1-hydroxybenzotriazole (0.15 g, 1.1 mmol) and 1-(3-dimethylaminopropyl)-3-ethylcarbodiimide (0.23 g, 1.1 mmol) in dimethylformamide (13 mL) as described in Preparation 151 gave 0.67 g (100%) of the desired product as a foam: $^1$H-NMR is consistent with structure; MS (ion spray) 675 (M+1); Anal. Calc'd for $C_{27}H_{50}N_6O_6$: C, 65.85; H, 7.47; N, 12.45. Found: C, 66.09; H, 7.23; N, 12.53.

Examples 71 and 72

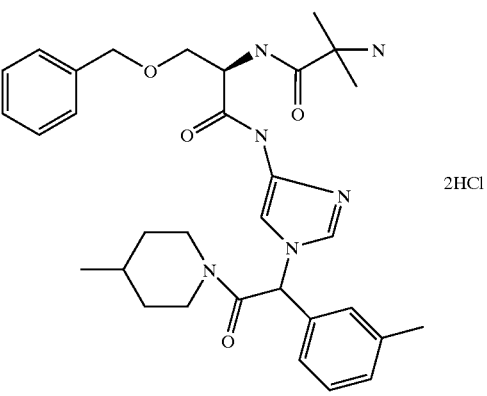

Reaction of the product of Preparation 168 (0.51 g, 0.76 mmol) with trifluoroacetic acid (4 mL) in dichloromethane (12 mL) as described in Example 63 gave 0.42 g (86%) of the desired product; $^1$H-NMR is consistent with structure; MS (ion spray) 574.1 (M+1); Anal. Calc'd for $C_{32}H_{42}N_6O_4 \cdot 2.25HCl$: C, 58.52; H, 6.79; N, 12.80. Found: C, 58.54; H, 6.68; N, 12.80. Resolution of the diastereomers (0.173 g, 0.32 mmol) by chiral HPLC gave the individual isomers which were individually treated with a saturated solution of hydrochloric acid in diethyl ether to give the desired products:

Example 71

Isomer 1

$^1$H-NMR is consistent with structure; $t_R$=6.22 min; MS (ion spray) 575.4 (M+1); Anal. Calc'd for $C_{32}H_{42}N_6O_4 \cdot 2.3HCl$: C, 58.36; H, 6.78; N, 12.76. Found: C, 58.23; H, 6.57; N, 12.53.

Example 72

Isomer 2

$^1$H-NMR is consistent with structure; $t_R$=8.53 min; MS (ion spray) 575.4 (M+1); Anal. Calc'd for $C_{32}H_{42}N_6O_4 \cdot 2.55HCl$: C, 57.56; H, 6.73; N, 12.59. Found: C, 57.95; H, 6.91; N, 12.29.

Preparation 169

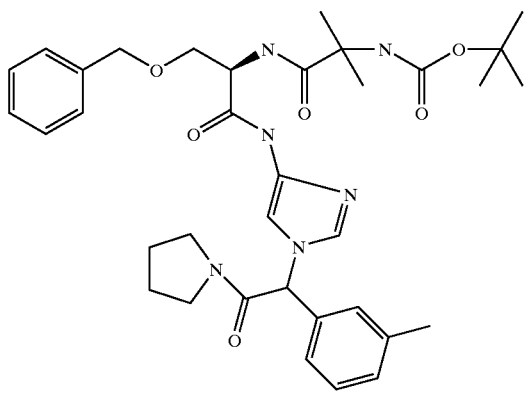

Reaction of the product of Preparation 166 (0.59 g, 1.0 mmol), pyrrolidine (0.071 g, 1.0 mmol), 1-hydroxybenzotriazole (0.15 g, 1.1 mmol) and 1-(3-dimethylaminopropyl)-3-ethylcarbodiimide (0.23 g, 1.1 ml) in dimethylformamide (13 mL) as described in Preparation 151 gave 0.57 g (88%) of the desired product: $^1$H-NMR is consistent with structure; MS (ion spray) 646 (M+1); Anal. Calc'd for $C_{35}H_{46}N_6O_6$: C, 65.00; H, 7.17; N, 12.99. Found: C, 64.95; H, 6.98; N, 13.19.

Example 73

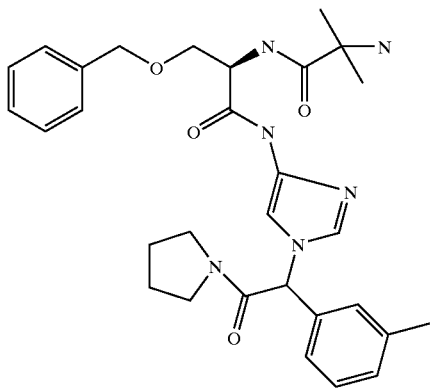

Reaction of the product of Preparation 170 (0.55 g, 0.85 mmol) and trifluoroacetic acid (4 mL) in dichloromethane (12 mL) as described in ale 63 gave 0.37 g (70%) of the desired product: $^1$H-NMR is consistent with structure; MS (ion spray) 546.1 (M+1); Anal. Calc'd for $C_{30}H_{38}N_6O_4 \cdot 2.4HCl$: C, 56.79; H, 6.42; N, 13.24. Found: C, 56.81; H, 6.35; N, 13.10.

Preparation 170

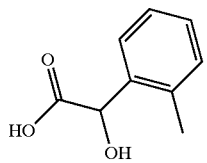

Reaction of 2-methylbenzaldehyde (12.0 g, 100 mmol), triethylbenzylammonium chloride (1.23 g, 0.5 mmol), chloroform (16 mL) and 50% sodium hydroxide (25 mL) as described in Preparation 145 gave 16.0 of an oil which was used without further purification.

Preparation 171

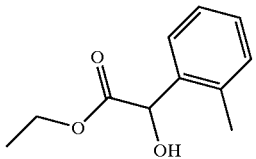

Reaction of the product of Preparation 170 (16.0 g, 96 mmol), concentrated sulfuric acid (10 mL) and absolute ethanol (100 mL) as described in Preparation 146 gave 15.2 g (78% over the two steps) of the desired product: $^1$H-NMR is consistent with structure; MS (ion spray) 194 (M+1).

Preparation 172

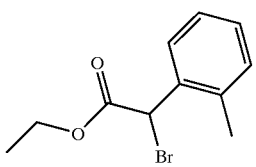

Reaction of the product of Preparation 171 (3.88 g, 20 mmol), phosphorus tribromide (2.2 mL, 22 mmol), chloroform (50 mL) as described in Preparation 147 gave 2.87 g (65%) of the desired product as a oil: $^1$H-NMR is consistent with structure; MS (ion spray) 256, 258 (M+).

Preparation 173

Reaction of the product of Preparation 172 (3.3 g, 12.8 mmol), 4-nitroimidazole (1.53 g, 13.5 mmol) and sodium hydride (0.32 g, 13.5 mmol) in dimethylformamide (30 mL) as described in Preparation 148 gave 3.1 g (84%) of the desired product as an oil: $^1$H-NMR is consistent with structure; MS (ion spray) 289 (M+1); Anal. Calc'd for $C_4H_{15}N_3O_4$: C, 58.13; H, 5.23; N, 24.52. Found: C, 58.41; H, 5.26; N, 14.47.

Preparation 174

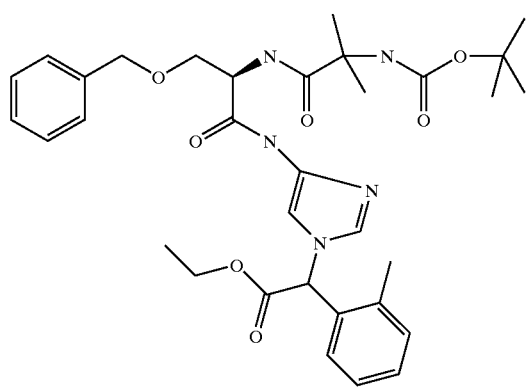

Reduction of the product of Preparation 173 (1.15 g, 3.96 mmol) under a hydrogen atmosphere with 5% palladium on carbon (0.59 g) in tetrahydrofuran (30 mL) followed by coupling with the product of Preparation 1d (1.5 g, 3.96 mmol), 1-hydroxybenzotriazole (0.59 g, 4.35 mmol), 1-(3-dimethylaminopropyl)-3-ethylcarbodiimide (0.9 g, 4.35 mmol) as described in Preparation 149 gave 2.43 g (99%) of the desired product as a foam: $^1$H-NMR is consistent with structure; MS (ion spray) 621.2 (M+1); Anal. Calc'd for $C_{33}H_{43}N_5O_7$: C, 63.75; H, 6.97; N, 11.26. Found: C, 63.59; H, 7.12; N, 11.38.

Preparation 175

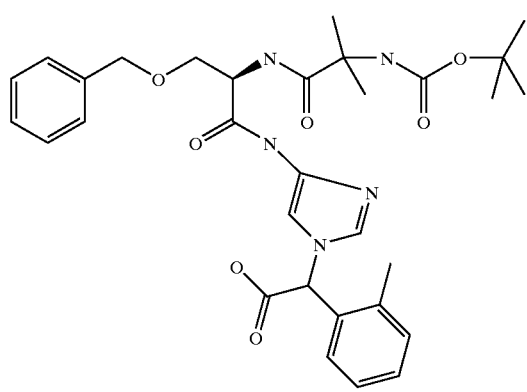

Reaction of the product of Preparation 174 (2.2 g, 3.6 mmol) with lithium hydroxide (0.096 g, 4.0 mmol) in dioxane (20 mL) and water (10 mL) as described in Preparation 150 gave 2.1 g (100%) of the desired product: $^1$H-NMR is consistent with structure; MS (ion spray) 594 (M+1); Anal. Calc'd for $C_{31}H_{39}N_5O_7 \cdot 0.4H_2O$: C, 61.27; H, 6.91; N, 10.57. Found: C, 60.93; H, 6.57; N, 10.92.

Preparation 176

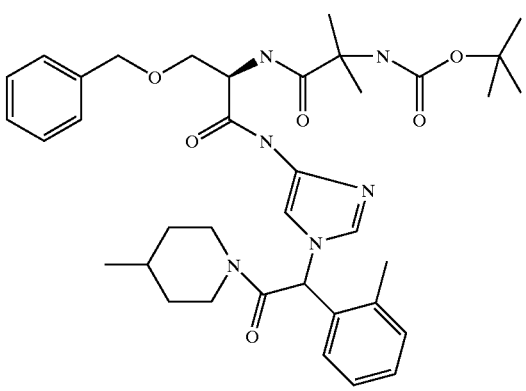

Reaction of the product of Preparation 175 (0.59 g, 1.0 mmol), 4-methylpiperidine (0.099 g, 1.0 mmol), 1-hydroxybenzotriazole (0.15 g, 1.1 mmol) and 1-(3-dimethylaminopropyl)-3-ethylcarbodiimide (0.23 g, 1.1 mmol) in dimethylformamide (10 mL) as described in Preparation 151 gave the desired product as an oil: $^1$H-NMR is consistent with structure; MS (ion spray) 674.3 (M+1); Anal. Calc'd for $C_{37}H_{50}N_6O_6$: C, 65.85; H, 7.47; N, 12.45. Found: C, 65.56; H, 7.53; N, 12.69.

Example 74

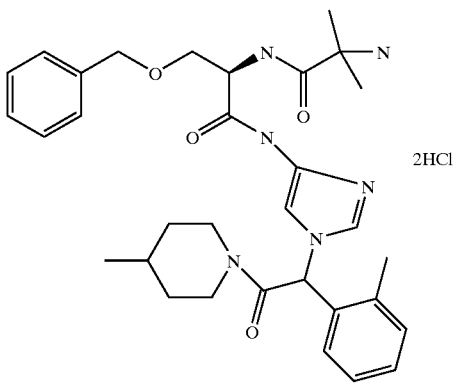

Reaction of the product of Preparation 176 (0.49 g, 0.72 mmol) with trifluoroacetic acid (4 mL) in dichloromethane (12 mL) as described in ale 63 gave 0.31 g (75%) of the desired product: $^1$H-NMR is consistent with structure; MS (ion spray) 574 (M+1); Anal. Calc'd for $C_{32}H_{42}N_6O_4 \cdot 2HCl$: C, 59.35; H, 6.85; N, 12.98. Found: C, 59.27; H, 6.76; N, 13.02.

Preparation 177

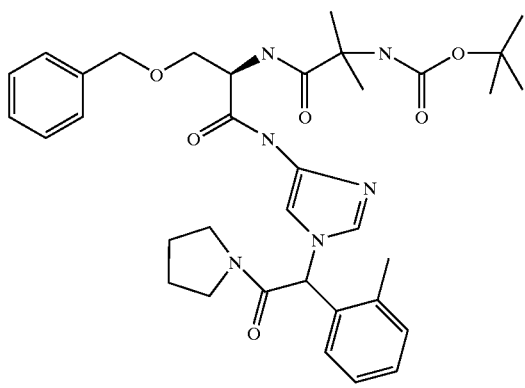

Reaction of the product of Preparation 175 (0.59 g, 1.0 mmol), pyrrolidine (0.071 g, 1.0 mmol), 1-hydroxybenzotriazole (0.15 g, 1.1 mmol) and 1-(3-dimethylaminopropyl)-3-ethylcarbodiimide (0.23 g, 1.1 mmol) in dimethylformamide (13 mL) as described in Preparation 151 gave 0.51 g (79%) of the desired product: $^1$H-NMR is consistent with structure; MS (ion spray) 646.2 (M+1); Anal. Calc'd for $C_{35}H_{36}N_6O_6$: C, 65.00; H, 7.17; N, 12.00. Found: C, 64.89; H, 7.15; N, 12.77.

Examples 75 and 76

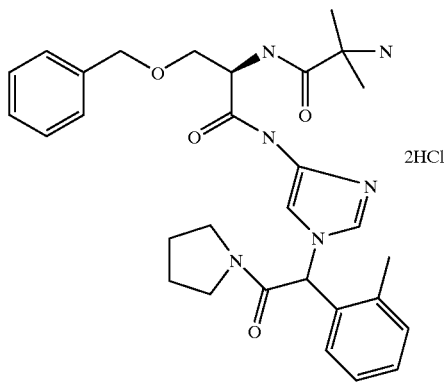

Reaction of the product of Preparation 177 (0.40 g, 0.62 mmol) with trifluoroacetic acid (4 mL) in dichloromethane (12 mL) as described in Example 63 gave 0.36 g (95%) of the desired product: $^1$H-NMR is consistent with structure; MS (ion spray) 546 (M+1); Anal. Calc'd for $C_{30}H_{38}N_6O_4$.2HCl: C, 58.16; H, 6.51; N, 13.56. Found: C, 58.09; H, 6.43; N, 13.60. Resolution of the diastereomers (0.17 g, 0.31 mmol) by chiral HPLC gave the respective isomers which were individually treated with a saturated solution of hydrochloric acid in diethyl ether to give the desired products:

Example 75

Isomer 1

0.039 g (20%), 1H-NMR is consistent with structure; $t_R$=6.50 min; MS (ion spray) 547.2 (M+1); Anal. Calc'd for $C_{30}H_{38}N_6O_4$.2.3HCl: C, 57.15; H, 6.44; N, 13.33. Found: C, 57.15; H, 6.17; N, 12.94.

Example 76

Isomer 2

0.054 g (28%) of the desired isomer as the hydrochloric acid salt. $^1$H-NMR is consistent with structure; $t_R$=7.52 min; MS (ion spray) 547.2 (M+1); Anal. Calc'd for $C_{30}H_{38}N_6O_4$.2.75HCl: C, 55.70; H, 6.35; N, 12.99. Found: C, 55.68; H, 6.35; N, 12.66.

Preparation 178

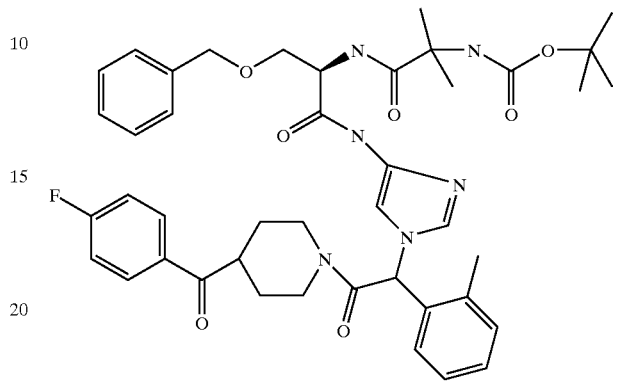

Reaction of the product of Preparation 175 (0.59 g, 1.0 mmol), 4-(4-fluorobenzoyl)piperidine hydrochloride (0.24 g, 1.0 mmol), triethylamine (0.11 g, 1.0 mmol), 1-hydroxybenzotriazole (0.15 g, 1.1 mmol) and 1-(3-dimethylaminopropyl)-3-ethylcarbodiimide (0.23 g, 1.1 mmol) in dimethylformamide (13 mL) as described in Preparation 151 gave 0.58 g (82%) of the desired product as a product: $^1$H-NMR is consistent with structure; MS (ion spray) 783 (M+1); Anal. Calc'd for $C_{43}H_{51}FN_5O_7$: C, 65.97; H, 6.57; N, 10.73. Found: C, 65.70; H, 6.69; N, 10.47.

Example 77

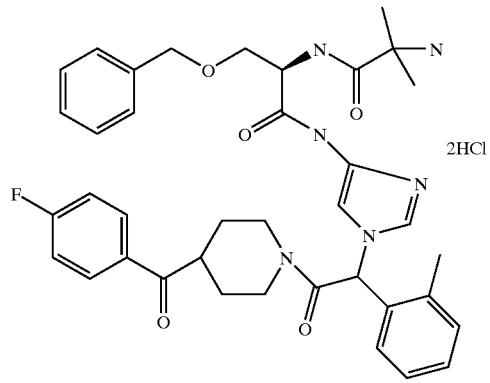

Reaction of the product of Preparation 178 (0.58 g, 0.74 mmol) with trifluoroacetic acid (4 mL) in dichloromethane (12 mL) as described in Example 63 gave 0.52 g (93%) of the desired product: $^1$H-NMR is consistent with structure; MS (ion spray) 682 (M+1); Anal. Calc'd for $C_{38}H_{43}FN_6O_5$.2HCl: C, 60.40; H, 6.00; N, 11.12; Cl, 9.38. Found: C, 60.35; H, 5.96; N, 11.17; Cl, 9.23.

Preparation 179

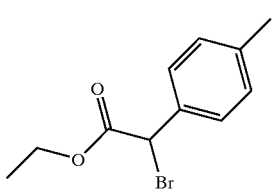

To a solution of 4-methylphenylacetic acid, (7.5 g, 50 mmol) in carbon tetrachloride (10 mL) was added thionyl chloride (14.4 mL, 200 mmol). The reaction was heated to reflux. After 30 min, the mixture was cooled to 20° C. and a solution of N-bromosuccinimide (8.9 g, 50 mmol) and HBr (8 drops of a 48% aqueous solution) in carbon tetrachloride (15 mL). The reaction was heated to reflux and after 30 min, cooled to ambient temperature, filtered and concentrated. The resulting oil was added to absolute ethanol at 0° C. and then concentrated. The residue was purified by flash chromatography (silica gel, 3% ethyl acetate/hexanes) to yield 5.1 g (40%) of the desired product as an oil: $^1$H-NMR is consistent with structure; MS (FD) 258 (M+); Anal. Calc'd for $C_{11}H_{13}BrO_2 \cdot 1.3CHCl_3$: C, 44.44; H, 4.34. Found: C, 44.58; H, 4.51.

Preparation 180

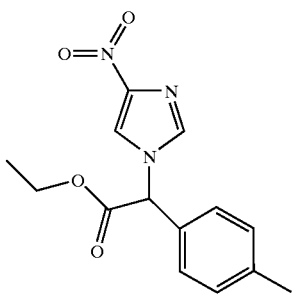

Reaction of the product of Preparation 179 (5.0 g, 19.5 mmol), 4-nitroimidazole (2.2 g, 19.5 mmol) and sodium hydride (0.47 g, 19.5 mmol) in dimethylformamide (50 mL) as described in Preparation 148 gave 1.9 g (33%) of the desired product as a yellow oil: $^1$H-NMR is consistent with structure; MS (FD) 289 (M+); Anal. Calc'd for $C_{14}H_{15}N_3O_4$: C, 58.13; H, 5.23; N, 14.52. Found: C, 58.33; H, 5.17; N, 14.70.

Preparation 181

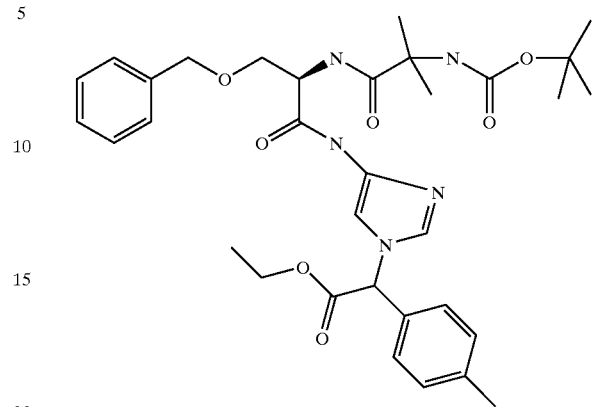

Reduction of the product of Preparation 180 (4.9 g, 17.0 mmol) under a hydrogen atmosphere with 10% palladium on carbon (3.5 g) in tetrahydrofuran (120 mL) followed by coupling of the product of Preparation 1d (6.43 g, 17.0 mmol), 1-hydroxybenzotriazole (2.6 g, 18.7 mmol), 1-(3-dimethylaminopropyl)-3-ethylcarbodiimide (3.9 g, 18.7 mmol) as described in Preparation 149 gave 6.54 g (62%) of the desired compound as an orange foam: $^1$H-NMR is consistent with structure; MS (ion spray) 622.5 (M+1); Anal. Calc'd for $C_{33}H_{43}N_5O_7$: C, 63.75; H, 6.97; N, 11.26. Found: C, 63.80; H, 7.09; N, 11.36.

Preparation 182

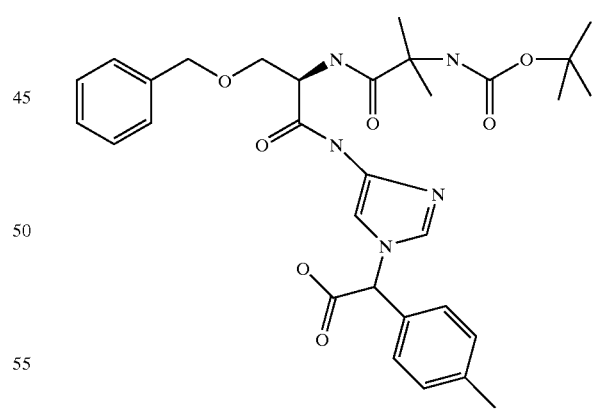

Reaction of the product of Preparation 181 (6.49 g, 10.0 mmol) with lithium hydroxide (0.3 g, 12.0 mmol) in dioxane (90 mL) and water (50 mL) as described in Preparation 150 gave 5.93 g (100%) of the desired product: $^1$H-NMR is consistent with structure; MS (ion spray) 594.6 (M+1); Anal. Calc'd for $C_{31}H_{39}N_5O_7 \cdot 0.4$ dioxane: C, 62.26; H, 6.76; N, 11.14. Found: C, 62.33; H, 6.41; N, 11.19.

Preparation 183

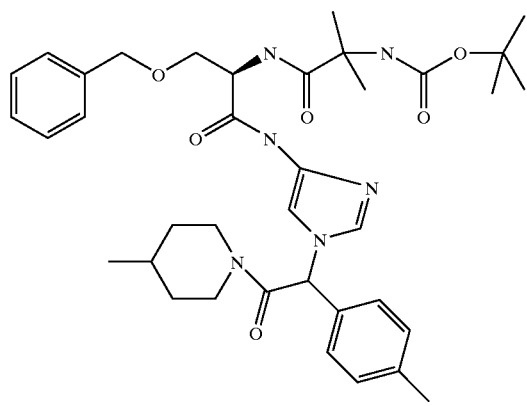

Reaction of the product of Preparation 182 (5.0 g, 8.4 mmol), 4-methylpiperidine (1.0 mL, 8.4 mmol), 1-hydroxybenzotriazole (1.3 g, 9.24 mmol) and 1-(3-dimethylaminopropyl)-3-ethylcarbodiimide (1.9 g, 9.24 mmol) in dimethylformamide (80 mL) as described in Preparation 151 gave 4.44 g (78%) of the desired product as a tan foam: $^1$H-NMR is consistent with structure; MS (ion spray) 675.7 (M+1); Anal. Calc'd for $C_{37}H_{50}N_6O_6 \cdot 0.3H_2O$: C, 65.33; H, 7.50; N, 12.35. Found: C, 65.28; H, 7.37; N, 12.30.

Examples 78 and 79

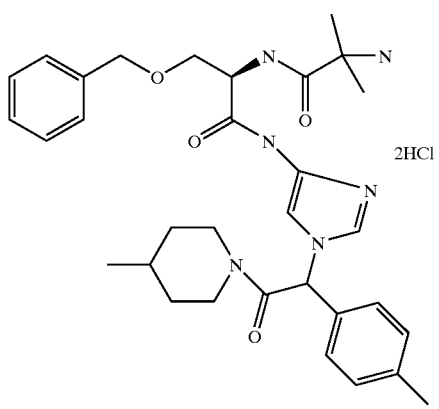

Reaction of the product of Preparation 183 (4.17 g, 6.4 mmol) and trifluoroacetic acid (20 mL) in dichloromethane (50 mL) as described in Example 63 gave 2.59 g (65%) of the desired product: $^1$H-NMR is consistent with structure; MS (ion spray) 575.5 (M+1). Resolution of the diastereomers (0.22 g, 0.34 mmol) by chiral HPLC gave the respective isomers which were individually treated with a saturated solution of hydrochloric acid in diethyl ether to give the desired products:

Example 78

Isomer 1

0.091 g (36%). $^1$H-NMR is consistent with structure; $t_R$=4.40 min; MS (ion spray) 575.3 (M+1); Anal. Calc'd for $C_{32}H_{42}N_6O_4$: C, 66.88; H, 7.37; N, 14.62. Found: C, 66.30; H, 7.20; N, 14.40.

Example 79

Isomer 2

0.059 g (24%); $^1$H-NMR is consistent with structure; $t_R$=5.3 min; MS (ion spray) 575.3 (M+1); Anal. Calc'd for $C_{32}H_{42}N_6O_4$: C, 66.86; H, 7.37; N, 14.62. Found: C, 67.02; H, 7.34; N, 14.40.

Preparation 184

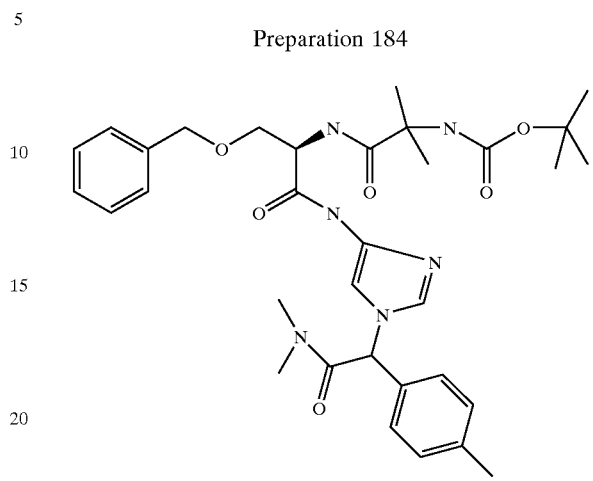

Reaction of the product of Preparation 182 (0.7 g, 1.2 mmol), dimethylamine hydrochloride (0.1 g, 1.2 mmol), triethylamine (0.2 mL, 1.32 mmol), 1-hydroxybenzotriazole (0.18 g, 1.32 mmol) and 1-(3-dimethylaminopropyl)-3-ethylcarbodiimide (0.27 g, 1.32 mmol) in dimethylformamide (30 mL) as described in Preparation 151 gave 0.55 g (75%) of the desired product as a tan foam: $^1$H-NMR is consistent with structure; MS (ion spray) 621.7 (M+1); Anal. Calc'd for $C_{33}H_{44}N_6O_6$: C, 63.85; H, 7.15; N, 13.54. Found: C, 63.56; H, 7.37; N, 13.35.

Example 80

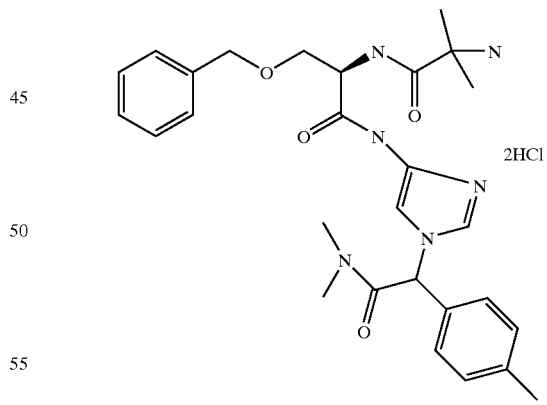

Reaction of the product of Preparation 184 (0.46 g, 0.74 mmol) with trifluoroacetic acid (2 mL) in dichloromethane (6 mL) as described in Example 63 gave 0.22 g (50%) of the desired product as a yellow solid: $^1$H-NMR is consistent with structure; MS (ion spray) 521.4 (M+1); Anal. Calc'd for $C_{28}H_{36}N_6O_4 \cdot 2.5HCl$: C, 54.97; H, 6.34; N, 13.74. Found: C, 54.85; H, 6.23; N, 13.58.

Preparation 185

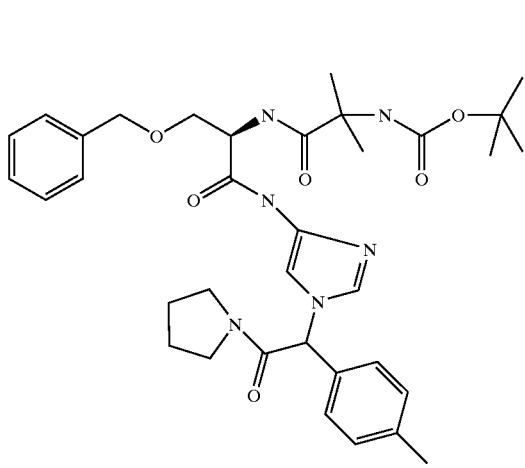

Reaction of the product of Preparation 182 (0.59 g, 1 mmol), pyrrolidine (0.078 g, 1.1 mmol), 1-hydroxybenzotriazole (0.15 g, 1.1 mmol) and 1-(3-dimethylaminopropyl)-3-ethylcarbodiimide (0.27 g, 1.1 mmol) in dimethylformamide (12 mL) as described in Preparation 151 gave 0.52 g (80%) of the desired product: $^1$H-NMR is consistent with structure; MS (ion spray) 646 (M+1); Anal. Calc'd for $C_{35}H_{46}N_6O_6$: C, 65.00; H, 7.17; N, 12.99. Found: C, 65.00; H, 7.05; N, 12.82.

Example 81

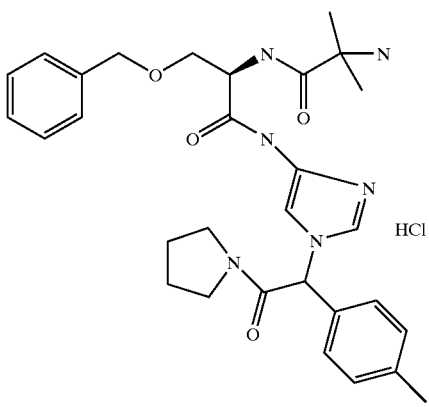

Reaction of the product of Preparation 185 (0.39 g, 0.61 mmol) with trifluoroacetic acid (3.5 mL) indichloromethane (12 mL) an described in Example 63 gave 0.3 g (90%) of the desired product as a white solid: $^1$H-NMR is consistent with structure; MS (ion spray) 546 (M+1); Anal. Calc'd for $C_{30}H_{36}N_6O_4 \cdot 1.4HCl$: C, 60.99; H, 6.69; N, 14.22. Found: C, 61.08; H, 6.51; N, 13.89.

Preparation 186

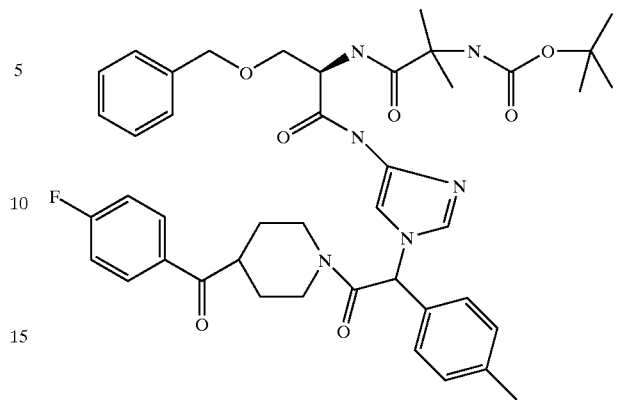

Reaction of the product of Preparation 182 (0.7 g, 1.32 mmol), 4-(4-fluorobenzoyl)piperidine hydrochloride (0.3 g, 1.2 mmol), triethylamine (0.2 mL, 1.32 ml), 1-hydroxybenzotriazole (0.18 g, 1.32 mmol) and 1-(3-dimethylaminopropyl)-3-ethylcarbodiimide (0.27 g, 1.32 mmol) in dimethylformamide (30 mL) as described in Preparation 151 gave 0.68 g (72%) of the desired product as a tan foam: $^1$H-NMR is consistent with structure; MS (ion spray) 783.6 (M+1); Anal. Calc'd for $C_{43}H_{51}FN_6O_7$: C, 65.97; H, 6.57; N, 10.73. Found: C, 65.86; H, 6.62; N, 10.62.

Examples 82 and 83

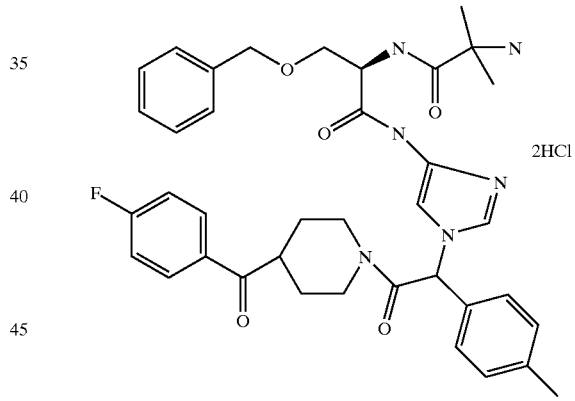

Reaction of the product of Preparation 186 (0.7 g, 0.89 mmol) with trifluoroacetic acid (2 mL) in dichloromethane (6 mL), as in Example 63 from Examples Part 2A. 0.45 g (66%) of the desired product as a yellow solid: $^1$H-NMR is consistent with structure; MS (ion spray) 683.4 (M+1); Anal. Calc'd for $C_{38}H_{43}N_6O_5 \cdot 2.4HCl$: C, 59.25; H, 5.94; N, 10.91. Found: C, 59.24; H, 5.66; N, 11.09. Resolution of the diastereomers (0.21 g, 0.32 mmol) by chiral HPLC gave the respective isomers which were individually treated with a saturated solution of hydrochloric acid in diethyl ether to give the desired products:

Example 82

Isomer 1

0.092 g (38%); $^1$H-NMR is consistent with structure; $t_R$=5.83 min; MS (ion spray) 683.4 (M+1); Anal. Calc'd for $C_{38}H_{43}FN_6O_5 \cdot 2HCl$: C, 60.40; H, 6.00; N, 11.12. Found: C, 60.11; H, 6.12; N; 10.98.

Example 83

Isomer 2

0.065 g (27%) of the desired isomer as a white solid: $^1$H-NMR is consistent with structure; $t_R$=7.62 min; MS (ion spray) 683.4 (M+1); Anal. Calc'd for $C_{38}H_{43}FN_6O_5 \cdot 2HCl$: C, 60.40; H, 6.00; N, 11.12. Found: C, 60.15; H, 5.82; N, 10.96.

Preparation 187

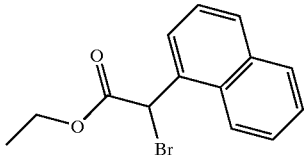

Reaction of 1-naphthylacetic acid (9.3 g, 50 mmol), thionyl chloride (14.4 mL, 200 mmol), carbon tetrachloride (35 mL), N-bromosuccinimide (8.9 g, 50 mmol), 48% HBr (8 drops) as described in Preparation 179 gave 12.6 g (86%) of the desired product as an oil: $^1$H-NMR is consistent with structure.

Preparation 188

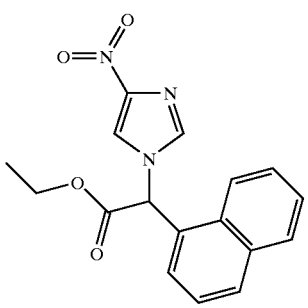

Reaction of the product of Preparation 187 (11.8 g, 40 mmol), 4-nitroimidazole (4.5 g, 40 mmol) and sodium hydride (1.6 g, 40 mmol) in dimethylformamide (50 mL) as described in Preparation 148 gave 6.03 g (50%) of the desired product as an oil: $^1$H-NMR is consistent with structure; MS (ion spray) 325.1 (M+1); Anal. Calc'd for $C_{17}H_{15}N_3O_4 \cdot 0.37H_2O$: C, 61.50; H, 4.78; N, 12.66. Found: C, 61.46; H, 4:60; N, 12.73.

Preparation 189

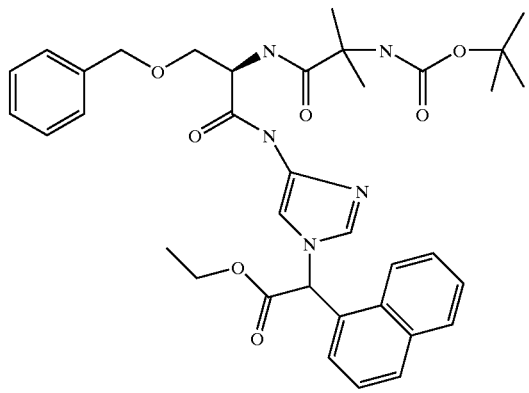

Reduction of the product of Preparation 188 (1.28 g, 4.0 mmol) under a hydrogen atmosphere with 5% palladium on carbon (0.6 g) followed by coupling with the product of Preparation 1d (1.5 g, 4.0 mmol), 1-hydroxybenzotriazole (0.59 g, 4.35 mmol) and 1-(3-dimethylaminopropyl)-3-ethylcarbodiimide (0.9 g, 4.35 mmol) in tetrahydrofuran (30 mL) as described in Preparation 149 gave 1.99 g (77%) of the desired product as an orange foam: $^1$H-NMR is consistent with structure; MS (ion spray) 657 (M+1); Anal. Calc'd for $C_{36}H_{43}H_5O_7$: C, 65.74; H, 6.59; N, 10.65. Found: C, 65.67; H, 6.53; N, 10.87.

Preparation 190

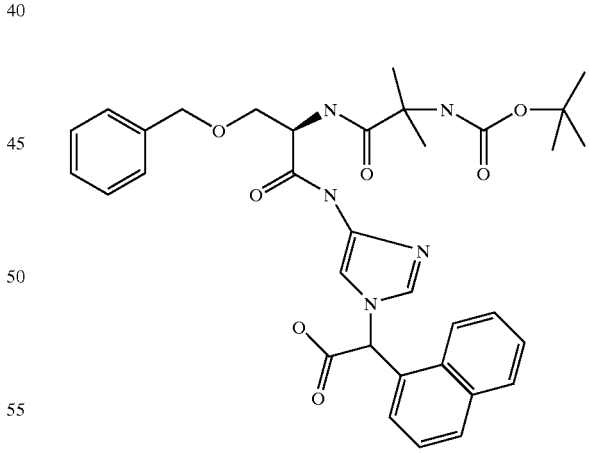

The product of Preparation 189 (1.97 g, 3.0 mmol), lithium hydroxide (0.08 g, 3.3 mmol), dioxane (20 mL), water (10 mL), as in Preparation 150. 1.8 g (95%) of the desired product. $^1$H-NMR is consistent with structure; MS (ion spray) 630 (M+1); Anal. Calc'd for $C_{34}H_{39}N_5O_7 \cdot 1.05H_2O$: C, 62.96; H, 6.39; N, 10.80. Found: C, 63.09; H, 6.39; N, 10.40.

Preparation 191

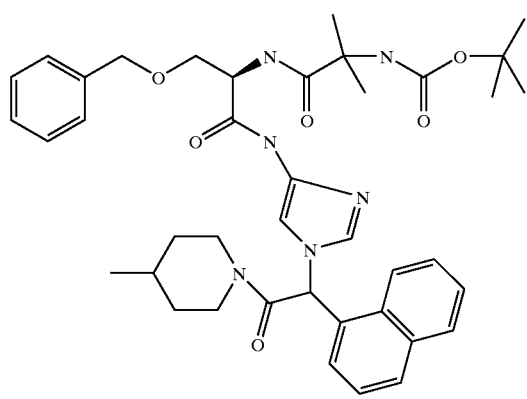

Reaction of the product of Preparation 190 (0.63 g, 1.0 mmol), 4-methylpiperidine (0.099 g, 1.0 mmol), 1-hydroxybenzotriazole (0.15 g, 1.1 mmol) and 1-(3-dimethylaminopropyl)-3-ethylcarbodiimide (0.23 g, 1.1 mmol) in dimethylformamide (12 mL) as described in Preparation 151 gave 0.60 g (85%) of the desired material as a white solid; $^1$H-NMR is consistent with structure; MS (ion spray) 710 (M+1); Anal. Calc'd for $C_{40}H_{50}N_6O_6$: C, 67.58; H, 7.09; N, 11.82. Found: C, 67.33; H, 6.94; N, 11.58.

Preparation 192

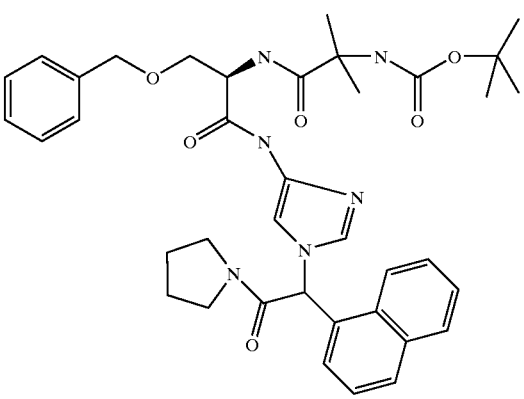

Reaction of the product of Preparation 190 (0.63 g, 1.0 mmol), pyrrolidine (0.071 g, 1.0 mol), 1-hydroxybenzotriazole (0.15 g, 1.1 mmol) and 1-(3-dimethylaminopropyl)-3-ethylcarbodiimide (0.23 g, 1.1 mmol) in dimethylformamide (12 mL) as described in Preparation 151 gave 0.54 g (78%) of the desired product as a solid: $^1$H-NMR is consistent with structure; MS (ion spray) 682 (M+1); Anal. Calc'd for $C_{38}H_{46}N_6O_6$: C, 66.84; H, 6.79; N, 12.31. Found: C, 66.59; H, 6.78; N, 12.29.

Example 84

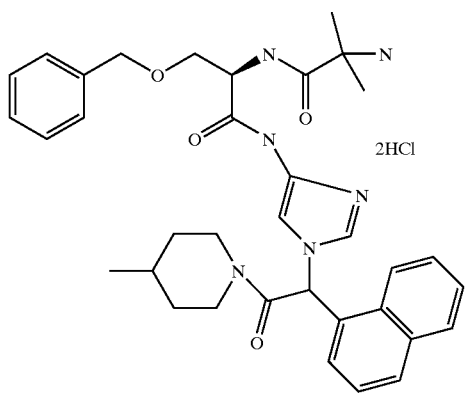

Reaction of the product of Preparation 191 (0.60 g, 0.84 mmol) with trifluoroacetic acid (4 mL) in dichloromethane (12 mL) as described in Example 63 gave 0.47 g (92%) of the desired product as a white solid: $^1$H-NMR is consistent with structure; MS (ion spray) 610 (M+1); Anal. Calc'd for $C_{35}H_{42}N_6O_4$·2.7HCl: C, 59.28; H, 6.35; N, 11.85. Found: C, 59.34; H, 6.57; N, 11.75.

Example 85

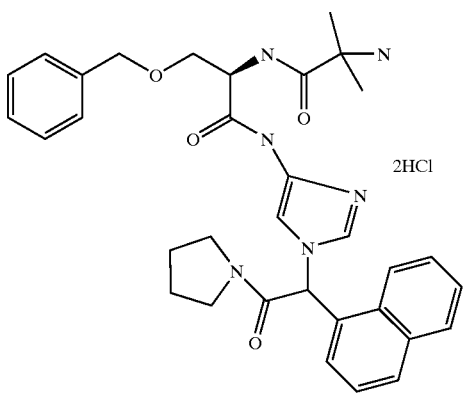

Reaction of the product of Preparation 192 (0.443 g, 0.65 mmol) with trifluoroacetic acid (4 mL) in dichloromethane (12 mL) as described in ale 63 gave 0.27 g (65%) of the desired product as a white solid; $^1$H-NMR is consistent with structure; MS (ion spray) 582 (M+1); Anal. Calc'd for $C_{33}H_{38}N_6O_4$·2.8HCl: C, 57.88; H, 6.01; N, 12.27. Found: C, 57.83; H, 6.47; N, 12.11.

Preparation 193

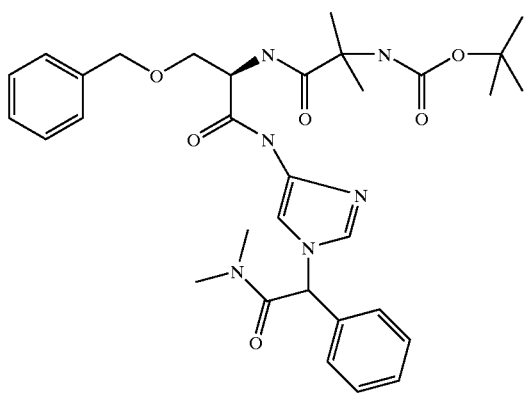

To a solution of Preparation 8 from Examples Part 1 (1.0 g, 1.7 mmol), N,N-dimethylamine hydrochloride, 0.14 g (1.7 mmol), triethylamine, 0.26 mL (1.9 mmol) and 1-hydroxybenzotriazole, 0.26 g (1.9 mmol) in 70 mL of dimethylformamide was added 0.4 g (1.9 mmol) of 1-(3-dimethylaminopropyl)-3-ethylcarbodiimide. The reaction mixture was stirred overnight then concentrated. The residue was slurried in ethyl acetate, filtered and water was added. The mixture was extracted with ethyl acetate. The combined organic extracts were washed with brine, dried over sodium sulfate, filtered and concentrated. The residue was chromatographed on silica gel using 4% methanol/chloroform as eluant to yield 0.58 g (56%) of the desired compound as a white foam: 1H-NMR is consistent with structure; MS (FD) 606 (M+); Anal. Calc'd for $C_{32}H_{42}N_6O_6$: C, 63.35; H, 6.98; N, 13.85. Found: C, 63.18; H, 7.03; N, 13.84.

Example 86

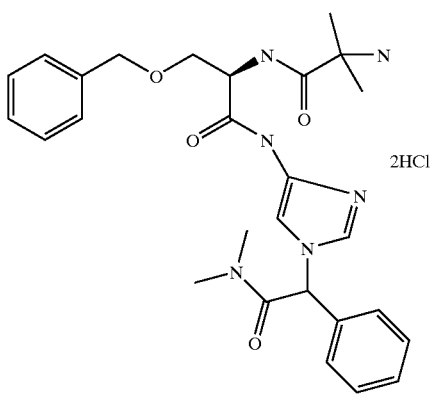

To a solution of the product of Preparation 193, 0.5 g (0.82 mmol) in 12 mL of dichloromethane was added 4 mL of trifluoroacetic acid. After stirred for 1 h, water was added. The reaction was quenched with solid sodium bicarbonate and was extracted with chloroform. The combined organic extracts were washed with brine, dried over sodium sulfate, filtered and concentrated. The residue was dissolved in ethyl acetate and hydrochloric acid-saturated ether was added. The resulting slurry was concentrated to yield 0.4 g (85%) of the desired product as a yellow solid: $^1$H-NMR is consistent with structure; MS (FD) 506.4 (M+); Anal. Calc'd for $C_{27}H_{34}N_6O_4$·2.9HCl: C, 53.85; H, 4.50; N, 13.95. Found: C, 53.91; H, 6.14; N, 13.76.

Preparation 194

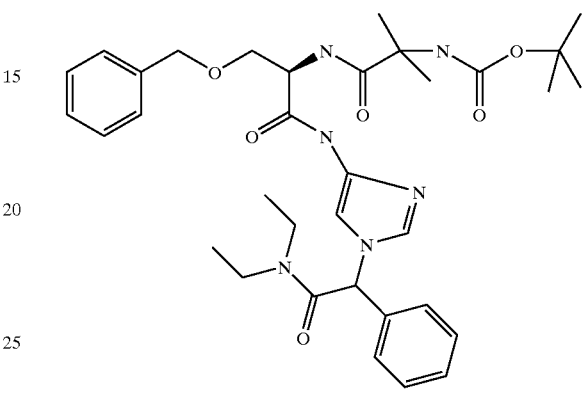

Reaction of the product of Preparation 8 from Examples Part 1 (1.0 g, 1.7 mmol), diethylamine (0.18 mL, 1.7 mmol), 1-hydroxybenzotriazole (0.26 g, 1.9 mmol), 1-(3-dimethylaminopropyl)-3-ethylcarbodiimide (0.4 g, 1.9 mmol, dimethylformamide (80 mL) as described in Preparation 193 gave 0.53 g (49%) of the desired product as a yellow foam: $^1$H-NMR is consistent with structure; MS (FD) 634.3 (M+).

Example 87

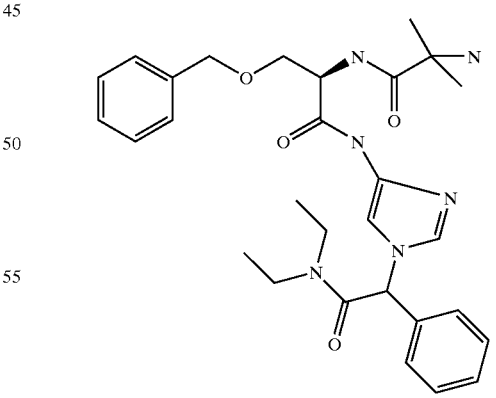

mL) as described in Example 86 gave 0.47 g (100%) of the desired product as a white solid: $^1$H-NMR is consistent with structure; MS (FD) 534.1 (M+); Anal. Calc'd for $C_{29}H_{38}N_6O_4$·2.4HCl: C, 55.99; H, 6.54; N, 13.51. Found: C, 55.88; H, 6.91; N, 13.32.

Preparation 195

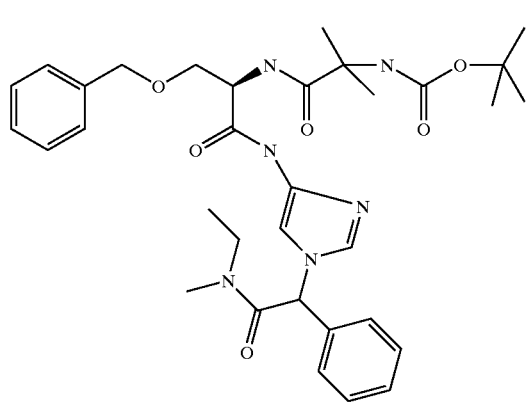

Reaction of the product of Preparation 8 from Examples Part 1 (1.0 g, 1.7 mmol), N,N-methylethylamine (0.15 mL, 1.7 mmol), 1-hydroxybenzotriazole (0.26 g, 1.9 mmol), 1-(3-dimethylaminopropyl)-3-ethylcarbodiimide (0.4 g, 1.9 mmol), dimethylformamide (40 mL) as in Preparation 193 gave 0.56 g (56%) of the desired product as a tan foam: $^1$H-NMR is consistent with structure; MS (FD) 620 (M+); Anal. Calc'd for $C_{33}H_{44}N_6O_6$: C, 63.85; H, 7.15; N, 13.54. Found: C, 63.45; H, 7.19; N, 13.15.

Preparation 196

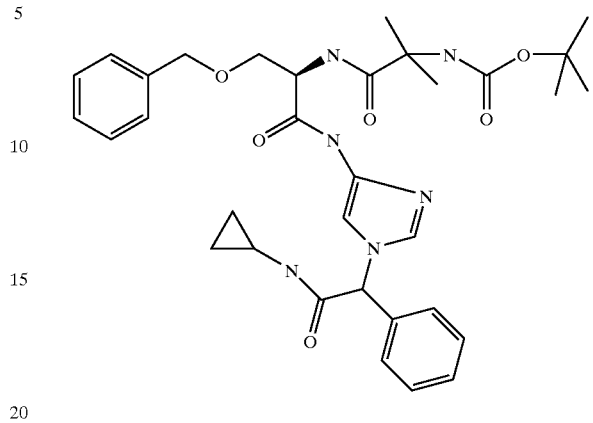

Reaction of the product of Preparation 8 from Examples Part 1 (0.6 g, 1.0 mmol), cyclopropylamine (0.07 mL, 1.0 mmol), 1-hydroxybenzotriazole (0.15 g, 1.1 mmol), 1-(3-dimethylaminopropyl)-3-ethylcarbodiimide (0.23 g, 1.1 mmol), dimethylformamide (30 mL) as described in Preparation 193 gave 0.31 g (50%) of the desired product as a white foam: $^1$H-NMR is consistent with structure; MS (ion spray) 619.6 (M+1); Anal. Calc'd for $C_{33}H_{42}N_6O_6 \cdot 1.1H_2O$: C, 62.07; H, 6.98; N, 13.15. Found: C, 62.19; H, 6.43; N, 12.82.

Example 88

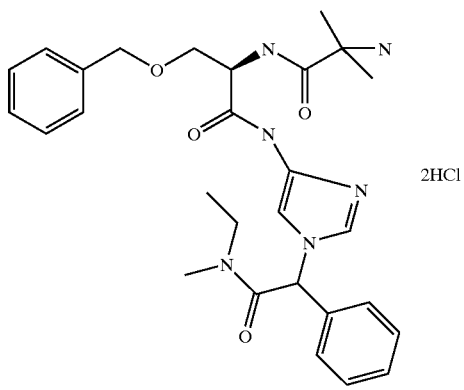

(0.4 g, 0.64 mmol), trifluoroacetic acid (2 ml), dichloromethane (6 mL), as in Example 86 gave 0.32 g (84%) of the desired product as a yellow solid: $^1$H-NMR is consistent with structure; MS (FD) 520 (M+); Anal. Calc'd for $C_{28}H_{36}N_6O_4 \cdot 2.2HCl$: C, 55.97; H, 6.41; N, 13.99. Found: C, 56.11; H, 6.23; N, 13.60.

Example 89

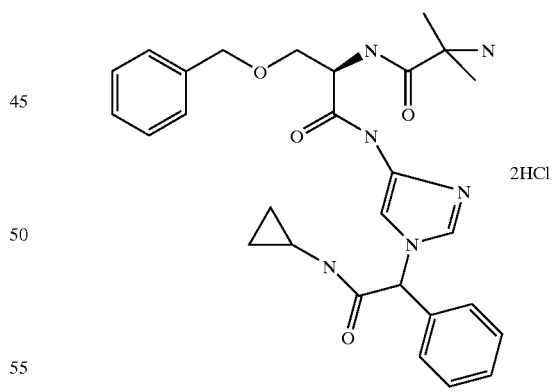

Reaction of the product of Preparation 196 (0.31 g, 0.5 mmol), trifluoroacetic acid (2 mL), dichloromethane (6 mL) as described in example 86 gave 0.27 g (90%) of the desired product as a white solid: $^1$H-NMR is consistent with structure; MS (ion spray) 518 (M+1); Anal. Calc'd for $C_{28}H_{34}N_6O_4 \cdot 2.4HCl$: C, 55.49; H, 6.05; N, 13.87. Found: C, 55.63; H, 5.27; N, 13.29.

Preparation 197

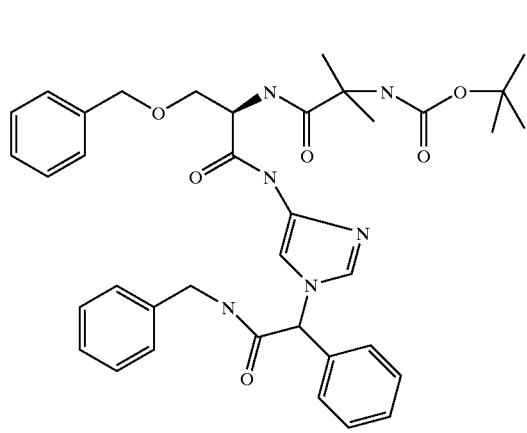

Reaction of the product of Preparation 8 from Examples Part 1 (1.0 g, 1.7 mmol), benzylamine (0.2 mL, 1.7 mmol), 1-hydroxybenzotriazole (0.26 g, 1.7 mmol), 1-(3-dimethylaminopropyl)-3-ethylcarbodiimide (0.4 g, 1.9 mmol), dimethylformamide (80 mL) as in Preparation 193 gave 0.86 g (75%) of the desired product as a white foam: $^1$H-NMR is consistent with structure; MS (FD) 669 (M+).

Preparation 198

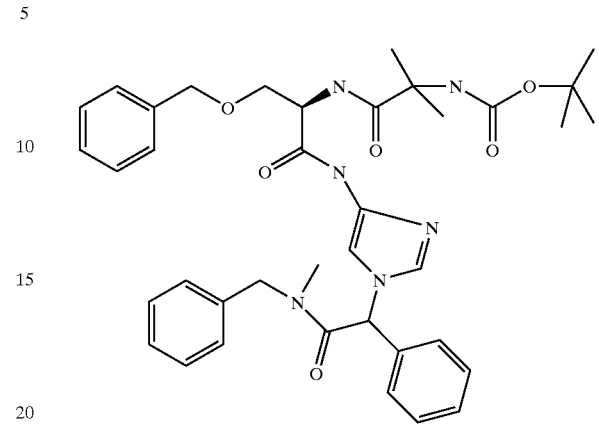

Reaction of the product of Preparation 8 from Examples Part 1 (1.0 g, 1.7 mmol), N,N-benzylmethylamine (0.22 mL, 1.7 mmol), 1-hydroxybenzotriazole (0.26 g, 1.9 mmol), 1-(3-dimethylaminopropyl)-3-ethylcarbodiimide (0.4 g, 1.9 mmol), dimethylformamide (80 mL) as in Preparation 193 gave 0.65 g (56%) of the desired product as a white foam: $^1$H-NMR is consistent with structure; MS (FD) 682.5 (M+).

Example 90

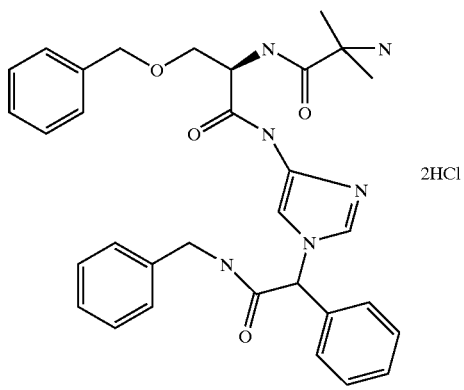

2HCl

Reaction of the product 197 (0.76 g, 1.1 mmol), trifluoroacetic acid (4 mL), dichloromethane (12 mL) as described in Example 86 gave 0.52 g (79%) of the desired product as a yellow solid: $^1$H-NMR is consistent with structure; MS (FD) 568 (M+); Anal. Calc'd for $C_{32}H_{35}N_6O_4 \cdot 2.5HCl$: C, 58.25; H, 5.88; N, 12.74. Found: C, 57.95; H, 6.02; N, 13.18.

Example 91

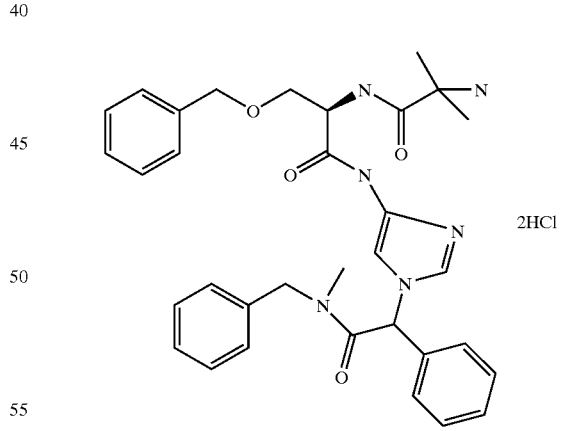

2HCl

Reaction of the product of Preparation 198 (0.6 g, 0.88 mmol), trifluoroacetic acid (4 mL), dichloromethane (12 mL) as described in Example 86 gave 0.53 g (96%) of the desired product as a white solid: $^1$H-NMR is consistent with structure; MS (FD) 582.2 (M+); Anal. Calc'd for $C_{33}H_{37}N_6O_4 \cdot 2.5HCl$: C, 58.82; H, 6.08; N, 12.47. Found: C, 58.85; H, 6.27; N, 12.39.

Preparation 199

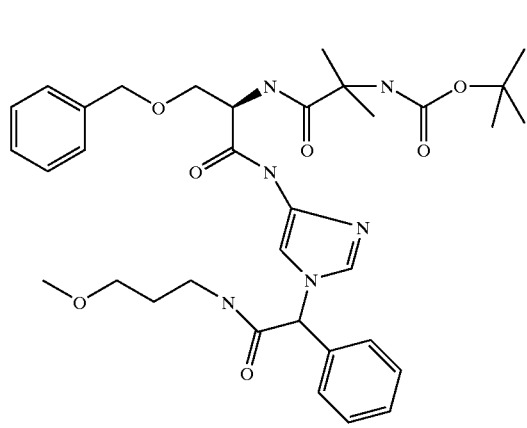

Reaction of the product of Preparation 8 from Examples Part 1 (1.0 g, 1.7 mmol), methoxypropylamine (0.18 mL, 1.7 mmol), 1-hydroxybenzotriazole (0.26 g, 1.9 mmol) 1-(3-dimethylaminopropyl)-3-ethylcarbodiimide (0.4 g, 1.9 mmol), dimethylformamide (40 mL) as in Preparation 193 gave 0.8 g (73%) of the desired product as a white foam: $^1$H-NMR is consistent with structure MS (FD) 650, (M+).

Preparation 200

Reaction of the product of Preparation 8 from Examples Part 1 (0.6 g, 1.0 mmol), 2-(ethylthio)ethylamine hydrochloride (0.15 g, 1.0 mmol), triethylamine (0.16 mL, 1.1 mmol), 1-hydroxybenzotriazole (0.15 g, 1.1 mmol), 1-(3-dimethylaminopropyl)-3-ethylcarbodiimide (0.23 g, 1.1 mmol), dimethylformamide (30 mL) as in Preparation 193 gave 0.42 g (63%) of the desired product as a white foam: $^1$H-NMR is consistent with structure; MS (FD) 663.3 (M+); Anal. Calc'd for $C_{34}H_{46}N_6O_6S$: C, 61.24; H, 6.95; N, 12.60. Found: C, 61.00; H, 6.83; N, 12.48.

Example 92

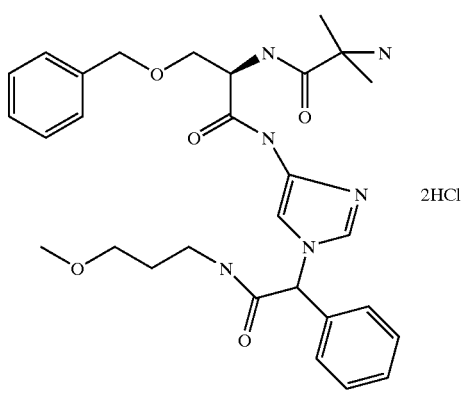

Reaction of the product of Preparation 199 (0.75 g (1.16 mmol), trifluroacetic acid (4 mL), dichloromethane (12 mL) as described in Example 86 gave 0.52 g (72%) of the desired product as a yellow a solid: $^1$H-NMR is consistent with structure; MS (FD) 550 (M+); Anal. Calc'd for $C_{29}H_{38}N_6O_5 \cdot 2.7HCl$: C, 53.66; H, 6.32; N, 12.95. Found: C, 53.93; H, 6.27; N, 13.14.

Example 93

Reaction of the product of Preparation 200 (0.36 g, 0.54 mmol), trifluoroacetic acid (2 mL), dichloromethane (6 mL), as described in Example 86 gave 0.28 g (80%) of the desired product as a white solid: $^1$H-NMR is consistent with structure; MS (FD) 566 (M+); Anal. Calc'd for $C_{29}H_{38}N_6O_4S \cdot 2.2HCl$: C, 53.84; H, 6.26; N, 12.99. Found: C, 53.99; H, 6.03; N, 12.79.

Preparation 201

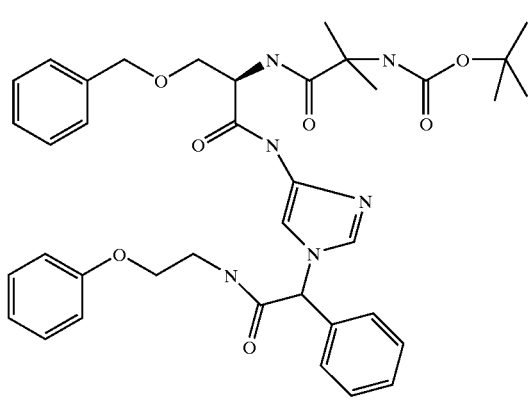

Reaction of the product of Preparation 8 from Examples Part 1 (0.6 g, 1.0 mmol), phenoxyethylamine (0.14 g, 1.0 mmol), 1-hydroxybenzotriazole (0.15 g, 1.1 mmol), 1-(3-dimethylaminopropyl)-3-ethylcarbodiimide (0.23 g, 1.1 mmol), dimethylformamide (20 mL) as described in Preparation 193 gave 0.53 g (76%) of the desired product as a tan foam: $^1$H-NMR is consistent with structure; MS (FD) 698 (M+).

Preparation 202

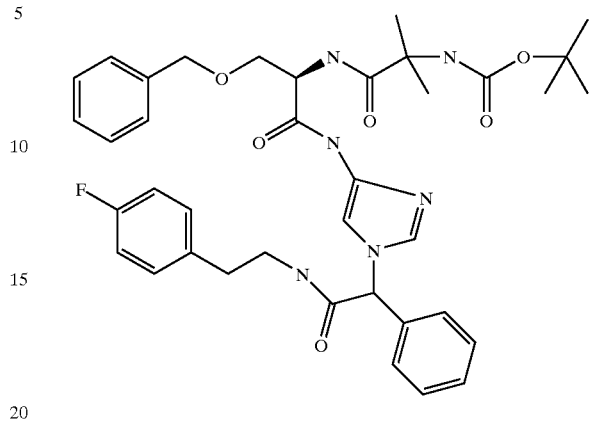

Reaction of the product of Preparation 9 from Examples Part 1 (0.6 g, 1.0 mmol), 4-fluorophenethylamine (0.13 mL, 1.0 mmol), 1-hydroxybenzotriazole (0.15 g, 1.1 mmol), 1-(3-dimethylaminopropyl)-3-ethylcarbodiimide (0.23 g, 1.1 mmol), dimethylformamide (30 mL) as described in Preparation 193 gave 0.5 g (71%) of the desired product as a yellow foam: $^1$H-NMR is consistent with structure; MS (FD) 700.5 (M+); Anal. Calc'd for $C_{38}H_{45}FN_6O_6 \cdot 0.5H_2O$: C, 64.30; H, 6.53; N, 11.84. Found: C, 64.12; H, 6.38; N, 11.73.

Example 94

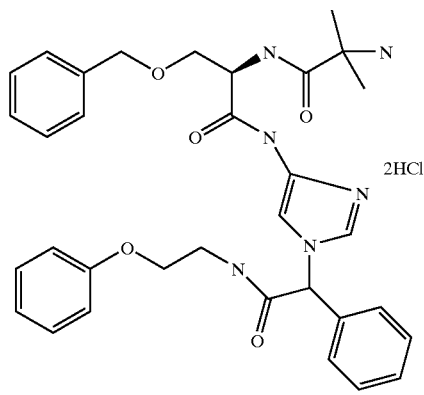

Reaction of the product of Preparation 201 (0.46 g, 0.67 mmol), trifluoroacetic acid (2 mL), dichloromethane (6 mL) as described in Example 86 gave 0.28 g (62%) of the desired product as a white solid: $^1$H-NMR is consistent with structure; MS (FD) 598 (M+); Anal. Calc'd for $C_{33}H_{38}N_6O_5 \cdot 2.0HCl$: C, 59.01; H, 6.00; N, 12.51. Found: C, 58.97; H, 6.09; N, 12.40.

Example 95

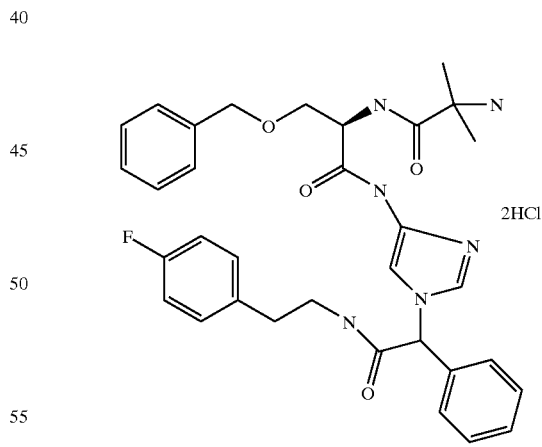

Reaction of the product of Preparation 202 (0.5 g, 0.71 mmol), trifluoroacetic acid (2 mL), dichloromethane (6 mL) as described in Example 86 gave 0.28 g (58%) of the desired product as a white solid: $^1$H-NMR is consistent with structure; MS (FD) 600 (M+); Anal. Calc'd for $C_{33}H_{37}FN_6O_4 \cdot 2.2HCl$: C, 58.21; H, 5.80; N, 12.34. Found: C, 58.32; H, 5.92; N, 12.07.

Preparation 203

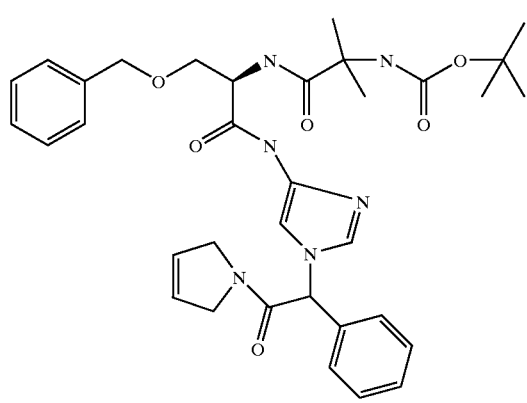

Reaction of the product of Preparation 8 from Examples Part 1 (1.0 g, 1.7 mmol), 3-pyrroline (0.13 mL, 1.7 mmol), 1-hydroxybenzotriazole (0.25 g, 1.9 mmol), 1-(3-dimethylaminopropyl)-3-ethylcarbodiimide (0.4 g, 1.9 mmol), dimethylformamide (80 mL) as described in Preparation 193 gave 0.75 g (70%) of the desired product as a white foam: $^1$H-NMR is consistent with structure; MS (FD) 630.2 (M+).

Preparation 204

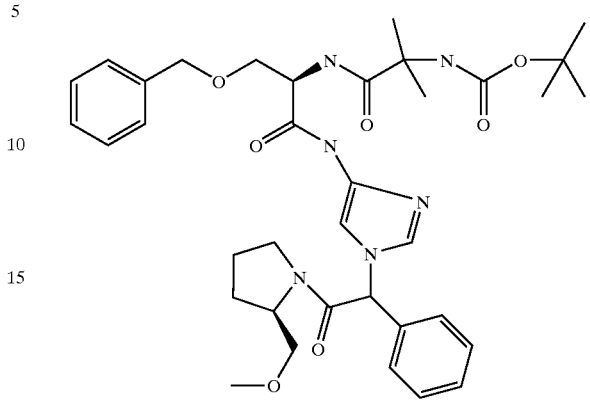

Reaction of the product of Preparation 8 from Examples Part 1 (1.0 g, 1.7 mmol), R-2-methoxymethylpyrrolidine (0.2 mL, 1.7 mmol), 1-hydroxybenzotriazole (0.26 g, 1.9 mmol), 1-(3-dimethylaminopropyl)-3-ethylcarbodiimide (0.4 g, 1.9 mmol), dimethylformamide (80 mL), as described in Preparation 193 gave 0.82 g (71%) of the desired compound as a white foam: $^1$H-NMR is consistent with structure; MS (FD) 676.4 (M+).

Example 96

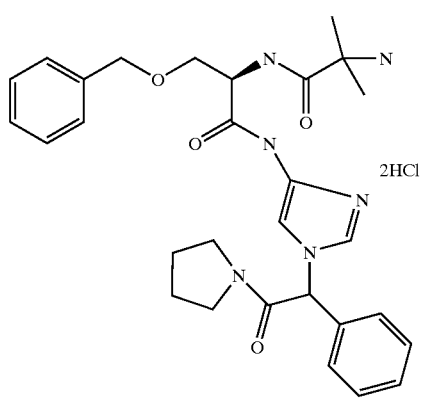

Reaction of the product of Preparation 203 (0.7 g, 1.1 mmol), trifluoroacetic acid (4 ml), dichloromethane (12 mL) as described in Example 86 gave 0.52 g (84%) of the desired product as a yellow solid: $^1$H-NMR is consistent with structure; MS (FD) 530 (M+). Anal. Calc'd for $C_{29}H_{33}N_6O_4 \cdot 2.7HCl$: C, 55.37; H, 5.88; N, 13.36. Found: C, 55.49; H, 5.95; N, 13.56.

Example 97

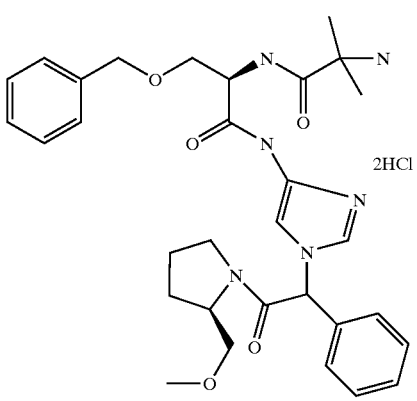

Reaction of the product of Preparation 204 (0.7 g, 1.0 mmol), trifluoroacetic acid (4 mL), dichloromethane (12 mL), as described in Example 86 gave 0.56 g (92%) of the desired product as a white solid: $^1$H-NMR is consistent with structure; MS (FD) 576 (M+); Anal. Calc'd for $C_{31}H_{39}N_6O_5 \cdot 2.5HCl$: C, 55.75; H, 6.41; N, 12.58. Found: C, 55.45; H, 6.36; N, 13.17.

Preparation 205

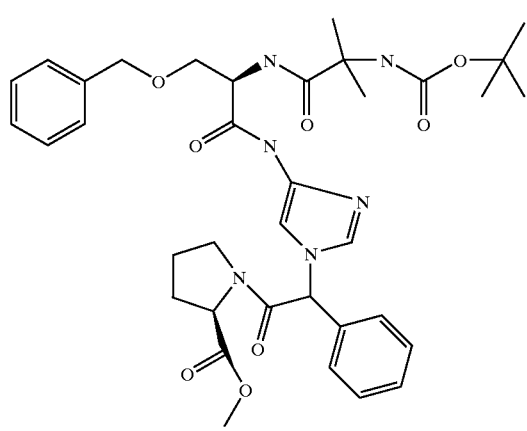

Reaction of the product of Preparation 8 from Examples Part 1 (1.0 g, 1.7 mmol), D-proline methyl ester (0.22 g, 1.7 mmol), 1-hydroxybenzotriazole (0.23 g, 1.7 mmol), 1-(3-dimethylaminopropyl)-3-ethylcarbodiimide (0.4 g, 1.9 mmol), dichloromethane (50 mL) as described in Example 86 gave 0.2 g (17%) of the desired compound as a yellow foam: $^1$H-NMR is consistent with structure; MS (FD) 690 (M+).

Preparation 206

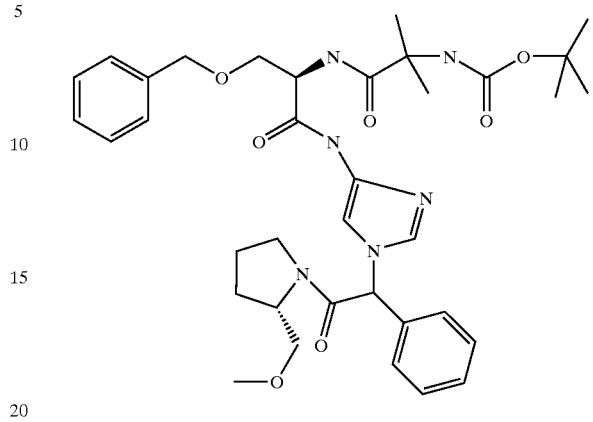

Reaction of the product of Preparation 8 from Examples Part 1 (1.0 g, 1.7 mmol), (S)-2-methoxymethylpyrrolidine (0.2 mL, 1.7 mmol), 1-hydroxybenzotriazole (0.26 g, 1.9 mmol), 1-(3-dimethylaminopropyl)-3-ethylcarbodiimide (0.4 g, 1.9 mmol), dimethylformamide (80 mL) as described in Preparation 193 gave 0.87 g (76%) of the desired product as a tan foam: $^1$H-NMR is consistent with structure; MS (FD) 676 (M+).

Example 98

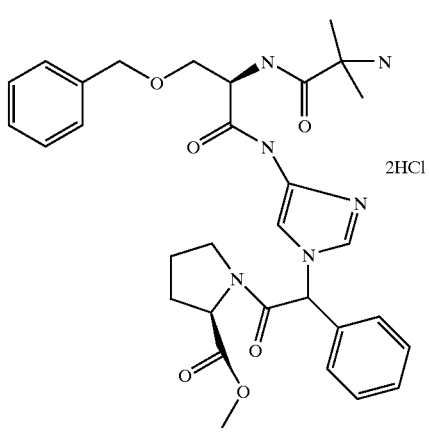

Reaction of the product of Preparation 205 (0.18 g, 0.26 mmol), trifluoroacetic acid (3.3 mL), dichloromethane (10 mL) as described in Example 86 gave 0.16 g (93%) of the desired product as a white foam: $^1$H-NMR is consistent with structure; MS (FD) 590 (M+).

Example 99

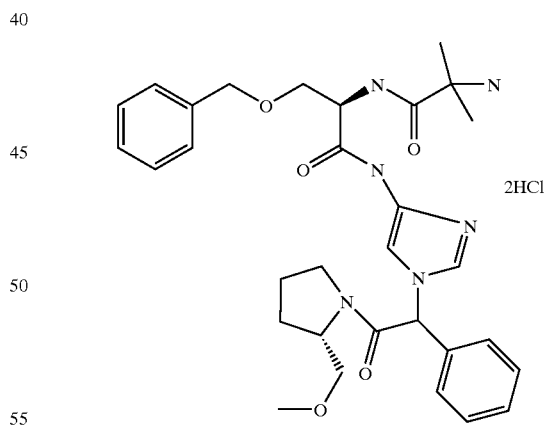

Reaction of the product of Preparation 206 (0.77 g, 1.1 mmol), trifluoroacetic acid (4 mL), dichloromethane (12 mL) as described in Example 86 gave 0.54 g (77%) of the desired product as a tan solid: $^1$H-NMR is consistent with structure; MS (FD) 576.1 (M+); Anal. Calc'd for $C_{31}H_{39}N_6O_5 \cdot 2.3HCl$: C, 56.37; H, 6.45; N, 12.72. Found: C, 56.28; H, 6.04; N, 13.36.

Preparation 208

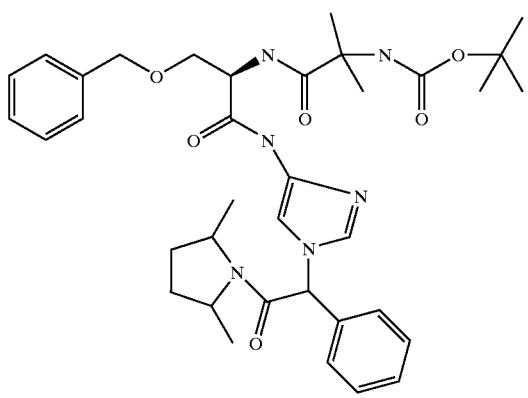

Reaction of the product of Preparation 8 from Examples Part 1 (1.0 g, 1.7 mmol), 3,5-dimethylpyrrolidine (0.2 mL, 1.7 mmol), 1-hydroxybenzotriazole (0.26 g, 1.9 mmol), 1-(3-dimethylaminopropyl)-3-ethylcarbodiimide (0.4 g, 1.9 mmol), dimethylformamide (80 mL), as described in Preparation 193 gave 0.95 g (95%) of the desired product as a tan foam: $^1$H-NMR is consistent with structure; MS (FD) 661 (M+); Anal. Calc'd for $C_{36}H_{48}N_6O_6C$, 65.43; H, 7.32; N, 12.72. Found: C, 65.22; H, 7.19; N, 12.87.

Preparation 209

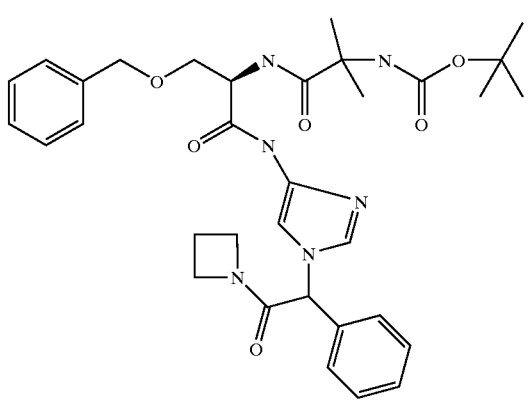

Reaction of the product of Preparation 8 from Examples Part 1 (1.0 g, 1.7 mmol), azetidine (0.11 mL, 1.7 mmol), 1-hydroxybenzotriazole (0.26 g, 1.9 mmol), 1-(3-dimethylaminopropyl)-3-ethylcarbodiimide (0.4 g, 1.9 mmol), dimethylformamide (80 mL) as described in Preparation 193 gave 0.64 g (61%) of the desired product as a tan foam: $^1$H-NMR is consistent with structure; MS (FD) 618 (M+).

Example 100

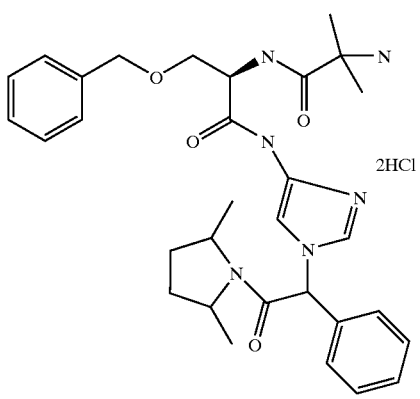

Reaction of the product of Preparation 208 (0.9 g, 1.4 mmol), trifluoroacetic acid (4 mL), dichloromethane (12 mL) as described in Example 86 gave 0.69 g (83%) of the desired product as a yellow solid: $^1$H-NMR is consistent with structure: MS (FD) 561 (M+); Anal. Calc'd for $C_{31}H_{39}N_6O_4 \cdot 2.2HCl$: C, 59.10; H, 6.64; N, 13.11. Found: C, 58.04; H, 6.75; N, 13.53.

Example 101

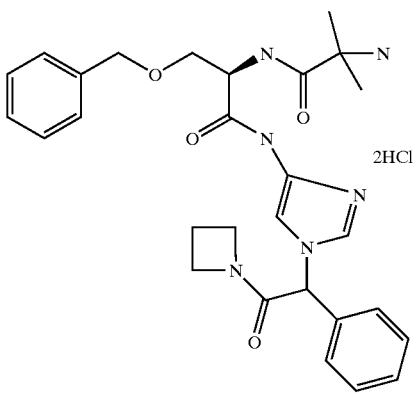

Reaction of the product of Preparation 209 (0.5 g, 0.81 mmol), trifluoroacetic acid (4 mL), dichloromethane (12 mL) as described in Example 86 gave 0.42 g (93%) of the desired product as a white solid: $^1$H-NMR is consistent with structure; MS (FD) 518 (M+); Anal. Calc'd for $C_{29}H_{33}N_6O_4 \cdot 2.5HCl$: C, 55.15; H, 6.03; N, 13.78. Found: C, 55.36; H, 5.87; N, 14.01.

Preparation 210

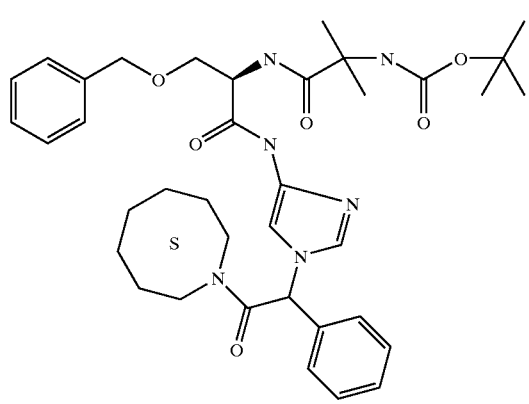

Reaction of the product of Preparation 8 from Examples Part 1 (1.0 g, 1.7 mmol), heptamethyleneimine (0.22 mL, 1.7 mmol), 1-hydroxybenzotriazole (0.26 g, 1.9 mmol), 1-(3-dimethylaminopropyl)-3-ethylcarbodiimide (0.4 g, 1.9 mmol), dimethylformamide (80 mL) as described in Preparation 193 gave 0.89 g (77%) of the desired product as a tan foam: $^1$H-NMR is consistent with structure; MS (FD) 674 (M+); Anal. Calc'd for $C_{37}H_{50}N_6O_6 \cdot 0.6H_2O$: C, 64.82; H, 7.53; N, 12.26. Found: C, 64.59; H, 7.39; N, 12.83.

Preparation 211

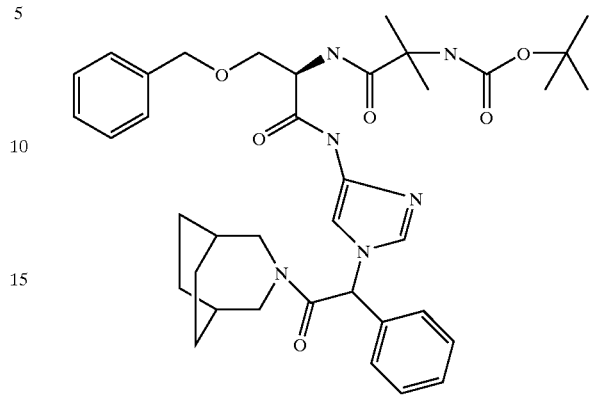

Reaction of the product of Preparation 8 from Examples Part 1 (1.0 g, 1.7 mmol), 3-azabicyclo(3.2.2)nonane (0.21 g, 1.7 mmol), 1-hydroxybenzotriazole (0.26 g, 1.9 mmol), 1-(3-dimethylaminopropyl)-3-ethylcarbodiimide (0.4 g, 1.9 mmol), dimethylformamide (80 mL) as described in Preparation 193 gave 1.0 g (85%) of the desired compound as a yellow foam: $^1$H-NMR is consistent with structure; MS (FD) 686 (M+); Anal. Calc'd for $C_{38}H_{50}N_6O_6$: C, 66.45; H, 7.34; N, 12.24. Found: C, 66.65; H, 7.42; N, 12.34.

Example 102

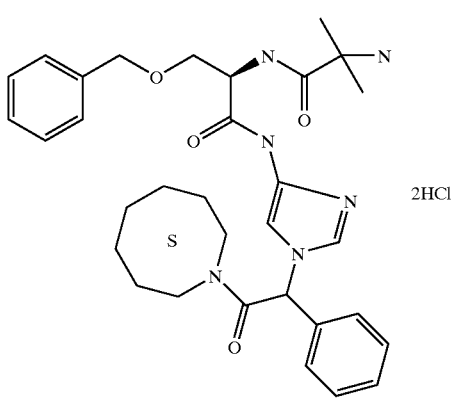

2HCl

Reaction of the product of Preparation 210 (0.83 g, 1.2 mmol), trifluoroacetic acid (4 mL), dichloromethane (12 mL) as described in Example 86 gave 0.67 g (92%) of the desired product as a tan solid: $^1$H-NMR is consistent with structure; MS (high res) calc'd for $C_{32}H_{43}N_6O_4$: 575.3346. Found: 575.3352.

Example 103

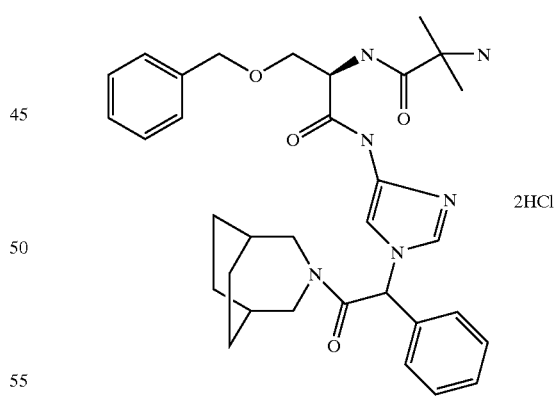

2HCl

Reaction of the product of Preparation 211 (0.95 g, 1.4 mmol), trifluoroacetic acid (4 mL), dichloromethane (12 mL) as described in Example 86 gave 0.75 g (86%) of the desired product as a yellow solid: $^1$H-NMR is consistent with structure; MS (FD) 586 (M+); Anal. Calc'd for $C_{33}H_{41}N_6O_4 \cdot 2.2HCl$: C, 59.43; H, 6.68; n, 12.60. Found: C, 59.54; H, 6.86; N, 12.73.

Preparation 212

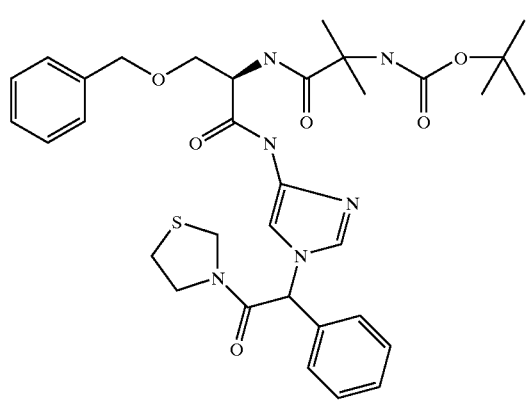

Reaction of the product of Preparation 8 from Examples Part 1 (1.0 g, 1.7 mmol), thiazolidine (0.134 mL, 1.7 mmol), 1-hydroxybenzotriazole (0.26 g, 1.9 mmol), 1-(3-dimethylaminopropyl)-3-ethylcarbodiimide (0.4 g, 1.9 mmol), dimethylformamide (40 mL) as described in Preparation 193 gave 0.33 g (30%) of the desired product as a white foam: $^1$H-NMR is consistent with structure; MS (FD) 650 (M+).

Preparation 213

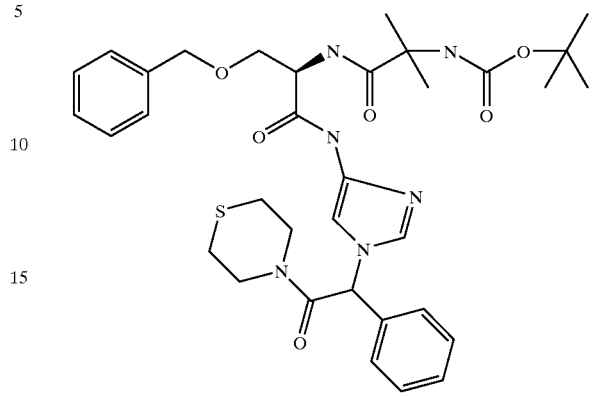

Reaction of the product of Preparation 8 from Examples Part 1 (0.6 g, 1.0 mmol), thiomorpholine (0.1 mL, 1.0 mol), 1-hydroxybenzotriazole (0.15 g, 1.1 mmol), 1-(3-dimethylaminopropyl)-3-ethylcarbodiimide (0.23 g, 1.1 ml), dimethylformamide (40 mL) as described in Preparation 193 gave 0.34 g (55%) of the desired product as a tan foam: $^1$H-NMR is consistent with structure; MS (FD) 664 (M+); Anal. Calc'd for $C_{34}H_{44}N_6O_6S \cdot 0.1H_2O$: C, 61.43; H, 6.67; N, 12.64. Found: 59.81; H, 6.79; N, 12.31.

Example 104

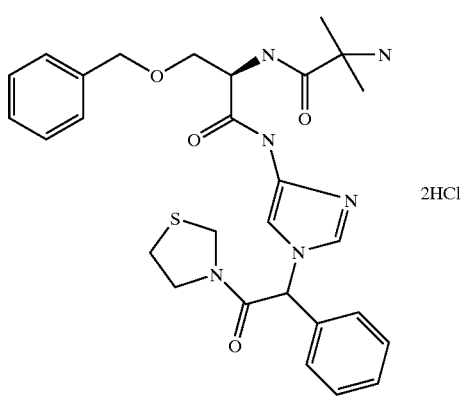

2HCl

Reaction of the product of Preparation 212 (0.31 g, 0.48 mmol), trifluoroacetic acid (4 ml), dichloromethane (12 mL) as described in Example 86 gave 0.28 g (93%) of the desired product as a white solid: $^1$H-NMR is consistent with structure; MS (FD) 550 (M+); Anal. Calc'd for $C_{28}H_{34}N_6O_4S \cdot 2.6HCl$: C, 52.10; H, 5.72; N, 13.01. Found: C, 52.01; H, 5.78; N, 13.23.

Example 105

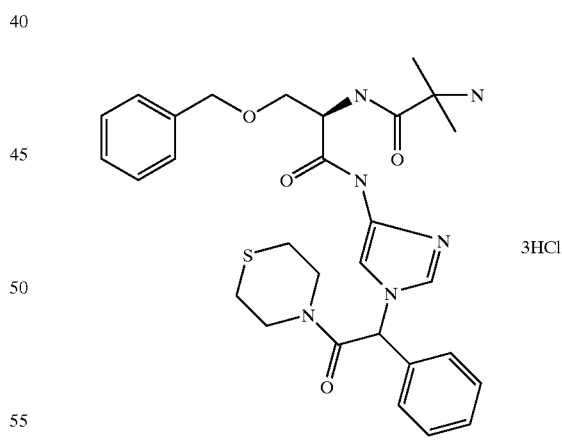

3HCl

Reaction of the product of Preparation 213 (0.3 g, 0.45 mmol), trifluoroacetic acid (4 mL), dichloromethane (12 mL) as described in Example 86 gave 0.26 g (100%) of the desired product as a yellow solid: $^1$H-NMR is consistent with structure; MS (FD) 564.1 (M+); Anal. Calc'd for $C_{29}H_{36}N_6O_5 \cdot 3HCl$: C, 51.67; H, 5.83; N, 12.47. Found: C, 52.08; H, 6.24; N, 12.48.

Preparation 214

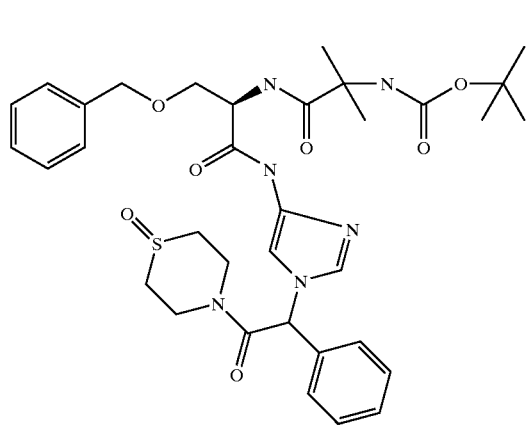

To a solution of the product of Preparation 213, 0.52 g (0.78 mmol) in 10 mL of dichloromethane was added 0.36 mL (3.12 mmol) of 30% hydrogen peroxide. The solution was heated to reflux for 4 h, then quenched with sodium bisulfite and concentrated. The residue was chromatographed on silica gel using 10% methanol/chloroform as eluant to yield 0.16 g (30%) of the desired product as a white foam: $^1$H-NMR is consistent with structure; MS (FD) 681 (M+); Anal. Calc'd for $C_{34}H_{44}N_6O_7S \cdot 1.5H_2O$: C, 56.42; H, 6.54; N, 11.61. Found: C, 56.39; H, 6.15; N, 11.67.

Example 106

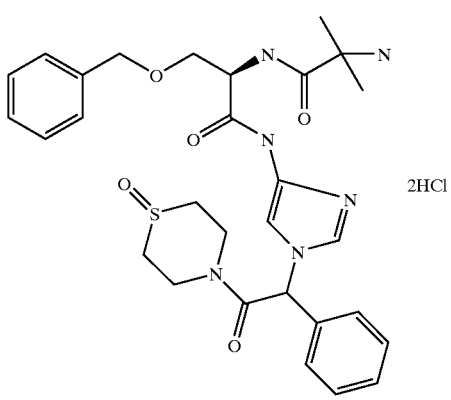

Reaction of the product of Preparation 214 (0.15 g, 0.21 mmol), trifluoroacetic acid (4 mL), dichloromethane (12 mL) as described in Example 86 gave 0.13 g (100%) of the desired product as a white solid: $^1$H-NMR is consistent with structure; MS (FD) 580 (M+); Anal. Calc'd for $C_{29}H_{36}N_6O_5S \cdot 2.5HCl$: C, 51.84; H, 5.78; N, 12.51. Found: C, 51.81; H, 5.79; N, 11.94.

Preparation 215

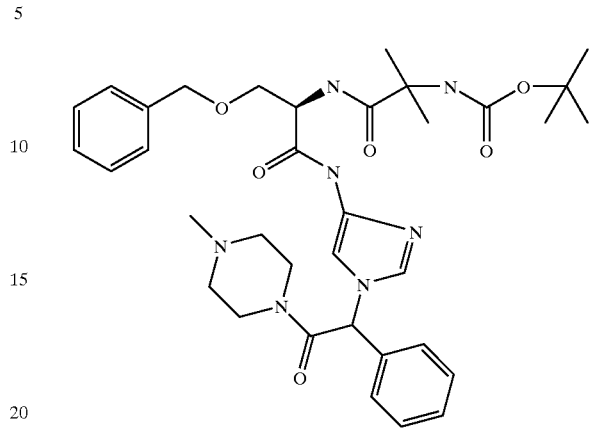

Reaction of the product of Preparation 8 from Examples Part 1 (0.5 g, 0.9 mmol), N-methylpiperazine (0.1 mL, 0.9 mmol), 1-hydroxybenzotriazole (0.13 g, 1.0 mmol), 1-(3-dimethylaminopropyl)-3-ethylcarbodiimide (0.2 g, 1.0 mmol), dimethylformamide (30 mL) as described in Preparation 193 gave 0.12 g (20%) of the desired product as a clear oil: $^1$H-NMR is consistent with structure; MS (FD) 662 (M+).

Example 107

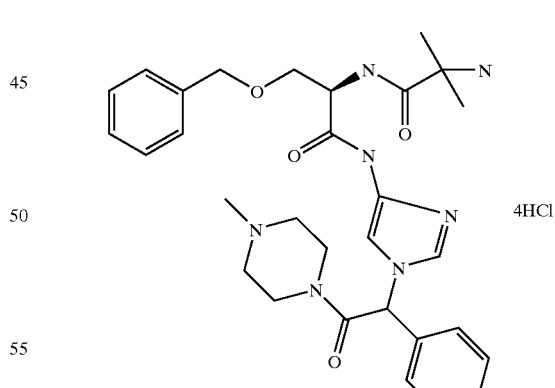

Reaction of the product of Preparation 215 (0.1 g, 0.15 mmol), trifluoroacetic acid (4 mL), dichloromethane (12 mL) as described in Example 86 gave 0.085 g (94%) of the desired product as a yellow solid: $^1$H-NMR is consistent with structure; MS (FD) 561 (M+).

Preparation 216

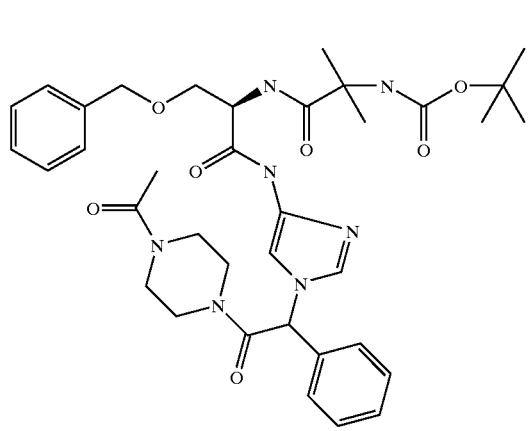

Reaction of the product of Preparation 8 from Examples Part 1 (0.6 g, 1.0 mmol), 1-acetylpiperazine (0.13 g, 1.0 mmol), 1-hydroxybenzotriazole (0.15 g, 1.1 mmol), 1-(3-dimethylaminopropyl)-3-ethylcarbodiimide (0.23 g, 1.1 mmol), dimethylformamide (40 mL) as described in Preparation 193 gave 0.52 g (75%) of the desired compound as a tan foam: $^1$H-NMR is consistent with structure; MS (FD) 689.4 (M+).

Preparation 217

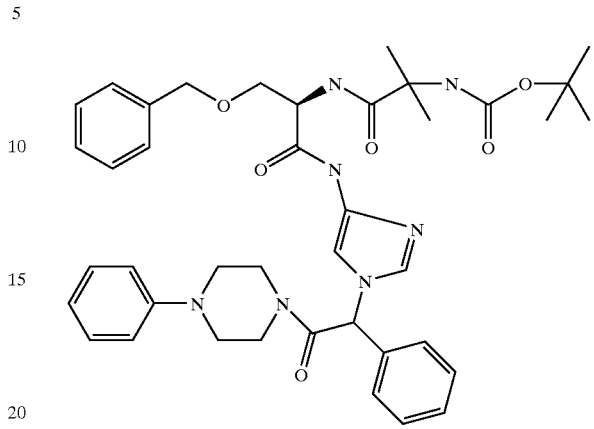

Reaction of the product of Preparation 8 from Examples Part 1 (0.5 g, 0.9 mmol), N-phenylpiperazine (0.14 mL, 0.9 mmol), 1-hydroxybenzotriazole (0.13 g, 1.0 mmol), 1-(3-dimethylaminopropyl)-3-ethylcarbodiimide (0.2 g, 1.0 mol), dimethylformamide (30 mL) as described in Preparation 193 gave 0.42 g (65%) of the desired product as a tan foam: $^1$H-NMR is consistent with structure; MS (FD) 723.7 (M+); Anal. Calc'd for $C_{40}H_{49}N_7O_6$: C, 66.37; H, 6.82; N, 13.55. Found: C, 62.92; H, 6.87; N, 13.24.

Example 108

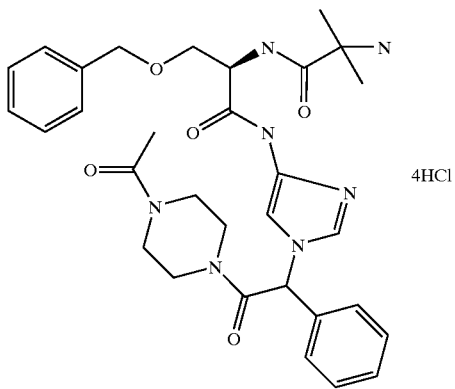

Reaction of the product of Preparation 216 (0.47 g, 0.68 mmol), trifluoroacetic acid (4 mL), dichloromethane (12 mL) as described in Example 86 gave 0.2 g (50%) of the desired product as a tan solid: $^1$H-NMR is consistent with structure; MS (FD) 589.3 (M+); Anal. Calc'd for $C_{31}H_{39}N_7O_5 \cdot 4.5HCl$: C, 49.40; H, 5.82; N, 13.01. Found: C, 49.84; H, 5.99; N, 12.57.

Example 109

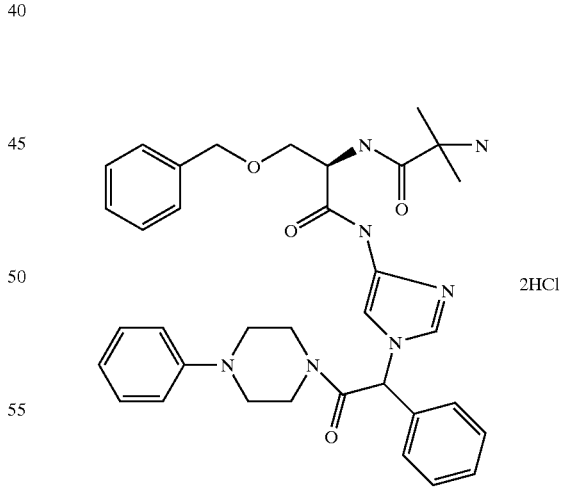

Reaction of the product of Preparation 217 (0.38 g, 0.5 mmol), trifluoroacetic acid (4 mL), dichloromethane (12 mL) as described in Example 86 gave 0.2 g (87%) of the desired product as a tan foam: $^1$H-NMR is consistent with structure; MS (FD) 623 (M+).

Preparation 218

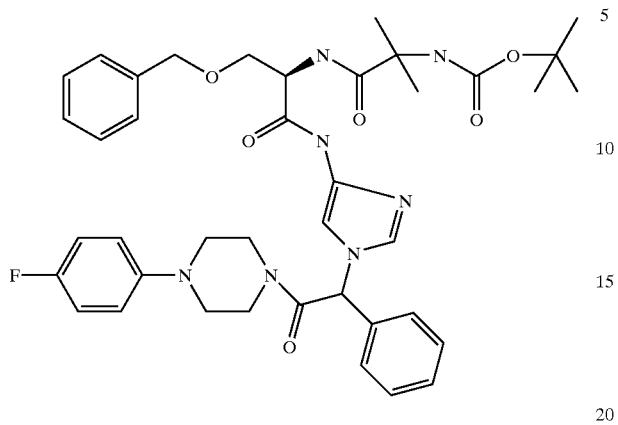

Reaction of the product of Preparation 8 from Examples Part 1 (0.6 g, 1.0 mmol), 1-(4-fluorophenyl)piperazine (0.18 g, 1.0 mmol), 1-hydroxybenzotriazole (0.15 g, 1.1 mmol), 1-(3-dimethylaminopropyl)-3-ethylcarbodiimide (0.23 g, 1.1 mmol), dimethylformamide (30 mL) as described in Preparation 193 gave 0.42 g (57%) of the desired product as a tan foam: $^1$H-NMR is consistent with structure; MS (FD) 742 (M+); Anal. Calc'd for $C_{40}H_{48}N_7O_6F.0.4H_2O$: C, 64.14; H, 6.57; N, 13.09. Found: C, 64.06; H, 6.35; N, 12.75.

Preparation 219

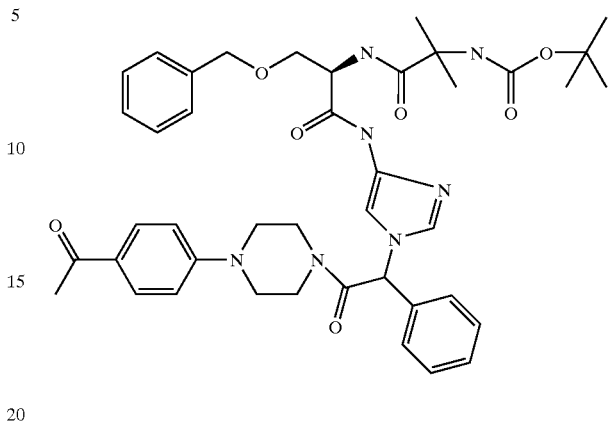

Reaction of the product of Preparation 8 from Examples Part 1 (0.6 g, 1.0 mmol), 4-piperazinoacetophenone (0.2 g, 1.0 mmol), 1-hydroxybenzotriazole (0.15 g, 1.1 mmol), 1-(3-dimethylaminopropyl)-3-ethylcarbodiimide (0.23 g, 1.1 mmol), dimethylformamide (30 mL) as described in Preparation 193 gave 0.42 g (55%) of the desired compound as a tan foam: $^1$H-NMR is consistent with structure; MS (ion spray) 766.2 (M+1); Anal. Calc'd for $C_{42}H_{52}N_7O_7.0.8H_2O$: C, 64.56; H, 6.91; N, 12.55. Found: C, 64.59; H, 6.59; N, 12.31.

Example 110

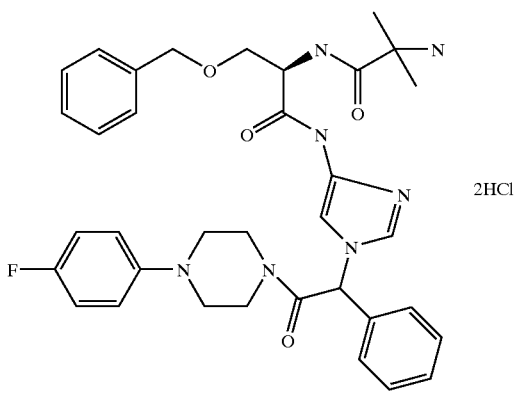

2HCl

Reaction of the product of Preparation 218 (0.37 g, 0.5 mmol), trifluoroacetic acid (2 mL), dichloromethane (6 mL) as described in Example 86 gave 0.36 g (100%) of the desired product as a white solid: $^1$H-NMR is consistent with structure; MS (FD) 641 (M+); Anal. Calc'd for $C_{35}H_{40}N_7O_4F.2.8HCl$: C, 56.52; H, 5.80; N, 13.18. Found: C, 56.92; H, 5.79; N, 12.86.

Example 111

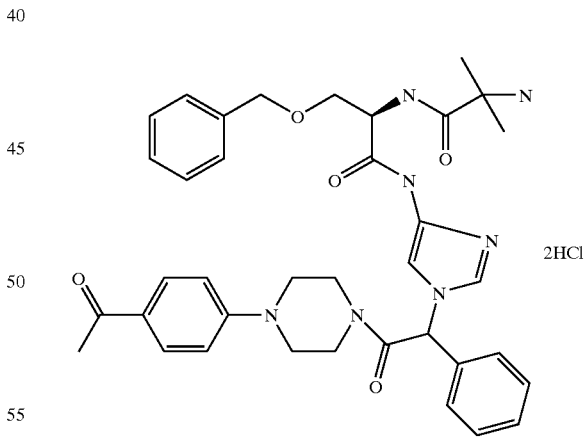

2HCl

Reaction of the product of Preparation 219 (0.36 g, 0.47 mmol), trifluoroacetic acid (2 mL), dichloromethane (6 mL) as described in Example 86 gave 0.33 g (94%) of the desired product as a yellow solid: $^1$H-NMR is consistent with structure; MS (ion spray) 666 (M+1); Anal. Calc'd for $C_{37}H_{43}N_7O_5.2.5HCl$: C, 58.71; H, 6.06; N, 12.95. Found: C, 58.56; H, 6.44; N, 12.60.

Preparation 220

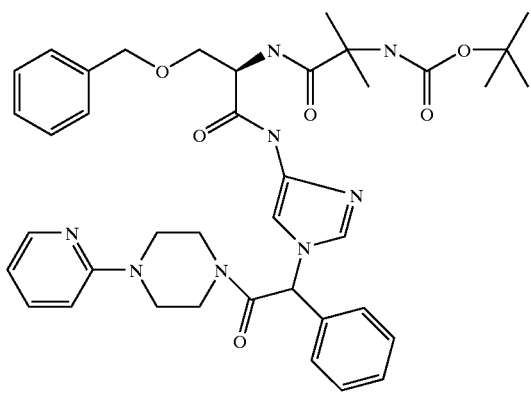

Reaction of the product of Preparation 8 from Examples Part 1 (0.6 g, 1.0 mmol), 1-(2-pyridyl)piperazine (0.16 mL, 1.0 mmol), 1-hydroxybenzotriazole (0.15 g, 1.1 mmol), 1-(3-dimethylaminopropyl)-3-ethylcarbodiimide (0.23 g, 1.1 mmol), dimethylformamide (40 mL) as described in Preparation 193 gave 0.48 g (66%) of the desired product as a white foam: $^1$H-NMR is consistent with structure; MS (ion spray) 725 (M+1); Anal. Calc'd for $C_{39}H_{48}N_6O_7 \cdot 0.5H_2O$: C, 63.83; H, 6.73; N, 15.27. Found: C, 63.85; H, 6.76; 20. N, 15.09.

Preparation 221

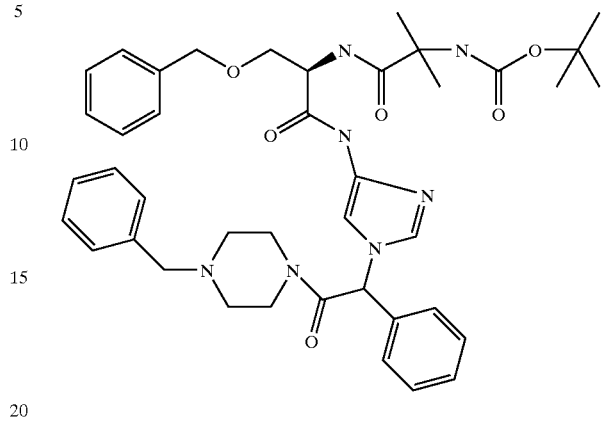

Reaction of the product of Preparation 8 from Examples Part 1 (0.6 g, 1.0 mmol), 1-benzylpiperazine (0.18 mL, 1.0 mmol), 1-hydroxybenzotriazole (0.15 g, 1.1 mmol), 1-(3-dimethylaminopropyl)-3-ethylcarbodiimide (0.23 g, 1.1 mmol), dimethylformamide (30 mL) as described in Preparation 193 gave 0.3 g (40%) of the desired product as a tan foam: $^1$H-NMR is consistent with structure; MS (FD) 737.6 (M+); Anal. Calc'd for $C_{41}H_{51}N_7O_6$: C, 66.74; H, 6.97; N, 13.29. Found: C, 66.67; H, 7.08; N, 13.09.

Example 112

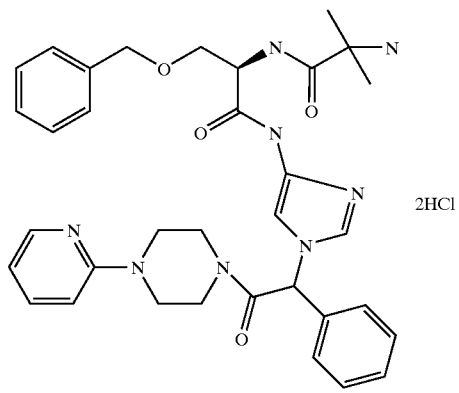

Reaction of the product of Preparation 220 (0.42 g, 0.58 mmol), trifluoroacetic acid (2 mL), dichloromethane (6 mL) as described in Example 86 gave 0.35 g (88%) of the desired product as a white foam: $^1$H-NMR is consistent with structure; MS (high res) calc'd for $C_{34}H_4:N_3O_4$: 625.3251. Found: 625.3256.

Example 113

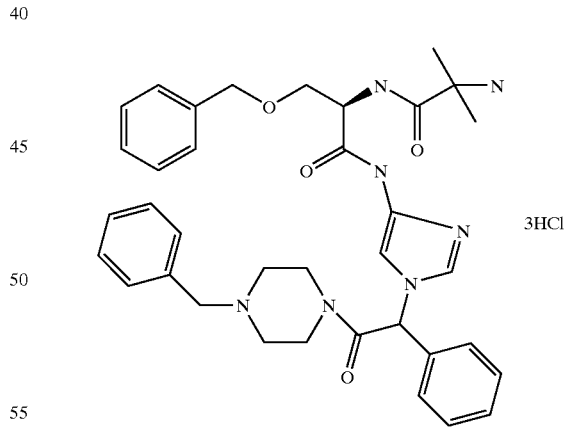

Reaction of the product of Preparation 221 (0.28 g, 0.38 mmol), trifluoroacetic acid (2 mL), dichloromethane (6 mL) as described in Example 86 gave 0.19 g (70%) of the desired product as a yellow solid: $^1$H-NMR is consistent with structure; MS (FD) 637 (M+); Anal. Calc'd for $C_{36}H_{43}N_7O_4 \cdot 3.5HCl$: C, 56.49; H, 6.12; N, 12.81. Found: C, 56.77; H, 6.44; N, 12.31.

Preparation 222

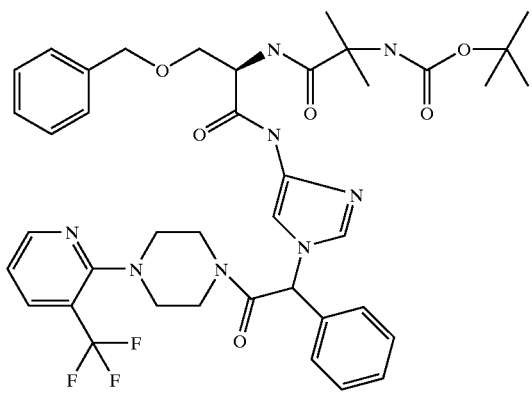

Reaction of the product of Preparation 8 from Examples Part 1 (0.6 g, 1.0 mmol), 1-((3-trifluoromethyl)-2-pyridyl)piperazine (0.23 g, 1.0 mmol), 1-hydroxybenzotriazole (0.15 g, 1.1 mmol), 1-(3-dimethylaminopropyl)-3-ethylcarbodiimide (0.23 g, 1.1 mmol), dimethylformamide (40 mL) as described in Preparation 193 gave 0.5 g (63%) of the product as a tan foam: $^1$H-NMR is consistent with structure; MS (ion spray) 793 (M+1).

Example 114

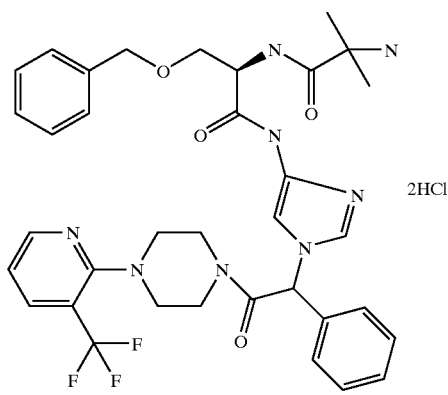

Reaction of the product of Preparation 222 (0.42 g, 0.53 mmol), trifluoroacetic acid (2 mL), dichloromethane (6 mL) as described in Example 86 gave 0.34 g (85%) of the desired product as a yellow solid: $^1$H-NMR is consistent with structure; MS (ion spray) 693 (M+1); Anal. Calc'd for $C_{35}H_{39}N_6O_4F_3 \cdot 2.3HCl$: C, 54.13; H, 5.36; N, 14.43. Found: C, 54.00; H, 5.55; N, 14.07.

Preparation 223

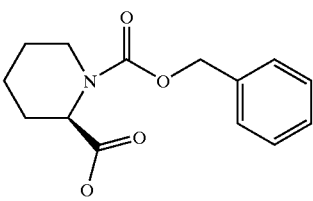

To a solution of d-pipecolinic acid, 2.0 g (15.5 mmol) in 30 mL of 4N sodium hydroxide as 0° C. was added 2.9 mL of benzyl chloroformate dropwise. The mixture was stirred overnight slowly warming to ambient temperature then was quenched into 5N hydrochloric acid. The mixture was extracted with chloroform. The combined organic extracts were washed with brine, dried over sodium sulfate, filtered and concentrated to yield 4.1 g (100%) of the desired product as a colorless oil: $^1$H-NMR is consistent with structure; MS (FD) 264 (M+).

Preparation 224

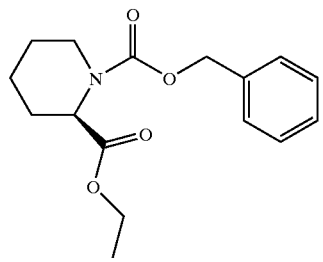

A solution of the product of Preparation 223, 4.1 g (15.5 mmol) and p-toluenesulfonic acid, 0.6 g in 100 mL of absolute ethanol was refluxed for 7 h. The mixture was quenched with solid sodium bicarbonate and concentrated. The residue was partitioned between ethyl acetate and water and extracted with ethyl acetate. The combined organic extracts were washed with brine, dried over sodium sulfate, filtered and concentrated. The residue was chromatographed on silica gel using chloroform as eluant to yield 0.91 g (20%) of the desired product as a colorless oil: $^1$H-NMR is consistent with structure; MS (FD) 291 (M+); Anal. Calc'd for $C_{16}H_{21}NO_4$: C, 65.96; H, 7.27; N, 4.81. Found: C, 66.21; H, 7.23; N, 4.93.

Preparation 225

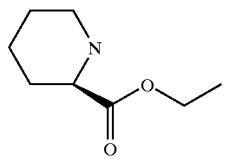

A solution of the product of Preparation 224, 0.9 g (3.0 mmol) in 20 mL of ethyl acetate and 40 mL of absolute ethanol was added to a slurry of 10% palladium on carbon, 0.5 g in 20 mL of ethyl acetate. The slurry was hydrogenated at 40 psi for 40 min, then was filtered through celite and concentrated to yield 0.3 g (64%) of the desired product as a colorless oil: This material was carried on without purification.

Preparation 226

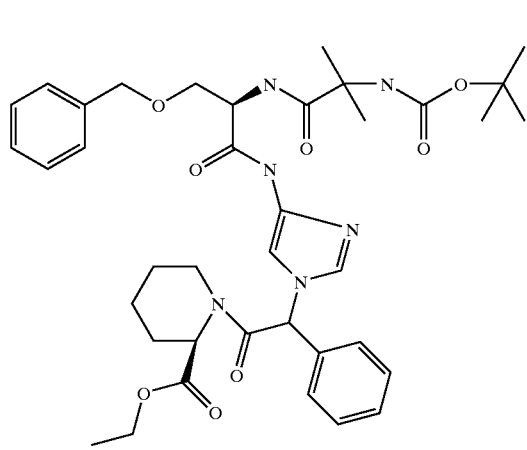

Reaction of the product of Preparation 8 from Examples Part 1 (1.1 g, 1.9 mmol), the product of Preparation 225 (0.3 g, 1.9 mmol), 1-hydroxybenzotriazole (0.28 g, 2.1 mmol), 1-(3-dimethylaminopropyl)-3-ethylcarbodiimide (0.43 g, 2.1 mmol), dimethylformamide (40 mL), as described in Preparation 193 gave 0.81 g (59%) of the desired product as a tan foam: $^{1}$H-NMR is consistent with structure; MS (FD) 719 (M+); Anal. Calc'd for $C_{38}H_{50}N_{6}O_{9}$: C, 63.49; H, 7.01; N, 11.69. Found: C, 62.98; H, 7.33; N, 11.51.

Preparation 227

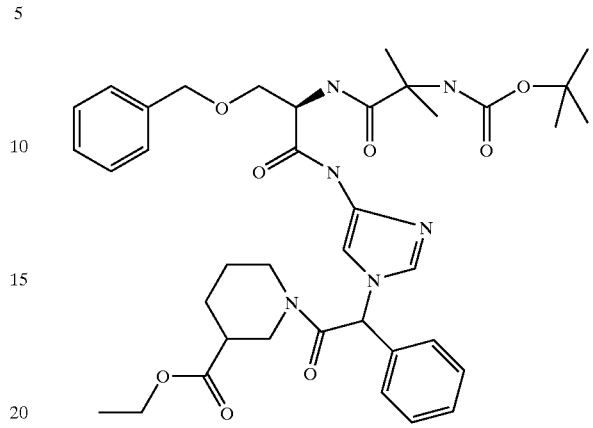

Reaction of the product of Preparation 8 from Examples Part 1 (1.0 g, 1.7 mmol), ethyl nipecotate (0.27 mL, 1.7 mmol), 1-hydroxybenzotriazole (0.25 g, 1.9 mmol), 1-(3-dimethylaminopropyl)-3-ethylcarbodiimide (0.4 g, 1.9 mmol), dimethylformamide (80 mL) as described in Preparation 193 gave 0.97 g (79%) of the desired product as a tan foam: $^{1}$H-NMR is consistent with structure; MS (FD) 718 (M+).

Example 115

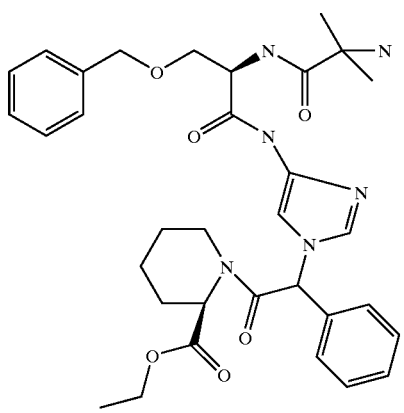

Reaction of the product of Preparation 226 (0.75 g, 1.0 mmol), trifluoroacetic acid (2 mL), dichloromethane (6 mL) as described in Example 86 gave 0.6 g (87%) of the desired product as a white solid: $^{1}$H-NMR is consistent with structure; MS (FD) 619 (M+); Anal. Calc'd for $C_{33}H_{42}N_{6}O_{6}\cdot 2HCl$: C, 57.31; H, 6.41; N, 12.15. Found: C, 57.09; H, 6.50; N, 12.04.

Example 116

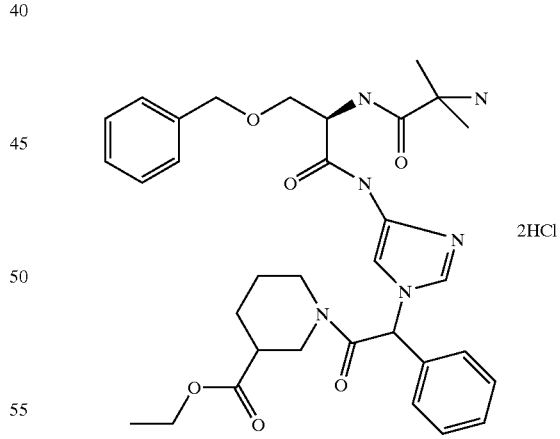

Reaction of the product of Preparation 227 (0.91 g, 1.26 mmol), trifluoroacetic acid (4 mL), dichloromethane (12 mL) as described in Example 86 gave 0.7 g (84%) of the desired product as a white solid: $^{1}$H-NMR is consistent with structure; MS (FD) 618 (M+); Anal. Calc'd for $C_{33}H_{42}N_{6}O_{6}\cdot 2.2HCl$: C, 56.71; H, 6.37; N, 12.02. Found: C, 56.71; H, 6.44; N, 12.45.

Preparation 228

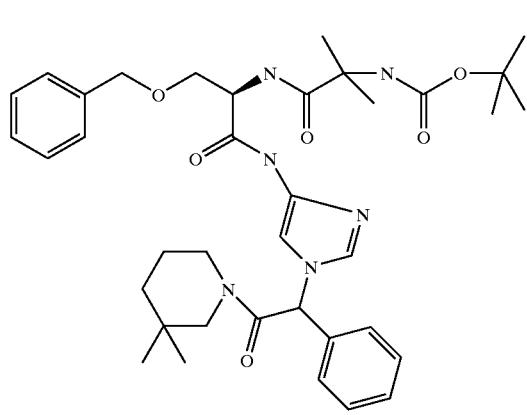

Reaction of the product of Preparation 8 from Examples Part 1 (0.7 g, 1.2 mmol), 3,5-dimethylpiperidine (0.16 mL, 1.2 mmol), 1-hydroxybenzotriazole (0.18 g, 1.32 mmol), 1-(3-dimethylaminopropyl)-3-ethylcarbodiimide (0.27 g, 1.32 mmol), dimethylformamide (80 mL) as described in Preparation 193 gave 0.8 g (100%) of the desired product as a tan solid: $^1$H-NMR is consistent with structure; MS (FD) (674 (M+).

Preparation 229

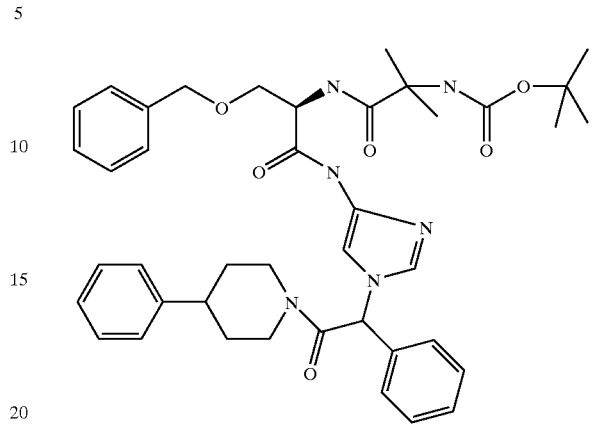

Reaction of the product of Preparation 8 from Examples Part 1 (1.0 g, 1.7 mmol), 4-phenylpiperidine (0.28 g, 1.7 mmol), 1-hydroxybenzotriazole (0.26 g, 1.9 mmol), 1-(3-dimethylaminopropyl)-3-ethylcarbodiimide (0.4 g, 1.9 mmol), dimethylformamide (80 mL) as described in Preparation 193 gave 0.92 g (75%) of the desired compound as a tan foam: $^1$H-NMR is consistent with structure; MS (FD) 722 (M+).

Example 117

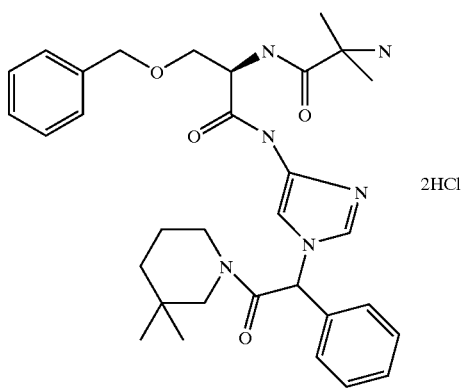

2HCl

Example 118

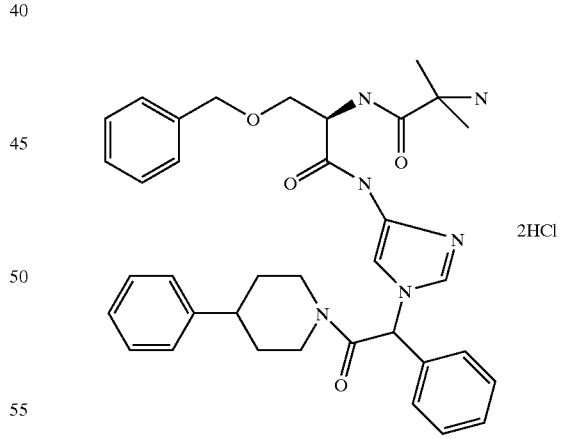

2HCl

Reaction of the product of Preparation 228 (0.47 g, 0.7 mmol), trifluoroacetic acid (4 mL), dichloromethane (12 mL) as in Example 86 gave 0.4 g (93%) of the desired product as a yellow solid: $^1$H-NMR is consistent with structure; MS (high res) calc'd for C32H43N6O4: 575.3346. Found: 575.3341.

Reaction of the product of Preparation 229 (0.88 g, 1.2 mmol), trifluoroacetic acid (4 mL), dichloromethane (12 mL) as described in Example 86 gave 0.77 g (96%) of the desired product as a yellow solid: $^1$H-NMR is consistent with structure; MS (FD) 622.2 (M+); Anal. Calc'd for $C_{36}H_{42}N_6O_4 \cdot 2.3HCl$: C, 61.19; H, 6.33; N, 11.89. Found: C, 61.02; H, 6.35; N, 11.97.

Preparation 229A

Preparation 230

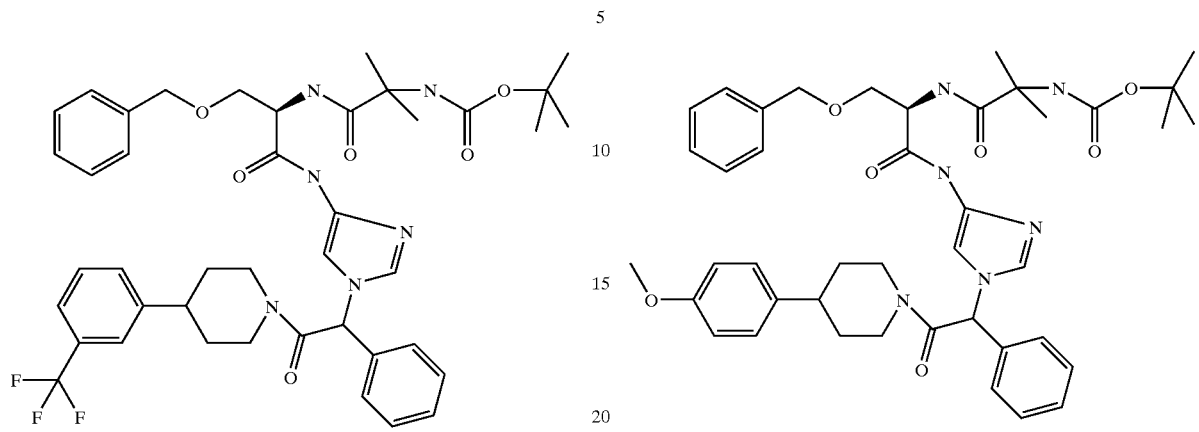

Reaction of the product of Preparation 8 from Examples Part 1 (0.6 g, 1.0 tool), 4-(3-trifluoromethylphenyl)piperidine hydrochloride (DE 3500898, DE 2048589) (0.27 g, 1.0 mmol), triethylamine (0.16 mL, 1.1 mmol), 1-hydroxybenzotriazole (0.15 g, 1.1 mmol), 1-(3-dimethylaminopropyl)-3-ethylcarbodiimide (0.23 g, 1.1 mmol), dimethylformamide (40 mL) as described in Preparation 193 gave 0.4 g (50%) of the desired product as a tan foam: $^1$H-NMR is consistent with structure; MS (FD) 791 (M+); Anal. Calc'd for $C_{42}H_{49}F_3N_6O_6$: C, 63.79; H, 6.35; N, 10.63. Found: C, 63.56; H, 6.53; N, 10.57.

Reaction of the product of Preparation 8 from Examples Part 1 (0.6 g, 1.0 mmol), 4-(4-methoxyphenyl)piperidine hydrochloride (WO 9518118, EP 630887)(0.27 g, 1.0 mmol), triethylamine (0.16 mL, 1.1 mmol), 1-hydroxybenzotriazole (0.15 g, 1.1 mmol), 1-(3-dimethylaminopropyl)-3-ethylcarbodiimide (0.23 g, 1.1 mmol), dimethylformamide (40 mL), as described in Preparation 193 gave 0.45 g (60%) of the desired product as a tan foam: $^1$H-NMR is consistent with structure; MS (FD) 754 (M+); Anal. Calc'd for $C_{42}H_{52}N_6O_7$: C, 67.00; H, 6.96; N, 11.16. Found: C, 66.66; H, 7.40; N, 10.95.

Example 119

Example 120

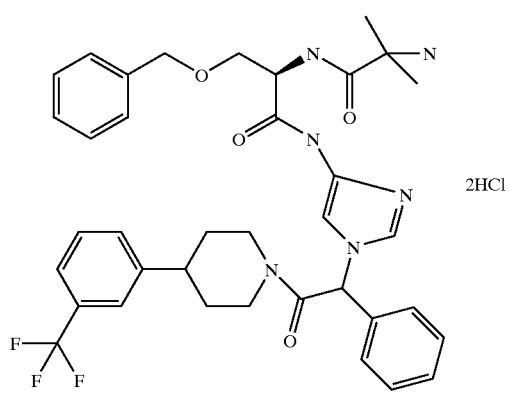

2HCl

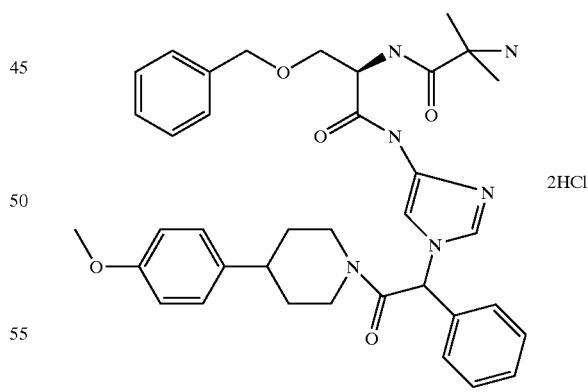

2HCl

Reaction of the product of Preparation 229A (0.36 g, 0.45 mmol), trifluoroacetic acid (2 mL), dichloromethane (6 mL) as described in Example 86 gave 0.34 g (100%) of the desired product. $^1$H-NMR is consistent with structure; MS (FD) 690 (M+); Anal. Calc'd for $C_{37}H_{41}N_6O_4F_3$.2.5HCl: C, 56.86; H, 5.61; N, 10.75. Found: C, 56.72; H, 5.88; N, 10.48.

Reaction of the product of Preparation 230 (0.4 g, 0.53 mmol), trifluoroacetic acid (2 mL), dichloromethane (6 mL), as described in Example 86 gave 0.32 g (84%) of the desired product as a white solid: $^1$H-NMR is consistent with structure; MS (FD) 652 (M+); Anal. Calc'd for $C_{37}H_{44}N_6O_5$.2HCl: C, 61.24; H, 6.39; N, 11.58. Found: C, 60.97; H, 6.38; N, 11.33.

Preparation 231

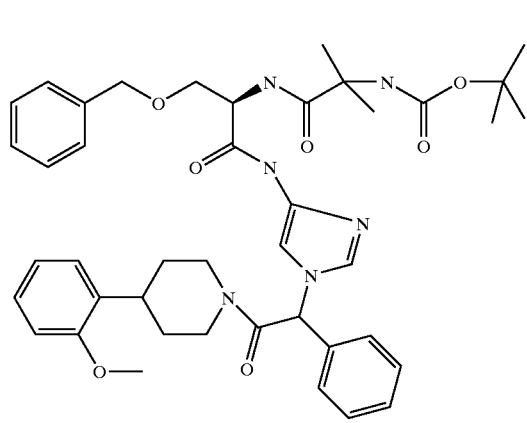

Reaction of the product of preparation 8 from Examples Part 1 (0.6 g, 1.0 mmol), 4-(2-methoxyphenyl)piperidine (0.19 g, 1.0 mmol), 1-hydroxybenzotriazole (0.15 g, 1.1 mmol), 1-(3-dimethylaminopropyl)-3-ethylcarbodiimide (0.23 g, 1.1 mmol), dimethylformamide (30 mL) as described in Preparation 193 gave 0.63 g (84%) of the desired product as a white foam: $^1$H-NMR is consistent with structure; MS (FD) 752 (M+); Anal. Calc'd for $C_{42}H_{52}N_6O_7 \cdot 0.1H_2O$: C, 65.44; H, 7.06; N, 10.90. Found: C, 65.56; H, 7.13; N, 10.89.

Example 121

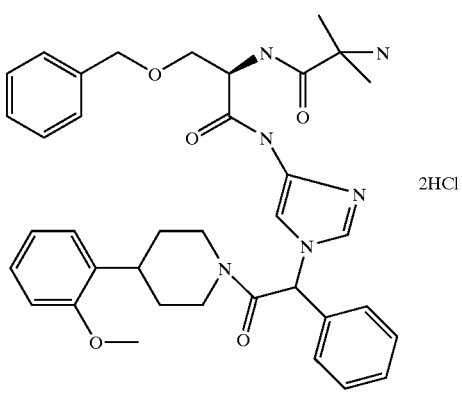

Reaction of the product of Preparation 231 (0.59 g, 0.78 mmol), trifluoroacetic acid (2 mL), dichloromethane (6 mL) as described in Example 86 gave 0.42 g (74%) of the desired product as a white solid: 1H-NMR is consistent with structure; MS (FD) 652 (M+); Anal. Calc'd for $C_{37}H_{44}N_6O_5 \cdot 2HCl$: C, 61.24; H, 6.39; N, 11.58. Found: C, 60.94; H, 6.35; N, 11.33.

Preparation 232

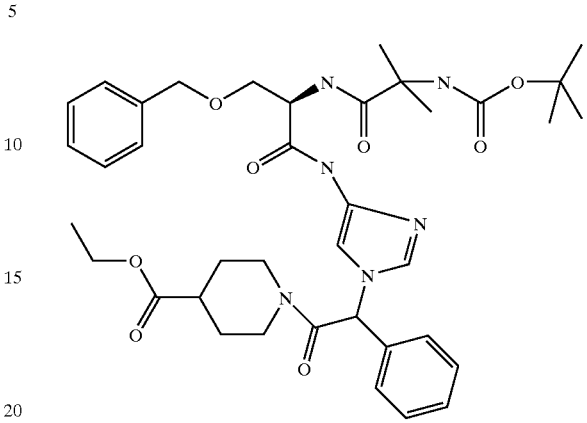

Reaction of the product of Preparation 8 from Examples Part 1 (1.0 g, 1.7 mmol), ethyl isonipecotate (0.27 mL, 1.7 mmol), 1-hydroxybenzotriazole (0.26 g, 1.9 mmol), 1-(3-dimethylaminopropyl)-3-ethylcarbodiimide (0.4 g, 1.9 mmol), dimethylformamide (60 mL) as described in Preparation 193 gave 0.87 g (71%) of the desired product as a yellow foam: $^1$H-NMR is consistent with structure; MS (FD) 718 (M+).

Example 122

Reaction of the product of Preparation 232 (0.85 g, 1.2 mmol), trifluoroacetic acid (4 mL), dichloromethane (12 mL) as in Example 86 gave 0.72 g (91%) of the desired product as a white solid., $^1$H-NMR is consistent with structure; MS (FD) 618 (M+); Anal. Calc'd for $C_{33}N_{42}N_6O_6 \cdot 2.6HCl$: C, 55.56; H, 6.30; N, 11.78. Found: C, 55.89; H, 6.34; N, 12.27.

Preparation 233

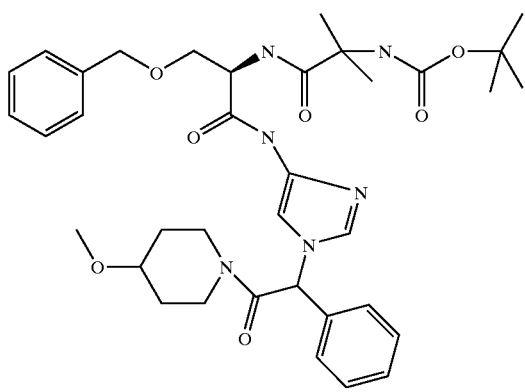

Reaction of the product of Preparation 8 from Examples Part 1 (0.84 g, 1.45 mmol), 4-methoxypiperidine hydrochloride (Baker, et al.; *J. Med. Chem.* 1992, 35(10), 1722–34) (0.22 g, 1.45 mmol), triethylamine (0.22 mL, 1.45 mmol), 1-hydroxybenzotriazole (0.21 g, 1.6 mmol), 1-(3-dimethylaminopropyl)-3-ethylcarbodiimide (0.32 g, 1.6 mmol), dimethylformamide (40 mL) as described in Preparation 193 gave 0.74 g (76%) of the desired product as a white foam: $^1$H-NMR is consistent with structure; MS (FD) 676.6 (M+); Anal. Calc'd for $C_{36}H_{48}N_6O_7$: C, 63.89; H, 7.15; N, 12.42. Found: C, 63.84; H, 7.17; N, 12.12.

Example 123

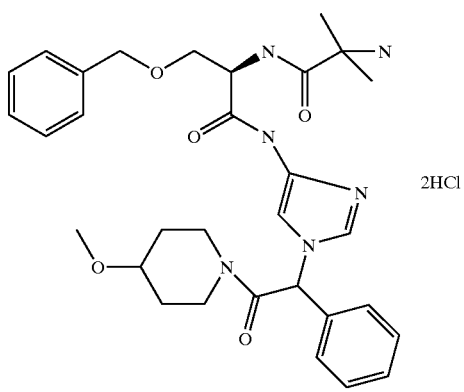

Reaction of the product of Preparation 233 (0.66 g, 1.0 mmol), trifluoroacetic acid (4 mL), dichloromethane (12 mL) as described in Example 86 gave 0.54 g (84%) of the desired product as a white solid: $^1$H-NMR is consistent with structure; MS (FD) 576.3 (M+); Anal. Calc'd for $C_{31}H_{40}N_6O_5 \cdot 2.5HCl$: C, 55.75; H, 6.41; N, 12.58. Found: C, 55.86; H, 6.52; N, 12.27.

Preparation 234

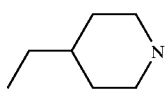

A slurry of 4-ethylpyridine, 10 g (93.3 mmol) and 5% Rh/C, 5 g in 135 mL of absolute ethanol was hydrogenated at 60 psi and 50° C. overnight. The reaction mixture was filtered through celite and distilled at atmospheric pressure to yield 3.6 g (34%) of the desired product as a colorless oil: $^1$H-NMR is consistent with structure; MS (FD) 114 (M+); b.p.=153–155° C.

Preparation 235

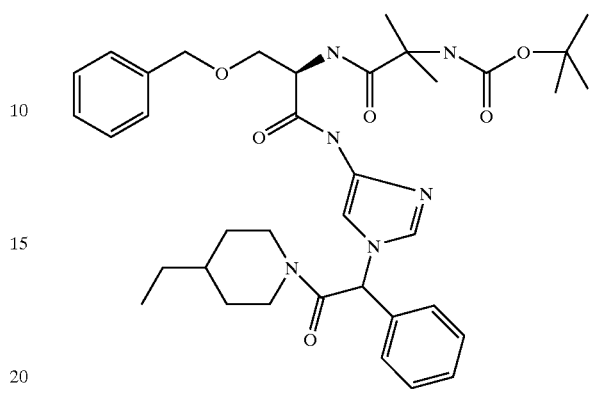

Reaction of the product of Preparation 8 from Examples Part 1 (0.6 g, 1.0 mmol), 4-ethylpiperidine (0.13 g, 1.0 mmol), 1-hydroxybenzotriazole (0.15 g, 1.1 mmol), 1-(3-dimethylaminopropyl)-3-ethylcarbodiimide (0.23 g, 1.1 mmol), dimethylformamide (40 mL) as described in Preparation 193 gave 0.57 g (85%) of the desired product as a tan foam: $^1$H-NMR is consistent with structure; MS (ion spray) 675.4 (M+1). Anal. Calc'd for $C_{37}H_{50}N_6O_6 \cdot 0.1CHCl_3$: C, 64.88; H, 7.35; N, 12.24. Found: C, 65.01; H, 6.95; N, 12.16.

Example 124

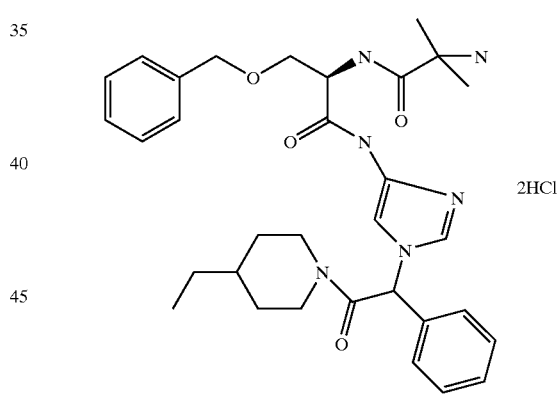

Reaction of the product of Preparation 235 (0.57 g, 0.84 mmol), trifluoroacetic acid (2 mL), dichloromethane (6 mL) as described in Example 86 gave 0.34 g (63%) of the desired product as a white solid: $^1$H-NMR is consistent with structure; MS (ion spray) 575 (M+1); Anal. Calc'd for $C_{32}H_{42}N_6O_4 \cdot 2HCl$: C, 59.35; H, 6.85; N, 12.98. Found: C, 59.19; H, 6.65; N, 12.80.

Preparation 236

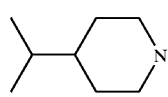

A slurry of 4-isopropylpyridine, 15.8 g (130 mmol) and 5% Rh/C, 16 g in 125 mL of absolute ethanol was hydrogenated at 60 psi and 50° C. for 18 h. The reaction mixture was filtered through celite and distilled at atmospheric pressure to yield 2.4 g (14.4%) of the desired product as a colorless oil: ¹H-NMR is consistent with structure; MS (FD) 127 (M+); b.p.=178–180° C.; Anal. Calc'd for $C_9H_{17}N$: C, 75.52; H, 13.47; N, 11.01. Found: C, 75.36; H, 13.40; N, 11.09.

Preparation 237

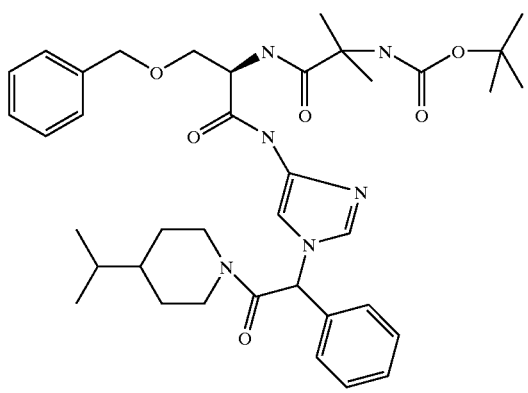

Reaction of the product of Preparation 8 from Examples Part 1 (0.6 g, 1.0 mmol), 4-isopropylpiperidine (0.13 g, 1.0 mmol), 1-hydroxybenzotriazole (0.15 g, 1.1 mmol), 1-(3-dimethylaminopropyl)-3-ethylcarbodiimide (0.23 g, 1.1 mmol), dimethylformamide (20 mL) as described in Preparation 193 gave 0.55 g (80%) of the desired product as a tan foam: ¹H-NMR is consistent with structure; MS (ion spray) 689.5 (M+1). Anal. Calc'd for $C_{38}H_{50}N_6O_6 \cdot 2HCl$: C, 66.26; H, 7.61; N, 12.20. Found: C, 66.16; H, 7.46; N, 12.03.

Example 125

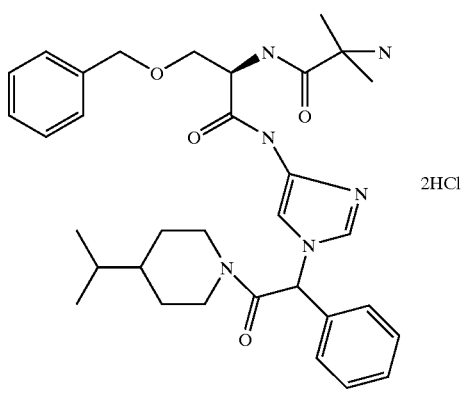

2HCl

Reaction of the product of Preparation 237 (0.45 g, 0.65 mmol), trifluoroacetic acid 12 mL), dichloromethane (6 mL), as described in Example 86 gave 0.37 g (86%) of the desired product as a white solid: ¹H-NMR is consistent with structure; MS (high res) calc'd for $C_{33}H_{43}N_6O_4$: 589.3502. Found: 589.3509.

Preparation 238

A slurry of 4-t-butylpyridine, 17.4 g (128 mmol) and 5% $Rh/Al_2O_3$, 6.8 g in 130 mL of absolute ethanol was hydrogenated at 60 psi and 50° C. overnight. The reaction mixture was filtered through celite and distilled at atmospheric pressure to yield 7.0 g (39%) of the desired product as a colorless oil: ¹H-NMR is consistent with structure; MS (FD) 142 (M+); b.p.=155° C.

Preparation 239

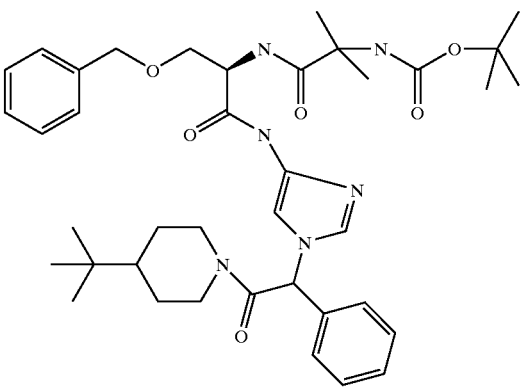

Reaction of the product of Preparation 8 from Examples Part 1 (0.6 g, 1.0 mmol), 4-t-butylpiperidine (0.14 g, 1.0 mmol), 1-hydroxybenzotriazole (0.15 g, 1.1 mmol), 1-(3-dimethylaminopropyl)-3-ethylcarbodiimide (0.23 g, 1.1 mmol), dimethylformamide (20 mL) as described in Preparation 193 gave 0.59 g (84%) of the desired product as a white foam: ¹H-NMR is consistent with structure; MS (ion spray) 703.6 (M+1). Anal. Calc'd for $C_{39}H_{52}N_6O_6 \cdot 0.5H_2O$: C, 65.80; H, 7.79; N, 11.80. Found: C, 65.63; H, 7.55; N, 11.88.

Example 126

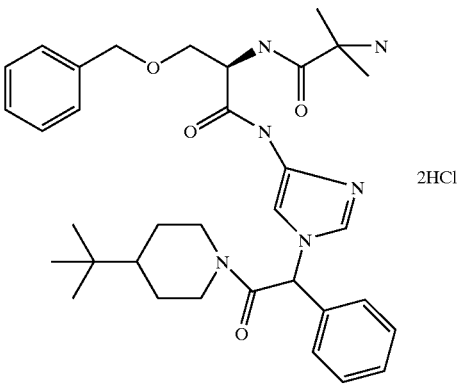

2HCl

Reaction of the product of Preparation 239 (0.48 g, 0.68 mmol), trifluoroacetic acid (2 mL), dichloromethane (6 mL) as described in Example 86 gave 0.33 g (72%) of the desired product as a white foam: ¹H-NMR is consistent with structure; MS (ion spray) 603.4 (M+1); Anal. Calc'd for $C_{34}H_{46}N_6O_4 \cdot 2.2HCl$: C, 59.80; H, 7.11; N, 12.30. Found: C, 59.63; H, 7.03; N, 12.37.

Preparation 240

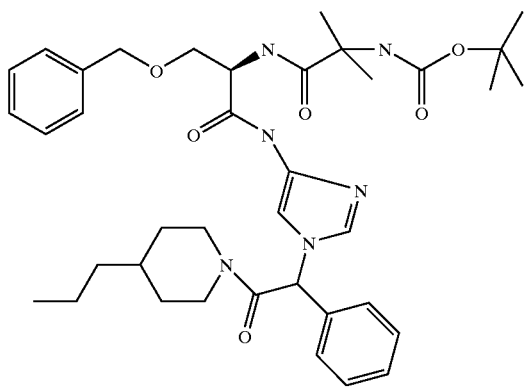

Reaction of the product of Preparation 8 from Examples Part 1 (1.0 g, 1.7 mmol), 4-propylpiperidine (0.22 g, 1.7 mmol), 1-hydroxybenzotriazole (0.26 g, 1.9 tool), 1-(3-dimethylaminopropyl)-3-ethylcarbodiimide (0.4 g, 1.9 mmol), dimethylformamide (60 mL) as described in Preparation 193 gave 0.93 g (80%) of the desired product as a yellow foam: $^1$H-NMR is consistent with structure; MS (FD) 689.5 (M+); Anal. Calc'd for $C_{38}H_{52}N_6O_6$: C, 66.20; H, 7.61; N, 12.20. Found: C, 66.19; H, 7.64; N, 12.47.

Example 127

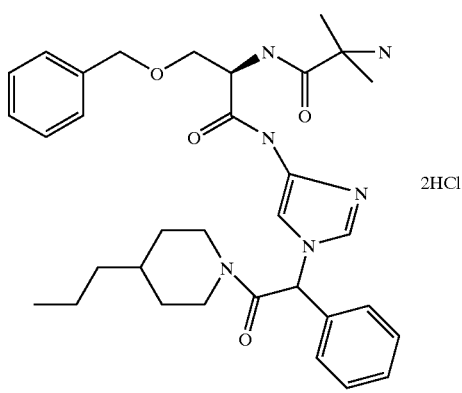

2HCl

Reaction of the product of Preparation 240 (0.93 g, 1.4 mmol), trifluoroacetic acid (4 mL), dichloromethane (12 mL), as described in Example 86, gave 0.8 g (92%) of the desired product as a yellow solid: $^1$H-NMR is consistent with structure; MS (FD) 588.2 (M+); Anal. Calc'd for $C_{33}H_{43}N_6O_4 \cdot 2.2HCl$: C, 59.58; H, 6.98; N, 12.63. Found: C, 59.26; H, 7.19; N, 12.82.

Preparation 241

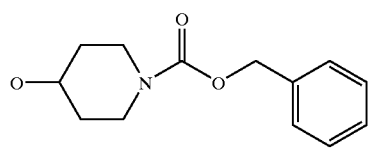

To a solution of 4-hydroxypiperidine, 5.0 g (50 mmol) in 80 mL of 4N sodium hydroxide at 0° C. was added 9.3 mL (65 mmol) of benzyl chloroformate dropwise. The reaction mixture was stirred overnight while slowly warming to ambient temperature, then was poured into 100 mL of 5N hydrochloric acid. The mixture was extracted with chloroform. The combined organic extracts were washed with brine, dried over sodium sulfate, filtered and concentrated. The residue was chromatographed on silica gel using a gradient of chloroform to 5% methanol/chloroform as eluant to yield 11.5 g (97%) of the desired product as a colorless oil: $^1$H-NMR is consistent with structure: MS (FD) 235 (M+); Anal. Calc'd for $C_{13}H_{17}NO_3$: C, 66.36; H, 7.28; N, 5.95. Found: C, 66.39; H, 7.19; N, 5.95.

Preparation 242

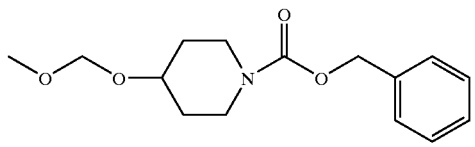

To a solution of the product of Preparation 241, 10.6 g (45 mmol) in 100 mL of ether and 100 mL of dimethylformamide at 0° C. was added 2.16 g (54 mmol) of sodium hydride. After stirring for 15 min at 0° C., 4.1 mL (54 mmol) of chloromethyl methyl ether was added dropwise. The reaction mixture was stirred overnight while slowly warming to ambient temperature and was then concentrated. The residue was partitioned between ethyl acetate and water and was extracted with ethyl acetate. The combined organic extracts were washed with brine, dried over sodium sulfate, filtered and concentrated. The residue was chromatographed on silica gel using 3–5% methanol/chloroform as eluant to yield 6.64 g (65%) of the desired product as a colorless oil: $^1$H-NMR is consistent with structure; MS (FD) 279.1 (M+); Anal. Calc'd for $C_{15}H_{21}NO_4$: C, 64.50; H, 7.58; N, 5.01. Found: C, 65.00; H, 7.20; N, 5.30.

Preparation 243

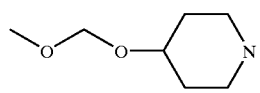

A solution of the product of Preparation 242, 2.0 g (7.1 mmol) in 20 mL of ethyl acetate and 40 mL of absolute ethanol was added to a slurry of 10% palladium on carbon, 1.0 g in 20 mL of ethyl acetate. The mixture was hydrogenated at 40 psi for 4 h then filtered through celite and concentrated to yield 0.71 g (68%) of the desired product as a colorless oil: $^1$H-NMR is consistent with structure and was carried on without further characterization.

Preparation 244

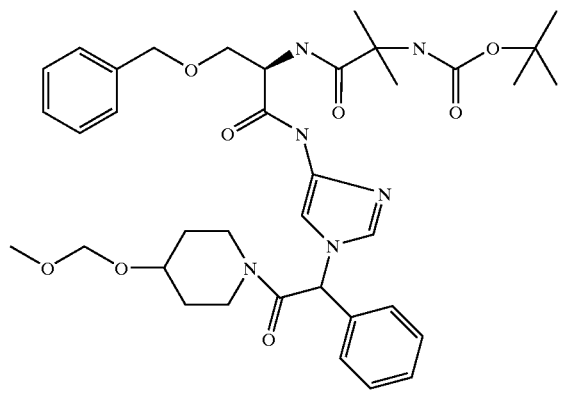

Reaction of the product of Preparation 8 from Examples Part 1 (1.0 g, 1.7 mmol), the product of Preparation 243 (0.25 g, 1.7 mmol), 1-hydroxybenzotriazole (0.26 g, 1.9 mmol), 1-(3-dimethylaminopropyl)-3-ethylcarbodiimide (0.4 g, 1.1 mmol), dimethylformamide (30 mL), as described in Preparation 193, gave 0.63 g (53%) of the desired product as a tan foam: $^1$H-NMR is consistent with structure: MS (FD) 706.5 (M+); Anal. Calc'd for $C_{37}H_{50}N_6O_8 \cdot 0.5H_2O$: C, 62.08; H, 7.18; N, 11.74. Found: C, 62.12; H, 7.32; N, 11.56.

Example 128

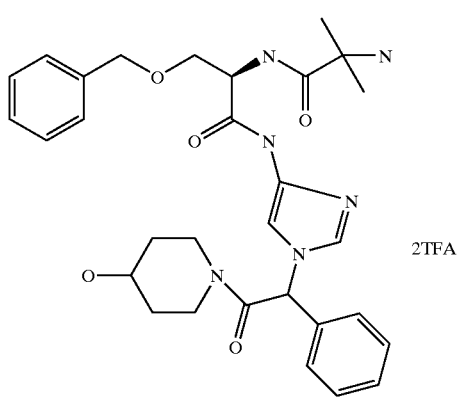

To a solution of the product of Preparation 244, 0.53 g (0.75 mmol) 12 mL of dichloromethane was added 6 mL of trifluoroacetic acid. The reaction mixture was stirred for 2 h, then concentrated. The residue was slurried in ether and filtered to yield 0.5 g (85%) of the desired product as a white solid: $^1$H-NMR is consistent with structure; MS (FD) 561.9 (M+); Anal. Calc'd for $C_{30}H_{38}N_6O_5 \cdot 2$ trifluoroacetic acid: C, 51.65; H, 5.10; N, 10.63. Found: C, 51.88; H, 5.36; N, 10.61.

Preparation 245

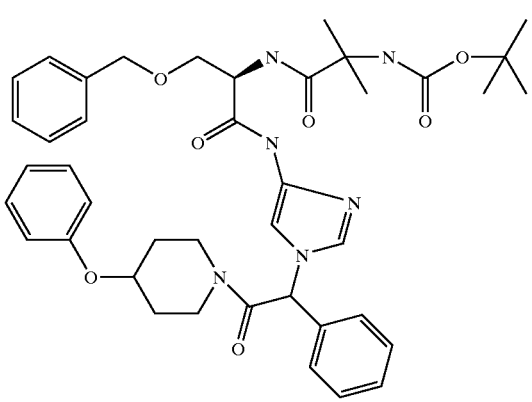

Reaction of the product of Preparation 8 from Examples Part 1 (0.6 g, 1.0 mmol), 4-phenoxypiperidine hydrochloride (Boswell, et al.; *J. Med. Chem.* 1974, 17(9), 1000–8) (0.2 g, 1.0 mmol), triethylamine (0.16 mL, 1.1 mmol), 1-hydroxybenzotriazole (0.15 g, 1.1 mmol), 1-(3-dimethylaminopropyl)-3-ethylcarbodiimide (0.23 g, 1.1 mmol), dimethylformamide (40 mL) as described in Preparation 193, gave 0.55 g (74%) of the desired product as a tan foam: $^1$H-NMR is consistent with structure; MS (FD) 738 (M+); Anal. Calc'd for $C_{41}H_{50}N_6O_7$: C, 66.65; H, 6.82; N, 11.37. Found: C, 66.35; H, 6.64; N, 11.28.

Example 129

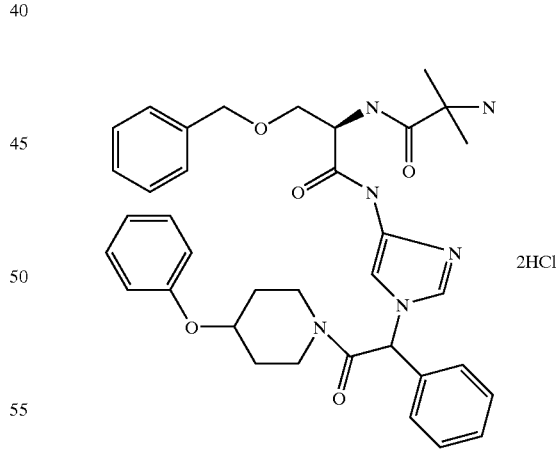

Reaction of the product of Preparation 245 (0.46 g, 0.6 mmol), trifluoroacetic acid (2 mL), dichloromethane (6 mL), as described in Example 66, gave 0.3 g (70%) of the desired product as a white solid: $^1$H-NMR is consistent with structure; MS (FD) 638.3 (M+); Anal. Calc'd for $C_{36}H_{42}N_6O_5 \cdot 2HCl$: C, 60.76; H, 6.23; N, 11.81. Found: C, 60.62; H, 6.32; N, 11.63.

Preparation 246

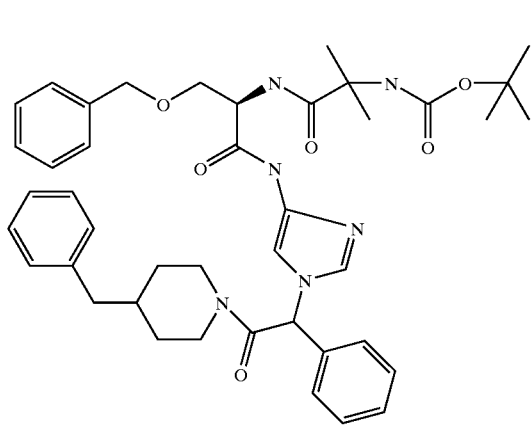

Reaction of the product of Preparation 8 from Examples Part 1 (1.0 g, 1.7 mmol), 4-benzylpiperidine (0.3 mL, 1.7 mmol), 1-hydroxybenzotriazole (0.26 g, 1.9 mmol), 1-(3-dimethylaminopropyl)-3-ethylcarbodiimide (0.4 g, 1.9 mmol), dimethylformamide (80 mL), as described in Preparation 193, gave 0.82 g (66%) of the desired product as a yellow foam: $^1$H-NMR is consistent with structure; MS (FD) 736.3 (M+); Anal. Calc'd for $C_{42}H_{52}N_6O_6 \cdot 1.1H_2O$: C, 66.66; H, 7.22; N, 11.11. Found: C, 66.47; H, 6.92; N, 11.67.

Preparation 247

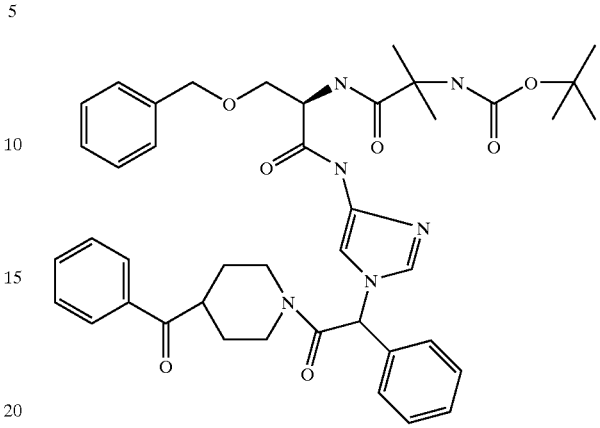

(0.7 g, 1.2 mmol), 4-benzoylpiperidine hydrochloride (0.27 g, 1.2 mmol), triethylamine (0.18 mL, 1.32 mmol), 1-hydroxybenzotriazole (0.18 g, 1.32 mmol), 1-(3-dimethylaminopropyl)-3-ethylcarbodiimide (0.27 g, 1.32 mmol), dimethylformamide (30 mL), as described in Preparation 193 gave 0.65 g (72%) of the desired product as a tan foam: $^1$H-NMR is consistent with structure; MS (FD) 751 (M+).

Example 130

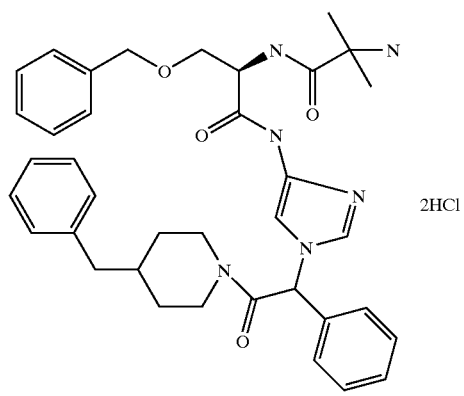

2HCl

Reaction of the product of Preparation 246 (0.8 g, 1.1 mmol), trifluoroacetic acid (4 mL), dichloromethane (12 mL), as described in Example 86, gave 0.65 g (88%) of the desired product as a white solid: $^1$H-NMR is consistent with structure; MS (FD) 637 (M+); Anal. Calc'd for $C_{37}H_{44}N_6O_4 \cdot 2.1HCl$: C, 62.30; H, 6.51; N, 11.78. Found: C, 62.21; H, 6.59; N, 12.12.

Example 131

2HCl

Reaction of the product of Preparation 247 (0.51 g, 0.68 mmol), trifluoroacetic acid (4 mL), dichloromethane (12 mL), as described in Example 86, gave 0.47 g (96%) of the desired product as a yellow solid: $^1$H-NMR is consistent with structure; MS (FD) 651 (M+); Anal. Calc'd for $C_{37}H_{42}N_6O_5 \cdot 2HCl$: C, 60.49; H, 6.08; N, 11.44. Found: C, 60.44; H, 6.00; N, 11.41.

Preparation 248

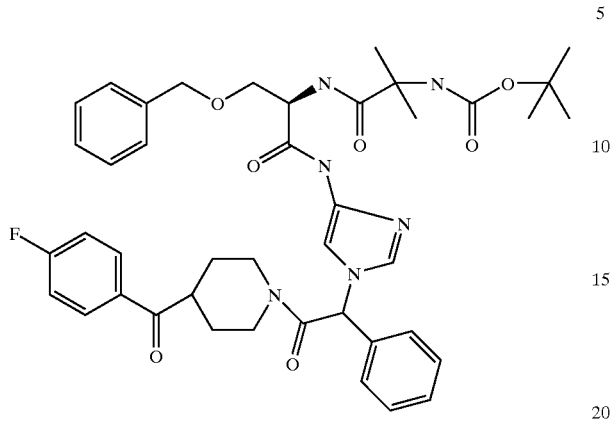

Reaction of the product of Preparation 8 from Examples Part 1 (1.0 g, 1.7 mmol), 4-(4-fluorobenzoyl)piperidine hydrochloride (0.42 g, 1.7 mmol), triethylamine (0.26 mL, 1.9 mmol), 1-hydroxybenzotriazole (0.26 g, 1.9 mmol), 1(3-dimethylaminopropyl)-3-ethylcarbodiimide (0.4 g, 1.9 mmol), dimethylformamide (80 mL), as described in Preparation 193, gave 0.97 g (75%) of the desired product as a tan foam: $^1$H-NMR is consistent with structure; MS (FD) 768.9 (M+).

Preparation 249

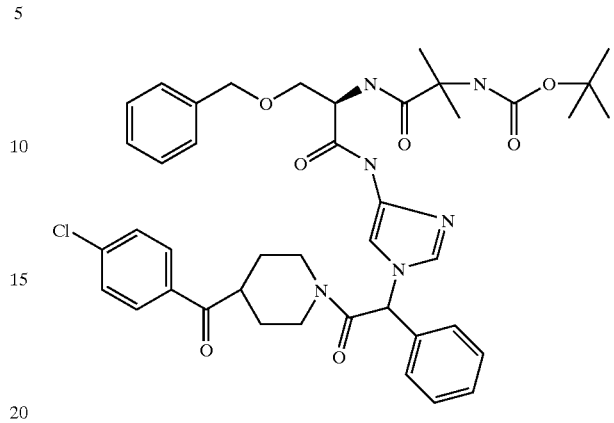

Reaction of the product of Preparation 8 from Examples Part 1 (0.7 g, 1.2 mmol), 4-(4-chlorobenzoyl)piperidine hydrochloride (0.32 q, 1.2 mmol), triethylamine (0.18 mL, 1.32 mmol), 1-hydroxybenzotriazole (0.18 g, 1.32 mmol), 1-(3-dimethylaminopropyl)-3-ethylcarbodiimide (0.27 g, 1.32 mmol), dimethylformamide (30 mL), as described in Preparation 193, gave 0.83 g (89%) of the desired product as a tan foam: $^1$H-NMR is consistent with structure; MS (FD) 785 (M+).

Example 132

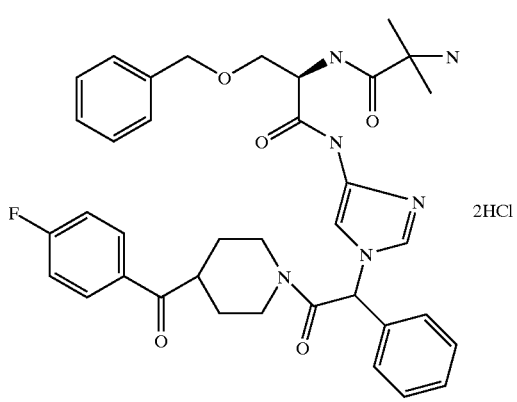

Reaction of the product of Preparation 248 (0.92 g, 1.2 mmol), trifluoroacetic acid (4 mL), dichloromethane (12 mL), as described in Example 86, gave 0.75 g (88%) of the desired product as a yellow solid: $^1$H-NMR is consistent with structure; MS (FD) 669 (M+); Anal. Calc'd for $C_{37}H_{42}FN_6O_5 \cdot 2.7HCl$: C, 57.93; H, 5.74; N, 10.95. Found: C, 57.83; H, 5.81; N, 11.20.

Example 133

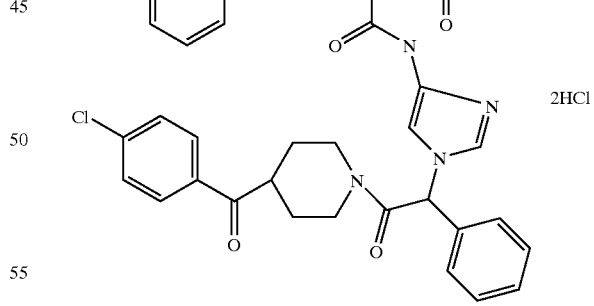

Reaction of the product of Preparation 249 (0.64 g, 0.82 mmol), trifluoroacetic acid (4 mL), dichloromethane (12 mL), as described in Example 86, gave 0.51 g (82%) of the desired product as a yellow solid: $^1$H-NMR is consistent with structure; MS (FD) 685 (M+); Anal. Calc'd for $C_{37}H_{41}N_6O_5Cl \cdot 2HCl$: C, 58.61; H, 5.72; N, 11.08. Found: C, 58.34; H, 5.93; N, 11.00.

Preparation 250

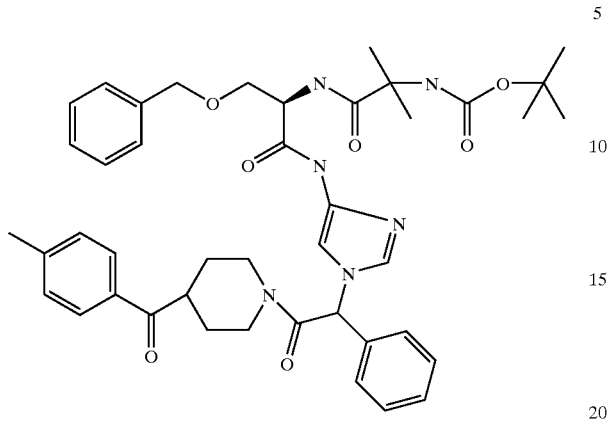

Reaction of the product of Preparation 8 from Examples Part 1 (0.6 g, 1.0 mmol), 4-(4-methylbenzoyl)piperidine hydrochloride (0.24 g, 1.0 mmol), triethylamine (0.16 mL, 1.1 mmol), 1-hydroxybenzotriazole (0.15 g, 1.1 mmol), 1-(3-dimethylaminopropyl)-3-ethylcarbodiimide (0.23 g, 1.1 mmol), dimethylformamide (30 mL), as described in Preparation 193, gave 0.54 g (71%) of the desired product as a tan foam: $^1$H-NMR is consistent with structure; MS (FD) 765.4 (M+); Anal. Calc'd for $C_{43}H_{52}N_6O_7$: C, 67.52; H, 6.85; N, 10.99. Found: C, 67.32; H, 6.65; N, 10.76.

Preparation 251

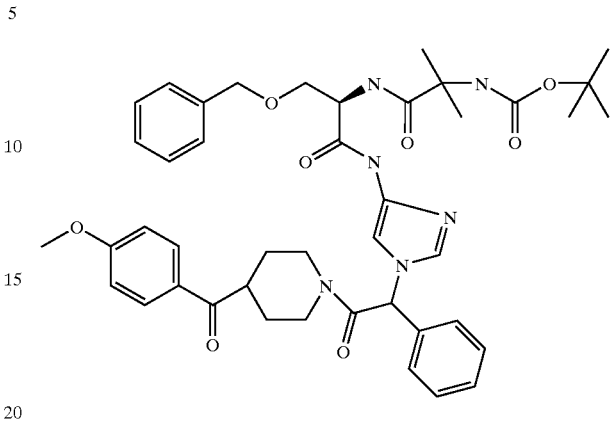

Reaction of the product of Preparation 8 from Examples Part 1 (0.6 g, 1.0 mmol), 4-(4-methoxybenzoyl)piperidine hydrochloride (0.26 g, 1.0 mmol), triethylamine (0.16 mL, 1.1 mmol), 1-hydroxybenzotriazole (0.15 g, 1.1 mmol), 1-(3-dimethylaminopropyl)-3-ethylcarbodiimide (0.23 g, 1.1 mmol), dimethylformamide (40 mL), as described in Preparation 193, gave 0.23 g (29%) of the desired product as a tan foam: $^1$H-NMR is consistent with structure; MS (FD) 780.8 (M+); Anal. Calc'd for $C_{43}H_{52}N_6O_8$: C, 66.14; H, 6.71; N, 10.76. Found: C, 66.14; H, 6.60; N, 10.65.

Example 134

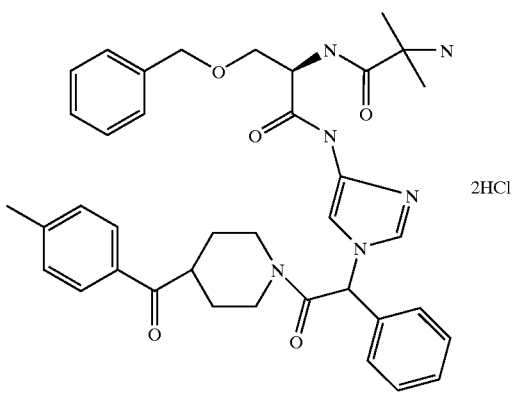

Reaction of the product of Preparation 250 (0.5 g, 0.65 mmol), trifluoroacetic acid (2 mL), dichloromethane (6 mL), as described in Example 86, gave 0.33 g (69%) of the desired product as a white solid: $^1$H-NMR is consistent with structure; (FD) 655.2 (M+); Anal. Calc'd for $C_{38}H_{44}N_6O_5Cl$·2.3HCl: C, 60.96; H, 6.23; N, 11.23. Found: C, 60.92; H, 6.55; N, 11.10.

Example 135

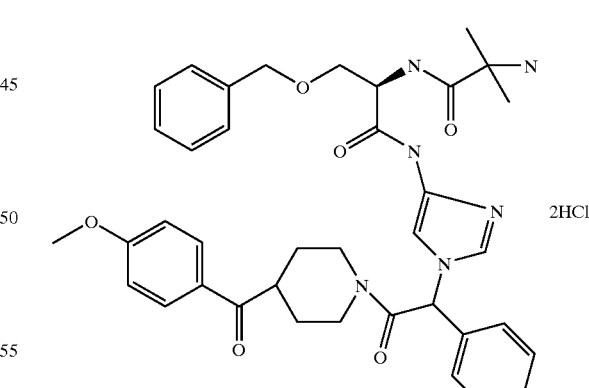

Reaction of the product of Preparation 251 (0.2 g, 0.26 mmol), trifluoroacetic acid (2 mL), dichloromethane (6 mL), as described in Example 86, gave 0.19 g (100%) of the desired product. $^1$H-NMR is consistent with structure; MS (FD) 681.3 (M+); Anal. Calc'd for $C_{38}H_{44}N_6O_4$·2HCl: C, 60.56; H, 6.15; N, 11.15. Found: C, 60.43; H, 6.29; N, 10.89.

Preparation 252

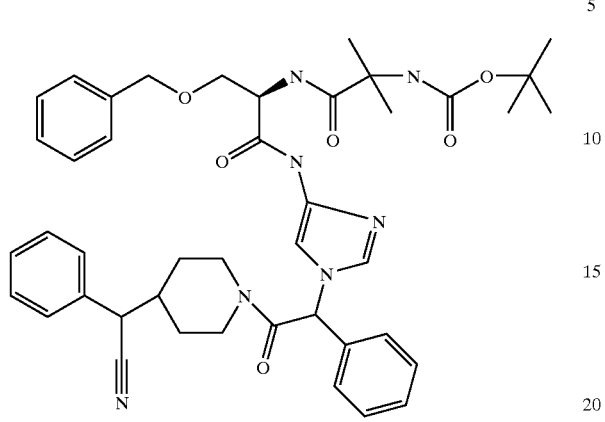

Reaction of the product of Preparation 8 from Examples Part 1 (0.6 g, 1.0 mmol), 4-(alpha-cyanobenzyl)piperidine hydrochloride (0.24 g, 1.0 mmol), triethylamine (0.16 mL, 1.1 mmol), 1-hydroxybenzotriazole (0.15 g, 1.1 mmol), 1-(3-dimethylaminopropyl)-3-ethylcarbodiimide (0.23 g, 1.1 mmol), dimethylformamide (40 mL), as described in Preparation 193, gave 0.4 g (53%) of the desired product as a tan foam: $^1$H-NMR is consistent with structure; MS (FD) 761.7 (M+); Anal. Calc'd for $C_{43}H_{51}N_7O_6$: C, 67.79; H, 6.75; N, 12.87. Found: C, 67.54; H, 6.45; N, 12.67.

Preparation 253

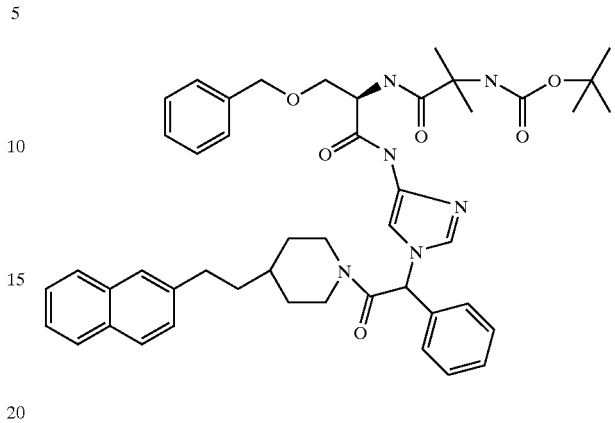

Reaction of the product of Preparation 8 from Examples Part 1 (0.6 g, 1.0 mmol), 4-(2-ethyl-2-naphthyl))piperidine hydrochloride (Efange et al., *J. Med Chem.* 1993 36(9), 1278–83) (0.28 g, 1.0 mmol), triethylamine (0.16 mL, 1.1 mmol), 1-hydroxybenzotriazole (0.15 g, 1.1 mmol), 1-(3-dimethylaminopropyl)-3-ethylcarbodiimide (0.23 g, 1.1 mmol), dimethylformamide (40 mL), as described in Preparation 193, gave 0.58 g (74%) of the desired product as a tan foam: $^1$H-NMR is consistent with structure; MS (FD) 801 (M+); Anal. Calc'd for $C_{47}H_{56}N_6O_6$: C, 70.48; H, 7.05; N, 10.49. Found: C, 70.52; H, 6.87; N, 10.50.

Example 136

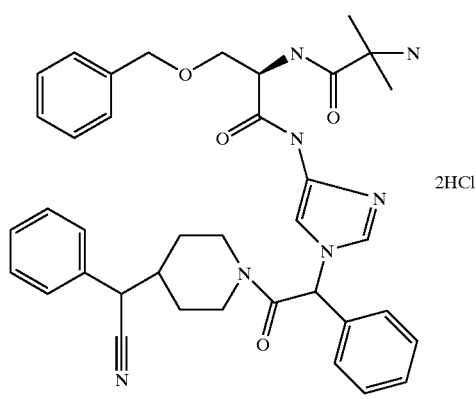

2HCl

Reaction of the product of Preparation 252 (0.31 g, 0.4 mmol), trifluoroacetic acid (2 mL), dichloromethane (6 mL), as described in Example 86, gave 0.22 g (76%) of the desired product as a tan foam: $^1$H-NMR is consistent with structure; MS (FD) 661.1 (M+); Anal. Calc'd for $C_{38}H_{43}N_{74} \cdot 2HCl$: C, 62.12; H, 6.17; N, 13.35. Found: C, 61.95; H, 8.38; H, 13.19.

Example 137

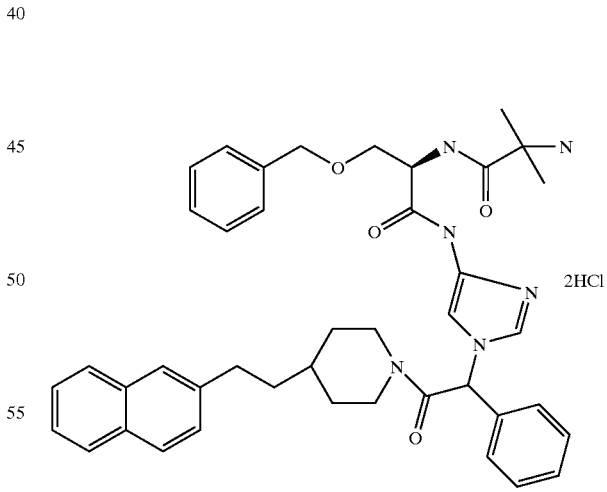

2HCl

Reaction of the product of Preparation 253 (0.5 g, 0.62 mmol), trifluoroacetic acid (2 mL), dichloromethane (6 mL), as described in Example 86, gave 0.22 g (46%) of the desired product as a yellow solid: $^1$H-NMR is consistent with structure; MS (FD) 701 (M+).

Preparation 254

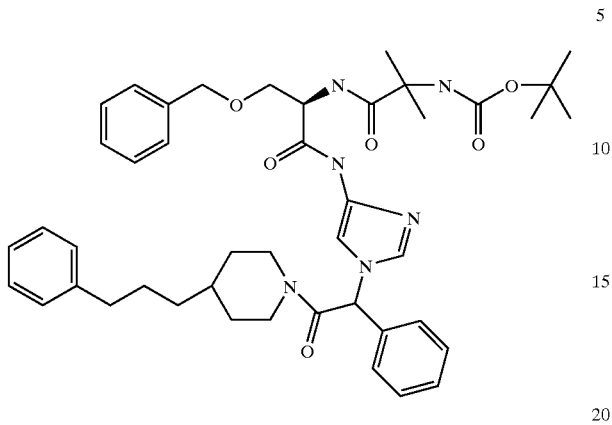

Reaction of the product of Preparation 8 from Examples Part 1 (0.6 g, 1.0 mmol), 4-(phenpropyl)piperidine (0.2 g, 1.0 mmol), triethylamine (0.16 mL, 1.1 mmol), 1-hydroxybenzotriazole (0.15 g, 1.1 mmol), 1-(3-dimethylaminopropyl)-3-ethylcarbodiimide (0.23 g, 1.1 mmol), dimethylformamide (40 mL), as described in Preparation 193, gave 0.58 g (761) of the desired product as a tan foam: $^1$H-NMR is consistent with structure; MS (FD) 765.4 (M+); Anal. Calc'd for $C_{44}H_{56}N_6O_6$: C, 69.09; H, 7.38; N, 10.99. Found: C, 68.95; H, 7.29; N, 11.04.

Preparation 255

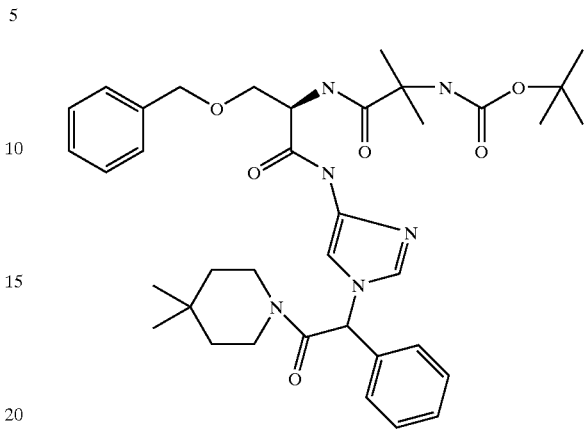

Reaction of the product of Preparation 8 from Examples Part 1 (1.0 g, 1.7 mmol), 4,4-dimethylpiperidine hydrochloride (0.26 g, 1.7 mmol), triethylamine (0.26 ml, 1.9 mmol), 1-hydroxybenzotriazole (0.26 g, 1.9 mmol), 1-(3-dimethylaminopropyl)-3-ethylcarbodiimide (0.4 g, 1.9 mmol), dimethylformamide (80 mL), as described in Preparation 193, gave 0.84 g (73%) of the desired product as a tan solid: $^1$H-NMR is consistent with structure; MS (FD) 674 (M+).

Example 138

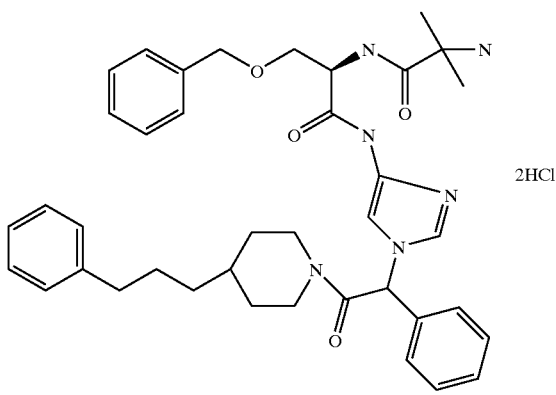

2HCl

Reaction of the product of Preparation 254 (0.41 g, 0.5 mmol), trifluoroacetic acid (2 mL), dichloromethane (6 mL), as described in Example 86, gave 0.32 g (87%) of the desired product as a white solid: $^1$H-NMR is consistent with structure; MS (FD) 664 (M+); Anal. Calc'd for $C_{39}H_{48}N_6O_4 \cdot 2HCl$: C, 63.49; H, 6.83; N, 11.39. Found: C, 63.30; H, 6.77; N, 11.29.

Example 139

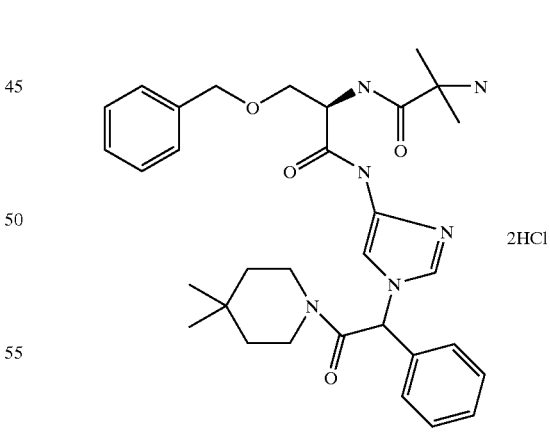

2HCl

Reaction of the product of Preparation 255 (0.82 g, 1.2 mmol), trifluoroacetic acid (4 mL), dichloromethane (12 mL), as described in Example 86, gave 0.65 g (89%) of the desired product as a yellow solid: $^1$H-NMR is consistent with structure; MS (FD) 574.2 (M+).

Preparation 257

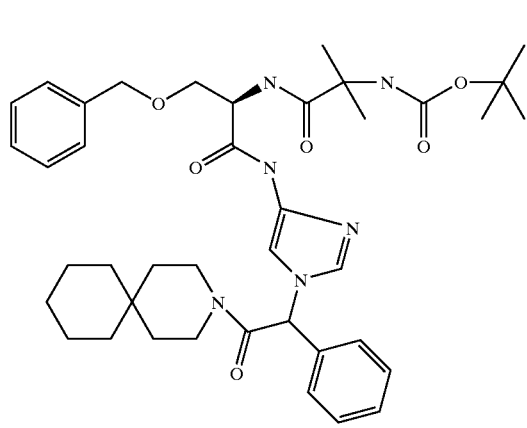

Reaction of the product of Preparation 8 from Examples Part 1 (0.6 g, 1.0 mmol), 3-azaspiro(5.5)undecane hydrochloride (Knoelker, et al; *Synlett.* 1992, Issue 5, 371–87) (0.19 g, 1.0 mmol), triethylamine (0.16 mL, 1.1 mmol), 1-hydroxybenzotriazole (0.15 g, 1.1 mmol), 1-(3-dimethylaminopropyl)-3-ethylcarbodiimide (0.23 g, 1.1 mmol), dimethylformamide (40 mL), as described in Preparation 193, gave 0.42 g (60%) of the desired compound as a tan foam: $^1$H-NMR is consistent with structure; MS (FD) 715 (M+); Anal. Calc'd for $C_{40}H_{54}N_6O_6$: C, 67.21; H, 7.61; N, 11.76. Found: C, 67.13; H, 7.38; N, 11.71.

Preparation 250

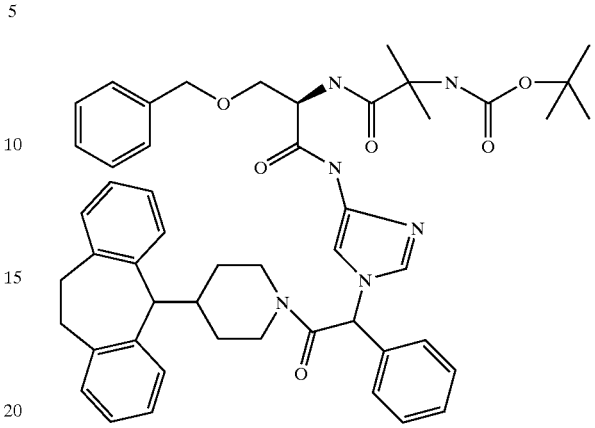

Reaction of the product of Preparation 8 from Examples Part 1 (0.6 g, 1.0 mmol), 4-(10,11-dihydro-5H-dibenzo(A,D)cyclohepten-5-yl)piperidine (U.S. Pat. No. 4,626,542) (0.28 g, 1.0 mmol), 1-hydroxybenzotriazole (0.15 g, 1.1 mmol), 1-(3-dimethylaminopropyl)-3-ethylcarbodiimide (0.23 g, 1.1 mmol), dimethylformamide (40 mL), as described in Preparation 193, gave 0.69 g (82%) of the desired compound as a tan foam: $^1$H-NMR is consistent with structure; MS (FD) 839 (M+).

Example 140

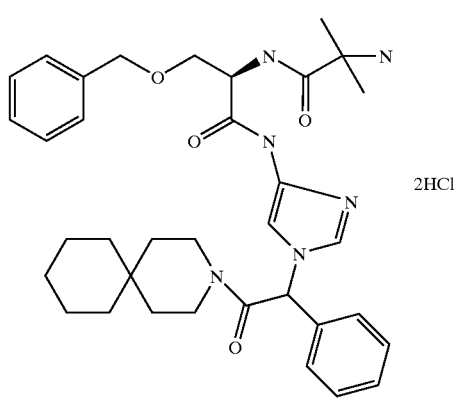

Reaction of the product of Preparation 257 (0.37 g, 0.5 mmol), trifluoroacetic acid (2 mL), dichloromethane (6 mL), as described in Example 86, gave 0.32 g (94%) of the desired product as a white solid: $^1$H-NMR is consistent with structure; MS (FD) 614 (M+); Anal. Calc'd for $C_{35}H_{46}N_6O_4 \cdot 2.3HCl$: C, 60.17; H, 6.97; N, 12.03. Found: C, 60.14; H, 7.13; N, 11.82.

Example 141

Reaction of the product of Preparation 258 (0.63 g, 0.75 mmol), trifluoroacetic acid (2 mL), dichloromethane (6 mL), as described in Example 86, gave 0.44 g (72%) of the desired product as a white solid: $^1$H-NMR is consistent with structure; MS (FD) 739 (M+); Anal. Calc'd for $C_{45}H_{50}N_6O_4 \cdot 2HCl$: C, 66.58; H, 6.46; N, 10.35. Found: C, 66.41, H, 6.62; N, 10.25.

Preparation 259

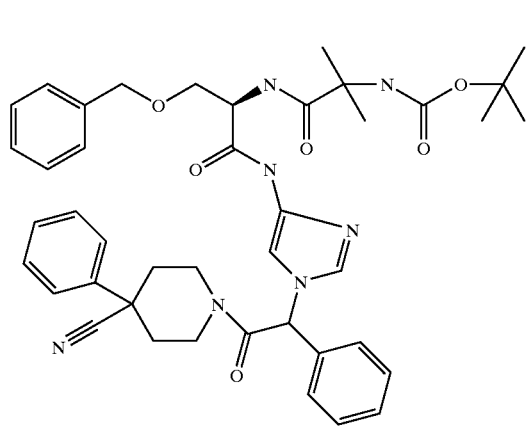

Reaction of the product of Preparation 8 from Examples Part 1 (1.0 g, 1.0 mmol), 4-cyano, 4-phenylpiperidine hydrochloride (0.38 g, 1.7 mmol), triethylamine (0.26 mL, 1.9 mmol), 1-hydroxybenzotriazole (0.26 g, 1.9 mmol), 1-(3-dimethylaminopropyl)-3-ethylcarbodiimide (0.4 g, 1.9 mmol), dimethylformamide (40 mL), as described in Preparation 193, gave 1.0 g (79%) of the desired product as a white foam: $^1$H-NMR is consistent with structure; MS (FD) 747.8 (M+).

Preparation 260

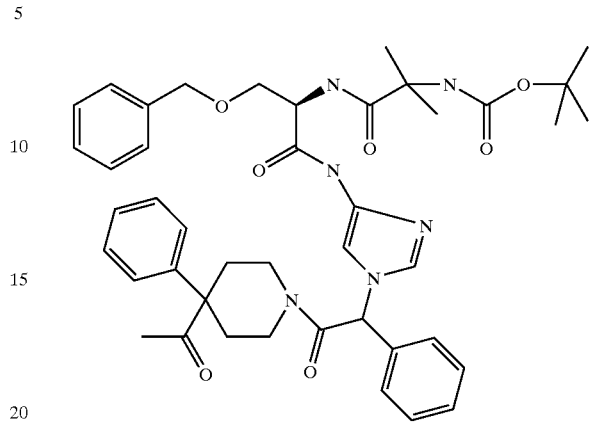

Reaction of the product of Preparation 8 from Examples Part 1 (1.0 g, 1.0 mmol), 4-acetyl-4-phenylpiperidine hydrochloride (0.4 g, 1.7 mmol), triethylamine (0.26 mL, 1.9 mmol), 1-hydroxybenzotriazole (0.26 g, 1.9 mmol), 1-(3-dimethylaminopropyl)-3-ethylcarbodiimide (0.4 g, 1.9 mmol), dimethylformamide (80 mL), as described in Preparation 193, gave 0.52 g (40%) of the desired product as a white foam: $^1$H-NMR is consistent with structure; MS (FD) 765 (M+); Anal. Calc'd for $C_{43}H_{52}N_6O_7 \cdot 0.1H_2O$: C, 65.97; H, 6.95; N, 10.73. Found: C, 65.68; H, 6.93; N, 11.17.

Example 142

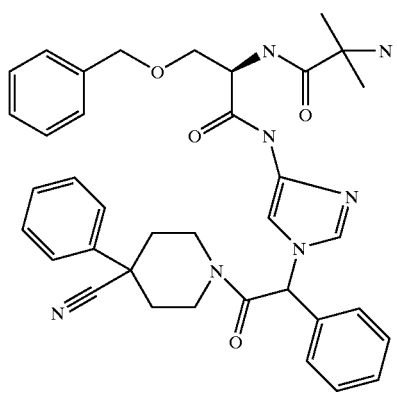

Reaction of the product of Preparation 259 (1.0 g, 1.3 mmol), trifluoroacetic acid (4 mL), dichloromethane (12 mL), as described in Example 86, gave 0.71 g (76%) of the desired product as a white solid: $^1$H-NMR is consistent with structure; MS (FD) 647.2 (M+); Anal. Calc'd for $C_{37}H_{41}N_7O_4 \cdot 2.6HCl$: C, 59.85; H, 5.92; N, 13.20. Found: C, 59.76; H, 5.88; N, 13.10.

Example 143

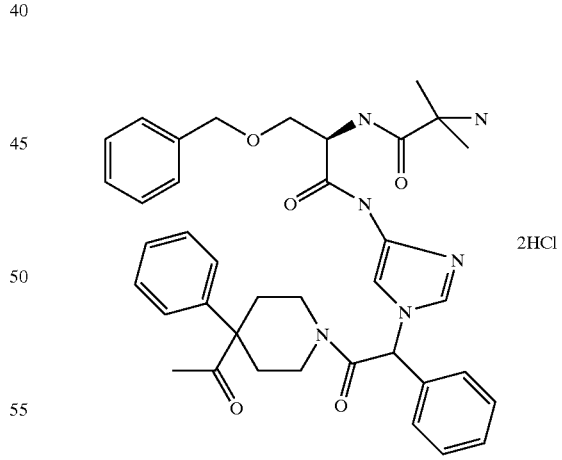

Reaction of the product of Preparation 260 (0.5 g, 0.65 mmol), trifluoroacetic acid (4 mL), dichloromethane (12 mL), as described in Example 86, gave 0.44 g (96%) of the desired product as a yellow solid: $^1$H-NMR is consistent with structure; MS (FD) 664.4 (M+); Anal. Calc'd for $C_{38}H_{43}N_6O_5 \cdot 2.7HCl$: C, 59.80; H, 6.17; N, 11.01. Found: C, 59.61; H, 6.18; N, 11.24.

Preparation 261

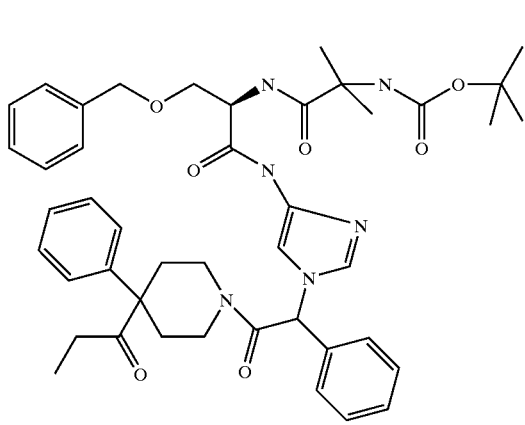

Reaction of the product of Preparation 8 from Examples Part 1 (0.7 g, 1.2 mmol), 4-phenyl-4-propionylpiperidine hdyrochloride (0.3 g, 1.2-mol), triethylamine (0.18 mL, 1.32 mmol), 1-hydroxybenzotriazole (0.18 g, 1.32 mmol), 1-(3-dimethylaminopropyl)-3-ethylcarbodiimide (0.27 g, 1.32 mmol), dimethylformamide (40 ml), as described in Preparation 193, gave 0.71 g (76%) of the desired product as a tan foam: $^1$H-NMR is consistent with structure; MS (FD) 779 (M+); Anal. Calc'd for $C_{44}H_{54}N_6O_7$: C, 67.85; H, 6.99; N, 10.79. Found: C, 67.56; H, 7.10; N, 10.95.

Preparation 262

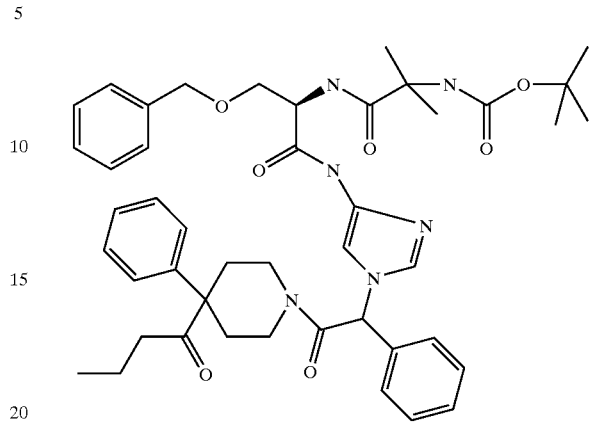

Reaction of the product of Preparation 8 from Examples Part 1 (0.7 g, 1.2 mmol), 4-butyryl-4-phenylpiperidine hdyrochloride (0.3 g, 1.2 mmol), triethylamine (0.18 mL, 1.32 mmol), 1-hydroxybenzotriazole (0.18 g, 1.32 mmol), 1-(3-dimethylaminopropyl)-3-ethylcarbodiimide (0.27 g, 1.32 mmol), dimethylformamide (40 mL), as described in Preparation 193, gave 0.76 g (80%) of the desired product as a tan foam: $^1$H-NMR is consistent with structure; MS (FD) 793 (M+).

Example 144

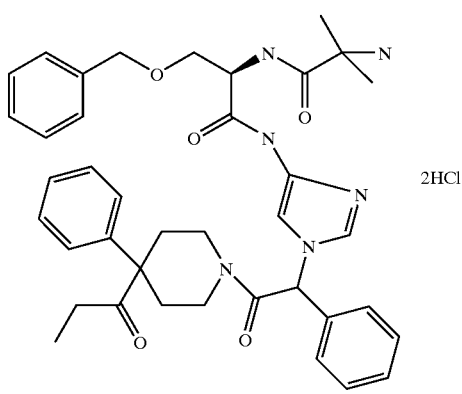

2HCl

Reaction of the product of Preparation 261 (0.58 g, 0.74 mmol), trifluoroacetic acid (4 mL), dichloromethane (12 mL), as described in Example 86, gave 0.54 g (100%) of the desired product. $^1$H-NMR is consistent with structure; MS (FD) 678 (M+); Anal. Calc'd for $C_{39}H_{46}N_6O_5 \cdot 2.6HCl$: C, 60.55; H, 6.33; N, 10.86. Found: C, 60.40; H, 6.27; N, 10.79.

Example 145

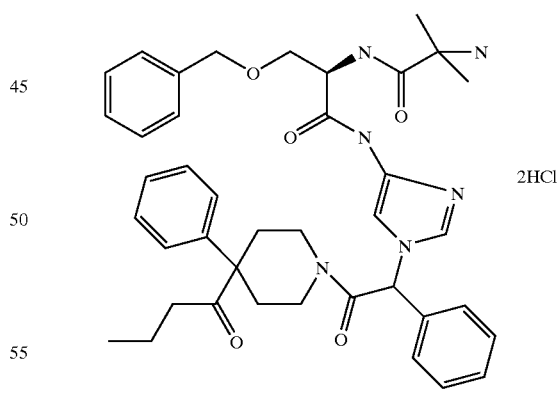

2HCl

Reaction of the product of Preparation 262 (0.65 g, 0.82 mmol), trifluoroacetic acid (4 mL), dichloromethane (12 mL), as described in Example 86, gave 0.5 g (80%) of the desired product as a white solid: $^1$H-NMR is consistent with structure; MS (FD) 692 (M+); Anal. Calc'd for $C_{40}H_{48}N_6O_5 \cdot 2.3HCl$: C, 61.86; H, 6.53; N, 10.82. Found: C, 61.96; H, 6.63; N, 10.60.

Preparation 263

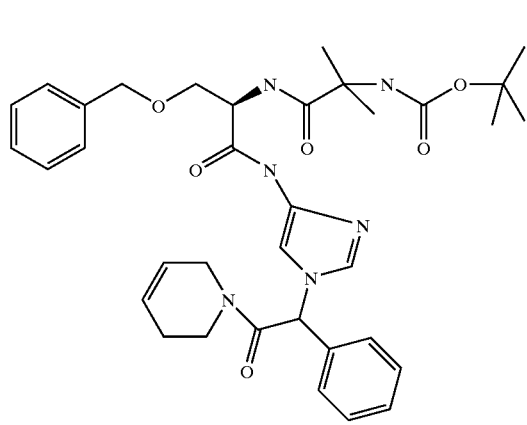

Reaction of the product of Preparation 8 from Examples Part 1 (1.0 g, 1.7 mmol), 1,2,3,6-tetrahydropyridine (0.16 mL, 1.7 mmol), 1-hydroxybenzotriazole (0.26 g, 1.9 mmol), 1-(3-dimethylaminopropyl)-3-ethylcarbodiimide (0.4 g, 1.9 mmol), dimethylformamide (80 mL), as described in Preparation 193, gave 0.63 g (57%) of the desired product as a tan solid: $^1$H-NMR is consistent with structure: MS (FD) 644 (M+); Anal. Calc'd for $C_{35}H_{44}N_6O_6$: C, 65.20; H, 6.88; N, 13.03. Found: C, 65.30; H, 7.04; N, 13.14.

Preparation 264

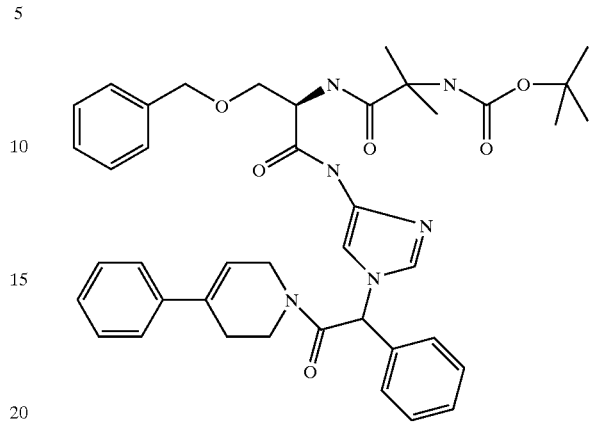

Reaction of the product of Preparation 8 from Examples Part 1 (0.7 g, 1.2 mmol), 4-phenyl-1,2,3,6-tetrahydropyridine (0.16 g, 1.2 mmol), 1-hydroxybenzotriazole (0.18 g, 1.32 mmol), 1-(3-dimethylaminopropyl)-3-ethylcarbodiimide (0.27 g, 1.32 mmol), dimethylformamide (40 mL), as described in Preparation 193, gave 0.36 g (50%) of the desired product as a tan foam: $^1$H-NMR is consistent with structure; MS (FD) 721.2 (M+); Anal. Calc'd for $C_{41}H_{48}N_6O_6 \cdot 0.5H_2O$: C, 67.47; H, 6.77; N, 11.51. Found: C, 67.56; 6.81; N, 11.20.

Example 146

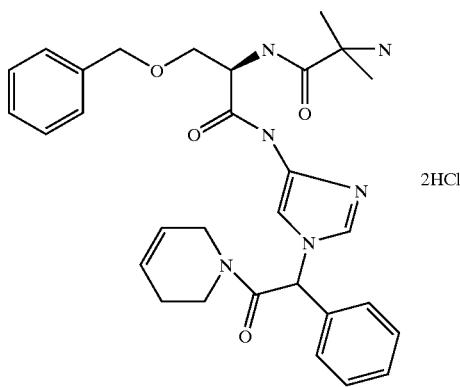

Reaction of the product of Preparation 263 (0.62 g, 0.96 mmol), trifluoroacetic acid (4 mL), dichloromethane (12 mL), as described in Example 86, gave 0.53 g (95%) of the desired product as a white solid: $^1$H-NMR is consistent with structure; MS (high res) calc'd for $C_{50}H_{37}N_6O_4$: 545.2876. Found: 545.2683.

Example 147

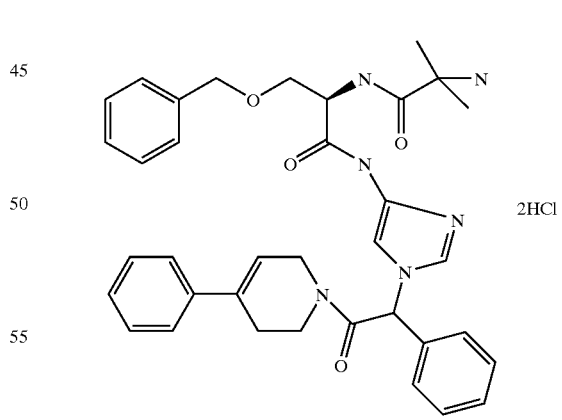

Reaction of the product of Preparation 264 (0.34 g, 0.47 mmol), trifluoroacetic acid (2 mL), dichloromethane (6 mL), as described in Example 86, gave 0.28 g (85%) of the desired product as a white solid: $^1$H-NMR is consistent with structure; MS (ion spray) 621.4 (M+1).

Preparation 265

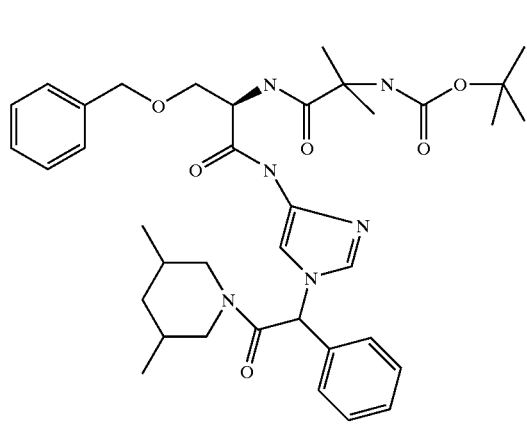

Reaction of the product of Preparation 8 from Examples Part 1 (1.0 g, 1.7 mmol), 3,5-dimethylpiperidine (0.23 ml, 1.7 mmol), 1-hydroxybenzotriazole (0.26 g, 1.9 mmol), 1-(3-dimethylaminopropyl)-3-ethylcarbodiimide (0.4 g, 1.9 mmol), dimethylformamide (80 mL), as described in Preparation 193, gave 0.93 g (81%) of the desired product as a tan solid: $^1$H-NMR is consistent with structure; MS (FD) 674 (M+).

Example 148

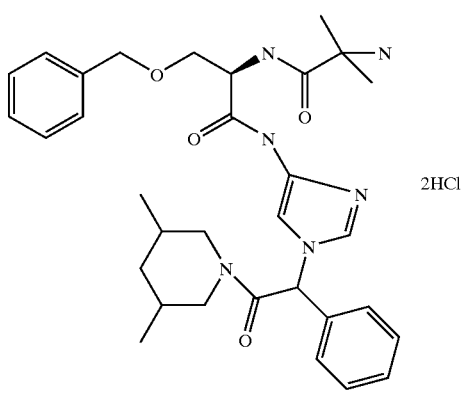

2HCl

Reaction of the product of Preparation 265 (0.78 g, 1.16 mmol), trifluoroacetic acid (4 mL), dichloromethane (12 mL), as described in Example 86, gave 0.63 g (89%) of the desired product as a yellow solid: $^1$H-NMR is consistent with structure; MS (FD) 574 (M+); Anal. Calc'd for $C_{32}H_{41}N_6O_4 \cdot 2.8HCl$: C, 56.79; H, 6.67; N, 12.42. Found: C, 56.75; H, 6.70; N, 12.12.

Preparation 266

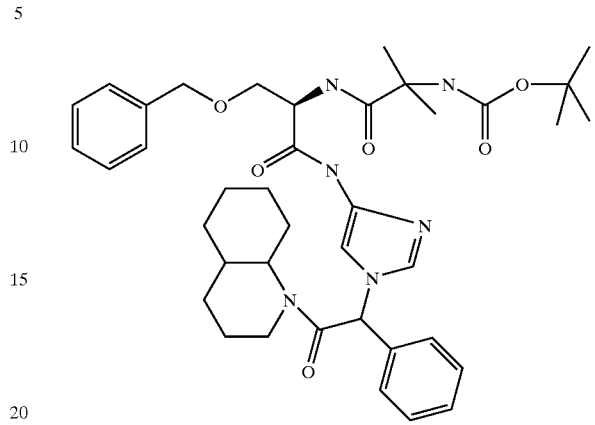

Reaction of the product of Preparation 8 from Examples Part 1 (1.0 g, 1.7 mmol), decahydroquinoline (0.26 mL, 1.7 mmol), 1-hydroxybenzotriazole (0.26 g, 1.9 mmol), 1-(3-dimethylaminopropyl)-3-ethylcarbodiimide (0.4 g, 1.9 mmol), dimethylformamide (80 mL), as described in Preparation 193, gave 1.0 g (83%) of the desired product as a tan solid: $^1$H-NMR is consistent with structure; MS (FD) 700.5 (M+); Anal. Calc'd for $C_{39}H_{52}N_6O_6$: C, 66.84; H, 7.48; N, 11.99. Found: C, 66.69; H, 7.48; N, 12.15.

Example 149

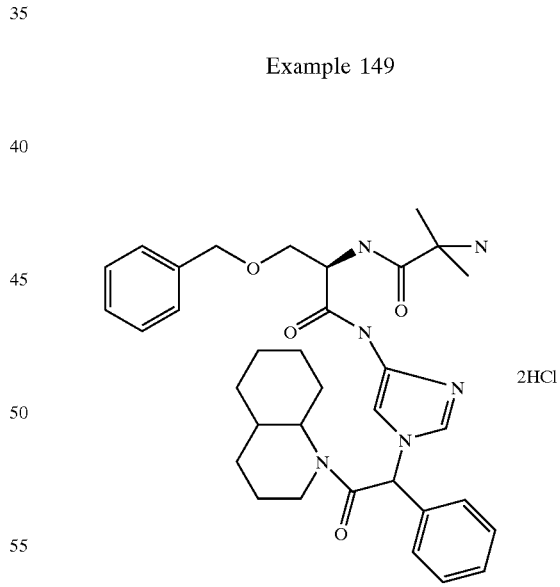

2HCl

Reaction of the product of Preparation 266 (0.93 g, 1.3 mmol), trifluoroacetic acid (4 mL), dichloromethane (12 mL), as described in Example 86, gave 0.77 g (93%) of the desired product as a yellow solid: $^1$H-NMR is consistent with structure; MS (FD) 600 (M+); Anal. Calc'd for $C_{34}H_{43}N_6O_4 \cdot 2.6HCl$: C, 58.71; H, 6.75; N, 12.08. Found: C, 58.54; H, 6.98; N, 11.93.

Preparation 267

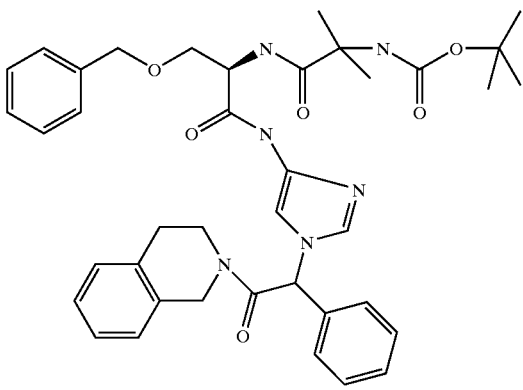

Reaction of the product of Preparation 8 from Examples Part 1 (1.0 g, 1.7 mmol), 1,2,3,4-tetrahydroisoquinoline (0.22 mL, 1.7 mmol), 1-hydroxybenzotriazole (0.26 g, 1.9 mmol), 1-(3-dimethylaminopropyl)-3-ethylcarbodiimide (0.4 g, 1.9 mmol), dimethylformamide (40 mL), as described in Preparation 193, gave 0.91 g (77%) of the desired product as a white foam: $^1$H-NMR is consistent with structure; MS (FD) 694.8 (M+).

Example 150

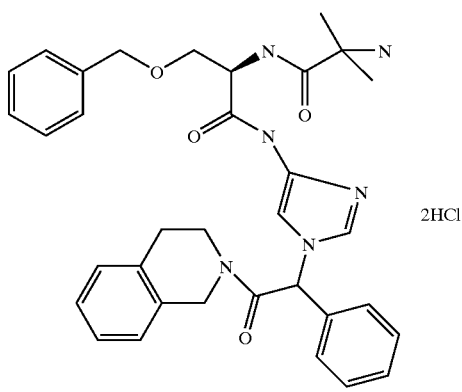

2HCl

Reaction of the product of Preparation 267 (0.88 g, 1.3 mmol), trifluoroacetic acid (4 mL), dichloromethane (12 mL), as described in Example 86, gave 0.87 g (100%) of the desired product as a white solid: $^1$H-NMR is consistent with structure; MS (FD) 594.3 (M+); Anal. Calc'd for $C_{34}H_{38}N_6O_4 \cdot 2.5HCl$: C, 59.54; H, 5.95; N, 12.25. Found: C, 59.31; H, 6.02; N, 12.06.

Preparation 268

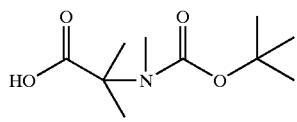

To a solution of tert-butylcarbonyl-alpha-aminoisobutic acid (10.0 g, 50 mmol) and methyl iodide, 3.6 mL (55 mmol) In 200 mL of tetrahydrofuran stirring at 0° C. was added 4.4 g (55 mmol) of sodium hydride. After 1 h, the mixture was warmed to ambient temperature and stirred overnight. The reaction mixture was quenched with water, concentrated, and dissolved in water. The aqueous solution was acidified to pH=3.4 with solid citric acid. Ethyl acetate was added and the mixture was extracted with ethyl acetate. The combined organic extracts were washed with brine, dried over sodium sulfate, filtered and concentrated to yield 10.8 g (100%) of the desired product as a white solid: $^1$H-NMR is consistent with structure; MS (ion spray) 218 (M+1).

Preparation 269

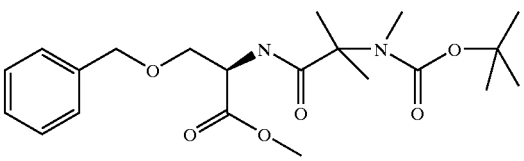

To a solution of the product of Preparation 268, 9.75 g (45.0 mmol), tert-butyloxycarbonyl-O-benzyl-D-serin, 11.0 g (45.0 mmol), Hunig's base, 28 mL (157.5 mmol) and 1-hydroxybenzotriazole, 6.8 g (49.5 mmol) in 100 mL of dimethylformamide at 0° C., was added 9.5 g (49.5 mmol) of 1-(3-(dimethylamino)propyl)-3-ethylcarbodiimide hydrochloride. The reaction mixture was slowly warmed to ambient temperature, stirred overnight, then concentrated. The residue was partitioned between ethyl acetate and water and extracted with ethyl acetate. The combined organic extracts were washed with 0.1 N hydrochloric acid, saturated sodium bicarbonate and brine, dried over sodium sulfate, filtered and concentrated. The residue was chromatographed on silica gel using 3% methanol/chloroform as eluant to yield 13.8 g (75%) of the desired product as a tan oil: $^1$H-NMR is consistent with structure; MS (ion spray) 409.4 (M+1); Anal. Calc'd for $C_{21}H_{32}N_2O_6$: C, 61.60; H, 8.12; N, 6.84. Found: C, 61.45; H, 8.10; N, 6.87.

Preparation 270

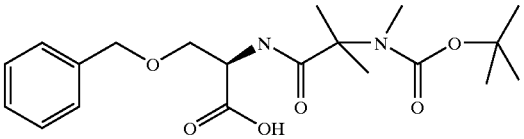

To a solution of the product of Preparation 269, 0.5 g (1.22 mmol) in 10 mL of tetrahydrofuran was added a solution of lithium hydroxide, 0.09 g (3.7 mmol) in 5 mL of water. The reaction mixture was stirred for 2 h and acidified to pH=2.4 with 1N hydrochloric acid. Water was added and the mixture was extracted with ethyl acetate. The combined organic extracts were washed with brine, dried over sodium sulfate, filtered, and concentrated to yield 0.48 g (100%) of the desired product as a clear oil: $^1$H-NMR is consistent with structure; MS (ion spray) 395.2 (M+1); Anal. Calc'd for $C_{20}H_{30}N_2O_4$: C, 60.90; H, 7.67; N, 7.10. Found: C, 61.04; H, 7.70; N, 7.34.

Preparation 271

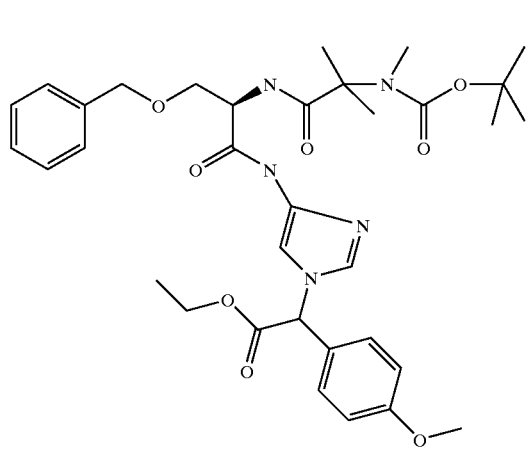

Reaction of the product of Preparation 165 (4.5 g, 14.7 mmol), 10% palladium on carbon (5.8 g), tetrahydrofuran (120 mL), the product of Preparation 270 (5.8 g, 14.7 mmol), 1-hydroxybenzotriazole (2.2 g, 16.2 mmol), dicyclohexylcarbodiimide (3.3 g, 16.2 mmol), as in Example 63, gave 6.55 g (68%) of the desired compound as a tan foam: $^1$H-NMR is consistent with structure; MS (ion spray) 652.4 (M+1).

Preparation 272

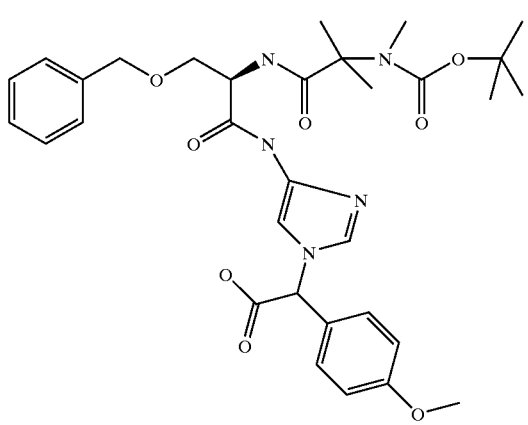

Reaction of the product of Preparation 271 (6.5 g, 10.0 mmol), lithium hydroxide (0.3 g, 12.0 mmol), dioxane (100 mL), water 150 mL), as in Example 63, gave 6.24 g (100%) of the desired compound as a tan foam: $^1$H-NMR is consistent with structure; MS (ion spray) 624.4 (M+1): Anal. Calc'd for $C_{43}NH_{41}N_5O_9$: C, 61.62; H, 6.63; N, 11.23. Found: C, 61.34; H, 6.68; N, 11.33.

Preparation 273

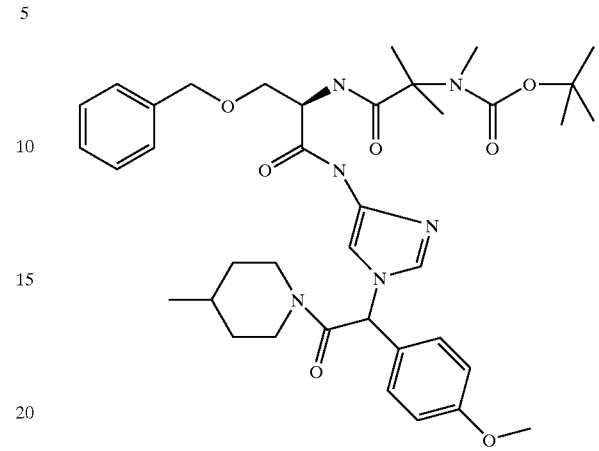

Reaction of the product of Preparation 272 (6.1 g, 1.0 mmol), 4-methylpiperidine (1.2 mL, 1.0 mmol), 1-hydroxybenzotriazole (1.5 g, 1.1 mmol), dicyclohexylcarbodiimide (2.3 g, 1.1 mmol), dimethylformamide (90 mL), as in Example 63, gave 6.18 g (88%) of the desired product as a tan foam: $^1$H-NMR is consistent with structure; MS (ion spray) 705.6 (M+1); Anal. Calc'd for $C_{38}H_{52}N_6O_7$: C, 64.75; H, 7.44; N, 11.92. Found: C, 64.63; H, 7.39; N, 11.99.

Examples 151 and 152

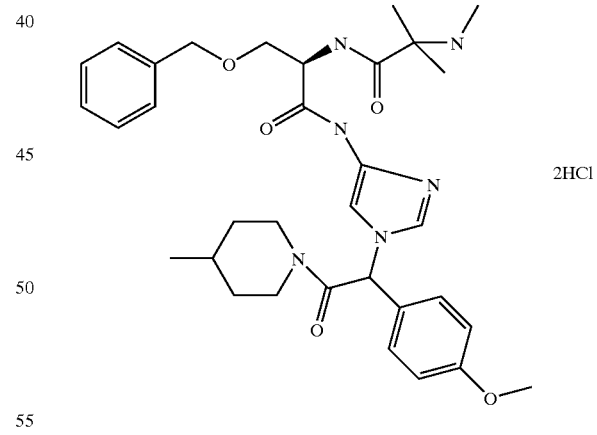

2HCl

Reaction of the product of Preparation 273 (5.65 g, 8.0 mmol), trifluoroacetic acid (16 mL), dichloromethane (40 mL), as in Example 63, gave 4.08 g (85%) of the desired product as the free base: $^1$H-NMR is consistent with structure; MS (ion spray) 605.4 (M+1); Anal. Calc'd for $C_{33}H_{44}N_6O_5$: C, 65.54; H, 7.33; N, 13.90. Found: C, 65.30; H, 7.54; N, 13.93. Resolution of the diastereomers (3.5 g, 5.9 mmol) by chiral HPLC gave the respective isomers which were individually treated with a saturated solution of hydrochloric acid in diethyl ether to give the desired products:

Example 151

Isomer 1

1.4 g (36%); ¹H-NMR is consistent with structure; $t_R$=6.50 min; MS (ion spray) 605.1 (M+1); Anal. Calc'd for $C_{33}H_{44}N_6O_5 \cdot 2.4HCl$: C, 57.26; H, 6.76; N, 12.14. Found: C, 57.30; H, 6.67; N, 12.00.

Example 152

Isomer 2

1.43 g (36%); ¹H-NMR is consistent with structure; $t_R$=7.91 min; MS (ion spray) 605.1 (M+1); Anal. Calc'd for $C_{33}H_{44}N_6O_5 \cdot 2.2HCl$: C, 57.87; H, 6.80; N, 12.27. Found: C, 57.71; H, 6.84; N, 12.09.

Preparation 274

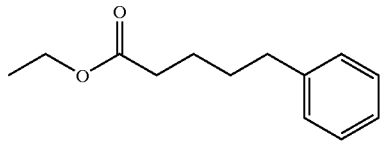

To a solution of 5-phenylvaleric acid, 19.55 g (110 mmol) in 100 ml of absolute ethanol was added 2.0 g (10.4 mmol) of p-toluenesulfonic acid. The mixture was heated to reflux overnight, cooled to ambient temperature and concentrated. The residue was chromatographed on silica gel using 20% ethyl acetate/hexanes as eluant to yield 21.3 g (94%) of the desired product as a colorless oil: ¹H-NMR is consistent with structure; MS (FD) 206 (M+); Anal. Calc'd for $C_{12}H_{18}O_2$: C, 75.69; H, 8.81. Found: C, 75.69; H, 8.91.

Preparation 275

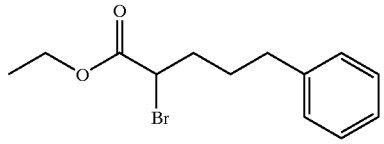

To a solution of diisopropylamine, 11.5 mL (80 mL) in 250 mL of tetrahydrofuran at −78° C. was added 50.0 mL of 1.0 M n-butyl lithium dropwise. After stirring at −78° C. for 20 minutes, 15.0 mL (116 mmol) of trimethylsilyl chloride was added followed by a solution of the product of Preparation 274 (15.0 g, 72.5 mmol) in 50 mL of tetrahydrofuran. The reaction mixture was stirred 1 h at −78° C. and was then concentrated. To a slurry of the resulting white solid in 500 mL of ethylene glycol dimethylether at −78° C. was added 13.5 g (76.1 mmol) of N-bromosuccinimide. The reaction mixture was stirred 3 h at −78° C., then was quenched with water and extracted with ethyl acetate. The combined organic extracts were washed with brine, dried over sodium sulfate, filtered and concentrated. The residue was chromatographed on silica gel using 2.5% ethyl acetate/hexanes to yield 14.8 g (72%) of the desired product as a yellow oil: ¹H-NMR is consistent with structure; MS (FD) 284, 286 (M+).

Preparation 276

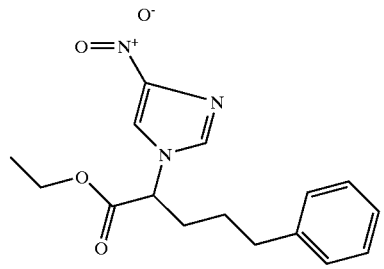

To a slurry of sodium hydride, 2.4 g (60 mmol) in 300 mL of dimethylformamide at 0° C. was added 6.8 g (60 mmol) of 4-nitroimidazole. After stirring for 20 min at 0° C., a solution of 14.1 g (50 mmol) of the product of Preparation 275 in 30 mL of dimethylformamide was added. The reaction mixture was stirred overnight, slowly warming to ambient temperature and was concentrated. The residue was partitioned between ethyl acetate and water and was extracted with ethyl acetate. The combined organic extracts were washed with brine, dried over sodium sulfate, filtered and concentrated. The resulting residue was chromatographed on silica gel using a chloroform as eluant to yield 12.7 g (71%) of the desired product as an orange oil: ¹H-NMR is consistent with structure; MS (FD) 317 (M+); Anal. Calc'd for $C_{16}H_{19}N_3O_4$: C, 60.56; H, 6.04; N, 13.24. Found: C, 60.78; H, 6.09; N, 12.98.

Preparation 277

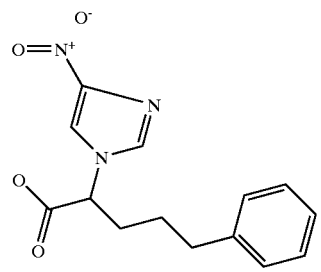

To a solution of the product of Preparation 276, 12.2 g (38.4 mmol) in 60 mL of tetrahydrofuran was added 40 mL of 5N sodium hydroxide. The mixture was stirred at ambient temperature for 1 h, then acidified to pH=0.3 with 5N hydrochloric acid and extracted with ethyl acetate. The combined organic extracts were washed with brine, dried over sodium sulfate, filtered and concentrated to yield 9.3 g (84%) of the desired product as an orange oil: ¹H-NMR is consistent with structure; MS (FD) 290 (M+).

Preparation 278

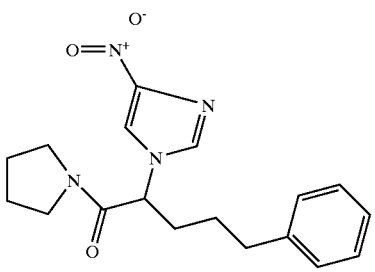

To a solution of the product of Preparation 277, 9.0 g (31 mmol), pyrrolidine, 2.6 mL (31 mmol) and 1-hydroxybenzotriazole, 4.6 g (34.1 mmol) in 200 mL of dimethylformamide was added 7.0 g (34.1 mmol) of dicyclohexylcarbodiimide. The reaction mixture was stirred overnight at ambient temperature and was then concentrated in vacuo. The residue was partitioned between ethyl acetate and water and was extracted with ethyl acetate. The combined organic extracts were washed with brine, dried over sodium sulfate, filtered and concentrated. The residue was chromatographed on silica gel using 5% methanol/chloroform as eluant to yield 10.3 g (97%) of the desired product as a tan oil: $^1$H-NMR is consistent with structure; MS (FD) 312 (M+).

Preparation 278A

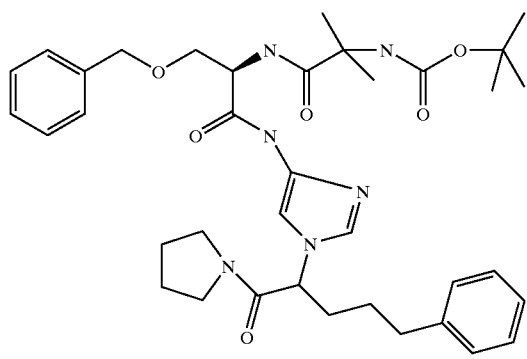

To a slurry of 0.8 g of 10% palladium on carbon in 20 mL of dioxane was added a solution of 0.6 g (3.5 mmol) of the product of Preparation 278 in 20 mL of dioxane. The mixture was hydrogenated at 40 psi of hydrogen for 3 h and filtered through celite. To this solution was added 1.2 g (5.8 mmol) of the product of Preparation 1d, 0.52 g (3.85 mmol) of 1-hydroxybenzotriazole and 0.8 g (3.85 mmol) of dicyclohexylcarbodiimide. The reaction was stirred overnight at ambient temperature, filtered and concentrated. The residue was partitioned between ethyl acetate and water and was extracted with ethyl acetate. The combined organic extracts were washed with brine, dried over sodium sulfate, filtered and concentrated. The resulting residue was chromatographed on silica gel using 2.5% methanol/chloroform as eluant to yield 0.65 g (16%) of the desired product as a red foam: $^1$H-NMR is consistent with structure; MS (FD) 674 (M+).

Example 153

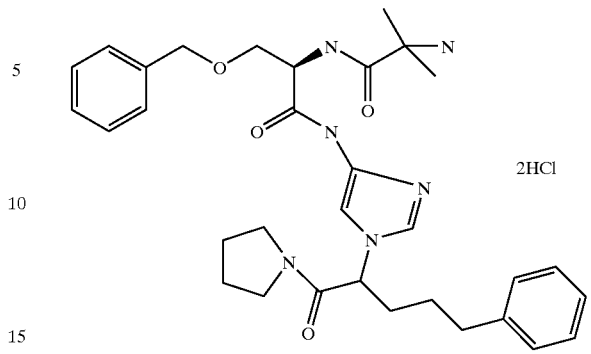

To a solution of the product of Preparation 278A, 0.55 g (0.8 mmol) in 24 mL of dichloromethane was added 8 mL of trifluoroacetic acid. The reaction mixture was stirred for 2 h, quenched with aqueous sodium carbonate and extracted with chloroform. The combined organic extracts were washed with brine, dried over sodium sulfate, filtered and concentrated. To a solution of the residue in ethyl acetate was added ether/hydrochloric acid. The resultant slurry was concentrated to yield 0.47 g (94%) of the desired product as a tan solid: $^1$H-NMR is consistent with structure; MS (FD) 573.9 (M+); Anal. Calc'd for $C_{32}H_{42}N_4O_4 \cdot 0.2HCl$: C, 59.35; H, 6.85; N, 12.98. Found: C, 59.04; H, 6.96; N, 12.52.

Preparation 279

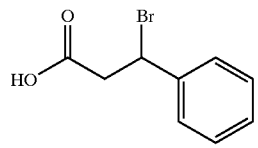

To a solution of hydrocinnamic acid, 12.35 g (82.2 mmol) in 300 mL of dichloromethane was added 4.2 mL (82.2 mmol) of bromine dropwise. The reaction mixture was illuminated for 15 min and then stirred an additional 15 min and concentrated. The residue was triturated with ether/hexanes to yield 14.7 g (78%) of the desired product as a white solid: $^1$H-NMR is consistent with structure; MS (FD) 228, 230 (M+); Anal. Calc'd for $C_9H_9O_2Br$: C, 47.19; H, 3.96. Found: C, 47.28; H, 4.02.

Preparation 280

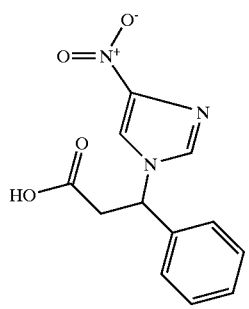

To a slurry of sodium hydride, 1.1 g (27.3 mmol) in 50 mL of dimethylformamide at 0° C. was added 3.1 g (27.3 mmol)

of 4-nitroimidazole. The resulting mixture was stirred 20 min, then 3.0 g (13.0 mmol) of product of Preparation 279 was added. The reaction mixture was stirred overnight slowly warming to ambient temperature, then concentrated. The residue was partitioned between ethyl acetate and 1N hydrochloric acid and was basified to pH=3.0 with 1N sodium hydroxide. The aqueous layer was extracted with ethyl acetate. The combined organic extracts were washed with brine, dried over sodium sulfate, filtered and concentrated. The residue was absorbed onto a silica pad and chromatographed on silica gel using a gradient of 10–40% methanol/chloroform to yield 0.55 g (14.4%) of the desired product as a white solid: $^1$H-NMR is consistent with structure; MS (FM) 261 (M+).

Preparation 281

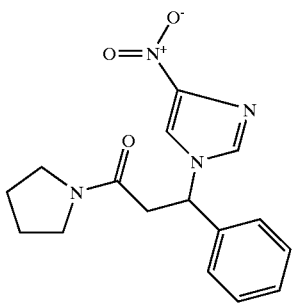

To a solution of the product of Preparation 280, 2.4 g (9.3 mmol), pyrrolidine, 0.77 mL (9.3 mmol) and 1-hydroxybenzotriazole, 1.6 g (10.2 mmol) in 200 mL of dimethylformamide was added 2.1 g (10.2 mmol) of dicyclohexylcarbodiimide. The reaction mixture was stirred overnight at ambient temperature and was then concentrated in vacuo. The residue was partitioned between ethyl acetate and water and extracted with ethyl acetate. The combined organic extracts were washed with brine, dried over sodium sulfate, filtered and concentrated. The residue was chromatographed on silica gel using 2.5% methanol/chloroform as eluant to yield 0.84 g (29%) of the desired product as a white foam: $^1$H-NMR is consistent with structure; MS (FD) 314 (M+).

Preparation 282

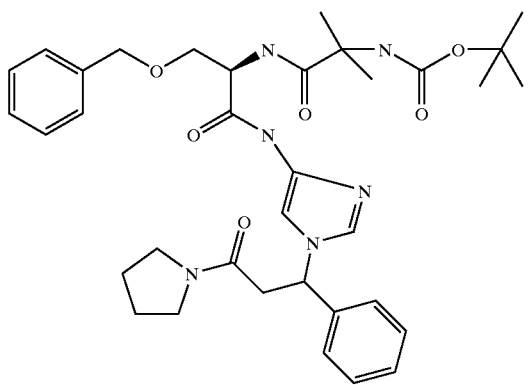

To a slurry of 0.7 g of 10% palladium on carbon in 30 mL of ethyl acetate was added a solution of 0.8 g (2.5 mmol) of the product of Preparation 281 in 30 mL of ethyl acetate, 60 mL of tetrahydrofuran and 60 mL of ethanol. The mixture was hydrogenated at 40 psi of hydrogen for 1 h, filtered through celite and concentrated. The residue was dissolved in 60 mL of dimethylformamide. To this solution was added 0.95 g (2.5 mmol) of the product of Preparation 1d, 0.37 g (2.75 mmol) of 1-hydroxybenzotriazole and 0.57 g (2.75 mmol) of dicyclohexylcarbodiimide. The reaction was stirred overnight at ambient temperature, filtered and concentrated. The residue was partitioned between ethyl acetate and water and was extracted with ethyl acetate. The combined organic extracts were washed with brine, dried over sodium sulfate, filtered and concentrated. The resulting residue was chromatographed on silica gel using 2.5% methanol/chloroform as eluant to yield 0.32 g (20%) of the desired product as a tan foam: $^1$H-NMR is consistent with structure; MS (FD) 646.3 (M+).

Example 154

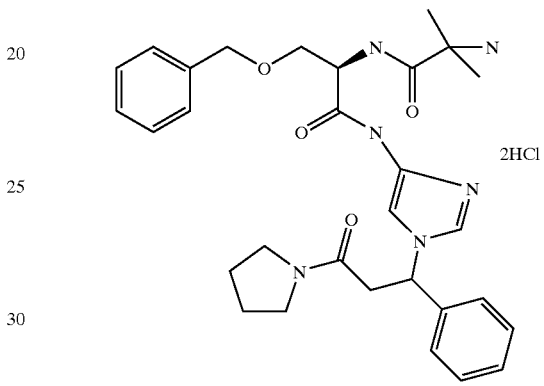

To a solution of the product of Preparation 282, 0.25 g (0.38 mmol) in 12 mL of dichloromethane was added 4 mL of trifluoroacetic acid. The reaction mixture was stirred for 2 h, quenched with aqueous sodium carbonate and extracted with chloroform. The combined organic extracts were washed with brine, dried over sodium sulfate, filtered and concentrated. To a solution of the residue in 20 mL of ethyl acetate was added 40 mL of ether hydrochloric acid. The resultant slurry was concentrated to yield 0.22 g (96%) of the desired product as a tan solid: $^1$H-NMR is consistent with structure; MS (high res) calc'd for $C_{30}H_{39}N_6O_4$: 547.3033. Found: 547.3037.

Preparation 283

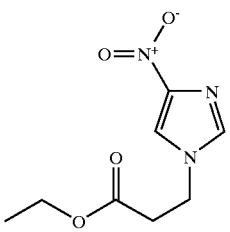

To a slurry of sodium hydride, 6.72 g (168 mmol) in 400 mL of dimethylformamide at 0° C. was added 19.0 g (168 mmol) of 4-nitroimidazole. The resulting slurry was stirred 20 min, then a solution of 25 g (140 mmol) of ethyl 3-bromopropionate in 10 mL of dimethylformamide was added dropwise. The reaction mixture was stirred overnight slowly warming to ambient temperature, then concentrated. The residue was partitioned between ethyl acetate and was extracted with ethyl acetate. The combined organic extracts were washed with brine, dried over sodium sulfate, filtered and concentrated. The residue was absorbed onto a silica pad and chromatographed on silica gel using a gradient of 20–70% ethyl acetate/hexanes to yield 22.71 g (76%) of the desired product as a yellow oil: $^1$H-NMR is consistent with structure; MS (FD) 213 (M+); Anal. Calc'd for $C_8H_{11}N_3O_4$: C, 45.07; H, 5.20; N, 19.71. Found: C, 45.08; H, 5.18; N, 19.42.

Preparation 294

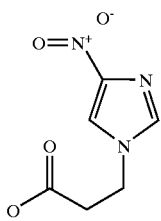

To a solution of the product of Preparation 283, 22.46 g (100 mmol) in 100 mL of tetrahydrofuran and 100 mL of ethanol was added 100 mL of 5N sodium hydroxide. The mixture was stirred at ambient temperature for 1 h, then acidified to pH=2.5 with 5N hydrochloric acid and extracted with ethyl acetate. The combined organic extracts were washed with brine, dried over sodium sulfate, filtered and concentrated to yield 7.8 g (42%) of the desired product as an orange oil: $^1$H-NMR is consistent with structure; MS (FD) 185 (M+).

Preparation 285

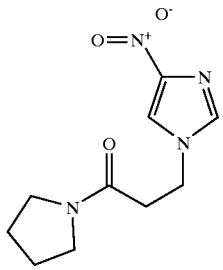

To a solution of the product of Preparation 284, 5.3 g (29 mmol), pyrrolidine, 2.4 mL (29 mmol) and 1-hydroxybenzotriazole, 4.3 g (32 mmol) in 50 mL of dimethylformamide was added 6.6 g (32 mmol) of dicyclohexylcarbodiimide. The reaction mixture was stirred overnight at ambient temperature and was then concentrated in vacuo. The residue was partitioned between ethyl acetate and water and was extracted with ethyl acetate. The combined organic extracts were washed with brine, dried over sodium sulfate, filtered and concentrated. The residue was absorbed onto a silica pad and chromatographed on silica gel using a gradient of 2.5–5% methanol/chloroform as eluant to yield 0.69 g (10%) of the desired product as a yellow solid: $^1$H-NMR is consistent with structure; MS (FD) 238 (M+); Anal. Calc'd for $C_{10}H_{14}N_4O_3$: C, 50.41; H, 5.92; N, 23.52. Found: C, 50.59; H, 5.75; N, 23.47.

Preparation 286

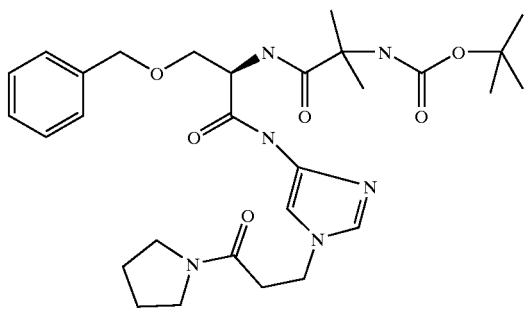

To a slurry of 0.66 g of 10% palladium on carbon in 15 mL of ethyl acetate was added a solution of 0.66 g (2.8 mmol) of the product of Preparation 285 in 6 mL of dichloromethane and 15 mL of ethanol. The mixture was hydrogenated at 40 psi of hydrogen for 40 min and filtered through celite and concentrated. The residue was dissolved in 30 mL of dimethylformamide. To this solution was added 1.1 g (2.8 mmol) of the product of Preparation 1d, 0.42 g (3.1 mmol) of 1-hydroxybenzotriazole and 0.63 g (3.1 mmol) of dicyclohexylcarbodiimide. The reaction was stirred overnight at ambient temperature, filtered and concentrated. The residue was partitioned between ethyl acetate and water and was extracted with ethyl acetate. The combined organic extracts were washed with brine, dried over sodium sulfate, filtered and concentrated. The resulting residue was chromatographed on silica gel using a gradient of chloroform to 3% methanol/chloroform as eluant to yield 0.67 g (42%) of the desired product as a tan foam: $^1$H-NMR is consistent with structure; MS (FD) 570.2 (M+); Anal. Calc'd for $C_{29}H_{42}N_6O_6$: C, 61.03; H, 7.42; N, 14.73. Found: C, 60.94; H, 7.26; N, 14.55.

Example 155

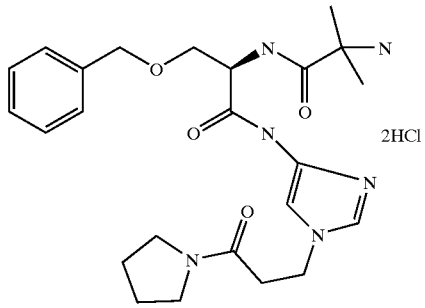

To a solution of the product of Preparation 286, 0.6 g (1.1 mmol) in 12 mL of dichloromethane was added 4 mL of trifluoroacetic acid. The reaction mixture was stirred for 2 h, quenched with solid sodium carbonate and extracted with chloroform. The combined organic extracts were washed with brine, dried over sodium sulfate, filtered and concentrated. To a solution of the residue in 10 mL of ethyl acetate was added 10 mL of ether-hydrochloric acid. The resultant slurry was concentrated to yield 0.52 g (94%) of the desired product as a tan foam: $^1$H-NMR is consistent with structure; MS (FD) 471 (M+1); Anal. Calc'd for $C_{24}H_{34}N_6O_4 \cdot 2.25HCl$: C, 52.16; H, 6.61; N, 15.21. Found: C, 52.48; 6.87; N, 14.81.

Preparation 287

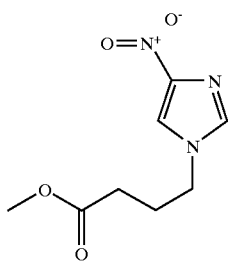

Ethyl-4-bromobutyrate (18.4 mL, 156-mol), 4-nitroimidazole (17.6 g, 130 mmol), sodium hydride (6.24 g, 156 mmol), dimethylformamide (400 mL), as described Preparation 283 gave 23.4 g (80%) of the desired product as a yellow oil: $^1$H-NMR is consistent with structure; MS (FD) 227 (M+); Anal. Calc'd for $C_9H_{13}N_3O_4$: C, 47.58; H, 5.77; N, 18.49. Found: C, 47.48; H, 5.50; N, 18.30.

Preparation 288

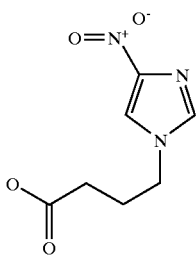

Reaction of the product of Preparation 287 (22.84 g, 100 mmol), 5N sodium hydroxide (100 mL), tetrahydrofuran (100 mL), ethanol (100 mL), as described in Preparation 284 gave 9.8 g (50%) of the desired product as an orange solid: $^1$H-NMR is consistent with structure; MS (FD) 200.1 (M+); Anal. Calc'd for $C_7H_9N_3O_4$: C, 42.22; H, 4.56; N, 21.10. Found: C, 41.97; H, 4.63; N, 21.04.

Preparation 289

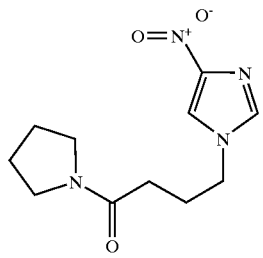

Reaction of the product of Preparation 288 (4.87 g, 25 mmol), pyrrolidine (2.4 mL, 25 mmol), 1-hydroxybenzotriazole (3.7 g, 27.5 mmol), dicyclohexylcarbodiimide (5.6 g, 27.5 mmol), dimethylformamide (50 mL), as described in Preparation 285, gave 0.65 g (11%) of the desired product as a tan oil: $^1$H-NMR is consistent with structure; MS (FD) 252 (M+); Anal. Calc'd for $C_{11}H_{16}N_4O_3$: C, 52.37; H, 6.39; N, 22.21. Found: C, 52.59; H, 6.50; N, 22.44.

Preparation 290

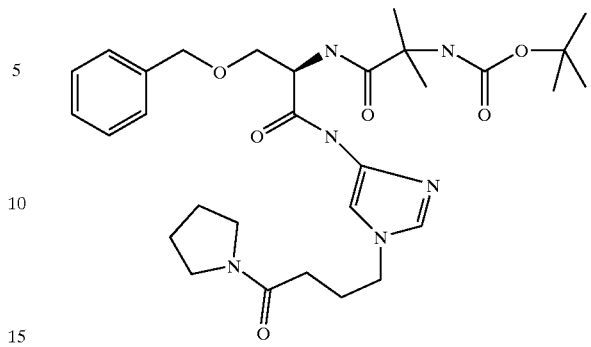

Reaction of the product of Preparation 289 (0.6 g, 2.4 mmol), 10% palladium on carbon (0.3 g), dichloromethane (6 mL), ethyl acetate (20 mL), absolute ethanol (20 mL), 386979 (0.91 g, 2.4 mmol), 1-hydroxybenzotriazole (0.36 g, 2.64 mmol), dicyclohexylcarbodiimide (0.54 g, 2.64 mmol), dimethylformamide (40 mL), as described in Preparation 286 gave 0.69 g (50%) of the desired product as a tan oil: $^1$H-NMR is consistent with structure; MS (FD) 585.4 (M+); Anal. Calc'd for $C_{30}H_{44}N_4O_6$: C, 61.63; H, 7.58; N, 14.37. Found: C, 61.35; H, 7.50; N, 14.30.

Example 156

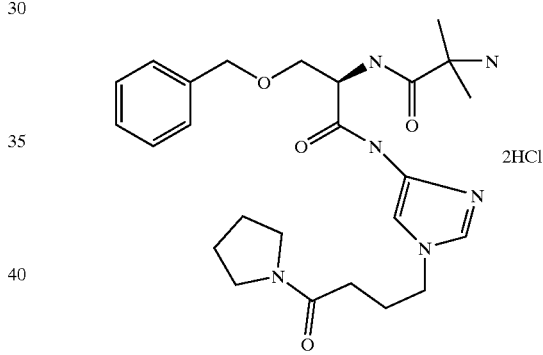

Reaction of the product of Preparation 290 (0.65 g, 1.1 mmol), trifluoroacetic acid (4 mL), dichloromethane (12 mL), as described in Example 155 gave 0.58 g (98%) of the desired hydrochloric acid salt as an oil: $^1$H-NMR is consistent with structure; MS (FD) 484 (M+): Anal. Calc'd for $C_{15}H_{36}N_6O_4$·2.3HCl: C, 52.821 H, 6.79; N, 14.78. Found: C, 53.01; H, 6.88; N, 14.40.

Preparation 291

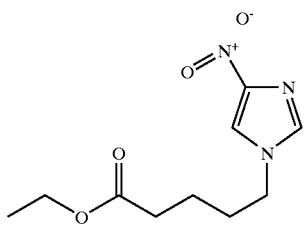

Reaction of ethyl-5-bromovalerate (25 g, 120 mmol), 4-nitroimidazole ((16.3 g, 144 mmol), sodium hydride 15.8 g, 144 mmol) dimethylformamide (400 mL), as described Preparation 283 gave 21.9 g (75%) of the desired product as a colorless oil: $^1$H-NMR is consistent with structure; MS (FD) 241.1 (M+); Anal. Calc'd for $C_{10}H_{15}N_3O_4$: C, 49.79; H, 6.27; N, 17.42. Found: C, 49.63; H, 6.16; N, 17.22.

Preparation 292

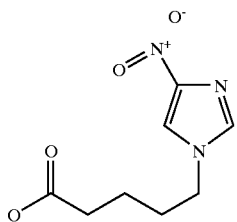

Reaction of the product of Preparation 291 (21.08 g, 87 mmol), 5N sodium hydroxide (100 mL), tetrahydrofuran (100 ml), ethanol (100 mL), as described in Preparation 284 gave 11.9 g (64%) of the desired product as a tan solid: $^1$H-NMR is consistent with structure; MS (FD) 214 (M+); Anal. Calc'd for $C_8H_{11}N_3O_4^-$: C, 45.07; H, 5.20; N, 19.71. Found: C, 44.89; H, 4.92; N, 19.44.

Preparation 293

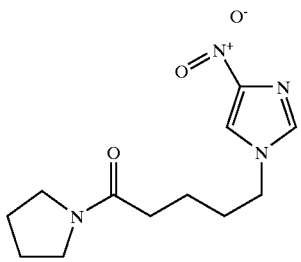

Reaction of the product of Preparation 292 (9.9 g, 46.4 mmol), pyrrolidine (4 mL, 46.4 mmol), 1-hydroxybenzotriazole (7.0 g, 51.0 mmol), dicyclohexyl-carbodiimide (10.6 g, 51.0 mmol)), triethylamine (3.23 mL, 46.4 mmol), as described in Preparation 285 gave 8.4 g (69%) of the desired product as a colorless oil: $^1$H-NMR is consistent with structure; MS (FD) 266 (M+); Anal. Calc'd for $C_{12}H_{18}N_4O_3^-$: C, 54.12; H, 6.81; N, 21.04. Found: C, 54.35; H, 6.91; N, 20.91.

Preparation 294

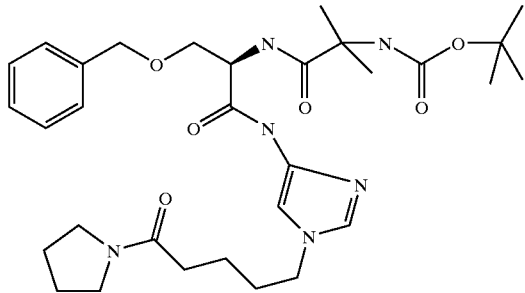

Reaction of the product of Preparation 293 (1.0 g, 3.8 mmol), 10% palladium on carbon (0.5 g), dichloromethane (5 mL), ethyl acetate (10 mL), ethanol (20 mL), the product of Preparation 1d (1.45 g, 3.9 mmol), 1-hydroxybenzotriazole (0.56 g, 4.2 mmol), dicyclohexyl-carbodiimide (0.86 g, 1.1 mmol), dimethylformamide (40 mL), as described in Preparation 286 gave 0.8 g (35%) of the desired product as a yellow oil: $^1$H-NMR is consistent with structure; MS (FM) 598.2 (M+).

Example 157

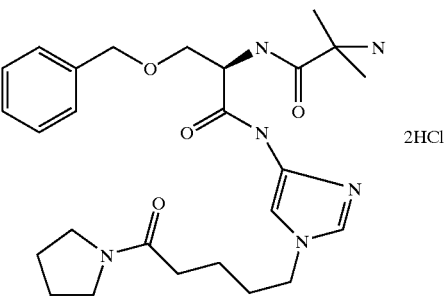

Reaction of the product of Preparation 294 (0.75 g, 1.2 mmol), trifluoroacetic acid (4 mL), dichloromethane (12 mL), as described in Example 155 gave 0.57 g (100%) of the desired product as the hydrochloric acid salt as a white solid: $^1$H-NMR is consistent with structure; MS (FD) 499 (M+).

Preparation 295

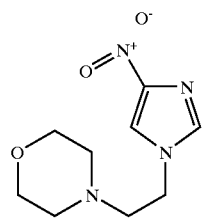

Reaction of N-(2-chloroethyl)morpholine hydrochloride (6.9 g, 37.0 mmol), 4-nitroimidazole (5.0 g, 44.0 mmol), sodium hydride (3.27 g, 80.7 mmol), dimethylformamide (150 mL), as described in Preparation 283 gave 1.1 g (13%) of the desired product as a yellow solid: $^1$H-NMR is consistent with structure; MS (FD) 226.1 (M+1); Anal. Calc'd. for $C_9H_{14}N_4O_3$: C, 47.78; H, 6.24; N, 24.77. Found: C, 48.01; H, 6.13; N, 24.56

Preparation 296

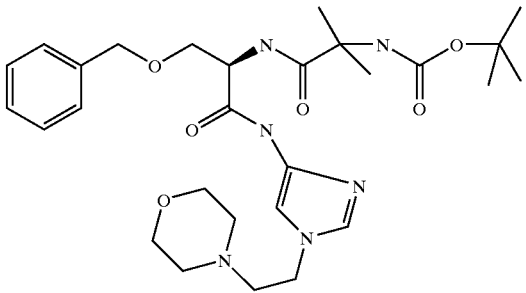

Reaction of the product of Preparation 295 (0.6 g, 2.6 mmol), 10% palladium on carbon (0.6 g), ethyl acetate (20 mL), ethanol (10 mL), the product of Preparation 1d (1.0 g, 2.6 mmol), 1-hydroxybenzotriazole (0.4 g, 2.9 mmol), dicyclohexylcarbodiimide (0.6 g, 2.9 mmol), dimethylformamide (40 mL), as described in. Preparation 286 gave 0.34 g (24%) of the desired product as a yellow foam: $^1$H-NMR is consistent with structure; MS (FD) 558 (M+1).

Example 158

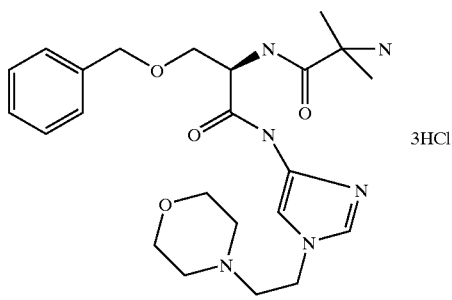

3HCl

Reaction of the product of Preparation 296 (0.14 g, 0.25 mmol), trifluoroacetic acid (2 mL), dichloromethane (6 mL), as described in Example 155 gave 0.13 g (100%) of the desired product as the hydrochloric acid salt as a white solid: $^1$H-NMR is consistent with structure; MS (FD) 458.2 (M+).

Preparation 297

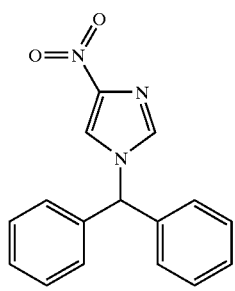

To a solution of 4-nitroimidazole, 4.6 g (40 mmol) and bromodiphenylmethane, 10.0 g (40 mmol) in 150 mL of dimethylformamide was added 16.6 g (120 mmol) of potassium carbonate. The reaction mixture was stirred overnight at ambient temperature, filtered and concentrated. The residue was partitioned between ethyl acetate and water and was extracted with ethyl acetate. The combined organic extracts were washed with brine, dried over sodium sulfate, filtered and concentrated. The resulting crude material was absorbed onto a silica pad and chromatographed on silica gel using 25–60% ethyl acetates/hexanes as eluant to yield 3.2 g (27%) of the desired product as a clear oil: $^1$H-NMR is consistent with structure; MS (ion spray) 280 (M+1).

Preparation 298

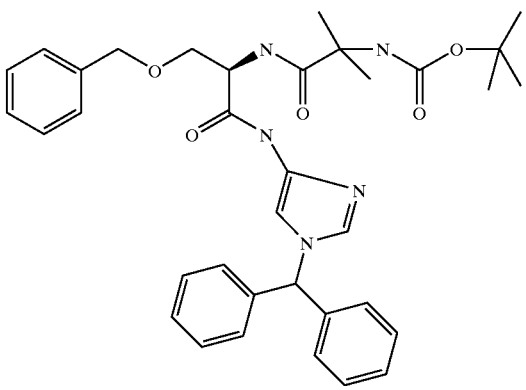

To a slurry of 0.8 g of 10% palladium on carbon in 30 mL of tetrahydrofuran was added a solution of 1.2 g (4.3 mmol) of the product of Preparation 297 in 40 mL of tetrahydrofuran. The mixture was hydrogenated at 40 psi of hydrogen for 1 h and filtered through celite. To this solution was added 1.64 g (4.3 mmol) of Preparation 4 from Examples Part 1, 0.7 g (4.7 mmol) of 1-hydroxybenzotriazole and 1.04 g (4.7 mmol) of dicyclohexylcarbodiimide. The reaction was stirred overnight at ambient temperature, filtered and concentrated. The resulting residue was chromatographed on silica gel using 4% methanol/chloroform as eluant to yield 1.57 g (60%) of the desired product. $^1$H-NMR is consistent with structure; MS (ion spray) 612.4 (M+1); Anal. Calc'd for $C_{35}H_{41}N_5O_5$: C, 68.72; H, 6.76; N, 11.45. Found: C, 68.44; H, 6.72; N, 11.15.

Example 159

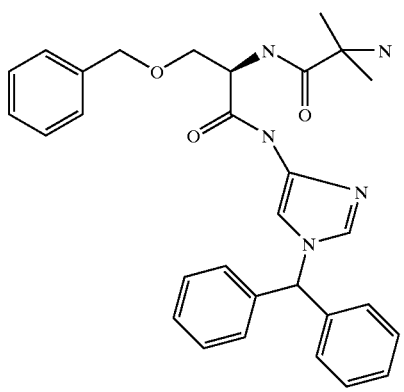

To a solution of the product of Preparation 298, 0.56 g (0.91 mmol) in 6 mL of dichloromethane was added 2 mL of trifluoroacetic acid. The reaction mixture was stirred for 2.5 h, then poured into a solution of saturated sodium carbonate and extracted with chloroform. The combined organic extracts were washed with brine, dried over sodium sulfate, filtered and concentrated. The desired product was triturated with ethyl acetate/hexanes to yield 0.45 g (96%) of the desired product as a tan solid: $^1$H-NMR is consistent with structure; MS (ion spray) 512.6 (M+1); Anal. Calc'd for $C_{30}H_{33}N_5O_3 \cdot 0.2H_2O$: C, 69.94; H, 6.53; N, 13.59. Found: C, 69.88; H, 6.36; N, 13.25.

Preparation 299

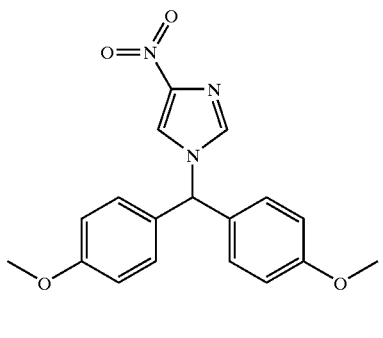

To a solution of 4,4'-dimethoxybenzhydrol, 5.0 g (20 mmol), 4-nitroimidazole, 2.31 g (20 mmol) and triphenylphosphine, 5.3 g (20 mmol) in 200 mL of tetrahydrofuran at 0° C. was added 5.0 mL (32 mmol) of diethyl azodicarboxylate dropwise. The resulting mixture was slowly warmed to ambient temperature, stirred overnight and concentrated. The residue was partitioned between ethyl acetate and water and extracted with ethyl acetate. The combined organic extracts were washed with brine, dried over sodium sulfate, filtered and concentrated. The residue was absorbed onto a silica pad and chromatographed on silica gel using 20–40% ethyl acetates/hexane as eluant. The resulting residue was chromatographed on silica gel using 3% methanol/chloroform as eluant to yield 4.92 g (72%) of the desired product as a yellow oil: $^1$H-NMR is consistent with structure; MS (ion spray) 340 (M+1); Anal. Calc'd for $C_{18}H_{17}N_3O_4 \cdot 0.3H_2O$: C, 62.71; H, 5.15; N, 12.19. Found: C, 62.48; H, 4.83; N, 11.84.

Preparation 300

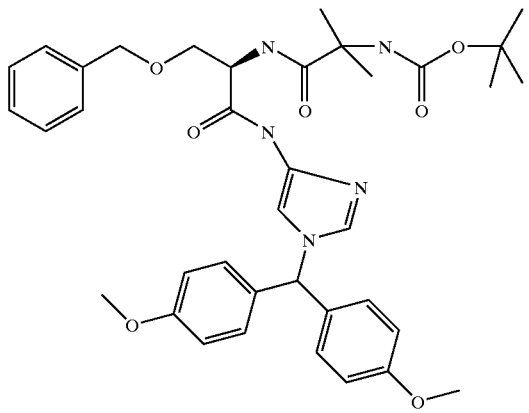

Reaction of the product of Preparation 299 (1.8 g, 5.3 mmol), 10% palladium on carbon (1.0 g), tetrahydrofuran (60 mL), 386979 (2.0 g, 5.3 mmol), 1-hydroxybenzotriazole (0.8 g, 5.83 mmol), dicyclohexylcarbodiimide (1.2 g, 5.83 mmol), as described in Preparation 159 gave 1.3 g (36%) of the desired product as a tan foam: $^1$H-NMR is consistent with structure; MS (ions spray) 672.7 (M+1); Anal. Calc'd for $C_{37}H_{45}N_5O_7$: C, 66.15; H, 6.75; N, 10.43. Found: C, 66.29; H, 6.82; N, 10.63.

Example 160

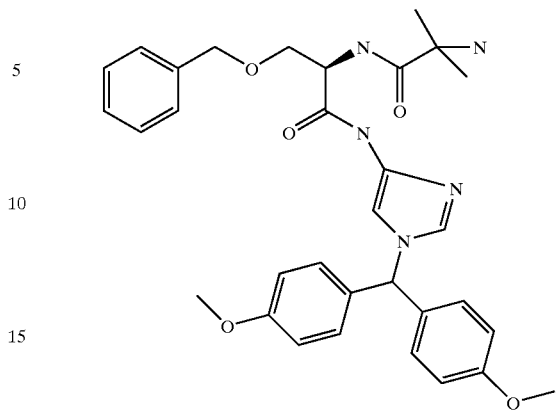

Reaction of the product of Preparation 300 (1.24 g, 1.8 mmol), trifluoroacetic acid (2 mL), dichloromethane (6 mL), as described in Example 159, Chromatographed over silica gel (5% methanol/chloroform) to yield 0.73 g (69%) of the desired product as a white foam: $^1$H-NMR is consistent with structure; MS (ion spray) 572.4 (M+1); Anal. Calc'd for $C_{32}H_{37}N_5O_5$: C, 67.23; H, 6.52; N, 12.25. Found: C, 67.05; H, 6.59; N, 11.97.

Preparation 301

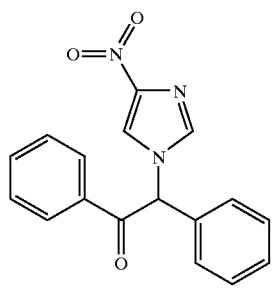

To a slurry of sodium hydride, 2.64 g (66.0 mmol) in 300 mL of dimethylformamide at 0° C. was added 7.4 g (66.0 mmol) of 4-nitroimidazole. After stirring for 20 min at 0° C., 15.0 g (55.0 mmol) of desyl bromide was added. The reaction mixture was stirred 65 h, as it warmed to ambient temperature and was concentrated. The residue was partitioned between ethyl acetate and water and was extracted with ethyl acetate. The combined organic extracts were washed with brine, dried over sodium sulfate, filtered and concentrated. The resulting residue was chromatographed on silica gel using a gradient of chloroform to 5% methanol/chloroform as eluant to yield 10.1 g (60%) of the desired product as a yellow oil which solidifies upon standing. $^1$H-NMR is consistent with structure; MS (ion spray) 307.1 (M+1); Anal. Calc'd for $C_{17}H_{13}N_3O_3$: C, 66.44; H, 4.26; N, 13.67. Found: C, 66.31; H, 4.22; N, 13.39.

Preparation 302

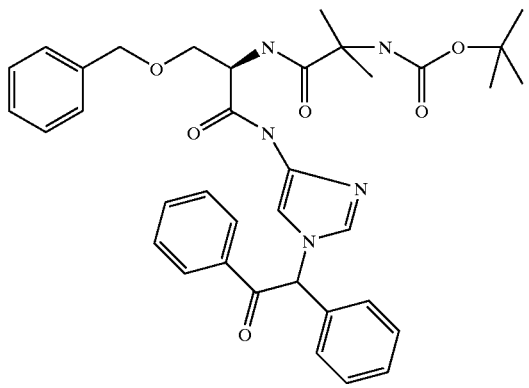

To a slurry of 0.3 g of 10% palladium on carbon in 20 mL of tetrahydrofuran was added a solution of 0.8 g (2.6 mmol) of the product of Preparation 301 in 20 mL of tetrahydrofuran. The mixture was hydrogenated at 40 psi of hydrogen for 1 h and filtered through celite. To this solution was added 1.0 g (2.6 mmol) of the product of Preparation 1d, 0.4 g (2.9 mmol) of 1-hydroxybenzotriazole and 0.6 g (2.9 mmol) of dicyclohexylcarbodiimide. The reaction was stirred overnight at ambient temperature, filtered and concentrated. The resulting residue was chromatographed on silica gel using a gradient from chloroform to 5% methanol/chloroform as eluant to yield 1.3 g (76%) of the desired product. $^1$H-NMR is consistent with structure; MS (FD) 639.4 (M+); Anal. Calc'd for $C_{36}H_{41}N_5O_6$: C, 65.74; H, 6.59; N, 10.65. Found: C, 65.91; H, 6.21; N, 10.67.

Example 161

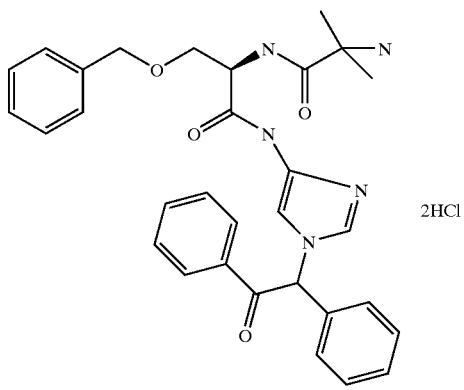

To a solution of the product of Preparation 302, 1.0 g (1.56 mmol) in 12 mL of dichloromethane was added 4 mL of trifluoroacetic acid. The reaction mixture was stirred for 1.5 h, then quenched with solid sodium carbonate and extracted with chloroform. The combined organic extracts were washed with brine, dried over sodium sulfate, filtered and concentrated. The residue was dissolved in ethyl acetate and ether hydrochloric acid was added. The mixture was concentrated to yield 0.68 g (71%) of the desired product as a tan solid: $^1$H-NMR is consistent with structure; MS (FD) 539 (M+); Anal. Calc'd for $C_{31}H_{33}N_5O_4 \cdot 2HCl$: C, 60.78; H, 5.76; N, 11.43. Found: C, 60.51; H, 5.84; N, 11.12.

Preparation 303

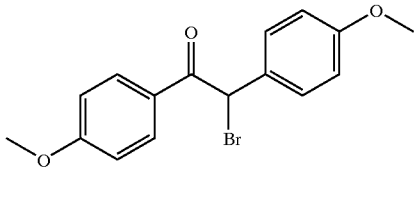

To a slurry of desoxyanisoin, 20 g (78 mmol) in 200 mL of carbon tetrachloride at 0° C. was added 4 mL (78 mmol) of bromine, dropwise over 30 min. The reaction mixture was stirred overnight while slowly warming to ambient temperature, then concentrated. The residue was absorbed onto a silica pad and chromatographed on silica gel using a gradient of 10–30% ethyl acetate/hexanes as eluant to yield 18 g (69%) of the desired product as a white solid: $^1$H-NMR is consistent with structure; MS (ion spray) 335, 337 (M+1).

Preparation 304

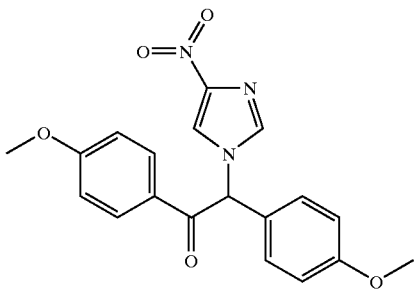

Reaction of the product of Preparation 303 (7.0 g, 20.0 mmol), 4-nitroimidazole (2.34 g, 20.0 mmol), sodium hydride (1.0 g, 24.0 mmol), dimethylformamide (100 mL), as described in Preparation 301. The crude material was absorbed onto a silica pad and chromatographed over silica gel using a gradient of 30–80% ethyl acetate/hexanes to yield 2.8 g (38%) of the desired product as a tan foam: $^1$H-NMR is consistent with structure; MS (ion spray) 366.1 (M+1); Anal. Calc'd for $C_{19}H_{17}N_3O_5$: C, 62.12; H, 4.66; N, 11.44. Found: C, 62.05; H, 4.55; N, 11.57.

Preparation 305

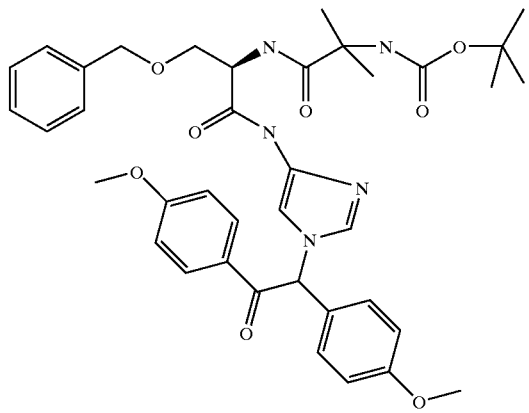

Reaction of the product of Preparation 304 (1.5 g, 4.1 mmol), 10% palladium on carbon (1.0 g), tetrahydrofuran (40 mL), the product of Preparation 1d (1.56 g, 4.1 mmol), 1-hydroxybenzotriazole (0.61 g, 4.51 mmol), dicyclohexylcarbodiimide (0.93 g, 4.51 mmol), as in described in Preparation 302. The residue was chromatographed on silica gel using 3% methanol/chloroform as eluant to yield 1.95 g (68%) of the desired product as a tan foam: $^1$H-NMR is consistent with structure; MS (ion spray) 700.8 (M+1); Anal. Calc'd for $C_{38}H_{45}N_5O_8$: C, 65.22; H, 6.48; N, 10.01. Found: C, 65.05; H, 6.20; N, 10.25.

Examples 162 and 163

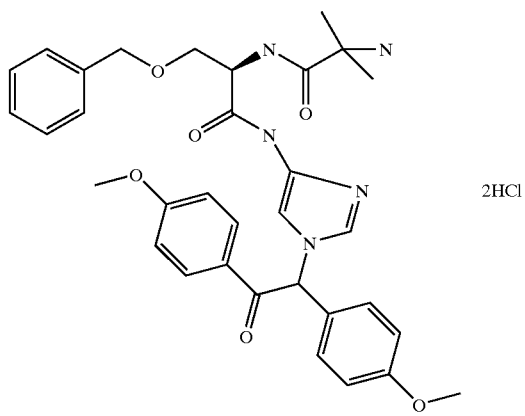

2HCl

Reaction of the product of Preparation 305 (1.85 g, 2.6 mmol), trifluoroacetic acid (10 mL), dichloromethane (24 mL), as in described in Example 161, gave 1.56 g (88%) of the desired product as a product as the hydrochloric acid salt. $^1$H-NMR is consistent with structure; MS (ion spray) 599.2 (M+1); Anal. Calc'd for $C_{33}H_{37}N_5O_6 \cdot 2HCl$: C, 58.93; H, 5.84; N, 10.41. Found: C, 59.05; H, 5.87; N, 10.43. Resolution of the diastereomers (0.21 g, 0.38 mmol) by chiral HPLC gave the respective isomers which were individually treated with a saturated solution of hydrochloric acid in diethyl ether to give the desired products:

Examples 162

Isomer 1

0.104 g (40%); $^1$H-NMR is consistent with structure; $t_R$=9.45 min; MS (ion spray) 600.3 (M+1); Anal. Calc'd for $C_{33}H_{37}N_5O_6 \cdot 2HCl$: C, 58.93; H, 5.84; N, 10.41. Found: C, 58.66; H, 5.80; N, 10.20.

Example 163

Isomer 2

0.066 g (25%); $^1$H-NMR is consistent with structure; $t_R$=12.93 min; MS (ion spray) 600.3 (M+1); Anal. Calc'd for $C_{33}H_{37}N_5O_6 \cdot 2.3HCl$: C, 57.99; H, 5.80; N, 10.25. Found: C, 57.94; H, 5.80; N, 10.12.

Preparation 306

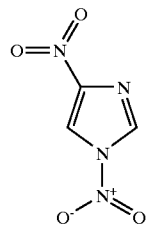

To a slurry of 4-nitroimidazole, 10.0 g (89 mmol) in 30 mL of glacial acetic acid was slowly added 10 mL of fuming nitric acid. To this mixture was added 20 mL of acetic anhydride at a rate such that the temperature remained below 50° C. The reaction mixture was stirred for one hour then poured into 300 g of ice/water. A white solid precipitated out over a period of 30 min. The solid was filtered and dried to yield 6.8 g of the desired product. The filtrate was extracted with dichloromethane. The combined organic extracts were washed with saturated sodium bicarbonate and water, then dried over sodium sulfate, filtered and concentrated to yield an additional 5.1 g of the desired white solid, affording a total of 11.9 g (85%) of the desired product. $^1$H-NMR is consistent with structure; MS (FD) 159 (M+); Anal. Calc'd for $C_3H_2N_4O_4 \cdot 0.3H_2O$: C, 22.04; H, 1.60; N, 34.27. Found: C, 22.35; H, 1.52; N, 33.87.

Preparation 307

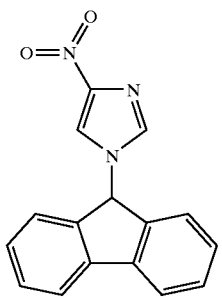

To a slurry of 9-aminofluorene hydrochloride, 2.1 g (10.0 mmol) in 20 mL of methanol and 20 mL of water at 0° C. was added 0.8 g (10.0 mmol) of sodium bicarbonate. After stirring for 10 min at 0° C., 1.5 g (10.0 mmol) of the product of Preparation 306 was added. The reaction mixture was stirred overnight, slowly warming to ambient temperature, then concentrated. The residue was partitioned between ethyl acetate and water and extracted with ethyl acetate. The combined organic extracts were washed with brine, dried over sodium sulfate and concentrated. The residue was absorbed onto a silica pad and chromatographed on silica gel using a gradient of 25–80% ethyl acetate/hexanes as eluant to yield 2.39 g (88%) of the desired product as a tan solid: $^1$H-NMR is consistent with structure; MS (ion spray) 276.2 (M+1); Anal. Calc'd for $C_{14}H_{11}N_3O_2$: C, 69.31; H, 4.00; N, 15.15. Found: C, 69.53; H, 4.08; N, 14.93.

Preparation 308

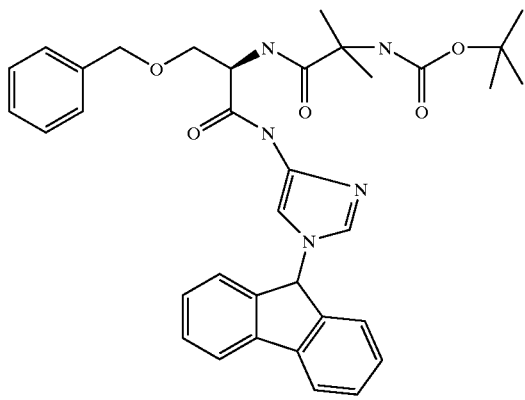

To a slurry of 0.95 g of 10% palladium on carbon in 30 mL of tetrahydrofuran was added a solution of 1.1 g (4.0 mmol) of the product of Preparation 307 in 30 mL of tetrahydrofuran. The mixture was hydrogenated at 40 psi of hydrogen for 1 h and filtered through celite. To this solution was added 1.5 g (4.0 mmol) of the product of Preparation 1d, 0.6 g (4.4 mmol) of 1-hydroxybenzotriazole and 0.9 g (4.4 mmol) of dicyclohexylcarbodiimide. The reaction was stirred overnight at ambient temperature, filtered and concentrated. The residue was slurried in ethyl acetate, filtered and water was added. The mixture was extracted with ethyl acetate. The combined organic extracts were washed with brine, dried over sodium sulfate, filtered and concentrated. The resulting residue was chromatographed on silica gel using 5% methanol/chloroform as eluant to yield 1.16 g (49%) of the desired product. $^1$H-NMR is consistent with structure; MS (ion spray) 610 (M+1); Anal. Calc'd for $C_{35}H_{39}N_5O_5$: C, 68.95; H, 6.59; N, 11.49. Found: C, 68.83; H, 6.46; N, 11.27.

Example 164

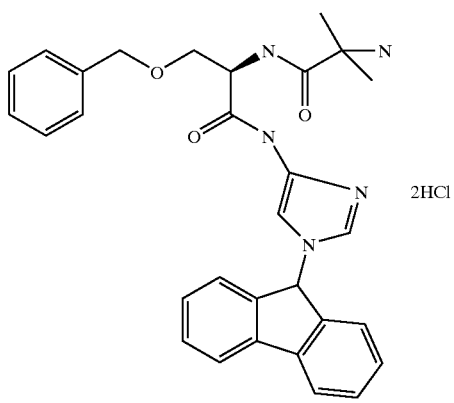

To a solution of the product of Preparation 308, 1.1 g (1.8 mmol) in 6 mL of dichloromethane was added 2 mL of trifluoroacetic acid. The reaction mixture was stirred for 3 h, then poured into a solution of saturated sodium carbonate. The mixture was extracted with chloroform. The combined organic extracts were washed with brine, dried over sodium sulfate, filtered and concentrated. The residue was dissolved in ethyl acetate and ether/hydrochloric acid was added. The mixture was concentrated to yield 0.9 g (90%) of the desired product as a pink solid: $^1$H-NMR is consistent with structure; MS (ion spray) 510.4 (M+1); Anal. Calc'd for $C_{30}H_{31}N_5O_3 \cdot 2HCl$: C, 61.86; H, 5.71; N, 12.02. Found: C, 61.70 H, 5.79; N, 11.86.

Preparation 309

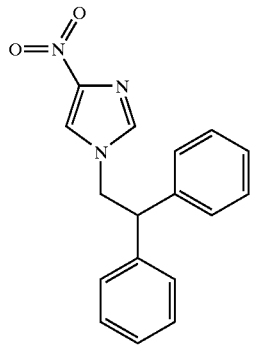

Reaction of 2,2-diphenylethylamine (2.5 g, 12.7 mmol), sodium bicarbonate (1.07 g, 12.7 mmol), the product of Preparation 306 (2.0 g, 12.7 mmol), methanol (20 mL), water (10 mL), as described in Preparation 307 gave 2.75 g (74%) of the desired product as a tan solid: $^1$H-NMR is consistent with structure; MS (ion spray) 294.2 (M+1).

Preparation 310

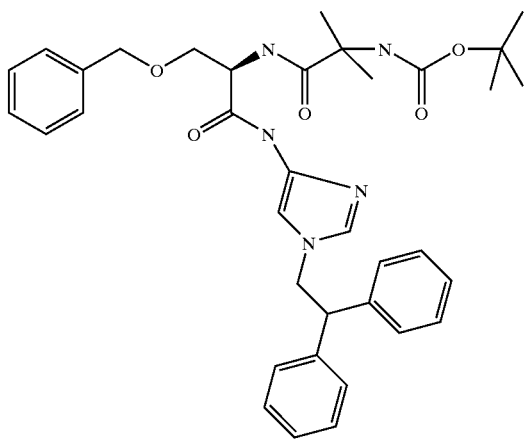

Reaction of the product of Preparation 309 (1.0 g, 3.4 mmol), 10% palladium on carbon (1.2 g), tetrahydrofuran (40 mL), the product of Preparation 1d (1.3 g, 3.4 mmol), 1-hydroxybenzotriazole (0.51 g, 3.74 mmol), dicyclohexylcarbodiimide (0.8 g, 3.74 mmol), as in Example Preparation 308. 1.42 g (67%) of the desired product as a tan foam: $^1$H-NMR is consistent with structure; MS (ion spray) 626.3 (M+1); Anal. Calc'd for $C_{36}H_{43}N_5O_5$: C, 69.10; H, 6.93; N, 11.19. Found: C, 68.92; H, 6.70; N, 11.21.

Example 165

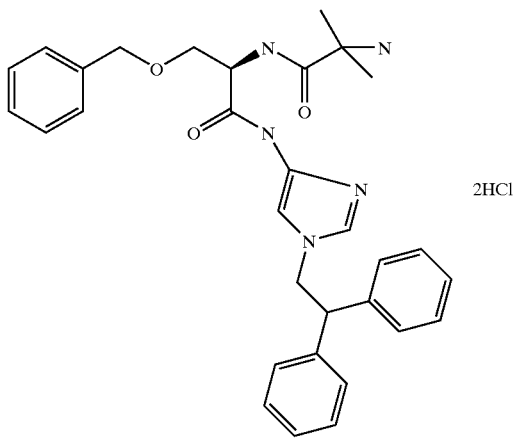

2HCl

Reaction of the product of Preparation 310 (1.37 g, 2.2 mmol), trifluoroacetic acid (4 mL), dichloromethane (12 mL), as described in Example 164–426737 gave 1.14 g (87%) of the desired product as a tan solid: $^{1}$H-NMR is consistent with structure; MS (ion spray) 526 (M+1); Anal. Calc'd for $C_{31}H_{35}N_5O_3 \cdot 2.2HCl$: C, 61.46; H, 6.19; N, 11.56. Found: C, 61.72; H, 5.95; N, 11.11.

Preparation 311

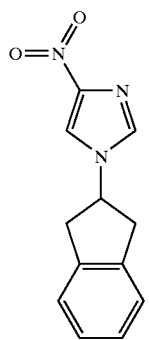

To a slurry of 2-aminoindan hydrochloride, 2.0 g (12.7 mmol) in 20 mL of methanol and 10 mL of water at 0° C. was added 1.4 g (16.4 mmol) of sodium bicarbonate. After stirring for 10 min at 0° C., 2.0 g (12.7 mmol) of the product of Preparation 306 was added. The reaction mixture was stirred overnight, slowly warming to ambient temperature, then concentrated. The residue was partitioned between ethyl acetate and water and extracted with ethyl acetate. The combined organic extracts were washed with brine, dried over sodium sulfate and concentrated. The residue was absorbed onto a silica pad and chromatographed on silica gel using a gradient of 50–80% ethyl acetate/hexanes as eluant to yield 1.91 g (66%) of the desired product as a tan solid: $^{1}$H-NMR is consistent with structure, MS (ion spray) 230.2 (M+1); Anal. Calc'd for $C_{12}H_{11}N_3O_2$: C, 62.88; H, 4.84; N, 18.33. Found: C, 63.28; H, 4.90; N, 17.89.

Preparation 312

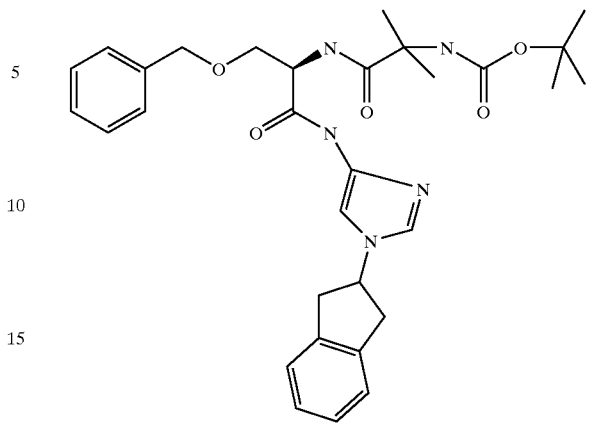

To a slurry of 1.3 g of 10% palladium on carbon in 30 mL of tetrahydrofuran was added a solution of 1.2 g (5.3 mmol) of the product of Preparation 311 in 30 mL of tetrahydrofuran. The mixture was hydrogenated at 40 psi of hydrogen for 40 min and filtered through celite. To this solution was added 2.0 g (5.3 mmol) of the product of Preparation 1d, 0.8 g (5.8 mmol) of 1-hydroxybenzotriazole and 1.2 g (5.8 mmol) of dicyclohexylcarbodiimide. The reaction was stirred overnight at ambient temperature, filtered and concentrated. The residue was slurried in ethyl acetate, filtered and water was added. The mixture was extracted with ethyl acetate. The combined organic extracts were washed with brine, dried over sodium sulfate, filtered and concentrated. The resulting residue was chromatographed on silica gel using 3% methanol/chloroform as eluant to yield 1.38 g (486) of the desired product: $^{1}$H-NMR is consistent with structure; MS (ion spray) 562.4 (M+1); Anal. Calc'd for $C_{32}H_{39}N_5O_3 \cdot 0.1CHCl3$: C, 65.12; H, 6.87; N, 12.21. Found: C, 65.39; H, 7.18; N, 11.97.

Example 166

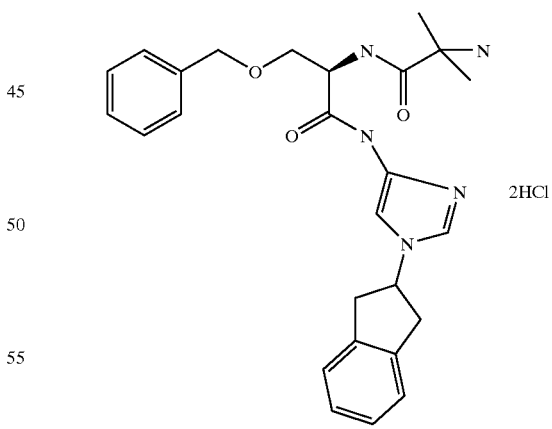

2HCl

To a solution of the product of Preparation 312, 1.4 g (2.5 mmol) in 12 mL of dichloromethane was added 4 mL of trifluoroacetic acid. The reaction mixture was stirred for 2 h, then concentrated. The residue was partitioned between ethyl acetate and saturated sodium carbonate and was extracted with ethyl acetate. The combined organic extracts were washed with brine, dried over sodium sulfate, filtered and concentrated. The residue was dissolved in ethyl acetate and ether hydrochloric acid was added. The mixture was concentrated to yield 1.2 g (90%) of the desired product as a yellow solid: ¹H-NMR is consistent with structure; MS (ion spray) 462.4 (M+1); Anal. Calc'd for C$_{26}$H$_{31}$N$_5$O$_3$.2HCl: C, 57.99; H, 6.93; N, 12.01. Found: C, 57.87; H, 6.82; N, 12.73.

Preparation 313

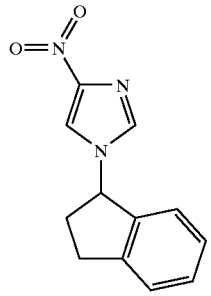

To a slurry of 1-aminoindan, 1.25 mL (10.0 mmol) in 20 mL of methanol and 20 mL of water at 0° C., was added 1.5 g (10.0 mmol) of the product of Preparation 306. The reaction mixture was stirred overnight, slowly warming to ambient temperature and concentrated. The residue was partitioned between ethyl acetate and water and extracted with ethyl acetate. The combined organic extracts were washed with brine, dried over sodium sulfate, filtered and concentrated. The residue was absorbed onto a silica pad and chromatographed on silica gel using 30–80% ethyl acetate/hexanes as eluant to yield 1.13 g (49%) of the desired product as a tan oil: ¹H-NMR is consistent with structure; MS (ion spray) 230.2 (M+1).

Preparation 314

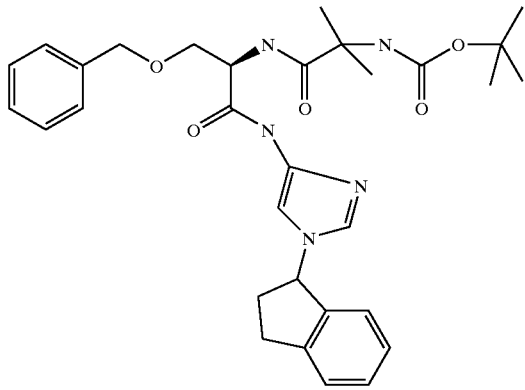

To a slurry of 1.0 g of 10% palladium on carbon in 20 mL of tetrahydrofuran was added a solution of 1.07 g (4.7 mmol) of the product of Preparation 313 in 20 mL of tetrahydrofuran. The mixture was hydrogenated at 40 psi of hydrogen, for 30 min and filtered through celite. To this solution was added 1.8 g (4.7 mmol) of the product of Preparation 1d, 0.7 g (5.2 mmol) of 1-hydroxybenzotriazole and 1.06 g (5.2 mmol) of dicyclohexylcarbodiimide. The reaction was stirred overnight at ambient temperature, filtered and concentrated. The residue was dissolved in ethyl acetate, filtered, then water was added. The mixture was extracted with ethyl acetate. The combined organic extracts were washed with brine, dried over sodium sulfate, filtered and concentrated. The resulting residue was chromatographed on silica gel using 3% methanol/chloroform as eluant to yield 0.99 g (38%) of the desired product: ¹H-NMR is consistent with structure; MS (ion spray) 562 (M+1); Anal. Calc'd for C$_{31}$H$_{39}$N$_5$O$_5$: C, 66.29; H, 7.00; N, 12.47. Found: C, 66.05; H, 7.12; N, 12.58.

Example 167

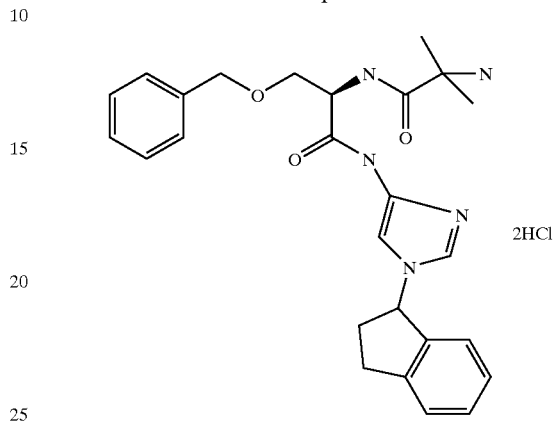

To a solution of the product of Preparation 314, 0.97 g (1.7 mmol) in 6 mL of dichloromethane was added 2 mL of trifluoroacetic acid. The reaction mixture was stirred for 2 h, then poured into a solution of saturated sodium carbonate. The mixture was extracted with chloroform. The combined organic extracts were washed with brine, dried over sodium sulfate, filtered and concentrated. The residue was dissolved in ethyl acetate and a saturated solution of hydrochloric acid in diethyl ether was added. The resulting mixture was concentrated to yield 0.73 g (76%) of the desired mixture of isomers as a white solid: ¹H-NMR is consistent with structure; MS (ion spray) 462.4 (M+1); Anal. Calc'd for C$_{26}$H$_{31}$N$_5$O$_3$.2.3HCl: C, 57.26; H, 6.15; N, 12.84. Found: C, 57.53; H, 6.04; N, 12.57.

Preparation 315

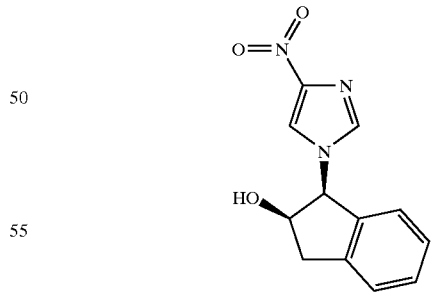

Reaction of (1S,2R)-(−)-cis-1-Amino-2-indanol (0.9 g, 6.3 mmol), sodium bicarbonate (0.53 g, 6.3 mmol), the product of Preparation 306, (1.0 g, 6.3 mmol) in methanol (10 mL) and water (5 mL), as described in Preparation 311 gave 1.02 g (66%) of the desired product as a tan foam: ¹H-NMR is consistent with structure; MS (ion spray) 246.3 (M+1).

Preparation 316

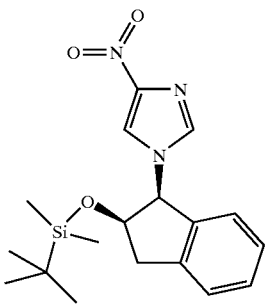

To a solution of the product of Preparation 315, 2.33 g (9.5 mmol) and imidazole, 2.0 g (36.9 mmol) in 100 mL of dimethylformamide was added 1.86 g (12.3 mmol) of t-butyldimethylsilyl chloride. The reaction mixture was stirred overnight at ambient temperature then concentrated. The residue was partitioned between ethyl acetate and water and was extracted with ethyl acetate. The combined organic extracts were washed with brine, dried over sodium sulfate, filtered and concentrated. The residue was chromatographed over silica gel using 50% ethyl acetate/hexanes as eluent to yield 3.07 g (90%) of the desired product as a tan oil: 1H-NMR is consistent with structure; MS (ion spray) 360.2 (M+1); Anal. Calc'd for $C_{18}H_{25}N_3O_3Si$: C, 60.14; H, 7.01; N, 11.69. Found: C, 60.37; H, 6.92; N, 11.43.

Preparation 317

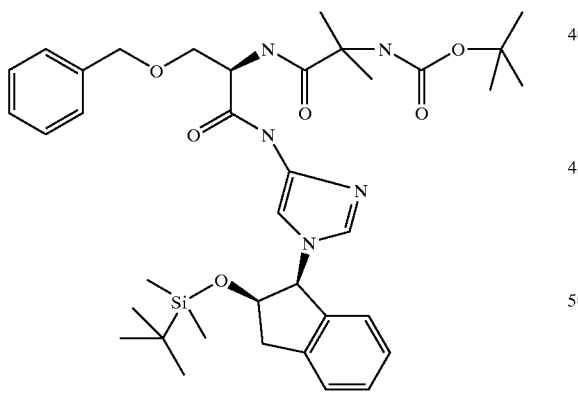

Reaction of the product of Preparation 316 (1.5 g, 4.2 mmol), 10% palladium on carbon (1.0 g), tetrahydrofuran (80 mL), the product of Preparation 1d, (1.6 g, 4.2 mmol), 1-hydroxybenzotriazole (0.63 g, 4.6 mmol), dicyclohexylcarbodiimide (0.95 g, 4.6 mmol), as described in Preparation 314 gave 0.72 g (25%) of the desired product as a reddish foam: 1H-NMR is consistent with structure; MS (ion spray) 692.1 (M+1); Anal. Calc'd for $C_{37}H_{53}N_5O_6Si$: C, 64.34; H, 7.72; N, 10.12. Found: C, 64.14; H, 7.65; N, 10.05.

Example 168

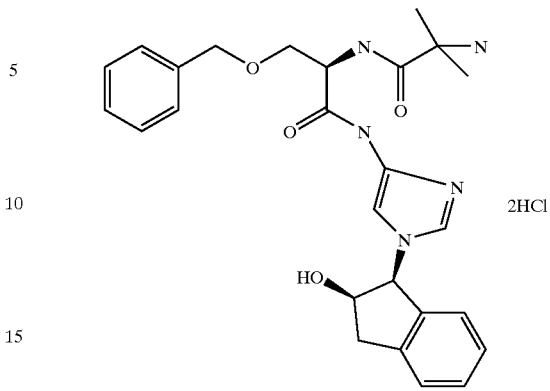

A solution of the product of Preparation 317, 0.65 g (0.94 mmol) in 10 mL of a saturation solution of hydrochloric acid in acetic acid was stirred at ambient temperature. After 1.5 h, the solution was concentrated. The residue was partitioned between ethyl acetate and saturated sodium bicarbonate and was extracted with ethyl acetate. The combined organic extracts were washed with brine, dried over sodium sulfate and concentrated. The residue was chromatographed on silica gel using a gradient of 5–10% methanol/chloroform/ammonia as eluant to yield the desired product as the free base. The resulting foam was dissolved in ethyl acetate and a saturated solution of hydrochloric acid in diethyl ether was added. The resulting slurry was concentrated to yield 0.18 g (35%) of the desired product as a white solid: 1H-NMR is consistent with structure; MS (ion spray) 478.3 (M+1): Anal. Calc'd for $C_{26}H_{31}N_5O_4 \cdot 2.5HCl$: C, 47.85; H, 5.53; N, 10.73. Found: C, 48.08; H, 5.17; N, 10.40.

Preparation 318

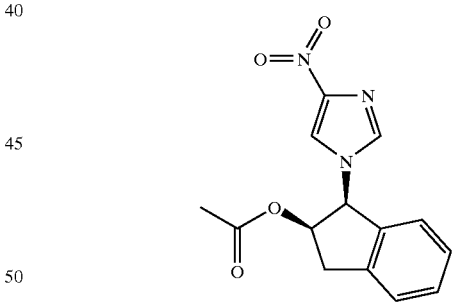

To a solution of the product of Preparation 315, 1.71 g. (7.0 mmol) and triethylamine, 2.2 mL (15.6 mmol) in 80 mL of dichloromethane at 0° C. was added 0.9 mL (12.6 mL) of acetyl chloride. The reaction mixture was stirred 2.5 h at 0° C., then was quenched with saturated sodium bicarbonate. The mixture was extracted with ethyl acetate. The combined organic extracts were washed with brine, dried over sodium sulfate, filtered and concentrated. The residue was absorbed onto a silica pad and chromatographed on silica gel using a gradient of 30–80% ethyl acetate/hexanes as eluant to yield 1.06 g (53%) of the desired product as a yellow oil: 1H-NMR is consistent with structure; MS (ion spray) 288.0 (M+1); Anal. Calc'd for $C_{14}H_{13}O_4$: C, 58.53; H, 4.56; N, 14.63. Found: C, 58.78; H, 4.58; N, 14.36.

Preparation 319

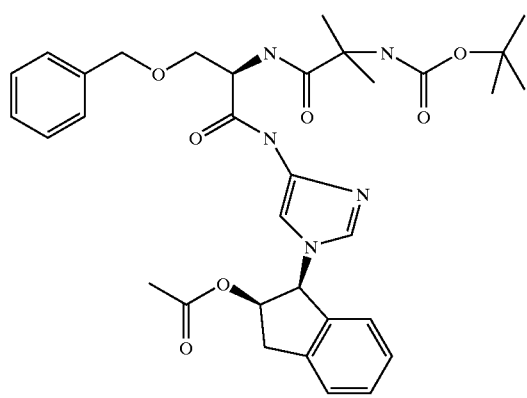

Reaction of the product of Preparation 318 (1.0 g, 3.5 mmol), 10% palladium on carbon (2.0 g), tetrahydrofuran (60 mL), the product of Preparation 1d, (1.33 g, 3.5 mmol), 1-hydroxybenzotriazole (0.52 g, 3.9 mmol), dicyclohexylcarbodiimide (0.8 g, 3.9 mmol), described in Preparation 314 gave 0.53 g (25%) of the desired product as a tan foam: $^1$H-NMR is consistent with structure; MS (ion spray) 620.4 (M+1); Anal. Calc'd for $C_{33}H_{41}N_5O_7 \cdot 0.15CHCl_3$: C, 62.44; H, 6.50; N, 10.98. Found: C, 62.42; H, 6.51; N, 11.16.

Example 169

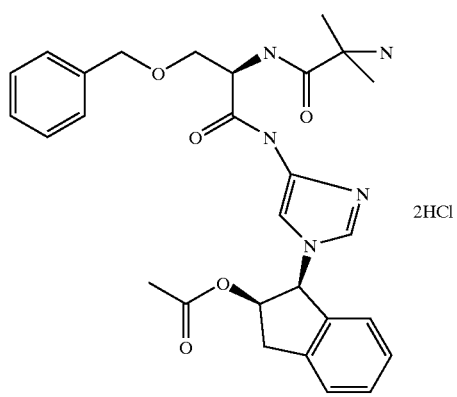

A solution of the product of Preparation 319, 0.43 g (0.7 mmol) in 8 mL of a saturated solution of hydrochloric acid in glacial acetic acid was stirred for 1.5 h at ambient temperature then concentrated. The residue was dissolved in toluene and concentrated to yield 0.26 g (61%) of the desired product as a tan solid: $^1$H-NMR is consistent with structure; MS (ion spray) 520.3 (M+1); Anal. Calc'd for $C_{29}H_{33}N_5O_5 \cdot 2HCl$: C, 56.76; H, 5.95; N, 11.82. Found: C, 56.87; H, 6.07; N, 11.52.

Preparation 320

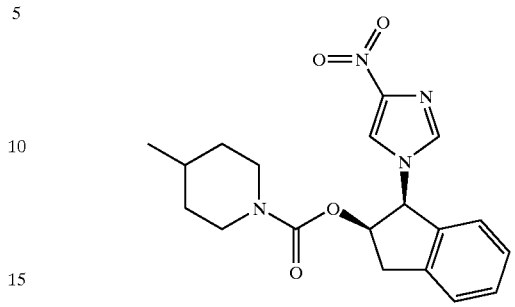

To a solution of the product of Preparation 315, 1.36 g (5.6 mmol) in 50 mL of dichloromethane was added 1.09 g (6.72 mmol) of 1,1'-carbonyldiimidazole. The reaction mixture was stirred overnight at ambient temperature then 3.3 mL (28 mmol) of 4-methylpiperidine was added. The reaction mixture was stirred overnight, washed with a 0.1N aqueous solution of hydrochloric acid, brine, dried over sodium sulfate, filtered and concentrated. The residue was chromatographed on silica gel using a gradient of chloroform to 1% methanol/chloroform as eluant to yield 1.4 g (67%) of the desired product as a tan foam: $^1$H-NMR is consistent with structure; MS (ion spray) 371.1 (M+1); Anal. Calc'd for $C_{19}H_{22}N_4O_4$: C, 61.61; H, 5.99; N, 15.13. Found: C, 61.95; H, 6.01; N, 14.95.

Preparation 321

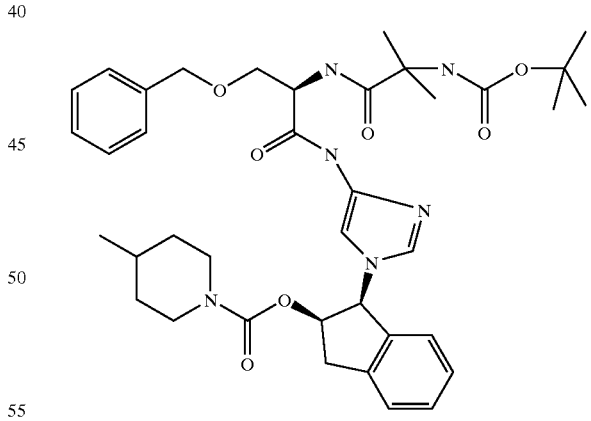

Reaction of the product of Preparation 320 (0.87 g, 2.3 mmol), 10% palladium on carbon (2.0 g), tetrahydrofuran (80 mL), the product of Preparation 1d, (0.9 g, 2.3 mmol), 1-hydroxybenzotriazole (0.35 g, 2.53 mmol), dicyclohexylcarbodiimide (0.52 g, 2.53 mmol), as described in Preparation 314, gave 0.23 g (14%) of the desired product as a tan foam: $^1$H-NMR is consistent with structure; MS (ion spray) 703.6 (M+1); Anal. Calc'd for $C_{38}H_{50}N_6O_7 \cdot 0.15CHCl_3$: C, 63.57; H, 7.01; N, 11.66. Found: C, 63.60; H, 7.32; N, 11.31.

Example 170

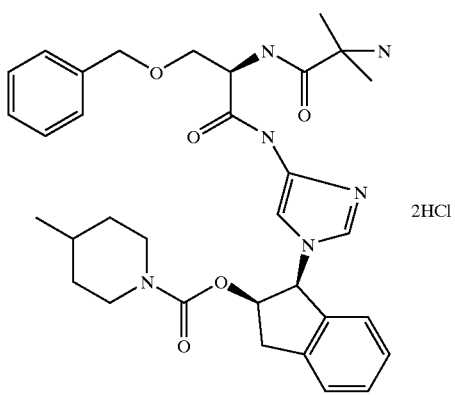

2HCl

To a solution of the product of Preparation 321, 0.21 g (0.3 mmol) in 6 mL of dichloromethane was added 2 mL of trifluoroacetic acid. The mixture was stirred 40 min at ambient temperature then concentrated. The resulting residue was partitioned between ethyl acetate and saturated sodium bicarbonate and extracted with ethyl acetate. The combined organic extracts were washed with brine, dried over sodium sulfate, filtered and concentrated. The crude product was chromatographed on silica gel using 10% methanol/chloroform as eluant. To a solution of the product in chloroform was added a saturates solution of hydrochloric acid in diethyl ether. The slurry was concentrated to yield the desired product as a white solid: $^1$H-NMR is consistent with structure; MS (ion spray) 603.4 (M+1); Anal. Calc'd for $C_{33}H_{42}N_6O_3 \cdot 2.3HCl$: C, 57.73; H, 6.50; N, 12.24. Found: C, 57.80; H, 6.34; N, 12.15.

Preparation 322

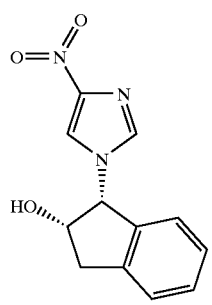

Reaction of (1R,2S)-(+)-1-amino-2-indanol (3.8 g, 26.0 mmol), sodium bicarbonate (2.2 g, 26.0 mmol), the product of Preparation 306. (4.0 g, 26.0 mmol), methanol (28 mL), water (12 mL), as in Preparation 313 gave 4.0 g (63%) of the desired product as a tan foam: $^1$H-NMR is consistent with structure; MS (ion spray) 246.3 (M+1): Anal. Calc'd for $C_{12}H_{11}N_3O_3$: C, 58.77; H, 4.52; N, 17.13. Found: C, 58.68; H, 4.48; H, 17.00.

Preparation 323

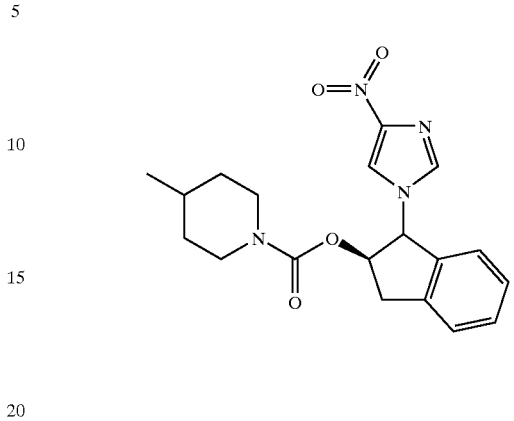

Reaction of the product of Preparation 322 (2.2 g, 9.0 mmol), 1,1'-carbonyldiimidazole (1.73 g, 10.8 mmol), 4-methylpiperidine (5.3 mL, 45.0 mmol), dichloromethane (80 mL), as described in Preparation 320, gave 2.3 g (70%) of the desired product as an orange foam: $^1$H-NMR is consistent with structure; MS (ion spray) 371.1 (M+1); Anal. Calc'd for $C_{19}H_{22}N_4O_4 \cdot 0.15CHCl_3$: C, 59.23; H, 5.75; N, 14.43. Found: C, 59.38; H, 5.87; N, 14.55.

Preparation 324

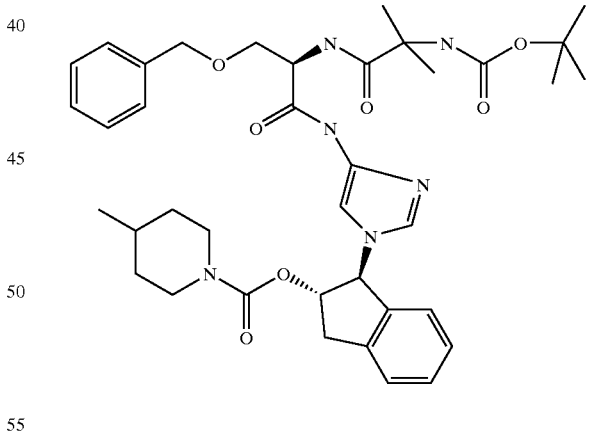

Reaction of the product of Preparation 323 (2.22 g, 6.0 mmol), 10% palladium on carbon (3.0 g), tetrahydrofuran (60 mL), the product of Preparation 1d, (2.3 g, 6.0 mmol), 1-hydroxybenzotriazole (0.9 g, 6.6 mmol), dicyclohexylcarbodiimide (1.4 g, 6.6 mmol), as described in Preparation 314 gave 1.0 g (24%) of the desired product as a tan foam: $^1$H-NMR is consistent with structure; MS (ion spray) 703.6 (M+1); Anal. Calc'd for $C_{38}H_{50}N_6O_7$: C, 64.94; H, 7.17; N, 11.96. Found: C, 64.81; H, 7.09; N, 11.83.

Example 171

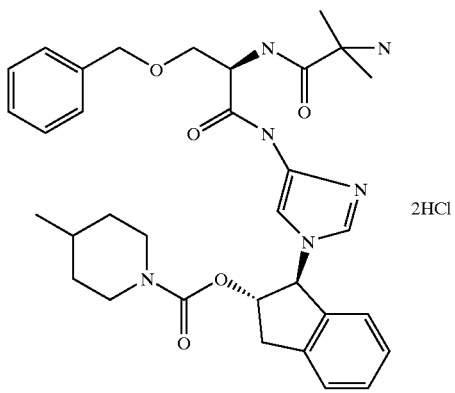

2HCl

Reaction of the product of Preparation 324 (0.97 g, 1.4 mmol), trifluoroacetic acid (4 mL), dichloromethane (12 mL), as in described in Example 170 gave 0.95 g (100%) of the desired product as a white solid: $^1$H-NMR is consistent with structure; MS (ion spray) 603.3 (M+1); Anal. Calc'd for $C_{33}H_{42}N_6O_5 \cdot 2.3HCl$: C, 57.73; H, 6.50; N, 12.24. Found: C, 57.46; H, 6.53; N, 11.90

Preparation 325

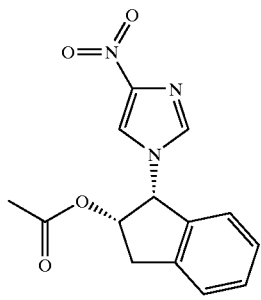

Prepared as shown in Preparation 1 in Examples Part 4. $^1$H-NMR consistent with structure.

Preparation 326

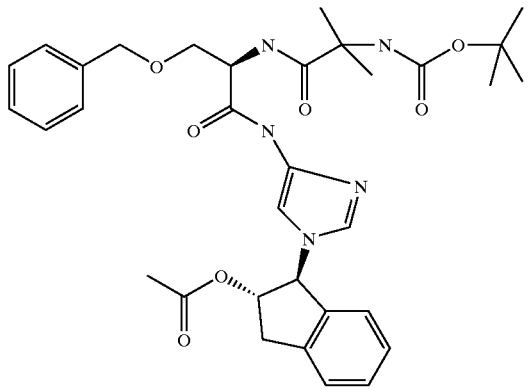

Reaction of the product of Preparation 4 from Examples Part 4 (0.4 g, 1.4 mmol), 10% palladium on carbon (0.8 g), tetrahydrofuran (40 mL), the product of Preparation 1d, (0.53 g, 1.4 mmol), 1-hydroxybenzotriazole (0.21 g, 1.54 mmol), dicyclohexylcarbodiimide (0.32 g, 1.54 mmol), as described in Preparation 314 gave 0.25 g (29%) of the desired product as a tan foam: $^1$H-NMR is consistent with structure; MS (ion spray) 620.7 (M+1); Anal. Calc'd for $C_{33}H_{41}N_5O_7$: C, 63.96; H, 6.67; N, 11.30. Found: C, 63.91; H, 6.72; N, 11.04.

Example 172

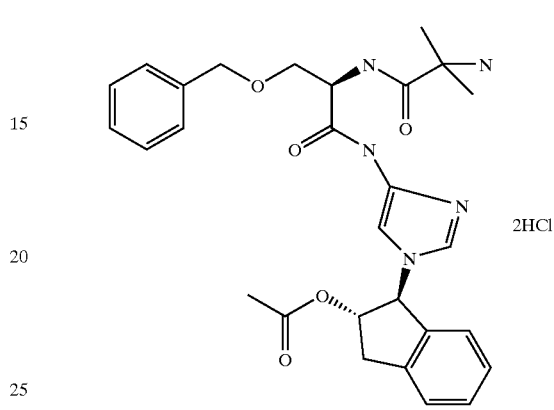

2HCl

A solution of the product Preparation 326, 0.22 g (0.35 mmol) in 10 mL of a saturated solution of hydrochloric acid in glacial acetic acid was stirred for 2 h at ambient temperature and then concentrated. The residue was dissolved in toluene and concentrated, then triturated with hexanes to yield 0.187 g (89%) of the desired product as a tan solid: $^1$H-NMR is consistent with structure; MS (ion spray) 520.3 (M+1); Anal. Calc'd for $C_{29}H_{33}N_5O_5 \cdot 2HCl$: C, 56.76; H, 5.95; N, 11.82. Found: C, 56.96; H, 6.06; N, 11.83.

Preparation 327

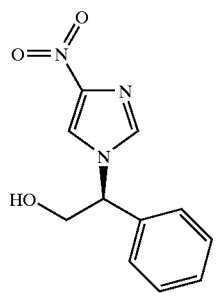

To a solution of R-(−)-2-phenylglycinol, 2.75 g (20 mmol) in 20 mL of methanol and 10 mL of water at 0° C., was added 1.7 g (20 mmol) of sodium bicarbonate. The reaction mixture was stirred for 20 min at 0° C., then 3.16 g (20 mmol) of the product of Preparation 306 was added. The residue was absorbed onto silica and chromatographed on silica gel using 80% ethyl acetate/hexanes as eluant to yield 3.5 g (74%) of the desired product as a colorless oil: $^1$H-NMR is consistent with structure; MS (ion-spray) 234 (M+1).

Preparation 328

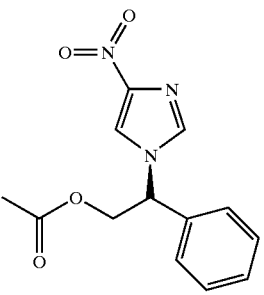

To a solution of the product of Preparation 327, 3.08 g (13.0 mmol), triethylamine, 2.4 mL (16.9 mmol) and 4-dimethylaminopyridine, 0.3 g (2.6 mmol) in 150 mL of dichloromethane at 0° C. was added 1.5 mL (15.6 mmol) of acetic anhydride dropwise. The reaction mixture was stirred overnight slowly warming to ambient temperature, then concentrated. The residue was partitioned between ethyl acetate and saturated sodium bicarbonate and extracted with ethyl acetate. The combined organic extracts were washed with brine, dried over sodium sulfate and concentrated. The residue was chromatographed on silica gel using 80% ethyl acetate/hexanes as eluant to yield 3.4 g (95%) of the desired product as a tan oil: $^1$H-NMR is consistent with structure; MS (ion spray) 276.2 (95%); Anal. Calc'd for $C_{13}H_{13}N_3O_4$: C, 56.73; H, 4.76; N, 15.27. Found: C, 56.46; H, 4.89; N, 15.17.

Preparation 329

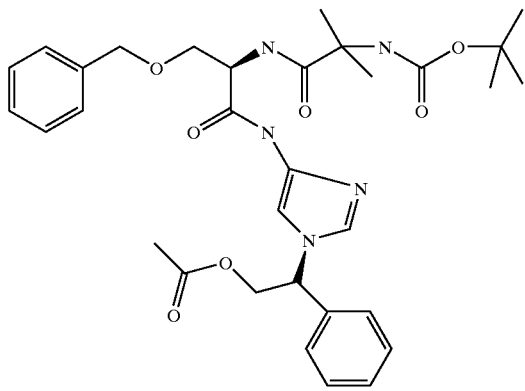

To a slurry of 4.0 g of 10% palladium on carbon in 60 mL of tetrahydrofuran was added a solution of 3.1 g (11.3 mmol) of the product of Preparation 328 in 60 mL of tetrahydrofuran. The mixture was hydrogenated at 40 psi of hydrogen for 1.5 h and filtered through celite. To this solution was added 4.3 g (11.3 mmol) of the product of Preparation 1d, 1.7 g (12.4 mmol) of 1-hydroxybenzotriazole and 2.6 g (12.4 mmol) of dicyclohexylcarbodiimide. The reaction was stirred overnight at ambient temperature, filtered and concentrated. The reaction mixture was stirred overnight, slowly warming to ambient temperature, then was concentrated. The residue was dissolved in ethyl acetate, filtered, then water was added. The mixture was extracted with ethyl acetate. The combined organic extracts were washed with brine, dried over sodium sulfate, filtered and concentrated. The resulting residue was chromatographed on silica gel using 3% methanol/chloroform as eluant to yield 2.41 g (35%) of the desired product: $^1$H-NMR is consistent with structure; MS (ion spray) 608.3 (M+1); Anal. Calc'd for $C_{32}H_{41}N_5O_7$: C, 63.25; H, 6.80; N, 11.52. Found: C, 63.51; H, 6.79; N, 11.74.

Example 173

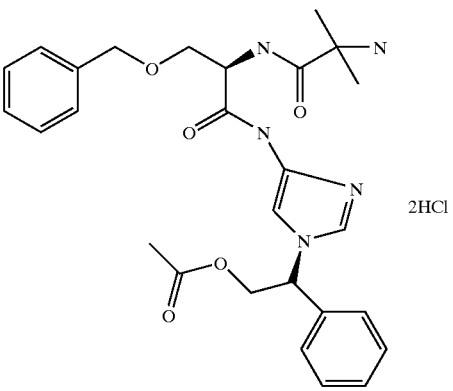

To a solution of the product of Preparation 329, 2.2 g (3.6 mmol) in 25 mL of dichloromethane was added 8 mL of trifluoroacetic acid. The reaction mixture was stirred for 1 h, then concentrated. The residue was partitioned between chloroform and saturated sodium carbonate and was extracted with chloroform. The combined organic extracts were washed with brine, dried over sodium sulfate, filtered and concentrated. The residue was dissolved in ethyl acetate and a saturated solution of hydrochloric acid in diethyl ether was added. The mixture was concentrated to yield 1.7 g (81%) of the desired isomer as a white solid: $^1$H-NMR is consistent with structure; MS (ion spray) 508.3 (M+1); Anal. Calc'd for $C_{27}H_{31}N_5O_5 \cdot 2.3HCl$: C, 55.00; H, 5.69; N, 11.89. Found: C, 55.06; H, 6.01; N, 11.41.

Preparation 330

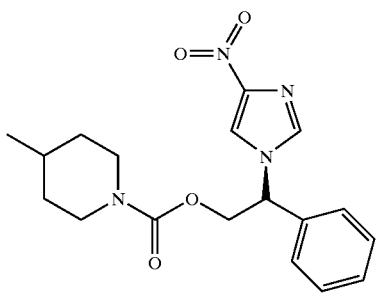

To a solution of the product of Preparation 327, 3.45 g (15.0 mmol) in 100 mL of dichloromethane was added 3.0 g (18.0 mmol) of 1,1'-carbonyldiimidazole. The reaction mixture was stirred overnight at ambient temperature then 8.9 mL (75 mmol) of 4-methylpiperidine was added. The reaction mixture was stirred overnight at ambient temperature then concentrated. The residue was partitioned between ethyl acetate and 0.1N aqueous hydrochloric acid and washed with 0.1N aqueous hydrochloric acid. The combined aqueous layers were extracted with ethyl acetate. The combined organic extracts were washed with brine, dried over sodium sulfate, filtered and concentrated. The residue was chromatographed on silica gel using 80% ethyl acetate/hexanes as eluant to yield 4.4 g (85%) of the desired product as a yellow oil: ¹H-NMR is consistent with structure; MS (ion spray) 359.2 (M+1); Anal. Calc'd for C₁₈H₂₂N₄O₄·0.3CHCl₃: C, 56.46; H, 5.789 N, 14.43. Found: C, 56.81; H, 5.981 N, 14.42.

Preparation 331

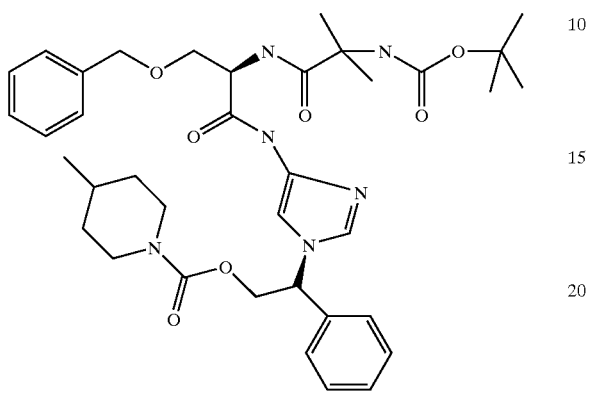

Reaction of the product of Preparation 330 (4.2 g, mmol), 10% palladium on carbon (5.2 g), tetrahydrofuran (80 mL), the product of Preparation 1d, (4.5 g, 11.7 mmol), 1-hydroxybenzotriazole (1.8 g, 12.9 mmol), dicyclohexylcarbodiimide (2.7 g, 12.9 mmol), as in described in Preparation 329 gave 2.2 g (27%) of the desired product as a tan foam: ¹H-NMR is consistent with structure; MS (ion spray) 691.3 (M+1); Anal. Calc'd for C₃₇H₅₀N₆O₇: C, 64.33; H, 7.30; N, 12.17. Found: C, 64.04; H, 7.41; N, 11.88.

Example 174

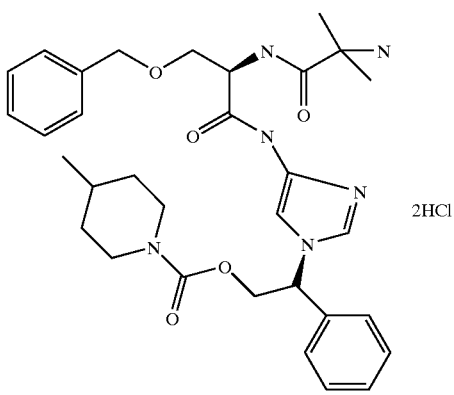

2HCl

Reaction of the product of Preparation 331 (1.95 g, 2.8 mmol), trifluoroacetic acid (8 mL), dichloromethane (25 mL), as described in Example 173 gave 1.7 g (90%) of the desired product as a white solid: ¹H-NMR is consistent with structure; MS (ion spray) 591.6 (M+1); Anal. Calc'd for C₃₂H₄₂N₆O₅·2.4HCl: C, 56.67; H, 6.60; N, 12.39. Found: C, 56.94; H, 6.63; N, 12.04.

Example 175

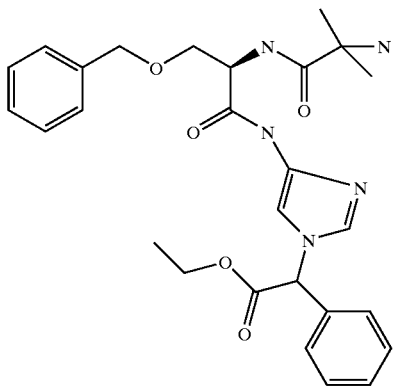

To a solution of the product of Preparation 8, Examples, Part 1, 2.5 g (4.1 mmol) in 12 mL of dichloromethane was added 4 mL of trifluoroacetic acid. The solution was stirred for 2 h and was then concentrated. The residue was partitioned between ethyl acetate and saturated sodium bicarbonate and was then extracted with ethyl acetate. The combined organic extracts were washed with brine, dried over sodium sulfate, filtered and concentrated to yield 1.88 g (90%) of the desired product as a white foam: ¹H-NMR is consistent with structure; MS (ion spray) 508.3 (M+1); Anal. Calc'd for C₂₇H₃₃N₅O₅·1H₂O: C, 61.70; H, 6.71; N, 13.32. Found: C, 61.79; H, 6.25; N, 13.07.

Example 176

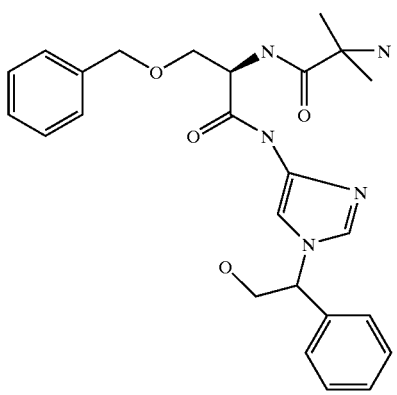

To a solution of the product of Example 175–438377, 1.66 g (3.3 mmol) in 50 mL of methanol was added 0.6 g of lithium borohydride. The reaction mixture was stirred 10 min. then concentrated. The residue was partitioned between ethyl acetate and water and was extracted with ethyl acetate. The combined organic extracts were washed with brine, dried over sodium sulfate, filtered and concentrated. The desired product was recrystallized from ethyl acetate/hexanes to yield 0.9 g (58%) of a white solid: ¹H-NMR is consistent with structure; MS (ion spray) 466.3 (M+1); Anal. Calc'd for C₂₅H₃₁N₅O₄·0.3H₂O: C, 63.76; H, 6.76; N, 14.87. Found: C, 63.87; H, 6.90; N, 14.77.

Preparation 332

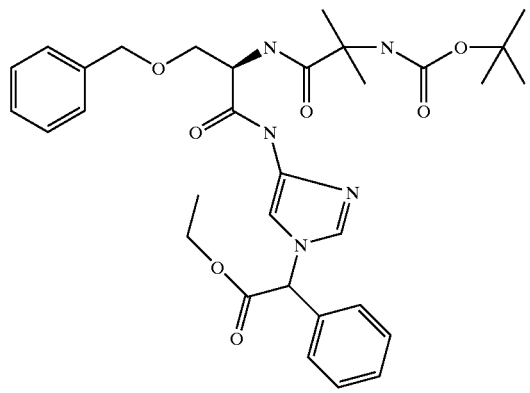

To a solution of the product of Preparation 8 from Examples Part 1, 3.0 g (5.2 mmol), N-methylmorpholine, 0.63 mL (5.7 mmol) and 4-dimethylaminopyridine, 20 mg in 30 mL of dichloromethane at 0° C. was added 0.55 mL (5.7 mmol) of ethyl chloroformate. After stirring at 0° C. for 1 h, the reaction mixture was concentrated to dryness. The residue was partitioned between ethyl acetate and 1N HCl and was extracted with ethyl acetate. The combined organics were washed with 1N HCl, brine, dried over sodium sulfate, filtered and concentrated to dryness. The crude material was chromatographed on silica gel using 3% methanol/chloroform as eluant to yield 2.7 g (85%) of the desired product as a white foam: $^1$H-NMR is consistent with structure; MS (ion spray) 608.1 (M+1); Anal. Calc'd for $C_{32}H_{41}N_5O_7$: C, 63.

Preparation 333

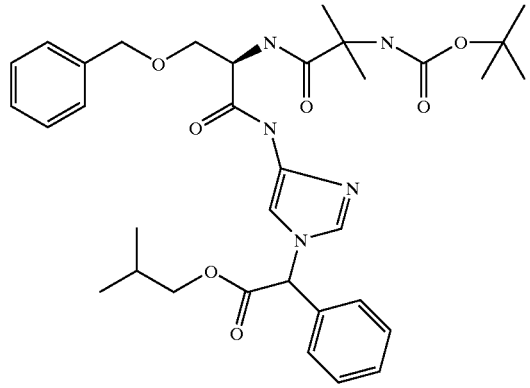

Reaction of the product of Preparation 8 (0.4 g, 0.69 mmol), N-methylmorpholine (0.08 ml, 0.69 mmol), isobutyl chloroformate (0.1 mL, 0.76 mmol) in dichloromethane (6 mL), as described in Preparation 332, gave 0.37 g (84%) of the desired product as a tan foam: $^1$H-NMR is consistent with structure; MS (FD) 635 (M+); Anal. Calc'd for $C_{34}H_{45}N_5O_7$: C, 64.23; H, 7.13; N, 11.02. Found: C, 64.15; H, 7.02; N, 10.94.

Example 177

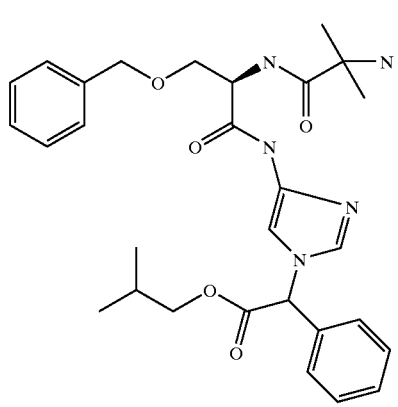

2HCl

Reaction of the product of Preparation 333 (0.31 g, 0.5 mmol), trifluoroacetic acid (2 mL), dichloromethane (6 mL), as described in Preparation 175, gave 0.25 g (83%) of the desired product as a tan solid: $^1$H-NMR is consistent with structure; MS (FD) 535 (M+).

Preparation 334

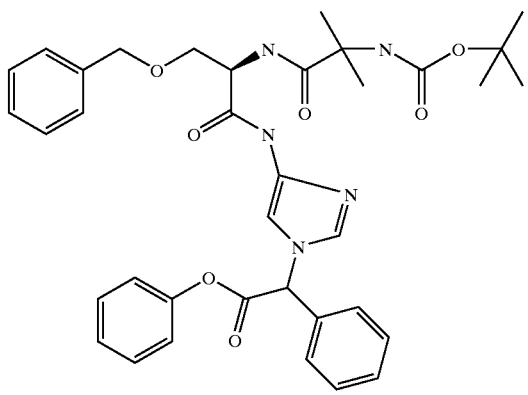

Reaction of the product of Preparation 8 from Examples Part 1 (0.6 q, 1.0 mmol), N-methylmorpholine (0.1 mL, 1.0 mmol), phenyl chloroformate (0.14 ml, 1.1 mmol), dichloromethane (6 mL), as described in Preparation 332 gave 0.4 g (61%) of the desired mixture of isomers as a tan foam: $^1$H-NMR is consistent with structure; MS (FD) 655.3 (M+); Anal. Calc'd for $C_{36}H_{41}N_5O_7$: C, 65.94; H, 6.30; N, 10.68. Found: C, 65.64; H, 6.42; N, 10.43.

Example 178

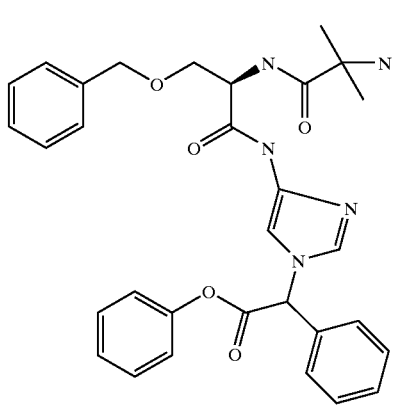

Reaction of the product of Preparation 334 (0.37 g, 0.56 mmol), trifluoroacetic acid (2 mL), dichloromethane (6 mL), as in described in Example 175 gave 0.32 g (91%) of the desired product as a white solid: $^1$H-NMR is consistent with structure; MS (FD) 555 (M+); Anal. Calc'd for $C_{31}H_{33}N_5O_5 \cdot 2HCl$: C, 59.24; H, 5.61; N, 11.14. Found: C, 59.30; H, 5.88; N, 10.97.

Example 179

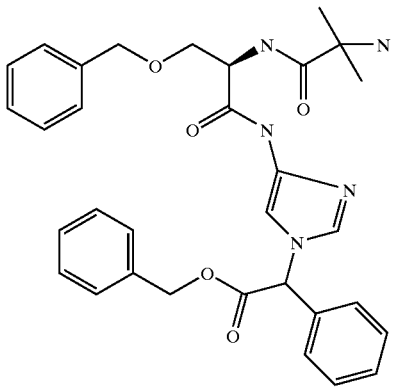

Reaction of the product of Preparation 335 (0.27 g, 0.4 mmol), trifluoroacetic acid (2 mL), dichloromethane (6 mL), as described in Preparation 175, gave 0.24 g (92%) of the desired product as a tan solid: $^1$H-NMR is consistent with structure; MS (FD) 569. (M+); Anal. Calc'd for $C_{32}H_{35}N_5O_5 \cdot 2HCl$: C, 59.81; H, 5.80; N, 10.90. Found: C, 60.05; H, 6.07; N, 10.66.

Preparation 335

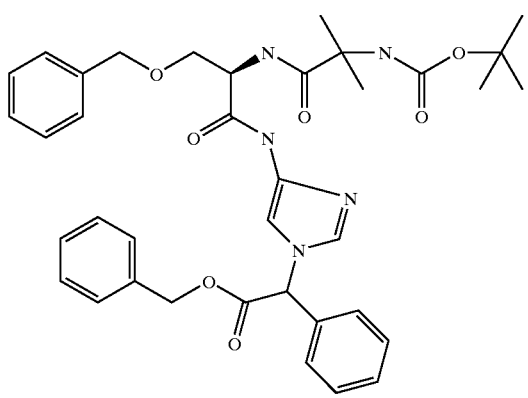

Reaction of the product of Preparation 8 from Examples Part 1 (0.4 g, 0.69 mmol), N-methylmorpholine (0.08 mL, 0.69 mmol), benzyl chloroformate (0.11 ml, 0.76 mmol), dichloromethane (6 mL), as described in Preparation 332 gave 0.32 g (70%) of the desired product as a white foam: $^1$H-NMR is consistent with structure; MS (FD) 669 (M+).

Preparation 336

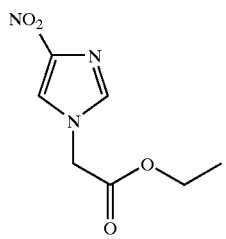

To a suspension of 60% sodium hydride in mineral oil (26.0 g, 0.6 mmol) stirring in dimethylformamide (500 mL) at −5° C. was slowly added 4-nitroimidazole (73.5 g, 0.650 mol). After 30 min, ethyl bromoacetate (100 g, 0.599 mol) was added neat over 15 minutes via addition funnel. After 24 h, the solution was concentrated, diluted with ethyl acetate washed with water. The organic extract was dried over sodium sulfate and concentrated then triturated in ether to collect 67.1 g (56%) of the desired product as pale yellow needles: $^1$H-NMR consistent with structure; MS FD+=199; Anal. Calcd. for $C_7H_9N_3O_4$: C, 42.21; H, 4.55; N, 21.20. (Found) C, 43.90; H, 4.58; N, 22.02.

Preparation 337

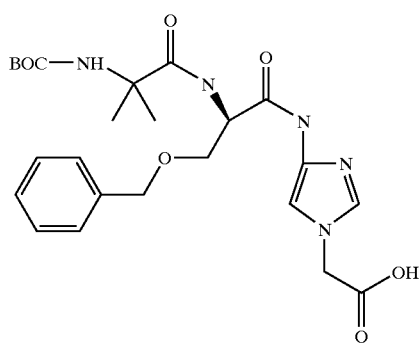

The product of Preparation 336 was reduced and coupled to give the ester which was then dissolved in methanol (400 ml) at room temp. 1 M lithium hydroxide (45.2 ml, 45.3 mmol) was added drop-wise over 10 minutes. After 20 min, the mixture was concentrated then diluted with 150 mL 10% acetic acid/ethyl acetate and concentrated and extracted with ethyl acetate. The combined organic extracts were dried over sodium sulfate, and concentrated to give 9.26 g (81%) of the desired material as a white amorphous powder: $^1$H NMR consistent with structure; MS FD+=504; Anal. Calcd. For $C_{24}H_{33}N_5O_7$: C, 57.25; H, 6.61; N, 13.91. (Found) C, 57.04; H, 6.83; N, 14.07.

Preparation 338

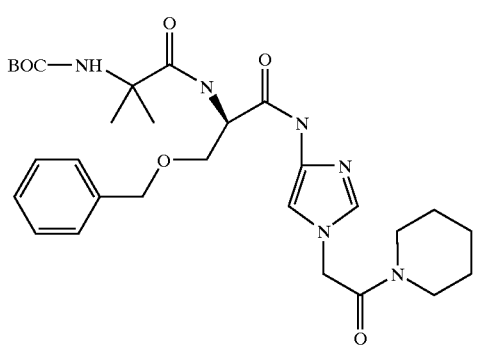

To a solution of the product of Preparation 337 (250 mgs, 0.49 mmol) and 1-hydroxybenzotriazole (67 mgs, 0.5 mmol) stirring in dry dioxane (5 mL) was added dicyclohexylcarbodiimide (107 mg, 0.521). After 15 min. piperidine (49 mg, 0.5 mmol) was added neat. After 18 h, the reaction mixture was filtered and concentrated. Purification by via radial chromatography (4 mm silica gel plate, 6% methanol/methylene chloride) gave 105 mg (36%) of a white amorphous foam: used in the next reaction without further purification.

Example 180

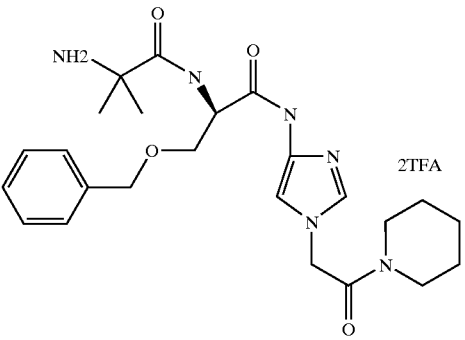

To a solution of the product of Preparation 338 (105 mg, 0.18 mmol) stirring in dichloromethane (5 mL) at room temperature was added anisole 0.2 mL) followed by trifluoroacetic acid (2 mL). After 2 h, the reaction mixture was concentrated and triturated with diethyl ether to give 86 mg (67%) of desired product as a white amorphous solid: $^1$H NMR consistent with structure; MS FD+=484; Anal. Calcd. for $C_{25}H_{36}N_6O_4 \times 2$ trifluoroacetic acid: C, 48.87; H, 5.38; N, 11.79. (Found) C, 48.71; H, 5.30; N, 11.59.

Example 181

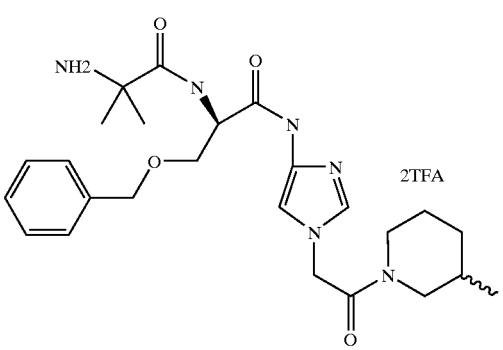

Reaction of the product of Preparation 337 (250 mg, 0.5 mmol) and 3-methyl piperidine (49 mg, 0.5 mmol) as described in Preparation 338 gave the corresponding amide which deprotected according to Example 180 to provide the desired product as a white amorphous solid: $^1$H NMR consistent with structure; MS FD+=485; Anal. Calcd. for $C_{25}H_{36}N_6O_4 \times 2$ trifluoroacetic acid: C, 48.87; H, 5.38; N, 11.79. (Found) C, 48.61; H, 5.25; N, 11.61.

Example 182

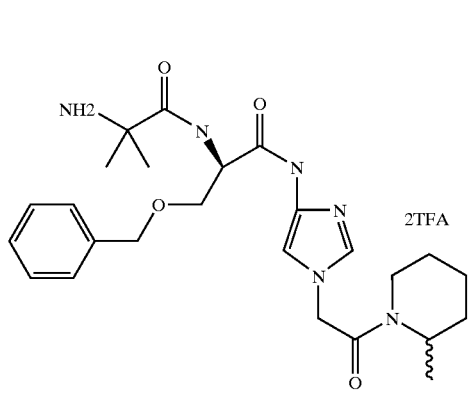

Reaction of the product of Preparation 337 (250 mg, 0.5 mmol) and 2-methyl piperidine (49 mg, 0.5 mol) as described in Preparation 338 gave the corresponding amide which deprotected according to Example 180 to provide the desired product as a white amorphous solid: $^1$H NMR consistent with structure; MS FD+=485; Anal. Calcd. for $C_{25}H_{36}N_6O_4 \times 2$ trifluoroacetic acid: C, 48.87; H, 5.38; N, 11.79. (Found) C, 48.65; H, 5.39; N, 11.64.

Example 183

Reaction of the product of Preparation 337 (250 mg, 0.5 mmol) and 2-methyl pyrrolidine (42 mg, 0.5 mmol) as described in Preparation 338 gave the corresponding amide which deprotected according to Example 180 to provide the desired product as a white amorphous solid: $^1$H NMR consistent with structure; MS FD+=470; Anal. Calcd. for $C_{24}H_{34}N_6O_4 \times 2$ trifluoroacetic acid: C, 48.14; H, 5.19; N, 12.03. (Found) C, 47.21; H, 5.37; N, 11.73.

Example 184

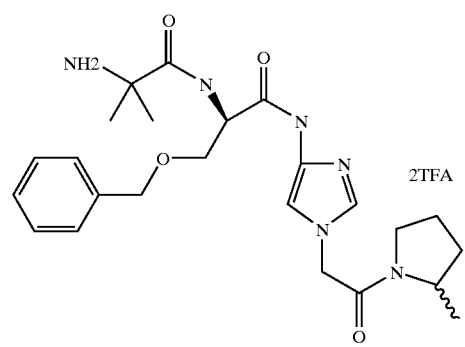

Reaction of the product of Preparation 337 (250 mg, 0.5 mmol) and 3-methyl pyrrolidine (42 mg, 0.5 mmol) as described in Preparation 338 gave the corresponding amide which deprotected according to Example 180 to provide the desired product as a white amorphous solid: $^1$H NMR consistent with structure; MS IS+=471; Anal. Calcd. for $C_{24}H_{34}N_6O_4 \times 2$ trifluoroacetic acid: C, 48.14; H, 5.19; N, 12.03. (Found) C, 48.02; H, 5.11; N, 11.83.

Example 185

Reaction of the product of Preparation 337 (250 mg, 0.5 mmol) and 4-propylpiperidine (63 mg, 0.5 mmol) as described in Preparation 338 gave the corresponding amide which deprotected according to Example 180 to provide the desired product as an off-white solid: $^1$H NMR consistent with structure; MS IS+=513; Anal. Calcd. for $C_{27}H_{40}N_6O_4 \times 2$ trifluoroacetic acid: C, 50.27; H, 5.72; N, 11.35. (Found) C, 52.30; H, 6.37; N, 12.29.

Example 186

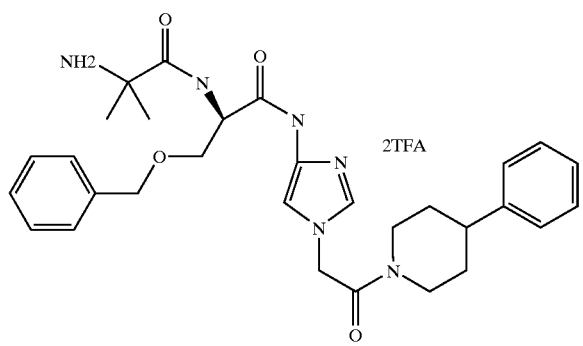

Reaction of the product of Preparation 337 (250 mg, 0.5 mmol) and piperidine (49 mg, 0.5 mmol) as described in Preparation 338 gave the corresponding amide which deprotected according to Example 180 to provide the desired product as an off-white amorphous solid: $^1$H NMR consistent with structure; MS FD+=546; Anal. Calcd. for $C_{30}H_{38}N_6O_4\times2$ trifluoroacetic acid: C, 48.14; H, 5.19; N, 12.03. (Found) C, 48.02; H, 5.11; N, 11.83.

Example 187

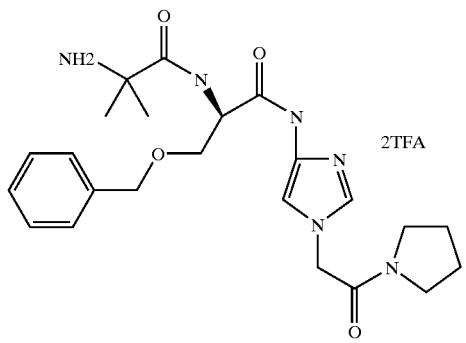

Reaction of the product of Preparation 337 (1.75 g, 3.48 mmol), dicyclohexylcarbodiimide (717 mg, 3.48 mmol), 1-hydroxybenzotriazole (470 mg, 3.48 mmol), and pyrrolidine (0.29 mL, 3.48 mmol) as described in Preparation 338 gave 870 mg (45%) of the corresponding amide which was deprotected according to Example 180 using anisole (1 mL) and trifluoroacetic acid (10 mL) to yield 580 mg (54%) of final product as a tan amorphous solid: $^1$H NMR consistent with structure; MS IS+=457; Anal. Calcd. for $C_{23}H_{32}N_6O_4\times2$ trifluoroacetic acid: C, 47.37; H, 5.01; N, 12.28. (Found) C, 51.40; H, 5.81; N, 14.34.

Example 188

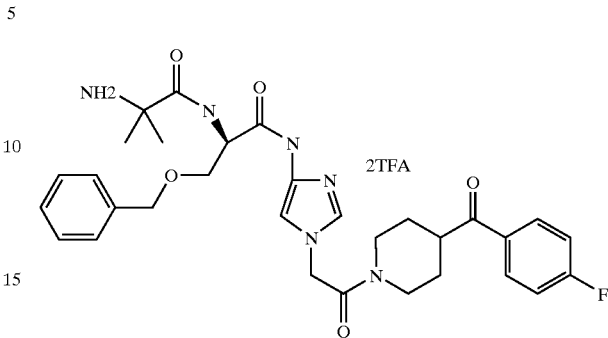

Reaction of the product of Preparation 337 (1.7 g, 3.38 mmol), dicyclohexylcarbodiimide (697 mg, 3.38 mmol), 1-hydroxybenzotriazole (456 mg, 3.38 mmol), 4-(p-fluorobenzoyl) piperidine hydrochloride (823 mg, 3.38 mmol), and triethylamine (0.47 mL, 3.38 mmol) as described in Preparation 338 gave 1.96 g (84%) of the corresponding amide which was deprotected according to Example 180 using anisole (1 mL) and trifluoroacetic acid (10 mL) to yield 1.28 g (55%) of final product as an off-white powder: $^1$H NMR consistent with structure; MS IS+=593; Anal. Calcd. for $C_{31}H_{37}FN_6O_5\times2$ trifluoroacetic acid: C, 51.22; H, 4.79; N, 10.24. (Found) C, 52.71; H, 5.07; N, 10.92.

Example 189

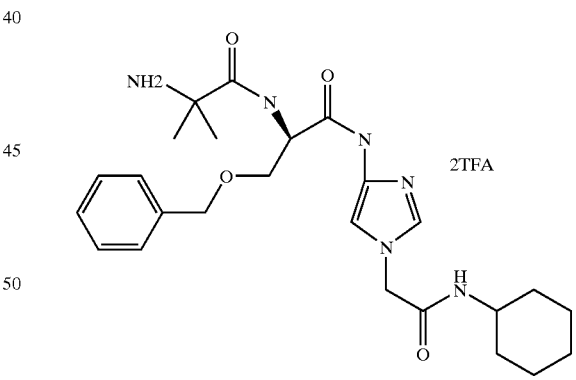

Reaction of the product of Preparation 337 (400 mg, 0.79 mmol), dicyclohexylcarbodiimide (164 mg, 0.79 mmol), 1-hydroxybenzotriazole (107 mg, 0.79 mmol), and cyclohexylamine (78 mg, 0.79 mmol) as described in Preparation 338 gave 234 mg (50%) of the corresponding amide which was deprotected according to Example 180 using anisole (0.05 mL) and trifluoroacetic acid (4 mL) to yield 220 mg (77%) of final product as a white amorphous solid: $^1$H NMR consistent with structure; MS IS+=485; Anal. Calcd. for $C_{25}H_{36}N_6O_4\times2$ trifluoroacetic acid: C, 48.88; H, 5.38; N, 11.79. (Found) C, 48.70: H, 5.52; N, 11.81.

Example 190

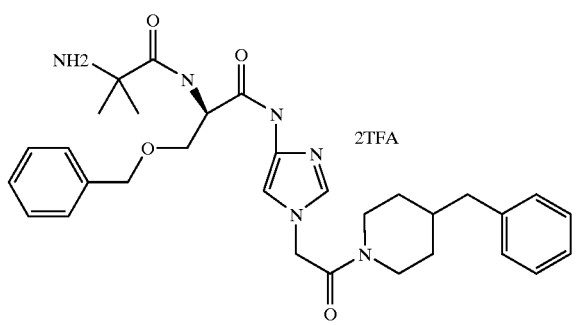

Reaction of the product of Preparation 337 (400 mg, 0.79 mmol), dicyclohexylcarbodiimide (164 mg, 0.79 mmol), 1-hydroxybenzotriazole (107 mg, 0.79 mmol), and 4-benzylpiperidine (139 mg, 0.79 mmol) as described in Preparation 338 gave 196 mg (68%) of the corresponding amide which was deprotected according to Example 180 using anisole (0.05 mL) and trifluoroacetic acid (4 mL) to yield 196 mg (68%) of final product as a white amorphous solid: $^1$H NMR consistent with structure; MS IS+=561; Anal. Calcd. for $C_{31}H_{40}N_6O_4 \times 2$ trifluoroacetic acid: C, 52.37; H, 5.02; N, 10.47. (Found) C, 52.55; H, 5.33; N, 10.56.

Example 191

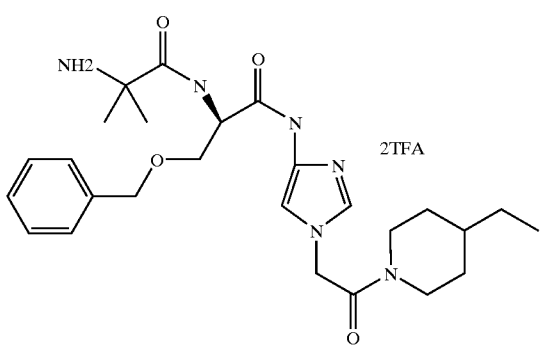

Reaction of the product of Preparation 337 (400 mg, 0.79 mmol), dicyclohexylcarbodiimide (164 mg, 0.79 mmol), 1-hydroxybenzotriazole (107 mg, 0.79 mmol), and 4-ethylpiperidine (89 mg, 0.79 mmol) as described in Preparation 338 gave 236 mg (50%) of the corresponding amide which was deprotected according to Example 180 using anisole (0.05 mL) and trifluoroacetic acid (4 mL) to yield 204 mg (71%) of final product as a white amorphous solid: $^1$H NMR consistent with structure; MS FD+=498; Anal. Calcd. for $C_{26}H_{38}N_6O_4 \times 2$ trifluoroacetic acid: C, 49.59; H, 5.55; N, 11.57. (Found) C, 48.77; H, 5.29; N, 11.37.

Example 192

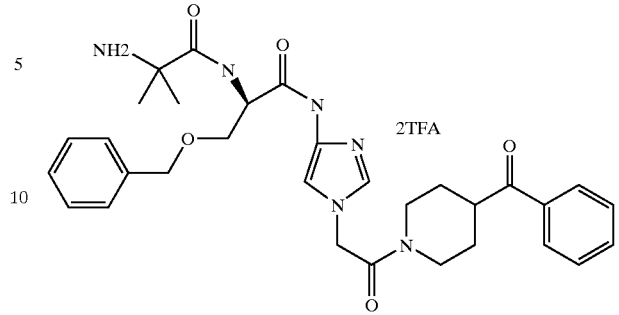

Reaction of the product of Preparation 337 (400 mg, 0.79 mmol), dicyclohexylcarbodiimide (164 mg, 0.79 mmol), 1-hydroxybenzotriazole (107 mg, 0.79 mmol), 4-benzoylpiperidine hydrochloride (179 mg, 0.79 mmol), and triethylamine (0.11 mL, 0.79 mmol) as described in Preparation 338 gave 175 mg (33%) of the corresponding amide which was deprotected according to Example 180 using anisole (0.05 mL) and trifluoroacetic acid (4 mL) to yield 170 mg (82%) of final product as a white amorphous solid: $^1$H NMR consistent with structure; MS IS+=575; Anal. Calcd. for $C_{31}H_{38}N_6O_5 \times 2$ trifluoroacetic acid: C, 52.37; H, 4.99; N, 10.47. (Found) C, 52.13; H, 5.03; N, 10.62.

Example 193

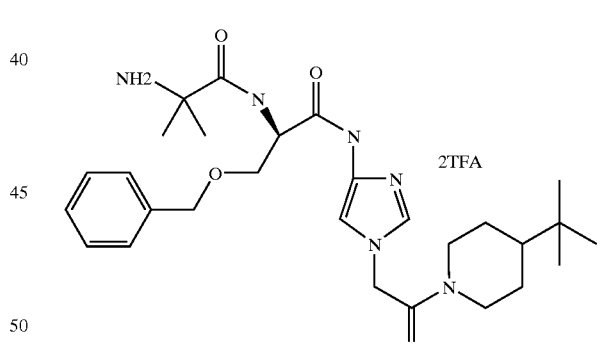

Reaction of the product of Preparation 337 (400 mg, 0.79 mmol), dicyclohexylcarbodiimide (164 mg, 0.79 mmol), 1-hydroxybenzotriazole (107 mg, 0.79 mmol), and 4-t-butylpiperidine (112 mg, 0.79 mmol) as described in Preparation 338 gave 342 mg (69%) of the corresponding amide which was deprotected according to Example 180 using anisole (0.05 mL) and trifluoroacetic acid (4 mL) to yield 287 mg (70%) of final product as a white amorphous solid: $^1$H NMR consistent with structure; MS IS+=527; Anal. Calcd. for $C_{28}H_{42}N_6O_4 \times 2$ trifluoroacetic acid: C, 50.93; H, 5.84; N, 11.14. (Found) C, 50.65; H, 5.99; N, 11.28.

Example 194

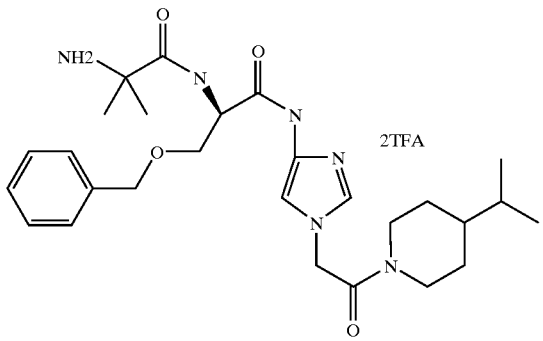

Reaction of the product of Preparation 337 (400 mg, 0.79 mmol), dicyclohexylcarbodiimide (164 mg, 0.79 mmol), 1-hydroxybenzotriazole (107 mg, 0.79 mmol), and 4-isopropylpiperidine (101 mg, 0.79 mmol)) as described in Preparation 338 gave 206 mg (43%) of the corresponding amide which was deprotected according to Example 180 using anisole (0.05 mL) and trifluoroacetic acid (4 mL) to yield 197 mg (78%) of final product as a white amorphous solid: $^1$H NMR consistent with structure; MS IS+=513; Anal. Calcd. for $C_{27}H_{40}N_6O_4 \times 2$ trifluoroacetic acid: C, 50.27; H, 5.68; N, 11.35. (Found) C, 50.21; H, 5.78; N, 11.64.

Preparation 339

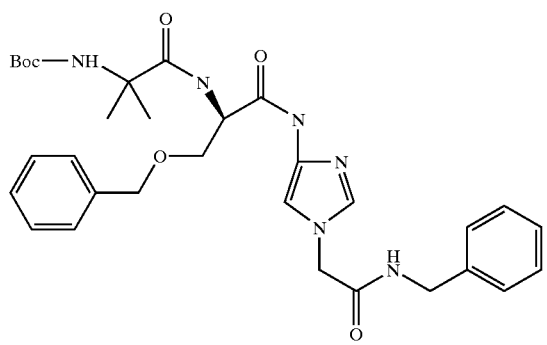

To a solution of the product of Preparation 337 (400 mg, 0.79 mmol) and N-methyl morpholine (0.1 mL) stirring in dichloromethane (20 mL) at 0° C. was added isobutyl chloroformate (0.13 mL, 1 mmol). After 15 min, benzylamine (0.11 mL, 1 mmol) was added drop-wise and after 30 min the reaction mixture was quenched with water and washed with saturated sodium bicarbonate solution, water, and 1N HCl. The organic extract was then dried over sodium sulfate, concentrated and then purified by flash chromatography (silica gel, 5% methanol/dichloromethane) to yield 199 (42%) mg of the desired product as a yellow foam: $^1$H NMR consistent with structure; MS FD+=592; Anal. Calcd. for $C_{31}H_{40}N_6O_6$: C, 62.82; H, 6.80; N, 14.18. (Found) C, 61.82; H, 6.72; N, 13.75.

Example 195

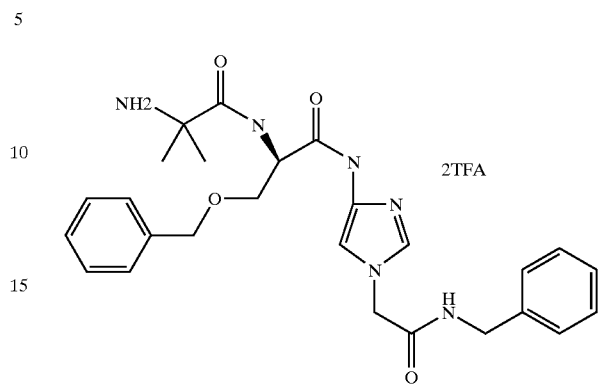

To a solution of the product of Preparation 339 (183 mg, 0.31) stirring in dichloromethane (5 mL) at room temperature was added anisole (0.2 mL) followed by trifluoroacetic acid (2 mL). After 2 h, the reaction mixture was concentrated and subsequently triturated with diethyl ether to provide 93 mg (42%) of desired product as a white amorphous solid: $^1$H NMR consistent with structure; MS FD+=492; Anal. Calcd. for $C_{26}H_{32}N_6O_4 \times 2$ trifluoroacetic acid: C, 50.00; H, 4.76; N, 11.66. (Found) C, 50.28; H, 4.93; N, 11.59.

Preparation 338

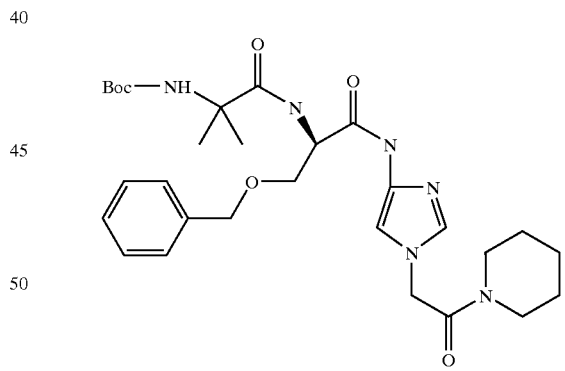

To a solution of the product of Preparation 337 (250 mgs, 0.49 mmol) and 1-hydroxybenzotriazole (67 mgs, 0.5 mmol) stirring in dry dioxane (5 mL) was added dicyclohexylcarbodiimide (107 mg, 0.521). After 15 min, piperidine (49 mg, 0.5 mmol) was added neat. After 18 h, the reaction mixture was filtered and concentrated. Purification by via radial chromatography (4 mm silica gel plate, 6% methanol/methylene chloride) gave 105 mg (36%) of a white amorphous foam: used in the next reaction without further purification.

Example 180

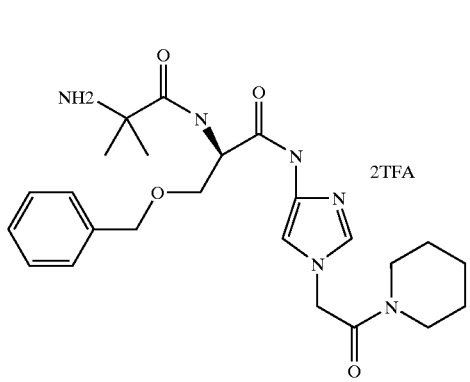

To a solution of the product of Preparation 338 (105 mg, 0.18 mmol) stirring in dichloromethane (5 mL) at room temperature was added anisole 0.2 mL) followed by trifluoroacetic acid (2 mL). After 2 h, the reaction mixture was concentrated and triturated with diethyl ether to give 86 mg (67%) of desired product as a white amorphous solid: $^1$H NMR consistent with structure; MS FD+=484; Anal. Calcd. for $C_{25}H_{36}N_6O_4 \times 2$ trifluoroacetic acid: C, 48.87; H, 5.38; N, 11.79. (Found) C, 48.71; H, 5.30; N, 11.59.

Example 181

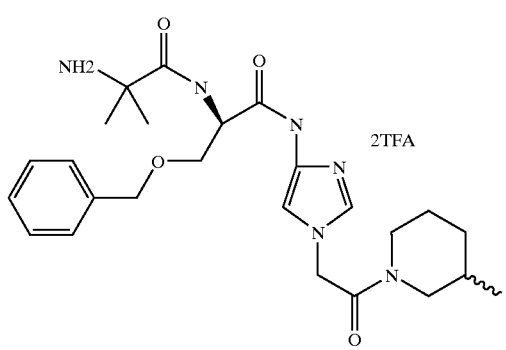

Reaction of the product of Preparation 337 (250 mg, 0.5 mmol) and 3-methyl piperidine (49 mg, 0.5 mmol) as described in Preparation 338 gave the corresponding amide which deprotected according to Example 180 to provide the desired product as a white amorphous solid: $^1$H NMR consistent with structure; MS FD+=485; Anal. Calcd. for $C_{25}H_{36}N_6O_4 \times 2$ trifluoroacetic acid: C, 48.87; H, 5.38; N, 11.79. (Found) C, 48.61; H, 5.25; N, 11.61.

Example 182

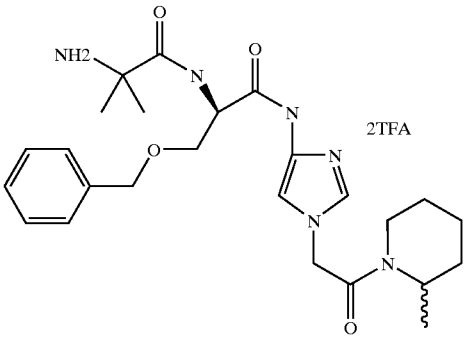

Reaction of the product of Preparation 337 (250 mg, 0.5 mmol) and 2-methyl piperidine (49 mg, 0.5 mmol) as described in Preparation 338 gave the corresponding amide which deprotected according to Example 180 to provide the desired product as a white amorphous solid: $^1$H NMR consistent with structure; MS FD+=485; Anal. Calcd. for $C_{25}H_{36}N_6O_4 \times 2$ trifluoroacetic acid: C, 48.87; H, 5.38; N, 11.79. (Found) C, 48.65; H, 5.39; N, 11.64.

Example 183

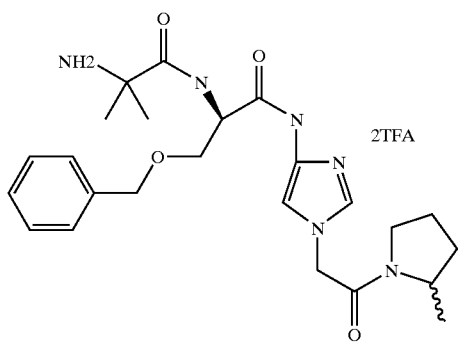

Reaction of the product of Preparation 337 (250 mg, 0.5 mmol) and 2-methyl pyrrolidine (42 mg, 0.5 mmol) as described in Preparation 338 gave the corresponding amide which deprotected according to Example 180 to provide the desired product as a white amorphous solid: $^1$H NMR consistent with structure; MS FD+=470; Anal. Calcd. for $C_{24}H_{34}N_6O_4 \times 2$ trifluoroacetic acid: C, 48.14; H, 5.19; N, 12.03. (Found) C, 47.21; H, 5.37; N, 11.73.

Example 184

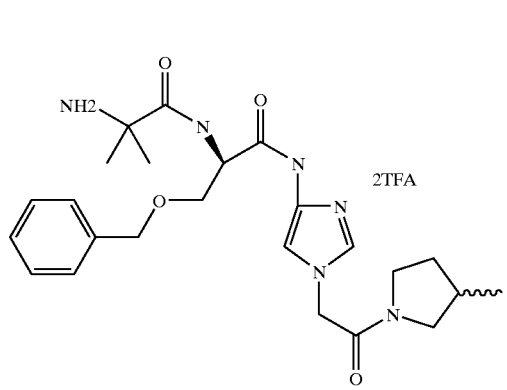

Reaction of the product of Preparation 337 (250 mg, 0.5 mmol) and 3-methyl pyrrolidine (42 mg, 0.5 mmol) as described in Preparation 338 gave the corresponding amide which deprotected according to Example 180 to provide the desired product as a white amorphous solid: $^1$H NMR consistent with structure; MS IS+=471; Anal. Calcd. for $C_{24}H_{34}N_6O_4\times 2$ trifluorcacetic acid: C, 48.14; H, 5.19; N, 12.03. (Found) C, 48.02; H, 5.11; N, 11.83.

Example 185

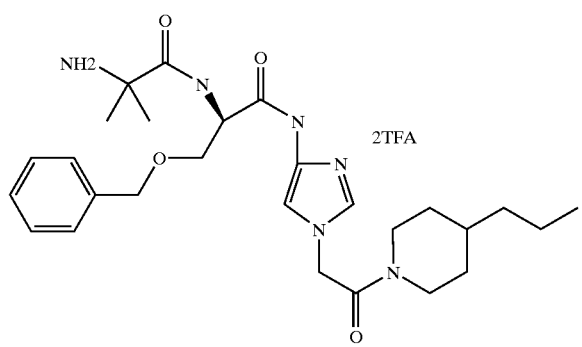

Reaction of the product of Preparation 337 (250 mg, 0.5 mmol) and 4-propylpiperidine (63 mg, 0.5 mmol) as described in Preparation 338 gave the corresponding amide which deprotected according to Example 180 to provide the desired product as an off-white solid: $^1$H NMR consistent with structure; MS IS+=513; Anal. Calcd. for $C_{27}H_{40}N_6O_4\times 2$ trifluoroacetic acid: C, 50.27; H, 5.72; N, 11.35. (Found) C, 52.30; H, 6.37; N, 12.29.

Example 186

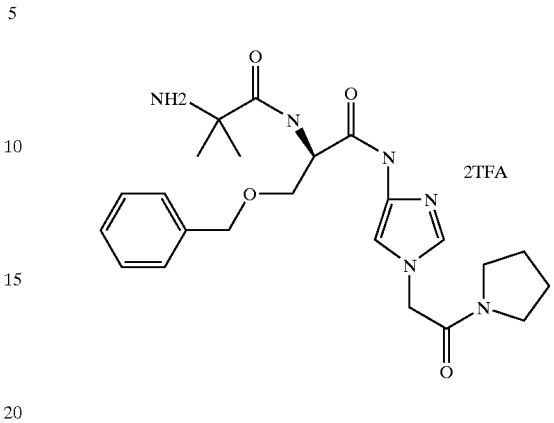

Reaction of the product of Preparation 337 (250 mg, 0.5 mmol) and piperidine (49 mg, 0.5 mmol) as described in Preparation 338 gave the corresponding amide which deprotected according to Example 180 to provide the desired product as an off-white amorphous solid: $^1$H NMR consistent with structure; MS FD+=546; Anal. Calcd. for $C_{30}H_{38}N_6O_4\times 2$ trifluoroacetic acid: C, 48.14; H, 5.19; N, 12.03. (Found) C, 48.02; H, 5.11; N, 11.83.

Example 187

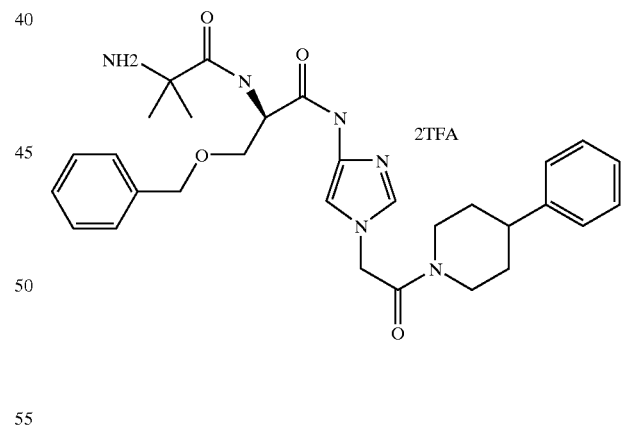

Reaction of the product of Preparation 337 (1.75 g, 3.48 mmol), dicyclohexylcarbodiimide (717 mg, 3.48 mmol), 1-hydroxybenzotriazole (470 mg, 3.48 mmol), and pyrrolidine (0.29 mL, 3.48 mmol) as described in Preparation 338 gave 870 mg (45%) of the corresponding amide which was deprotected according to Example 180 using anisole (1 mL) and trifluoroacetic acid (10 mL) to yield 580 mg (54%) of final product as a tan amorphous solid. $^1$H NMR consistent with structure; MS IS+=457; Anal. Calcd. for $C_{23}H_{32}N_6O_4\times 2$ trifluoroacetic acid: C, 47.37; H, 5.01; N, 12.28. (Found) C, 51.40; H, 5.81; N, 14.34.

Example 188

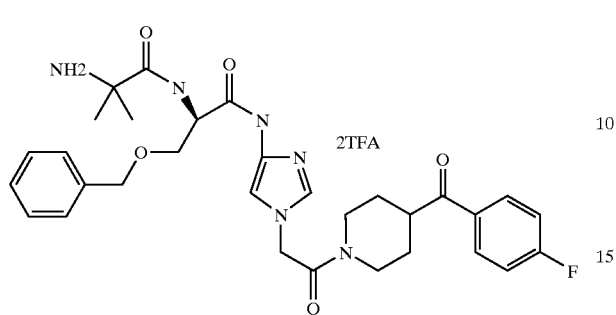

Reaction of the product of Preparation 337 (1.7 g, 3.38 mmol), dicyclohexylcarbodiimide (697 mg, 3.38 mmol), 1-hydroxybenzotriazole (456 mg, 3.38 mmol), 4-(p-fluorobenzoyl) piperidine hydrochloride (823 mg, 3.38 mmol), and triethylamine (0.47 mL, 3.38 mmol) as described in Preparation 338 gave 1.96 g (84%) of the corresponding amide which was deprotected according to Example 180 using anisole (1 mL) and trifluoroacetic acid (10 mL) to yield 1.28 g (55%) of final product as an off-white powder: $^1$H NMR consistent with structure; MS IS+=593; Anal. Calcd. for $C_{31}H_{37}FN_6O_5 \times 2$ trifluoroacetic acid: C, 51.22; H, 4.79; N, 10.24. (Found) C, 52.71; H, 5.07; N, 10.92.

Example 189

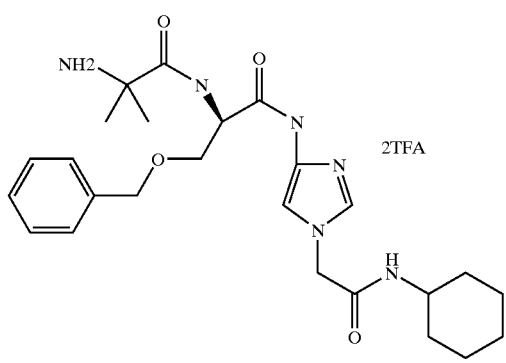

Reaction of the product of Preparation 337 (400 mg, 0.79 mmol), dicyclohexylcarbodiimide (164 mg, 0.79 mmol), 1-hydroxybenzotriazole (107 mg, 0.79 mmol), and cyclohexylamine (78 mg, 0.79 mmol) as described in Preparation 338 gave 234 mg (50%) of the corresponding amide which was deprotected according to Example 180 using anisole (0.05 mL) and trifluoroacetic acid (4 mL) to yield 220 mg (77%) of final product as a white amorphous solid: $^1$H NMR consistent with structure; MS IS+=485; Anal. Calcd. for $C_{25}H_{36}N_6O_4 \times 2$ trifluoroacetic acid: C, 48.88; H, 5.38; N, 11.79. (Found) C, 48.70; H, 5.52; N, 11.81.

Example 190

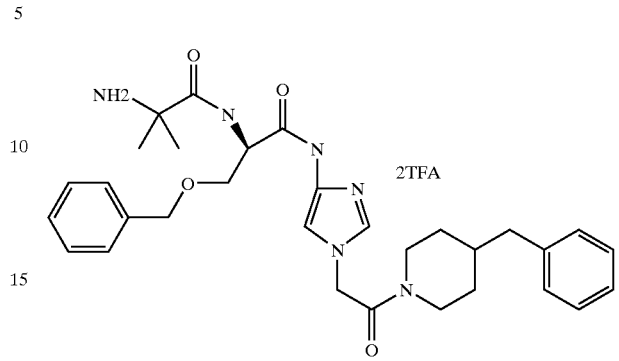

Reaction of the product of Preparation 337 (400 mg, 0.79 mmol), dicyclohexylcarbodiimide (164 mg, 0.79 mmol), 1-hydroxybenzotriazole (107 mg, 0.79 mmol), and 4-benzylpiperidine (139 mg, 0.79 mmol) as described in Preparation 338 gave 196 mg (68%) of the corresponding amide which was deprotected according to Example 180 using anisole (0.05 mL) and trifluoroacetic acid (4 mL) to yield 196 mg (68%) of final product as a white amorphous solid: $^1$H NMR consistent with structure; MS IS+=561; Anal. Calcd. for $C_{31}H_{40}H_6N_6O_4 \times 2$ trifluoroacetic acid: C, 52.37; H, 5.02; N, 10.47. (Found) C, 52.55; H, 5.33; N, 10.56.

Example 191

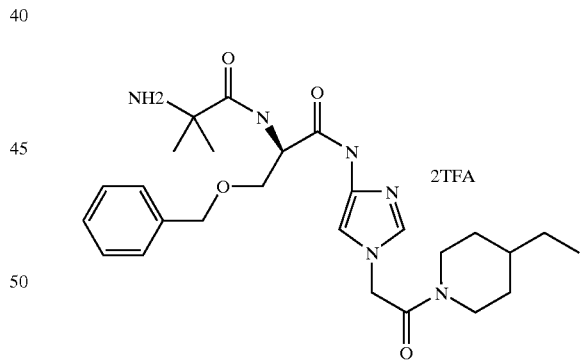

Reaction of the product of Preparation 337 (400 mg, 0.79 mmol), dicyclohexylcarbodiimide (164 mg, 0.79 mmol), 1-hydroxybenzotriazole (107 mg, 0.79 mmol), and 4-ethylpiperidine (89 mg, 0.79 mmol) as described in Preparation 338 gave 236 mg (50%) of the corresponding amide which was deprotected according to Example 180 using anisole (0.05 mL) and trifluoroacetic acid (4 mL) to yield 204 mg (71%) of final product as a white amorphous solid: $^1$H NMR consistent with structure; MS FD+=498; Anal. Calcd. for $C_{24}H_{38}N_6O_4 \times 2$ trifluoroacetic acid: C, 49.59; H, 5.55; N, 11.57. (Found) C, 48.77; H, 5.29; N, 11.37.

Example 192

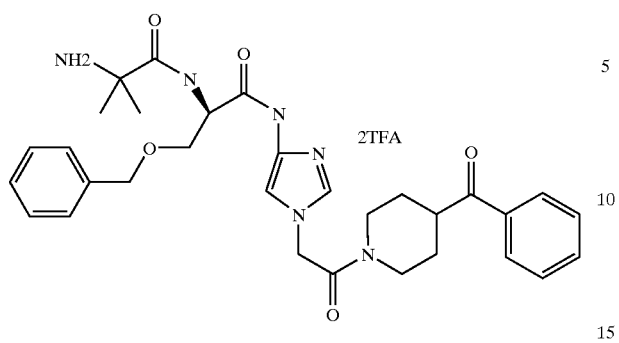

Reaction of the product of Preparation 337 (400 mg, 0.79 mmol), dicyclohexylcarbodiimide (164 mg, 0.79 mmol), 1-hydroxybenzotriazole (107 mg, 0.79 mmol), 4-benzoylpiperidine hydrochloride (179 mg, 0.79 mmol), and triethylamine (0.11 mL, 0.79 mmol) as described in Preparation 338 gave 175 mg (33%) of the corresponding amide which was deprotected according to Example 180 using anisole (0.05 mL) and trifluoroacetic acid (4 mL) to yield 170 mg (82%) of final product as a white amorphous solid: $^1$H NMR consistent with structure; MS IS+=575; Anal. Calcd. for $C_{31}H_{38}N_6O_5 \times 2$ trifluoroacetic acid: C, 52.37; H, 4.99; N, 10.47. (Found) C, 52.13; H, 5.03; N, 10.62.

Example 193

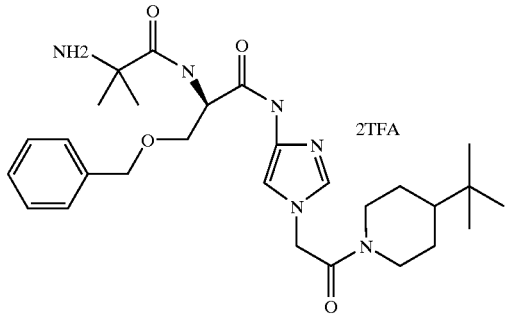

Reaction of the product of Preparation 337 (400 mg, 0.79 mmol), dicyclohexylcarbodiimide (164 mg, 0.79 mmol), 1-hydroxybenzotriazole (107 mg, 0.79 mmol), and 4-t-butylpiperidine (112 mg, 0.79 mmol) as described in Preparation 338 gave 342 mg (69%) of the corresponding amide which was deprotected according to Example 180 using anisole (0.05 mL) and trifluoroacetic acid (4 mL) to yield 287 mg (70%) of final product as a white amorphous solid: $^1$H NMR consistent with structure; MS IS+=527; Anal. Calcd. for $C_{28}H_{42}N_4O_4 \times 2$ trifluoroacetic acid: C, 50.93; H, 5.84; N, 11.14. (Found) C, 50.65; H, 5.99; N, 11.28.

Example 194

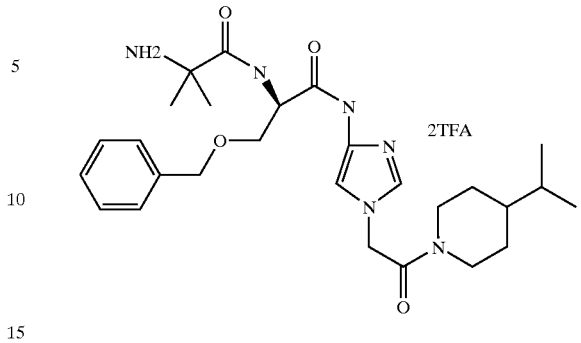

Reaction of the product of Preparation 337 (400 mg, 0.79 mmol), dicyclohexylcarbodiimide (164 m, 0.79 mmol), 1-hydroxybenzotriazole (107 mg, 0.79 mmol), and 4-isopropylpiperidine (101 mg, 0.79 mmol) as described in Preparation 338 gave 208 mg (43%) of the corresponding amide which was protected according to Example 180 using anisole (0.05 mL) and trifluoroacetic acid (4 mL) to yield 197 mg (78%) of final product as a white amorphous solid: $^1$H NMR consistent with structure; MS IS+=513; Anal: Calcd. for $C_{27}H_{40}N_6O_4 \times 2$ trifluoroacetic acid: C, 50.27; H, 5.68; N, 11.35. (Found) C, 50.21; H, 5.78; N, 11.64.

Preparation 339

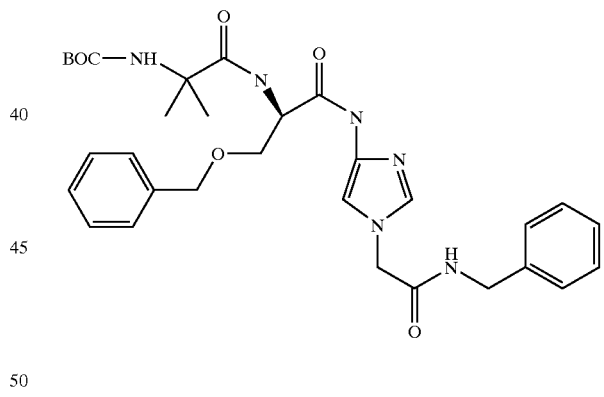

To a solution of the product of Preparation 337 (400 mg, 0.79 mmol) and N-methyl morpholine (0.1 mL) stirring in dichloromethane (20 mL) at 0° C. was added isobutyl chloroformate (0.13 mL, 1 mmol). After 15 min, benzylamine (0.11 mL, 1 mmol) was added drop-wise and after 30 min the reaction mixture was quenched with water and washed with saturated sodium bicarbonate solution, water, and 1N HCl. The organic extract was then dried over sodium sulfate, concentrated and then purified by flash chromatography (silica gel, 5% methanol/dichloromethane) to yield 199 (42%) mg of the desired product as a yellow foam: $^1$H NMR consistent with structure; MS FD+=592; Anal. Calcd. for $C_{33}H_{40}N_6O_6$: C, 62.82; H, 6.80; N, 14.18. (Found) C, 61.82; H, 6.72; N, 13.75.

Example 195

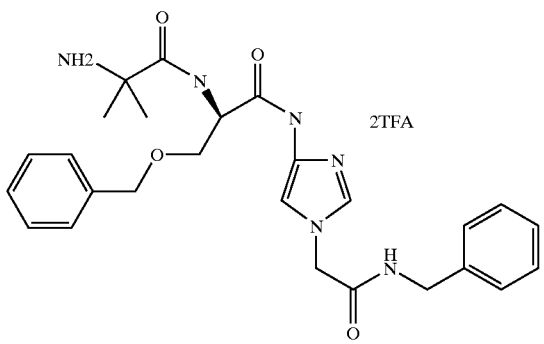

To a solution of the product of Preparation 339 (183 mg, 0.31) stirring in dichloromethane (5 mL) at room temperature was added anisole (0.2 mL) followed by trifluoroacetic acid (2 mL). After 2 h, the reaction mixture was concentrated and subsequently triturated with diethyl ether to provide 93 mg (42%) of desired product as a white amorphous solid: $^1$H NMR consistent with structure; MS FD+=492; Anal. Calcd. for $C_{26}H_{32}N_6O_4 \times 2$trifluoroacetic acid: C, 50.00; H, 4.76; N, 11.66. (Found) C, 50.28; H, 4.93; N, 11.59.

Preparation 340

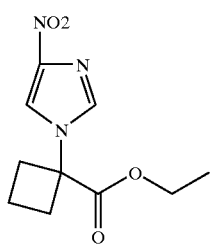

To a mixture of potassium t-butoxide (16.2 g, 145 mmol) stirring in dimethylformamide (100 mL) was added 4-nitroimidazole (13.6 g, 120.7 mmol portion-wise over 30 min. After 1 h, ethyl-1-bromocyclobutanecarboxylate (25 g, 120.7 mmol) was slowly added. The mixture was heated to 100° C., and after 36 h, the mixture was cooled to room temperature and concentrated. The resulting solid was triturated in diethyl ether and filtered. The filtrate was concentrated and purified by flash chromatography (silica gel; 60% ethyl acetate/hexanes) to yield 3.86 g (13%) of the desired product as a clear yellow oil: $^1$H NMR consistent with structure; MS FD+=239; Anal. Calcd. for $C_{10}H_{13}N_3O_4$: C, 50.21; H, 5.48; N, 17.56; (Found) C, 50.36; H, 5.60; N, 17.54.

Preparation 341

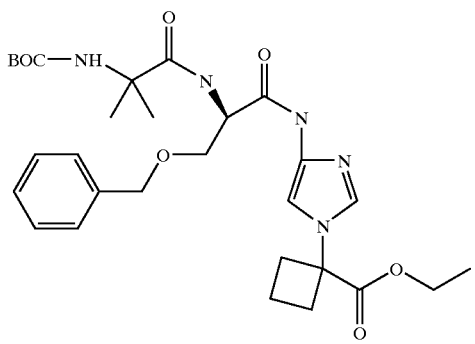

To a solution of the product of Preparation 340 (3.6 g, mmol) in dioxane (50 mL) was added 5% palladium on carbon (0.9 g). The resulting mixture was hydrogenated at room temperature at 40 p.s.i on a Parr apparatus for 30 min. This mixture was then filtered through celite and added to solution of the product of Preparation 1d (5.73 g, 15.05 mmol), 1-hydroxybenzotriazole (2.03 g, 15.05 mmol), and dicyclohexylcarbodiimide (3.11 g, 15.05 mmol) in dioxane (75 mL). After 18 h, the reaction was filtered and the filtrate concentrated. The resulting orange foam was purified by flash chromatography (silica gel; methanol/dichloromethane) to yield 2.63 g of the desired product as a yellow foam: $^1$H NMR consistent with structure; MS IS+=572.

Preparation 342

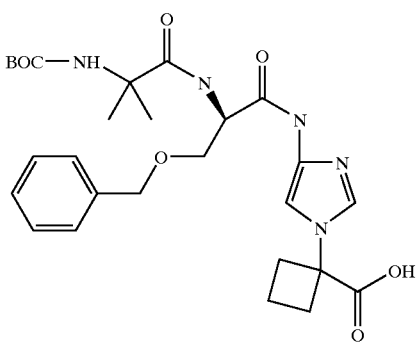

To a solution of the product of Preparation 341 (2.6 g, 4.55 mmol) stirring in methanol (80 mL) at room temperature was slowly added 1M LiOH (9.1 mL, 9.1 mmol) drop-wise. After 90 min, the reaction mixture was concentrated then diluted with 30 mL 10% acetic acid/ethyl acetate and concentrated. The resulting concentrate was diluted with 50 mL 10% acetic acid/ethyl acetate and washed with water. The organic extract was dried over sodium sulfate and then concentrated. Triturate the solid in diethyl ether gave 620 mg (25%) of desired product as a white amorphous powder: $^1$H NMR consistent with structure; MS IS+=544.

Preparation 343

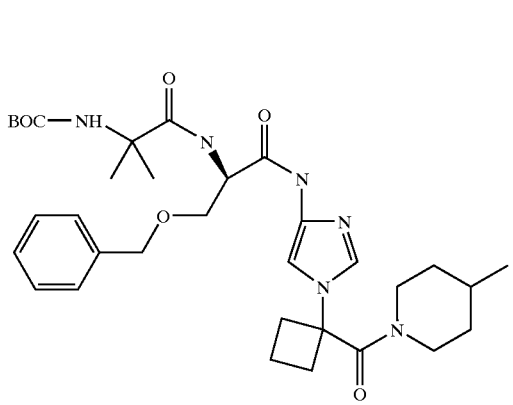

To a solution of the product of Preparation 342 (600 mg, 1.10 mmol) and 1-hydroxybenzotriazole (149 mg, 1.10 mmol) stirring in dioxane (10 mL) at room temperature was added dicyclohexylcarbodiimide (228 mg, 1.10 mmol). After 15 min, 4-methylpiperidine (109 mg, 1.10 mmol) was added. After 18 h, the mixture was filtered and the filtrate concentrated. The resulting material was purified by radial chromatography to yield 200 mg (29%) of the desired product as a white amorphous foam: $^1$H NMR consistent with structure; MS IS+=625.

Example 196

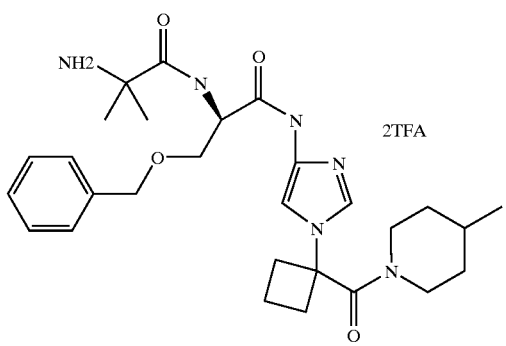

To a solution of the product of Preparation 343 (200 mg, 0.32 mmol) stirring in dichloromethane (5 mL) at room temperature was added anisole (0.05 mL) followed by trifluoroacetic acid (2 mL). After 2 h, the reaction mixture was concentrated then triturate in diethyl ether to provide 118 mg (49%) of desired product as a white amorphous solid: $^1$H NMR consistent with structure; MS IS+=525; Anal. Calcd. for $C_{28}H_{40}N_6O_4 \times 2$trifluoroacetic acid: C, 51.06; H, 5.62; N, 11.16. (Found) C, 53.40; H, 6.06; N, 11.99.

Preparation 344

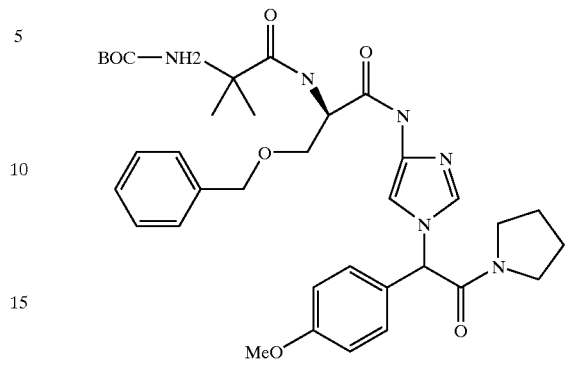

To a solution of the product of Preparation 5 (10.0 g, 16.4 mmol) stirring in tetrahydrofuran (150 mL) at room temperature was added 1-hydroxybenzotriazole (2.22 g, 16.4 mmol) and 1,3-dicyclohexylcarbodiimide (3.38 g, 16.4 mmol). After 15 min, pyrrolidine (1.37 mL, 16.4 mmol) was added. After 16 h, the reaction mixture was filtered and concentrated. The resulting crude material was purified by flash chromatography (silica gel, 5% methanol/dichloromethane) to yield 7.05 g (65%) of the desired product as a yellow foam: $^1$H-NMR consistent with product; MS (ion spray) 663 (M+1); Anal. Calcd for $C_{35}H_{46}N_6O_7$: C, 63.43; H, 7.00; N, 12.68. (Found) C, 62.69; H, 6.87; N, 12.91.

Examples 197 and 198

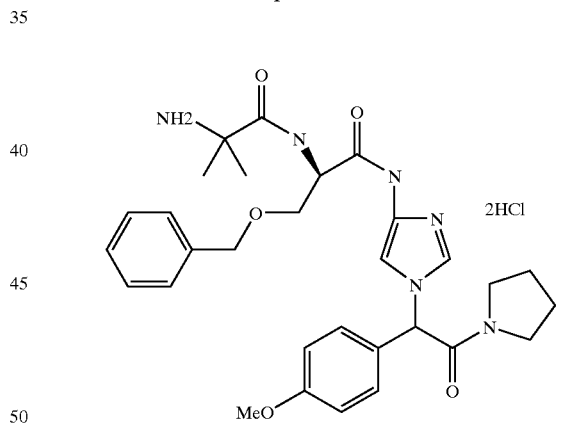

To the product of Preparation 344 (7.0 g, 10.6 mmol) was added a saturated solution of HCl(g)/acetic acid (100 mL). After 4 h, the reaction mixture was concentrated then partitioned between ethyl acetate and saturated sodium bicarbonate. The organic layer was removed, dried over sodium sulfate and concentrated to yield 5.59 g (94%) of the free base as a light yellow foam. The diastereomeric material (3.45 g) was chromatographed on an 8×15 cm Prochrom column packed with Kromsil CHI-DIMETHYLFORMAMIDE chiral phase using an eluent mixture of 3A alcohol and dimethylethylamine in heptane to provide the individual diastereomers in pure form: $^1$H NMR consistent with product; MS (ion spray) 563 (M+1); Anal. Calcd. for $C_{30}H_{38}N_6O_5$: C, 64.04; H, 6.81; N, 14.94. (Found) C, 63.98; H, 6.82; N, 14.87.

Example 197

Isomer 1

To a solution of the purified isomer in ethyl acetate was added a saturated solution of hydrochloric acid in ethyl acetate. The resulting slurry was concentrated to dryness to yield 1.50 g (39%) of the desired product as an off-white solid: $^1$H NMR consistent with product; MS (ion spray) 563 (M+1); Anal. Calcd. for $C_{30}H_{38}N_6O_5 \times 2HCl$: C, 56.69; H, 6.34; N, 13.22. (Found) C, 55.81; H, 6.40; N, 12.68.

Example 198

Isomer 2

To a solution of the purified isomer in ethyl acetate was added a saturated solution of hydrochloric acid in ethyl acetate. The resulting slurry was concentrated to dryness to yield 1.43 g (38%) of the desired product as an off-white solid: $^1$H NMR consistent with structure; MS (ion spray) 563 (M+1); Anal. Calcd. for $C_{30}H_{38}N_6O_5 \times 2HCl$: C, 56.69; H, 6.34; N, 13.22. (Found) C, 55.71; H, 6.38; N, 12.74.

Preparation 345

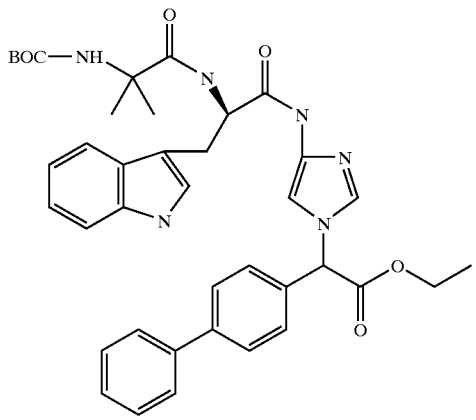

To a mixture of the product of Preparation 99 (6.0 g, 17.1 mmol) and 10% palladium on carbon (6.0 g) in tetrahydrofuran (100 mL). The reaction mixture was placed under a hydrogen atmosphere (40 psi) using a Parr apparatus for 30 min then filtered through Celite. The resulting solution was then added to a previously prepared mixture of the product of Preparation 1L (6.66 g, 17.1 mmol), 1-hydroxybenzotriazole 12.31 g, 17.1 mmol), and 1,3-dicyclohexylcarbodiimide (3.53 g, 17.1 mmol) in tetrahydrofuran (75 mL). After 16 h at room temperature, the reaction mixture was concentrated and the crude material purified by flash chromatography (silica gel, 4% methanol/dichloromethane) to yield 6.17 g (52%) of the desired product as a brown foam: $^1$H NMR consistent with structure; MS (ion spray) 693 (M+1).

Preparation 346

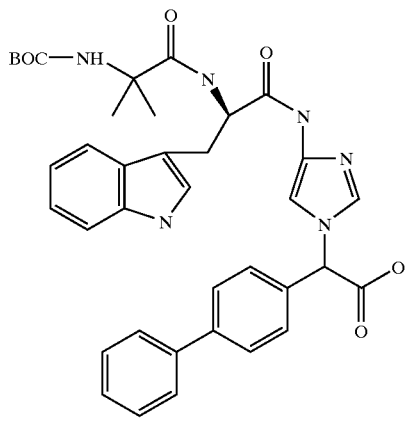

To a solution of the product Preparation 345 (4.6 g, 6.64 mmol) stirring in tetrahydrofuran (100 mL) at room temperature was added a solution of lithium hydroxide in water (40 mL of 1M). After 30 min, the reaction mixture was acidified with 5N HCl (8.5 mL). The resulting mixture diluted with water and extracted with ethyl acetate. The combined organic extracts were dried over sodium sulfate and concentrated to yield 4.4 g (99%) of the desired product as a yellow foam.

Preparation 347

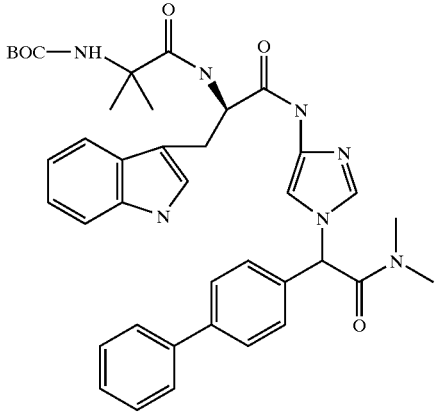

To a solution of the product Preparation 346 (4.0 g, 6.02 mol) stirring in tetrahydrofuran (50 mL) at room temperature was added 1-hydroxybenzotriazole (813 mg, 6.02 mmol) and 1,3-dicyclohexylcarbodiimide (1.24 g, 6.02 mmol). After 15 min, dimethylamine (3.0 mL of a 2M soln in tetrahydrofuran, 6.02 mmol) was added. After stirring for 16 h in a sealed flask, the reaction mixture was filtered and concentrated. The resulting crude material was purified by flash chromatography (silica gel, 5% methanol/dichloromethane) to yield 2.79 g (68%) of the desired product as a yellow foam.

Examples 199 and 200

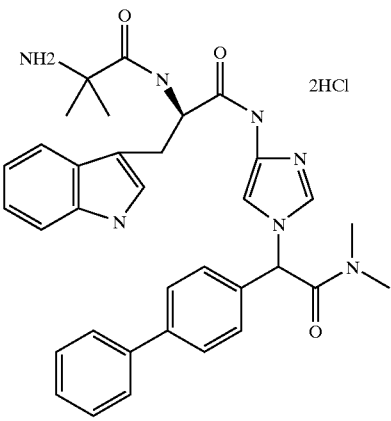

To the product of Preparation 347 (3.4 g, 5.0 mmol) was added a saturated solution of HCl(g)/acetic acid (50 mL). After 1.5 h, the reaction mixture was concentrated then partitioned between ethyl acetate and saturated sodium bicarbonate. The organic layer was removed, dried over sodium sulfate and concentrated to yield 2.45 g (84%) of the free base as a light yellow foam. The diastereomeric material (2.45 g) was chromatographed on an 8×15 cm Prochrom column packed with Kromsil CHI chiral phase using an eluent mixture of 3A alcohol and dimethylethylamine in heptane to provide the individual diastereomers in pure form: $^1$H NMR consistent with product; MS (ion spray) 592 (M+1); Anal. Calcd. for $C_{34}H_{37}N_7O_3$: C, 69.02; H, 6.30; N, 16.57. (Found) C, 67.93; H, 6.29; N, 15.80.

Example 199

Isomer 1

To a solution of the purified isomer in ethyl acetate was added a saturated solution of hydrochloric acid in ethyl acetate. The resulting slurry was concentrated to dryness to yield 992 mg (37%) of the desired product as an off-white solid: $^1$H NMR consistent with product; MS (ion spray) 592 (M+1); Anal. Calcd. for $C_{34}H_{37}N_7O_3 \times 2HCl$: C, 61.44; H, 5.91; N, 14.75. (Found) C, 59.54; H, 5.92; N, 13.76.

Example 200

Isomer 2

To a solution of the purified isomer in ethyl acetate was added a saturated solution of hydrochloric acid in ethyl acetate. The resulting slurry was concentrated to dryness to yield 1.17 g (40%) of the desired product as an off-white solid: $^1$H NMR consistent with structure; MS (ion spray) 592 (M+1); Anal. Calcd. for $C_{34}H_{37}N_7O_3 \times 2HCl$: C, 61.44; H, 5.91; N, 14.75. (Found) C, 59.03; H, 6.04; N, 13.84.

Preparation 348

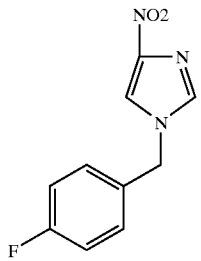

To a suspension of sodium hydride (1.8 g of a 60% dispersion in mineral oil, 45 mmol) stirring at 0° C. in dimethylformamide (50 mL) was slowly added 4-nitroimidazole (5.0 g, 44.2 mmol). After 1 h, a solution of 4-fluorobenzyl bromide (5.5 mL, 44.2 mmol) in dimethylformamide (10 mL) was added dropwise over 10 min. After 16 h, the reaction mixture was warmed to room temperature and concentrated. The resultant crude material was then diluted with hot methanol, filtered, allowed to cool, then filtered to yield 5.0 g (51%) of pale yellow crystals: $^1$H NMR consistent with structure; MS (ion spray) 222 (M+1); Anal. Calcd. for $C_{10}H_8FN_3O_2$: C, 54.31; H, 3.65; N, 19.00. Found: C, 53.81; H, 3.92; N, 17.48.

Preparation 349

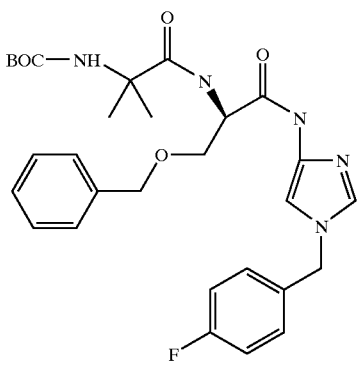

To a slurry of Raney Nickel (116 mg) in dioxane (15 mL) was added a slurry of the product of Preparation 348 (582 mg, 2.63 mmol) in dioxane (20 mL). The reaction mixture was placed under a hydrogen atmosphere (60 psi) using a Parr apparatus. After 30 min, the solution was filtered through Celite and the filtrate immediately added to a previously prepared mixture of the product of Preparation 1d (1.0 g, 2.63 mmol), 1-hydroxybenzotriazole (355 mg, 2.63 mmol), and 1,3-dicyclohexylcarbodiimide (543 mg, 2.63 mmol) in dioxane (25 mL). After 16 h, the reaction mixture was concentrated and the crude material purified by flash chromatography (silica gel, 5% methanol/dichloromethane) to give the desired product. This material was then crystallized from diethyl ether to yield 150 mg (10%) of the desired product as a white powder: $^1$H NMR consistent with structure.

Example 201

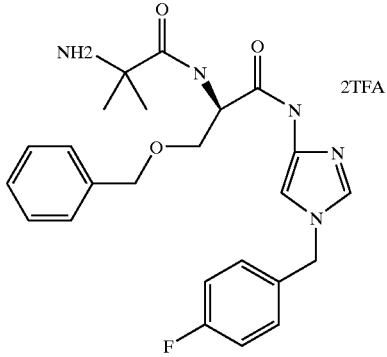

To the product of Preparation 349 (150 mg, 0.27 mmol) stirring in dichloromethane (5 mL) at room temperature was added anisole (0.05 mL) and trifluoroacetic acid (2 mL). After 3 h, the mixture was concentrated, triturated extensively in diethyl ether, and the product collected via filtration to provide 101 mg (55%) of desired product as a white powder: $^1$H NMR consistent with structure; MS (ion spray) 454 (M+1); Anal. Calcd. For $C_{24}H_{28}FN_5O_3 \times 2TFA$: C, 49.34; H, 4.44; N, 10.28. Found: C, 49.64; H, 4.58; N, 10.36.

Preparation 350

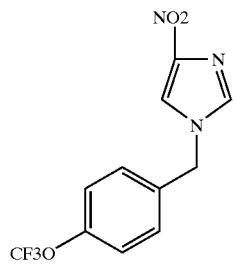

To a suspension of sodium hydride (1.56 g of a 60% dispersion in mineral oil, 39 mmol) stirring in DIMETHYLFORMAMIDE (50 mL) at 0° C. was slowly added 4-nitroimidazole (4.0 g, 35.4 mmol). After 1 h, a solution of 4-trifluoro-methoxybenzyl bromide 9.03 g, 35.4 mmol) in dimethylformamide (10 mL) was added dropwise over 10 min. After 16 h, the reaction mixture was warmed to room temperature then concentrated. The resultant crude material was then purified by flash chromatography (silica gel, 100% dichloromethane) and the product subsequently crystallized from diethyl ether to yield 3.95 g (39%) of desired product as white needles: $^1$H NMR consistent with structure; MS (ion spray) 288 (M+1); Anal. Calcd. for $C_{11}H_8F_3N_3O_3$: C, 45.99; H, 2.79; N, 14.63; F, 19.86. (Found) C, 46.27; H, 2.86; N, 14.86; F, 19.74.

Preparation 351

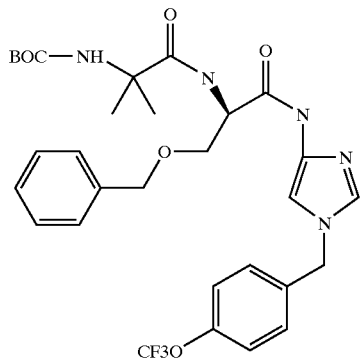

To a slurry of Raney Nickel (150 mg) in dioxane (15 mL) was added a slurry of the product of Preparation 350 (755 mg, 2.63 mmol) in dioxane (20 mL). The reaction mixture was placed under a hydrogen atmosphere (60 psi) using a Parr apparatus. After 30 min. the solution was filtered through Celite and the filtrate immediately added to a previously prepared mixture of the product of Preparation 1d (1.0 g, 2.63 mmol), 1-hydroxybenzotriazole (355 mg, 2.63 mmol), and 1,3 dicyclohexylcarbodiimide (543 mg, 2.63 mmol) in dioxane (25 mL). After 16 h, the reaction mixture was concentrated and the crude material purified by flash chromatography (silica gel, 5% methanol/dichloromethane) to provide 171 mg (10%) of the desired product as a white foam: $^1$H NMR consistent with structure; used without further characterization.

Example 202

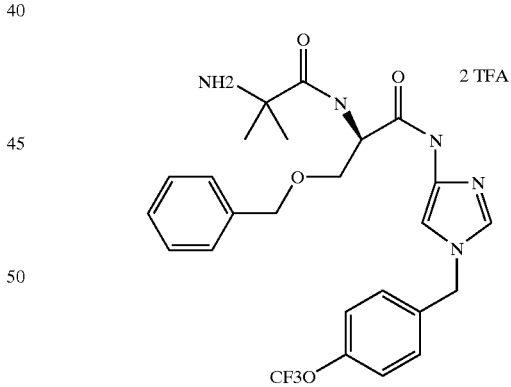

To the product of Preparation 351 (171 mg, 0.28 mmol) stirring in dichloromethane (5 mL) at room temperature was added anisole (0.05 mL) and trifluoroacetic acid (2 mL). After 3 h, the mixture was concentrated, triturated extensively in diethyl ether, and the product collected via filtration to provide 84 mg (40%) of desired product as a white powder: 1H NMR consistent with structure; MS (ion spray) 520 (M+1); Anal. Calcd. For $C_{25}H_{28}F_3N_5O_4 \times 2TFA$: C, 46.59; H, 4.04; N, 9.37. Found: C, 48.48; H, 4.48; N, 10.04.

Preparation 352

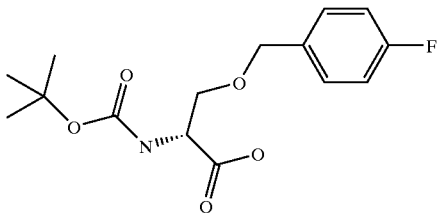

A cold (0–5° C.) solution of 5.0 g (24.37 mmol) of Boc-D-serine in 20 mL of dry N,N-dimethylformamide was added to a stirred suspension of sodium hydride (60% dispersion in mineral oil, 2.2 g, 55 mmol) in 60 mL of dry dimethylformamide at 0–5° C. under nitrogen over 5 min. The resulting light yellow brown suspension was stirred at 0–5° C. until gas evaluation nearly ceased (~15 min). Then a cold (0–5° C.) solution of 4-fluorobenzyl bromide (3.12 mL, 25 mmol) in 10 mL of dry N,N-dimethylformamide (Additional 10 mL of dimethylformamide was used as washings) was added to the stirred mixture over 5 min. The resulting off white suspension was stirred at 0–5° C. for 2 h, during which time the mixture turned to a thick suspension and the magnetic stirring became ineffective. The reaction flask was shaken by hand several times. The cooling bath was removed and the mixture was allowed to warm to room temperature while shaking the reaction flask occasionally by hand. By the time the mixture reached the room temperature, the suspension thinned and the magnetic stirring became effective. The mixture was stirred at ambient temperature for additional 1 h (total 5 hours). The mixture was concentrated and the oily residue was dissolved in 150 mL of water and extracted with ether. The aqueous layer was cooled to 0–5° C., acidified to pH~3 with cold (0–5° C.) 0.5N HCl, and quickly extracted with ethyl acetate. The aqueous layer was saturated with sodium chloride and extracted with ethyl acetate. The ethyl acetate extracts were combined, washed with brine, dried over anhydrous sodium sulfate, filtered, and concentrated to dryness to give 6.86 g (89.9%) of the desired product as a light yellow viscous oil which was used in the next step without further purification: $^1$H-NMR ($\delta$, DMSO) 1.38 (s, 9H), 3.60–3.70 (m, 2H), 4.15–4.25 (m, 1H), 4.45 (s, 2H), 6.97 (d, J=8.3 Hz, 1H), 7.16 (t, J≅8.7 Hz and 9.0 Hz, 2H), 7.30–7.40 (m, 2H), 12.65 (br s, 1H); MS (ion spray) 314 (M+1).

Preparation 353

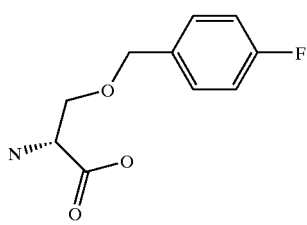

Trifluoroacetic acid (40 mL) was added to a stirred solution of 6.5 g (20.75 mmol) of the product of Preparation 352 in 40 mL of dichloromethane and the mixture was stirred at ambient temperature for 1 h, then it was concentrated to dryness. The resulting oily residue was dissolved in 30 mL of deionized water, cooled in ice-water bath, neutralized to pH~7, and the separated white precipitate was filtered. The precipitate was washed with ether (5×10 mL) to remove the yellow brown impurity and the resulting white precipitate was dried to a constant weight to give 2.45 g (55.4%) of the desired product as a white powder: $^1$H-NMR ($\delta$, DMSO) 3.37 (dd, J=3.4, 7.9 Hz, 1H), 3.60 (dd, J=7.9 Hz, 1H), 3.77 (dd, J=3.4 Hz, 1H), 4.47 (s, 2H), 7.15–7.25 (m, 2H), 7.35–7.48 (m, 2H), 7.65 (br s, 1H); MS (ion spray) 214 (M+1); Anal. Calc'd for $C_{10}H_{12}FNO_3$: C, 56.33; H, 5.67; N, 6.57. Found: C, 56.32; H, 5.66; N, 6.39.

Preparation 354

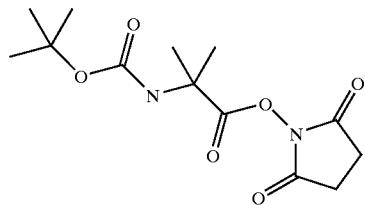

A solution of 1,3-dicyclohexylcarbodiimide (6.18 g, 30 mmol) in 30 mL of tetrahydrofuran was added to a stirred solution of 6.1 g (30 mmol) of Boc-a-methylalanine and 4.14 g (36 mmol) of N-hydroxysuccinimide in 60 mL of tetrahydrofuran at ambient temperature under nitrogen and the mixture was stirred at ambient temperature under nitrogen for overnight. The mixture was cooled to ~0° C. and filtered through celite. The precipitate was washed with cold (0–5° C.) tetrahydrofuran. The filtrate was concentrated to dryness and purified by flash chromatography (5% acetone/dichloromethane) to give 7.25 g (80.6%) of the desired product as a white powder: $^1$H-NMR ($\delta$, DMSO) 1.39 (s, 9H), 1.48 (s, 6H), 2.78 (s, 4H), 7.57 (br s, ~0.5H); MS (ion spray) 301 (M+1); Anal. Calc'd for $C_{13}H_{20}FN_2O_6$: C, 51.99; H, 6.71; N, 9.33. Found: C, 52.70; H, 6.67; N, 9.30.

Preparation 355

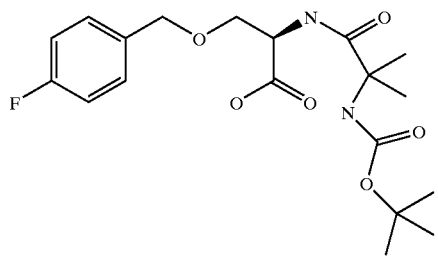

Forty mL of tetrahydrofuran was added to a stirred suspension of 4.26 g (20 mmol) of the product of Preparation 353 in 100 mL 1N sodium bicarbonate and the mixture was stirred for 15 min to give a fine suspension. Forty mL of water was added to the reaction mixture to dissolve the suspension to form a clear solution. To this stirred solution at ambient temperature under nitrogen atmosphere was added a solution of 5.71 g (19 mmol) of the product of Preparation 354 in 60 mL of tetrahydrofuran over 3 h and the resulting mixture was stirred at ambient temperature under nitrogen for 4 h. The resulting turbid solution was diluted with 150 mL of water to form a clear solution which was extracted with petroleum ether (2×200 mL). The aqueous layer was cooled to 0–5° C., acidified to pH~3.0 with cold (0–5° C.) 1N HCl (~100 mL) followed by 0.5N HCl (~15 mL)+, and the separated white precipitate was quickly extracted with ethyl acetate (1×200 mL). The aqueous layer was saturated with sodium chloride, further acidified to pH~1, and quickly extracted with ethyl acetate (1×200 mL). The ethyl acetate extracts were combined, washed with brine, dried over anhydrous sodium sulfate, filtered and concentrated to dryness to give 7.03 g (92.9%) of the desired product as a white foam: $^1$H-NMR ($\delta$, DMSO) 1.29 (s, 6H), 1.33 (s, 9H), 3.66 (dd, J=4.0 Hz, 1H), 3.75 (dd, J=4.3 Hz, 1H), 4.38–4.48 (m, 1H), 4.44 (s, 2H), 7.00–7.20 (m, 3H), 7.28–7.42 (m, 3H), 12.8 (br s, ~0.5H); MS (ion spray) 399 (M+1); Anal. Calc'd for $C_{19}H_{27}FN_2O_6$: C, 57.28; H, 6.83; N, 7.03. Found: C, 57.05; H, 6.84; N, 6.87.

Preparation 356

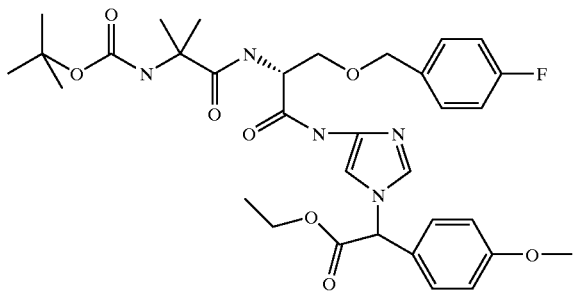

7.0 g of 5% palladium on carbon (dry) was added under nitrogen atmosphere to a solution of 6.7 g (22 mmol) of the product of Preparation 3 from Examples Part 1 in 35 mL of tetrahydrofuran and the resulting slurry was hydrogenated at ~50 psi of hydrogen for 2 h. The mixture was filtered through celite and the catalyst was washed with tetrahydrofuran (15×25 mL). The resulting yellow brown filtrate (~300 mL) was added to a mixture of 6.6 g (16.57 mmol) of the product of Preparation 355 and 2.97 g (22 mmol) of 1-hydroxybenzotriazole. To this stirred brown solution was added 3.7 g (18 mmol) of 1,3-dicyclohexylcarbodiimide as solid in one lot and the mixture was stirred at ambient temperature for 20 h, then it was concentrated. The residue was dissolved in 150 mL of ethyl acetate and filtered through celite. The brown filtrate was washed with 1N sodium bicarbonate, brine, dried over anhydrous sodium sulfate, filtered, and concentrated to dryness to give 12.3 g of crude product as a tan foam which was purified by flash chromatography (silica gel, 3% methanol in dichloromethane) to give 7.75 g (71.3%) of the desired product as a tan foam: $^1$H-NMR ($\delta$, DMSO) 1.17 (t, J=7.2 Hz, 3H), 1.25–1.35 (m, 15H); 3.52–3.65 (m, 1H), 3.66–3.72 (m, 1H), 3.76 (s, 3H), 4.21 (q, J=7.2, 2H), 4.42 (d, J=3.4 Hz, 2H), 4.53–4.62 (m, 1H), 6.35 (d, J=3.4 Hz, 1H), 6.98 (d, J=8.7 Hz, 2H), 7.05–7.30 (m, 5H), 7.32 (d, J=8.7 Hz), 7.51 (s, 1H), 10.20 (br s, 1H); MS (ion spray) 656 (M+1); Anal. Calc'd for $C_{33}H_{42}FN_5O_8$: C, 60.45; H, 6.46; N, 10.68. Found: C, 61.35; H, 6.57; N, 10.98.

Preparation 357

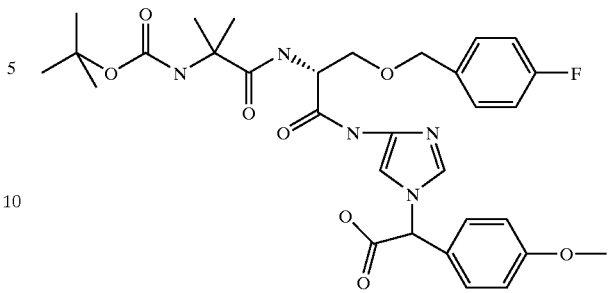

14 mL (14 mmol) of 1M solution of lithium hydroxide was added in one lot to a stirred solution of the product of Preparation 356 (7.2 g, 11 mmol) in 51 mL of dioxane and 30 mL of deionized water. The mixture was stirred at ambient temperature for 20 min and extracted it with ether (3×40 mL). The light yellow colored ether extracts were discarded. The brown aqueous layer (pH~12) was cooled in ice-water bath and acidified to pH~4 with cold 0.5N HCl and quickly extracted the separated light brown precipitate with ethyl acetate (1×150 mL). The light yellow colored aqueous layer was saturated with sodium chloride, further acidified to pH~3 and extracted with ethyl acetate. The aqueous layer was discarded. The organic extracts were combined, washed with brine, dried over anhydrous sodium sulfate, filtered, and concentrated to dryness to give 6.9 g (100%) of the desired product as a tan foam: $^1$H-NMR ($\delta$, DMSO) 1.20–1.45 (m, 15H), 3.50–3.60 (m, 1H), 3.65–3.72 (m, 1H), 3.76 (s, 3H), 4.425 (d, J=3 Hz, 2H), 4.50–4.65 (m, 1H), 6.205 (d, 1.9 Hz, 1H), 6.99 (d, J=8.7 Hz, 2H), 7.05–7.32 (m, 5H), 7.33 (d, J=8.7 Hz, 2H), 7.51 (t, J=1.9 Hz, 1H), 10.20 (br s, 1H), 13.48 (br s, 1H); MS (ion spray) 628 (M+1), 629 (M+2); Anal. Calc'd for $C_{31}H_{38}FN_5O_8$ 0.5H$_2$O: C, 58.31; H, 6.33; N, 10.99. Found: C, 58.75; H, 6.26; N, 10.56.

Preparation 358

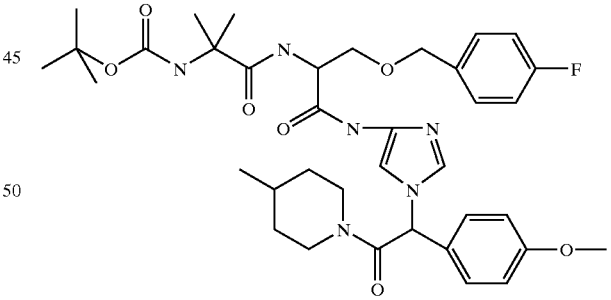

To a solution of 7.0 g (11 mmol) of the product of Preparation 357 in 130 mL of N,N-dimethylformamide was added 1.42 mL (12 mmol) of 4-methylpiperidine, 1.62 g (12 mmol) of 1-hydroxybenzotriazole hydrate, and 2.37 g (11.5 mmol) of dicyclohexylcarbodiimide. The reaction mixture was stirred at ambient temperature for 38 h, then filtered, the precipitate was washed with ethyl acetate (2×20 mL) and the filtrate was concentrated on rotavap. The resulting brown syrup was partitioned between ethyl acetate (200 mL) and 0.5N HCl (100 mL) and the layers were quickly separated. The organic extract was washed with 100 mL each of saturated sodium bicarbonate and brine. The organic extract was dried over anhydrous sodium sulfate, filtered, and concentrated to give 7 g of crude product as a tan foam which was purified by flash chromatography (silica gel, 3% methanol/dichloromethane) to give 5.7 g (73%) of the desired product as light brown foam: $^1$H-NMR (δ, DMSO) 0.12–0.30 (m, 0.5H), 0.75 (d, J=6.4 Hz, 1.5H), 0.88 (d, J=6.0 Hz, 1.5H), 0.80–1.15 (m, 2H), 1.20–1.40 (m, 15 H), 1.45–1.67 (m, 2.5H), 2.55–2.75 (m, 1.5H), 2.93–3.07 (m, 0.5H), 3.50–3.60 (m, 1H), 3.60–3.70 (m, 1H), 3.75 (d, J=3.4 Hz, 3H), 3.60–3.85 (m, 1H), 4.30–4.45 (m, 1H), 4.425 (d, J=3.0 Hz, 2H), 4.50–4.65 (m, 1H), 6.62 (d, J=12 Hz, 1H), 6.98 (t, J=9.4 Hz, 2H), 7.05–7.45 (m, 10H), 10.13 (br s, 1H); MS (ion spray) 709 (M+1); Anal. Calc'd for $C_{37}H_{49}FN_6O_7$: C, 62.70; H, 6.97; N, 11.86. Found: C, 62.44; H, 6.99; N, 11.89.

Examples 203 and 204

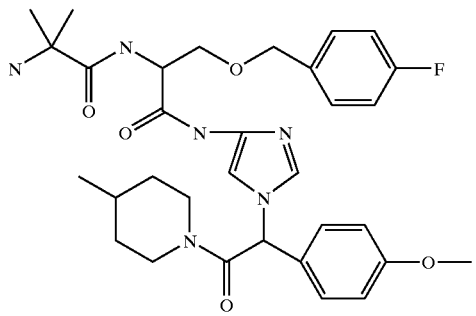

Trifluoroacetic acid (6 mL) was added to a solution of the product of Preparation 358 (3.88 g, 5.47 mmol) in 15 mL of dichloromethane and the resulting brown solution was stirred at ambient temperature for 4 h. The mixture was poured into 300 mL of saturated sodium bicarbonate and extracted with ethyl acetate (1×150 mL). The yellow brown color organic layer was separated and the aqueous layer was saturated with sodium chloride and extracted with fresh ethyl acetate. The aqueous layer was discarded. The organic extracts were combined, washed with brine, dried over anhydrous sodium sulfate, filtered, and concentrated to give 3.2 g (96%) of diastereomeric mixture of the desired product as a light brown foam: $^1$-NMR (δ, DMSO) consistent with the structure; MS (ion spray) 609 (M+1); Anal. Calc'd for $C_{32}H_{41}FN_6O_5 \cdot 0.5H_2O$: C, 62.22; H, 6.85; N, 13.60. Found: C, 62.14; H, 6.62; N, 13.62. This material (3.0 g) was purified by HPLC (8×15 cm Prochrom column packed with Kromsil CHI-DMP chiral phase, eluted with a mixture of 3A alcohol and dimethylethylamine in heptane) to provide the individual diastereomers which were converted to their respective hydrochloride salts as described below:

Example 203

Isomer 1

1.28 g (2.1 mmol) of pure free amine of isomer 1 (lot #CJ4-LFK-53B) was dissolved in 21 mL of 1N HCl, diluted with 21 mL of deionized water, and the resulting solution was freeze-dried to give 1.3 g (96%) of the desired product as a light brown powder: $^1$H-NMR (δ, DMSO) 0.1–0.25 (m, 0.5H), 0.75 (d, J=6.4 Hz, 1.5H), 0.88 (d, J=6.0 Hz, 1.5H), 0.8–1.22 (m, 1.5H), 1.22–1.40 (m, 0.5H), 1.40–1.75 (m, 8.5H), 2.55–2.75 (m, 1.5H), 2.95–3.10 (m, 0.5H), 3.60–3.75 (m, 3H), 3.76 (d, J=3.4 Hz, 3H), 4.25–4.45 (m, 1H), 4.50 (s, 2H), 4.65–4.75 (m, 1H), 6.79 (d, J=12.8 Hz, 1H), 6.95–7.45 (m, 9H), 7.80–7.95 (m, 1H), 8.19 (br s, 3H, exchangeable with deuterium), 8.52 (d, J=6.8 Hz, 1H, exchangeable with deuterium), 10.86 (br s, 1H, exchangeable with deuterium); $t_R$=7.40 min; MS (ion spray) 610 (M+1); Anal. Calc'd for $C_{32}H_{41}FN_6O_5 \cdot 2HCl \cdot 0.5H_2O$: C, 55.73; H, 6.43; N, 12.19. Found: C, 55.50; H, 6.33; N, 12.12.

Example 204

Isomer 2

1.1 g (1.8 mmol) of pure free amine of isomer 2 (lot #CJ4-LFK-53A) was dissolved in 20 mL of 1N HCl, diluted with 20 mL of deionized water, and the resulting solution was freeze-dried to give 1.1 g (95%) of the desired product as a light brown powder: $^1$H-NMR (δ, DMSO) 0.05–0.25 (m, 0.5H), 0.75 (d, J=6.4 Hz, 1.5H), 0.89 (d, J=6.0 Hz, 1.5H), 0.8–1.40 (m, 2H), 1.40–1.70 (m, 8.5H), 2.55–2.75 (m, 1.5H), 2.95–3.10 (m, 0.5H), 3.60–3.75 (m, 3H), 3.77 (d, J=3.0 Hz, 3H), 4.30–4.45 (m, 1H), 4.49 (s, 2H), 4.68–4.78 (m, 1H), 6.87 (d, J=13.6 Hz, 1H), 6.98–7.18 (m, 4H), 7.25–7.45 (m, 5H), 8.05–8.20 (m, 1H), 8.27 (br s, 3H, exchangeable with deuterium), 8.57 (d, J=6.8 Hz, 1H, exchangeable with deuterium), 11.04 (br s, 1H, exchangeable with deuterium); $t_R$=9.43 min; MS (ion spray) 610 (M+1); Anal. Calc'd for $C_{32}H_{41}FN_6O_5 \cdot 2HCl \cdot 0.5H_2O$: C, 55.73; H, 6.43; N, 12.19. Found: C, 55.33; H, 6.40; N, 12.02.

Preparation 359

This is Preparation 457 from Examples Part 2C.

Preparation 360

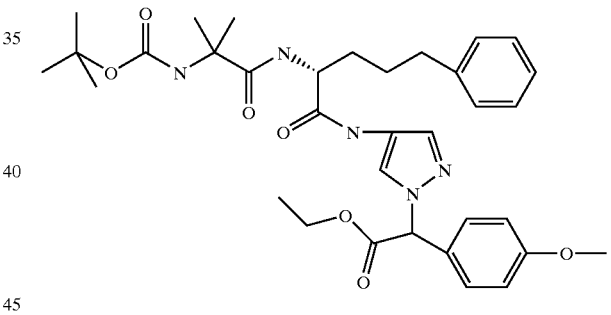

5.5 g of 5% palladium on carbon was added under nitrogen atmosphere to a solution of 4.49 g (18 cool) 4-nitropyrazole in 30 mL of tetrahydrofuran and the resulting slurry was hydrogenated at ~50 psi of hydrogen for 2 h. The mixture was filtered through celite and the catalyst was washed with tetrahydrofuran (10×25 mL). The resulting yellow brown filtrate (~300 mL) was added to a mixture of 6.05 g (16 mmol) of the product of Preparation 1j and 2.43 g (18 mmol) of 1-hydroxybenzotriazole. To this stirred brown solution was added 3.5 g (17 mmol) of 1,3-dicyclohexylcarbodiimide and the mixture was stirred at ambient temperature for 21 h, then concentrated. The residue was dissolved in 150 mL of ethyl acetate and filtered through celite. The brown filtrate was washed successively with 100 mL each of 0.5N HCl, 1N sodium bicarbonate, brine, dried over anhydrous sodium sulfate, filtered, and concentrated to dryness to give 11.6 g of crude product as a tan foam which was purified by flash chromatography (silica gel, 3% methanol in dichloromethane) to give 9.8 g (96%) of the desired product as a tan foam: $^1$H-NMR (δ, DMSO) 1.15 (t, J=7.1, 6.8 Hz, 3H), 1.20–1.40 (m, 15H), 1.45–1.90

(m, 4H), 2.45–2.65 (m, 2H), 3.77 (s, 3H), 4.10–4.28 (m, 3H), 6.30 (s, 1H), 6.98 (d, J=9.0 Hz, 2H), 7.10–7.30 (m, 6H), 7.36 (d, J=8.7 Hz, 2H), 7.54 (d, J=5.3 Hz, 1H), 7.69 (d, J=0.75 Hz, 1H), 7.82 (be s, 1H), 9.70 (br s, 1H); MS (ion spray) 636 (M+1); Anal. Calc'd for $C_{34}H_{45}N_5O_7$: C, 64.23; H, 7.13; N, 11.02. Found: C, 64.50; H, 7.25; N, 11.06.

Preparation 361

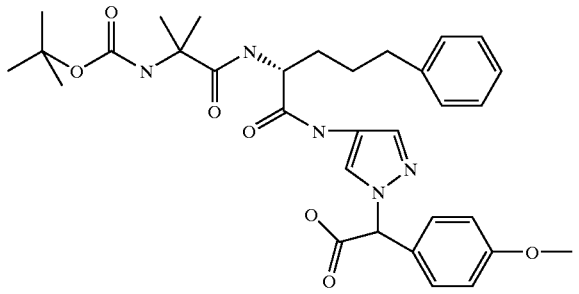

16.5 mL (16.5 mmol) of 1M solution of lithium hydroxide was added in one lot to a stirred solution of the product of Preparation 360 (8.3 g, 13 mmol) in 60 mL of dioxane and 35 mL of deionized water. The mixture was stirred at ambient temperature for 20 min and extracted it with ether (3×40 mL). The light yellow colored ether extracts were discarded. The brown aqueous layer (pH~12) was cooled in ice-water bath and acidified to pH~4 with cold 0.5N HCl and quickly extracted the separated light brown precipitate with ethyl acetate (1×200 mL). The light yellow colored aqueous layer was saturated with sodium chloride, further acidified to pH~1–2 and extracted with ethyl acetate. The aqueous layer was discarded. The organic extracts were combined, washed with brine, dried over anhydrous sodium sulfate, filtered, and concentrated to dryness to give 7.9 g (100%) the desired product as a tan foam: $^1$H-NMR (δ, DMSO/D$_2$O) 1.25–1.35 (m, 15H), 1.40–1.85 (m, 4H), 2.45–2.60 (m, 2H), 3.75 (s, 3H), 4.12–4.27 (m, 1H), 6.14 (s, 1H), 6.97 (d, J=8.7 Hz, 2H), 7.10–7.18 (m, 3H), 7.20–7.30 (m, 2H), 7.35 (d, J=8.7 Hz, 2H), 7.53 (d, J=6.4 Hz, 1H), 7.67 (d, J=3.0 Hz, 1H), 7.80 (br s, 1H, exchangeable with deuterium), 9.70 (br s, 1H, exchangeable with deuterium), 13.30 (br s, 1H, exchangeable with deuterium): MS (ion spray) 608 (M+1); Anal. Calc'd for $C_{32}H_{41}N_5O_7$: C, 63.25; H, 6.80; N, 11.52. Found: C, 63.18; H, 6.98; N, 10.64.

Preparation 362

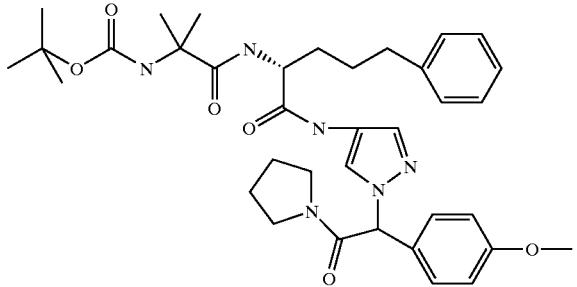

To a solution of 6.08 g (10 mmol) of the product of Preparation 361 in 100 mL of N,N-dimethylformamide was added 1.25 mL (15 mmol) of pyrrolidine, 1.62 g (12 mmol) of 1-hydroxybenzotriazole hydrate, and 2.27 g (11 mmol) of dicyclohexylcarbodiimide. The reaction mixture was stirred at ambient temperature for 46 h, then concentrated. The resulting brown syrup was disolved in ethyl acetate (150 mL) and filtered. The filtrate was washed successively with 0.5N HCl (2×25 mL), saturated sodium bicarbonate (2×25 mL) and brine (1×30 mL). The organic layer was dried over anhydrous sodium sulfate, filtered, and concentrated to dryness to give 5.96 g of crude product as a off white foam which was purified by flash chromatography (silica gel, 3% methanol/dichloromethane) to give 5.7 g (80.6%) of the desired product as white foam: $^1$H-NMR (δ, DMSO) 1.20–1.40 (m, 15H), 1.45–1.95 (m, 8H), 2.45–2.60 (m, 2H), 2.98–3.10 (m, 1H), 3.25–3.43 (m, 2H), 3.45–3.60 (m, 1H), 3.76 (s, 3H), 4.15–4.30 (m, 1H), 6.36 (s, 1H), 6.98 (d, J=8.7 Hz, 2H), 7.10–7.30 (m, 6H, 1H exchangeable with deuterium), 7.34 (dd, J=8.7, 1.9 Hz, 2H), 7.50 (d, J=10.6 Hz, 1H), 7.63 (d, J=6.4 Hz, 1H), 7.70–7.90 (m, 1H, exchangeable with deuterium), 9.66 (m, 1H, exchangeable with deuterium); MS (ion spray) 662 (M+1); Anal. Calc'd for $C_{36}H_{48}N_6O_6$: C, 65.43; H, 7.32; N, 12.72. Found: C, 65.14; H, 7.09; N, 12.91.

Example 205

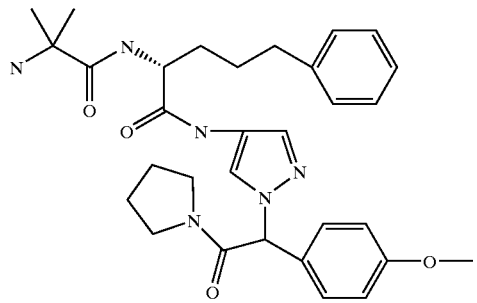

Trifluoroacetic acid (7 mL) was added to a solution of the product of Preparation 363 (4.05 g, 6.13 mmol) in 18 mL of dichloromethane and the resulting clear brown solution was stirred at ambient temperature for 4 h. The mixture was poured into 300 mL of saturated sodium bicarbonate and extracted with ethyl acetate (1×150 mL). The yellow brown color organic layer was separated and the aqueous layer was saturated with sodium chloride and extracted with fresh ethyl acetate. The aqueous layer was discarded. The organic extracts were combined, washed with brine, dried over anhydrous sodium sulfate, filtered, and concentrated to give 3.48 g (99%) of diastereomeric mixture of the desired product (free base form) as a white foam: $^1$H-NMR (δ, DMSO) 1.15–1.25 (m, 6H), 1.45–1.95 (m, 8H), 2.45–2.60 (m, 2H), 2.97–3.07 (m, 1H), 3.25–3.45 (m, 2H), 3.47–3.60 (m, 1H), 3.77 (s, 3H), 4.27–4.37 (m, 1H), 6.36 (s, 1H), 6.98 (d, J=8.7 Hz, 2H), 7.10–7.18 (m, 3H), 7.20–7.30 (m, 2H), 7.35 (d, J=8.7 Hz, 2H), 7.42 (s, 1H), 7.65 (s, 1H), 8.10 (br s, 1H, exchangeable with deuterium), 10.10 (s, 1H, exchangeable with deuterium); MS (ion spray) 562 (M+1); Anal. Calc'd for $C_{31}H_{40}N_6O_4 \cdot 0.5H_2O$: C, 65.35; H, 7.25; N, 14.75. Found: C, 65.39; H, 7.27; N, 14.12.

Example 206

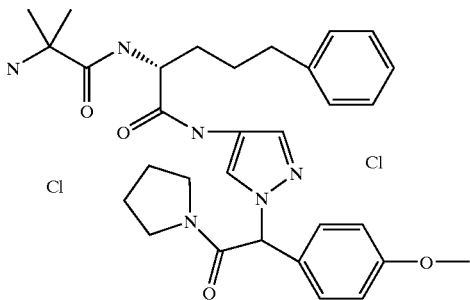

82 mg (0.146 mmol) of the product of Example 205 was dissolved in 2 mL of 1N HCl and diluted with 2 mL of deionized water and the resulting slightly turbid solution was freeze-dried to give 89.5 mg (97%) of the desired product as a off-white crystalline solid: $^1$H-NMR ($\delta$, DMSO) consistent with the structure; MS (ion spray) 562 (Free base) (M+1); Anal. Calc'd for $C_{31}H_{40}N_6O_4 \cdot H_2O$: C, 57.14; H, 6.50; N, 12.90. Found: C, 57.35; H, 6.77; N, 12.89.

Preparation 363

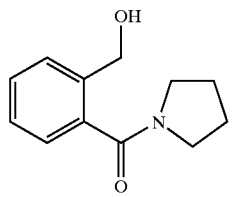

To a solution of phthalide (6.0 g, 44.8 mmol) in ethanol (150 ml) was added pyrrolidine (15.0 mL, 180 mmol) and the mixture stirred for 48 h at ambient temperature. The mixture was then concentrated and the residue purified by flash chromatography (silica gel, ethyl acetate) to yield 8.50 g (92%) of the desired product as an oil.

ESMS: (M+1)$^+$ 206.2. $^1$H NMR (DMSO-d$_6$) $\delta$ 7.53–7.45 (m, 1H), 7.42–7.33 (m, 1H), 7.31–7.25 (m, 1H), 7.23–7.17 (m, 1H), 5.11 (t, J=5.65 Hz, 1H), 4.44 (d, J=5.65 Hz, 2H), 3.45 (t, J=6.78 Hz, 2H), 3.09 (t, J=6.78 Hz, 2H), 1.92 (m, 4H). Anal. Calcd. for $C_{12}H_{15}NO_2 \cdot 0.1EtOAc$: C, 69.57; H, 7.44; N, 6.54. Found: C, 69.67; H, 7.41; N, 6.54.

Preparation 364

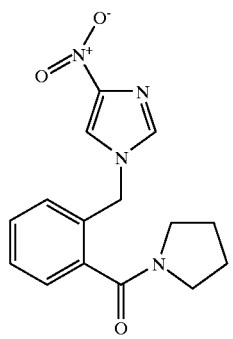

The compound from Preparation 363 (2.05 g, 10.0 mmol) was combined with 4-nitroimidazole (1.13 g, 10.0 mmol) and triphenylphosphine (2.62 g, 10.0 mmol) in tetrahydrofuran (75 mL) and the mixture cooled in an ice bath. Diethylazodicarboxylate (2.00 mL, 13.0 mmol) was then added via syringe and the mixture stirred overnight while warming to ambient temperature. The mixture was concentrated and the residue purified by flash chromatography (silica gel, ethyl acetate) to provide 1.16 g of the desired product as a yellow solid: ESMS: (M+1)$^+$ 301.2; $^1$H NMR was consistent with product.

Preparation 365

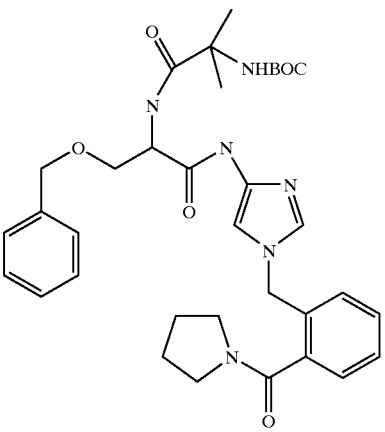

The product of Preparation 364 (0.50 g, 1.7 mmol) was added to a mixture of 10% palladium/carbon (0.20 g) and palladium/black (0.05 g) in tetrahydrofuran (30 mL) and the mixture shaken under hydrogen (40 psi) in a Parr apparatus. After the reduction was complete, the reaction mixture was filtered through celite and the filtrate immediately combined with 1,3-dicyclohexylcarbodiimide (0.344 g, 1.7 mmol), 1-hydroxybenzotriazole mono-hydrate (0.225 g, 1.7 mmol), and the product of Preparation 1d, (0.633 g, 1.7 mmol). After stirring overnight at ambient temperature, the mixture was concentrated and the resulting residue slurried in ethyl acetate and filtered. The filtrate was concentrated and the residue purified by flash chromatography (silica gel, chloroform/methanol) which provided 0.68 g (64%) of product as a white solid. ESMS: (M+1)$^+$ 633.2. 634.2. $^1$H NMR was consistent with product. Anal. Calcd. for $C_{34}H_{44}N_6O_6$: C, 64.54; H, 7.01; N, 13.28. Found: C, 64.78; H, 7.21; N, 13.31.

Example 207

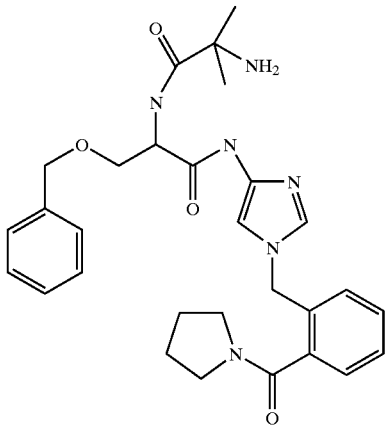

To a solution of the compound from Preparation 365 (0.58 g, 0.92 mmol) stirring in dichloromethane (20 mL) at room temperature was added trifluoroacetic acid (5 mL). After stirring for 1.5 h, the reaction mixture was concentrated and the residue treated with excess aqueous sodium bicarbonate. The mixture was extracted with ethyl acetate and chloroform. The extracts were concentrated and the residue purified by flash chromatography (silica gel, chloroform/methanol) to give 0.40 g of the product. ESMS: (M+1)⁺ 533.3, 534.0. ¹H NMR was consistent with product.

Anal. Calcd. for $C_{29}H_{36}N_6O_4 \cdot 0.23CHCl_3$: C, 62.68; H, 6.52; N, 15.00. Found: C, 62.84; H, 6.56; N, 14.62.

Preparation 366

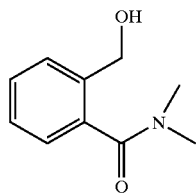

To a solution of phthalide (2.10 g, 15.7 mmol) in ethanol (50 mL) was added dimethyl amine (40% aqueous, 5.0 mL, 40 ml) and the mixture stirred for 72 hours at ambient temperature. The mixture was then concentrated and the residue purified by flash chromatography (silica gel, ethyl acetate) to yield 1.46 g (52%) of the desired product as an oil. ESMS: (M+1)⁺ 180.1. ¹H NMR was consistent with product.

Preparation 367

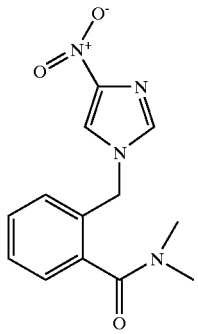

To the compound from Preparation 366 (1.40 g, 9.0 mmol) was dissolved in dichloromethane (25 mL) followed by the addition of triethylamine (1.25 mL, 9.0 mmol). Then methane sulfonylchloride (0.70 mL, 9.0 mmol) was added dropwise via syringe and the resulting mixture stirred for 0.5 h at ambient temperature. The mixture was then concentrated and the residue combined with potassium carbonate (1.24 g, 18.0 mmol) and 4-nitroimidazole (1.02 g, 9.0 mmol) in dimethylformamide (25 mL) and this mixture stirred overnight at ambient temperature. The mixture was concentrated and combined with water followed by extraction with ethyl acetate. Concentration of the combined extracts left crude product which was purified by flash chromatography (silica gel, chloroform/methanol) to give 0.40 g (15%) of the desired product: ESMS: (M+1)⁺ 275.3. ¹H NMR (300 MHz, DMSO-d₆) δ 8.33 (d, J=1.51 Hz, 1H), 7.85 (d, J=1.51 Hz, 1H), 7.50–7.37 (m, 3H), 7.35–7.28 (m, 1H), 5.24 (s, 2H), 2.97 (s, 3H), 2.65 (s, 3H). Anal. Calcd. for $C_{13}H_{14}N_4O_3$: C, 56.92; H, 5.14; N, 20.43. Found: C, 57.17; H, 5.16; N, 20.40.

Preparation 368

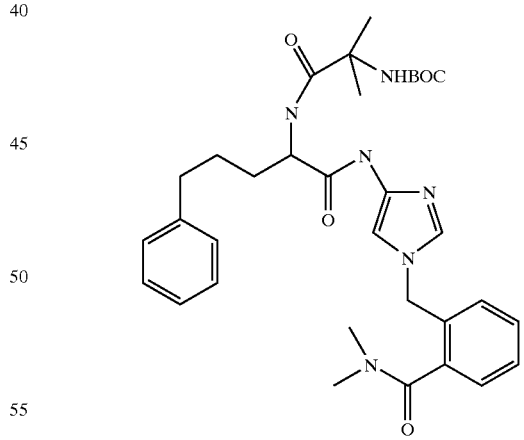

The product of Preparation 367 (1.70 g, 6.2 mmol) was added to a mixture of 10% palladium/carbon (1.2 g) and palladium/black (0.5 g) in tetrahydrofuran (100 mL) and the mixture shaken under hydrogen (38 psi) in a Parr apparatus. After the reduction was complete, the reaction mixture was filtered through celite and the filtrate immediately combined with 1,3-dicyclohexylcarbodiimide (1.28 g, 6.2 mmol), 1-hydroxybenzotriazole mono-hydrate (0.840 g, 6.2 mmol) and the product of Preparation 1j, (2.35 g, 6.2 mmol). After stirring overnight at ambient temperature, the mixture was concentrated and the resulting residue slurried in ethyl acetate and filtered. The filtrate was concentrated and the residue purified by flash chromatography (silica gel, chloroform/methanol) which provided 3.35 g (88%) of product as a white foam. ESMS: (M+1)⁺ 605.4, 606.5. ¹H NMR was consistent with product.

Example 208

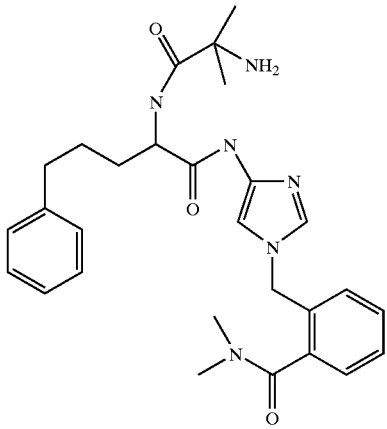

To a solution of the compound from Preparation 368 (3.30 g, 5.5 mmol) stirring in dichloromethane (40 mL) at room temperature was added trifluoroacetic acid (10 mL). After stirring for 2.5 h, the reaction mixture was concentrated and the residue treated with excess aqueous sodium bicarbonate. The mixture was extracted with ethyl acetate and the combined extracts were dried over sodium sulfate and concentrated. The residue was purified by flash chromatography (silica gel, chloroform/methanol) to give 1.10 g of the product as an off white solid: ESMS: (M+1)⁺ 505.2, 506.4. ¹H NMR was consistent with product. Anal. Calcd. for $C_{28}H_{36}N_6O_3 \cdot 0.1CHCl_3$: C, 65.34; H, 7.04; N, 16.27. Found: C, 65.67; H, 7.08; N, 15.94.

Preparation 369

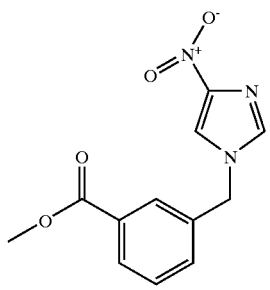

Methyl-3-bromomethyl benzoate (6.08 g, 26.5 mmol) was combined with 4-nitroimidazole (3.00 g, 26.5 mmol) and potassium carbonate (9.04 g, 26.5 mmol) in dimethylformamide (75 mL) and the mixture stirred overnight at ambient temperature. The mixture was then concentrated and the residue taken up in water and extracted with chloroform.

The combined extracts were dried over sodium sulfate and concentrated leaving a residue which was purified by flash chromatography (silica gel, chloroform/methanol) to give 5.77 g (83%) of product as an off white solid. ESMS: (M+1)⁺ 262.2; ¹H NMR (300 MHz, DMSO-d₆) δ 8.54 (s, 1H), 8.05 (s, 1H), 8.02 (d, 1H), 7.95 (d, J=7.7 Hz, 1H), 7.69 (d, J=7.7 Hz, 1H), 7.57 (t, J=7.7 Hz, 1H), 5.41 (s, 2H) 3.87 (s, 3H). Anal. Calcd. for: $C_{12}H_{11}N_3O_4 \cdot 0.15CHCl_3$: C, 65.54; H, 7.33; N, 13.90. Found: C, 65.41; H, 7.37; N, 13.48.

Preparation 370

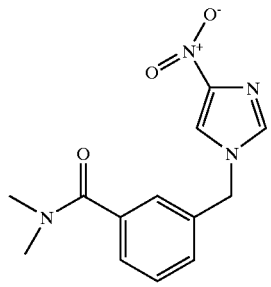

To a solution of Preparation 369 (4.00 g, 15.3 mmol) in ethanol (5 mL) and tetrahydrofuran (10 mL) was added sodium hydroxide (50 mL of 2 N aqueous solution) and the mixture stirred at ambient temperature until hydrolysis was complete. The aqueous mixture wag acidified to pH 2.0 with aqueous hydrochloric acid and the organics extracted with ethyl acetate. Concentration left the crude acid which was combined with 1,3-dicyclohexylcarbodiimide (3.15 g, 15.3 mmol), 1-hydroxybenzotriazole mono-hydrate (2.06 g, 15.3 mmol), and dimethylamine (40% aqueous, 1.75 mL, 14.0 mmol) in tetrahydrofuran (75 mL) and the mixture stirred overnight at ambient temperature. The mixture was concentrated and the resulting residue slurried in ethyl acetate and filtered. The filtrate was concentrated and the residue purified by flash chromatography (silica gel, chloroform/methanol) which provided 2.50 g (60%) of the desired product as a tan solid. ESMS: (M+1)⁺ 275.3; ¹H NMR (300 MHz, DMSO-d₆) δ 8.54 (d, J=1.25 Hz, 1H), 8.3 (d, J=1.25 Hz, 1H), 7.50–7.32 (m, 4H), 5.34 (s, 2H), 2.97 (s, 3H), 2.87 (s, 3H). Anal. Calcd. for: $C_{12}H_{11}N_3O_4$: C, 56.93; H, 5.14; N, 20.43. Found: C, 57.21; H, 5.34; N, 20.36.

Preparation 371

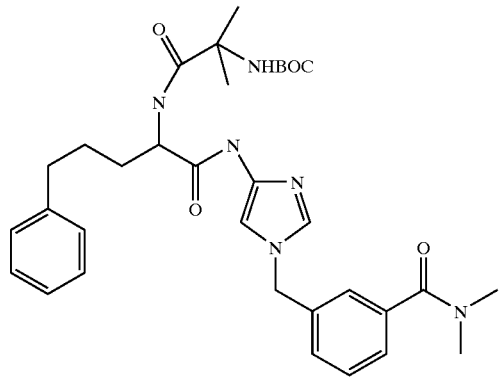

The product of Preparation 370 (1.0 g, 4.0 mmol) was added to a mixture of 10% palladium/carbon (0.80 g) and palladium/black (0.30 g) in tetrahydrofuran (100 mL) and the mixture shaken under hydrogen (39 psi) in a Parr apparatus.

After the reduction was complete, the reaction mixture was filtered through celite and the filtrate immediately combined with 1,3-dicyclohexylcarbodiimide (0.824 g, 4.0 mmol), 1-hydroxybenzotriazole mono-hydrate (0.540 g, 4.0 mmol), and the product of Preparation 1j, (1.51 g, 4.0 mmol). After stirring overnight at ambient temperature, the mixture was concentrated and the resulting residue slurried in ethyl acetate and filtered. The filtrate was concentrated and the residue purified by flash chromatography (silica gel, chloroform/methanol) which provided 2.05 g (84%) of the desired product as a white solid. ESMS: (M+1)$^+$ 605.4. 606.5. $^1$H NMR was consistent with product. Anal. Calcd. for $C_{33}H_{44}N_6O_5$: C, 65.54; H, 7.33; N, 13.90. Found: C, 65.41; H, 7.37; N, 12.73.

Example 209

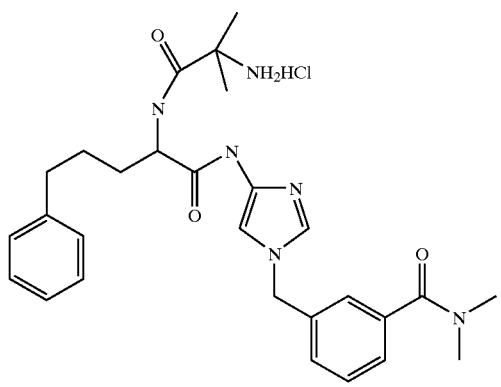

To a solution of the compound from Preparation 371 (2.00 g, 3.3 mmol) stirring in dichloromethane (30 mL) at room temperature was added trifluoroacetic acid (10 mL). After stirring for 2 h, the reaction mixture was concentrated and the residue treated with excess aqueous sodium bicarbonate. The mixture was extracted with ethyl acetate and the combined extracts were dried over sodium sulfate and concentrated. The residue was purified by flash chromatography (silica gel, chloroform/methanol) to give pure free base. This material was dissolved in minimal ethyl acetate/methanol and treated with diethyl ether saturated with hydrochloric acid. Concentration left a semi-solid which was taken up in chloroform, concentrated, and dried to give 0.765 g of a light yellow solid. ESMS: (M+1)$^+$ 505.2, 506.4. $^1$H NMR was consistent with product.

Anal. Calcd. for: $C_{28}H_{41}N_6O_3 \cdot 1CHCl_3$: C, 49.98; H, 5.64; N, 12.06. Found: C, 49.51; H, 6.14; N, 11.67.

Preparation 372

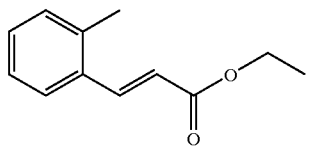

Triethylphosphonoacetate (13.44 g, 60 mmol) was dissolved in tetrahydrofuran (100 mL) and the mixture cooled, under a nitrogen atmosphere, to −50° C. in a dry ice/acetone bath.

Then n-butyllithium (37.5 mL, 1.6 M in hexanes, 60 mmol) was added via syringe and the mixture stirred at −40 to −50° C. for 20 min. before the addition of o-tolualdehyde (6.0 g, 50 mmol). After stirring for 3 h and warming to 10° C., the mixture was quenched with water and the product extracted with ethyl acetate. The combined extracts were dried over sodium sulfate and concentrated yielding an oil which was purified by flash chromatography (silica gel, ethyl acetate) to net 9.25 g (97%) of the desired product. FDMS: (M+) 190.1. $^1$H NMR (DMSO-d$_6$) δ 7.88 (d, J=15.83 Hz, 1H), 7.71 (d, J=7.91 Hz, 1H), 7.35–7.15 (m, 3H), 6.50 (d, J=15.83 Hz, 1H), 4.19 (q, J=7.16 Hz, 2H), 2.39 (s, 3H), 1.26 (t, J=7.16 Hz, 3H).

Anal. Calcd. for $C_{12}H_{14}O_2 \cdot 0.1EtOAc$: C, 74.82; H, 7.49. Found: C, 74.65; H, 7.75.

Preparation 373

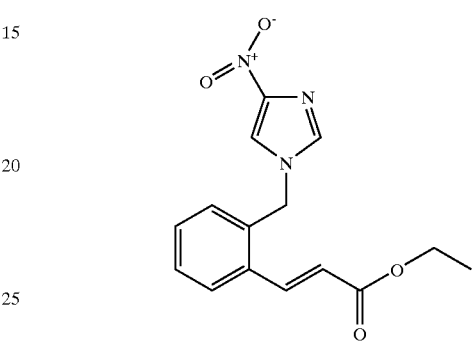

The product from Preparation 372 (3.00 g, 15.8 mmol) was dissolved in carbontetrachloride (50 mL) and N-bromosuccinimide (2.82 g, 15.8 mmol) and 2,2'-azobisisobutyronitrile (cat. 50 mg) were added. This mixture was heated at reflux for 7 h after which the mixture was cooled and filtered. The filtrate was concentrated and added together with potassium carbonate (4.40 g, 31.9 mmol) and 4-nitroimidazole (1.78 g, 15.8 mmol) in dimethylformamide (75 mL). After stirring for 72 h, the mixture was concentrated, water added, and extracted with ethyl acetate. The combined extracts were concentrated and the resulting residue purified by flash chromatography (chloroform/methanol) to give 2.60 g (55%) of the product as an oil. ESMS: (M+1)$^+$ 302.3.

$^1$H NMR (300 MHz, DMSO-d$_6$) δ 6.32 (d, J=1.5 Hz, 1H), 7.95 (d, J=15.6 Hz, 1H), 7.86 (d, J=1.5 Hz, 1H), 7.84–7.70 (m, 1H), 7.50–7.38 (m, 2H), 7.19–7.12 (m, 1H), 6.54 (d, J=15.6 Hz, 1H), 5.59 (s, 2H), 4.20 (q, J=7.0 Hz, 2H), 1.27 (t, J=7.0 Hz, 3H), Anal. Calcd. for $C_{15}H_{15}N_3O_4$: C, 55.31; H, 4.64; N, 12.69. Found: C, 55.37; H, 4.75; N, 12.80.

Preparation 374

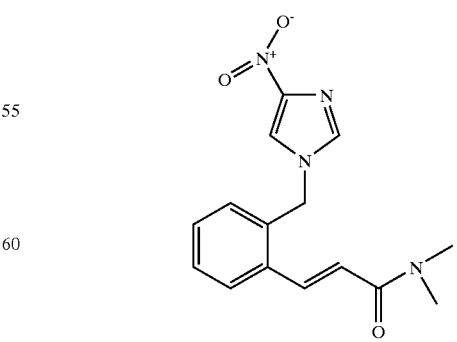

To a solution of Preparation 373 (2.50 g, 8.3 mmol) in ethanol (5 mL) and tetrahydrofuran (10 mL) was added sodium hydroxide (30 mL of 2 N aqueous solution) and the mixture stirred at ambient temperature until hydrolysis was complete. The aqueous mixture was acidified to pH 1.8 with aqueous hydrochloric acid and extracted with ethyl acetate. Concentration left the 2.20 g of the acid as a tan solid. ESMS: (M+1)$^+$ 264.2. $^1$H NMR (300 MHz, DMSO-d$_6$) δ 12.58 (bs, 1H), 8.32 (s, 1H), 7.90 (d, J=15.6 Hz, 1H), 7.87 (s, 1H), 7.80–7.70 (m, 1H), 7.50–7.37 (m, 2H), 7.17–7.10 (m, 1H), 6.44 (d, J=15.6 Hz, 1H), 5.58 (s, 2H).

The acid (2.00 g, 7.3 mmol) was combined with 1,3-dicyclo-hexylcarbodiimide (1.51 g, 7.3 mmol), 1-hydroxybenzotriazole mono-hydrate (0.98 g, 7.3 mmol), and dimethylamine (40% aqueous, 1.00 mL, 8.0 mmol) in tetrahydrofuran (100 mL) and the mixture stirred overnight at ambient temperature. The mixture was concentrated and the resulting residue purified by flash chromatography (silica gel, chloroform/methanol) which provided 1.78 g (81%) of the desired amide.

ESMS: (M+1)$^+$ 301.2, 302.3. Anal. Calcd. for C$_{15}$H$_{16}$N$_4$O$_3$: C, 59.99; H, 5.37; N, 18.66. Found: C, 59.79; H, 5.34; N, 18.51.

Preparation 375

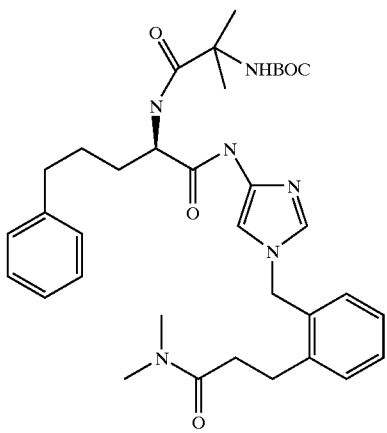

The product of Preparation 374 (1.20 g, 4.0 mmol) was added to a mixture of 10% palladium/carbon (0.95 g) and palladium/black (0.25 g) in tetrahydrofuran (100 mL) and the mixture shaken under hydrogen (38 psi) in a Parr apparatus.

After the reduction was complete, the reaction mixture was filtered through celite and the filtrate immediately combined with 1,3-dicyclohexylcarbodiimide (0.824 g, 4.0 mmol), 1-hydroxybenzotriazole mono-hydrate (0.540 g, 4.0 mmol), and the product of Preparation 1j, (1.51 g, 4.0 mmol). After stirring overnight at ambient temperature, the mixture was concentrated and the resulting residue slurried in ethyl acetate and filtered. The filtrate was concentrated and the residue purified by flash chromatography (silica gel, chloroform/methanol) which provided 1.75 g (69%) of product as a yellow solid. ESMS: (M+1)$^+$ 633.5, 634.5. $^1$H NMR was consistent with product. Anal. Calcd. for C$_{35}$H$_{48}$N$_6$O$_5$·0.2CHCl$_3$: C, 64.38; H, 7.40; N, 12.80. Found: C, 64.41; H, 7.63; N, 12.14.

Example 210

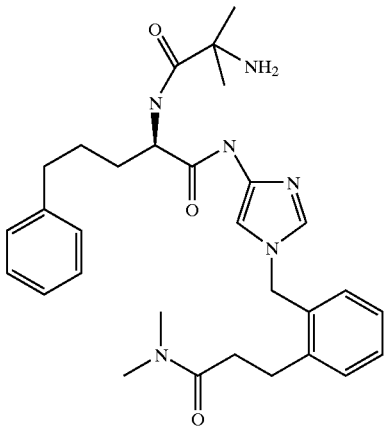

To a solution of the compound from Preparation 375 (1.6 g, 2.5 mmol) stirring in dichloromethane (20 mL) at room temperature was added trifluoroacetic acid (5 mL). After stirring for 1 h, the reaction mixture was concentrated and the residue treated with excess aqueous sodium bicarbonate. The mixture was extracted with ethyl acetate and the combined extracts were dried over sodium sulfate and concentrated. The residue was purified by flash chromatography (silica gel, dichloromethane/methanol) to give the free base. This compound was dissolved in minimal ethyl acetate and excess ether saturated with hydrochloric acid was added. Concentration and drying netted 0.53 g of the hydrochloride salt as a white solid. ESMS: (M+1)$^+$ 533.2. 534.3. $^1$H NMR was consistent with product.

Anal. Calcd. for C$_{30}$H$_{39}$N$_6$O$_3$·3HCl: C, 59.99; H, 5.37; N, 18.66. Found: C, 59.79; H, 5.34; N, 18.51.

Preparation 376

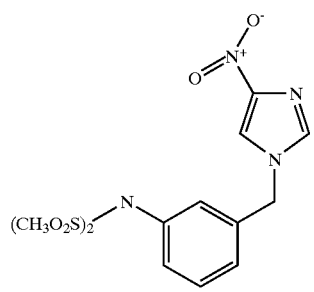

To 3-aminobenzyl alcohol (3.00 g, 24.4 mmol) in dichloromethane (55 mL) was added triethylamine (17 mL, 122 mmol) and 4-dimethylaminopyridine (cat. 50 mg) and the mixture cooled to 0° C. under a nitrogen atmosphere. Then methanesulfonyl chloride (9.4 mL, 122 mmol) was added dropwise via syringe and the resulting mixture stirred for 2 h while warming to ambient temperature. The mixture was concentrated in vacuo and the residue taken up in dimethylformamide (100 mL) and solid potassium carbonate (20 g, 146 mmol) added along with 4-nitro-imidazole (2.75 g, 24.3 mmol). This mixture stirred at ambient temperature for 90 h after which the mixture was concentrated and the residue taken up in water and the product extracted with ethyl acetate. The combined extracts were washed with water and dried over sodium sulfate. Concentration left a semi-solid which was tritruated in chloroform and filtered to yield the desired bis-sulfonamide (3.5 g, 38%) as a white solid. ESMS: (M+1)+ 375.2. ¹H NMR (300 MHz, DMSO-d₆) δ 8.51 (d, J=1.13 Hz, 1H), 8.02 (d, J=1.13 Hz, 1H), 7.65–7.45 (m, 4H), 5.36 (s, 2H) 3.54 (s, 6H).

Preparation 377

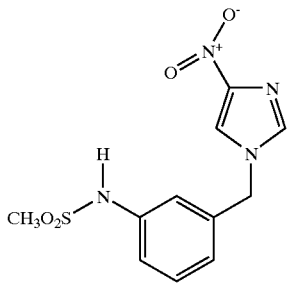

To a solution of Preparation 376 (0.75 g, 2.0 mmol) in ethanol (3 mL) and tetrahydrofuran (3 mL) was added sodium hydroxide (10 mL of 2 N aqueous solution) and the mixture stirred at ambient temperature until hydrolysis was complete. The aqueous mixture was acidified to pH 3.5 with aqueous hydrochloric acid and the organics extracted with ethyl acetate. Concentration left a residue which was purified by flash chromatography (silica gel, chloroform/methanol) which afforded 0.41 g (69%) of pure product as a yellow solid. ESMS: (M+1)+ 297.4; ¹H NMR (300 MHz, DMSO-d₆) δ 9.81 (s, 1H), 8.47 (d, J=1.51 Hz, 1H), 7.98 (d, J=1.51 Hz, 1H), 7.40–7.30 (m, 1H, 7.20–7.00 (m, 3H), 5.31 (s, 2H), 3.00 (s, 3H). Anal. Calcd. for C₁₁H₁₂N₄O₄S: C, 44.59, H, 4.08, N, 18.91. Found: C, 44.12; H, 4.28; N, 18.90.

Preparation 378

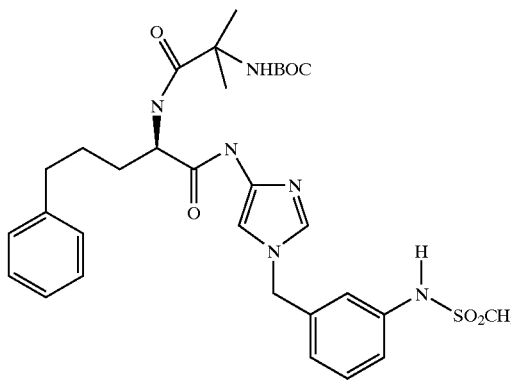

The product of Preparation 377 (0.55 g, 1.86 mmol) was added to a mixture of 10% palladium/carbon (0.40 g) and palladium/black (0.15 g) in tetrahydrofuran (50 mL) and the mixture shaken under hydrogen (40 psi) in a Parr apparatus. After the reduction was complete, the reaction mixture was filtered through celite and the filtrate immediately combined with 1,3-dicyclohexylcarbodiimide (0.384 g, 1.86 mmol), 1-hydroxybenzotriazole mono-hydrate (0.251 g, 1.86 mmol), the product of Preparation 1j, (0.70 g, 1.85 mmol), and additional tetrahydrofuran (30 mL). After stirring overnight at ambient temperature, the mixture was concentrated and the resulting residue slurried in ethyl acetate and filtered. The filtrate was concentrated and the residue purified by flash chromatography (silica gel, chloroform/methanol) which provided 0.66 g (57%) of the desired product as a white solid. ESMS: (M+1)+ 627.4, 628.5. ¹H NMR was consistent with product.

Example 211

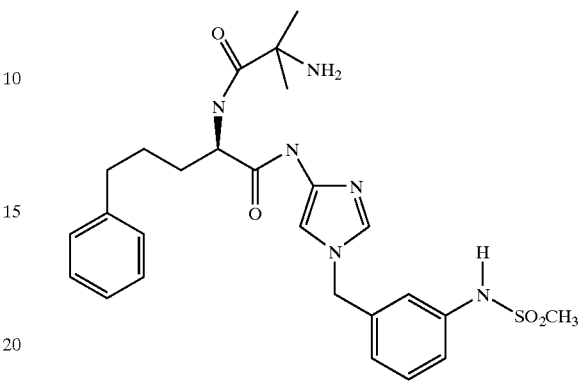

To a solution of the compound from Preparation 379 (0.60 g, 0.96 mmol) stirring in dichloromethane (25 mL) at room temperature was added trifluoroacetic acid (5 mL). After stirring for 2 h, the reaction mixture was concentrated and the residue treated with excess aqueous sodium bicarbonate. The mixture was extracted with ethyl acetate and the combined extracts were dried over sodium sulfate and concentrated. The residue was purified by flash chromatography (silica gel, chloroform/methanol) to give 0.25 g of the desired pure product as a white solid. ESMS: (M+1)+ 527.2. 528.3. ¹H NMR was consistent with product.

Anal. Calcd. for C₂₆H₃₄N₆O₄S: C, 59.30; H, 6.51; N, 15.96. Found: C, 59.13; H, 6.65; N, 15.66.

Preparation 380

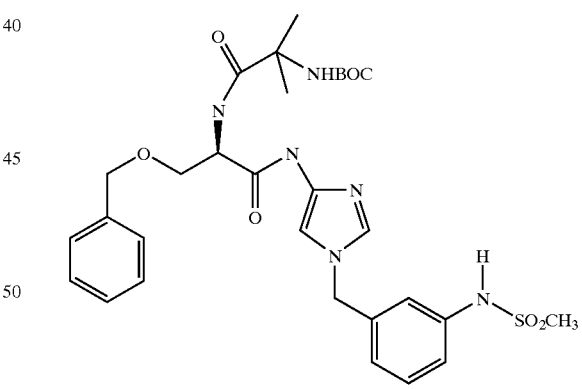

The product of Preparation 377 (0.60 g, 2.03 mmol) was added to a mixture of 10% palladium/carbon (0.50 g) and palladium/black (0.10 g) in tetrahydrofuran (40 mL) and the mixture shaken under hydrogen (39 psi) in a Parr apparatus. After the reduction was complete, the reaction mixture was filtered through celite and the filtrate immediately combined with 1,3-dicyclohexylcarbodiimide (0.418 g, 2.03 mmol), 1-hydroxybenzotriazole mono-hydrate (0.274 g, 2.03 mmol), the product of Preparation 1d, (0.77 g, 2.03 mmol), and additional tetrahydrofuran (40 mL). After stirring overnight at ambient temperature, the mixture was concentrated and the resulting residue slurried in ethyl acetate and filtered.

The filtrate was concentrated and the residue purified by flash chromatography (silica gel, chloroform/methanol) which provided 0.28 g (22%) of the desired product as a light tan solid. ¹H NMR was consistent with product.

Example 212

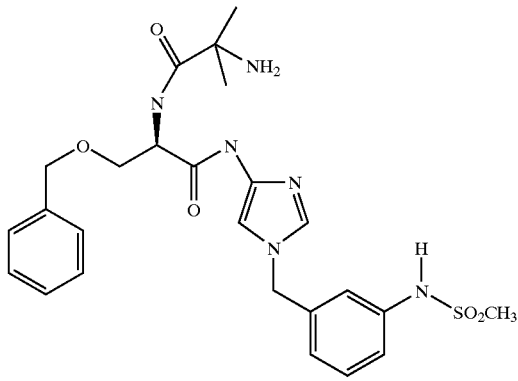

To a solution of the compound from Preparation 380 (0.28 g, 0.44 mmol) stirring in dichloromethane (10 mL) at room temperature was added trifluoroacetic acid (2.5 mL). After stirring for 2.5 h, the reaction mixture was concentrated and the residue treated with excess aqueous sodium bicarbonate. The mixture was extracted with ethyl acetate and the combined extracts were dried over sodium sulfate and concentrated. The residue was purified by flash chromatography (silica gel, chloroform/methanol) to give 45 mg of the desired product as an off white solid. ESMS: (M+1)⁺ 529.2. ¹H NMR was consistent with product. Anal. Calcd. for $C_{25}H_{32}N_6O_5S.2H_2O$: C, 53.18; H, 6.43; N, 14.88. Found: C, 53.40; H, 6.30; N, 13.53.

Preparation 381

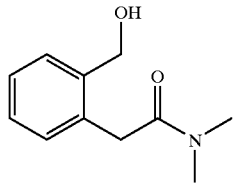

To a solution of 3-isochromanone (3.00 g, 20.0 mmol) in ethanol (40 mL) was added dimethyl amine (40% aqueous, 3.0 mL, 24 mmol) and the mixture stirred for 72 hours at ambient temperature. The mixture was then concentrated and the residue purified by flash chromatography (silica gel, chloroform/methanol) to yield 3.16 g (81%) of the desired product as an oil. ESMS: (M+1)⁺ 194.3. ¹H NMR (DMSO-d₆) δ 7.40–7.34 (m, 1H), 7.25–7.13 (m, 2H), 7.09–7.03 (m, 2H), 5.04 (t, J=5.3 Hz, 1H), 4.44 (d, J=5.3 Hz, 2H), 3.72 (s, 2H), 3.02 (s, 3H), 2.85 (s, 3H).

Preparation 382

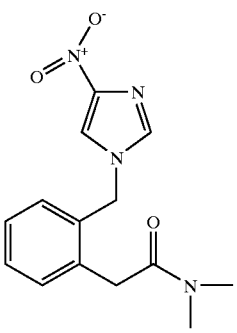

To the compound from Preparation 381 (2.00 g, 10.4 mmol) was dissolved in dichloromethane (40 mL) followed by the addition of triethylamine (1.74 mL, 12.5 mmol). Then methane sulfonylchloride (0.96 mL, 12.5 mmol) was added dropwise via syringe and the resulting mixture stirred for 2.5 h at ambient temperature. The mixture was then concentrated and the residue combined with potassium carbonate (2.85 g, 20.6 mmol) and 4-nitroimidazole (1.17 g, 10.4 mmol) in dimethylformamide (50 mL) and this mixture stirred overnight at ambient temperature. The mixture was concentrated and combined with water followed by extraction with ethyl acetate. Concentration of the combined extracts left crude product which was purified by flash chromatography (silica gel, chloroform/methanol) to give 0.88 g of the desired product as a light solid. ESMS: (M+1)⁺ 289.1. ¹H NMR (300 MHz, DMSO-d₆) δ 8.32 (s, 1H), 7.88 (s, 1H), 7.30–7.05 (m, 4H), 5.27 (s, 2H), 3.85 (s, 2H), 3.06 (s, 3H), 2.82 (s, 3H). Anal. Calcd. for $C_{14}H_{16}N_4O_3.0.05CHCl_3$: C, 57.35. H, 5.50; N, 19.04. Found: C, 57.10; H, 5.53; N, 18.80.

Preparation 383

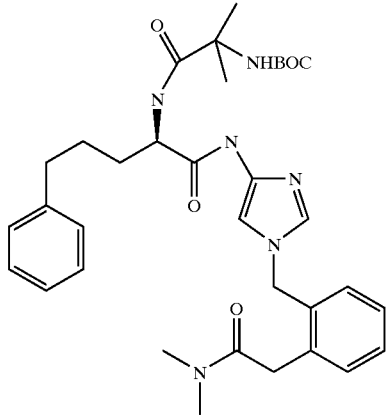

The product of Preparation 382 (0.75 g, 2.6 mmol) was added to a mixture of 10% palladium/carbon (0.60 g) and palladium/black (0.15 g) in tetrahydrofuran (0.40 mL) and the mixture shaken under hydrogen (37 psi) in a Parr apparatus.

After the reduction was complete, the reaction mixture was filtered through celite and the filtrate immediately combined with 1,3-dicyclohexylcarbodiimide (0.537 g, 2.6 mmol), 1-hydroxybenzotriazole mono-hydrate (0.351 g, 2.6 mmol), and the product of Preparation 1j, (0.983 g, 2.6 mmol). After stirring overnight at ambient temperature, the mixture was concentrated and the resulting residue slurried in ethyl acetate and filtered. The filtrate was concentrated and the residue purified by flash chromatography (silica gel, chloroform/methanol) which provided 0.87 g (84%) of product as a tan foam. ESMS: (M+1)+ 619.7, 620.8. ¹H NMR was consistent with product.

Example 213

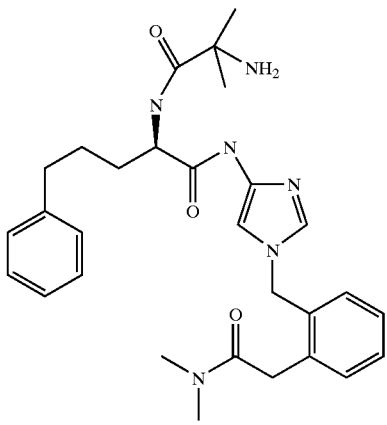

To a solution of the compound from Preparation 383 (0.80 g, 1.3 mmol) stirring in dichloromethane (15 mL) at room temperature was added trifluoroacetic acid (3 mL). After stirring for 1 h, the reaction mixture was concentrated and the residue treated with excess aqueous sodium bicarbonate. The mixture was extracted with ethyl acetate and the combined extracts were dried over sodium sulfate and concentrated. The residue was purified by flash chromatography (silica gel, dichloromethane/methanol) to give 0.14 g of the desired product as a white solid.

ESMS: (M+1)+ 519.3, 520.4. ¹H NMR was consistent with product. Anal. Calcd. for $C_{29}H_{38}N_6O_3 \cdot 0.2CHCl_3$: C, 65.48; H, 7.23; N, 15.69. Found: C, 65.06; H, 7.29; N, 15.62.

Preparation 384

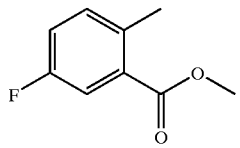

To a solution of 5-flouro-2-methylbenzoic acid (9.00 g, 58.4 mmol) in methanol (200 mL) was added tosic acid mono-hydrate (cat. 0.50 g) and the mixture heated overnight at reflux. The mixture was then concentrated and the residue purified by flash chromatography (silica gel, chloroform/methanol) to yield 5.80 g of the desired ester as an oil.

ESMS: (M+1)+ 167.9; ¹H NMR (300 MHz, DMSO-d₆) δ 7.56 (dd, J=9.4 and 2.6 Hz, 1H), 7.40–7.33 (m, 2H), 3.83 (s, 3H), 2.48 (s, 3H).

Preparation 385

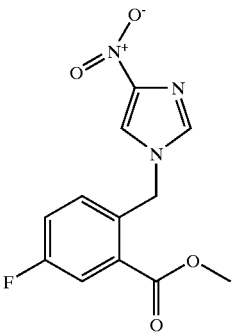

The product from Preparation 384 (5.30 g, 31.5 mmol) was dissolved in carbontetrachloride (75 mL) and N-bromosuccinimide (5.60 g, 31.5 mmol) and 2,2'-azabisisobuytronitrile (cat. 70 mg) were added. This mixture was heated at reflux for 4 h after which the mixture was cooled and filtered. The filtrate was concentrated and added together with potassium carbonate (5.00 g, 36.2 mmol) and 4-nitroimidazole (3.56 g, 31.5 mmol) in dimethylformamide (50 mL). After stirring for overnight at ambient temperature, the mixture was concentrated, water added, and extracted with ethyl acetate. The combined extracts were concentrated and the resulting residue purified by flash chromatography (chloroform/methanol) to give 6.25 g of product as a white solid. ESMS: (M+1)+ 280.1. ¹H NMR (300 MHz, DMSO-d₆) δ 8.36 (d, J=1.51 Hz, 1H), 7.90 (d, J=1.51 Hz, 1H), 7.73 (dd, J=9.42 and 2.64 Hz, 1H), 7.57–7.45 (m, 1H), 7.35–7.25 (m, 1H), 5.60 (s, 2H), 3.87 (s, 3H). Anal. Calcd. for $C_{12}H_{10}N_3O_4F$: C, 51.62; H, 3.61; N, 15.05. Found: C, 52.19; H, 3.75; N, 14.87.

Preparation 386

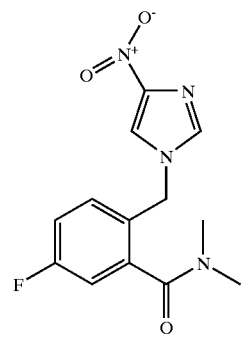

To a solution of Preparation 385 (3.25 g, 11.6 mmol) in ethanol (5 mL) and tetrahydrofuran (5 mL) was added sodium hydroxide (25 mL of 2 N aqueous solution) and the mixture stirred at ambient temperature until hydrolysis was complete. The aqueous mixture was acidified to pH 2.5 with aqueous hydrochloric acid and the organics extracted with ethyl acetate. Concentration left the crude acid as a solid. The acid (2.30 g, 8.7 mmol) was combined with 1,3-dicyclohexylcarbodiimide (1.79 g, 8.7 mmol), 1-hydroxybenzotriazole mono-hydrate (1.17 g, 8.7 mmol), and dimethylamine (40% aqueous, 2.00 mL, 40.0 mmol) in tetrahydrofuran (60 mL) and the mixture stirred overnight at ambient temperature. The mixture was concentrated and the resulting residue slurried in ethyl acetate and filtered. The filtrate was concentrated and the residue purified by flash chromatography (silica gel, chloroform/methanol) which provided for recovery of the desired amide, 1.85 g.

ESMS: (M+1)$^+$ 293.1. $^1$H NMR (300 MHz, DMSO-d$_6$) δ 8.32 (d, J=1.51 Hz, 1H), 7.84 (d, J=1.51 Hz, 1H), 7.55–7.45 (m, 1H), 7.35–7.20 (m, 2H), 5.21 (s, 2H), 2.96 (s, 3H), 2.65 (s, 3H).

Preparation 386A

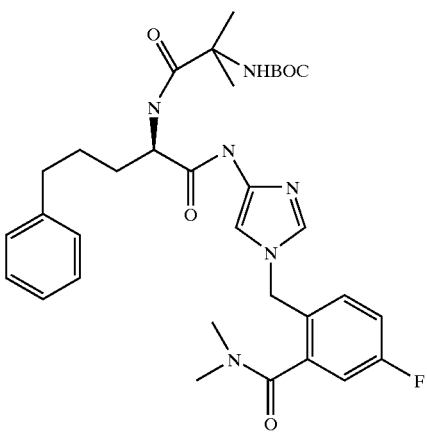

The product of Preparation 386 (0.60 g, 2.0 mmol) was added to a mixture of 10% palladium/carbon (0.50 g) and palladium/black (0.10 g) in tetrahydrofuran (100 mL) and the mixture shaken under hydrogen. (38 psi) in a Parr apparatus. After the reduction was complete, the reaction mixture was filtered through celite and the filtrate immediately combined with 1,3-dicyclohexylcarbodiimide (0.422 g, 2.0 mmol), 1-hydroxybenzotriazole mono-hydrate (0.277 g, 2.0 mmol), and the product of Preparation 1j, (0.775 g, 2.0 mmol). After stirring 72 h at ambient temperature, the mixture was concentrated and the resulting residue slurried in ethyl acetate and filtered. The filtrate was concentrated and the residue purified by flash chromatography (silica gel, chloroform/methanol) which provided 0.78 g (62%) of product. ESMS: (M+1)$^+$ 623.5. $^1$H NMR was consistent with product.

Example 214

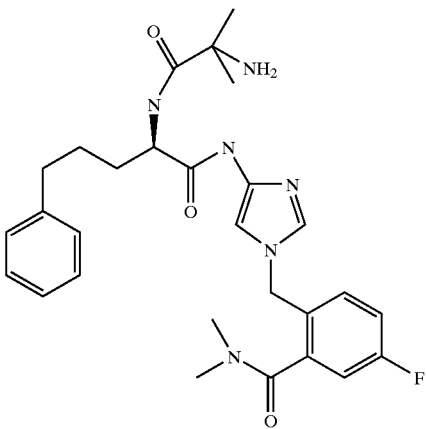

To a solution of the compound from Preparation 386A (0.65 g, 1.0 mmol) stirring in dichloromethane (20 mL) at room temperature was added trifluoroacetic acid (4 mL). After stirring for 2 h, the reaction mixture was concentrated and the residue treated with excess aqueous sodium bicarbonate. The mixture was extracted with ethyl acetate and the combined extracts were dried over sodium sulfate and concentrated. The residue was purified by flash chromatography (silica gel, dichloromethane/methanol) to give 0.05 g of the desired product. ESMS: (M+1)$^+$ 523.4. 524.5. $^1$NMR was consistent with product. Anal. Calcd. for $C_{28}H_{35}N_6O_3F\cdot 0.4CHCl_3$: C, 63.86; H, 6.70; N, 15.93. Found: C, 64.28; H, 6;96; N, 15.54.

Preparation 387

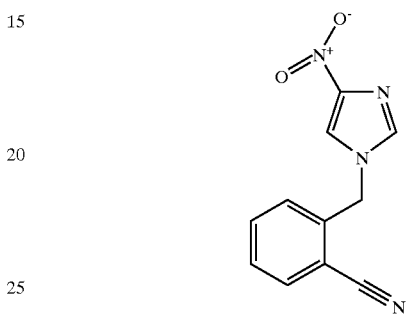

Potassium carbonate (6.90 g, 50 mmol) was combined with 4-nitroimidazole (5.65 g, 50 mmol) and 2-cyanobenzyl bromide (9.80 g, 50 mmol) in dimethylformamide (100 mL) and the mixture stirred overnight at ambient temperature. The mixture was then concentrated and the residue taken up in water and extracted with ethyl acetate. The combined extracts were dried over sodium sulfate and concentrated leaving a tan solid which was purified by flash chromatography (silica gel, chloroform/methanol) to give 9.76 g (85%) of product. ESMS: (M+1)$^+$ 229.3. $^1$H NMR (300 MHz, DMSO-d$_6$) δ 8.42 (d, J=1.51 Hz, 1H), 7.95 (d, J=1.51 Hz, 1H), 7.92 (dd, J=7.91 Hz, 1.13 Hz, 1H), 7.77–7.69 (m, 1H), 7.60–7.52 (m, 1H), 7.31 (d, J=7.91 Hz, 1H), 5.57 (s, 2H). Anal. Calcd. for $C_{11}H_9N_4O_2$: C, 57.89; H, 3.53; N, 24.55. Found: C, 57.65; H, 3.53; N, 24.33.

Preparation 388

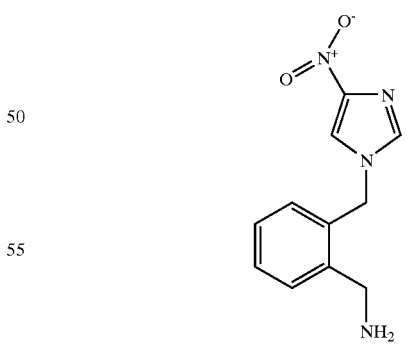

The compound of Preparation 387 (2.50 g, 11 mmol) was dissolved in tetrahydrofuran (40 mL) and borane added (1.0 M in tetrahydrofuran, 15 mL, 15 mmol) and the mixture stirred overnight at ambient temperature. The reaction was then quenched by the slow addition of methanol. After hydrogen evolution had ceased, the mixture was concentrated and the residue purified by flash chromatography (silica gel, chloroform/methanol). Recovered 0.61 g (17%) of the desired amine as a light oil.

ESMS: (M+1)⁺ 233.1. ¹H NMR (300 MHz, DMSO-d₆) δ 8.42 (d, J=1.13 Hz, 1H), 7.96 (d, J=1.13 Hz, 1H), 7.43 (d, J=7.16 Hz, 1H), 7.38–7.15 (m, 2H), 7.09 (d, J=7.16 Hz, 1H), 5.42 (s, 2H), 3.81 (s, 2H), 3.30 (bs, 2H).

Preparation 389

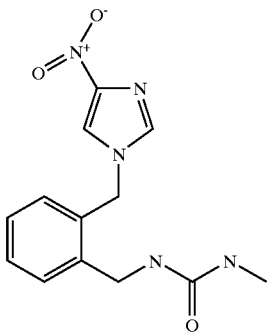

The amine from Preparation 388 (0.90 g, 3.88 mmol) was dissolved in tetrahydrofuran (40 mL) and methyl isocyanate (0.50 mL, 8.5 mmol) was added dropwise via syringe and the mixture stirred overnight at ambient temperature. The resulting precipitate was filtered and dried which netted 0.89 g, (79%) of the desired urea. ESMS: (M+1)⁺ 290.2. ¹H NMR (300 MHz, DMSO-d₆) δ 8.35 (d, J=1.51 Hz, 1H), 7.92 (d, J=1.51 Hz, 1H), 7.37–7.20 (m, 3H), 7.12 (d, J=7.54 Hz, 1H), 6.45–6.35 (m, 1H), 5.90–5.78 (m, 1H), 5.39 (s, 2H), 4.28 (d, J=6.03 Hz, 2H), 2.56 (d, J=4.90 Hz, 3H). Anal. Calcd. for C₁₃H₁₅N₅O₃: C, 53.97; H, 5.23; N, 24.21. Found: C, 53.71; H, 5.14; N, 24.10.

Preparation 390

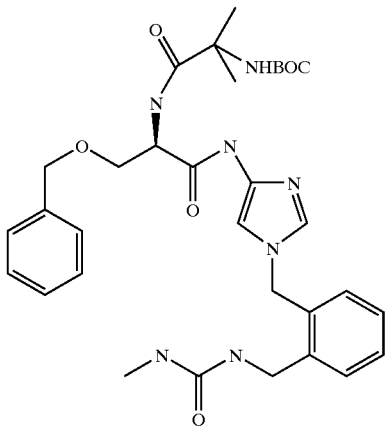

The product of Preparation 389 (0.50 g, 1.73 mmol) was added to a mixture of 10% palladium/carbon (0.40 g) and palladium/black (0.10 g) in tetrahydrofuran (80 mL) and the mixture shaken under hydrogen (39 psi) in a Parr apparatus. After 6 h, the reaction mixture was filtered through celite to remove catalyst and undissolved starting material (0.15 g, poor solubility). The filtrate was immediately combined with 1,3-dicyclohexylcarbodiimide (0.356 g, 1.73 mmol), 1-hydroxybenzotriazole mono-hydrate (0.233 g, 1.73 mmol), and the product of Preparation 1d, (0.657 g, 1.73 mmol). After stirring for 72 h at ambient temperature, the mixture was concentrated and the resulting residue slurried in ethyl acetate and filtered. The filtrate was concentrated and the residue purified by flash chromatography (silica gel, chloroform/methanol) which provided 0.25 g of product.

ESMS: (M+1)⁺ 622.5. ¹H NMR was consistent with product.

Example 215

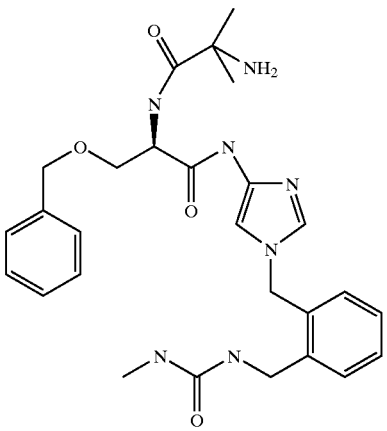

To a solution of the compound from Preparation 390 (0.24 g, 0.34 mmol) stirring in dichloromethane (10 mL) at room temperature was added trifluoroacetic acid (1.5 mL). After stirring for 2 h, the reaction mixture was concentrated and the residue treated with excess aqueous sodium bicarbonate. The mixture was extracted with ethyl acetate. The extracts were concentrated and the residue purified by flash chromatography (silica gel, chloroform/methanol) to give 0.065 g of product as a white solid. ESMS: (M+1)⁺ 522.3, 523.5. ¹H NMR was consistent with product.

Preparation 391

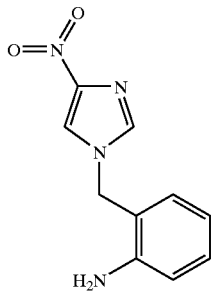

To a solution of 2-aminobenzylamine, 3.0 g (24.6 mmol) in 50 mL of methanol and 15 mL of water at 0° C. was added 2.1 g of sodium bicarbonate. The resulting slurry was stirred for 10 min. then 3.9 g of the product of Preparation 306 was added. The reaction mixture was stirred overnight while slowly warming to ambient temperature and was then concentrated to dryness. The resulting residue was absorbed onto a silica pad and was chromatographed using 80% ethyl acetate/hexanes as eluant to yield 2.66 g (50%) of the desired product as an orange solid. ¹H-NMR is consistent with structure; MS (ion spray) 219.2 (M+1); Anal. Calc'd for C₁₀H₁₀N₄O₂C, 55.04; H, 4.62; N, 25.67. Found: C, 55.31; H, 4.72; N, 25.76.

Preparation 392

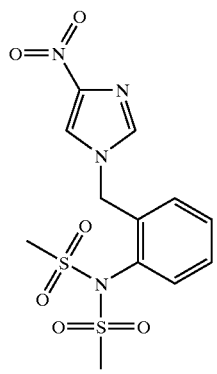

To a solution of the product of Preparation 391, 2.5 g (11.5 mmol) and triethylamine, 4 mL (28.8 mmol) in 200 mL of dichloromethane at 0° C. was added 2.25 mL (28.8 mmol) of methanesulfonyl chloride. The resulting slurry was stirred overnight, slowly warming to ambient temperature and was then concentrated to dryness. The residue was slurried in water and filtered, then slurried in chloroform, filtered and dried under vacuum to yield 3.1 g (72%) of the desired product as a white solid. $^1$H-NMR is consistent with structure; MS (ion spray) 375.2 (M+1); Anal. Calc'd for $C_{12}H_{14}N_4O_6S_2$: C, 38.50; H, 3.77; N, 14.96. Found: C, 38.45; H, 3.66; N, 14.74.

Preparation 393

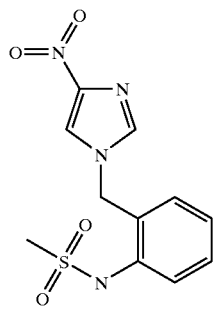

To a slurry of the product of Preparation 392, 1.7 g (4.6 mmol) in 60 mL of absolute ethanol and 60 mL of tetrahydrofuran was added 23 mL (23 mmol) of 1N sodium hydroxide. The resulting solution was stirred 90 min then was concentrated to dryness. The residue was partitioned between ethyl acetate and water and acidified to pH=3 with 1N HCl. The mixture was extracted with ethyl acetate. The combined organics were washed with brine, dried over sodium sulfate, filtered and concentrated to dryness. The residue was chromatographed on silica gel using a gradient of 3–10% methanol/chloroform as eluant to yield 0.7 g (51%) of the desired product as a yellow solid. $^1$H-NMR is consistent with structure; MS (ion spray) 297.4 (M+1); Anal. Calc'd for $C_{11}H_{12}N_4O_4S$: C, 44.59; H, 4.08; N, 18.91. Found: C, 44.38; H, 4.23; N, 18.65.

Preparation 394

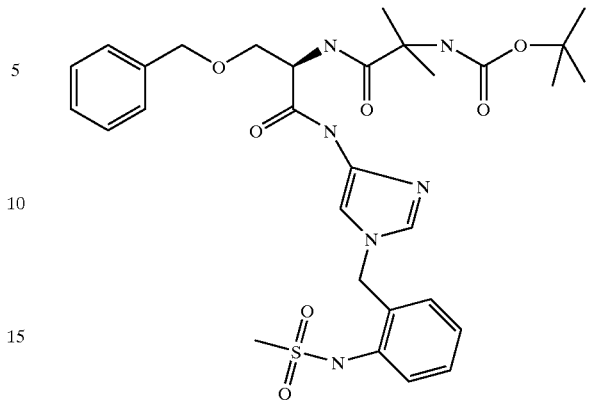

A solution of the product of Preparation 393, 0.59 g (2.0 mmol) in 40 mL of tetrahydrofuran was added to a slurry of 10% palladium on carbon (1.0 g) in 40 mL of tetrahydrofuran. The mixture was hydrogenated at 40 psi for 40 min, then filtered through celite. To this solution was added 0.76 g (2.0 mmol) of the product of Preparation 1d, 0.3 g (2.2 mmol) of 1-hydroxybenzotriazole and 0.46 g (2.2 mmol) of dicylohexylcarbodiimide. The reaction mixture was stirred overnight at ambient temperature and was then concentrated to dryness. The residue was partitioned between ethyl acetate and water and was then extracted with ethyl acetate. The combined organics were washed with brine, dried over sodium sulfate, filtered and concentrated to dryness. The residue was chromatographed on silica gel using a gradient of 3–10% methanol/chloroform to yield 0.45 g (36%) of the desired product as a tan foam. $^1$H-NMR is consistent with structure; MS (ion spray) 629.3 (M+1).

Example 216

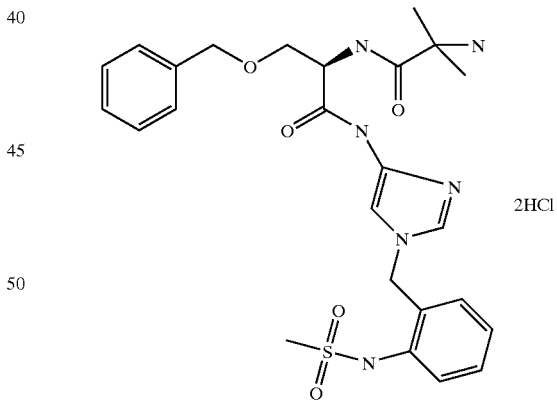

2HCl

To a solution of the product of Preparation 394, 0.35 g (0.56 mmol) in 12 mL of dichloromethane was added 4 mL of trifluoroacetic acid. The resulting mixture was stirred for 1 h, then was concentrated to dryness. The residue was partitioned between ethyl acetate and saturated sodium bicarbonate end was then extracted with ethyl acetate. The combined organics were washed with brine, dried over sodium sulfate, filtered and concentrated to dryness. To a solution of the residue in chloroform was added HCl-saturated ether. The slurry was concentrated to dryness to yield 0.34 g (100%) of the desired product as a tan solid.

¹H-NMR is consistent with structure; MS (ion spray) 529.2 (M+1); Anal. Calc'd for C₂₅H₃₂N₆O₅S.2.3HCl: C, 49.03; H, 5.64; N, 13.72. Found: C, 48.94; H, 5.62; N, 13.39.

Preparation 395

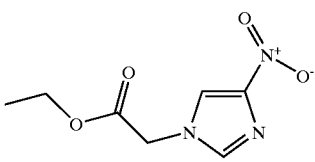

To a solution of 4-nitroimidazole (12.76 g, 112.8 mmol) in anhydrous dimethylformamide (350 mL) was added sodium hydride (4.96 g, 124.1 mmol, 60% in mineral oil), followed by ethyl bromoacetate dropwise over a period of five minutes, and the reaction was stirred at room temperature overnight. The solution was concentrated and the residue was dissolved in a solution of 20% isopropanol in chloroform, washed with 1N HCl, dried over magnesium sulfate, and concentrated to give 35.0 g crude product as an orange solid. These solids were treated with anhydrous diethyl ether (100 mL), sonicated, heated on a steam bath, and cooled in a 0° C. refrigerator overnight. The mixture was filtered and the solids washed with ice cold diethyl ether, then dried to give 16.56 g of the title compound as a white solid, 74% yield: ¹H NMR (d⁶-DMSO, δ): 1.19 (t, J=6.1 Hz, 3H), 4.15 (q, J=6.1 Hz, 2H), 5.02 (s, 2H), 7.80 (s, 1H), 8.32 (s, 1H); MS (ion spray) 200 (M⁺+1).

Preparation 396

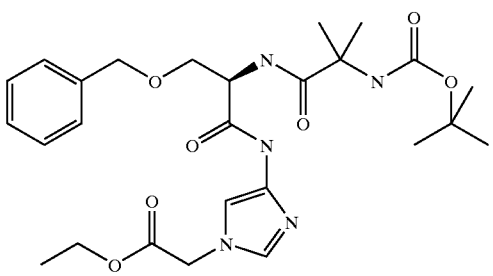

To a mixture of 4.0 g 10% palladium on carbon in 100 mL tetrahydrofuran was added the product of Preparation 395 (9.96 g, 50.0 mmol). The mixture was subjected to 60 psi hydrogen on a Parr apparatus for 2 h, then filtered through celite to remove the catalyst. The filtrate was concentrated and the resulting oil was dissolved in anhydrous dimethylformamide (10 mL). This solution was added to a solution of the product of Preparation 1d from Examples Part 2A (20.92 g, 55.0 mmol) and 1-hydroxybenzotriazole (8.42, 55.0 mmol) in anhydrous dimethylformamide (150 mL) which had been cooled to −13° C. in an ice/acetone bath. Dicyclohexyl carbodiimide (11.35 g, 55.0 mmol) was then added, and the stirred solution was allowed to warm to room temperature overnight. The solvent was removed, ethyl acetate was added, and the insoluble dicyclohexyl urea was removed by filtration. The filtrate was washed with 1N HCl, saturated aqueous sodium bicarbonate solution, brine, dried over magnesium sulfate, and concentrated. Purification by flash chromatography on silica gel (eluting with 5% methanol/dichloromethane) gave 5.39 g of the title compound as a tan solid, 31% yield: ¹H NMR (d⁶-DMSO, δ): 1.17 (t, J=6.1 Hz, 3H), 1.25 (m, 15H), 3.55 (q, J=3.7 Hz, 1H), 3.65 (m, 1H), 4.08 (q, J=3.7 Hz, 2H), 4.40 (s, 2H), 4.56 (brs, 1H), 4.84 (s, 2H), 7.15 (s, 1H), 7.22 (m, 6H), 7.38 (s, 1H), 7.42 (m, 1H), 10.10 (brs, 1H): MS (ion spray) 532 (M⁺+1).

Preparation 396

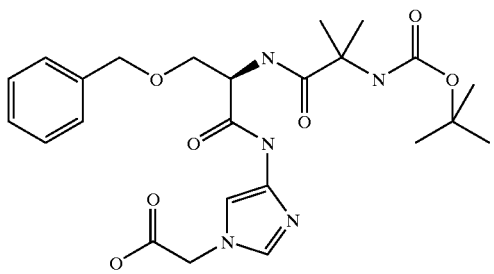

To a solution of the product of Preparation 396 (7.17 g, 13.49 mmol) in dioxane (100 mL) was added a solution of lithium hydroxide (623 mg, 14.84 mmol) in water (50 mL). After 1 h, more lithium hydroxide (60 mg, 1.42 mmol) was added. After 30 min, the reaction was quenched with 1N HCl and concentrated. The resulting oil was dissolved in a 20% isopropanol/chloroform solution, washed with 1N HCl, water, dried over magnesium sulfate, and concentrated to give 6.12 g of the title compound as a golden yellow solid, 90% yield: ¹H NMR (d⁶-DMSO, δ): 1.32 (m, 15H), 3.62 (m, 1H), 3.73 (m, 1H), 4.48 (s, 2H), 4.62 (brs, 1H), 4.85 (s, 2H), 7.19 (s, 1H), 7.30 (m, 6H), 7.51 (m, 1H), 7.59 (s, 1H), 10.24 (brs, 1H): MS (ion spray) 504 (M⁺+1).

Preparation 397

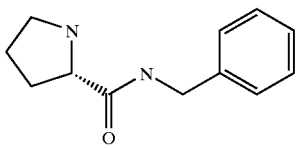

To a solution of L-proline (5.38 g, 25.0 mmol) in anhydrous tetrahydrofuran (75 mL) was added carbonyl diimidazole (4.05 g 25.0 mmol), and the solution stirred at room temperature. After 30 minutes, benzylamine (2.73 mL, 25.0 mmol) was added dropwise, and the reaction stirred at room temperature overnight. The solvent was removed and the residue dissolved dichloromethane, washed with 1N HCl, saturated aqueous sodium bicarbonate solution, brine, dried over magnesium sulfate, and concentrated to give 6.29 g of a white solid. This solid dissolved in diethyl ether saturated with dry HCl₍g₎ (35 mL, ~3N in HCl) and stirred vigorously at room temperature for 2 h. The volatiles were removed and the residue dissolved in 20% isopropanol/chloroform, washed with saturated aqueous sodium bicarbonate solution, dried over magnesium sulfate and concentrated to give 2.7 g of the title compound as a yellow oil, 64% yield: ¹H NMR (d⁶-DMSO, δ): 1.55 (m, 1H), 1.62 (m, 1H), 1.90 (m, 1H), 2.75 (m, 2H), 3.00 (brs, 1H), 3.23 (brs, 1H), 3.48 (m, 1H), 4.20 (d, J=5.4 Hz, 2H), 7.17 (m, 3H), 7.22 (t, J=5.0 Hz, 2H), 8.34 (s, 1H); MS(ion spray) 205 (M⁺+1).

Preparation 398

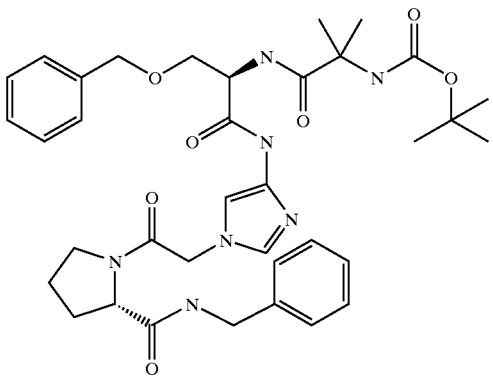

To a 0° C. solution of the product of Preparation 396A (1.01 g, 2.0 mmol) in anhydrous tetrahydrofuran (10 mL) was added the product of Preparation 397 (409 mg, 2.0 mmol), 1-hydroxybenzotriazole (322 mg, 2.1 mmol), and dicyclohexyl carbodiimide (433 mg, 2.1 mmol). The stirred reaction was allowed to warm to room temperature overnight. The insoluble dicyclohexyl urea was removed by filtration, and the filtrate was concentrated. The resulting foam was dissolved in ethyl acetate, washed with 1N HCl, saturated aqueous sodium bicarbonate solution, brine, dried over magnesium sulfate, and concentrated. Purification by flash chromatography on silica gel (eluting with 4–7% methanol/dichloromethane) gave 636 mg of the title compound as a faintly yellow solid, 46% yield: $^1$H NMR (d$^6$-DMSO, δ): 1.32 (m, 15H), 1.93 (m, 4H), 2.07 (m, 1H), 3.50 (m, 1H), 3.64 (m, 1H), 3.72 (m, 1H), 4.28 (d, J=6.3 Hz, 2H), 4.34 (m, 2H), 4.47 (s, 2H), 4.63 (brs, 1H), 4.93 (s, 2H), 7.21 (d, J=12.5 Hz, 2H), 7.30 (m, 10H), 7.45 (s, 1H), 8.38 (m, 1H), 10.16 (brs, 1H): MS(ion spray) 690 (M$^+$+1). Anal. (C$_{36}$H$_{47}$N$_7$O$_7$): H, N; C: calcd 62.68, found 62.13.

Example 217

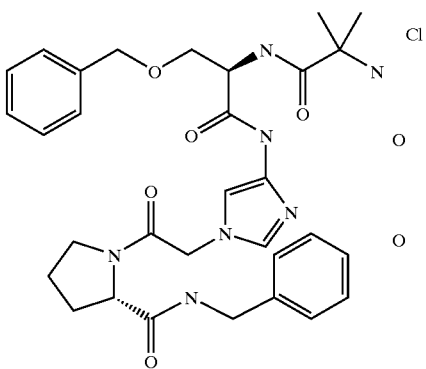

To a solution of the product of Preparation 398 (627 mg, 0.91 mmol) was added acetic acid saturated with HCl$_{(g)}$ (20 mL, ~3N in HCl) and the solution stirred vigorously at room temperature for 2 h. The solution was concentrated toluene was added and the mixture concentrated to assist in removal of acetic acid. The resulting white solid was treated with diethyl ether, sonicated, and 700 mg yellow solid was isolated by filtration. The solid was dried overnight to give 626 mg of the title compound as a yellow powder, 100% yield: $^1$H NMR (d$^6$-DMSO, δ): consistent with structure; MS(ion spray) 590 (M$^+$+1 of free base); Anal. (C$_{31}$H$_{44}$N$_7$O$_7$Cl): C, H; N: calcd. 14.81, found 13.83.

Preparation 399

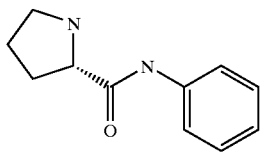

To a solution of L-proline (5.38 g, 25.0 mmol) in anhydrous tetrahydrofuran (75 mL) was added carbonyl diimidazole (4.05 g 25.0 mmol), and the solution stirred at room temperature. After 30 min, aniline (2.28 mL, 25.0 mmol) was added dropwise, and the reaction stirred at room temperature overnight. The solvent was removed and the residue dissolved in dichloromethane, washed with 1N HCl, saturated aqueous sodium bicarbonate solution, brine, dried over magnesium sulfate, and concentrated to give 6.30 g of a white solid. The solid was dissolved in dichloromethane (50 mL) and treated with trifluoroacetic acid (15 mL). The solution was stirred vigorously at room temperature for 1 h. The volatiles were removed and the residue dissolved in dichloromethane, washed with saturated aqueous sodium bicarbonate solution, dried over magnesium sulfate, and concentrated to give 1.62 g of the title compound as a white solid, 39% yield: $^1$H NMR (d$^6$-DMSO, δ): consistent with structure; MS(ion spray) 191 (M$^+$+1).

Preparation 400

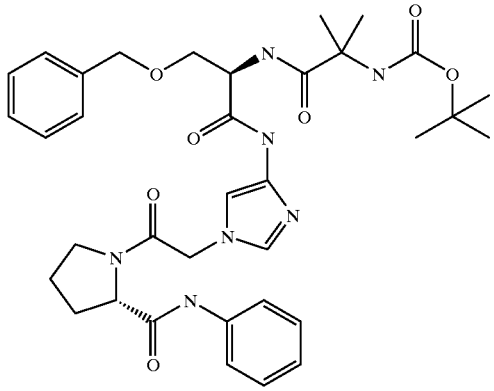

To a solution of the product of Preparation 396A (504 mg, 1.00 mmol) in anhydrous tetrahydrofuran (20 mL) was added the product of Preparation 399 (173 mg, 0.91 mmol), PyBOP® (473 mg, 0.91 mmol), and diisopropylethyl amine (0.48 mL, 2.73 mmol). The reaction was stirred at room temperature overnight. The solution was concentrated and the resulting residue was dissolved in ethyl acetate, washed with 1N HCl, saturated aqueous sodium bicarbonate solution, brine, dried over magnesium sulfate, and reconcentrated. Purification by flash chromatography on silica gel (eluting with 4–7% methanol/dichloromethane) gave 244 mg of the title compound as an orange solid, 40% yield: $^1$H NMR (d$^6$-DMSO, δ): consistent with structure; MS(ion spray) 676 (M$^+$+1); Anal. (C$_{35}$H$_{45}$N$_7$O$_7$): C, H, N.

Example 218

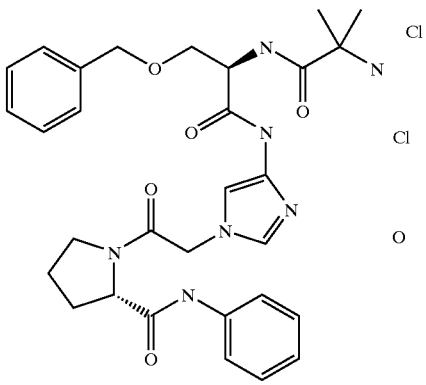

To the product of Preparation 400 (234 mg, 0.35 mmol) was added acetic acid saturated with HCl$_{(g)}$ (10 mL, ~3N in HCl) and the solution stirred vigorously at room temperature for 1 h. The solution was concentrated, toluene was added and the mixture concentrated to assist in removal of acetic acid. The residue was then treated with diethyl ether, sonicated and 235 mg a light tan solid was isolated by filtration. The solid was dried to give 230 mg of the title compound, 100% yield: $^1$H NMR (d$^6$-DMSO, δ): consistent with structure; MS(ion spray) 576 (M$^+$+1 of free base); Anal. (C$_{30}$H$_{39}$N$_7$O$_5$Cl$_2$): C, H; N: theory 14.71, found 14.13.

Preparation 401

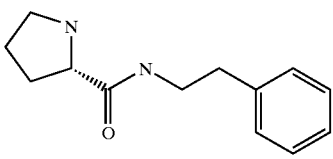

To a solution of L-proline (5.38 g, 25.0 mmol) in anhydrous tetrahydrofuran (75 mL) was added carbonyl diimidazole (4.05 g 25.0 mmol), and the solution stirred at room temperature. After 30 minutes, phenethylamine (3.14 mL, 25.0 mmol) was added dropwise, and the reaction stirred at room temperature overnight. The solvent was removed and the residue dissolved in dichloromethane, washed with 1N HCl, saturated aqueous sodium bicarbonate solution, brine, dried over magnesium sulfate, and concentrated to give 6.77 g of a white solid. The solid was dissolved in anhydrous dichloromethane (50 mL) and treated with trifluoroacetic acid (15 mL). The solution was stirred vigorously at room temperature for 1 h. The volatiles were removed and the residue dissolved in dichloromethane, washed with saturated aqueous sodium bicarbonate solution, dried over magnesium sulfate, and concentrated to give 1.08 g of the title compound as a white solid, 23% yield: $^1$H NMR (d$^6$-DMSO, δ): consistent with structure; MS(ion spray) 219 (M$^+$+1).

Preparation 402

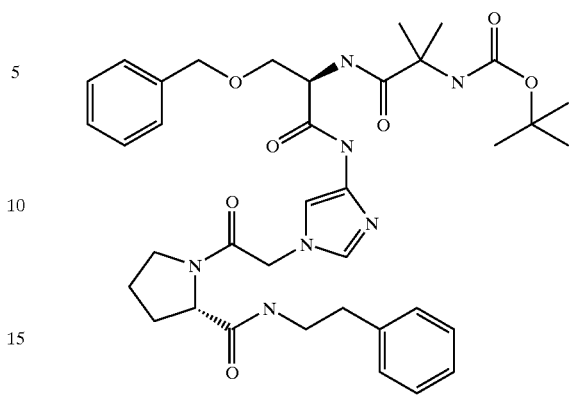

To a solution of the product of Preparation 396A (504 mg, 1.00 mmol) in anhydrous tetrahydrofuran (20 mL) was added the product of Preparation 401 (198 mg, 0.91 mmol), PyBOP® (473 mg, 0.91 mmol), and diisopropylethyl amine (0.48 mL, 2.73 mmol). The reaction was stirred at room temperature overnight. The solution was concentrated and the resulting orange residue was dissolved in ethyl acetate, washed with 1N HCl, saturated aqueous sodium bicarbonate solution, brine, dried over magnesium sulfate, and concentrated. Purification by flash chromotography on silica gel (eluting with 4–7% methanol/dichloromethane) gave 272 mg of the title compound as an light orange solid, 42% yield: $^1$H NMR (d$^6$-DMSO, δ): consistent with structure; MS(ion spray) 704 (M$^+$+1); Anal. (C$_{37}$H$_{49}$N$_7$O$_7$): C, H, N.

Example 219

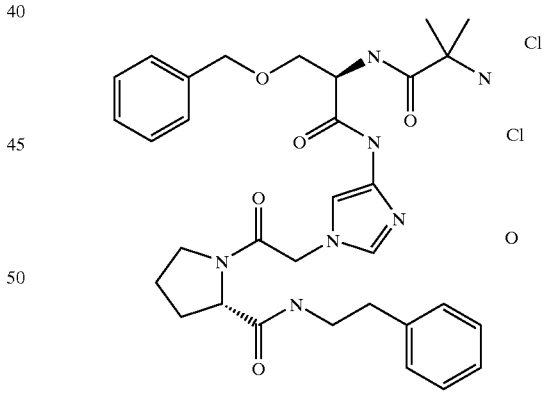

To the product of Preparation 402 (262 mg, 0.37 mmol) was added acetic acid saturated with HCl$_{(g)}$ (15 mL, ~3N in HCl) and the solution stirred vigorously at room temperature for 1 h. The solution was concentrated, toluene was added and the mixture concentrated. The residue was then treated with diethyl ether to give 243 mg of the desired compound, 94% yield: $^1$H NMR (d$^6$-DMSO, δ): consistent with structure; MS(ion spray) 603 (M$^+$+1 of free base); Anal. (C$_{32}$H$_{45}$N$_7$O$_6$Cl$_2$): C, H, N.

Preparation 403

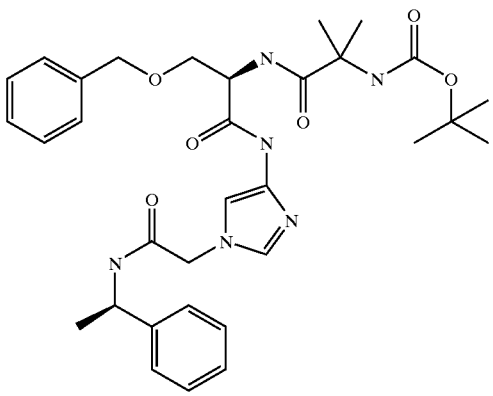

To a solution of the product of Preparation 396A (504 mg, 1.00 mmol) in tetrahydrofuran (20 mL) was added S-alpha-methylbenzylamine (0.14 mL, 0.91 mmol); PyBOP® (473 mg, 0.91 mmol), and diisopropylethyl amine (0.48 mL, 2.73 mmol). The reaction was stirred at room temperature overnight. The solution was concentrated and the resulting orange residue was dissolved in dichloromethane, washed with 1N HCl, saturated aqueous sodium bicarbonate solution, brine, dried over magnesium sulfate, and concentrated. Purification by flash chromotography on silica gel (eluting with 5% methanol/dichloromethane) gave 232 mg of the title compound as a white solid, 42% yield: $^1$H NMR (d$^6$-DMSO, δ): consistent with structure; MS(ion spray) 607 (M$^+$+1); Anal. ($C_{32}H_{429}N_6O_6$): H, N; C: theory 63.35, found 62.64.

Preparation 404

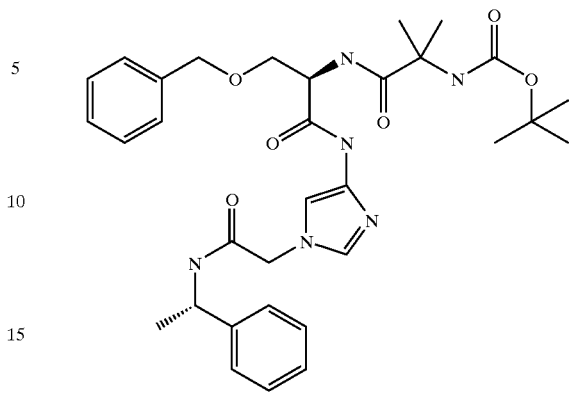

To a solution of the product of Preparation 396A (504 mg, 1.00 mmol) in tetrahydrofuran (20 mL) was added S-alpha-methylbenzylamine (0.14 mL, 0.91 mmol), PyBOP® (benzotriazol-1-yl-oxytripyrrolidinephosphonium hexafluorophosphate) (473 mg, 0.91 mmol), and diisopropylethyl amine (0.48 mL, 2.73 mmol). The reaction was stirred at room temperature overnight. The solution was concentrated and the resulting orange residue was dissolved in dichloromethane, washed with 1N HCl, saturated aqueous sodium bicarbonate solution, brine, dried over magnesium sulfate, and reconcentrated. Purification by flash chromotography on silica gel (eluting with 15% methanol/1:1 diethyl ether:hexane) gave 168 mg of the title compound as a white solid, 30% yield: $^1$H NMR (d$^6$-DMSO, δ): consistent with structure; MS (ion spray) 607 (M$^+$+1).

Example 220

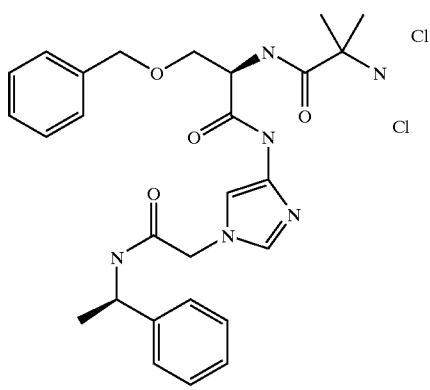

To the product of Preparation 403 (222 mg, 0.37 mmol) was added acetic acid saturated with HCl$_{(g)}$ (15 mL, ~3N in HCl) and the solution stirred vigorously at room temperature for 1 h. The solution was concentrated, toluene was added and the mixture concentrated. The residue was then treated with diethyl ether and sonicated to give 218 mg of the title compound as a tan solid, 100% yield: $^1$H NMR (d$^6$-DMSO, δ): consistent with structure; MS(ion spray) 607 (M$^+$+1 of free base); Anal. ($C_{27}H_{36}N_6O_4Cl_2$): C, H, N.

Example 221

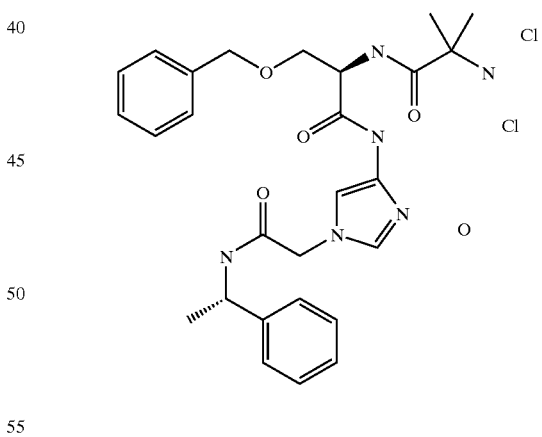

To the product of Preparation 404 (164 mg, 0.237 mmol) was added acetic acid saturated with HCl$_{(g)}$ (15 mL, ~3N in HCl) and the mixture stirred vigorously at room temperature for 1 h. The solution was concentrated, toluene was added and the mixture concentrated to assist in removal of acetic acid. The residue was then treated with diethyl ether, sonicated, and 161 mg of the title compound was isolated by filtration as a yellow solid, 100% yield: $^1$H NMR (d$^6$-DMSO, δ): consistent with structure; MS(ion spray) 507 (M$^+$+1 of free base); Anal. ($C_{27}H_{36}N_6O_4Cl_2$): C, H; N: theory 14.06, found 13.15.

Preparation 405

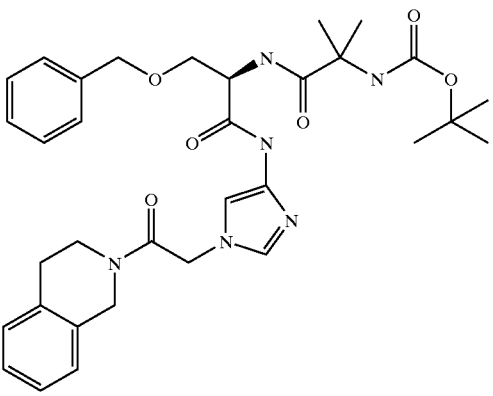

To a solution of the product of Preparation 396A (504 mg, 1.00 mmol) in tetrahydrofuran (20 mL) was added 1,2,3,4-tetrahydroisoquinoline (0.13 mL, 0.91 mmol), PyBOP® (473 mg, 0.91 mmol), and diisopropylethyl amine (0.48 mL, 2.73 mmol). The reaction was stirred at room temperature overnight. The solution was concentrated and the resulting orange residue was dissolved in dichloromethane, washed with 1N HCl, saturated aqueous sodium bicarbonate solution, brine, dried over magnesium sulfate, and reconcentrated. Purification by flash chromotography on silica gel (eluting with 5% methanol/dichloromethane) gave 560 mg of the title compound as a yellow solid, 99% yield: $^1$H NMR (d$^6$-DMSO, δ): consistent with structure; MS (ion spray) 619 (M$^+$+1).

Preparation 406

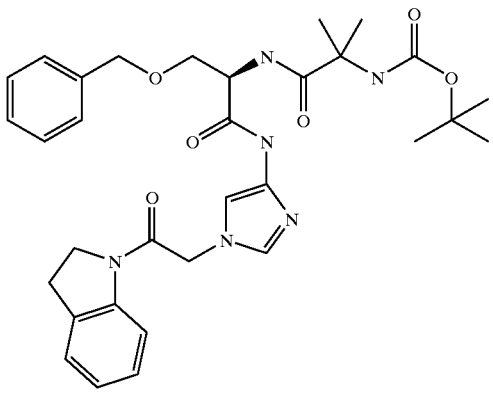

To a solution of the product of Preparation 396A (504 mg, 1.00 mmol) in anhydrous tetrahydrofuran (20 mL) was added indoline (0.10 mL, 0.91 mmol), PyBOP® (473 mg, 0.91 mmol), and diisopropylethyl amine (0.48 mL, 2.73 mmol). The reaction was stirred at room temperature overnight. The solution was concentrated and the resulting orange residue was dissolved in dichloromethane, washed with 1N HCl, saturated aqueous sodium bicarbonate solution brine, dried over magnesium sulfate, and reconcentrated. Purification by flash chromatography on silica gel (eluting with 4–7% methanol/dichloromethane) gave 543 mg of the title compound as a yellow solid, 99% yield: $^1$H NMR (d$^6$-DMSO, δ): consistent with structure; MS(ion spray) 605 (M$^+$+1).

Example 222

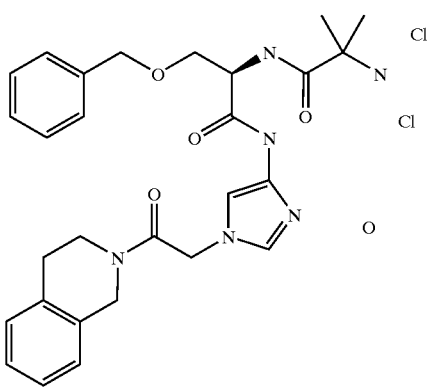

To the product of Preparation 405 (583 mg, 0.94 mmol) was added acetic acid saturated with HCl$_{(g)}$ (15 mL, ~3N in HCl) and the mixture stirred vigorously at room temperature for 1 h. The solution was concentrated, toluene was added and the mixture concentrated to assist in removal of acetic acid. The residue was then treated with diethyl ether, sonicated, and 573 mg of the title compound was isolated by filtration as a yellow solid, 100% yield: $^1$H NMR (d$^6$-DMSO, δ): consistent with structure; Ion spray MS (M$^+$+1 of free base): 519; Anal. (C$_{27}$H$_{37}$N$_6$O$_4$Cl$_3$): C, N; H: calcd 5.94, found 6.68.

Example 223

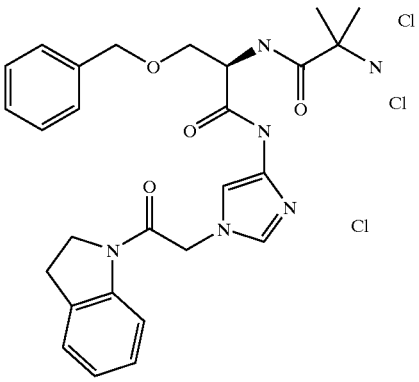

To the product of Preparation 406 (534 mg, 0.89 mmol) was added acetic acid saturated with HCl$_{(g)}$ (15 mL, ~3N in HCl) and the mixture stirred vigorously at room temperature for 1 h. The solution was concentrated, toluene was added and the mixture concentrated to assist in removal of acetic acid. The residue was then treated with diethyl ether, sonicated, and 336 mg of the title compound was isolated by filtration as a yellow solid, 62% yield: $^1$H NMR (d$^6$-DMSO, δ): consistent with structure; MS(ion spray) 505 (M$^+$+1 of free base); Anal. (C$_{27}$H$_{35}$N$_6$O$_4$Cl$_3$): C, H, N.

Preparation 407

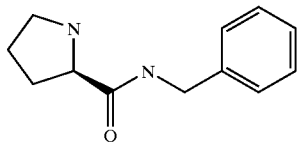

To a solution of D-proline (1.08 g, 5.0 mmol) in anhydrous tetrahydrofuran (20 mL) was added carbonyl diimidazole (0.81 g, 5.0 mmol), and the solution stirred at room temperature. After 30 min, benzylamine (0.55 mL, 5.0 mmol) was added dropwise, and the reaction stirred at room temperature overnight. The solvent was removed and the residue dissolved in dichloromethane, washed with 1N HCl, saturated aqueous sodium bicarbonate solution, brine, dried over magnesium sulfate, and concentrated to give 1.31 g of a white solid. This solid was dissolved in dichloromethane (20 mL) and treated with trifluoroacetic acid (5 mL). The reaction was stirred vigorously at room temperature for 1 h. The mixture was concentrated and the residue dissolved in 20% isopropanol/chloroform, washed with saturated aqueous sodium bicarbonate solution, dried over magnesium sulfate, and concentrated to give 600 mg of the title compound as a yellow oil, 59% yield: $^1$H NMR (d$^6$-DMSO, δ): consistent with structure; MS(ion spray) 205 (M$^+$+1).

Preparation 408

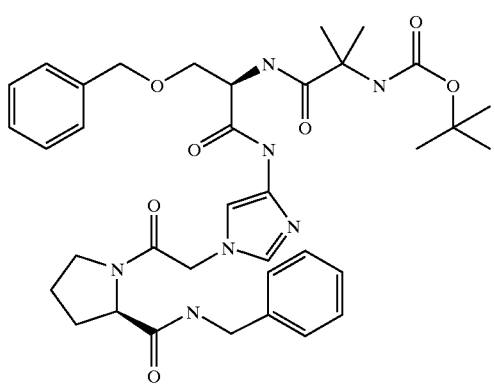

To a solution of the product of Preparation 396A (504 mg, 1.00 mmol) in tetrahydrofuran (20 mL) was added the product of Preparation 407 (186 mg, 0.91 mmol), PyBOP® (473 mg, 0.91 mmol), and diisopropylethyl amine (0.48 mL, 2.73 mmol). The reaction was stirred at room temperature overnight. The solution was concentrated and the resulting orange residue was dissolved in 20% isopropanol/chloroform, washed with 1N HCl, saturated aqueous sodium bicarbonate solution, brine, dried over magnesium sulfate, and reconcentrated. Purification by flash chromotography on silica gel (eluting with 5–10% methanol/dichloromethane) gave 454 mg of the title compound as a white solid, 72% yield: $^1$H NMR (d$^6$-DMSO, δ): consistent with structure; MS(ion spray) 690 (M$^+$+1); Anal. (C$_{36}$H$_{47}$N$_7$O$_7$): H, N; C: calcd 62.68, found 61.72.

Example 224

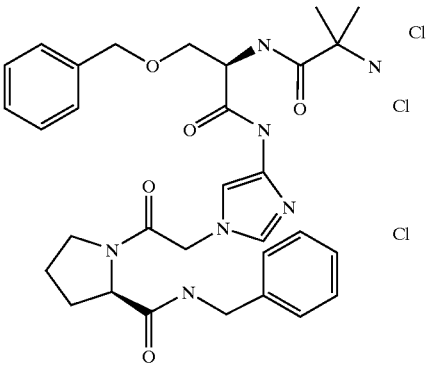

To the product of Preparation 408 (441 mg, 0.64 mmol) was added acetic acid saturated with HCl$_{(g)}$ (20 mL, ~3N in HCl) and the solution stirred vigorously at room temperature for 2 h. The solution was concentrated, toluene was added and the mixture concentrated. The residue was then treated with diethyl ether, sonicated, and 459 mg of white solid was isolated by filtration. The solid was dried to give 431 mg of the title compound as a white powder, 96% yield: $^1$H NMR (d$^6$-DMSO, δ): consistent with structure; MS(ion spray) 590 (M$^+$+1); Anal. (C$_{31}$H$_{42}$N$_7$O$_5$Cl$_3$): C, H, N.

Preparation 409

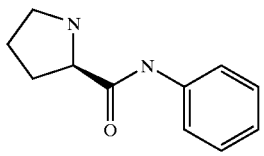

To a solution of D-proline (1.08 g, 5.0 mmol) in anhydrous tetrahydrofuran (20 mL) was added carbonyl diimidazole (0.81 g, 5.0 mmol), and the solution stirred at room temperature. After 30 minutes, aniline (0.46 mL, 5.0 mmol) was added dropwise, and the reaction stirred at room temperature overnight. The solvent was removed and the residue dissolved in dichloromethane, washed with 1N HCl, saturated aqueous sodium bicarbonate solution, brine, dried over magnesium sulfate, and concentrated to give 1.20 g of a white solid. This solid was dissolved in anhydrous dichloromethane (10 mL) and treated with trifluoroacetic acid (10 mL). The reaction was stirred vigorously at room temperature for 1 h. The volatiles were removed and the residue dissolved in 20% isopropanol/chloroform, washed with saturated aqueous sodium bicarbonate solution, dried over magnesium sulfate, and concentrated to give 281 mg of the title compound as a white solid, 46% yield: $^1$H NMR (d$^6$-DMSO, δ): 1.60 (p, J=8.6 Hz, 2H), 1.73 (m, 1H), 1.98 (m, 1H), 2.82 (t, J=7.6 Hz, 2H), 3.30 (brs, 1H), 3.63 (dd, J=7.6, 4.3 Hz, 1H), 6.99 (t, J=8.2 Hz, 1H), 7.22 (t, J=8.2 Hz, 2H), 7.59 (d, J=8.2 Hz, 1H); MS(ion spray) 191 (M$^+$+1).

Preparation 410

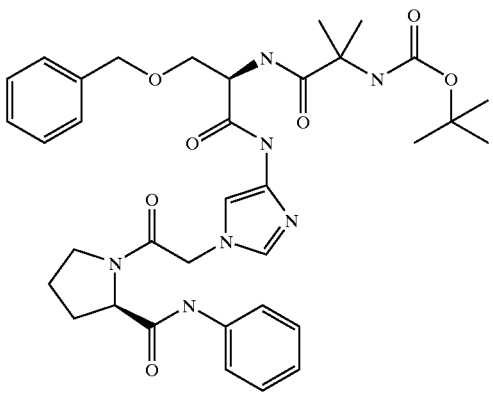

To a solution of the product of Preparation 396A (619 mg, 1.23 mmol) in dimethylformamide (25 mL) was added the product of Preparation 409 (281 mg, 1.48 mmol), PyBOP® (640 mg, 1.23 mmol), and diisopropylethyl amine (0.44 mL, 2.50 mmol). The reaction was stirred at room temperature overnight. The solution was concentrated and the resulting residue was dissolved in dichlormethane, washed with 0.1N HCl, saturated aqueous sodium bicarbonate solution, brine, dried over magnesium sulfate, and reconcentrated. Purification by flash chromotography on silica gel (eluting with 3–6% methanol/dichloromethane) gave 265 mg of the title compound as a yellow solid, 32% yield: $^1$H NMR (d$^6$-DMSO, δ: consistent with structure. MS(ion spray) 676 (M$^+$+1).

Example 225

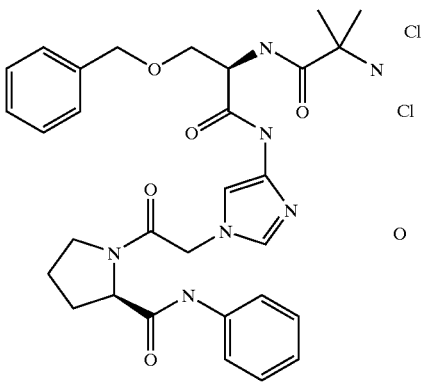

To the product of Preparation 410 (262 mg, 0.39 mmol) was added acetic acid saturated with HCl$_{(g)}$ (15 mL, ~3N in HCl) and the mixture stirred vigorously at room temperature for 1 h. The solution was concentrated, toluene was added and the mixture. The residue was then treated with diethyl ether, sonicated, to provide 267 mg of the desired product by a tan solid which was dried to give 225 mg of the title compound, 87% yield: $^1$H NMR (d$^6$-DMSO, δ); consistent with structure; MS(ion spray) 576 (M$^+$+1 of free base); Anal. ($C_{30}H_{41}N_7O_6Cl_2$): C, H, N.

Preparation 411

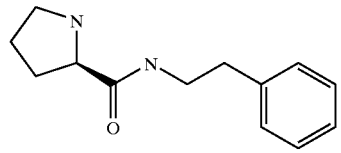

To a solution of L-proline (1.08 g, 5.0 mmol) in anhydrous tetrahydrofuran (20 mL) was added carbonyl diimidazole (0.81 g, 5.0 mmol), and the solution stirred at room temperature. After 30 minutes, phenethylamine (0.63 mL, 5.0 mmol) was added dropwise, and the reaction stirred at room temperature overnight. The solvent was removed and the residue dissolved in dichloromethane, washed with 1N HCl, saturated aqueous sodium bicarbonate solution, brine, dried over magnesium sulfate, and concentrated to give 1.39 g of a white solid. This solid was dissolved in anhydrous dichloromethane (10 mL) and treated with trifluoroacetic acid (10 mL). The reaction was stirred vigorously at room temperature for 1 h. The volatiles were removed and the residue dissolved in 20% isopropanol/chloroform, washed with saturated aqueous sodium bicarbonate solution, dried over magnesium sulfate, and concentrated to give 386 mg of the title compound as a yellow oil, 35% yield: $^1$H NMR (d$^6$-DMSO, δ): consistent with structure; MS(ion spray) 219 (M$^+$+1).

Preparation 412

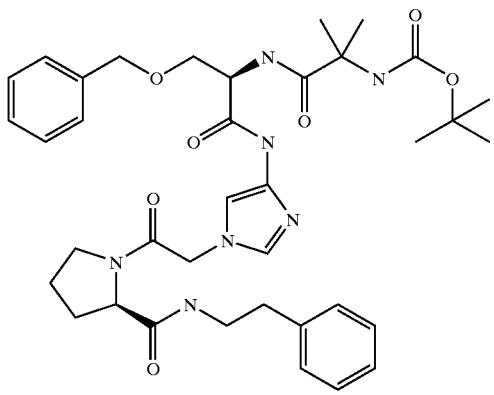

To a solution of the product of Preparation 396A (360 mg, 0.71 mmol) in dimethylformamide (25 mL) was added the product of Preparation 411 (156 mg, 0.71 mmol), PyBOP® (372 mg, 0.71 mmol), and diisopropylethylamine (0.25 mL, 1.42 mmol). The reaction was stirred at room temperature overnight. The solution was concentrated and the resulting orange residue was dissolved in dichloromethane, washed with 0.1N HCl, saturated aqueous sodium bicarbonate solution, brine, dried over magnesium sulfate, and reconcentrated. Purification by flash chromatography on silica gel (eluting with 4–8% methanol/dichloromethane) gave 304 mg of the title compound as a light tan solid, 60% yield: $^1$H NMR (d$^6$-DMSO, δ): consistent with structure; MS(ion spray) 704 (M$^+$+1).

Example 226

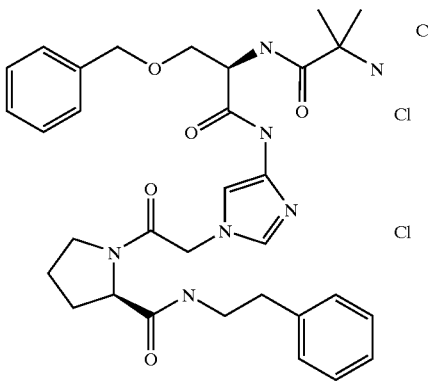

To the product of Preparation 412 (262 mg, 0.37 mmol) was added acetic acid saturated with HCl$_{(g)}$ (15 mL, ~3N in HCl) and the mixture stirred vigorously at room temperature for 1 h. The solution was concentrated, toluene was added and the mixture concentrated. The residue was then treated with diethyl ether, sonicated, and 281 mg of the title compound was isolated by filtration as a yellow solid, 92% yield: $^1$H NMR (d$^6$-DMSO, δ): consistent with structure; MS(ion spray) 604 (M$^+$+1 of free base); Anal. (C$_{32}$H$_{44}$N$_7$O$_5$Cl$_3$): C, H; N: calcd 13.75, found 12.96.

Preparation 413

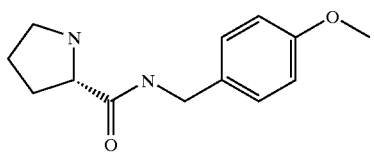

To a solution of L-proline (5.38 g, 25.0 mmol) in anhydrous tetrahydrofuran (75 mL) was added carbonyl diimidazole (4.05 g, 25.0 mmol), and the solution stirred at room temperature. After 30 min, p-methoxybenzylamine (3.26 mL, 25.0 mmol) was added dropwise, and the reaction stirred at room temperature overnight. The solvent was removed and the residue dissolved in dichloromethane, washed with 1N HCl, saturated sodium bicarbonate solution, dried over magnesium sulfate, and concentrated. The resulting solids were dissolved in anhydrous dichloromethane (50 mL) and treated with trifluoroacetic acid (20 mL). The reaction was stirred vigorously at room temperature for 1 h. The volatiles were removed and the residue dissolved in dichloromethane, washed with saturated aqueous sodium bicarbonate solution, dried over magnesium sulfate, and concentrated to give 0.95 g of the title compound as a yellow oil, 16% yield: $^1$H NMR (d$^6$-DMSO, δ): consistent with structure; MS(ion spray) 235 (M$^+$+1).

Preparation 414

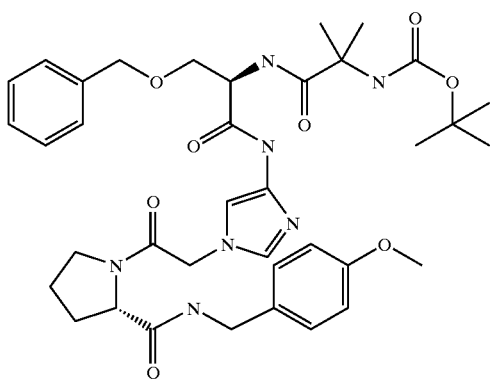

To a solution of the product of Preparation 396A (1.01 g, 2.0 mmol) in anhydrous tetrahydrofuran (10 mL) was added the product of Preparation 413 (469 mg, 2.0 mmol), 1-hydroxybenzotriazole (322 mg, 2.1 ml), and dicyclohexyl carbodiimide (433 mg, 2.1 mmol). The reaction was stirred at room temperature overnight then filtered and concentrated. The resulting orange residue was dissolved in dichloromethane, washed with 1N HCl, saturated aqueous sodium bicarbonate solution, brine, dried over magnesium sulfate, and reconcentrated. Purification by flash chromatography on silica gel (eluting with 10% methanol/dichloromethane) gave 370 mg of the title compound as a light yellow foam, 26% yield: $^1$H NMR (d$^6$-DMSO, δ): consistent with structure; MS(ion spray) 720 (M$^+$+1); Anal. (C$_{37}$H$_{49}$N$_7$O$_8$): H, N; C: calcd 61.74, found 60.96.

Example 227

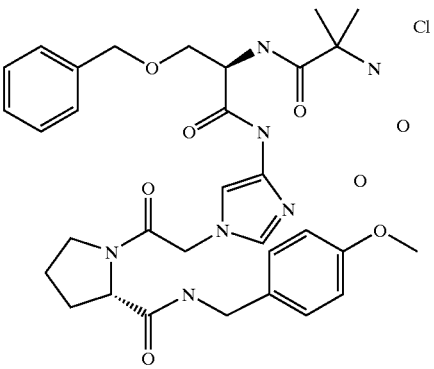

To the product of Preparation 414 (360 mg, 0.50 mmol) was added acetic acid saturated with HCl$_{(g)}$ (15 mL, ~3N in HCl) and the solution stirred vigorously at room temperature for 1 h. The solution was concentrated, toluene was added and the mixture concentrated. The residue was then treated with diethyl ether and sonicated to give 349 mg of the title as a yellow solid, 99% yield: $^1$H NMR (d$^6$-DMSO, δ): consistent with structure; MS(ion spray) 620 (M$^+$+1 of free base); Anal. (C$_{32}$H$_{46}$N$_7$O$_7$Cl): C, H; N: calcd 14.16, found 13.26.

Preparation 415

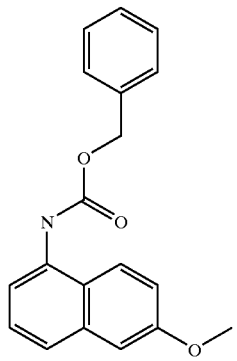

To a solution of 5-amino-2-napthol (7.96 g, 50.0 mmol) in anhydrous tetrahydrofuran (200 mL) was added benzyl chloroformate (7.14 mL, 50.0 mL) and diisopropylethylamine (9.6 mL, 55.0 mmol). The reaction was stirred at room temperature overnight. The reaction was quenched with 0.1N HCl, concentrated, treated with anhydrous diethyl ether (150 mL), and 11.49 g of gray solid was isolated by filtration. This material was dissolved in anhydrous tetrahydrofuran (120 mL), cooled to −13° C. in an ice/acetone bath, treated with sodium hydride (60% dispersion in mineral oil, 1.88 g, 47.0 mmol), and stirred for 30 min. To this solution was added a solution of methyl iodide (2.6 mL, 41.0 mmol) in tetrahydrofuran (30 mL) and the reaction was allowed to warm to room temperature overnight. The reaction was quenched with 0.1N HCl and concentrated. The resulting residue was dissolved in dichloromethane, washed with 1N HCl, saturated aqueous sodium bicarbonate solution, dried over magnesium sulfate, and reconcentrated. Purification by flash chromotography on silica gel (eluting with 20% ethyl acetate/hexane) followed by sonication in diethyl ether gave 2.66 g of the title compound as a white solid, 17% yield: $^1$H NMR (d$^6$-DMSO, d): consistent with structure; MS(ion spray) 308 (M$^+$+1).

Preparation 416

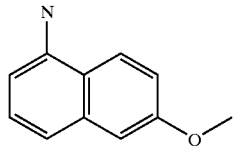

To a solution of 5% palladium on carbon (1.00 g) in anhydrous tetrahydrofuran (45 mL) and acetic acid (45 mL) was added the product of Preparation 415 (2.66 g, 8.65 mmol). The mixture was subjected to 60 psi hydrogen on a Parr apparatus for 2 h, then filtered through celite to remove the catalyst. The solvent was removed and the resulting black oil was dissolved in dichloromethane, washed with saturated aqueous sodium bicarbonate solution, dried over magnesium sulfate, and concentrated. Purification by flash chromotography on silica gel (eluting with 20% ethyl acetate/hexanes) gave 537 mg of the title compound as a purple solid, 36% yield: $^1$H NMR (d$^6$-DMSO, d): consistent with structure; MS(ion spray) 619 (M$^+$+1).

Preparation 417

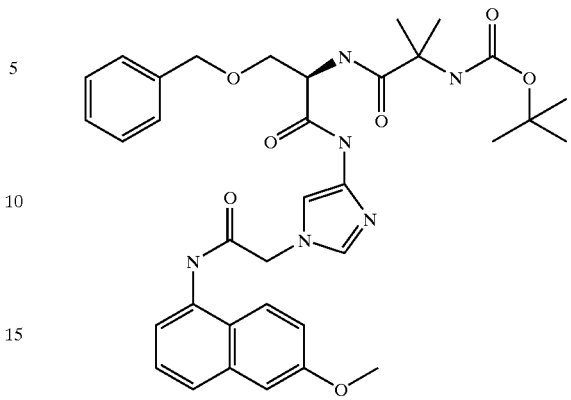

To a solution of the product of Preparation 396A (1.01 g, 2.0 mmol) in tetrahydrofuran (20 mL) was added the product of Preparation 416 (346 mg, 2.0 mmol), 1-hydroxybenzotriazole (322 mg, 2.1 mmol), and dicyclohexyl carbodiimide (433 mg, 2.1 mmol). The reaction was stirred at room temperature overnight. The insoluble dicyclohexyl urea was removed by filtration, and the filtrate concentrated. The resulting residue was dissolved in ethyl acetate, washed with 1N HCl, saturated aqueous sodium bicarbonate solution, brine, dried over magnesium sulfate, and reconcentrated. Purification by flash chromatography on silica gel (eluting with 5% methanol/dichloromethane) gave 372 mg of the title compound as a foam, 28% yield: $^1$H NMR (d$^6$-DMSO, d): consistent with structure; MS(ion spray) 659 (M$^+$+1); Anal. ($C_{35}H_{42}N_6O_7$): C, H, N.

Example 228

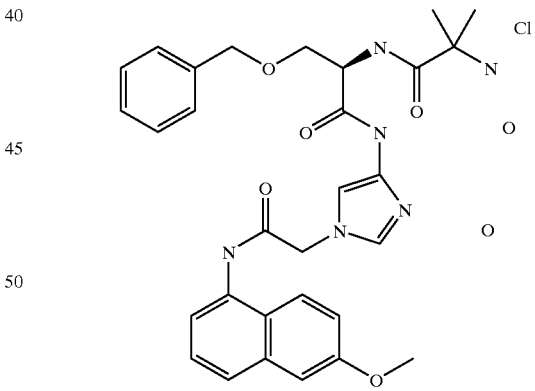

To a solution of the product of Preparation 417 (362 mg, 0.55 mmol) was added acetic acid saturated with HCl$_{(g)}$ (15 mL, ~3N in HCl) and the mixture stirred vigorously at room temperature for 1 h. The solution was concentrated, toluene was added and the mixture concentrated. The residue was then treated with diethyl ether and sonicated to give 351 mg of the title compound as a lavender solid, 100% yield: $^1$H NMR (d$^6$-DMSO, d): consistent with structure; MS(ion spray) 559 (M$^+$+1 of free base); Anal. ($C_{30}H_{39}N_6O_7Cl$): C, H,; N: calcd 13.32, found 11.61.

Preparation 418

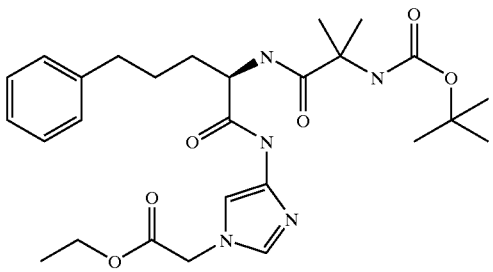

To a mixture of 1.0 g 10% palladium on carbon in 100 mL tetrahydrofuran was added the product of Preparation 395 (1.78 g, 6.94 mmol). The mixture was subjected to 60 psi hydrogen on a Parr apparatus for 2 h, then filtered through celite to remove the catalyst. The majority of solvent was removed (50 mL of tetrahydrofuran remained) and to the resulting solution was added the product of Preparation from Examples Part 2A (3.78 g, 10.0 mmol), 1-hydroxybenzotriazole (1.53 g, 10.0 mmol), and dicyclohexyl carbodiimide (2.06 g, 10.0 mmol). The solution was stirred at room temperature overnight. The insoluble dicyclohexyl urea was removed by filtration and the solvent was removed. The resulting oil was dissolved in ethyl acetate, washed with 1N HCl, saturated aqueous sodium bicarbonate solution, brine, dried over magnesium sulfate, and concentrated. Purification by flash chromotography on silica gel (eluting with 6% methanol/dichloromethane) gave 3.17 g of the title compound as a yellow solid, 67% yield: $^1$H NMR (d$^6$-DMSO, d): consistent with structure; MS(ion spray) 530 (M$^+$+1); Anal. ($C_{27}H_{39}N_5O_6$): C, H; N: calcd 13.22, found 12.69.

Preparation 419

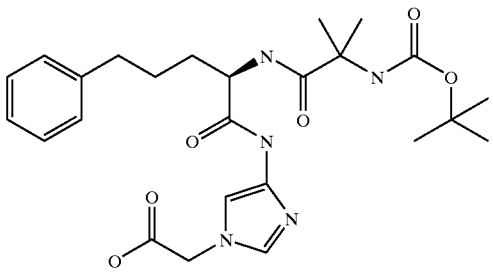

A solution of the product of Preparation 418 (3.17 g, 5.99 mmol) in dioxane (50 mL) was treated with a solution of lithium hydroxide (301 mg, 7.18 mmol) in water (20 mL) and stirred vigorously. After 1 h, the reaction was quenched with 1N HCl, and concentrated. The resulting oil was dissolved in ethyl acetate, washed with 1N HCl, water, brine, dried over magnesium sulfate, and concentrated to give 2.88 g of the title compound as a white foam, 96% yield: $^1$H NMR (d$^6$-DMSO, δ): consistent with structure; MS(ion spray) 502 (M$^+$+1).

Preparation 420

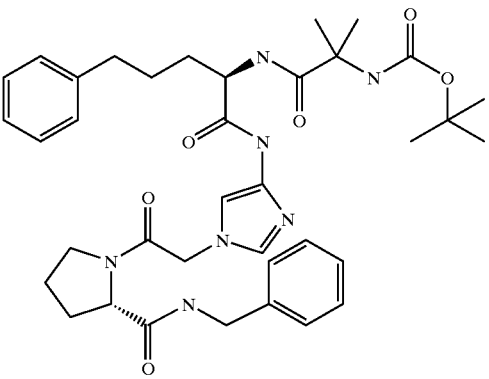

To a solution of the product of Preparation 419 (1.0 g, 2.0 mmol) stirring in tetrahydrofuran (15 mL) was added the product of Preparation 397 (409 mg, 2.0 mmol), 1-hydroxybenzotriazole (337 mg, 2.2 mmol), and dicyclohexyl carbodiimide (454 mg, 2.2 mmol). The reaction was allowed to warm to room temperature overnight. The insoluble dicyclohexyl urea was removed by filtration, and the filtrate was concentrated. The resulting foam was dissolved in ethyl acetate, washed with 1N HCl, saturated aqueous sodium bicarbonate solution, brine, dried over magnesium sulfate, and concentrated. Purification by flash chromatography on silica gel (eluting with 4–7% methanol/dichloromethane) gave 794 mg of the title compound as a white solid, 58% yield: $^1$H NMR (d$^6$-DMSO, δ): consistent with structure; MS(ion spray) 688 (M$^+$+1).

Example 229

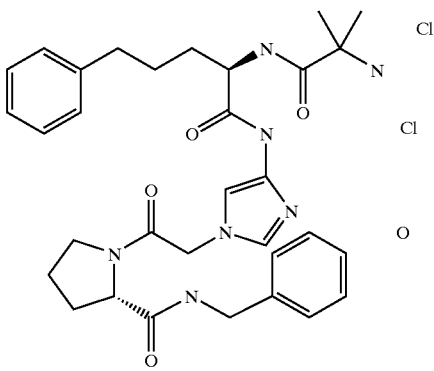

To the product of Preparation 420 (785 mg, 1.14 mmol) was added acetic acid saturated with HCl$_{(g)}$ (20 mL, ~3N in HCl and the mixture stirred vigorously at room temperature for 1 h. The solution was concentrated, toluene was added and the mixture concentrated. The residue was then treated with diethyl ether and sonicated to precipitate give 695 mg of the title compound as a light pink powder after drying, 90% yield: $^1$H NMR (d$_6$-DMSO, δ): consistent with structure; MS(ion spray) 588 (M$^+$+1 of free base); Anal. ($C_{32}H_{45}N_7O_5Cl_2$): H, N; C: calcd 56.63, found 57.53.

Example 230

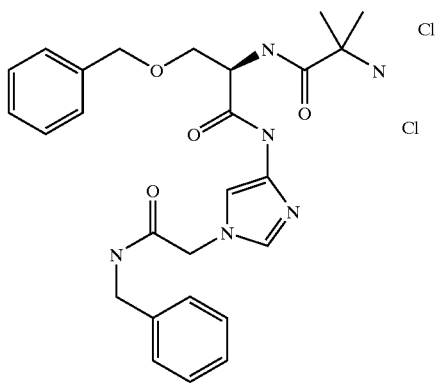

To a solution of the product of Preparation 396A (504 mg, 1.0 mmol) in anhydrous acetonitrile (20 mL) was added benzylamine (0.11 mL, 1.0 mmol), 1-hydroxy-7-azabenzotriazole (150 mg, 1.1 mol), and 1-ethyl-3-(3-dimethylaminopropyl)carbodiimide hydrochloride (211 mg, 1.1 mol). The reaction was stirred at room temperature overnight. The solution was concentrated and the resulting residue was dissolved in dichloromethane, washed with 1N HCl, saturated aqueous sodium bicarbonate solution, brine, dried over magnesium sulfate, and reconcentrated. Purification by flash chromatography on silica gel (eluting with 7% methanol/dichloromethane) gave 356 mg of a white solid. The solids were dissolved in acetic acid saturated with $HCl_{(g)}$ (20 mL, ~3N in HCl) and the mixture stirred vigorously at room temperature for 1 h. The solution was concentrated, toluene was added and the mixture concentrated. The residue was then treated with diethyl ether and sonicated to precipitate 302 mg of the title compound as a light tan solid, 53% yield: $^1$H NMR (d$^6$-DMSO, δ): consistent with structure; MS(ion spray) 493 (M$^+$+1 of free base); Anal. ($C_{26}H_{34}N_6O_4Cl_2$): C, H; N: calcd 14.86, found 14.21.

Preparation 421

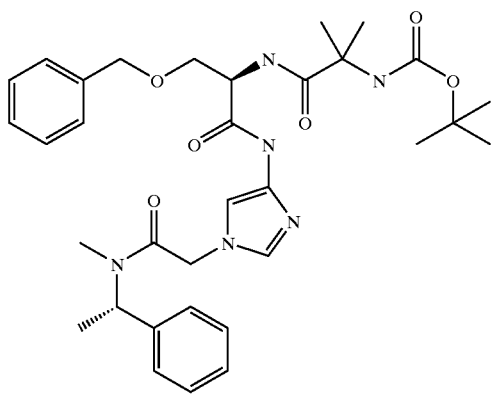

To a solution of the product of Preparation 396A (504 mg, 1.0 mmol) in anhydrous acetonitrile (20 mL) was added (S)-(−)-N,alpha-dimethylbenzylamine (0.15 mL, 1.0 mmol), 1-hydroxy-7-azabenzo-triazole (150 mg. 1.1 mmol), and 1-ethyl-3-(3-dimethylaminopropyl)carbodiimide hydrochloride (211 mg, 1.1 mmol). The reaction was stirred at room temperature overnight. The solution was concentrated and the resulting residue was dissolved in ethyl acetate, washed with 1N HCl, saturated aqueous sodium bicarbonate solution, brine, dried over magnesium sulfate, and concentrated. Purification by flash chromotography on silica gel (eluting with 5% methanol/1:1 diethyl ether:hexane) gave 289 mg of the title compound as a white solid, 47% yield: $^1$H NMR (d$^6$-DMSO, δ): consistent with structure; MS(ion spray) 621 (M$^+$+1); Anal. ($C_{33}H_{44}N_6O_6$): C, H, N.

Example 231

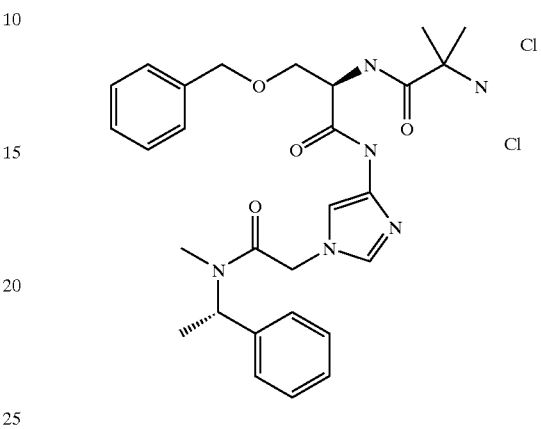

To a solution of the product of Preparation 421 (279 mg, 0.237 mmol) was added acetic acid saturated with $HCl_{(g)}$ (20 mL, ~3N in HCl) and the mixture stirred vigorously at room temperature for 1 h. The solution was concentrated toluene was added and the mixture concentrated. The residue was then treated with diethyl ether and sonicated to precipitate 235 mg of the title compound as a light red solid, 88% yield: $^1$H NMR (d$^6$-DMSO, δ): consistent with structure; MS(ion spray) 521 (M$^+$+1 of free base); Anal. ($C_{28}H_{38}N_6O_4Cl_2$): C, H; N: calcd 14.16, found 13.24.

Preparation 422

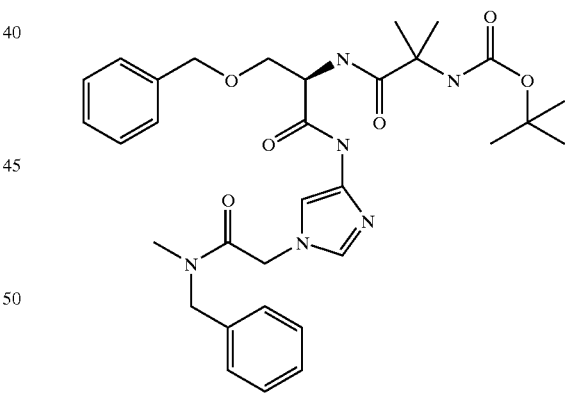

To a solution of the product of Preparation 396A (400 mg, 0.79 mmol) in anhydrous acetnitrile (20 mL) was added N-benzylmethylamine (0.11 mL, 0.87 mmol), 1-hydroxy-7-azabenzo-triazole (119 mg, 0.87 mmol), and 1-ethyl-3-3-dimethylaminopropyl) carbodiimide hydrochloride (168 mg, 0.87 mmol). The reaction was stirred at room temperature overnight. The solution was concentrated and the resulting residue was dissolved in dichloromethane, washed with 1N HCl, saturated aqueous sodium bicarbonate solution, brine, dried over magnesium sulfate, and reconcentrated. Purification by flash chromatography on silica gel (eluting with 2–7.5% methanol/dichloromethane) gave 122 mg of a white solid: $^1$H NMR (d$^6$-DMSO, δ): consistent with structure; MS(ion spray) 607 (M$^+$+1); Anal. (C$_{32}$H$_{42}$N$_6$O$_6$): H, N; C: calcd 63.35, found 62.77.

Example 232

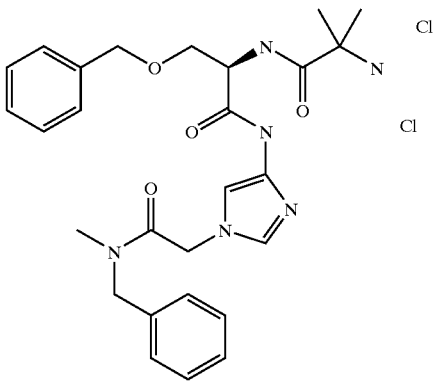

To a solution of the product of Preparation 422 (110 mg, 0.18 mmol) was added acetic acid saturated with HCl$_{(g)}$ (20 mL, ~3 N in HCl) and the mixture stirred vigorously at room temperature for 1 h. The solution was concentrated, toluene was added and the mixture concentrated. The residue was then treated with diethyl ether and sonicated to precipiate 95 mg of the title compound as a white solid, 90% yield: $^1$H NMR (d$^6$-DMSO, δ): consistent with structure; MS(ion spray) 507 (M$^+$+1 of free base); Anal. (C$_{27}$H$_{36}$N$_6$O$_4$Cl$_2$): C,H; N: calcd 14.50, found 13.24.

Preparation 423

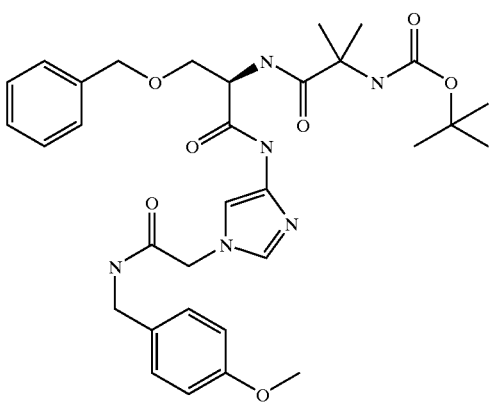

To a solution of the product of Preparation 396A (504 mg, 1.0 mmol) in anhydrous tetrahydrofuran (20 mL) was added p-methoxybenzylamine (0.13 mL, 1.0 mmol), 1-hydroxybenzotriazole (184 mg, 1.2 mmol), and dicyclohexyl carbodiimide (248 mg, 1.2 mmol). The reaction was stirred at room temperature overnight. Dicyclohexyl urea was removed by filtration and the filtrate was concentrated. The resulting residue was dissolved in dichloromethane, washed with 1N HCl, saturated aqueous sodium bicarbonate solution, brine, dried over magnesium sulfate, and reconcentrated. Purification by flash chromotography on silica gel (eluting with 2–7% methanol/dichloromethane) gave 236 mg of the title compound as a white solid, 38% yield: $^1$H NMR (d$^6$-DMSO, δ): consistent with structure; MS(ion spray) 623 (M$^+$+1); Anal. (C$_{32}$H$_{42}$N$_6$O$_7$): C, H, N.

Example 233

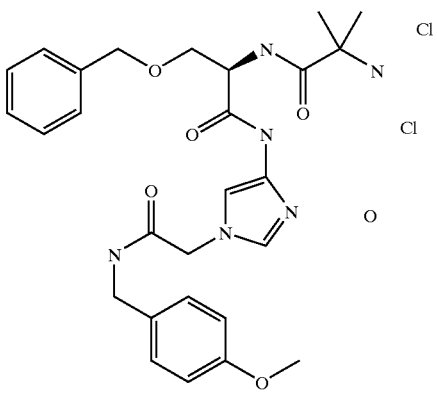

To the product of Preparation 423 (226 mg, 0.36 mmol) was added acetic acid saturated with HCl$_{(g)}$ (20 mL, ~3N in HCl) and the mixture stirred vigorously at room temperature for 1 h. The solution was concentrated, toluene was added and the mixture concentrated. The residue was then treated with diethyl ether and sonicated to precipitate 139 mg of the title compound as a white solid, 65% yield: $^1$H NMR (d$^6$-DMSO, δ): consistent with structure; MS(ion spray) 523 (M$^+$+1 of free base).

EXAMPLES PART 2C

Preparation 424

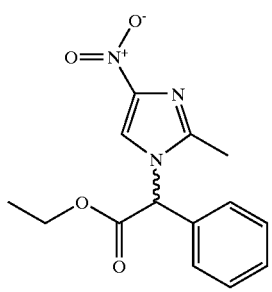

To a stirring slurry of sodium hydride (0.66 g of a 60% dispersion in mineral oil, 16.5 mmol) in N,N-dimethylformamide (30 mL) at 0° C., was added a solution of 2-methyl-5-nitroimidazole (2.0 g, 15.7 mmol) in N,N-dimethylformamide (10 mL). This solution stirred at 0° C. for 10 min then a solution of the product of Preparation 5 from Examples Part 1 (4.21 g, 17.3 mmol) in N,N-dimethylformamide (10 mL) was added. The reaction stirred for 3 h at room temperature, at which time it was quenched with brine and extracted with ethyl acetate. The combined extracts were washed with brine, dried (sodium sulfate) and evaporated in vacuo to provide a yellow oil. Flash chromatography (silica gel, 10%–50% ethyl acetate/hexanes) yielded the desired product as a light-yellow solid (2.53 g, 60%): $^1$H NMR consistent with structure; MS (IS) m/e 288 (M−1); Anal. Calc'd for C$_{14}$H$_{15}$N$_3$O$_4$: C, 58.13; H, 5.23; N, 14.53. Found: C, 58.18; H, 5.26; N, 14.56.

Preparation 425

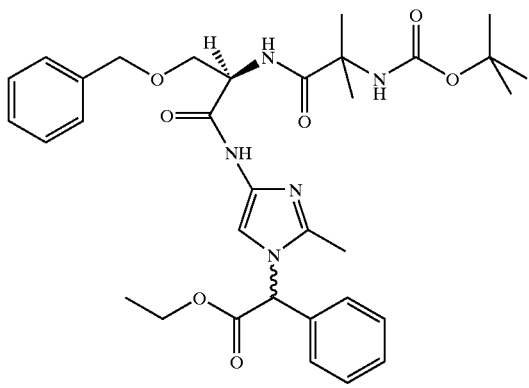

To a suspension of 5% palladium on carbon (1.50 g) and dioxane (120 mL), in a Parr reaction bottle, was added the product of Preparation 424 (2.70 g, 9.33 mmol) as a solid. The reaction bottle was placed on a Parr shaker, and shaken at room temperature for 2 h under a hydrogen atmosphere (35 psi). The reaction was filtered through a pad of Celite 521 and the filtrate was then added to a previously prepared mixture of the product of Preparation 1d from Examples Part 1 (2.79 g, 7.34 mmol) and 1-hydroxybenzotriazole hydrate (1.10 g, 8.10 mmol) in 50 mL dioxane at room temperature. This solution stirred for 15 min at which time 1,3-dicyclohexylcarbodiimide (1.66 g, 8.10 mmol) was added. The reaction was stirred for 16 h at room temperature, then the solvent was evaporated under reduced pressure. The residue was dissolved in ethyl acetate and filtered to remove the 1,3-dicyclohexylurea. The filtrate was purified by flash chromatography (silica gel, 50% ethyl acetate/hexanes—ethyl acetate) to give the desired product as a tan solid foam (3.10 g, 68%): $^1$H NMR consistent with structure; MS (IS) m/e 622 (M+1); Anal. Calc'd for $C_{33}H_{43}N_5O_7$: C, 63.75; H, 6.97; N, 11.26. Found: C, 63.46; H, 6.92; N, 11.54.

Preparation 426

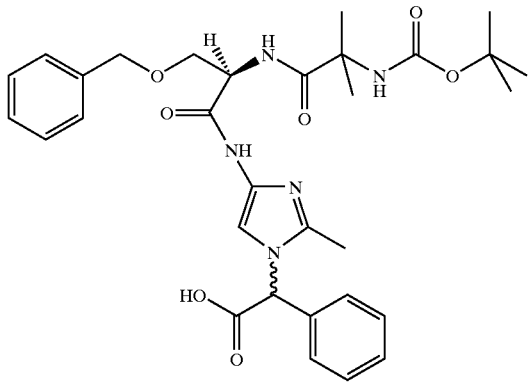

To a solution of the product of Preparation 425 (2.85 g, 4.59 mmol) in dioxane (100 mL) and water (50 mL) at room temperature was added lithium hydroxide (0.55 g, 13.0 mmol). The reaction stirred 30 min at room temperature, at which time the dioxane was evaporated under reduced pressure. The residue was diluted with water and extracted with diethyl ether (the ether extracts were discarded). The aqueous layer was acidified (pH 2–3) with 1N HCl and then extracted with diethyl ether and ethyl acetate. The combined organic layers were washed with brine, dried (sodium sulfate) and concentrated under reduced pressure to provide the desired product as a light tan solid foam which was used without further purification (2.64 g, 97%): $^1$H NMR consistent with structure; MS (IS) m/e 594 (M+1); Anal. Calc'd for $C_{31}H_{39}N_5O_7$: C, 62.72; H, 6.62; N, 11.80. Found: C, 60.94; H, 6.40; N, 11.50.

Preparation 427

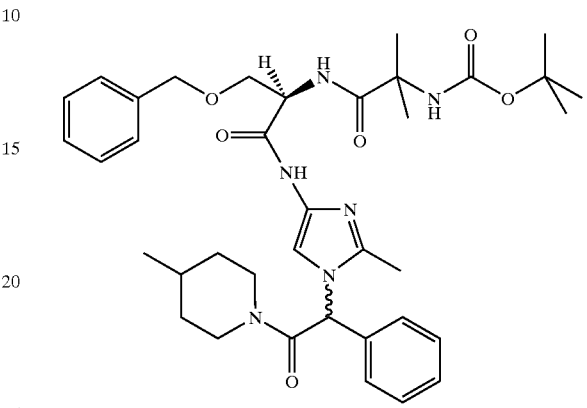

To a solution of the product of Preparation 426 (0.70 g, 1.18 mmol) in anhydrous N,N-dimethylformamide (20 mL) at room temperature was added 1-hydroxybenzotriazole hydrate (0.17 g, 1.22 mmol) and 4-methylpiperidine (0.13 mL, 1.11 mmol). This mixture stirred for 15 min at room temperature, at which time 1,3-dicyclohexylcarbodiimide (0.25 g, 1.22 mmol) was added. The reaction was stirred at room temperature for 15 h, at which time it was quenched with brine and extracted with ethyl acetate. The combined extracts were washed with brine, dried (sodium sulfate) and evaporated to provide a light-brown solid foam. The foam was dissolved in ethyl acetate, the 1,3-dicyclohexylurea was filtered away and the filtrate was purified by flash chromatography (silica gel, 75% ethyl acetate/hexanes—10% methanol/ethyl acetate) to give the desired product as a light tan solid foam (0.475 g, 60%): $^1$H NMR consistent with structure; MS (IS) m/e 673 (M−1); Anal. Calc'd for $C_{37}H_{50}N_6O_6$: C, 65.85; H, 7.47; N, 12.45. Found: C, 65.20; H, 7.26; N, 12.67.

Example 234

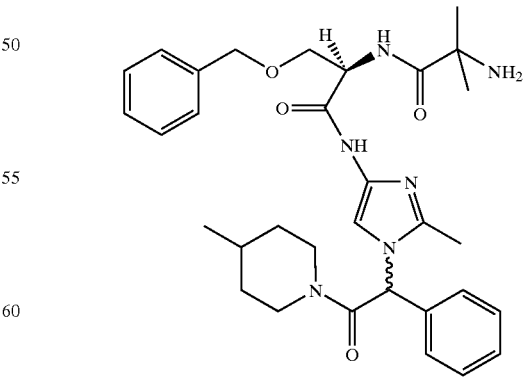

To a stirring solution of the product of Preparation 427 (0.41 g, 0.61 mmol) and anisole (0.05 mL, 0.47 mmol) in anhydrous dichloromethane (25 mL) at 0° C. was added trifluoroacetic acid (3 mL) via syringe. The reaction was stirred for 4 h, warming to room temperature and then was quenched by pouring over ice-cooled, saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, ethyl acetate—5% methanol/ethyl acetate—5% triethylamine/10% methanol/85% ethyl acetate) to provide the desired product as a white solid foam (0.26 g, 75%): $^1$H NMR consistent with structure; MS (IS) m/e 574 (M+1); Anal. Calc'd for $C_{32}H_{42}N_6O_4$: C, 66.88; H, 7.37; N, 14.62. Found: C, 66.64; H, 7.38; N, 14.34.

Preparation 428

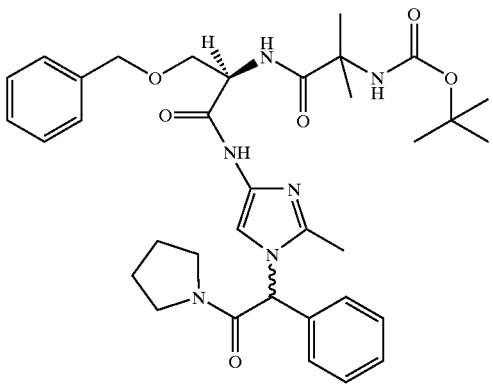

To a solution of the product of Preparation 427 (0.70 g, 1.18 mmol) in anhydrous N,N-dimethylformamide (25 mL) at room temperature was added 1-hydroxybenzotriazole hydrate (0.17 g, 1.22 mmol) and pyrrolidine (0.09 mL, 1.11 mmol). This mixture stirred for 15 min at room temperature, at which time 1,3-dicyclohexylcarbodiimide (0.25 g, 1.22 mmol) was added. The reaction was stirred at room temperature for 15 h, at which time it was quenched with brine and extracted with ethyl acetate. The combined extracts were washed with brine, dried (sodium sulfate) and evaporated to provide a light-brown solid foam. The foam was dissolved in ethyl acetate, the 1,3-dicyclohexylurea was filtered away and the filtrate was purified by flash chromatography (silica gel, 75% ethyl acetate/hexanes—10% methanol/ethyl acetate) to give the desired product as a light tan solid foam (0.58 g, 76%): $^1$H NMR consistent with structure; MS (IS) m/e 647 (M+1); Anal. Calc'd for $C_{35}H_{46}N_6O_6$: C, 65.00; H, 7.17; N, 12.99. Found: C, 63.16; H, 6.81; N, 12.91.

Example 235

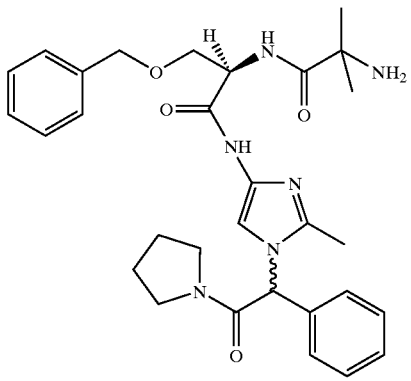

To a stirring solution of the product of Preparation 428 (0.49 g, 0.76 mmol) and anisole (0.05 mL, 0.47 mmol) in anhydrous dichloromethane (25 mL) at 0° C. was added trifluoroacetic acid (3 mL) via syringe. The reaction was stirred for 4 h, warming to room temperature and then was quenched by pouring over ice-cooled, saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The immune foam was purified by flash chromatography (silica gel, ethyl acetate—5% methanol/ethyl acetate—5% triethylamine/10% methanol/ethyl acetate) to provide the desired product as a white solid foam (0.27 g, 65%): $^1$H NMR consistent with structure; MS (IS) m/e 547 (M+1); Anal. Calc'd for $C_{30}H_{38}N_6O_4$: C, 65.91; H, 7.01; N, 25.37. Found: C, 65.37; H, 6.81; N, 14.83.

Preparation 429

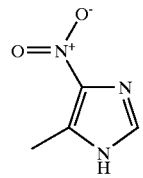

To a 0° C. solution of 4-methylimidazole (5.00 g, 61 mmol) and concentrated nitric acid (8.22 ml, 183 mmol) was added concentrated sulfuric acid (8.28 ml. 155 mmol), with stirring. After addition was complete, the ice bath was removed and the reaction was heated to a gentle reflux for 2 h. The reaction was allowed to cool and then poured into ice water. The bright yellow precipitate was collected by vacuum filtration and washed thoroughly with water to provide the desired product as a pale yellow solid (5.28 g, 68%): $^1$H NMR consistent with structure; MS (FD) m/e 127 (M+); Anal. Calc'd for $C_4H_5N_3O_2$: C, 37.80; H, 3.96; N, 33.06. Found: C, 37.73; H, 3.79; N, 33.32.

Preparation 430

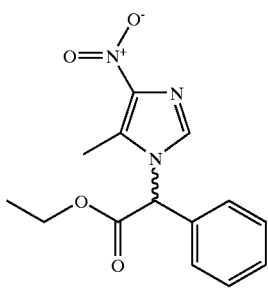

To a stirring slurry of sodium hydride (1.70 g of a 60% dispersion in mineral oil, 43 mmol) in N,N-dimethylformamide (50 mL) at 0° C. was added a solution of the product of Preparation 429 (5.15 g, 41 mmol) in N,N-dimethylformamide (50 mL). This solution stirred at 0° C. for 10 min then a solution of the product of Preparation 5 from Examples Part 1 (10.84 g, 45 mmol) in N,N-dimethylformamide (40 mL) was added. The reaction stirred for 1.5 h at room temperature, at which time it was quenched with brine and extracted with ethyl acetate. The combined extracts were washed with brine, dried (sodium sulfate) and evaporated to provide a yellow oil, which contained a 9:1 mixture of the desired regioisomer and the undesired 5-nitro-4-methyl regioisomer. Flash chromatography (silica gel, 25%–50% ethyl acetate/hexanes) yielded the desired product as a light-yellow solid (7.14 g, 60%): $^1$H NMR consistent with structure; MS (IS) m/e 290 (M+1); Anal. Calc'd for $C_{14}H_{15}N_3O_4$: C, 58.13; H, 5.23; N, 14.53. Found: C, 58.38; H, 5.33; N, 14.48.

Preparation 431

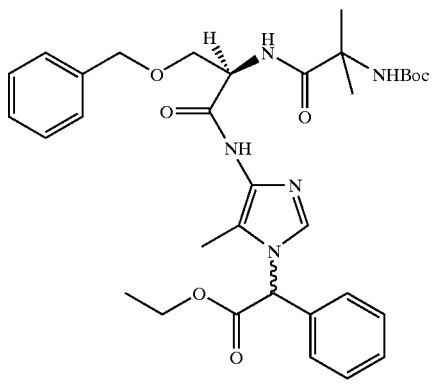

To a suspension of 5% palladium on carbon (1.10 g) and dioxane (55 mL), in a Parr reaction bottle, was added the product of Preparation 430 (1.55 g, 5.35 mmol) as a solid. The reaction bottle was placed on a Parr shaker, and shaken at room temperature for 3 h under a hydrogen atmosphere (40 psi). The reaction was filtered through a pad of Celite 521 and the filtrate was then added to a previously prepared mixture of the product of Preparation 1d from Examples Part 2A (2.03 g, 5.35 mmol) and 1-hydroxybenzotriazole hydrate (0.80 g, 5.88 mmol) in 25 mL dioxane at room temperature. This solution stirred for 15 min at which time 1,3-dicyclohexylcarbodiimide (1.21 g, 5.88 mmol) was added. The reaction was stirred at room temperature for 15 h, then the solvent was evaporated under reduced pressure. The residue was dissolved in ethyl acetate and the 1,3-dicyclohexylurea was filtered away. The filtrate was purified by flash chromatography (silica gel, 50% ethyl acetate/hexanes—ethyl acetate) to give the desired product as a light tan solid foam (1.91 g, 57%): $^1$H NMR consistent with structure; MS (IS) m/e 622 (M+1); Anal. Calc'd for $C_{33}H_{43}N_5O_7$: C, 63.75; H, 6.97; N, 11.26. Found: C, 62.75; H, 6.89; N, 11.76.

Preparation 432

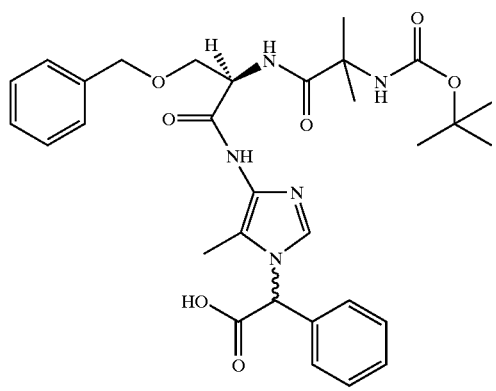

To a solution of the product of Preparation 431 (1.51 g, 2.41 mmol) in dioxane (75 mL) and water (35 mL) at room temperature was added lithium hydroxide (0.31 g, 7.24 mmol). The reaction stirred 25 min at room temperature, at which time the dioxane was evaporated under reduced pressure. The residue was diluted with water and extracted with diethyl ether (the ether extracts were discarded). The aqueous layer was acidified (pH 2–3) with 1N HCl and then extracted with diethyl ether and ethyl acetate. The combined organic layers were washed with brine, dried (sodium sulfate) and concentrated under reduced pressure to provide the desired product as a light tan solid foam that was used without further purification (1.18 g, 83%): $^1$H NMR consistent with structure; MS (IS) m/e 594 (M+1).

Preparation 433

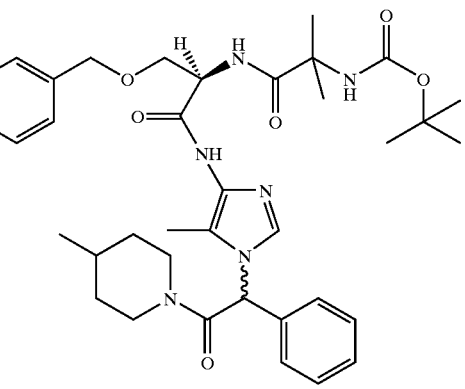

To a solution of the product of Preparation 432 (0.50 g, 0.84 mmol) in anhydrous N,N-dimethylformamide (20 mL) at room temperature was added 1-hydroxybenzotriazole hydrate (0.126 g, 0.93 mmol) and 4-methylpiperidine (0.10 mL, 0.84 mmol). This mixture stirred for 15 min at room temperature, at which time 1,3-dicyclohexylcarbodiimide (0.19 g, 0.93 mmol) was added. The reaction was stirred at room temperature for 15 h, at which time it was quenched with brine and extracted with ethyl acetate. The combined extracts were washed with brine, dried (sodium sulfate) and evaporated to provide a tan solid foam. The foam was dissolved in ethyl acetate, the 1,3-dicyclohexylurea was filtered away and the filtrate was purified by flash chromatography (silica gel, 90% ethyl acetate/hexanes—10% methanol/ethyl acetate) to give the desired product as an off-white solid foam (0.24 g, 44%): $^1$H NMR consistent with structure; MS (IS) m/e 675 (M+1); Anal. Calc'd for $C_{37}H_{50}N_6O_6$: C, 65.95; H, 7.47; N, 12.45. Found: C, 64.70; H, 6.86; N, 12.49.

Example 236

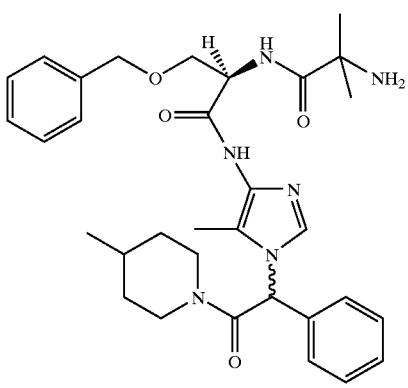

To a stirring solution of the product of Preparation 433 (0.18 g, 0.27 mmol) and anisole (0.05 mL, 0.47 mmol) in anhydrous dichloromethane (10 mL) at 0° C. was added trifluoroacetic acid (2 mL) via syringe. The reaction was stirred for 4 h, warming to room temperature and then was quenched by pouring over ice-cooled, saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, ethyl acetate—5% methanol/ethyl acetate—5% triethylamine/10% methanol/ethyl acetate) to provide the desired product as an off-white solid foam (0.12 g, 75%): $^1$H NMR consistent with structure; MS (IS) m/e 573 (M−1); Anal. Calc'd for $C_{32}H_{42}N_6O_4$: C, 66.88; H, 7.37; N, 14.62. Found: C, 65.86; H, 7.18; N, 13.82.

Preparation 434

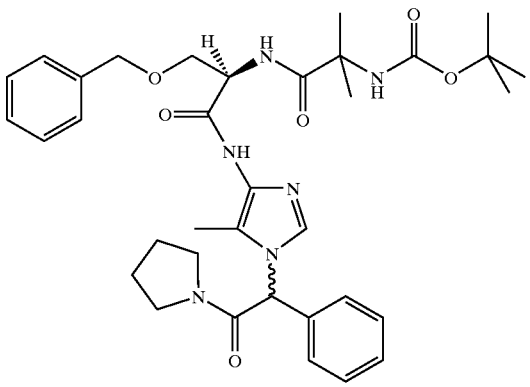

To a solution of the product of Preparation 433 (0.50 g, 0.84 mmol) in anhydrous N,N-dimethylformamide (20 mL) at room temperature was added 1-hydroxybenzotriazole hydrate (0.13 g, 0.93 mmol) and pyrrolidine (0.07 mL, 0.84 mmol). This mixture stirred for 15 min at room temperature, at which time 1,3-dicyclohexylcarbodiimide (0.19 g, 0.93 mmol) was added. The reaction was stirred at room temperature for 15 h, at which time it was quenched with brine and extracted with ethyl acetate. The combined extracts were washed with brine, dried (sodium sulfate) and evaporated to provide a light-brown solid foam. The foam was dissolved in ethyl acetate, the 1,3-dicyclohexylurea was filtered away and the filtrate was purified by flash chromatography (silica gel, 90% ethyl acetate/hexanes—10% methanol/ethyl acetate) to give the desired product as a off-white solid foam (0.28 g, 50%): $^1$H NMR consistent with structure; MS (IS) m/e 647 (M+1); Anal. Calc'd for $C_{35}H_{46}N_6O_6$: C, 65.00; H, 7.17; N, 12.99. Found: C, 64.08; H, 7.31; N, 12.81.

Example 237

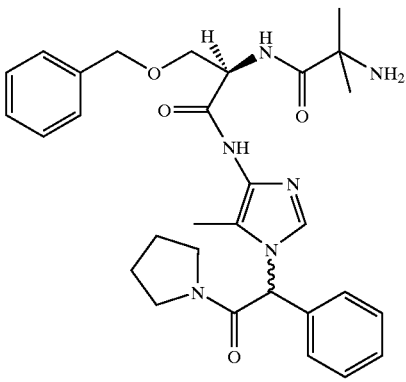

To a stirring solution of the product of Preparation 434 (0.20 g, 0.30 mmol) and anisole (0.05 mL, 0.47 mmol) in anhydrous dichloromethane (10 mL) at 0° C. was added trifluoroacetic acid (2 mL) via syringe. The reaction was stirred for 4 h, warming to room temperature and then was quenched by pouring over ice-cooled, saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, ethyl acetate—5% methanol/ethyl acetate—5% triethylamine/10% methanol/ethyl acetate) to provide the desired product as an off-white solid foam (0.12 g, 73%): $^1$H NMR consistent with structure; MS (FD) m/e 546 (M+); Anal. Calc'd for $C_{30}H_{38}N_6O_4$: C, 65.91; H, 7.01; N, 15.37. Found: C, 65.10; H, 7.10; N, 14.97.

Preparation 435

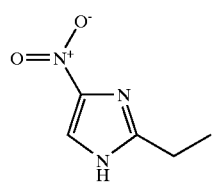

To a 0° C. solution of 2-ethylimidazole (10.0 g, 104 mmol) and concentrated nitric acid (15 ml, 312 mmol) was added concentrated sulfuric acid (14 ml, 265 mmol), with stirring. After addition was complete, the ice bath was removed and the reaction was heated to a gentle reflux for 1.5 h. The reaction was allowed to cool and was then poured into ice water and basified with 1N NaOH (pH~6). The aqueous mixture was extracted with ethyl acetate and the combined extracts were washed with brine, dried (sodium sulfate) and evaporated to provide an off-white solid. The crude solid was recrystallized in methanol to give the desired product as a white solid (6.26 g, 43%): $^1$H NMR consistent with structure; MS (IS) m/e 142 (M+1); Anal. Calc'd for $C_5H_7N_3O_2$: C, 42.55; H, 5.00; N, 29.77. Found: C, 42.43; H, 4.99; N, 29.48.

Preparation 436

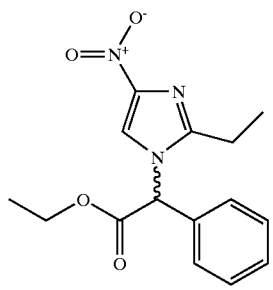

To a stirring slurry of sodium hydride (01.49 g of a 60% dispersion in mineral oil, 37.2 mmol) in N,N-dimethylformamide (30 mL) at 0° C., was added a solution of the product of Preparation 435 (5.0 g, 35.4 mmol) in N,N-dimethylformamide (30 mL). This solution stirred at 0° C. for 10 min then a solution of the product of Preparation 5 from Examples Part 1 (9.50 g, 39.0 mmol) in N,N-dimethylformamide (30 mL) was added. The reaction was stirred at room temperature for 15 h, at which time it was quenched with brine and extracted with ethyl acetate. The combined extracts were washed with brine, dried (sodium sulfate) and evaporated to provide a orange oil. Flash chromatography of the crude oil (silica gel, 20%–60% ethyl acetate/hexanes) yielded the desired product as a light-yellow solid (8.48 g, 79%): $^1$H NMR consistent with structure; MS (IS) m/e 302 (M−1); Anal. Calc'd for $C_{15}H_{17}N_3O_4$: C, 59.40; H, 5.65; N, 13.85. Found: C, 59.49; H, 5.43; N, 13.93.

Preparation 437

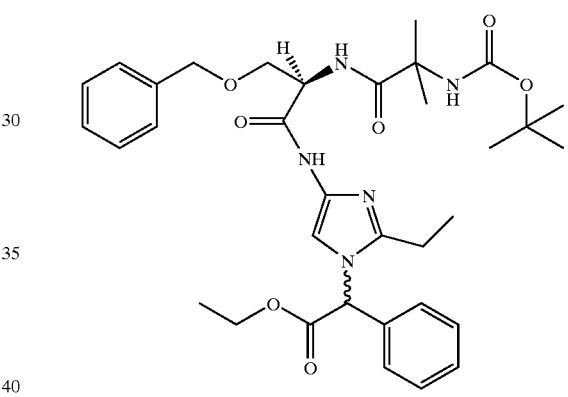

To a suspension of 5% palladium on carbon (0.75 g) and dioxane (60 mL), in a Parr reaction bottle, was added the product of Preparation 436 (0.93 g, 3.07 mmol) as a solid. The reaction bottle was placed on a Parr shaker, and shaken at room temperature for 2 h under a hydrogen atmosphere (35 psi). The reaction was filtered through a pad of Celite 521 and the filtrate was then added to a previously prepared mixture of the product of Preparation 1d from Examples Part 2A (1.16 g, 3.07 mmol) and 1-hydroxybenzotriazole hydrate (0.46 g, 3.37 mmol) in 30 mL dioxane at room temperature. This solution stirred for 15 min at which time 1,3-dicyclohexylcarbodiimide (0.70 g, 3.37 mmol) was added. The reaction was stirred at room temperature for 15 h, then the solvent was evaporated under reduced pressure. The residue was dissolved in ethyl acetate and the 1,3-dicyclohexylurea was filtered away. The filtrate was purified by flash chromatography (silica gel, 50% ethyl acetate/hexanes—ethyl acetate) to give the desired product as a light orange solid foam (1.18 g, 61%): $^1$H NMR consistent with structure; MS (IS) m/e 636 (M+1); Anal. Calc'd for $C_{34}H_{45}N_5O_7$: C, 64.23; H, 7.13; N, 11.02. Found: C, 63.45; H, 6.70; N, 10.91.

Preparation 438

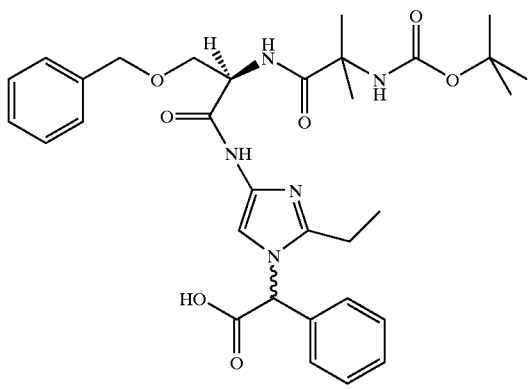

To a solution of the product of Preparation 437 (1.51 g, 2.38 mmol) in dioxane (75 mL) and water (35 mL) at room temperature was added lithium hydroxide (0.30 g, 7.13 mmol). The reaction stirred 25 min at room temperature, at which time the dioxane was evaporated under reduced pressure. The residue was diluted with water and extracted with diethyl ether (the ether extracts were discarded). The aqueous layer was acidified (pH 2–3) with 1N HCl and then extracted with diethyl ether and ethyl acetate. The combined organic layers were washed with brine, dried (sodium sulfate) and concentrated under reduced pressure to provide the desired product as a light tan solid foam that was used without further purification (1.40 g, 97%): $^1$H NMR consistent with structure; MS (IS) m/e 606 (M−1); Anal. Calc'd for $C_{32}H_{41}N_5O_7$: C, 63.25; H, 6.80; N, 11.52. Found: C, 61.13; H, 6.44; N, 11.40.

Preparation 439

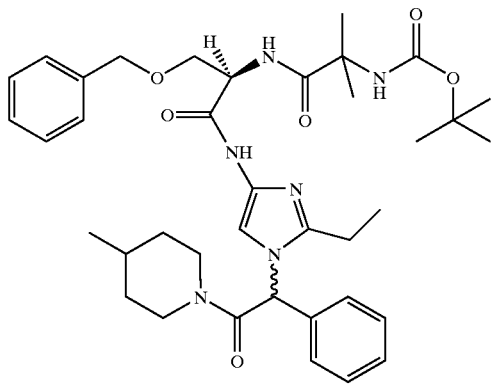

To a solution of the product of Preparation 438 (0.40 g, 0.66 mmol) in anhydrous N,N-dimethylformamide (20 mL) at room temperature was added 1-hydroxybenzotriazole hydrate (0.10 g, 0.72 mmol) and 4-methylpiperidine (0.08 mL, 0.66 mmol). This mixture stirred for 15 min at room temperature, at which time 1,3-dicyclohexylcarbodiimide (0.15 g, 0.72 mmol) was added. The reaction was stirred at room temperature for 15 h, at which time it was quenched with brine and extracted with ethyl acetate. The combined extracts were washed with brine, dried (sodium sulfate) and evaporated to provide a light-brown solid form. The foam was dissolved in ethyl acetate, the 1,3-dicyclohexylurea was filtered away and the filtrate was purified by flash chromatography (silica gel, 90% ethyl acetate/hexanes—10% methanol/ethyl acetate) to give the desired product as a white solid foam (0.372 g, 80%): $^1$H NMR consistent with structure; MS (IS) m/e 689 (M+1); Anal. Calc'd for $C_{38}H_{52}N_6O_6$: C, 66.26; H, 7.61; N, 12.20. Found: C, 65.31; H, 7.15; N, 11.85.

Example 238

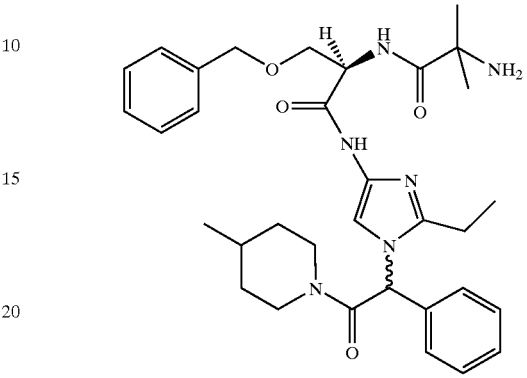

To a stirring solution of the product of Preparation 439 (0.30 g, 0.43 mmol) and anisole (0.06 mL, 0.58 mmol) in anhydrous dichloromethane (15 mL) at 0° C. was added trifluoroacetic acid (3 mL) via syringe. The reaction was stirred for 4 h, warming to room temperature and then was quenched by pouring over ice-cooled, saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, ethyl acetate—10% methanol/ethyl acetate—5% triethylamine/10% methanol/ethyl acetate) to provide the desired product as an white solid foam (0.19 g, 75%): $^1$H NMR consistent with structure; MS (FD) m/e 588 (M+); Anal. Calc'd for $C_{33}H_{44}N_6O_4$: C, 67.32; H, 7.53; N, 14.27. Found: C, 67.48; H, 7.32; N, 14.07.

Preparation 440

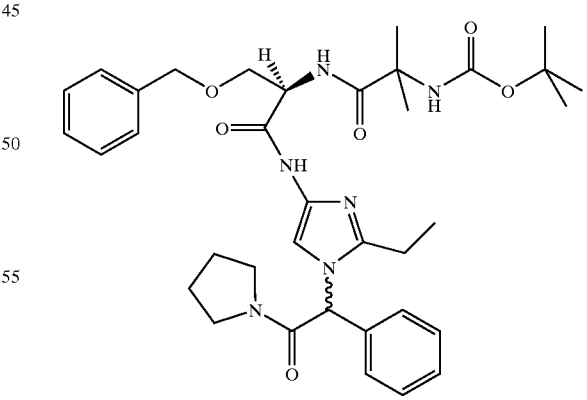

To a solution of the product of Preparation 438 (0.60 g, 1.00 mmol) in anhydrous N,N-dimethylformamide (20 mL) at room temperature was added 1-hydroxybenzotriazole hydrate (0.15 g, 1.09 mmol) and pyrrolidine (0.08 mL, 1.00 mmol). This mixture stirred for 15 min at room temperature, at which time 1,3-dicyclohexylcarbodiimide (0.23 g, 1.09 mmol) was added. The reaction was stirred at room temperature for 15 h, at which time it was quenched with brine and extracted with ethyl acetate. The combined extracts were washed with brine, dried (sodium sulfate) and evaporated to provide a tan solid foam. The foam was dissolved in ethyl acetate, the 1,3-dicyclohexylurea was filtered away and the filtrate was purified by flash chromatography (silica gel, 90% ethyl acetate/hexanes—10% methanol/ethyl acetate) to give the desired product as a tan solid foam (0.50 g, 76%): $^1$H NMR consistent with structure; MS (IS) m/e 661 (M+1); Anal. Calc'd for $C_{34}H_{45}N_5O_7$: C, 65.43; H, 7.32; N, 12.72. Found: C, 63.85; H, 7.03; N, 12.71.

Example 239

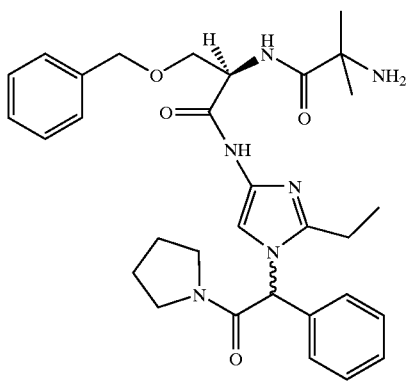

To a stirring solution of the product of Preparation 440 (0.35 g, 0.54 mmol) and anisole (0.07 mL, 0.65 mmol) in anhydrous dichloromethane (15 mL) at 0° C. was added trifluoroacetic acid (3 mL) via syringe. The reaction was stirred for 4 h, warming to room temperature and then was quenched by pouring over ice-cooled, saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, ethyl acetate—10% methanol/ethyl acetate—5% triethylamine/10% methanol/ethyl acetate) to provide the desired product as an off-white solid foam (0.26 g, 86%): $^1$H NMR consistent with structure; MS (FD) m/e 560 (M+); Anal. Calc'd for $C_{31}H_{40}N_6O_4$: C, 66.41; H, 7.19; N, 14.99. Found: C, 66.36; H, 7.16; N, 14.78.

Preparation 441

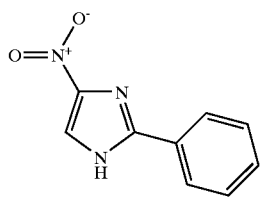

To a 0° C. solution of concentrated nitric acid (2.38 ml, 53 mmol) in 85 mL acetic anhydride was added solid 2-phenylimidazole (7.5 g, 52 mmol), with stirring. After addition was complete, the ice bath was removed and the reaction was heated at 95–100° C. for 0.5 h. The reaction was allowed to cool and was then poured into ice water and neutralized with 1N NaOH. The aqueous mixture was extracted with ethyl acetate and the combined extracts were washed with brine, dried (sodium sulfate) and evaporated to provide a beige solid. The crude solid was recrystallized in methanol to give the desired product as a off-white solid (1.55 g, 16%): $^1$H NMR consistent with structure; MS (IS) m/e 190 (M+1); Anal. Calc'd for $C_9H_7N_3O_2$: C, 57.14; H, 3.73; N, 22.21. Found: C, 57.17; H, 3.85; N, 21.95.

Preparation 442

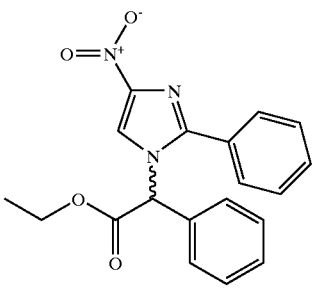

To a stirring slurry of sodium hydride (0.30 g of a 60% dispersion in mineral oil, 7.38 mmol) in N,N-dimethylformamide (30 mL) at 0° C., was added a solution of the product of Preparation 441 (1.33 g, 7.03 mmol) in N,N-dimethylformamide (20 mL). This solution stirred at 0° C. for 10 min then a solution of the product of Preparation 6 from Examples Part 1 (1.88 g, 7.73 mmol) in N,N-dimethylformamide (20 mL) was added. The reaction was stirred at room temperature for 15 h, at which time it was quenched with brine and extracted with ethyl acetate. The combined extracts were washed with brine, dried (sodium sulfate) and evaporated to provide a yellow oil. Flash chromatography (silica gel, 20%–50% ethyl acetate/ hexanes) yielded the desired product as a yellow solid (1.50 g, 61%): $^1$H NMR consistent with structure; MS (IS) m/e 352 (M+1); Anal. Calc'd for $C_{19}H_{17}N_3O_4$: C, 64.95; H, 4.88; N, 11.96. Found: C, 65.23; H, 5.04; N, 11.98.

Preparation 443

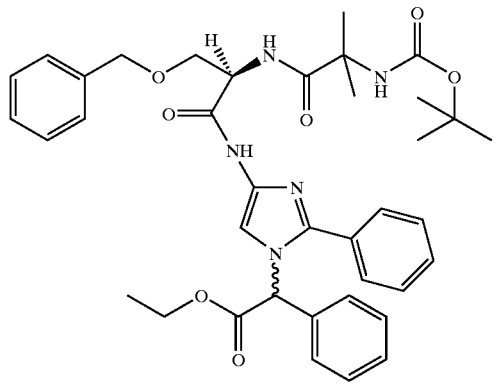

To a suspension of 5% palladium on carbon (0.68 g) and tetrahydrofuran (75 mL), in a Parr reaction bottle, was added the product of Preparation 442 (1.34 g, 3.81 mmol) as a solid. The reaction bottle was placed on a Parr shaker, and shaken at room temperature for 2 h under a hydrogen atmosphere (40 psi). The reaction was filtered through a pad of Celite 521 and the filtrate was then added to a previously prepared mixture of the product of Preparation 1d from Examples Part 2A (1.45 g, 3.81 mmol) and 1-hydroxybenzotriazole hydrate (0.57 g, 4.20 mmol) in 30 mL tetrahydrofuran at room temperature. This solution stirred for 15 min at which time 1,3-dicyclohexylcarbodiimide (0.87 g, 4.20 mmol) was added. The reaction was stirred at room temperature for 15 h, then the solvent was evaporated under reduced pressure. The residue was dissolved in ethyl acetate and the 1,3-dicyclohexylurea was filtered away. The filtrate was purified by flash chromatography (silica gel, 50% ethyl acetate/hexanes—ethyl acetate) to give the desired product as an orange-yellow solid foam (2.04 g, 78%): $^1$H NMR consistent with structure; MS (IS) m/e 684 (M+1); Anal. Calc'd for $C_{38}H_{45}N_5O_7$: C, 66.75; H, 6.63; N, 10.24. Found: C, 65.89; H, 6.26; N, 10.12.

Preparation 444

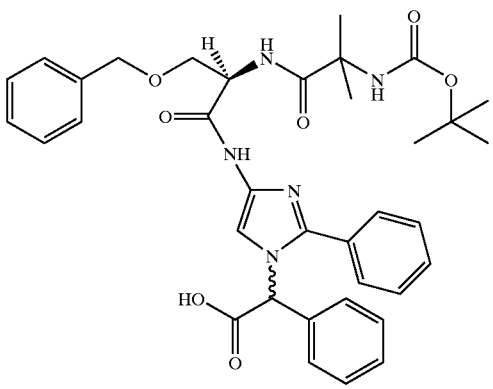

To a solution of the product of ration 443 (1.94 g, 2.84 mmol) in dioxane (60 mL) and water (30 mL) at room temperature was a lithium hydroxide (0.48 g, 1.14 mmol). The reaction stirred 25 mm at room temperature, at which time the dioxane was evaporated tinder reduced pressure. The residue was diluted with water and extracted with diethyl ether (the ether exacts were discarded). The aqueous layer was acidified (pH 2–3) with 1N HCl and then extracted with diethyl other and ethyl acetate. The combined organic layers were washed with brine, dried (sodium sulfate) and concentrated under reduced pressure to provide the desired product as an orange-yellow solid foam that was used without further purification (1.71 g, 92%): $^1$H NMR consistent with structure; MS (IS) m/e 656 (M+1); Anal. Calc'd for $C_{36}H_{41}N_5O_7$: C, 65.94; H, 6.30; N, 10.68. Found: C, 63.03; H, 5.86; N, 10.60.

Preparation 445

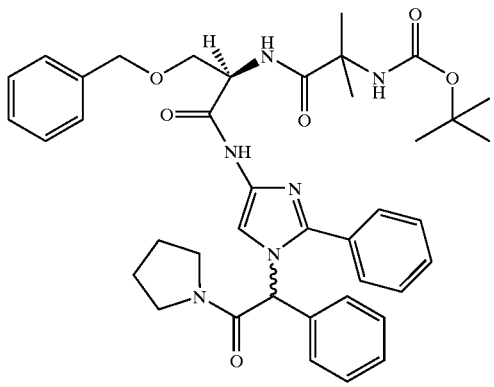

To a solution of the product of Preparation 444 (0.65 g, 0.99 mmol) in anhydrous N,N-dimethylformamide (20 mL) at room temperature was added 1-hydroxybenzotriazole hydrate (0.148 g, 1.09 mmol) and pyrrolidine (0.08 mL, 0.99 mmol). This mixture stirred for 15 min at room temperature, at which time 1,3-dicyclohexylcarbodiimide (0.23 g, 1.09 mmol) was added. The reaction was stirred at room temperature for 15 h, at which time it was quenched with brine and extracted with ethyl acetate. The combined extracts were washed with brine, dried (sodium sulfate) and evaporated to provide a light-tan solid foam. The foam was dissolved in ethyl acetate, the 1,3-dicyclohexylurea was filtered away and the filtrate was purified by flash chromatography (silica gel, 90% ethyl acetate/hexanes—10% methanol/ethyl acetate) to give the desired product as a white solid (0.31 g, 44%): $^1$H NMR consistent with structure; MS (IS) m/e 709 (M+1); Anal. Calc'd for $C_{40}H_{48}N_6O_6$: C, 67.78; H, 6.83; N, 11.86. Found: C, 67.17; H, 6.92; N, 11.67.

Example 240

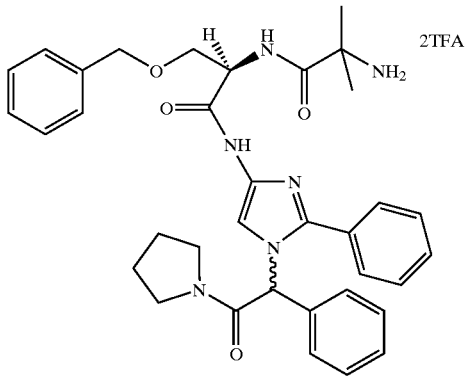

To a stirring solution of the product of Preparation 445 (0.27 g, 0.38 mmol) and anisole (0.07 mL, 0.65 mmol) in anhydrous dichloromethane (10 mL) at 0° C. was added trifluoroacetic acid (1.5 mL) via syringe. The reaction was

Preparation 446

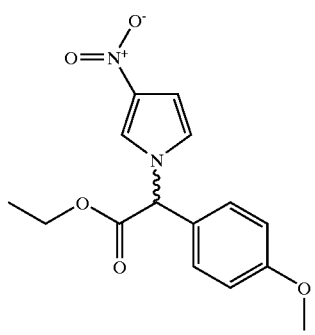

To a stirring slurry of sodium hydride (1.12 g of a 60% dispersion in mineral oil, 28 mmol) in N,N-dimethylformamide (50 mL) at 0° C., was added a solution of 3-nitropyrrole (3.00 g, 27 mmol) in N,N-dimethylformamide (30 mL). This solution stirred at 0° C. for 10 min then a solution of the product of Preparation 2 from Examples Part 2A (7.31 g, 27 mmol) in N,N-dimethylformamide (30 mL) was added. The reaction was stirred at room temperature for 15 h, at which time it was quenched with brine and extracted with ethyl acetate. The combined extracts were washed with brine, dried (sodium sulfate) and evaporated to provide an orange-yellow oil. Flash chromatography (silica gel, 30%–50% ethyl acetate/hexanes) yielded the desired product as a yellow oil (6.20 g, 75%): $^1$H NMR consistent with structure; MS (IS) m/e 303 (M−1); Anal. Calc'd for $C_{15}H_{16}N_2O_5$: C, 59.21; H, 5.30; N, 9.21. Found: C, 59.20; H, 5.40; N, 9.03.

Preparation 447

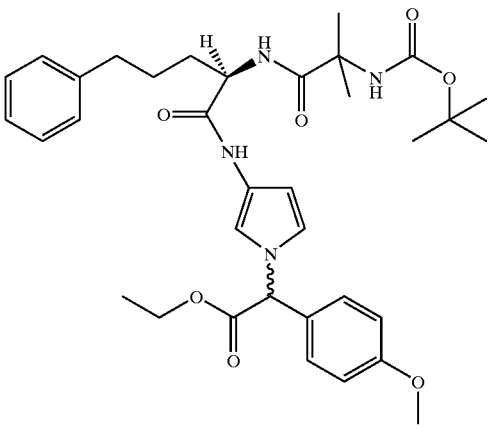

To a suspension of 5% palladium on carbon (2.00 g) and tetrahydrofuran (100 mL), in a Parr reaction bottle, was added the product of Preparation 446 (4.10 g, 13.5 mmol) as a solid. The reaction bottle was placed on a Parr shaker, and shaken at room temperature for 2 h under a hydrogen atmosphere (40 psi). The reaction was filtered through a pad of Celite 521 and the filtrate was then added to a previously prepared mixture of the product of Preparation 1j from Examples Part 2A (5.10 g, 13.5 mmol), 1,3-dicyclohexylcarbodiimide (3.06 g, 14.8 mmol) and 1-hydroxybenzotriazole hydrate (2.02 g, 14.8 mmol) in 50 mL tetrahydrofuran at 0° C. The reaction was stirred for 16 h at room temperature, then the solvent was evaporated under reduced pressure. The residue was dissolved in ethyl acetate and the 1,3-dicyclohexylurea was filtered away. The filtrate was purified by flash chromatography (silica gel, 50% ethyl acetate/hexanes—ethyl acetate) to give the desired product as a light orange solid foam (4.00 g, 47%). $^1$H NMR consistent with structure; MS (IS) m/e 635 (M+1); Anal. Calc'd for $C_{35}H_{46}N_4O_7$: C, 66.23; H, 7.30; N, 8.83. Found: C, 66.30; H, 7.31; N, 9.03.

Preparation 448

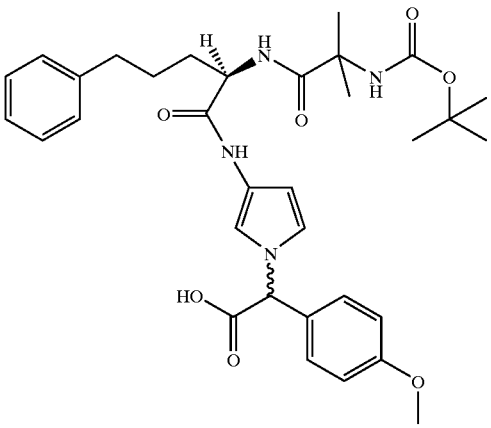

--- stirred for 4 h, warming to room temperature and then was quenched by pouring over ice-cooled, saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, ethyl acetate—10% methanol/ethyl acetate—5% triethylamine/10% methanol/ethyl acetate) to provide the desired product as a white solid foam (0.23 g, 99%): $^1$H NMR consistent with structure; MS (IS) m/e 609 (M+1); Anal. Calc'd for $C_{39}H_{42}N_6O_6F_6$: C, 55.98; H, 5.06; N, 10.04. Found: C, 56.21; H, 5.14; N, 10.12.

To a solution of the product of Preparation 447 (3.86 g, 6.08 mmol) in tetrahydrofuran (60 mL) and water (30 mL) at room temperature was added lithium hydroxide (0.64 g, 15.2 mmol). The reaction stirred 25 min at room temperature, at which time the tetrahydrofuran was evaporated under reduced pressure. The residue was diluted with water and extracted with diethyl ether (the ether extracts were discarded). The aqueous layer was acidified (pH 2–3) with 1N HCl and then extracted with diethyl ether and ethyl acetate. The combined organic layers were washed with brine, dried (sodium sulfate) and concentrated under reduced pressure to provide the desired product as a light tan solid foam that was used without further purification (3.54 g, 96%): $^1$H NMR consistent with structure; MS (IS) m/e 607 (M+1); Anal. Calc'd for $C_{33}H_{42}N_4O_7$: C, 65.33; H, 6.98; N, 9.23. Found: C, 64.83; H, 6.76; N, 8.65.

Preparation 449

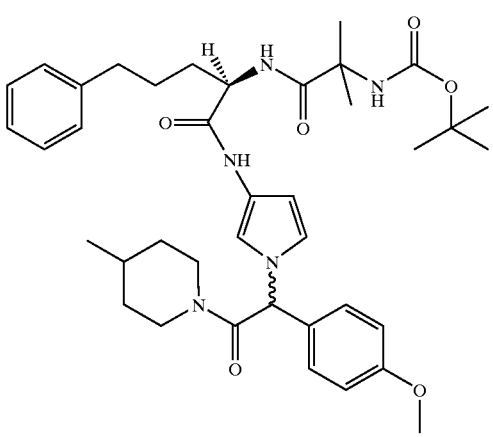

To a solution of the product of Preparation 448 (3.46 g, 5.71 mmol) in anhydrous dichloromethane (75 mL) at 0° C. was added N-methylmorpholine (0.76 mL, 6.86 mmol) and 2-chloro-4,6-dimethoxy-1,3,5-triazine (1.11 g, 6.29 mmol). This mixture stirred for 1 h, warming to room temperature, at which time 4-methylpiperidine (0.75 mL, 6.28 mmol) was added. The reaction stirred for 2 h at room temperature, then more 2-chloro-4,6-dimethoxy-1,3,5-triazine (0.20 g, 1.14 mmol) was added. The reaction was stirred for another 1 h and the solvent was evaporated under reduced pressure. The residue was dissolved in ethyl acetate, the solids were filtered away and the filtrate was purified by flash chromatography (silica gel, ethyl acetate—10% methanol/ethyl acetate) to give the desired product as an off-white solid foam (0.3.20 g, 82%): $^1$H NMR consistent with structure; MS (IS) m/e 688 (M+1); Anal. Calc'd for $C_{39}H_{53}N_5O_6$: C, 68.10; H, 7.77; N, 10.18. Found: C, 67.55; H, 7.72; N, 10.28.

Examples 241 and 242

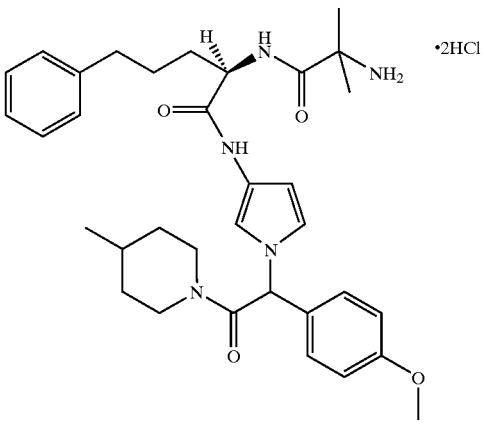

To a stirring solution of the product of Preparation 449 (3.10 g, 4.51 mmol) and anisole (0.52 mL, 4.73 mmol) in anhydrous dichloromethane (100 mL) at 0° C. was added trifluoroacetic acid (12 mL) via syringe. The reaction was stirred for 4 hours warming to room temperature and then quenched by pouring over ice-cooled saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, ethyl acetate—10% methanol/ethyl acetate—5% triethylamine/10% methanol/ethyl acetate) to provide the desired product as an off-white solid foam (2.05 g, 77%). $^1$H NMR consistent with structure; MS (IS) m/e 586 (M−1); Anal. Calc'd for $C_{34}H_{45}N_5O_4$: C, 69.48; H, 7.72; N, 11.92. Found: C, 69.27; H, 7.69; N, 11.70. Diastereomeric separation: The product was resolved by HPLC [Kromasil packing material, 15% 3A alcohol/85% heptane (w/0.2% DMEA)] to provide two diastereomers. The first diastereomer (0.80 g) (retention time=7.13 min) was dissolved in ethyl acetate (20 mL) and then a saturated solution of hydrochloric acid in diethyl ether (3 mL) was added, with stirring. The white precipitate was collected by vacuum filtration and rinsed with diethyl ether. Vacuum drying provided Example 241 (0.79 g) as a white amorphous solid: $^1$H NMR consistent with structure; MS (IS) m/e 588 (M+1); Anal. Calc'd for $C_{34}H_{45}N_5O_4\cdot$HCl: C, 65.42; H, 7.42; N, 11.22. Found: C, 64.26; H, 7.37; N, 10.93. The second diastereomer (0.65 g) (retention time=8.23 min) was dissolved in ethyl acetate (20 mL) and then a saturated solution of hydrochloric acid in diethyl ether (2 mL) was added, with stirring. The white precipitate was collected by vacuum filtration and rinsed with diethyl ether. Vacuum drying provided Example 242 (0.61 g) as a white amorphous solid: $^1$H NMR consistent with structure; MS (IS) m/e 588 (M+1); Anal. Calc'd for $C_{34}H_{45}N_5O_4\cdot$HCl: C, 65.42; H, 7.42; N, 11.22. Found: C, 64.52; H, 7.31; N, 10.72.

Preparation 250

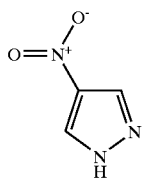

To a 0° C. solution of pyrazole (20.0 g, 294 mmol) and fuming nitric acid (40 ml, 881 mmol) was added concentrated sulfuric acid (40 ml, 750 mmol), with stirring. After addition was complete, the ice bath was removed and the reaction was heated to a gentle reflux for 1 h. The reaction was allowed to cool and was then poured into ice water, providing an off-white precipitate. The precipitate was collected by vacuum filtration and the crude solid was recrystallized in methanol to give the desired product as a white solid (20.4 g, 61%): $^1$H NMR consistent with structure; MS (IS) m/e 114 (M+1).

Preparation 451

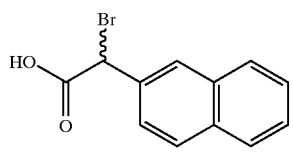

To a stirring slurry of 2-naphthyl acetic acid in carbon tetrachloride (100 mL) at 0° C. was added thionyl chloride (64.01 g, 538 mmol). The mixture was heated at 70° C. for 1 h, then cooled to 0° C. N-bromosuccinimide (57.4 g, 323 mmol), hydrobromic acid (48% aq, 1.7 mL) and carbon tetrachloride (100 mL) were added, and this mixture was heated to reflux for 2 h. After allowing the reaction mixture to cool to room temperature, the succinimide was filtered away and ethanol (150 mL) was added dropwise. This solution stirred for 1 h at room temperature and was then concentrated in vacuo to provide an orange oil. The crude oil was purified by flash chromatography (silica gel; 10% ethyl acetate/hexanes) to provide a yellow oil which solidified upon sitting. The solid was triturated with 5% ethyl acetate/hexanes to provide the desired product as a white solid (37.5 g, 48%): $^1$H NMR consistent with structure; MS (FD) m/e 292,294 (M+); Anal. Calc'd for $C_{14}H_{13}BrO_2$: C, 57.36; H, 4.47. Found: C, 58.27; H, 4.51.

Preparation 452

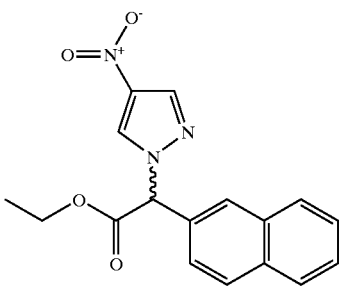

To a stirring slurry of sodium hydride (1.30 g of a 60% dispersion in mineral oil, 32.5 mmol) in N,N-dimethylformamide (35 mL) at 0° C., was added a solution of the product of Preparation 451 (3.50 g, 31.0 mmol) in N,N-dimethylformamide (25 mL). This solution stirred at 0° C. for 10 min then a solution of the product of Preparation 451 (9.98 g, 34.04 mmol) in N,N-dimethylformamide (50 mL) was added. The reaction stirred for 12 h at room temperature, at which time it was quenched with brine and extracted with ethyl acetate. The combined extracts were washed with brine, dried (sodium sulfate) and evaporated in vacuo to provide a yellow oil. Flash chromatography (silica gel, 15%–40% ethyl acetate/hexanes) yielded the desired product as a light-yellow oil (5.40 g, 54%): $^1$H NMR consistent with structure; MS (IS) m/e 326 (M+1).

Preparation 453

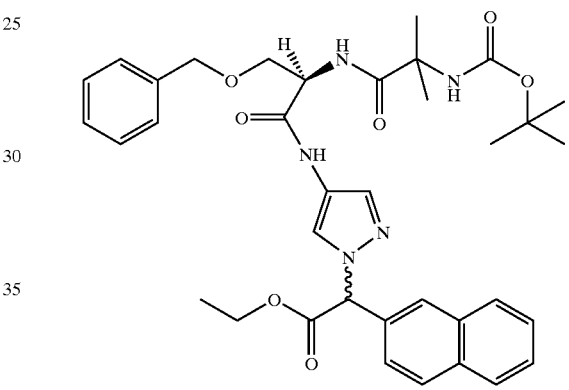

To a suspension of 5% palladium on carbon (5.00 g) and tetrahydrofuran (100 mL), in a Parr reaction bottle, was added the product of Preparation 452 (5.00 g, 15.4 mmol) as a solution in 50 mL tetrahydrofuran. The reaction bottle was placed on a Parr shaker, and shaken at room temperature for 3.5 h under a hydrogen atmosphere (35 psi). The reaction was filtered through a pad of Celite 521 the filtrate was then added to a previously prepared mixture of the product of Preparation 1d from Examples Part 2A (4.00 g, 10.5 mmol), 1,3-dicyclohexylcarbodiimide (2.44 g, 11.8 mmol) and 1-hydroxybenzotriazole hydrate (1.61 g, 11.8 mmol) in 50 mL tetrahydrofuran at room temperature. The reaction was stirred for 16 h at room temperature, then the solvent was evaporated under reduced pressure. The residue was dissolved in ethyl acetate and the remaining solids were filtered away. The filtrate was purified by flash chromatography (silica gel, 70% ethyl acetate/hexanes—ethyl acetate) to give the desired product as a white solid foam (4.75 g, 69%). $^1$H NMR consistent with structure; MS (IS) m/e 658 (M+1); Anal. Calc'd for $C_{36}H_{43}N_5O_7$: C, 65.74; H, 6.59; N, 10.65. Found: C, 65.11; H, 6.46; N, 10.66.

Preparation 454

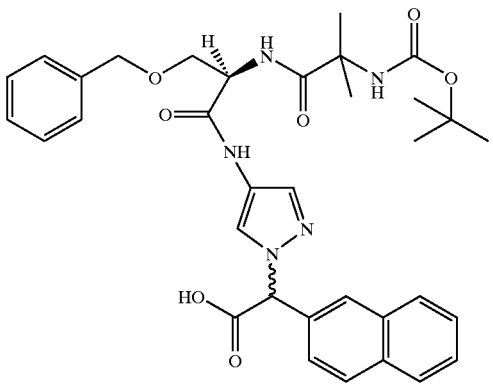

To a solution of the product of Preparation 453 (3.95 g, 6.01 mmol) in tetrahydrofuran (60 mL), water (30 mL) and ethanol (10 mL) at room temperature was added lithium hydroxide (1.01 g, 24.0 mmol). The reaction stirred 25 min at room temperature, at which time the tetrahydrofuran was evaporated under reduced pressure. The residue was diluted with water and extracted with diethyl ether (the ether extracts were discarded). The aqueous layer was acidified (pH 2~3) with 1N HCl and then extracted with diethyl ether and ethyl acetate. The combined organic layers were washed with brine, dried (sodium sulfate) and concentrated under reduced pressure to provide the desired product as a light tan solid foam that was used without further purification (3.55 g, 94%): $^1$H NMR consistent with structure; MS (IS) m/e 630 (M+1).

Preparation 455

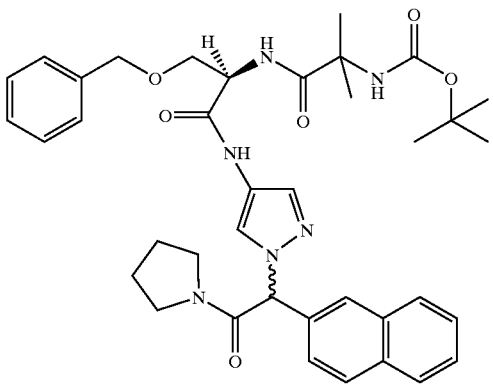

To a solution of the product of Preparation 454 (0.40 g, 0.64 mmol) in anhydrous dichloromethane (20 mL) at 0° C. was added N-methylmorpholine (0.08 mL, 0.76 mmol) and 2-chloro-4,6-methoxy-1,3,5-triazine (0.12 g, 0.70 mmol). This mixture stirred for 1 h, warming to room temperature, at which time pyrrolidine (0.06 mL, 0.70 mmol) was added. The reaction stirred for 4 h at room temperature, then the solvent was evaporated under reduced pressure. The residue was dissolved in ethyl acetate, the solids were filtered away and the filtrate was purified by flash chromatography (silica gel, ethyl acetate—10% methanol/ethyl acetate) to give the desired product as an off-white solid foam (0.21 g, 48%): $^1$H NMR consistent with structure; MS (IS) m/e 683 (M+1); Anal. Calc'd for $C_{34}H_{46}N_6O_6$: C, 66.84; H, 6.79; N, 12.31. Found: C, 64.83; H, 6.53; N, 12.64.

Example 243

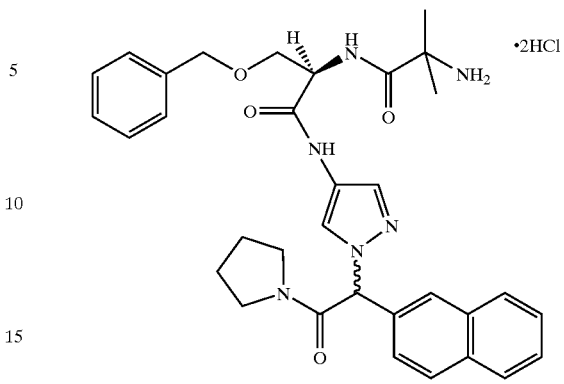

To a stirring solution of the product of Preparation 455 (0.19 g, 0.29 mmol) and anisole (0.03 mL, 0.30 mmol) in anhydrous dichloromethane (12 mL) at 0° C. was added trifluoroacetic acid (1.8 mL) via syringe. The reaction was stirred for 4 h, warming to room temperature and then was quenched by pouring over ice-cooled saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, ethyl acetate—10% methanol/ethyl acetate—5% triethylamine/10% methanol/ethyl acetate) to provide an off-white solid foam (0.11 g, 65%). The free based material was dissolved in ethyl acetate (5 mL) and then a saturated solution of hydrochloric acid in diethyl ether (1 mL) was added, with stirring. The white precipitate was collected by vacuum filtration and rinsed with diethyl ether. Vacuum drying provided the desired product (0.12 g) as a white amorphous solid: $^1$H NMR consistent with structure; MS (IS) m/e 583 (M+1); Anal. Calc'd for $C_{33}H_{38}N_6O_4 \cdot 2HCl$: C, 60.46; H, 6.15; N, 12.82. Found: C, 61.22; H, 6.50; N, 12.75.

Preparation 456

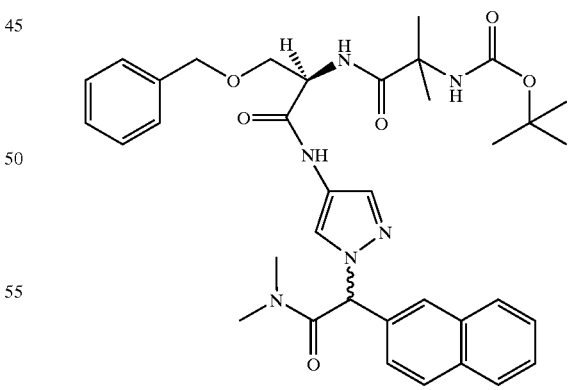

To a solution of the product of Preparation 454 (0.50 g, 0.80 mmol) in anhydrous dichloromethane (25 mL) at 0° C. was added N-methylmorpholine (0.11 mL, 0.95 mmol) and 2-chloro-4,6-dimethoxy-1,3,5-triazine (0.15 g, 0.87 mmol). This mixture stirred for 1 h, warming to room temperature, at which time a 2M solution of N,N-dimethylamine (0.83 mL, 1.67 mmol) was added. The reaction stirred for 4 h at room temperature, then the solvent was evaporated under reduced pressure. The residue was dissolved in ethyl acetate, the solids were filtered away and the filtrate was purified by flash chromatography (silica gel, ethyl acetate—10% methanol/ethyl acetate) to give the desired product as a light yellow solid foam (0.27 g, 52%): $^1$H NMR consistent with structure; MS (IS) m/e 657 (M+1); Anal. Calc'd for $C_{36}H_{44}N_6O_6$: C, 65.84; H, 6.75; N, 12.80. Found: C, 63.89; H, 6.65; N, 13.06.

Example 244

To a stirring solution of the product of Preparation 456 (0.26 g, 0.40 mmol) and anisole (0.04 mL, 0.42 mmol) in anhydrous dichloromethane (15 mL) at 0° C. was added trifluoroacetic acid (2.3 mL) via syringe. The reaction was stirred for 4 h, warming to room temperature and then was quenched by pouring over ice-cooled saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, ethyl acetate—10% methanol/ethyl acetate—5% triethylamine/10% methanol/ethyl acetate) to provide an off-white solid foam (0.16 g, 64%). The free based material was dissolved in ethyl acetate (5 mL) and then a saturated solution of hydrochloric acid in diethyl ether (1 mL) was added, with stirring. The white precipitate was collected by vacuum filtration and rinsed with diethyl ether. Vacuum drying provided the desired product (0.17 g) as an off-white amorphous solid: $^1$H NMR consistent with structure; MS (IS) m/e 557 (M+1); Anal. Calc'd for $C_{31}H_{36}N_6O_4$·2HCl: C, 59.14; H, 6.08; N, 13.35. Found: C, 59.87; H, 6.22; N, 13.16.

Preparation 457

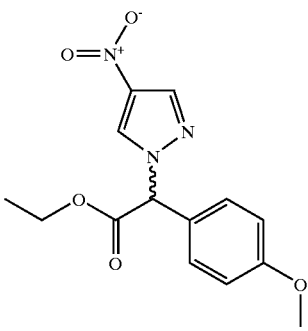

To a stirring slurry of sodium hydride (1.49 g of a 60% dispersion in mineral oil, 37.1 mmol) in N,N-dimethylformamide (35 mL) at 0° C., was added a solution of Preparation 450 (4.00 g, 35.4 mmol) in N,N-dimethylformamide (25 mL). This solution stirred at 0° C. for 10 min then a solution of the product of Preparation 2 from Examples Part 2A (10.6 g, 38.9 mmol) in N,N-dimethylformamide (50 mL) was added. The reaction stirred for 12 h at room temperature, at which time it was quenched with brine and extracted with ethyl acetate. The combined extracts were washed with brine, dried (sodium sulfate) and evaporated to provide a yellow oil. Flash chromatography (silica gel, 15%–40% ethyl acetate/hexanes) yielded the desired product as a light-yellow oil (9.90 g, 92%): $^1$H NMR consistent with structure; MS (IS) m/e 304 (M−1); Anal. Calc'd for $C_{14}H_{15}N_3O_5$: C, 55.08; H, 4.95; N, 13.76. Found: C, 55.26; H, 4.89; N, 13.62.

Preparation 458

To a suspension of 5% palladium on carbon (2.50 g) and tetrahydrofuran (60 mL), in a Parr reaction bottle, was added the product of Preparation 457 (2.60 g, 8.55 mmol) as a solution in 30 mL tetrahydrofuran. The reaction bottle was placed on a Parr shaker, and shaken at room temperature for 3.5 h under a hydrogen atmosphere (35 psi). The reaction

425 was filtered through a pad of Celite 521 and the filtrate was than added to a previously prepared mixture of the product of Preparation 1d from Examples Part 2A (3.25 g, 8.55 mmol), 1,3-dicyclohexylcarbodiimide (1.94 g, 9.40=mmol) and 1-hydroxybenzotriazole hydrate (1.28 g, 9.40 mmol) in 35 mL tetrahydrofuran at room temperature. The reaction was stirred for 16 h at room temperature, then the solvent was evaporated under reduced pressure. The residue was dissolved in ethyl acetate and the solids were filtered away. The filtrate was purified by flash chromatography (silica gel, 70% ethyl acetate/hexanes—ethyl acetate) to give the desired product as a white solid foam (4.14 g, 76%). $^1$H NMR consistent with structure; MS (IS) m/e 638 (M+1); Anal. Calc'd for $C_{33}H_{43}N_5O_8$: C, 62.15; H, 6.80; N, 10.98. Found: C, 62.05; H, 6.85; N, 11.07.

Preparation 459

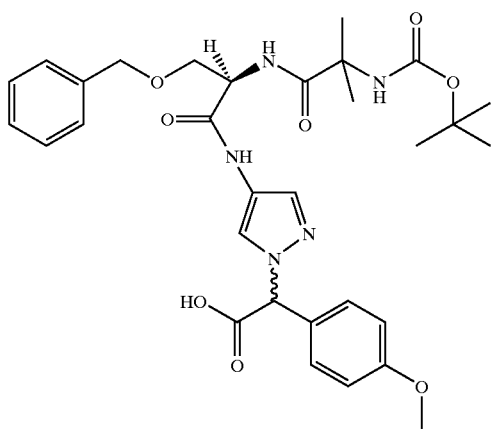

To a solution of the product of Preparation 458 (3.95 g, 6.21 mmol) in tetrahydrofuran (60 mL), water (30 mL) and ethanol (10 mL) at room temperature was added lithium hydroxide (1.04 g. 24.8 mmol). The reaction stirred 25 min at room temperature, at which time the tetrahydrofuran was evaporated under reduced pressure. The residue was diluted with water and extracted with diethyl ether (the ether extracts were discarded). The aqueous layer was acidified (pH 2–3) with 1N HCl and then extracted with diethyl ether and ethyl acetate. The combined organic layers were washed with brine, dried (sodium sulfate) and concentrated under reduced pressure to provide the desired product as an off-white solid foam that was used without further purification (3.53 g, 93%): $^1$H NMR consistent with structure; MS (IS) m/e 610 (M+1); Anal. Calc'd for $C_{31}H_{39}N_5O_8$: C, 61.07; H, 6.45; N, 11.49. Found: C, 59.51; H, 6.17; N, 11.86.

426

Preparation 460

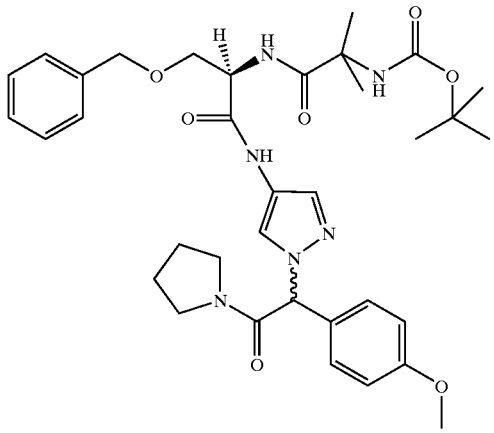

To a solution of the product of Preparation 458 (0.60 g, 0.99 ml) in anhydrous dichloromethane (35 mL) at 0° C. was added N-methylmorpholine (0.13 mL, 1.18 mmol) and 2-chloro-4,6-dimethoxy-1,3,5-triazine (0.19 g, 1.09 mmol). This mixture stirred for 1 h, warming to room temperature, at which time pyrrolidine (0.09 mL, 1.04 mmol) was added. The reaction stirred for 2 h at room temperature, then the solvent was evaporated under reduced pressure. The residue was dissolved in ethyl acetate, the solids were filtered away and the filtrate was purified by flash chromatography (silica gel, 90% ethyl acetate/hexanes—10% methanol/ethyl acetate) to give the desired product as an off-white solid foam (0.375 g, 57%): $^1$H NMR consistent with structure; MS (IS) m/e 661 (M−1); Anal. Calc'd for $C_{35}H_{46}N_6O_7$: C, 63.43; H, 7.00; N, 12.68. Found: C, 63.03; H, 7.00; N, 12.62.

Example 245

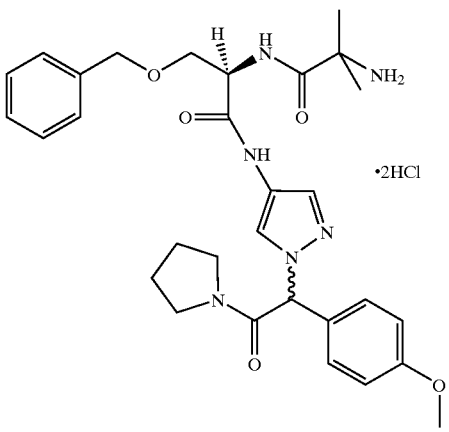

To a stirring solution of the product of Preparation 460 (0.26 g, 0.39 mmol) and anisole (0.04 mL, 0.42 mmol) in anhydrous dichloromethane (15 mL) at 0° C. was added trifluoroacetic acid (2.3 mL) via syringe. The reaction was stirred for 4 h, warming to room temperature and then was quenched by pouring over ice-cooled saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, ethyl acetate—10% methanol/ethyl acetate—5% triethylamine/10% methanol/ethyl acetate) to provide a white solid foam (0.17 g, 80%). The free based material was dissolved in ethyl acetate (5 mL) and then a saturated solution of hydrochloric acid in diethyl ether (1 mL) was added, with stirring. The white precipitate was collected by vacuum filtration and rinsed with diethyl ether. Vacuum drying provided the desired product (0.18 g) as a white amorphous solid: $^1$H NMR consistent with structure; MS (IS) m/e 563 (M+1); Anal. Calc'd for $C_{30}H_{38}N_6O_5$·2HCl: C, 56.69; H, 6.34; N, 13.22. Found: C, 58.29; H, 6.29; N, 13.52.

Preparation 461

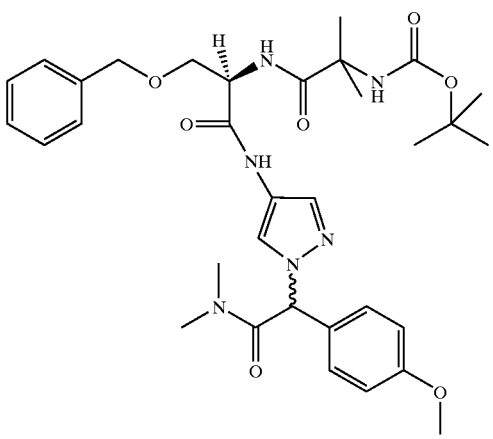

To a solution of the product of Preparation 459 (0.60 g, 0.99 mmol) in anhydrous dichloromethane (35 mL) at 0° C. was added N-methylmorpholine (0.13 mL, 1.18 mmol) and 2-chloro-4,6-dimethoxy-1,3,5-triazine (0.19 g, 1.09 mmol). This mixture stirred for 1 h, warming to room temperature, at which time a 2M solution of N,N-dimethylamine (0.52 mL, 1.04 mmol) was added. The reaction stirred for 2 h at room temperature, then the solvent was evaporated under reduced pressure. The residue was dissolved in ethyl acetate, the solids were filtered away and the filtrate was purified by flash chromatography (silica gel, 90% ethyl acetate/hexanes—10% methanol/ethyl acetate) to give the desired product as an off-white solid foam (0.35 g, 56%); $^1$H NMR consistent with structure; MS (IS) m/e 635 (M−1); Anal. Calc'd for $C_{33}H_{44}N_6O_7$: C, 62.25; H, 6.97; N, 13.20. Found: C, 61.78; H, 6.89; N, 13.05.

Example 246

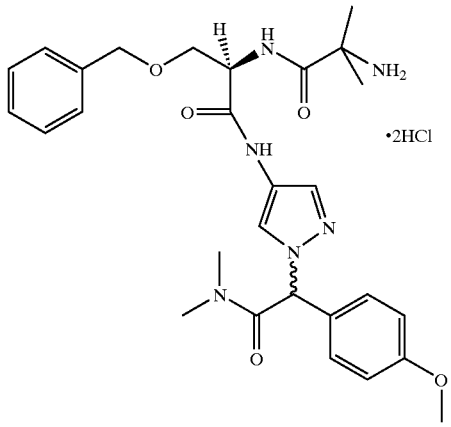

To a stirring solution of the product of Preparation 461 (0.25 g, 0.39 mmol) and anisole (0.04 mL, 0.42 mmol) in anhydrous dichloromethane (15 mL) at 0° C. was added trifluoroacetic acid (2.3 mL) via syringe. The reaction was stirred for 4 h, warming to room temperature and then was quenched by pouring over ice-cooled saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, ethyl acetate—10% methanol/ethyl acetate—5% triethylamine/10% methanol/ethyl acetate) to provide a white solid foam (0.19 g, 89%). The free based material was dissolved in (5 mL) ethyl acetate and then a saturated solution of hydrochloric acid in diethyl ether (1 mL) was added, with stirring. The white precipitate was collected by vacuum filtration and rinsed with diethyl ether. Vacuum drying provided the desired product (0.19 g) as a white amorphous solid: $^1$H NMR consistent with structure; MS (IS) m/e 537 (M+1); Anal. Calc'd for $C_{28}H_{36}N_6O_5$·2HCl: C, 55.17; H, 6.28; N, 13.79. Found: C, 56.27; H, 6.15; N, 14.06.

Preparation 462

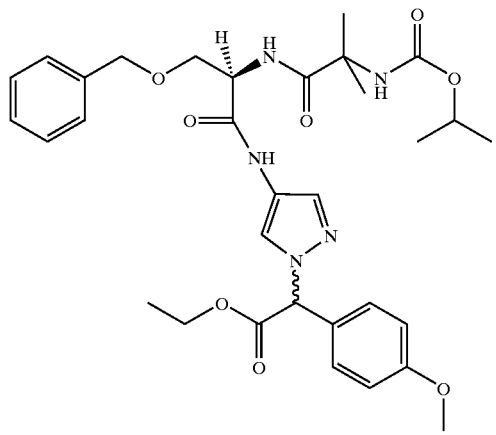

To a suspension of 5% palladium on carbon (0.65 g) and tetrahydrofuran (40 mL), in a Parr reaction bottle, was added the product of Preparation 457 (0.65 g, 2.14 mmol) as a solution in 20 mL tetrahydrofuran. The reaction bottle was placed on a Parr shaker, and shaken at room temperature for 2.5 h under a hydrogen atmosphere (35 psi). The reaction was filtered through a pad of Celite 521 and the filtrate was then added to a previously prepared mixture of the product of Preparation 1j from Examples Part 2A (0.81 g, 2.14 mmol), 1,3-dicyclohexylcarbodiimide (0.49 g, 2.35 mmol) and 1-hydroxybenzotriazole hydrate (0.32 g, 2.35 mmol) in 30 mL tetrahydrofuran at room temperature. The reaction was stirred for 16 h at room temperature, then the solvent was evaporated under reduced pressure. The residue was dissolved in ethyl acetate and the solids were filtered away. The filtrate was purified by flash chromatography (silica gel, 70% ethyl acetate/hexanes—ethyl acetate) to give the desired product as a white solid foam (0.82 g, 60%): $^1$H NMR consistent with structure; MS (IS) m/e 636 (M+1); Anal. Calc'd for $C_{34}H_{45}N_5O_7$: C, 64.23; H, 7.13; N, 11.02. Found: C, 64.53; H, 7.04; N, 10.97.

Preparation 463

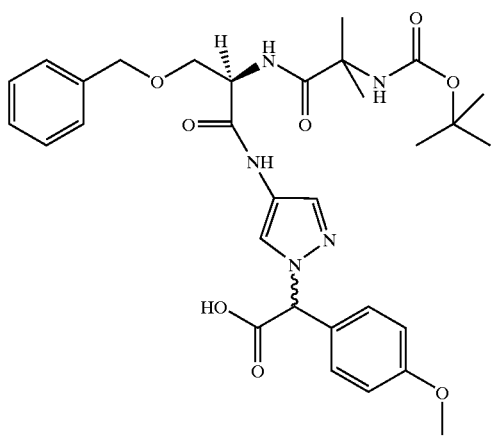

To a solution of the product of Preparation 462 (0.72 g, 1.14 mmol) in tetrahydrofuran (30 mL), water (15 mL) and ethanol (5 mL) at room temperature was added lithium hydroxide (0.19 g, 4.54 mmol). The reaction stirred 25 min at room temperature, at which time the tetrahydrofuran was evaporated under reduced pressure. The residue was diluted with water and extracted with diethyl ether (the ether extracts were discarded). The aqueous layer was acidified (pH 2–3) with 1N HCl and then extracted with diethyl ether and ethyl acetate. The combined organic layers were washed with brine, dried (sodium sulfate) and concentrated under reduced pressure to provide the desired product as a white solid that was used without further purification (0.71 g, 99%): $^1$H NMR consistent with structure; MS (IS) m/e 606 (M−1).

Preparation 464

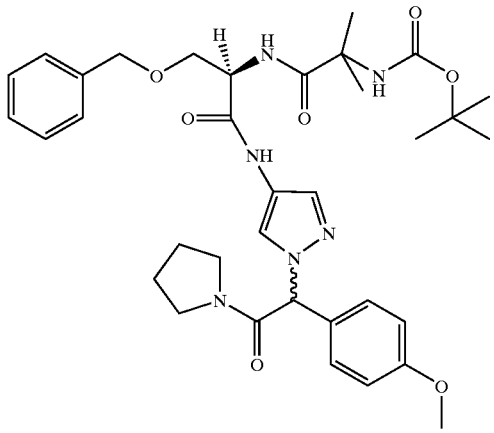

To a solution of the product of Preparation 463 (0.20 g, 0.32 mmol) in anhydrous dichloromethane (20 mL) at 0° C. was added N-methylmorpholine (0.05 mL, 0.39 mmol) and 2-chloro-4,6-dimethoxy-1,3,5-triazine (0.07 g, 0.35 mmol). This mixture stirred for 1 h, warming to room temperature, at which time pyrrolidine (0.03 mL, 0.35 mmol) was added. The reaction stirred for 2 h at room temperature, then the solvent was evaporated under reduced pressure. The residue was dissolved in ethyl acetate, the solids were filtered away and the filtrate was purified by flash chromatography (silica gel, 90% ethyl acetate/hexanes—10% methanol/ethyl acetate) to give the desired product as an off-white solid foam (0.18 g, 85%): $^1$H NMR consistent with structure; MS (IS) m/e 661 (M+1); Anal. Calc'd for $C_{36}H_{48}N_6O_6$: C, 65.43; H, 7.32; N, 12.72. Found: C, 64.37; H, 7.24; N, 12.47.

Example 247

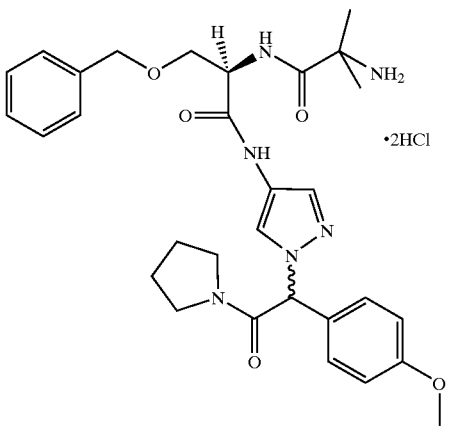

To a stirring solution of the product of Preparation 464 (0.21 g, 0.31 mmol) and anisole (0.04 mL, 0.42 mmol) in anhydrous dichloromethane (15 mL) at 0° C. was added trifluoroacetic acid (1.8 mL) via syringe. The reaction was stirred for 4 h, warming to room temperature and then was quenched by pouring over ice-cooled saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, ethyl acetate—10% methanol/ethyl acetate—5% triethylamine/10% methanol/ethyl acetate) to provide a white solid foam (0.15 g, 86%). The free based material was dissolved in ethyl acetate (5 mL) and then a saturated solution of hydrochloric acid in diethyl ether (1 mL) was added, with stirring. The white precipitate was collected by vacuum filtration and rinsed with diethyl ether. Vacuum drying provided the desired product (0.13 g) as a white amorphous solid: $^1$H NMR consistent with structure; MS (IS) m/e 561 (M+1); Anal. Calc'd for $C_{31}H_{40}N_6O_4 \cdot 2HCl$: C, 58.76; H, 6.68; N, 13.26. Found: C, 59.73; H, 6.63; N, 13.35.

Preparation 465

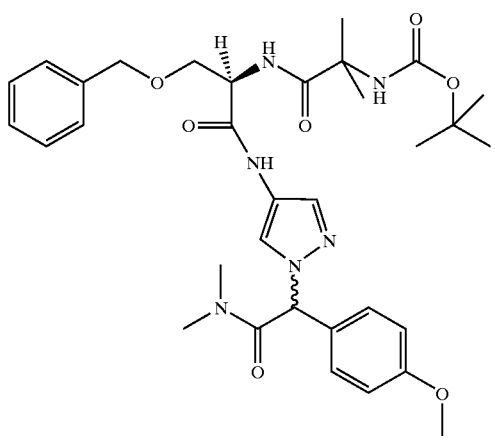

To a solution of the product of Preparation 463 (0.32 g, 0.52 mmol) in anhydrous dichloromethane (20 mL) at 0° C. was added N-methylmorpholine (0.07 mL, 0.62 mmol) and 2-chloro-4,6-dimethoxy-1,3,5-triazine (0.10 g, 0.57 mmol). This mixture stirred for 1 h, warming to room temperature, at which time a 2M solution of N,N-dimethylamine (0.29 mL, 0.57 mmol) was added. The reaction stirred for 2 h at room temperature, then the solvent was evaporated under reduced pressure. The residue was dissolved in ethyl acetate, the solids were filtered away and the filtrate was purified by flash chromatography (silica gel, 90% ethyl acetate/hexanes—10% methanol/ethyl acetate) to give the desired product as an off-white solid foam (0.19 g, 58%): $^1$H NMR consistent with structure; MS (IS) m/e 635 (M+1); Anal. Calc'd for $C_{34}H_{46}N_6O_6$: C, 64.33; H, 7.30; N, 13.24. Found: C, 63.64; H, 7.35; N, 12.95.

Example 248

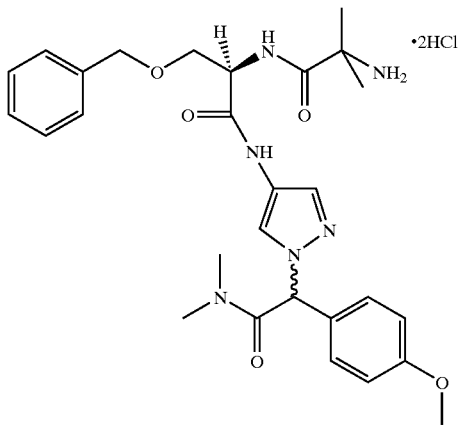

To a stirring solution of the product of Preparation 465 (0.19 g, 0.29 mmol) and anisole (0.03 mL, 0.33 mmol) in anhydrous dichloromethane (15 mL) at 0° C. was added trifluoroacetic acid (1.8 mL) via syringe. The reaction was stirred for 4 h, warming to room temperature and then was quenched by pouring over ice-cooled saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, ethyl acetate—10% methanol/ethyl acetate—5% triethylamine/10% methanol/ethyl acetate) to provide a white solid foam (0.14 g, 88%). The free based material was dissolved in ethyl acetate (5 mL) and then a saturated solution of hydrochloric acid in diethyl ether (1 mL) was added, with stirring. The white precipitate was collected by vacuum filtration and rinsed with diethyl ether. Vacuum drying provided the desired product (0.12 g) as a white amorphous solid: $^1$H NMR consistent with structure; MS (IS) m/e 535 (M+1); Anal. Calc'd for $C_{29}H_{38}N_6O_4 \cdot 2HCl$: C, 57.33; H, 6.64; N, 13.83. Found: C, 58.11 H, 6.61; N, 13.78.

Preparation 466

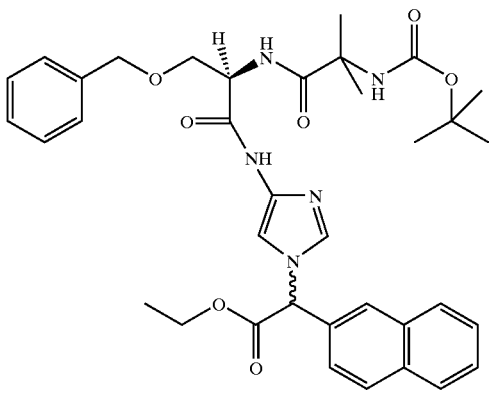

433

To a suspension of 5% palladium on carbon (2.60 g) and tetrahydrofuran (100 mL), in a Parr reaction bottle, was added the product of Preparation 136 from Examples Part 2A (5.00 g, 15.3 mmol) as a solid. The reaction bottle was placed on a Parr shaker, and shaken at room temperature for 2 h under a hydrogen atmosphere (40 psi). The reaction was filtered through a pad of Celite 521 and the filtrate was then added to a previously prepared mixture of the product of Preparation 1j from Examples Part 2A (5.80 g, 15.3 mmol) 1,3-dicyclohexylcarbodiimide (3.48 g, 16.9 mmol) and 1-hydroxybenzotriazole hydrate (2.29 g, 16.9 mmol) in 50 mL tetrahydrofuran at 0° C. The reaction was stirred for 16 h at room temperature, then the solvent was evaporated under reduced pressure. The residue was dissolved in ethyl acetate and the 1,3-dicyclohexylurea was filtered away. The filtrate was purified by flash chromatography (silica gel, 80% ethyl acetate/hexanes—5% methanol/ethyl acetate) to give the desired product as a light yellow solid foam (7.96 g, 80%): $^1$H NMR consistent with structure; MS (IS) m/e 656 (M+1); Anal. Calc'd for $C_{37}H_{44}N_5O_6$: C, 67.77; H, 6.92; N, 10.68. Found: C, 67.49; H, 6.88; N, 11.71.

Preparation 467

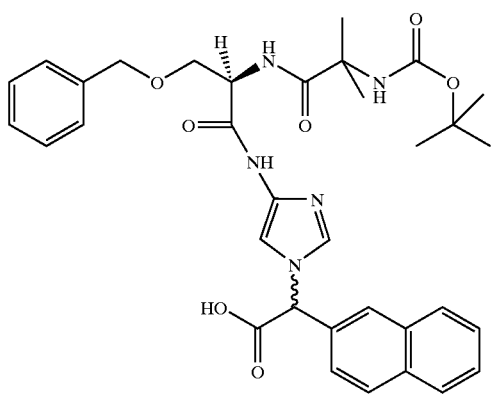

To a solution of the product of Preparation 466 (8.73 g, 13.3 mmol) in tetrahydrofuran (120 mL) and water (60 mL) at room temperature was added lithium hydroxide (2.23 g, 53.2 mmol). The reaction stirred 35 min at room temperature, at which time the tetrahydrofuran was evaporated under reduced pressure. The residue was diluted with water and extracted with diethyl ether (the ether extracts were discarded). The aqueous layer was acidified (pH 2–3) with 1N HCl and then extracted with diethyl ether and ethyl acetate. The combined organic layers were washed with brine, dried (sodium sulfate) and concentrated under reduced pressure to provide the desired product as a light yellow solid foam that was used without further purification (8.18 g, 98%): $^1$H NMR consistent with structure; MS (IS) m/e 628 (M+1); Anal. Calc'd for $C_{35}H_{41}N_5O_6$: C, 66.97; H, 6.58; N, 11.16. Found: C, 66.68; H, 6.75; N, 11.12.

434

Preparation 468

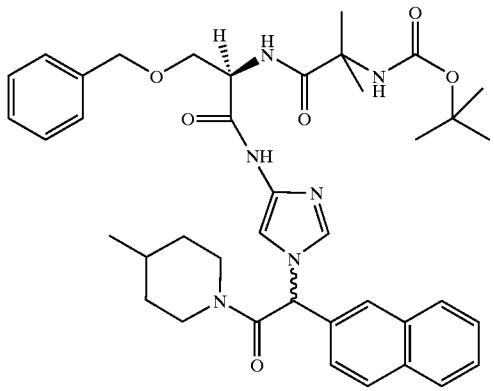

To a solution of the product of Preparation 467 (2.90 g, 4.61 mmol) in anhydrous dichloromethane (40 mL) at 0° C. was added N-methylmorpholine (0.61 mL, 5.53 mmol) and 2-chloro-4,6-dimethoxy-1,3,5-triazine (1.05 g, 5.99 mmol). This mixture stirred for 1 h, warming to room temperature, at which time 4-methylpiperidine (0.60 mL, 5.07 mmol) was added. The reaction stirred for 2 h at room temperature, then more 2-chloro-4,6-dimethoxy-1,3,5-triazine (0.20 g) was added. The reaction was stirred for another 1 h and the solvent was evaporated under reduced pressure. The residue was dissolved in ethyl acetate, the solids were filtered away and the filtrate was purified by flash chromatography (silica gel, ethyl acetate—10% methanol/ethyl acetate) to give the desired product as a light yellow solid foam (2.99 g, 92%): $^1$H NMR consistent with structure; MS (IS) m/e 709 (M+1); Anal. Calc'd for $C_{41}H_{52}N_6O_5$: C, 69.47; H, 7.39; N, 11.85. Found: C, 69.30; H, 7.47; N, 11.92.

Examples 249 and 250

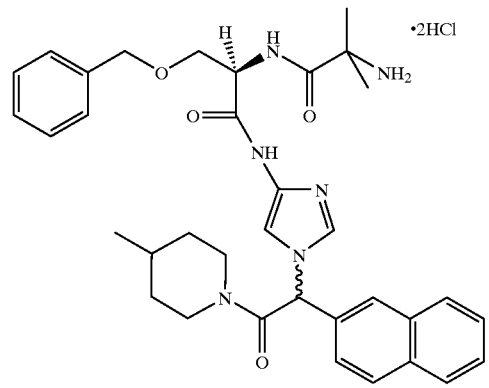

To a stirring solution of the product of Preparation 468 (4.40 g, 6.20 mmol) and anisole (0.71 mL, 6.50 mmol) in anhydrous dichlormethane (140 mL) at 0° C. was added trifluoroacetic acid (14 mL) via syringe. The reaction was stirred for 4 h warming to room temperature and then was quenched by pouring over ice-cooled saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, 5% methanol/ethyl acetate—5% triethylamine/10% methanol/ethyl acetate) to provide the desired product as a light yellow solid foam (3.75 g, 99%). $^1$H NMR consistent with structure; MS (IS) m/e 609 (M+1); Anal. Calc'd for $C_{36}H_{44}N_6O_3$: C, 71.03; H, 7.29; N, 13.80. Found: C, 69.83; H, 7.17; N, 13.54.

Diastereomeric separation: the desired product was resolved by HPLC [Kromasil packing material, 15% 3A alcohol/85% heptane (w/0.2% DMEA)] to provide two diastereomers. The first diastereomer (1.30 g) (retention time=6.77 min) was dissolved in ethyl acetate (20 mL) and then a saturated solution of hydrochloric acid in diethyl ether (3 mL) was added, with stirring. The white precipitate was collected by vacuum filtration and rinsed with diethyl ether. Vacuum drying provided Example 249 (1.10 g) as a white amorphous solid: $^1$H NMR consistent with structure; MS (IS) m/e 609 (M+1); Anal. Calc'd for $C_{36}H_{44}N_6O_3 \cdot HCl$: C; 67.02; H, 7.03; N, 13.03. Found: C, 66.53; H, 6.96; N, 12.80. The second diastereomer (1.50 g) (retention time=9.17 min) was dissolved in ethyl acetate (20 mL) and then a saturated solution of hydrochloric acid in diethyl ether (3 mL) was added, with stirring. The white precipitate was collected by vacuum filtration and rinsed with diethyl ether. Vacuum drying provided Example 250 (1.47 g) as a white amorphous solid: $^1$H NMR consistent with structure; MS (IS) m/e 609 (M+1); Anal. Calc'd for $C_{36}H_{44}N_6O_3 \cdot HCl$: C, 67.02; H, 7.03; N, 13.03. Found: C, 66.08; H, 6.95; N, 12.71.

Preparation 469

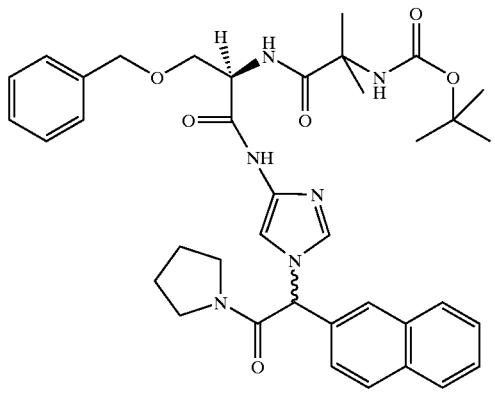

To a solution of the product of Preparation 467 (5.10 g, 8.11 mmol) in anhydrous dichloromethane (75 mL) at 0° C. was added N-methylmorpholine (1.07 mL. 9.73 mmol) and 2-chloro-4,6-dimethoxy-1,3,5-triazine (1.85 g, 10.5 mmol). This mixture stirred for 1 h, warming to room temperature, at which time pyrrolidine (0.75 mL, 8.93 mmol) was added. The reaction stirred for 2 h at room temperature, then more 2-chloro-4,6-dimethoxy-1,3,5-triazine (0.20 g) was added. The reaction was stirred for another 1 h and the solvent was evaporated under reduced pressure. The residue was dissolved in ethyl acetate, the solids were filtered away and the filtrate was purified by flash chromatography (silica gel, ethyl acetate—10% methanol/ethyl acetate) to give the desired product as a light yellow solid foam (5.30 g, 96%): $^1$H NMR consistent with structure; MS (IS) m/e 681 (M+1); Anal. Calc'd for $C_{39}H_{48}N_6O_5$: C, 68.80; H, 7.11; N, 12.34. Found: C, 68.07; H, 7.10; N, 12.85.

Examples 251 and 252

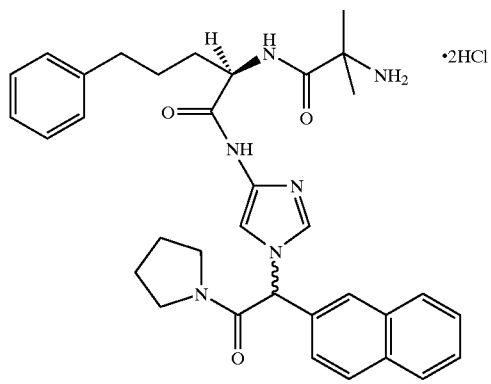

To a stirring solution of the product of Preparation 469 (5.15 g, 7.55 mmol) and anisole (0.86 mL, 7.93 mmol) in anhydrous dichlormethane (150 mL) at 0° C. was added trifluoroacetic acid (15 mL) via syringe. The reaction was stirred for 4 h warming to room temperature and then was quench by pouring over ice-cooled saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatograph (silica gel, 5% methanol/ethyl acetate—5% triethylamine/10% methanol/ethyl acetate) to provide the desired product as an off-white solid foam (4.11 g, 94%). $^1$H NMR consistent with structure; MS (IS) m/e 591 (M+1); Anal. Calc'd for $C_{34}H_{40}N_6O_3$: C, 70.32; H, 6.94; N, 14.47. Found: C, 70.34; H, 6.79; N, 13.70.

Diastereomeric separation: the desired product was resolved by HPLC [Kromasil packing material, 15% 3A alcohol/85% heptane (w/0.2% DMEA)] to provide two diastereomers. The first diastereomer (1.70 g) (retention time=7.72 min) was dissolved in ethyl acetate (20 mL) and then a saturated solution of hydrochloric acid in diethyl ether (3 mL) was added, with stirring. The white precipitate was collected by vacuum filtration and rinsed with diethyl ether. Vacuum drying provided Example 251 (1.27 g) as a off-white amorphous solid: $^1$H NMR consistent with structure; MS (IS) m/e 581 (M+1); Anal. Calc'd for $C_{34}H_{40}N_6O_3 \cdot 2HCl$: C, 66.17; H, 6.70; N, 13.62. Found: C, 65.65; H, 6.90; N, 13.48. The second diastereomer (1.40 g) (retention time=10.81) was dissolved in ethyl acetate (20 mL) and then a saturated solution of hydrochloric acid in diethyl ether (3 mL) was added, with stirring. The white precipitate was collected by vacuum filtration and rinsed with diethyl ether. Vacuum drying provided Example 252 (1.47 g) as a off-white amorphous solid: $^1$H NMR consistent with structure; MS (IS)=m/e 581 (M+1); Anal. Calc'd for $C_{34}H_{40}N_6O_3 \cdot 2HCl$: C, 66.17; H, 6.70; N, 13.62. Found: C, 65.73; H, 7.03; N, 13.31.

Preparation 470

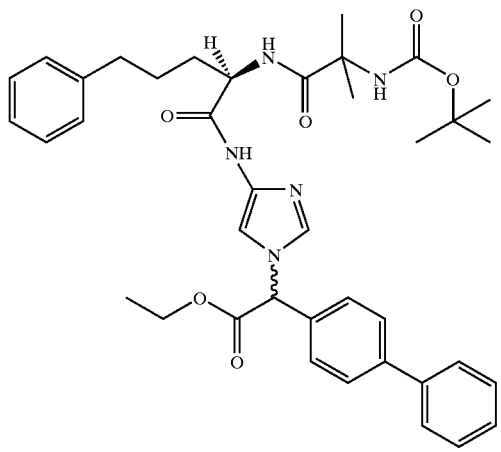

To a suspension of 5% palladium on carbon (2.60 g) and tetrahydrofuran (100 mL), in a Parr reaction bottle, was added the product of Preparation 99 from Examples Part 2A (5.00 g, 15.3 mmol) as a solid. The reaction bottle was placed on a Parr shaker, and shaken at room temperature for 2 h under a hydrogen atmosphere (40 psi). The reaction was filtered through a pad of Celite 521 and the filtrate was then added to a previously prepared mixture of the product of Preparation 1j from Examples Part 2A (5.80 g, 15.3 mmol), 1,3-dicyclohexylcarbodiimide (3.48 g, 16.9 mmol) and 1-hydroxybenzotriazole hydrate (2.29 g, 16.9 mmol) in 50 mL tetrahydrofuran at 0° C. The reaction was stirred for 16 h at room temperature, then the solvent was evaporated under reduced pressure. The residue was dissolved in ethyl acetate and the 1,3-dicyclohexylurea was filtered away. The filtrate was purified by flash chromatography (silica gel, 80% ethyl acetate/hexanes—5% methanol/ethyl acetate) to give the desired product as a light yellow solid foam (7.96 g, 80%): $^1$H NMR consistent with structure; MS (IS) m/e 682 (M+1); Anal. Calc'd for $C_{39}H_{47}N_5O_6$: C, 68.70; H, 6.95; N, 10.27. Found: C, 68.27; H, 6.86; N, 10.77.

Preparation 471

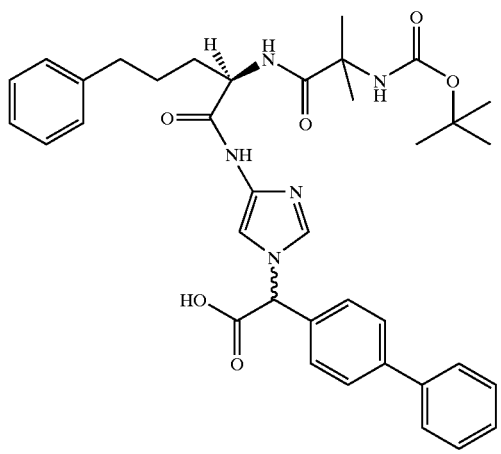

To a solution of the product of Preparation 470 (8.73 g, 13.3 mmol) in tetrahydrofuran (120 mL) and water (60 mL) at room temperature was added lithium hydroxide (2.23 g, 53.2 mmol). The reaction stirred 35 min at room temperature, at which time the tetrahydrofuran was evaporated under reduced pressure. The residue was diluted with water and extracted with diethyl ether (the ether extracts were discarded). The aqueous layer was acidified (pH 2–3) with 1N HCl and then extracted with diethyl ether and ethyl acetate. The combined organic layers were washed with brine, dried (sodium sulfate) and concentrated under reduced pressure to provide the desired product as a light yellow solid foam that was used without further purification (8.18 g, 98%): $^1$H NMR consistent with structure; MS (IS) m/e 654 (M+1); Anal. Calc'd for $C_{37}H_{43}N_5O_6$: C, 67.98; H, 6.63; N, 10.71. Found: C, 66.83; H, 6.59; N, 10.50.

Preparation 472

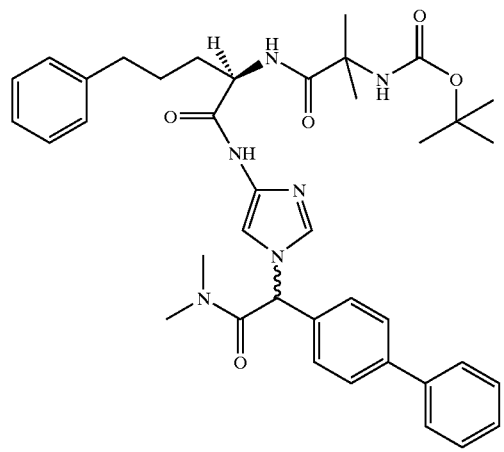

To a solution of the product of Preparation 471 (1.00 g, 1.52 mmol) in anhydrous dichloromethane (30 mL) at 0° C. was added N-methylmorpholine (0.20 mL, 1.82 mmol) and 2-chloro-4,6-dimethoxy-1,3,5-triazine (0.35 g, 1.98 mmol. This mixture stirred for 1 h, warming to room temperature, at which time a 2M solution of N,N-dimethylamine (0.84 mL, 1.68 mmol) was added. The reaction stirred for 2 h at room temperature, then more 2-chloro-4,6-dimethoxy-1,3,5-triazine (0.08 g) was added. The reaction was stirred for another 1 h and the solvent was evaporated under reduced pressure. The residue was dissolved in ethyl acetate, the solids were filtered away and the filtrate was purified by flash chromatography (silica gel, 90% ethyl acetate/hexanes—10% methanol/ethyl acetate) to give the desired product as a light yellow solid foam (0.83 g, 80%): $^1$H NMR consistent with structure; MS (IS) m/e 681 (M+1); Anal. Calc'd for $C_{39}H_{48}N_6O_5$: C, 68.80; H, 7.11; N, 12.34. Found: C, 68.23; H, 7.03; N, 12.66.

Example 253

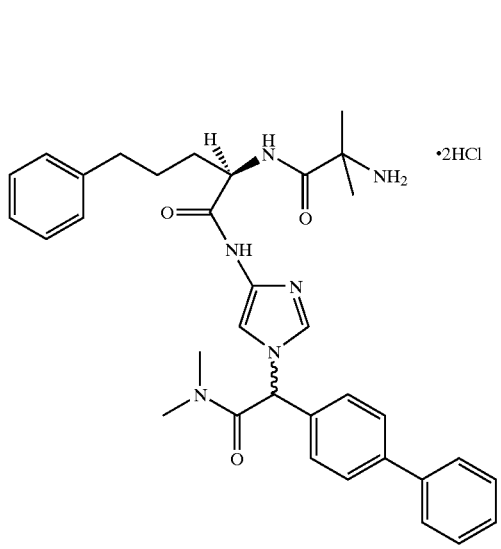

To a stirring solution of the product of Preparation 472 (3.10 g, 4.52 mmol) and anisole (0.52 mL, 4.75 mmol) in dichlormethane (100 mL) at 0° C. was added trifluoroacetic acid (10 mL) via syringe. The reaction was stirred for 4 h warming to room temperature and then was quenched by pouring over ice-cooled saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, 5% methanol/ethyl acetate~5% triethylamine/10% methanol/ethyl acetate) to provide the desired product as an off-white solid foam (2.40 g, 91%). $^1$H NMR consistent with structure; MS (IS) m/e 581 (M+1); Anal. Calc'd for $C_{34}H_{40}N_6O_3$: C, 70.32; H, 6.94; N, 14.47. Found: C, 69.36; H, 6.71; N, 14.10.

Diastereomeric separation: the desired product was resolved by HPLC [Kromasil packing material, 15% 3A alcohol/85% heptane (w/0.2% DMEA)] to provide two diastereomers. The second diastereomer (0.76 g) (retention time=9.98 min) was dissolved in ethyl acetate (15 mL) and then a saturated solution of hydrochloric acid in diethyl ether (2 mL) was added, with stirring. The white precipitate was collected by vacuum filtration and rinsed with diethyl ether. Vacuum drying provided Example 253 (0.70 g) as a white amorphous solid: $^1$H NMR consistent with structure; MS (IS) m/e 581 (M+1); Anal. Calc'd for $C_{34}H_{40}N_6O_3$·HCl: C, 66.18; H, 6.70; N, 13.62. Found: C, 64.39; H, 6.69; N, 13.19.

Preparation 473

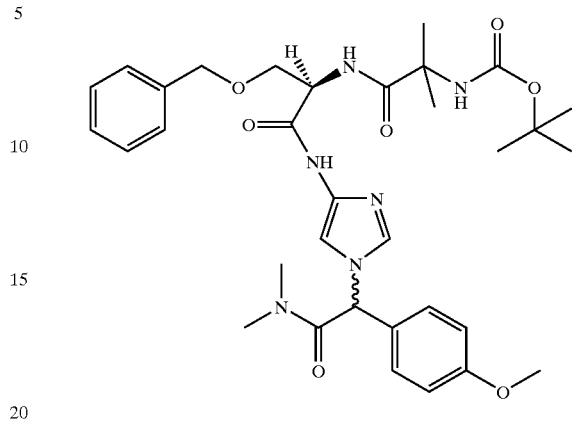

To a solution of the product of Preparation 5 from Examples Part 2A (3.60 g, 5.90 mmol) in anhydrous dichloromethane (60 mL) at 0° C. was added N-methylmorpholine (0.78 mL, 7.08 mmol) and 2-chloro-4,6-dimethoxy-1,3,5-triazine (1.35 g, 7.67 mmol). This mixture stirred for 1 h, warming to room temperature, at which time a 2M solution of N,N-dimethylamine (3.30 mL, 6.49 mmol) was added. The reaction stirred for 2 h at room temperature, then more 2-chloro-4,6-dimethoxy-1,3,5-triazine (0.30 g) was added. The reaction was stirred for another 1 h and the solvent was evaporated under reduced pressure. The residue was dissolved in ethyl acetate, the solids were filtered away and the filtrate was purified by flash chromatography (silica gel, ethyl acetate—10% methanol/ethyl acetate) to give the desired product as a light yellow solid foam (2.93 g, 78%): $^1$H NMR consistent with structure; MS (IS) m/e 637 (M+1); Anal. Calc'd for $C_{33}H_{44}N_6O_7$: C, 62.25; H, 6.97; N, 13.20. Found: C, 61.02; H, 6.67; N, 13.72.

Example 254

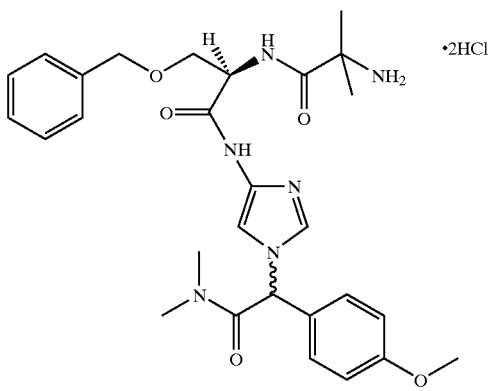

To a stirring solution of the product of Preparation 473 (3.60 g, 5.65 mmol) and anisole (0.65 mL, 5.93 mmol) in anhydrous dichloromethane (130 mL) at 0° C. was added trifluoroacetic acid (13 mL) via syringe. The reaction was stirred for 4 h warming to room temperature and then was quenched by pouring over ice-cooled saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, 5% methanol/ethyl acetate—5% triethylamine/10% methanol/ethyl acetate) to provide the desired product as an off-white solid foam (2.20 g, 73%). $^1$H NMR consistent with structure; MS (IS) m/e 537 (M+1); Anal. Calc'd for $C_{28}H_{36}N_6O_5$: C, 62.67; H, 6.76; N, 15.66. Found: C, 62.53; H, 6.62; N, 15.57.

Diastereomeric separation: the product was resolved by HPLC [Kromasil packing material, 15% 3A alcohol/85% heptane (w/0.2% DMEA)] to provide two diastereomers. The second diastereomer (0.45 g) (retention time=10.70 min) was dissolved in ethyl acetate (10 mL) and then a saturated solution of hydrochloric acid in diethyl ether (2 mL) was added, with stirring. The white precipitate was collected by vacuum filtration and rinsed with diethyl ether. Vacuum drying provided Example 254 (0.40 g) as a white amorphous solid: $^1$H NMR consistent with structure; MS (IS) m/e 537 (M+1); Anal. Calc'd for $C_{28}H_{36}N_6O_5 \cdot 2HCl$: C, 55.17; H, 6.28; N, 13.79. Found: C, 56.56; H, 6.38; N, 14.26.

Preparation 475

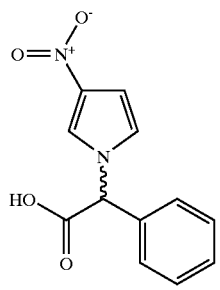

To a stirring solution of the product of Preparation 474 (1.01 g, 1.59 mmol) in dioxane (30 mL) and water (15 mL) at room temperature was added lithium hydroxide (0.26 g, 6.30 mmol). The reaction stirred 25 min at room temperature, at which time the dioxane was evaporated under reduced pressure. The residue was diluted with water and extracted with diethyl ether (the ether extracts were discarded). The aqueous layer was acidified (pH 2–3) with 1N HCl and then extracted with diethyl ether and ethyl acetate. The combined organic layers were washed with brine, dried (sodium sulfate) and concentrated under reduced pressure to provide the desired product as a light tan solid foam that was used without further purification (0.96 g, 99%):

Preparation 474

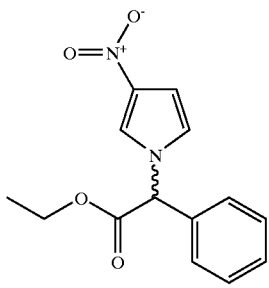

To a stirring slurry of sodium hydride (0.155 g of a 60% dispersion in mineral oil, 3.86 mmol) in N,N-dimethylformamide (30 mL) at 0° C., was added a solution of 3-nitropyrrole (0.600 g, 3.68 mmol) in N,N-dimethylformamide (10 mL). This solution stirred at 0° C. for 10 min then a solution of the product of Preparation 5, Examples Part 1, in N,N-dimethylformamide (10 mL) was added. The reaction was stirred at room temperature for 15 h, at which time it was quenched with brine and extracted with ethyl acetate. The combined extracts were washed with brine, dried (sodium sulfate) and evaporated to provide a yellow oil, which contained a 9:1 mixture of the desired regioisomer and the undesired 5-nitro-4-methyl regioisomer. Flash chromatography (silica gel, 20%–50% ethyl acetate/hexanes) yielded the desired product as a light-yellow solid (2.53 g, 60%).

Preparation 476

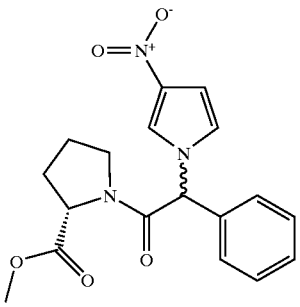

To a stirring solution of Preparation 475 (0.433 g, 1.46 mmol), L-proline methyl ester hydrochloride (0.241 g, 1.46 mmol), 1-hydroxybenzotriazole hydrate (0.200 g, 1.46 mmol) and N,N-diisopropylethylamine (0.660 g, 5.10 mmol) in anhydrous 1,2-dichlormethane (30 mL), at room temperature, was added 1(3-dimethylaminopropyl)-3-ethylcarbodiimide (0.310 g, 1.60 mmol). The reaction was stirred for 18 h at room temperature, quenched with water (50 mL) and the aqueous layer w extracted with ethyl acetate. The combined extracts were washed with 10% citric acid, saturated sodium bicarbonate, water and brine, dried (sodium sulfate) and evaporated to provide a yellow solid. Rotary chromatography (silica gel, 35% ethyl acetate/hexanes—85% ethyl acetate/hexanes) gave 0.250 g (42%) of the desired product as a white foam solid.

Preparation 477

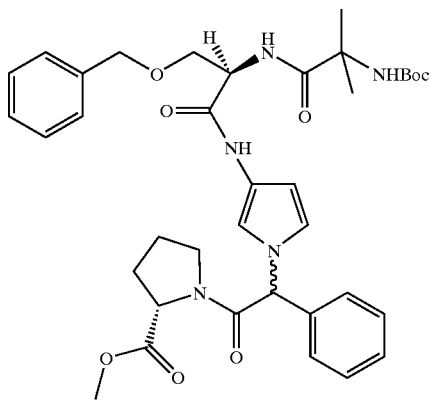

To a suspension of 5% palladium on carbon (1.75 g) ethyl acetate (90 mL) and ethanol (10 mL), in a Parr reaction bottle, was added the product of Preparation 476 (3.51 g, 11.5 mmol) as a solid. The reaction bottle was placed on a Parr shaker, and shaken at room temperature for 45 min under a hydrogen atmosphere (35 psi). The reaction was filtered through a pad of Celite 521. The filtrate was evaporated to an orange solid foam which was then added to a previously prepared mixture of the product of Preparation 1d (4.33 g, 11.5 mmol) and 1-hydroxybenzotriazole hydrate (1.72 g, 12.6 mmol) in 50 mL dioxane at room temperature. This solution stirred for 15 man at which time 1,3-dicyclohexylcarbodiimide (1.66 g, 10.3 mmol) was added. The reaction was stirred at room temperature for 15 h, then the solvent was evaporated under reduced pressure. The residue was dissolved in ethyl acetate and the 1,3-dicyclohexylurea was filtered away. The filtrate was purified by flash chromatography (silica gel, 75% ethyl acetate/hexanes—10% methanol/ethyl acetate) to give the desired product as a light tan solid foam (4.5 g, 62%):

Example 255

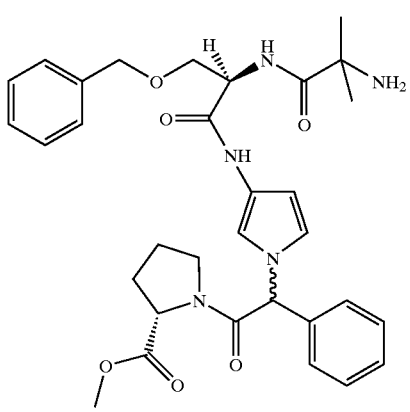

To a stirring solution of the product of Preparation 477 (0.77 g, 1.12 mmol) and anisole (0.05 mL, 0.47 mmol) in anhydrous dichloromethane (20 mL) at 0° C. was added trifluoroacetic acid via syringe. The reaction was stirred for 4 h, warming to room temperature and then was quenched by pouring over ice-cooled, saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, 100% ethyl acetate—5% methanol/95% ethyl acetate—5% triethylamine/10% methanol/85% ethyl acetate) to provide the desired product as an off-white solid foam (0.625 g, 95%).

Preparation 478

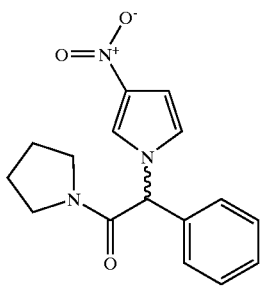

To a stirring solution of the product of Preparation 475 (0.433 g, 1.46 mmol), pyrrolidine (0.242 g, 1.46 mmol), 1-hydroxybenzotriazole hydrate (0.200 g, 1.46 mmol) and N,N-diisopropylethylamine (0.660 g, 5.10 mmol) in anhydrous 1,2-dichlormethane (30 mL), at room temperature, was added 1-(3-dimethylaminopropyl)-3-ethylcarbodiimide (0.310 g, 1.60 mmol). The reaction was stirred for 18 h at room temperature, quenched with water (50 mL) and the aqueous layer was extracted with ethyl acetate. The combined extracts were washed with 10% citric acid, saturated sodium bicarbonate, water and brine, dried (sodium sulfate) and evaporated to provide a yellow solid. Flash chromatography (silica gel, 40% ethyl acetate/hexanes—100% ethyl acetate) gave 0.250 g (42%) of the desired product as a white foam solid.

Preparation 479

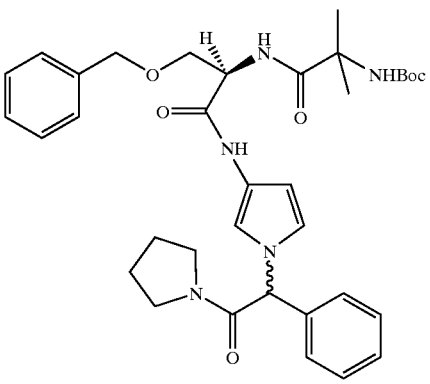

To a suspension of 5% palladium on carbon (1.75 g) ethyl acetate (50 mL) and ethanol (25 mL), in a Parr reaction bottle, was added Preparation 478 (3.51 g, 11.5 mmol) as a solid. The reaction bottle was placed on a Parr shaker, and shaken at room temperature for 45 min under a hydrogen atmosphere (35 psi). The reaction was filtered through a pad of Celite 521. The filtrate was evaporated to an orange solid foam which was then added to a previously prepared mixture of the product of Preparation 1d (4.33 g, 11.5 mmol) and 1-hydroxybenzotriazole hydrate (1.72 g, 12.6 mmol) in 50 mL dioxane at room temperature. This solution stirred for 15 min at which time 1,3-dicyclohexylcarbodiimide (1.66 g, 10.3 mmol) was added. The reaction was stirred at room temperature for 15 h, then the solvent was evaporated under reduced pressure. The residue was dissolved in ethyl acetate and the 1,3-dicyclohexylurea was filtered away. The filtrate was purified by flash chromatography (silica gel, 50% ethyl acetate/hexanes—100% ethyl acetate) to give the desired product as a light tan solid foam (4.5 g, 62%).

Example 256

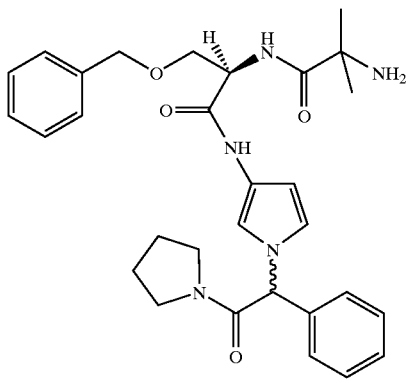

To a stirring solution of the product of Preparation 479 (0.77 g, 1.12 mmol) and anisole (0.05 mL, 0.47 mmol) in anhydrous dichloromethane (20 mL) at 0° C. was added trifluoroacetic acid via syringe. The reaction was stirred for 4 h, warming to room temperature and then was quenched by pouring over ice-cooled, saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, 100% ethyl acetate—5% methanol/95% ethyl acetate—5% triethylamine/10% methanol/85% ethyl acetate) to provide the desired product as an off-white solid foam (0.625 g, 95%).

Preparation 480

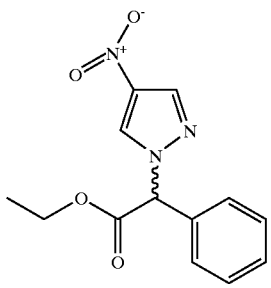

To a stirring slurry of sodium hydride (0.155 g of a 60% dispersion in mineral oil, 3.86 mmol) in N,N-dimethylformamide (30 mL) at 0° C., was added a solution of 3-nitropyrrole (0.600 g, 3.68 mmol in N,N-dimethylformamide (10 mL). This solution stirred at 0° C. for 10 min then a solution of the product of Preparation 5, Examples Part 1 in N,N-dimethylformamide (10 mL) was added. The reaction was stirred at room temperature for 15 h, at which time it was quenched with brine and extracted with ethyl acetate. The combined extracts were washed with brine, dried (sodium sulfate) and evaporated to provide a yellow oil, which contained a 9:1 mixture of the desired regioisomer and the undesired 5-nitro-4-methyl regioisomer. Flash chromatography (silica gel, 20%–50% ethyl acetate/hexanes) yielded the desired product as a light-yellow solid (2.53 g, 60%).

Preparation 481

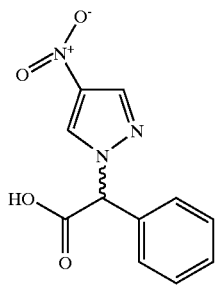

To a stirring solution of the product of Preparation 480 (1.01 g, 1.59 mmol) in dioxane (30 mL) and water (15 mL) at room temperature was added lithium hydroxide (0.26 g, 6.30 mmol). The reaction stirred 25 min at room temperature, at which time the dioxane was evaporated under reduced pressure. The residue was diluted with water and extracted with diethyl ether (the ether extracts were discarded). The aqueous layer was acidified (pH 2–3) with 1N HCl and then extracted with diethyl ether and ethyl acetate. The combined organic layers were washed with brine, dried (sodium sulfate) and concentrated under reduced pressure to provide the desired product as a light tan solid foam that was used without further purification (0.96 g, 99%).

Preparation 482

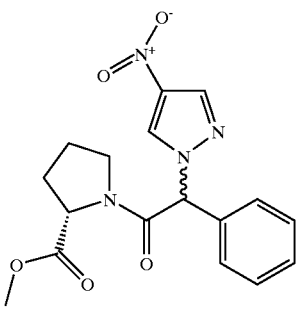

To a stirring solution of the product of Preparation 481 (0.433 g, 1.46 mmol), L-proline methyl ester hydrochloride (0.241 g, 1.46 mmol), 1-hydroxybenzotriazole hydrate (0.200 g, 1.46 mmol) and N,N-diisopropylethylamine (0.660 g, 5.10 mmol) in anhydrous 1,2-dichlormethane (30 mL), at room temperature, was added 1-(3-dimethylaminopropyl)-3-ethylcarbodiimide (0.310 g, 1.60 mmol). The reaction was stirred for 18 h at room temperature, quenched with water (50 mL) and the aqueous layer was extracted with ethyl acetate. The combined extracts were washed with 10% citric acid, saturated sodium bicarbonate, water and brine, dried (sodium sulfate) and evaporated to provide a yellow solid.

Rotary chromatography (silica gel, 35% ethyl acetate/hexanes—85% ethyl acetate/hexanes) gave 0.250 g (42%) of the desired product as a white foam solid.

Preparation 483

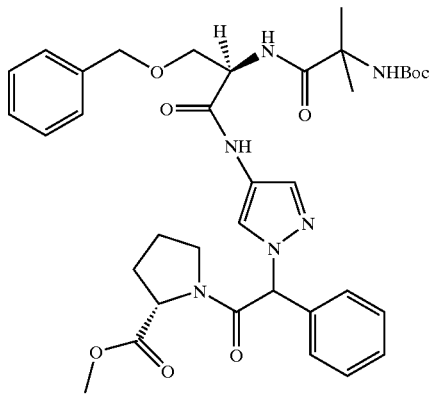

To a suspension of 5% palladium on carbon (1.75 g) methanol (25 mL), was added the product of Preparation 482 (3.51 g, 11.5 mmol) as a solid. The reaction was stirred at room temperature for 3–4 h under 1 atmosphere of $H_2$. The reaction filtered through a pad of Celite 521. The filtrate mm evaporated to an off-white solid foam which was then added to a previously prepared mixture of the product of Preparation 1d (14.33 g, 11.5 mmol) and 1-hydroxybenzotriazole hydrate (1.72 g, 12.6 mmol) in 50 mL N,N-dimethylformamide at room temperature. This solution stirred for 15 min at which time 1,3-dicyclohexylcarbodiimide (1.66 g, 10.3 mmol) was added. The reaction was stirred at room temperature for 15 h, then quenched with brine and extracted with ethyl acetate. The combined extracts were washed with brine, dried (sodium sulfate), and evaporated to give a tan solid foam. The crude foam was purified by flash chromatography (silica gel, 75% ethyl acetate/hexanes—10% methanol/ethyl acetate) to provide the separated diastereomers, Preparation 483A and Preparation 483B as off-white solid foams (4.5 g, 62%).

Example 257

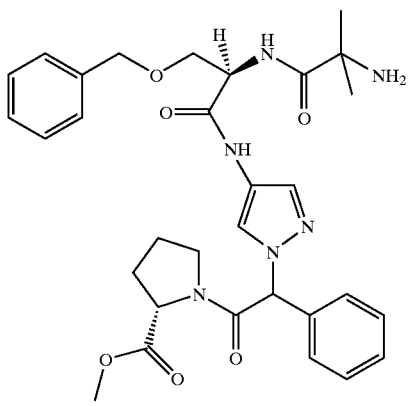

To a stirring solution of the product of Preparation 483A (0.77 g, 1.12 mmol) and anisole (0.05 mL, 0.47 mmol) in anhydrous dichloromethane (20 mL) at 0° C. was added trifluoroacetic acid via syringe. The reaction was stirred for 4 h, warming to room temperature and then was quenched by pouring over ice-cooled, saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, 100% ethyl acetate—5% methanol/95% ethyl acetate—5% triethylamine/10% methanol/85% ethyl acetate) to provide the desired product as an white solid foam (0.625 g, 95%).

Example 258

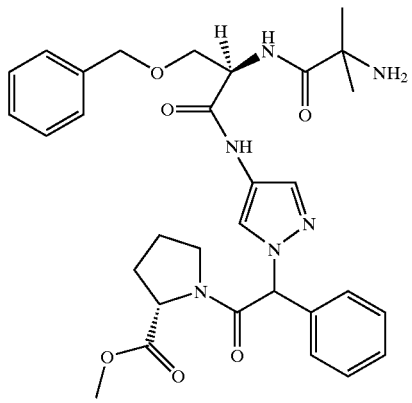

To a stirring solution of the product of Preparation 483B (0.77 g, 1.12 mmol) and anisole (0.05 mL, 0.47 mmol) in anhydrous dichlormethane (20 mL) at 0° C. was added trifluoroacetic acid via syringe. The reaction was stirred for 4 h, warming to room temperature and then was quenched by pouring over ice-cooled, saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, 100% ethyl acetate—5% methanol/95% ethyl acetate—5% triethylamine/10% methanol 85% ethyl acetate) to provide the desired product as an white solid foam (0.625 g, 95%).

Preparation 484

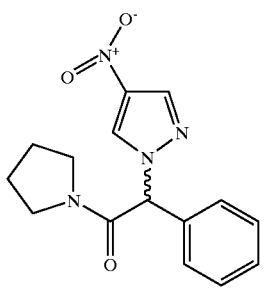

To a stirring solution of the product of Preparation 481 (0.433 g, 1.46 mmol), L-proline methyl ester hydrochloride (0.241 g, 1.46 mmol), 1-hydroxybenzotriazole hydrate (0.200 g, 1.46 mmol) and N,N-diisopropylethylamine (0.660 g, 5.10 mmol) in anhydrous 1,2-dichlormethane (30 mL), at room temperature, was added 1-(3-dimethylaminopropyl)-3-ethylcarbodiimide (0.310 g, 1.60 mmol). The reaction was stirred for 18 h at room temperature, quenched with water (50 mL) and the aqueous layer was extracted with ethyl acetate. The combined extracts were washed with 10% citric acid, saturated sodium bicarbonate, water and brine, dried (sodium sulfate) and evaporated to provide a yellow solid. Rotary chromatography (silica gel, 35% ethyl acetate/hexanes—85% ethyl acetate/hexanes) gave 0.250 g (42%) of the desired product as a white foam solid.

Preparation 485

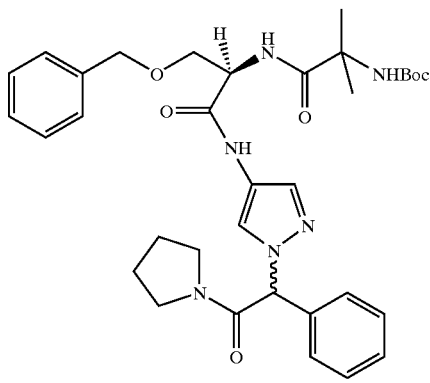

To a suspension of 5% palladium on carbon (1.75 g) methanol (25 mL), was added the product of Preparation 484 (3.51 g, 11.5 mmol) as a solid. The reaction was stirred at room temperature for 3–4 h under 1 atmosphere of $H_2$. The reaction was filtered through a pad of Celite 521. The filtrate was evaporated to an off-white solid foam which was then added to a previously prepared mixture of the product of Preparation 1d (4.33 g, 11.5 mmol) and 1-hydroxybenzotriazole hydrate (1.72 g, 12.6 mmol) in 50 mL N,N-dimethylformamide at room temperature. This solution stirred for 15 min at which time 1,3-dicyclohexylcarbodiimide (1.66 g, 10.3 mmol) was added. The reaction was stirred at room temperature for 15 h, then quenched with brine and extracted with ethyl acetate. The combined extracts were washed with brine, dried (sodium sulfate), and evaporated to give a tan solid foam. The crude foam was purified by flash chromatography (silica gel, 75% ethyl acetate/hexanes—10% methanol/ethyl acetate) to provide the desired product as an off-white solid foam (4.5 g, 62%).

Examples 259

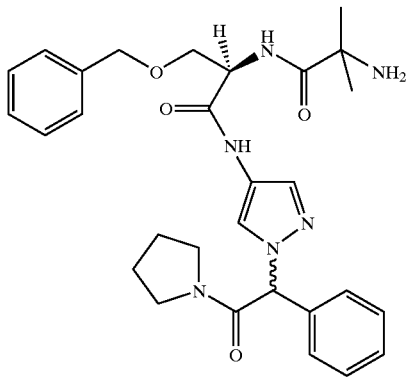

To a stirring solution of the product of Preparation 485 (0.77 g, 1.12 mmol) and anisole (0.05 mL, 0.47 mmol) in anhydrous dichloromethane (20 mL) at 0° C. was added trifluoroacetic acid via syringe. The reaction was stirred for 4 h, warming to room temperature and then was quenched by pouring over ice-cooled, saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, 100% ethyl acetate—5% methanol/95% ethyl acetate—5% triethylamine/10% methanol/85% ethyl acetate) to provide the desired product as a white solid foam (0.625 g, 95%).

EXAMPLES PART 2D

Preparation 486

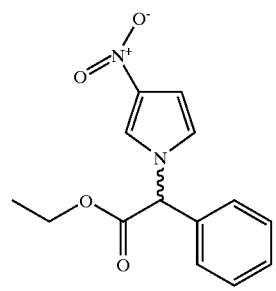

To a stirring slurry of sodium hydride (0.750 g of a 60% dispersion in mineral oil, 18.7 mmol) in N,N-dimethylformamide (40 mL) at 0° C., was added a solution of 3-nitropyrrole (2.00 g, 17.8 mmol) in N,N-dimethylformamide (25 mL). This solution stirred at 0° C. for 10 min then a solution of the product of Preparation 5 from Examples Part 1 (4.77 g, 19.6 mmol) in N,N-dimethylformamide (10 mL) was added. The reaction was stirred at room temperature for 15 h, at which time it was quenched with brine and extracted with ethyl acetate. The combined extracts were washed with brine, dried (sodium sulfate) and evaporated to provide a yellow oil. Flash chromatography (silica gel, 20%–50% ethyl acetate/hexanes) yielded the desired product as a light-yellow oil (4.77 g, 98%): $^1$H NMR consistent with structure; MS (IS) m/e 275 (M+1).

Preparation 487

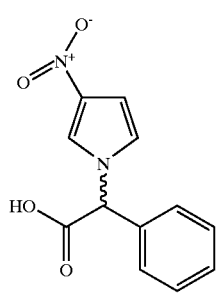

To a stirring solution of the product of Preparation 486 (4.70 g, 17.1 mmol) in dioxane (100 mL) and water (50 mL) at room temperature was added lithium hydroxide (2.88 g, 68.5 mmol). The reaction stirred 25 min at room temperature, at which time the dioxane was evaporated under reduced pressure. The residue was diluted with water and extracted with diethyl ether (the ether extracts were discarded). The aqueous layer was acidified (pH 2–3) with 1N HCl and then extracted with diethyl ether and ethyl acetate. The combined organic layers were washed with brine, dried (sodium sulfate) and concentrated under reduced pressure to provide the desired product as a light tan solid foam that was used without further purification (4.11 g, 98%): ¹H NMR consistent with structure; MS (IS) m/e 247 (M+1).

Preparation 488

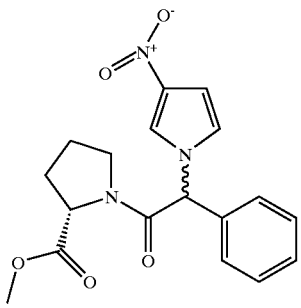

To a stirring solution of the product of Preparation 487 (2.50 g, 10.1 mmol), L-proline methyl ester hydrochloride (2.10 g, 12.7 mmol), 1-hydroxybenzotriazole hydrate (1.72 g, 12.7 mmol) and N,N-diisopropylethylamine (4.40 mL, 25.4 mmol) in anhydrous dichlormethane (90 mL), at room temperature, was added 1-(3-dimethylaminopropyl)-3-ethylcarbodiimide (2.63 g, 13.7 mmol). The reaction was stirred for 18 h at room temperature, then was quenched with water and the aqueous layer was extracted with ethyl acetate. The combined extracts were washed with 10% citric acid, saturated sodium bicarbonate, water and brine, dried (sodium sulfate) and evaporated to provide a yellow solid. Flash chromatography (silica gel, 35% ethyl acetate/hexanes—85% ethyl acetate/hexanes) gave 2.76 g (76%) of the desired product as a white foam solid: ¹H NMR consistent with structure; MS (IS) m/e 358 (M+1).

Preparation 489

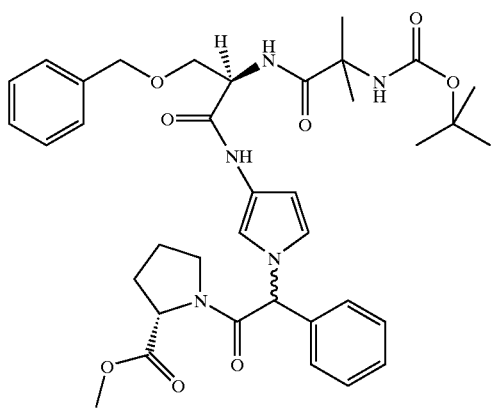

To a suspension of 5% palladium on carbon (1.30 g) in ethyl acetate (90 mL) and ethanol (10 mL), in a Parr reaction bottle, was added the product of Preparation 488 (1.30 g, 3.63 mmol) as a solid. The reaction bottle was placed on a Parr shaker, and shaken at room temperature for 45 min under a hydrogen atmosphere (35 psi). The reaction was filtered through a pad of Celite 521. The filtrate was evaporated to an orange solid foam which was then added to a previously prepared mixture of the product of Preparation 1d from Examples Part 2A (1.38 g, 3.63 mmol) and 1-hydroxybenzotriazole hydrate (0.54 g, 4.00 mmol) in dioxane (50 mL) at room temperature. This solution stirred for 15 min at which time 1,3-dicyclohexylcarbodiimide (0.83 g, 4.00 mmol) was added. The reaction was stirred at room temperature for 15 h, then the solvent was evaporated under reduced pressure. The residue was dissolved in ethyl acetate and the 1,3-dicyclohexylurea was filtered away. The filtrate was purified by flash chromatography (silica gel, 75% ethyl acetate/hexanes—10% methanol/ethyl acetate) to give the desired product as a tan solid foam (0.91 g, 40%): ¹H NMR consistent with structure; MS (IS) m/e 690 (M+1).

Example 260

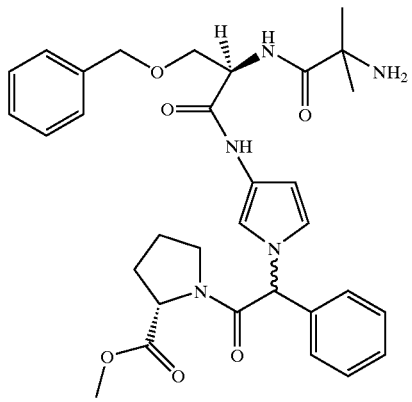

To a stirring solution of the product of Preparation 489 (0.88 g, 1.28 mmol) and anisole (0.15 mL; 1.28 mmol) in anhydrous dichloromethane (40 mL) at 0° C. was added trifluoroacetic acid (6 mL). The reaction was stirred for 4 h, warming to room temperature, and then was quenched by pouring over ice-cooled, saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, ethyl acetate—5% methanol/ethyl acetate—5% triethylamine/10% methanol/ethyl acetate) to provide the desired product as an light yellow solid foam (0.710 g, 94%): ¹H NMR consistent with structure; MS (IS) m/e 590 (M+1).

Preparation 490

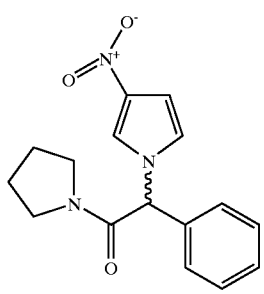

To a solution of the product of Preparation 487 (2.50 g, 10.0 mmol), in anhydrous dichloromethane (60 mL) at 0° C. was added N-methylmorpholine (1.34 mL, 12.0 mmol) and 2-chloro-4,6-dimethoxy-1,3,5-triazine (1.96 g, 11.0 mmol). This mixture stirred for 1 h, warming to room temperature, at which time pyrrolidine (0.93 mL, 11.0 mmol) was added. The reaction was then stirred for an additional 2.5 h at room temperature at which time the solvent was evaporated under reduced pressure. The resulting residue was dissolved in ethyl acetate and the remaining solids were filtered away. The filtrate was purified by flash chromatography (silica gel, 40% ethyl acetate/hexanes—ethyl acetate), to provide the desired product as a light yellow foam solid (2.57 g, 86%): $^1$H NMR consistent with structure; MS (IS) m/e 300 (M+1).

Preparation 491

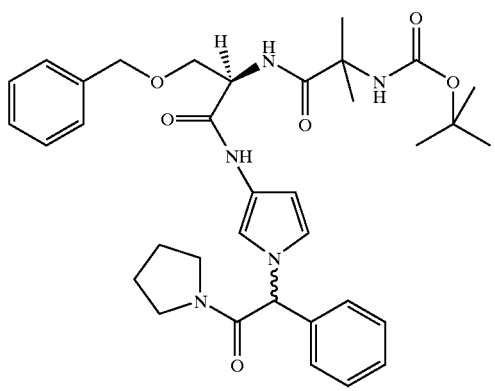

To a suspension of 5% palladium on carbo (0.40 g) in ethyl acetate (50 mL) and ethanol (25 mL), in a Parr reaction bottle, was added the product of Preparation 490 (0.65 g, 2.20 mmol) as a solid. The reaction bottle was Placed on a Parr shaker, and shaken at room temperature for 1 h under a hydrogen atmosphere (35 psi). The reaction was filtered through a pad of Celite 521. The filtrate was evaporated to an orange solid foam which was then added to a previously prepared mixture of the product of Preparation 1d from Examples Part 2A (0.81 g, 2.12 mmol) and 1-hydroxybenzotriazole hydrate (0.31 g, 2.30 mmol) in N,N-dimethylformamide (50 mL), at room temperature. This solution stirred for 15 min at which time 1,3-dicylohexylcarbodiimide (0.48 g, 2.30 mmol) was added. The reaction was stirred at room temperature for 15 h, then was quenched with brine, and extracted with ethyl acetate. The combined extracts were washed with brine, dried (sodium sulfate), and evaporated under reduced pressure to give a brown solid foam. The impure solid was purified by flash chromatography (silica gel, 50% ethyl acetate/hexanes—ethyl acetate) to give the desired product as a yellow solid foam (0.46 g, 42%): $^1$H NMR consistent with structure; MS (IS) m/e 632 (M+1).

Example 261

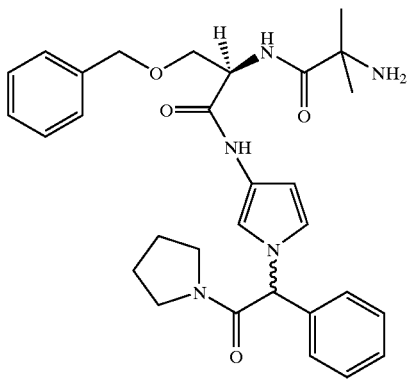

To a stirring solution of the product of Preparation 491 (0.37 g, 0.59 mmol) and anisole (0.03 mL, 0.30 mmol) in anhydrous dichloromethane (13 mL) at 0° C. was added trifluoroacetic acid (2 mL). The reaction was stirred for 4 h, warming to room temperature, and then was quenched by pouring over ice-cooled, saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, ethyl acetate—5% methanol/ethyl acetate—5% triethylamine/10% methanol/ethyl acetate) to provide the desired product as an light yellow solid foam (0.27 g, 86%): $^1$H NMR consistent with structure; MS (IS) m/e 532 (M+1); Anal. Calc'd for $C_{30}H_{37}N_5O_6$: C, 67.68; H, 7.01; N, 13.17. Found: C, 67.30; H, 7.02; N, 12.80.

Preparation 492

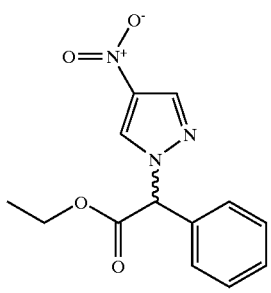

To a stirring slurry of sodium hydride (0.74 g of a 60% dispersion in mineral oil, 18.6 mmol) in N,N-dimethylformamide (30 mL) at 0° C., was added a solution of 4-nitropyrazole (2.00 g, 17.7 mmol) (from Preparation 450) in N,N-dimethylformamide (20 mL). This solution stirred at 0° C. for 10 min then a solution of the product of Preparation 5 of Examples Part 1 (4.75 g, 19.5 mmol) in N,N-dimethylformamide (20 mL) was added. The reaction was stirred at room temperature for 15 h, at which time it was quenched with brine and extracted with ethyl acetate.

The combined extracts were washed with brine, dried (sodium sulfate) and evaporated to provide a yellow oil. Flash chromatography (silica gel, 20%–50% ethyl acetate/hexanes) yielded the desired product as a colorless oil (4.76 g, 97%): ¹H NMR consistent with structure; MS (IS) m/e 276 (M+1).

Preparation 493

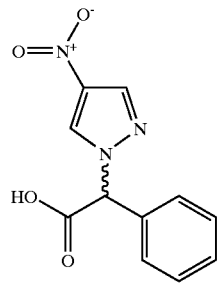

To a stirring solution of the product of Preparation 492 (4.65 g, 16.9 mmol) in dioxane (100 mL) and water (50 mL) at room temperature was added lithium hydroxide (2.83 g, 67.5 mmol). The reaction stirred 25 min at room temperature, at which time the dioxane was evaporated under reduced pressure. The residue was diluted with water and extracted with diethyl ether (the ether extracts were discarded). The aqueous layer was acidified (pH 2–3) with 1N HCl and then extracted with diethyl ether and ethyl acetate. The combined organic layers were washed with brine, dried (sodium sulfate) and concentrated under reduced pressure to provide the desired product as a light orange solid that was used without further purification (4.09 g, 98%): ¹H NMR consistent with structure; MS (IS) m/e 248 (M+1).

Preparation 494

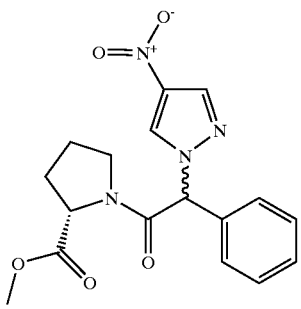

To a stirring solution of the product of Preparation 493 (2.00 g, 8.09 mmol), L-proline methyl ester hydrochloride (1.68 g, 10.1 mmol), 1-hydroxybenzotriazole hydrate (1.38 g, 10.1 mmol) and N,N-diisopropylethylamine (3.50 mL, 20.2 mmol) in anhydrous dichlormethane (80 mL), at room temperature, was added 1-(3-dimethylaminopropyl)-3-ethylcarbodiimide (2.09 g, 10.92 mmol). The reaction was stirred for 18 h at room temperature, then was quenched with water and the aqueous layer was extracted with ethyl acetate. The combined extracts were washed with 10% citric acid, saturated sodium bicarbonate, water and brine, dried (sodium sulfate) and evaporated to provide a yellow solid. Flash chromatography (silica gel, 35% ethyl acetate/hexanes—85% ethyl acetate/hexanes) gave the desired product as a white foam solid (1.80 g, 62%): ¹H NMR consistent with structure; MS (IS) m/e 359 (M+1).

Preparation 495

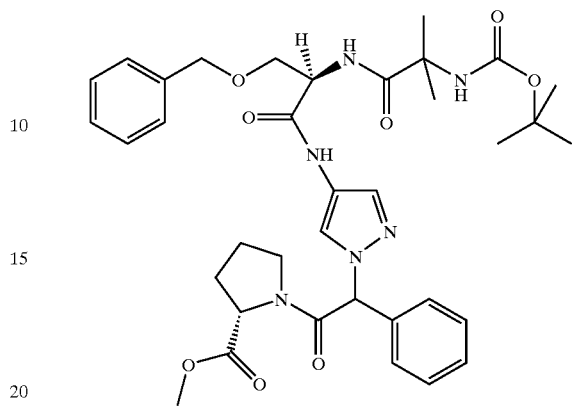

To a suspension of 5% palladium on carbon (0.20 g) in methanol (25 mL), was added the product of Preparation 494 (0.36 g, 1.01 mmol) as a solid. The reaction was stirred at room temperature for 4 h under a hydrogen atmosphere (1 atm). The reaction was filtered through a pad of Celite 521. The filtrate was evaporated to an off-white solid foam which was then added to a previously prepared mixture of the product of Preparation 1d from Examples Part 2A (0.30 g, 0.80 mmol) and 1-hydroxybenzotriazole hydrate (0.12 g, 0.88 mmol) in N,N-dimethylformamide (15 mL) at room temperature. This solution stirred for 15 min at which time 1,3-dicyclohexylcarbodiimide (0.18 g, 0.88 mmol) was added. The reaction was stirred at room temperature for 15 h, then quenched with brine and extracted with ethyl acetate. The combined extracts were washed with brine, dried (sodium sulfate), and evaporated to give a tan solid foam. The crude foam was purified by flash chromatography (silica gel, 75% ethyl acetate/hexanes—10% methanol/ethyl acetate) to provide the separated diastereomers, as off-white solid foams: 495A (0.18 g, 33%) ¹H NMR consistent with structure; MS (IS) m/e 691 (M+1); and 495S (0.19 g, 35%): ¹H NMR consistent with structure; MS (IS) m/e 691 (M+1).

Example 262

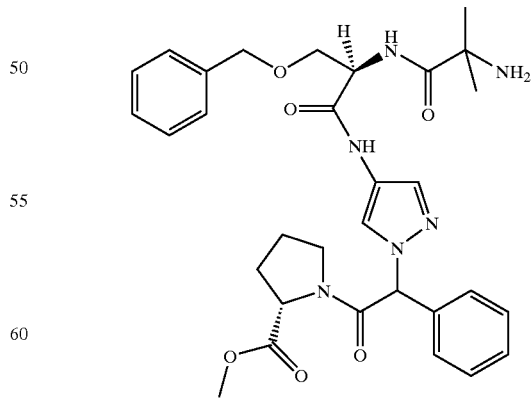

To a stirring solution of the product of Preparation 495A (0.15 g, 0.22 mmol) in anhydrous dichloromethane (15 mL) at 0° C. was added trifluoroacetic acid (3 mL). The reaction was stirred for 4 h, warming to room temperature, and then was quenched by pouring over ice-cooled, saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flesh chromatography (silica gel, ethyl acetate—5% methanol/ethyl acetate—5% triethylamine/10% methanol/ethyl acetate) to provide the desired product as a white solid foam (0.10 g, 77%): $^1$H NMR consistent with structure; MS (IS) m/e 591 (M+1).

Example 263

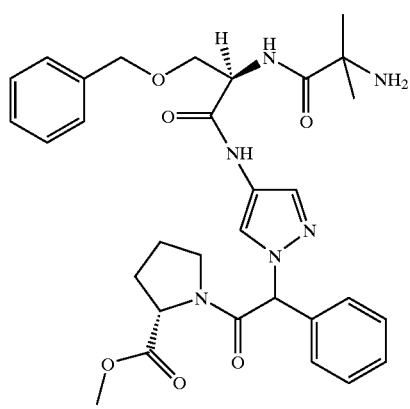

To a stirring solution of the product of Preparation 295B (0.15 g, 0.22 mmol) in anhydrous dichloromethane (15 mL) at 0° C. was added trifluoroacetic acid (3 mL). The reaction was stirred for 4 h, warming to room temperature, and then was quenched by pouring over ice-cooled, saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give an light yellow solid foam. The impure foam was purified by flash chromatography (silica gel, ethyl acetate—5% methanol/ethyl acetate—5% triethylamine/10% methanol/ethyl acetate) to provide the desired product as a white solid foam (0.08 g, 62%): $^1$H NMR consistent with structure; MS (IS) m/e 591 (M+1).

Preparation 496

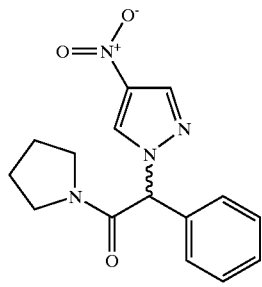

To a stirring solution of the product of Preparation 493 (0.75 g, 3.03 mmol), pyrrolidine (0.32 mL, 3.79 mmol), 1-hydroxybenzotriazole hydrate (0.52 g, 3.79 mmol) and N,N-diisopropylethylamine (1.10 mL), 6.07 mmol) in anhydrous dichlormethane (50 mL) at room temperature, was added 1-(3-dimethylaminopropyl)-3-ethylcarbodiimide (0.79 g, 4.10 mmol). The reaction was stirred for 18 h at room temperature, quenched with water and the aqueous layer was extracted with ethyl acetate. The combined extracts were washed with 10% citric acid, saturated sodium bicarbonate, water and brine, dried (sodium sulfate) and evaporated to provide a yellow solid. Flash chromatography (silica gel, 35% ethyl acetate/hexanes—85% ethyl acetate/hexanes) gave the desired product as a white foam solid (0.83 g, 91%): $^1$H NMR consistent with structure; MS (IS) m/e 301 (M+1).

Preparation 497

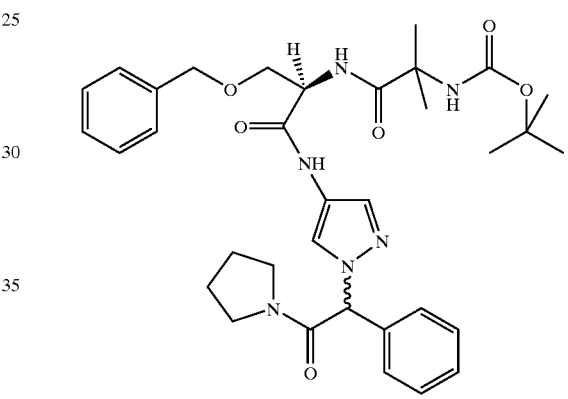

To a suspension of 5% palladium on carbon (0.40 g) in a mixture of ethyl acetate (55 mL) and ethanol (7 mL), was added the product of Preparation 496 (0.71 g, 2.35 mmol) as a solid. The reaction was shaken on a Parr shaker at room temperature for 1.5 h under a hydrogen atmosphere (35 psi). The reaction was filtered through a pad of Celite 521. The filtrate was evaporated to an off-white solid foam which was then added to a previously prepared mixture of the product of Preparation 1d from Examples Part 2A (0.89 g, 2.35 mmol) and 1-hydroxybenzotriazole hydrate (0.351 g, 2.58 mmol) in N,N-dimethylformamide (35 mL) at room temperature. This solution stirred for 15 min at which time 1,3-dicyclohexycarbodiimide (0.53 g, 2.58 mmol) was added. The reaction was stirred at room temperature for 15 h, then quenched with brine and extracted with ethyl acetate. The combined extracts were washed with brine, dried (sodium sulfate), and evaporated to give a tan solid foam. The crude foam was purified by flash chromatography (silica gel, 75% ethyl acetate/hexanes—10% methanol/ethyl acetate) to provide the desired product as an off-white solid foam (0.97 g, 65%): $^1$H NMR consistent with structure; MS (IS) m/e 633 (M+1).

Example 264

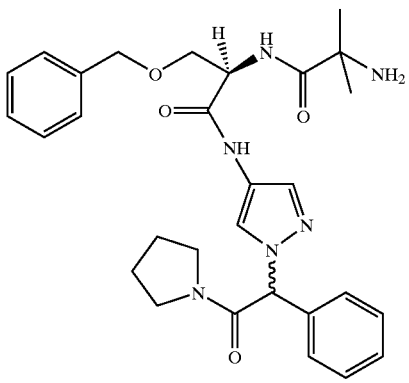

To a stirring solution of the product of Preparation 497 (0.75 g, 1.19 mmol) and anisole (0.04 mL, 0.39 mmol) in anhydrous dichloromethane (30 mL) at 0° C. was added trifluoroacetic acid (4 mL). The reaction was stirred for 4 h, warming to room temperature, and then was quenched by pouring over ice-cooled, saturated sodium bicarbonate. The organic layer was collected and the aqueous layer was extracted twice with dichloromethane. The combined organic layers were washed with sodium bicarbonate, water and brine, then dried (sodium sulfate) and evaporated in vacuo to give a light yellow solid foam. The impure foam was purified by flash chromatography (silica gel, ethyl acetate—5% methanol/ethyl acetate—5% triethylamine/10% methanol/ethyl acetate) to provide the desired product as a white solid foam (0.62 g, 98%): $^1$H NMR consistent with structure; MS (IS) m/e 533 (M+1).

EXAMPLES PART 3

Preparation of 1-N-alkylated-4-nitroimidazoles

Preparation 1

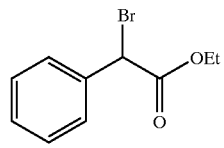

To a solution of α-bromophenylacetic acid (100 g, 466 mmol) stirring in absolute ethanol (500 mL) at room temperature was added p-toluenesulfonic acid monohydrate (10 g, 53 mmol). This solution was heated to reflux and, after 8 h, concentrated to dryness. The resulting residue was dissolved in ethyl acetate, washed with saturated aqueous sodium bicarbonate, brine, dried over sodium sulfate, filtered, and concentrated to yield 77 g (68%) of the desired product as an orange oil: $^1$H-NMR is consistent with structure; MS (FD) 241.9, 243.9.

Preparation 2

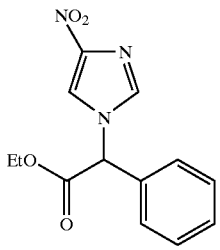

To a slurry of sodium hydride (13.6 g of a 60% dispersion in mineral oil, 341 mmol) stirring in N,N-dimethylformamide (240 mL) was carefully added 4-nitroimidazole (38.6 g, 341 mmol) such that the temperature during the addition was maintained below 40° C. This resulting slurry was stirred for 1 h and then cooled to 5° C. To this mixture was slowly added a compound of Preparation 1 (76 g, 310 mmol) at a rate such that the reaction temperature was maintained below 20° C. After 4 h, the reaction was concentrated and subsequently extracted with ethyl acetate. The combined organic extracts were filtered, washed with water, brine, dried over sodium sulfate, filtered and concentrated. The resulting residue was purified by silica gel chromatography (methanol/chloroform gradient) to yield the 60.1 g (70%) of the desired product as a white solid: $^1$H-NMR is consistent with structure; MS (FD) 275 (M+); Anal. Calc'd. for: C, 56.73; H, 4.73; N, 15.27. Found: C, 56.48; H, 4.78; N, 15.08.

Preparation 3

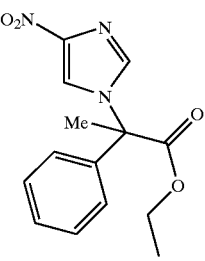

A solution of the product of Preparation 2 (10.00 g, 36.36 mmol) in DMF (50 mL) was added dropwise to a suspension of sodium hydride (1.60 g, 40.00 mmol) in DMF (50 mL) under nitrogen at 0° C. The mixture was stirred 10 min., then methyl iodide (2.5 mL, 40.00 mmol) was added dropwise. The reaction was stirred thirty minutes at 0° C., then 1 h at ambient temperature. The mixture was quenched with a saturated solution of sodium bicarbonate. Ethyl acetate was added and the mixture washed with bicarbonate followed by brine. The organic layer was dried over sodium sulfate, filtered, and concentrated in vacuo. The resulting foam was purified by flash chromatography (300 g silica, 2:3 ethyl acetate/hexanes) to yield the desired product (8.81 g, 84%) as a light yellow foam: $^1$H NMR (300 MHz, CDCl$_3$)— consistent with structure; Anal. calcd. for C$_{14}$H$_{15}$N$_3$O$_4$; 58.13 C, 5.23 H, 14.53 N; found 57.88 C, 5.36 H, 14.39 N; FDMS (M+)—289.

Preparation 4

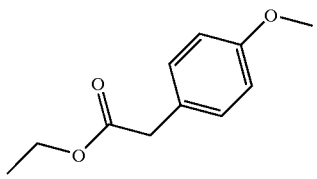

To a solution of 4-methoxyphenylacetic acid, 98 g (590 mmol) in 300 mL of absolute ethanol was added 20 g (105 mmol) of TsOH. The reaction mixture was refluxed for 5 h then concentrated to dryness. The resulting oil was chromatographed on silica gel using 20% ethyl acetate/hexanes as eluant to afford 102 g (89%) of the desired product as a colorless oil. $^1$H-NMR (d, DMSO) 1.17 (t, J=8.7 Hz, 3H), 3.56 (s, 2H), 3.73 (s, 3H), 4.05 (q, J=7.2 Hz, 2H), 6.87 (d, J=8.7 Hz, 2H), 7.17 (d, 8.7 Hz, 2H); MS (ion spray) 195.3 (M+1); Anal. Calc'd for $C_{11}H_{14}O_3$: C, 68.02; H, 7.27. Found: C, 67.95, 7.17.

Preparation 5

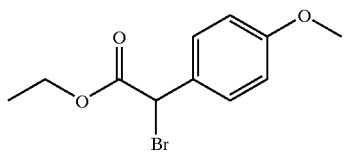

To a solution of the product of Preparation 4, 40 g (200 mmol) in 500 mL of carbon tetrachloride was added 37 g (206 mmol) of N-bromosuccinimide and 4 drops of 48% HBr. The reaction mixture was refluxed for 5 h, filtered and concentrated to dryness. The resulting oil was chromatographed on silica gel using chloroform as eluant to afford 51.1 g (94%) of the desired product as a colorless oil. 1H-NMR (d, DMSO) 1.19 (t, J=8.4 Hz, 3H), 3.77 (s, 3H), 4.18 (m, 2H), 5.88 (s, 1H), 6.95 (d, J=8.4 Hz, 2H), 7.50 (d, J=8.4 Hz, 2H); MS (FD) 272, 274 (M+); Anal. Calc'd for $C_{11}H_{13}BrO_3$: C, 48.37; H, 4.80. Found: C, 48.52, 4.77.

Preparation 6

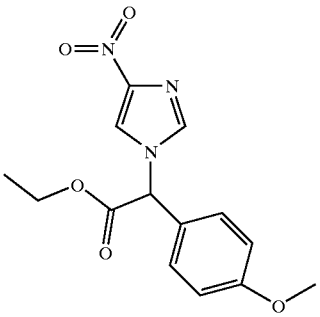

To a solution of the product of Preparation 5, 49.5 g (181 mmol) in 500 mL of DMF was added 20.5 g (181 mmol) of 4-nitroimidazole and 75 g (543 mmol) of potassium carbonate. The reaction mixture was stirred overnight at ambient temperature, filtered and concentrated to dryness. The resulting oil was partitioned between ethyl acetate and water and extracted with ethyl acetate. The combined organics were washed with brine, dried over sodium sulfate, filtered and concentrated to dryness. The resulting oil was absorbed onto a silica pad and chromatographed on silica gel using 30–70% ethyl acetates/hexanes as eluant to yield 33.6 g (61%) of the desired product as an orange oil that solidifies upon sitting. $^1$H-NMR (d, DMSO) 1.17 (t, J=7.2 Hz, 3H), 3.78 (s, 3H), 4.25 (q, J=7.2 Hz, 2H), 6.57 (s, 1H), 7.02 (d, J=8.7 Hz, 2H), 7.46 (d, J=8.7 Hz, 2H), 7.92 (s, 1H), 8.38 (s, 1H); MS (ion spray) 306 (M+1); Anal. Calc'd for $C_{14}H_{15}N_3O_5$: C, 55.08; H, 4.95; N, 13.76. Found: C, 54.93; H, 4.89; N, 13.82

Preparation 7

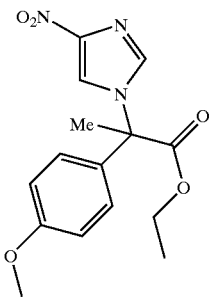

Prepared as in Preparation 3 using the product of Preparation 6 (5.00 g, 16.39 mmol) in DMF (25 mL) and sodium hydride (0.72 g, 18.03 mmol) and methyl iodide (1.12 ml, 18.03 mmol) in DMF (25 mL) to yield the desired product (4.81 g, 92%) as a light yellow foam: $^1$H NMR (300 MHz, CDCl$_3$)—consistent with structure; Anal. calcd. for $C_{15}H_{17}N_3O_5$; 56.42 C, 5.37 H, 13.16 N; found 56.13 C, 5.35 H, 13.01 N; ISMS (M+)—320.

Preparation 7A

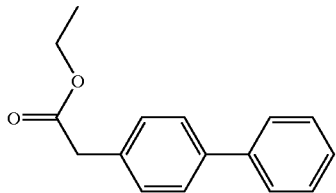

Biphenylacetic acid (25.2 g, 119 mmol), TsOH (3.3 g, 17 mmol), absolute ethanol (250 mL), as in Preparation 4. 25.4 g (89%) of the desired product as a yellow oil. $^1$H-NMR is consistent with structure; MS (FD) 240.1 (M+); Anal. Calc'd for $C_{16}H_{16}O_2$: C, 79.97; H, 6.71. Found: C, 79.75; H, 6.59.

Preparation 8

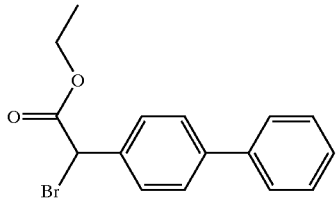

The product of Preparation 7A (18.0 g, 75.0 mmol), N-bromosuccinimide (13.7 g, 77.25 mL), 48% HBr (4 drops), carbon tetrachloride (80 mL), as in Preparation 5 gave 22.56 g (94%) of the desired product as a yellow oil. ¹H-NMR is consistent with structure; MS (FD) 318, 320 (M+); Anal. Calc'd for $C_{16}H_{15}BrO_2 \cdot 0.05CHCl_3$: C, 60.21; H, 4.74. Found: C, 59.50; H, 4.75.

Preparation 9

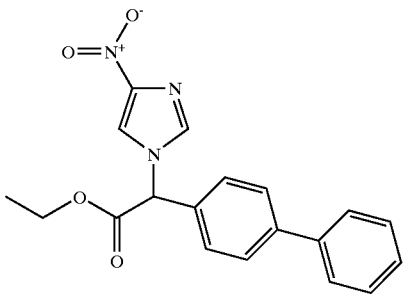

To a slurry of 2.42 g (60.5 mmol) of sodium hydride in 200 mL of DMF at ambient temperature was added 6.9 g (60.5 mmol) of 4-nitroimidazole. After 10 min, 17.62 g (55.0 mmol) of the product of Preparation 8 was added. The resulting mixture was stirred overnight at ambient temperature than concentrated to dryness. The residue was slurried in ethyl acetate and filtered. The resulting oil was partitioned between ethyl acetate and water and extracted with ethyl acetate. The combined organics were washed with brine, dried over sodium sulfate, filtered and concentrated to dryness. The resulting oil was absorbed onto a silica pad and chromatographed on silica gel using 30–50% ethyl acetate/hexanes as eluant to yield 12.0 g (62%) of the desired product as a yellow viscous oil. ¹H-NMR is consistent with structure; MS (FD) 351 (M+).

Preparation 10

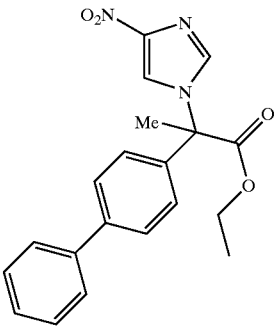

Prepared as described in Preparation 2 using the product of Preparation 9 (11.03 g, 31.39 mmol) in DMF (50 mL) and sodium hydride (1.25, 31.39 mmol) and methyl iodide (1.9 ml, 31.39 mmol) in DMF (50 mL) to yield the desired product (10.25 g, 89%) as a light yellow foam: ¹H NMR (300 MHz, CDCl₃)—consistent with structure; Anal. calcd. for $C_{20}H_{19}N_3O_4$; 65.75 C, 5.26 H, 11.50 N; found 63.84 C, 5.16 H, 10.94 N; ISMS (M+)—366.

Preparation 11

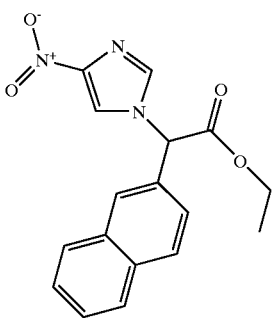

A suspension of 2-naphthyl acetic acid (49.37 g, 265.0 mmol) and thionyl chloride (80 mL) in carbon tetrachloride (55 mL) was heated to reflux for 20 minutes at which time all material went into solution. The reaction was cooled to ambient temperature. Carbon tetrachloride (125 mL). N-bromosuccinamide (56.60 g, 318.0 mmol), and hydrobromic acid (48% aq., catalytic, 0.5 mL) were added. The mixture was heated to reflux for 30 min., cooled to ambient temperature, filtered, and concentrated in vacuo. The material was redissolved in dichloromethane (200 mL) and excess ethanol (100 mL) was added dropwise. The mixture was stirred at ambient temperature 1 hour, then concentrated in vacuo. The crude material was chromatographed (700 g silica, 30% ethyl acetate/hexane) to yield a crude tan solid. This crude material was dissolved dimethylformamide (200 mL) and 4-nitroimidazole (29.78 g, 263.5 mmol) and potassium carbonate (72.70 g, 526.8 mmol) were added. The reaction was stirred at ambient temperature, then concentrated in vacuo to 100 mL. Ethyl acetate and water were added and the mixture washed with sodium bicarbonate and brine. The organic layer was dried over sodium sulfate and concentrated in vacuo. The crude material was chromatographed (1.0 kg silica, 30% ethyl acetate/hexane) to yield the desired product (40.2 g, 47%) as a brown foam: ¹H NMR (300 MHz, CDCl₃)—consistent with structure; Anal. calcd. for $C_{17}H_{15}N_3O_4$; 62.76 C, 4.65 H, 12.92 N; found 60.54 C, 4.35 H, 12.04 N. ISMS (M+)—326.

Preparation 12

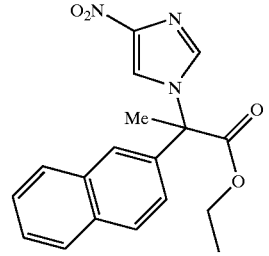

Prepared as described in Preparation 3 using the product of Preparation 10 (13.9 g, 42.65 mmol) in DMF (50 mL) and sodium hydride (1.71 g, 42.65 ml) and methyl iodide (2.64 ml, 42.65 mmol) in DMF (50 mL) to yield the desired product (10.94 g, 77%) as a light, yellow oil: ¹H NMR (300 MHz, CDCl₃)—consistent with structure; Anal. calcd. for $C_{18}H_{17}N_3O_4$; 63.71 C, 5.05 H, 12.38 N; found 63.80 C, 4.98 H, 12.41 N; ISMS (M+)—340.

Preparation 13

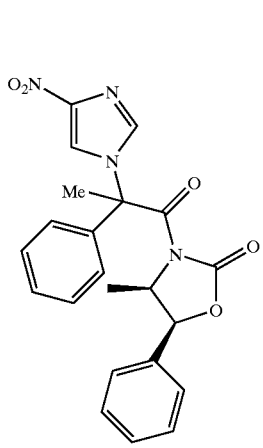

A solution of the product of Preparation 2 (8.35 g, 28.89 mmol) in THF (100 mL) was treated with lithium hydroxide (1.82 g, 43.34 mmol) and water (50 mL). The reaction was stirred at ambient temperature for 30 minutes. Water was added and the mixture washed with diethyl ether. The pH of the aqueous layer was adjusted to 3.0 with 10% sodium bisulfate. The mixture was saturated with sodium chloride and washed with ethyl acetate. The ethyl acetate washes were combined, dried over sodium sulfate, filtered, and concentrated in vacuo. The resulting crude solid was dissolved in anhydrous dichloromethane (100 mL) under nitrogen. To this solution was added catalytic DMF (0.1 mL) and excess oxalyl chloride (25 g). This mixture was stirred 3 hours, then concentrated in vacuo. The resulting crude foam was dissolved in THF (20 mL) and added dropwise to a solution of lithium (4R,5S)-(+)-4-methyl-5-phenyl-2-oxazolidinone (generated by adding n-BuLi (1.6M in hexanes, 19.9 mL, 31.82 mmol) dropwise to a solution of (4R,5S)-(+)-4-methyl-5-phenyl-2-oxazolidinone (5.64 g, 31.82 mmol) in THF (50 mL) at −78 C under nitrogen. This solution was stirred 20 min., then used without further purification.). The resulting mixture was stirred at −78 C for 30 min, then warmed to 0 C. The mixture was quenched with saturated sodium bicarbonate. Ethyl acetate and water were added and the mixture washed with sodium bicarbonate and brine. The organic layer was dried over sodium sulfate, filtered, and concentrated in vacuo. The resulting foam was purified by flash chromatography (400 g silica, 5% diethyl ether/dichloromethane) to yield diastereomer 1 (3.76 g, 31% yield) and diastereomer 2 (4.32 g, 36%) of the desired product an colorless foams: diastereomer 1—$^1$H NMR (300 MHz, CDCl$_3$)—consistent with structure; Anal. calcd. for C$_{22}$H$_{20}$N$_4$O$_5$; 62.85 C, 4.80 H, 13.33 N; found 60.97 C, 4.64 H, 12.44 N; FDMS (M+)—420: diastereomer 2—$^1$H NMR (300 MHz, CDCl$_3$)—consistent with structure; Anal. calcd. for C$_{22}$H$_{20}$N$_4$O$_5$; 62.85 C, 4.80 H, 13.33 N; found 62.41 C, 4.82 H, 11.92 N; FDMS (M+)—420.

Preparation 14

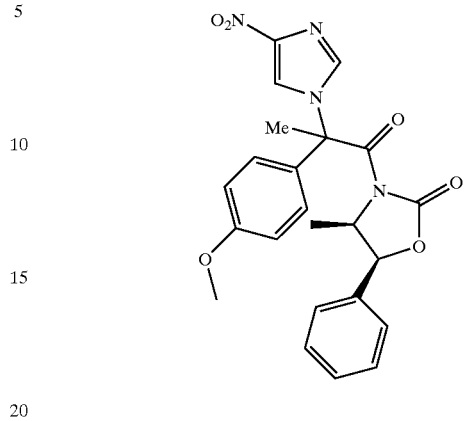

Prepared as described in Preparation 13 using the product of Preparation 7 (4.80 g, 15.03 mmol) in THF (50 mL) and lithium hydroxide (1.26 g, 30.06 mmol) in water (25 mL) to give the crude acid. This material was immediately reacted with anhydrous dichloromethane (100 mL), catalytic DMF (0.5 mL), and excess oxalyl chloride (12 mL) to give the crude acid chloride. This crude product was reacted with THF (20 mL), n-BuLi (1.6M in hexanes, 14.1 mL, 22.54 mmol), and (4R, 5S)-(+)-4-methyl-5-phenyl-2-oxazolidinone (4.00 g, 22.54 mmol) in THF (50 mL) to yield diastereomer 1 (2.79 g, 41% yield) and diastereomer 2 (2.80 g, 41%) of the desired product as colorless foams: diastereomer 1—$^1$H NMR (300 MHz, CDCl$_3$)—consistent with structure; Anal. calcd. for C$_{23}$H$_{22}$N$_4$O$_6$; 61.33 C, 4.92 H, 12.44 N; found 60.92 C, 4.82 H, 12.03 N; ISMS (M+)—451: $^1$H NMR (300 MHz, CDCl$_3$)—consistent with structure; Anal. calcd. for C$_{23}$H$_{22}$N$_4$O$_6$; 61.33 C, 4.92 H, 12.44 N; found 61.57 C, 4.98 H, 12.47 N; ISMS (M+)—451.

Preparation 15

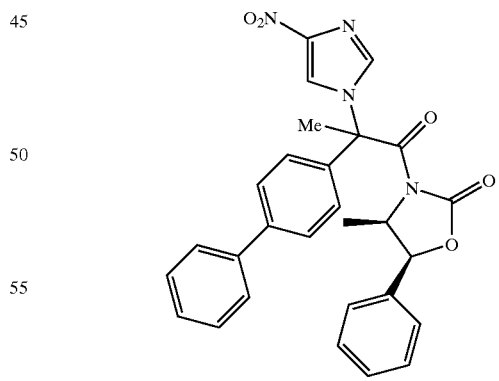

Prepared as in Preparation 13 using the product of Preparation 10 (10.20 g, 27.92 mmol) in THF (100 mL) and lithium hydroxide (2.34 g, 55.84 mmol) in water (50 mL) to give the crude acid. The resulting crude solid was dissolved in anhydrous dichloromethane (150 mL) and reacted with catalytic DMF (0.5 mL) and excess oxalyl chloride (23 mL). The resulting crude foam was dissolved in THF (50 mL) and reacted with n-BuLi (1.6M in hexanes, 25.1 mL, 40.28 mol), (4R,5S)-(+)-4-methyl-5-phenyl-2-oxazolidinone (7.14 g, 40.28 mmol), and THF (150 mL) to yield diastereomer 1 (6.21 g, 45% yield) and diastereomer 2 (6.20 g, 45%) of the desired product as colorless foams: $^1$H NMR (300 MHz, CDCl$_3$)—consistent with structure; Anal. calcd. for C$_{28}$H$_{24}$N$_4$O$_5$; 66.93 C, 4.99 H, 11.56 N; found 65.32 C, 5.06 H, 10.66 N; ISMS (M+)—497: $^1$H NMR (300 MHz, CDCl$_3$)—consistent with structure; Anal. calcd. for C$_{28}$H$_{24}$N$_4$O$_5$; 66.93 C, 4.99 H, 11.56 N; found 65.05 C, 4.92 H, 10.61 N; FDMS (M+)—497.

Preparation 16

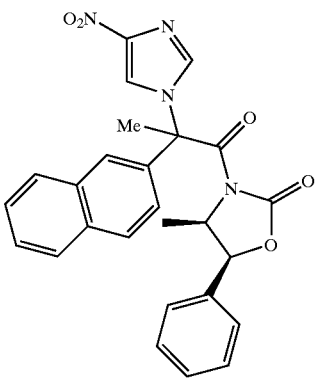

Prepared as in Preparation 13 using the product of Preparation 12 (10.9 g, 32.27 mmol) in THF (150 mL) and lithium hydroxide (1.63 g, 38.73 mmol) in water (75 mL) to give the crude acid. The resulting crude solid was dissolved in anhydrous dichloromethane (150 mL) and reacted with catalytic DMF (0.5 mL) and excess oxalyl chloride (23 mL). The resulting crude foam was dissolved in THF (50 mL) and reacted with n-BuLi (1.6M in hexanes, 30.1 mL, 48.23 mmol), (4R,5S)-(+)-4-methyl-1-5-phenyl-2-oxazolidinone (8.55 g, 48.23 mmol), and THF (150 mL) to yield diastereomer 1 (6.13 g, 41% yield) and diastereomer 2 (4.82 g, 32%) of the desired product as colorless foams: distereomer 1—$^1$H NMR (300 MHz, CDCl$_3$)—consistent with structure; Anal. calcd. for C$_{26}$H$_{22}$N$_4$O$_5$; 66.38 C, 4.71 H, 11.91 N; found 65.24 C, 4.72 N, 11.59 N; ISMS (M+)—471: distereomer 2—$^1$H NMR (300 MHz, CDCl$_3$)—consistent with structure; Anal. calcd. for C$_{26}$H$_{22}$N$_4$O$_5$; 66.38 C, 4.71 H, 11.91 N; found 66.45 C, 4.77 H, 12.20 N; ISMS (M+)—471.

Preparation 17

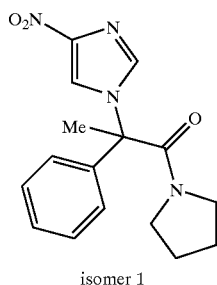

isomer 1

A solution of the product of Preparation 13, diastereomer 1 (2.30 g, 5.48 mmol) in THF (50 mL) was added to a solution of lithium hydroxide (0.25 g, 6.03 mmol) in water (25 mL). The resulting mixture was stirred at ambient temperature for 30 minutes. Water was added and the mixture washed with diethyl ether. The pH of the aqueous layer was adjusted to 3.0 with 10% aqueous sodium bisulfate. The mixture was saturated with sodium chloride and washed with ethyl acetate. The ethyl acetate washes were combined, dried over sodium sulfate, filtered, and concentrated in vacuo. The resulting crude solid was dissolved in anhydrous dichloromethane (50 mL) under nitrogen. To this solution was added catalytic DMF (0.1 mL) and excess oxalyl chloride (5 g). This mixture was stirred 3 hours, then concentrated in vacuo. The resulting crude foam was dissolved in Anhydrous dichloromethane (50 mL) and cooled to 0° C. 4-Dimethylaminopyridine (catalytic, 10 mg) and pyrrolidine (1.8 mL, 18.74 mmol) were added and the resulting solution stirred for 18 hours. Dichloromethane was then added and the mixture washed with sodium bicarbonate and brine. The organic layer was dried over sodium sulfate, filtered, and concentrated in vacuo. The crude foam was purified by flash chromatography (silica, 100 g, 5% methanol/dichloromethane) to yield the desired product (1.73 g, 88% yield) as a colorless foam: $^1$H NMR (300 MHz, CDCl$_3$)—consistent with structure; Anal. calcd. for C$_{16}$H$_{18}$N$_4$O$_3$; 61.14 C, 5.77 H, 17.82 N; found 60.67 C, 5.78 H, 16.03 N; FDMS (M+)—314.

Preparation 18

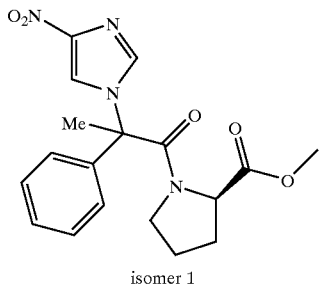

isomer 1

Prepared as in Preparation 17 using the product of Preparation 13, diastereomer 1 (1.88 g, 5.44 mmol) in THF (50 mL) and lithium hydroxide (0.23 g, 5.63 mmol) in water (25 mL) to give the crude acid. The resulting crude solid was dissolved in anhydrous dichloromethane (50 mL) and reacted with catalytic DMF (0.1 mL) and excess oxalyl chloride (5 g) to give the crude acid chloride. The resulting crude foam was dissolved in anhydrous dichloromethane (50 mL) and reacted with 4-Dimethylaminopyridine (catalytic, 10 mg), L-proline methyl enter hydrochloride (0.90 g, 5.44 mmol), and N,N-diisopropylethylamine (2.8 mL, 16.31 mmol) to yield the desired product (1.39 g, 69% yield) as a colorless foam: $^1$H NMR (300 MHz, CDCl$_3$)—consistent with structure; Anal. calcd. for C$_{18}$H$_{20}$N$_4$O$_5$; 58.60 C, 5.41 H, 15.04 N; found 57.95 C, 5.40 H, 13.45 N; FDMS (M+)—372.

Preparation 19

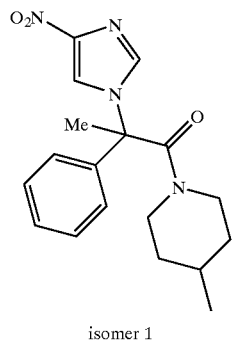

isomer 1

Prepared as in Preparation 17 using the product of Preparation 13, diastereomer 1 (1.88 g, 5.44 mmol) in THF (50 mL) and lithium hydroxide (0.23 g, 5.63 mmol) in water (25 mL) to give the crude acid. The resulting crude solid was dissolved in anhydrous dichloromethane (50 mL) and reacted with catalytic DMF (0.1 mL) and excess oxalyl chloride (5 g) to give the crude acid chloride. The resulting crude foam was dissolved in anhydrous dichloromethane (50 mL) and reacted with 4-Dimethylaminopyridine (catalytic, 10 mg), L-proline methyl ester hydrochloride (0.90 g, 5.44 mmol), and N,N-diethylisopropylamine (2.8 mL, 16.31 mmol) to yield the desired product (1.21 g, 65% yield) as a colorless foam: $^1$H NMR (300 MHz, CDCl$_3$)—consistent with structure; Anal. calcd. for $C_{18}H_{22}N_4O_3$; 63.14 C, 6.48 H, 16.36 N; found 63.29 C, 6.45 H, 15.29 N; FDMS (M+)—342.

Preparation 20

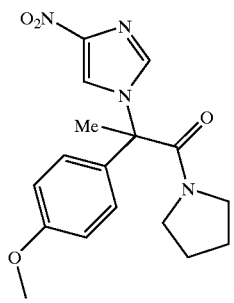

isomer 1

Prepared as in Preparation 17 using the product of Preparation 14, diastereomer 1 (1.25 g, 2.78 mmol) in THF (50 mL) and lithium hydroxide (0.14 g, 3.33 mmol) in water (25 mL) to give the crude acid. The resulting crude solid was dissolved in anhydrous dichloromethane (50 mL) and reacted with catalytic DMF (0.1 mL) and excess oxalyl chloride (5 g) to give the crude acid chloride. The resulting crude foam was dissolved in anhydrous dichloromethane (50 mL) and reacted with 4-Dimethylaminopyridine (catalytic, 10 mg) and pyrrolidine (0.24 mL, 2.89 mmol) to yield the desired product (0.78 g, 86% yield) as a colorless foam: $^1$H NMR (300 MHz, CDCl$_3$) consistent with structure; Anal. calcd. for $C_{17}H_{20}N_4O_4$; 59.59 C, 5.85 H, 16.27 N; found 59.59 C, 5.96 H, 16.19 N; ISMS (M+)—345.

Preparation 21

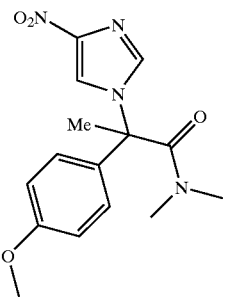

isomer 1

Prepared as in Preparation 17 using the product of Preparation 13, diastereomer 1 (2.31 g, 5.15 mmol) in THF (50 mL) and lithium hydroxide (0.26 g, 6.18 mmol) in water (25 mL) to give the crude acid. The resulting crude solid was dissolved in anhydrous dichloromethane (50 mL) and reacted with catalytic DMF (0.1 mL) and excess oxalyl chloride (5 g) to give the crude acid chloride. The resulting crude foam was dissolved in anhydrous dichloromethane (50 mL) and reacted with 4-Dimethylaminopyridine (catalytic, 10 mg) and dimethylamine (2.0 M in THF, 7.7 mL, 15.46 mmol) to yield the desired product (1.57 g, 96% yield) as a colorless foam: $^1$H NMR (300 MHz, CDCl$_3$)—consistent with structure; Anal. calcd. for $C_{15}H_{18}N_4O_4$; 56.60 C, 5.70 H, 17.60 N; found 57.04 C, 6.09 H, 16.82 N; ISMS (M+)—319.

Preparation 22

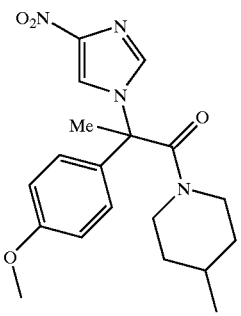

isomer 1

Prepared as in Preparation 17 using the product of Preparation 14, diastereomer 1 (1.00 g, 2.22 mmol) in THF (50 mL) and lithium hydroxide (0.10 g, 2.44 mmol) in water (25 mL) to give the crude acid. The resulting crude solid was dissolved in anhydrous dichloromethane (50 mL) and reacted with catalytic DMF (0.1 mL) and excess oxalyl chloride (5 g) to give the crude acid chloride. The resulting crude foam was dissolved in anhydrous dichloromethane (50 mL) and reacted with 4-Dimethylaminopyridine (catalytic, 10 mg) and 4-methylpiperidine (0.34 mL, 2.71 mmol) to yield the desired product (0.38 g, 50% yield) as a colorless foam: $^1$H NMR (300 MHz, CDCl$_3$)—consistent with structure; Anal. calcd. for $C_{19}H_{24}N_4O_4$; 61.28 C, 6.50 H, 15.05 N; found 61.38 C, 6.40 H, 15.11 N; FDMS (M+)—372.

Preparation 23

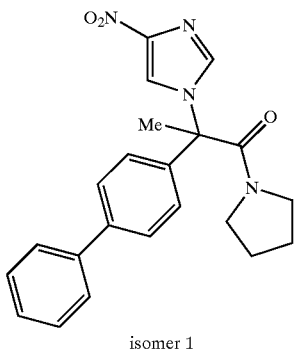

isomer 1

Prepared as in Preparation 17 using the product of Preparation 15, diastereomer 1 (1.00 g, 2.02 mmol) in THF (20 mL) and lithium hydroxide (0.13 g, 3.09 mmol) in water (10 mL) to give the crude acid. The resulting crude solid was dissolved in anhydrous dichloromethane (20 mL) and reacted with catalytic DMF (0.1 mL) and excess oxalyl chloride (5 g). The resulting crude foam was dissolved in anhydrous dichloromethane (20 mL) and reacted with 4-Dimethylaminopyridine (catalytic, 10 mg) and pyrrolidine (0.65 mL, 7.76 mmol) to yield the desired product (0.80 g, 98% yield) as a colorless foam: $^1$H NMR (300 MHz, CDCl$_3$)—consistent with structure; Anal. calcd. for C$_{22}$H$_{22}$N$_4$O$_3$; 67.68 C, 5.68 H, 14.34 N; found 65.36 C, 5.54 H, 13.43 N; ISMS (M+)—391.

Preparation 24

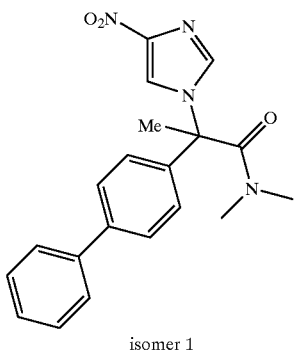

isomer 1

Prepared as in Preparation 17 using the product of Preparation 15, diastereomer 1 (0.50 g, 1.00 mmol) in THF (20 mL) and lithium hydroxide (0.05 g, 1.10 mmol) in water (10 mL) to give the crude acid. The resulting crude solid was dissolved in anhydrous dichloromethane (50 mL) and reacted with catalytic DMF (0.1 mL) and excess oxalyl chloride (5 g) to give the crude acid chloride. The resulting crude foam was dissolved in anhydrous dichloromethane (50 mL) and reacted with 4-Dimethylaminopyridine (catalytic, 10 mg), N-methylmorpholine (0.33 mL, 3.00 mmol), and dimethylamine hydrochloride (0.13 g, 1.50 mmol) to yield the desired product (0.30 g, 82% yield) as a colorless foam: $^1$H NMR (300 MHz, CDCl$_3$)—consistent with structure; Anal. calcd. for C$_{20}$H$_{20}$N$_4$O$_3$; 65.92 C, 5.53 H, 15.37 N; found 64.17 C, 5.41 H, 14.15 N; ISMS (M+)—365.

Preparation 25

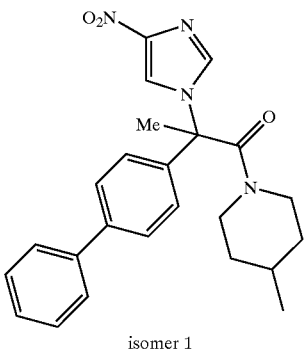

isomer 1

Prepared as in Preparation 17 using the product of Preparation 15, diastereomer 1 (0.40 g, 0.80 mmol) in THF (20 mL) and lithium hydroxide (0.04 g, 0.96 mmol) in water (10 mL) to give the crude acid. The resulting crude solid was dissolved in anhydrous dichloromethane (50 mL) and reacted with catalytic DMF (0.1 mL) and excess oxalyl chloride (5 g) to give the crude acid chloride. The resulting crude foam was dissolved in hydrous dichloromethane (50 mL) and reacted with 4-Dimethylaminopyridine (catalytic, 10 mg) and 4-methylpiperidine (0.24 mL, 2.89 mmol) to yield the desired product (0.30 g, 90% yield) as a colorless foam: $^1$H NMR (300 MHz, CDCl$_3$)—consistent with structure; Anal. calcd. for C$_{24}$H$_{26}$N$_4$O$_3$; 68.88 C, 6.26 H, 13.39 N; found 67.40 C, 6.72 H, 12.45 N; FDMS (M+)—419.

Preparation 26

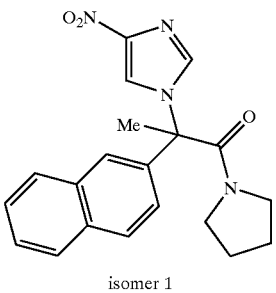

isomer 1

Prepared as in Preparation 17 using the product of Preparation 16, diastereomer 1 (1.00 g, 2.13 mmol) in THF (20 mL) and lithium hydroxide (0.10 g, 2.33 mmol) in water (10 mL) to give the crude acid. The resulting crude solid was dissolved in anhydrous dichloromethane (20 mL) and reacted with catalytic DMF (0.1 mL) and excess oxalyl chloride (5 g). The resulting crude foam was dissolved in anhydrous dichloromethane (20 mL) and reacted with 4-Dimethylaminopyridine (catalytic, 10 mg) and pyrrolidine (0.61 mL, 6.39 mmol) to yield the desired product (0.42 g, 54% yield) as a colorless foam: $^1$H NMR (300 MHz, CDCl$_3$)—consistent with structure; Anal. calcd. for C$_{20}$H$_{20}$N$_4$O$_3$; 65.92 C, 5.53 H, 15.38 N; found 61.50 C, 5.41 H, 13.91 N; ISMS (M+)—365.

Preparation of Dipeptide Acids

Preparation 27

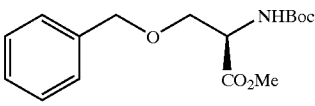

To a solution of boc-(OBz)-D-Ser-OH (25.0 g, 84.7 mmol) stirring in anhydrous N,N-dimethylformamide (500 mL) at room temperature was added sodium bicarbonate (14.2 g, 169 mmol) followed by methyl iodide (26.4 mL, 424 mmol). After 18 h, the reaction mixture was concentrated to approximately 100 mL. Ethyl acetate was added and the mixture washed with aqueous sodium bicarbonate and brine. The organic extract was dried and concentrated to give the desired compound (25 g, 96%) as a light yellow oil: $^1$H NMR (300 MHz, CDCl$_3$) d 1.45 (s, 9H), 3.70 (m, 1H), 3.75 (s, 3N), 3.85 (m, 1H), 4.50 (m, 3H), 7.30 (m, 5H); MS (FD) m/e 310; Anal. calc'd for C$_{16}$H$_{23}$NO$_5$: C, 62.12; H, 7.49; N, 4.53. Found: C, 62.31; H, 7.49; N, 4.43.

Preparation 28

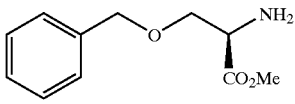

To a solution of the product of Preparation 27 (5.0 g, 16 mmol) stirring in dichloromethane (40 mL) and anisole (1 mL) at 0° C. was added trifluoroacetic acid (10 mL). After 4 h at room temperature, saturated sodium bicarbonate solution was added and the mixture extracted with ethyl acetate. The combined organic extracts were washed with brine, dried over sodium sufate, and concentrated. The crude product was used in the next step without further purification.

Preparation 29

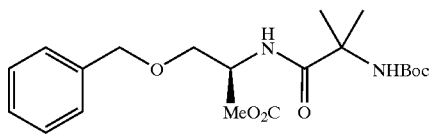

To a solution of the product of Preparation 28 (65.4 mmol), boc-α-aminoisobutyric acid (13.2 g, 65.4 mmol), 1-hydroxybenzotriazole (8.8 g, 65.4 mmol), and N,N-diisopropylethylamine (22.8 mL, 130.7 mmol) stirring in dichloromethane (500 mL) at 0° C. was added 1-(3-dimethylaminopropyl)-3-ethylcarbodiimide (12.3 g, 71.9 mmol). After 18 h, ethyl acetate and saturated ammonium chloride were added and the mixture extracted with ammonium chloride, sodium bicarbonate, and brine. The organic extracts were dried over sodium sulfate and concentrated. Purification by silica gel chromatography (25% ethyl acetate/hexanes) yielded the desired compound (21.6 g, 83%) as a white solid: $^1$H NMR (300 MHz, CDCl$_3$) d 1.39 (s, 9H), 1.48 (s, 6H), 3.62 (dd. J=3.4, 9.1 Hz, 1H), 3.70 (s, 3H), 3.85 (dd, J=3.4. 9.1 Hz, 1H), 4.48 (dd, J=12.5, 22.7 Hz, 2H), 4.75 (m, 1H), 4.92 (s, 1H), 7.11 (d. J=8.6 Hz, 1H), 7.35 (m, 5H); MS (FD) m/e 395; Anal. calc'd for C$_{20}$H$_{30}$N$_2$O$_6$: C, 60.90; H, 7.67; N, 7.10. Found: C, 61.02; H, 7.78; N, 7.10.

Preparation 30

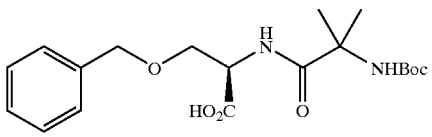

To a solution of the product of Preparation 29 (5.30 g, 13.4) stirring in dioxane (100 mL)/water (50 mL) at room temperature was added lithium hydroxide (2.80 g, 67.3 mmol). After 18 h, water was added and the solution concentrated. The resulting mixture was extracted with diethyl ether. Sodium chloride was added to the aqueous layer and the pH adjusted to 3.5 with 1N HCl. The resulting mixture was extracted with ethyl acetate and the combined organic extracts dried over sodium sulfate then concentrated to yield the title compound (4.40 g, 86%) as a white foam: $^1$H NMR (300 MHz, CDCl$_3$) d 1.39 (s, 9H), 1.45 (s, 3H), 1.47 (s, 3H), 3.68 (m, 1H), 3.95 (m, 1H), 4.54 (s, 2H), 4.70 (m, 1H), 5.51 (bs, 1H), 7.18 (d, J=9.1 Hz, 1H), 7.25 (m, 5H), 9.90 (bs, 1H); MS (FD) m/e 381; Anal. calc'd for C$_{19}$H$_{28}$N$_2$O$_6$: C, 59.99; H, 7.42; N, 7.36. Found: C, 59.74; H, 7.26; N, 7.30.

Preparation 31

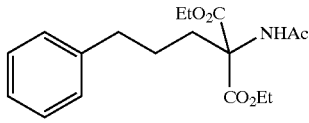

A solution of sodium ethoxide was generated by the addition of sodium metal (52.89 gram, 2.3007 mol) over 3 hours to ethanol (1500 mL). To the sodium ethoxide solution at ambient temperature was added a solution of diethylacetamidomalonate (499.75 grams, 2.3007 mmol) dissolved in ethanol (225 mL). The reaction mixture was stirred for 1.5 hours at ambient temperature. 1-bromo-3-phenylpropane (458.07 grass 2.3007 mol) was added over 15 minutes and the reaction a mixture was refluxed until complete as determined by hplc (16 hours). The reaction mixture was concentrated to dryness and the residue partitioned between ethyl acetate (1×1500 mL and 2×500 mL) and water (1500 mL). The ethyl acetate layers were combined, washed with saturated sodium chloride solution (4×500 mL), dried using sodium sulfate, and concentrated to give 752.1 grams (98%) of the desired, product as a light yellow solid. A 1.0 gram sample was recrystallized from hexane:ethyl acetate (19:1, v:v) to give a mp 84–86° C. $^1$H nmr (CDCl$_3$): δ 1.18–1.23 (t, 6H). 1.37–1.50 (m, 2H), 2.02 (s, 3H), 2.34–2.41 (m, 2H), 2.58–2.62 (t, 2H), 4.16–4.24 (q, 4H), 6.76 (s, broad, 1H). 7.11–7.28 (m, 5H). $^{13}$C nmr (CDCl$_3$): δ 13.95, 23.03, 25.67, 31.85, 35.45, 62.46, 66.49, 125.40, 125.90, 128.27, 128.35, 141.77, 168.11, 168.84, MS (FIA) m/z 336.3 ([M+H]$^+$). IR (KBr, cm$^{-1}$) 1645.98 (amide), 1744.76 (C=O), Anal. Calcd. for C$_{18}$H$_{25}$NO$_5$: C, 64.46; H, 7.51; N, 4.17. Found: C, 64.60; H, 7.37; N, 4.39.

Preparation 32

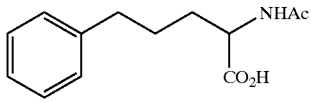

A slurry consisting of the product from Preparation 31 (249.15 grass, 0.7428 mmol) and 2.5N sodium hydroxide solution was heated at 100° C. for three hours. The reaction mixture was cooled to 30° C. and the pH adjusted to 5.0 using concentrated hydrochloric acid. The solution was heated to 100° C. and the pH was held at 5.0 using concentrated hydrochloric acid as needed until the reaction was complete as determined by hplc. The solution was filtered while hot through diatomaceous earth. The filtrate was cooled to 5–10° C. and the pH adjusted to 1.0 using concentrated hydrochloric acid. The resulting slurry was stirred for 1 hour at 5° C., filtered, and dried in vacuum at 50° C. to give 160.34 grams (92%) of (DL)-N-acetyl-2-amino-5-phenylpentanoic acid as a white powder, up 145–148° C. $^1$H nmr (DMSO-d$_6$): δ 1.60–1.71 (m, 4H), 1.86 (s, 3H), 2.56–2.59 (m, 2H), 4.19–4.23 (m, 1H), 7.16–7.30 (m, 5H), 8.14 (d, 1H). $^{13}$C nmr (DMSO-d$_6$): δ 23.17, 28.25, 31.55, 35.51, 52.55, 126.60, 129.14, 142.64, 170.25, 174.65. MS (FIA) m/z 236.2 (M$^+$). IR (KBr, cm$^{-1}$) 1609.17 (amide), 1741.12 (C=O). Anal. Calcd. for C$_{13}$H$_{17}$NO$_3$: C, 66.36; H, 7.28; N, 5.95. Found: C, 66.41; H, 7.15; N, 5.96.

Preparation 33

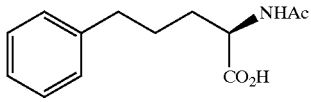

A solution consisting of (DL)-N-acetyl-2-amino-5-phenylpentanoic acid (438.0 grams, 1.862 mmol), cobalt chloride (1.10 grams), 2N potassium hydroxide solution (931 mL, 1.862 mmol), and water (8000 mL) was adjusted to a pH of 8.0 by the addition of 2N potassium hydroxide solution. To the reaction mixture was added Acylase I (*Aspergillus melleus*, 39.42 grams) and vigorously stirred for 24 hours at 40° C. while maintaining a pH of 8.0 by addition of 2N potassium hydroxide. The resulting slurry was filtered. The filtrate was adjusted to a pH of 2.0 giving a thick slurry. The product was isolated by filtration, washed with hexane (2000 mL) and dried in vacuum at 50° C. to give 188.52 grams (43%) of (D)-N-acetyl-2-amino-5-phenylpentanoic acid. $^1$H nmr (DMSO-d$_6$): δ 1.59–1.74 (m, 4H), 1.86 (s, 3H), 2.57–2.60 (m, 2H), 4.22–4.26 (m, 1H), 7.16–7.30 (m, 5H), 8.02 (d, 1H), 12.39 (s, broad, 1H). $^{13}$C nmr (DMSO-d$_6$): δ 23.18, 28.13, 31.66, 35.54, 52.58, 126.56, 129.10, 142.67, 170.12, 174.48. MS (FIA) m/z 236.1 (M$^+$). IR (KBr, cm$^{-1}$) 1625.08 (amide), 1700.24 (C=O). Anal. Calcd. for C$_{13}$H$_{17}$NO$_3$: C, 66.36; H, 7.28; N, 5.95. Found: C, 66.49; H, 7.00; N, 6.03.

Preparation 34

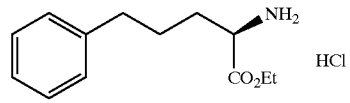

A solution consisting of (D)-N-acetyl-2-amino-5-phenylpentanoic acid (188.8 grams, 0.8024 mmol), ethanol (535 mL), and concentrated hydrochloric acid (268 mL, 3.21 mmol) was warmed to 85° C. and monitored by hplc. The reaction was determined to be incomplete by hplc at 14.5 hours and additional concentrated hydrochloric acid (50 mL) was added. The reaction was determined to be complete by hplc after 22.5 hours. Water was azeotropically distilled from the reaction by continuous addition and distillation of 8000 mL of ethanol. The ethanol was azeotropically distilled from the reaction by the continuous addition and distillation of ethyl acetate (2000 mL). Upon cooling the solution to 0° C. the product crystallized. The solution containing the product was stirred for 1 hour at 0° C., filtered, and the cake dried in vacuum at 40° C. to give 199.0 grams (96%) of 2-amino-5-phenylpentanoic acid, ethyl ester hydrochloride, mp 117–121° C. $^1$H nmr (DMSO-d$_6$): δ 1.15–1.21 (t, 3H), 1.50–1.89 (m, 4H), 2.48–2.67 (m, 2H), 3.92–3.98 (t, 1H), 4.08–4.25 (m, 2H), 7.12–7.29 (m, 5H), 8.76 (s, broad, 3H). $^{13}$C nmr (DMSO-d$_6$): δ 13.90, 25.97, 29.52, 34.41, 51.71, 61.56, 124.91, 125.81, 128.24, 141.27, 169.35. MS (FIA) m/z 222.3 (M$^+$). IR (KBr, cm$^{-1}$) 1741.14 (C=O). [α]$^{20}_D$=−11.17(c=30.62 mg/3 mL, MeOH). Anal. Calcd. for C$_{13}$H$_{20}$NO$_2$Cl: C, 60.58; H, 7.82; N, 5.43. Found: C, 60.45; H, 7.67; N, 5.55.

Preparation 35

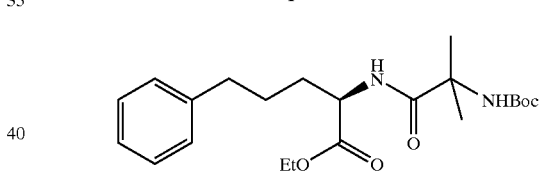

A slurry consisting of N-t-BOC-α-aminoisobutyric acid (90.64 grams, 0.446 mmol), 2-chloro-4,6-dimethoxy-1,3,5-triazine (75.90 grams, 0.425 mmol), N-methyl morpholine (88.13 grams, 0.871 mmol), and diethyl ether (1000 mL) was stirred at ambient temperature until complete as determined by hplc (3 hours). The 2-amino-5-phenylpentanoic acid, ethyl ester hydrochloride (109.55 grams, 0.425 mmol) was added and the reaction mixture stirred for 16 hours at ambient temperature. The reaction mixture was partitioned between 10% citric acid solution (1000 mL) and ethyl acetate (3×500 mL). The organic phase was washed with 10% citric acid solution (3×500 mL), saturated sodium bicarbonate solution (3×500 mL), water (1×500 mL), dried using sodium sulfate, and concentrated to dryness. The residue was recrystallized from hexane (3000 mL) to give 155.11 grams of compound 2, mp 97–99° C. $^1$H nmr (CDCl$_3$): δ 1.25–1.28 (t, 3H), 1.43 (s, 9H), 1.48 (s, 3H), 1.50 (s, 3H), 1.70–1.73 (m, 3H), 1.87–1.93 (m, 1H), 2.62–2.67 (m, 2H), 4.16–4.21 (m, 2H), 4.57–4.62 (m, 1H), 4.95 (s, 1H), 6.96 (s, broad, 1H), 7.16–7.19 (m, 3H), 7.26–7.33 (m, 2H). $^{13}$C nmr (CDCl$_3$): δ 14.53, 26.32, 27.17, 28.67, 32.47, 35.73, 52.54, 57.17, 61.62, 126.21, 128.69, 128.79, 142.12, 154.99, 172.81, 174.69. MS (FIA) m/z 407.5 ([M+H]$^+$). IR (KBr, cm$^{-1}$) 1652.75, 1685.52 (amides), 1741.73 (C=O).

[α]²⁰$_D$=7.83 (c=10.22 mg/1 mL, MeOH). UV (0.1% trifluoroacetic acid in water:acetonitrile) $\lambda_{max}$ 215.6 nm. Anal. Calcd. for $C_{22}H_{34}N_2O_5$: C, 65.00; H, 8.43; N, 6.89. Found: C, 65.23; H, 8.34; N, 6.94.

Preparation 36

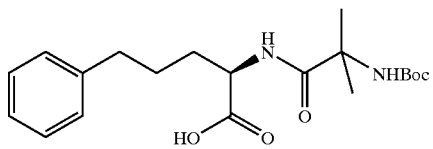

A solution consisting of the product of Preparation 35 (152.53 grams, 0.3752 mmol) and tetrahydrofuran (884 mL) was cooled to 5° C. A solution consisting of lithium hydroxide (26.96 grams, 1.126 mmol) and water (1419 mL) was added to the reaction dropwise over 10 minutes maintaining a temperature of 5–10° C. Ethanol (183 mL) was added and the reaction stirred at 5–10° C. until complete as determined by hplc (2 hours). The pH of the reaction mixture was adjusted to 2.0 using 6 N hydrochloric acid solution while maintaining 5–10° C. The product was extracted from solution with ethyl acetate (3×500 mL). The ethyl acetate extracts were combined, dried using sodium sulfate, and concentrated to dryness to give 141.51 grams (100%) of 427623. ¹H nmr (DMSO-d₆): δ 1.32–1.37 (m, 15H), 1.57–1.75 (m, 4H), 2.51–2.58 (m, 2H), 4.23–4.27 (m, 1H), 6.85 (s, broad, 1H), 7.15–7.28 (m, 5H), 7.42 (d, 1H), 12.5 (s, broad, 1H), ¹³C nmr (DMSO-d₆): δ 26.31, 27.85, 29.00, 31.86, 35.60, 52.53, 56.60, 78.95, 126.52, 129.05, 129.10, 142.69, 155.06, 174.40, 175.17. MS (FIA) m/z 379.5 ([M+H]⁺). IR (KBr, cm⁻¹) 1641.98, 1692.22 (amides), 1719.72 (C=O). [α]²⁰$_D$=−5.73 (c=10.48 mg/1 mL, MeOH).

Anal. Calcd. for $C_{20}H_{30}N_2O_5$: C, 63.47; H, 7.99; N, 7.40. Found: C, 63.25; H, 7.84; N, 7.46.

Preparation 37

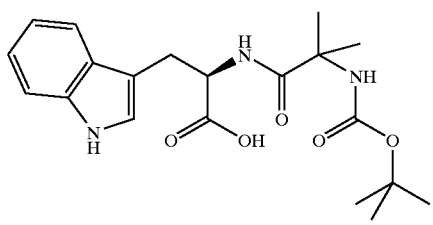

N-Methyl morpholine (4.79 mL, 2 eq, 47.3 mm) was added to a stirred slurry of N-Boc-a-aminoisobutyric acid (4.43 g, 21.7 mm, 1 eq) and 3.89 g (21.7 mm, 1.10 eq) of 2-chloro-(4,6)-dimethoxy-1,3,5-triazine (CDMT) in 100 mL of diethyl ether. After stirring the reaction mixture at ambient temperature for 1.5 hours, D-tryptophan ester hydrochloride was added. After stirring overnight, the reaction mixture was quenched by the addition of 150 mL of 10% aqueous citric acid solution. The layers were separated and the, ether layer was washed with 50 mL of saturated sodium bicarbonate solution and 50 mL of water. Lithium hydroxide (2.43 g, 5 eq) was dissolved in 100 ml of water and the solution was added to the diethyl ether solution and stirred vigorously for 4 hours at room temperature. The layers were separated and the pH of the aqueous layers was adjusted to 5.6 with 1M HCl. The pH was then adjusted to 3.95 with 10% citric acid solution and the aqueous layer was extracted with 100 mL of ethyl acetate. The ethyl acetate layers were washed with brine, dried over magnesium sulfate and filtered. The volatiles were removed under vacuum to give 82% yield of the desired product as a white foam. 1H-NMR consistent with structure.

Coupling of Dipeptide Acids to Nitroimidazoles

Preparation 38

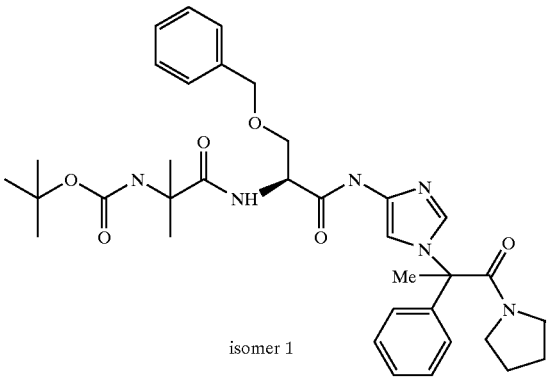

A solution of the product of Preparation 17 (1.66 g, 5.29 mmol) in THF (5 mL) was added to a suspension of 5% palladium on carbon (0.80 g, catalytic, 25 mL THF) under inert atmosphere. The resulting mixture was placed under hydrogen (40 psi) on a Parr shaker for 1.5 hours. The resulting mixture was placed under nitrogen and celite added. The mixture was then filtered and rinsed with THF. The filtrate was place under nitrogen and HOBT (0.71 g, 5.29 mmol), the product of Preparation 30 (2.01 g, 5.29 mmol), EDC (1.00 g, 5.81 mmol), and DIEA (1.0 mL, 5.81 mmol) were added. The resulting mixture was stirred 18 hours at ambient temperature, then concentrated in vacuo. The crude material was dissolved in ethyl acetate and washed with sodium bicarbonate and brine. The organic layer was dried over sodium sulfate, filtered, and concentrated in vacuo. The resulting crude foam was purified by flash chromatography (silica, 100 g, 2% methanol/dichloromethane) to yield the desired product (0.66 g, 19% yield) as a light yellow foam: ¹H NMR (300 MHz, CDCl₃)—consistent with structure; Anal. calcd. for $C_{35}H_{46}N_6O_6$; 65.00 C, 7.17 H, 12.99 N; found 63.21 C, 6.92 H, 12.54 N; FDMS (M+)—646.

Preparation 39

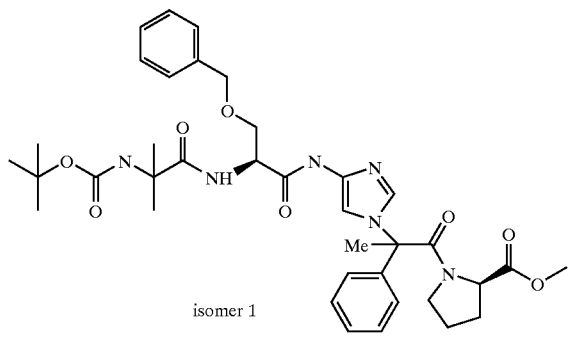

Prepared as in Preparation 38 using the product of Preparation 18 (1.39 g, 3.74 mmol) and 5% palladium on carbon (0.70 g, catalytic, 25 mL THF) to give the crude amine. The resulting filtrate was reacted with HOBT (0.50 g, 3.74 mmol), the product of Preparation 30 (1.42 g, 3.74 mmol), diisopropylethylamine (0.65 mL, 3.74 mmol), and EDCI (0.71 g, 4.11 mmol) to yield the desired product (0.86 g, 33% yield) as a light yellow foam: $^1$H NMR (300 MHz, CDCl$_3$)—consistent with structure; Anal. calcd. for C$_{37}$H$_{48}$O$_8$N$_6$; 63.05 C, 6.86 H, 11.92 N; found 63.01 C, 6.64 H, 11.85 N; FDMS (M+)—705.

Preparation 40

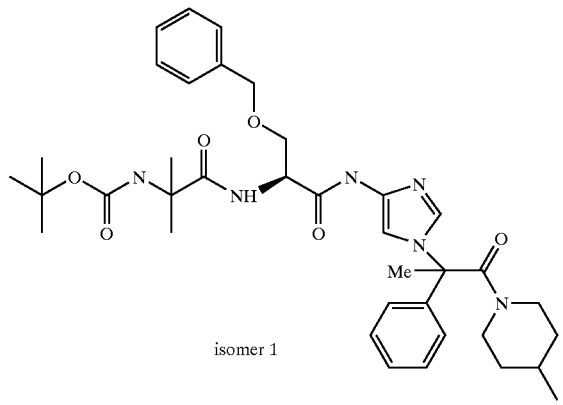

isomer 1

Prepared as in Preparation 38 using the product of Preparation 19 (1.21 g, 3.53 mmol) and 5% palladium on carbon (0.80 g, catalytic, 25 mL THF) to give the crude amine. The resulting filtrate was reacted with HOBT (0.48 g, 3.53 mmol), the product of Preparation 30 (1.34 g, 3.53 mmol), diisopropylethylamine (0.6 mL, 3.53 mmol), and EDCI (0.67 g, 3.88 mmol) to yield the desired product (0.97 g, 41% yield) as a light yellow foam: $^1$H NMR (300 MHz, CDCl$_3$)—consistent with structure; Anal. calcd. for C$_{37}$H$_{50}$N$_6$O$_6$; 65.85 C, 7.47 H, 12.45 N; found 64.96 C, 7.48 H, 12.04; FDMS (M+)—675.

Preparation 41

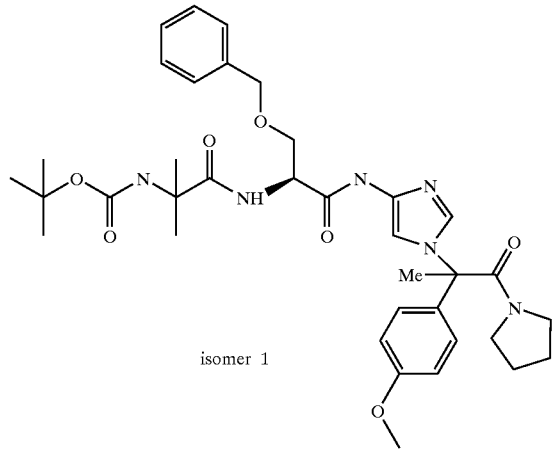

isomer 1

Prepared as in Preparation 38 using the product of Preparation 20 (0.77 g, 2.24 mmol) and 5% palladium on carbon (0.80 g, catalytic, 25 mL THF) to give the crude amine. The resulting filtrate was reacted with HOBT (0.30 g, 2.46 mmol), the product of Preparation 36 (0.85 g, 2.24 mmol), and DCC (0.51 g, 2.46 mmol) to yield the desired, product (0.70 g, 46% yield) as a light yellow foam: $^1$H NMR (300 MHz, CDCl$_3$)—consistent with structure; Anal. calcd. for C$_{37}$H$_{50}$N$_6$O$_6$; 65.85 C, 7.47 H, 12.45 N; found 65.83, C, 7.27 H, 12.38 N; ISMS (M+)—675.

Preparation 42

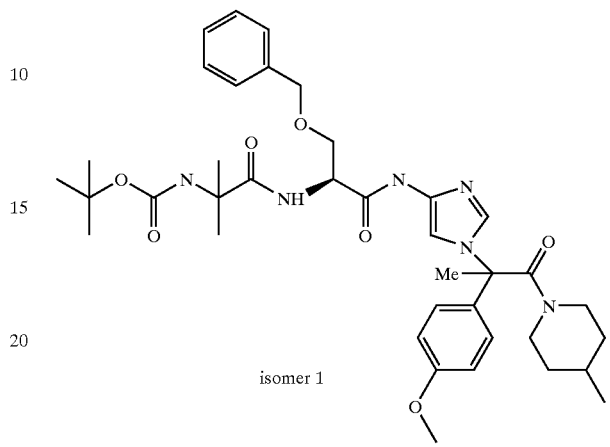

isomer 1

Prepared as in Preparation 38 using the product of Preparation 22 (0.92 g, 2.47 mmol) and 5% palladium on carbon (1.00 g, catalytic, 30 mL THF) to give the crude amine. The resulting filtrate was reacted with HOBT (0.35 g, 2.47 mmol), the product of Preparation 36 (0.94 g, 2.47 mmol), and DCC (0.56 g, 2.72 mmol) to yield the desired product (0.92 g, 53% yield) as a light yellow foam: $^1$H NMR (300 MHz, CDCl$_3$)—consistent with structure; Anal. calcd. for C$_{39}$H$_{54}$N$_6$O$_6$; 66.64 C, 7.74 H, 11.96 N; found 66.65 C, 7.65 H, 12.02 N; ISMS (M+)—702.

Preparation 43

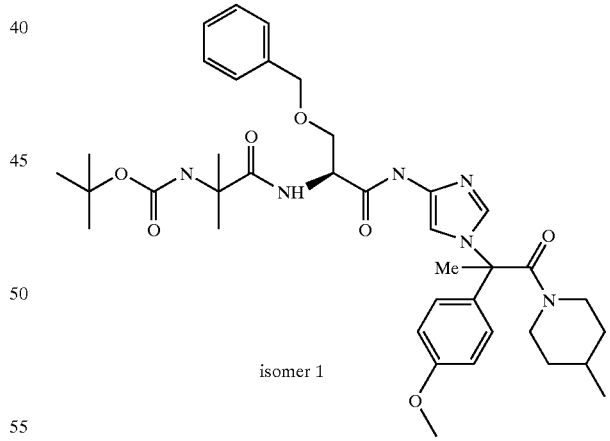

isomer 1

Prepared as in Preparation 38 using the product of Preparation 22 (1.32 g, 3.55 mmol) and 5% palladium on carbon (1.4 g, catalytic, 50 mL THF) to give the crude amine. The resulting filtrate was reacted with HOST (0.48 g, 3.55 mmol), the product of Preparation 30 (1.35 g, 3.55 mmol), and DCC (0.81 g, 3.91 mmol) to yield the desired product (0.82 g, 33% yield) as a light yellow foam: $^1$H NMR (300 MHz, CDCl$_3$)—consistent with structure; Anal. calcd. for C$_{38}$H$_{52}$N$_6$O$_7$; 64.75 C, 7.44 H, 11.92 N; found 66.19 C, 7.17 H, 12.10 N; ISMS (M+)—705.

Preparation 44

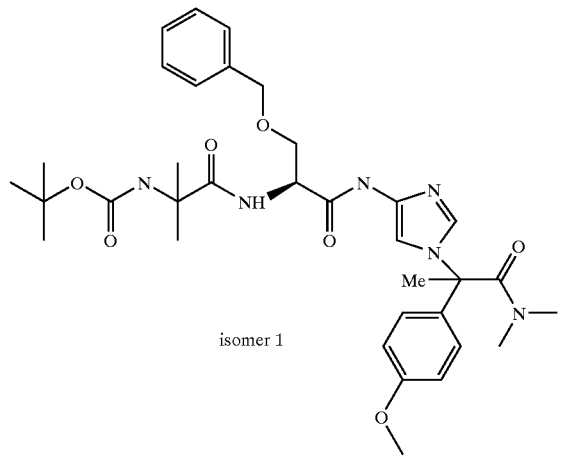

isomer 1

Prepared as in Preparation 38 using the product of Preparation 21 (0.27 g, 0.85 mmol) and 5% palladium on carbon (0.30 g, catalytic, 20 mL THF) to give the crude amine. The resulting filtrate was reacted with HOBT (0.11 g, 0.85 mmol), the product of Preparation 36 (0.32 g, 0.85 mmol), N-methylmorpholine (0.10 mL, 0.85 mmol), and EDCI (0.16 g, 0.93 mmol) to yield the desired product (0.70 g, 46% yield) as a light yellow foam: $^1$H NMR (300 MHz, CDCl$_3$)—consistent with structure; Anal. calcd. for $C_{35}H_{48}N_6O_6$; 66.43 C, 7.65 H, 13.28 N; found 63.53 C, 6.83 H, 12.38 N; ISMS (M+)—649.

Preparation 45

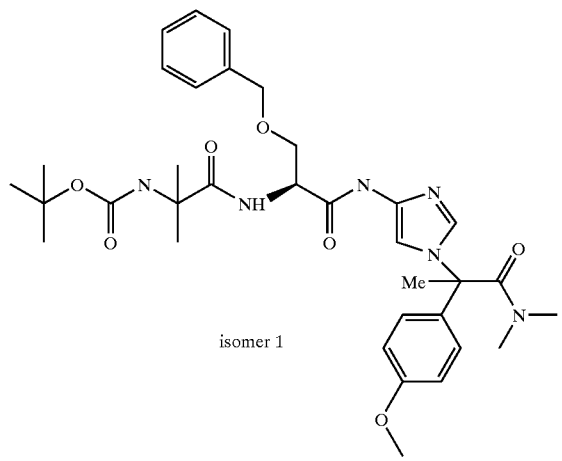

isomer 1

Prepared as in Preparation 38 using the product of Preparation 21 (0.75 g, 2.36 mmol) and 5% palladium on carbon (0.80 g, catalytic, 25 mL THF) to give the crude amine. The resulting filtrate was reacted with HOBT (0.32 g, 2.36 mmol), the product of Preparation 30 (0.90 g, 2.36 mmol), and DCC (0.54 g, 2.60 mmol) to yield the desired product (0.86 g, 56% yield) as a light yellow foam: $^1$H NMR (300 MHz, CDCl$_3$)—consistent with structure; Anal. calcd. for $C_{37}H_{50}N_6O_6$; 62.75 C, 7.12 H, 12.91 N; found 62.65 C, 6.95 H, 12.76 N; ISMS (M+)—651.

Preparation 46

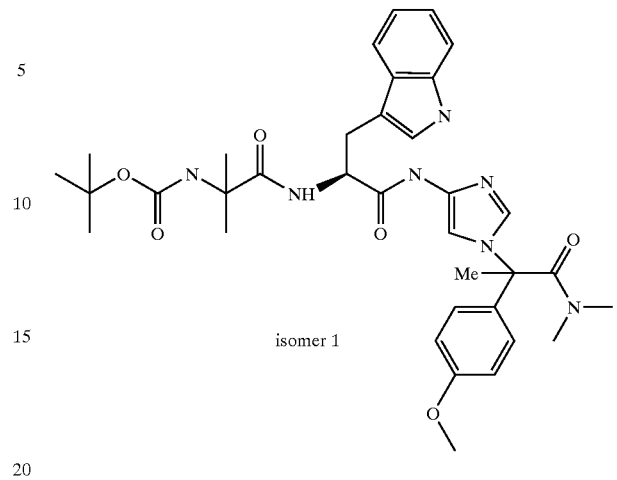

isomer 1

Prepared as in Preparation 38 using the product of Preparation 21 (0.80 g, 2.52 mmol) and 5% palladium on carbon (0.80 g, catalytic, 25 mL THF) to give the crude amine. The resulting filtrate was reacted with HOBT (0.34 g, 2.52 mmol), the product of Preparation 37 (0.99 g, 2.52 mmol), and DCC (0.57 g, 2.77 mmol) to yield the desired product (0.77 g, 46% yield) as a light yellow foam: $^1$H NMR (300 MHz, CDCl$_3$)—consistent with structure; Anal. calcd. for $C_{37}H_{50}N_6O_6$; 63.72 C, 6.87 H, 14.86 N; found 63.45 C, 6.86 H, 14.76 N; ISMS (M+)—660.

Preparation 47

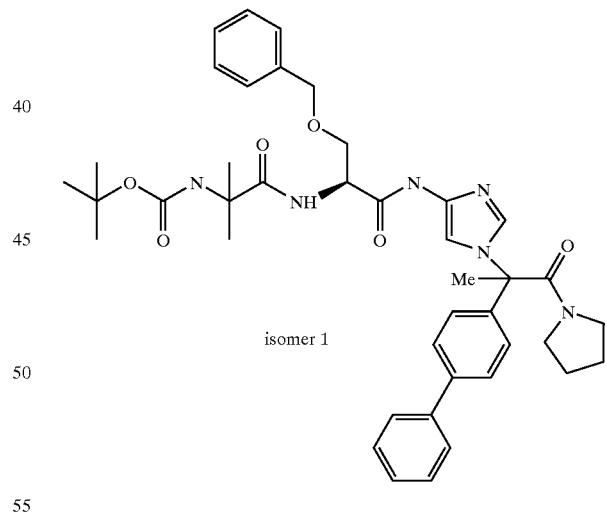

isomer 1

Prepared as in Preparation 38 using the product of Preparation 23 (0.60 g, 2.05 mmol) and 5% palladium on carbon (0.80 g, catalytic, 25 mL THF) to yield the crude amine. The filtrate was reacted with HOBT (0.28 g, 2.05 mmol), the product of Preparation 30 (0.78 g, 2.05 mmol), and DCC (0.46 g, 2.05 mmol) to yield the desired product (0.76 g, 51% yield) as a light yellow foam: $^1$H NMR (300 MHz, CDCl$_3$)—consistent with structure; Anal. calcd. for $C_{41}H_{50}N_6O_6$; 68.12 C, 6.97 H, 11.63 N; found 66.93 C, 6.74 H, 11.24 N; ISMS (M+)—723.

Preparation 48

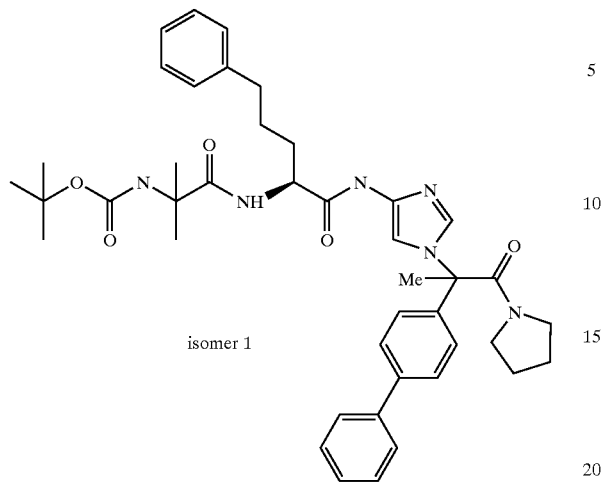

isomer 1

Prepared as in Preparation 38 using the product of Preparation 23 (0.60 g, 1.54 mmol) and 5% palladium on carbon (0.60 g, catalytic, 25 mL THF) to give the crude amine. The resulting filtrate was reacted with HOBT (0.21 g, 1.54 mmol), the product of Preparation 36 (0.58 g, 1.54 mmol), and DCC (0.35 g, 1.69 mmol) to yield the desired product (0.56 g, 50% yield) as a light yellow foam: $^1$H NMR (300 MHz, CDCl$_3$)—consistent with structure; Anal. calcd. for $C_{42}H_{52}N_6O_5$; 69.98 C, 7.27 H, 11.66 N; found 68.71 C, 6.92 H, 11.39 N; ISMS (M+)—721.

Preparation 49

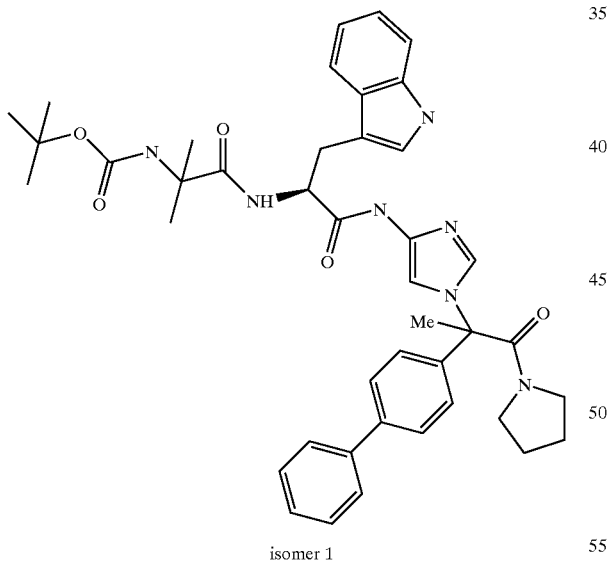

isomer 1

Prepared as in Preparation 38 using the product of Preparation 23 (0.20 g, 0.51 mmol) and 5% palladium on carbon (0.20 g, catalytic, 25 mL THF) to give the crude amine. The resulting filtrate was reacted with HOBT (0.07 g, 0.51 mmol), the product of Preparation 37 (0.20 g, 0.51 mmol), and DCC (0.12 g, 0.51 mmol) to yield the desired product (0.17 g, 45% yield) as a light yellow foam: $^1$H NMR (300 MHz, CDCl$_3$)—consistent with structure; Anal. calcd. for $C_{42}H_{49}N_7O_6$; 68.93 C, 6.75 H, 13.40 N; found 67.02 C, 6.54 H, 12.71 N; ISMS (M+)—732.

Preparation 50

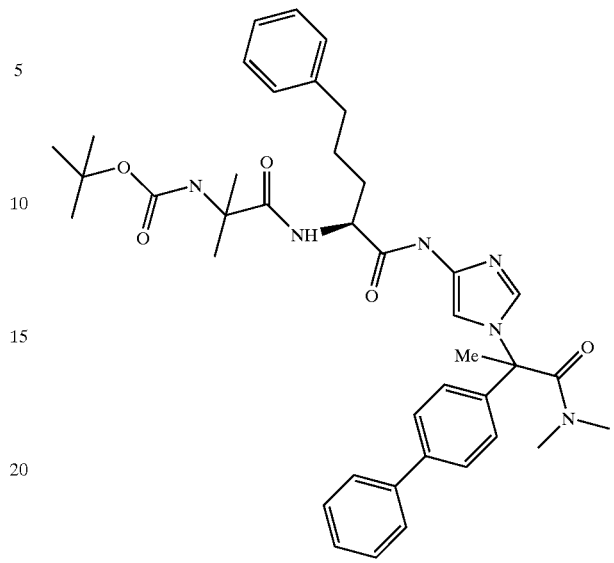

Prepared as in Preparation 38 using the product of Preparation 24 (0.30 g, 0.82 mmol) and 5% palladium on carbon (0.30 g, catalytic, 25 mL THF) to give the crude amine. The resulting filtrate was reacted with HOBT (0.11 g, 0.82 mmol), the product of Preparation 36 (0.31 g, 0.82 mmol), and DCC (0.19 g, 0.90 mmol) to yield the desired product (0.32 g, 56% yield) as a light yellow foam: $^1$H NMR (300 MHz, CDCl$_3$)—consistent with structure; Anal. calcd. for $C_{40}H_{50}N_6O_5$; 69.14 C, 7.25 H, 12.09 N; found 67.82 C, 7.07 H, 11.62 N; ISMS (M+)—695.

Preparation 51

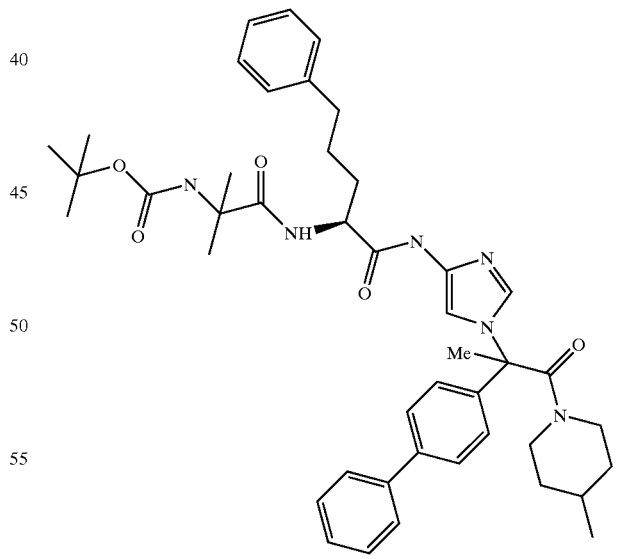

Prepared as in Preparation 38 using the product of Preparation 25 (0.35 g, 0.84 mmol) and 5% palladium on carbon (0.35 g, catalytic, 25 mL THF) to give the crude amine. The resulting filtrate was reacted with HOBT (0.11 g, 0.84 mmol), the product of Preparation 36 (0.32 g, 0.84 mmol), and DCC (0.17 g, 0.92 mmol) to yield the desired product (0.22 g, 35% yield) as a light yellow foam: $^1$H NMR (300

MHz, CDCl$_3$)—consistent with structure; Anal. calcd. for C$_{44}$H$_{56}$N$_6$O$_5$; 70.56 C, 7.54 H, 11.22 N; found 70.22 C, 7.58 H, 11.21 N; ISMS (M+)—749.

Preparation 52

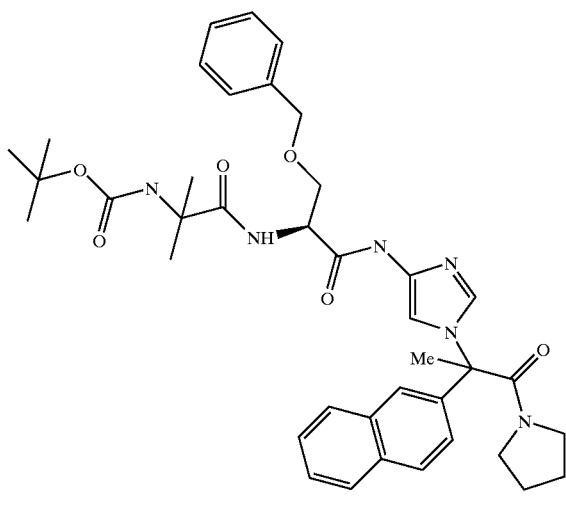

Prepared as in Preparation 38 using the product of Preparation 26 (0.42 g, 1.15 mmol) and 5% palladium on carbon (0.40 g, catalytic, 25 mL THF) to yield the crude amine. The filtrate was reacted with HOBT (0.16 g, 1.15 mmol), the product of Preparation 30 (0.44 g, 1.15 mmol), and DCC (0.26 g, 1.28 mmol) to yield the desired product (0.41 g, 51% yield) as a light yellow foam: $^1$H NMR (300 MHz, CDCl$_3$)—consistent with structure; Anal. calcd. for C$_{39}$H$_{48}$N$_6$O$_6$; 67.22 C, 6.94 H, 12.06 N; found 67.66 C, 6.95 H, 11.66 N; ISMS (M+)—697.

Example 1

A solution of the product of Preparation 38 (0.52 g, 0.80 mmol) in dichloromethane (20 mL) was stirred under nitrogen with anisole (0.4 mL) and trifluoroacetic acid (4.0 mL) at ambient temperature for 3 hours. The mixture was concentrated in vacuo to approximately 5 mL and excess diethyl ether added. The mixture was filtered and rinsed with diethyl ether to yield the desired product (0.40 g, 65% yield) as an off white solid: $^1$H NMR (300 MHz, CDCl$_3$)—consistent with structure; Anal. calcd. for C$_{34}$H$_{40}$N$_6$O$_8$F$_6$; 52.71 C, 5.20 H, 10.85 N; found 52.60 C, 5.08 H, 10.69 N; FDMS (M+)—546.

Example 2

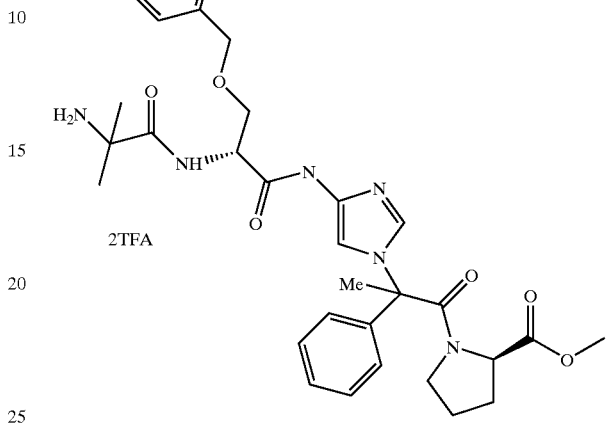

Prepared as in Example 1 using the product of Preparation 39 (0.86 g, 1.22 mmol), trifluoroacetic acid (4.0 mL), anisole (0.4 mL), and dichloromethane (20 mL) to yield the desired product (0.86 g, 85%) as a pale yellow solid: $^1$H NMR (300 MHz, CDCl$_3$)—consistent with structure; Anal. calcd. for C$_{36}$H$_{42}$N$_6$O$_{10}$F$_6$; 51.92 C, 5.08 H, 10.09 N; found 51.63 C, 4.96 H, 10.22 N; FDMS (M+)—604.

Example 3

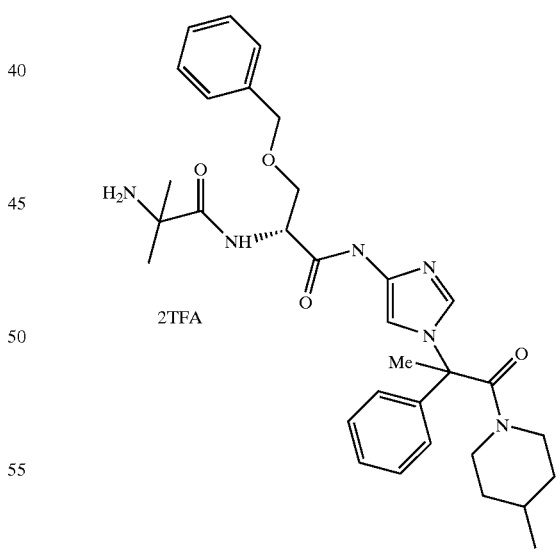

Prepared as in Example 1 using the product of Preparation 40 (0.95 g, 1.41 mmol), trifluoroacetic acid (4.0 mL), anisole (0.4 mL), and dichloroethane (20 mL) to yield the desired product (0.82 g, 92%) as a pale yellow solid: $^1$H NMR (300 MHz, CDCl$_3$)—consistent with structure; Anal. calcd. for C$_{36}$H$_{44}$N$_6$O$_8$F$_6$; 53.86 C, 5.53 H, 10.47 N; found 52.73 C, 5.50 H, 10.07 N; FDMS (M+)—574.

Example 4

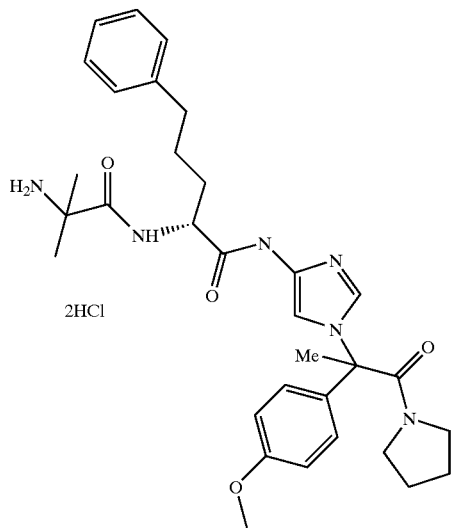

2HCl

A solution of the product of Preparation 41 (0.69 g, 1.02 mmol) in dichloroethane (10 mL) was stirred under nitrogen with anisole (0.2 mL) and trifluoroacetic acid (4.0 mL) at ambient temperature for 3 hours. The mixture was quenched with saturated sodium bicarbonate and stirred 10 min. at ambient temperature. Dichloromethane was added and the mixture washed with bicarbonante and brine. The organic layer was dried over sodium sulfate, concentrated in vacuo, and redissolved in 2 mL ethyl acetate. Diethyl ether (saturated HCl (g), 5 mL) was added and the mixture stirred 10 min. The mixture was filtered to yield the desired product (0.57 g, 86% yield) as a white solid: $^1$H NMR (300 MHz, CDCl$_3$)—consistent with structure; Anal. calcd. for C$_{32}$H$_{42}$N$_6$O$_4$Cl$_2$; 59.35 C, 6.85 H, 12.98 N; found 58.74 C, 6.77 H, 12.85 N; ISMS (M+)—575.

Example 5

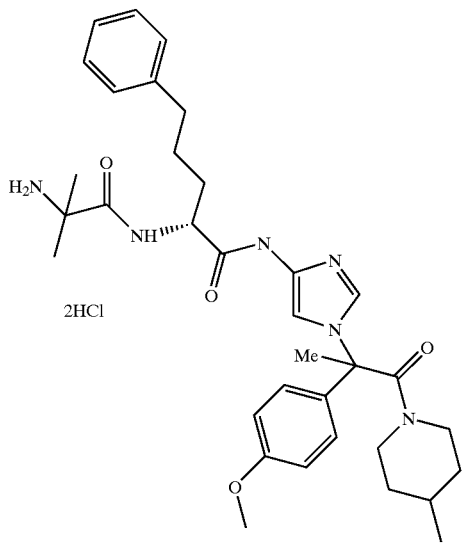

2HCl

Prepared as in Example 4 using the product of Preparation 42 (0.26 g, 0.37 mmol), trifluoroacetic acid (4.0 mL), anisole (0.4 mL), and dichloromethane (20 mL) to yield the desired product (0.19 g, 76%) as a pale yellow solid: $^1$H NMR (300 MHz, CDCl$_3$)—consistent with structure; Anal. calcd. for C$_{34}$H$_{48}$N$_6$O$_4$Cl$_2$; 60.44 C, 7.16 H, 12.44 N; found 60.08 C, 7.03 H, 12.06 N; ISMS (M+)—603.

Example 6

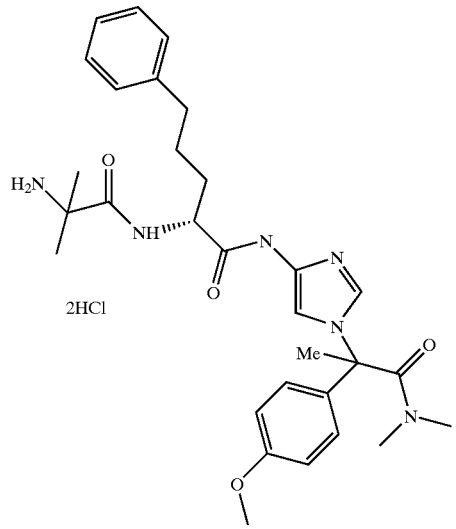

2HCl

Prepared as in Example 4 using the product of Preparation 44 (0.19 g, 0.29 mmol), trifluoroacetic acid (4.0 mL), anisole (0.4 mL) and dichloromethane (20 mL) to yield the desired product (0.16 g, 84%) as a pale yellow solid: $^1$H NMR (300 MHz, CDCl$_3$)—consistent with structure; Anal. calcd. for C$_{30}$H$_{42}$N$_6$O$_4$Cl$_2$; 57.97 C, 6.81 H, 13.52 N; found 57.54 C, 6.36 H, 13.04 N; FDMS (M+)—549.

Example 7

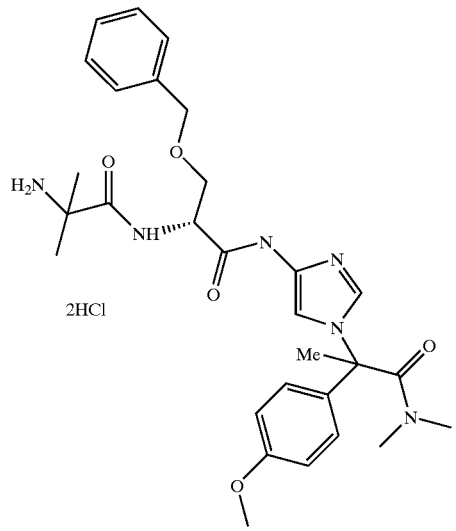

2HCl

Prepared as in Example 4 using the product of Preparation 45 (0.84 g, 1.29 mmol), trifluoroacetic acid (4.0 mL), anisole (0.4 mL), and dichloromethane (20 mL) to yield the desired product (0.69 g, 86%) as a pale yellow solid: $^1$H NMR (300 MHz, CDCl$_3$)—consistent with structure Anal. calcd. for C$_{29}$H$_{38}$N$_6$O$_5$Cl$_2$; 55.86 C, 6.47 H, 13.48 N; found 55.31 C, 6.52 H, 13.01 N; ISMS (M+)—551.

Example 8

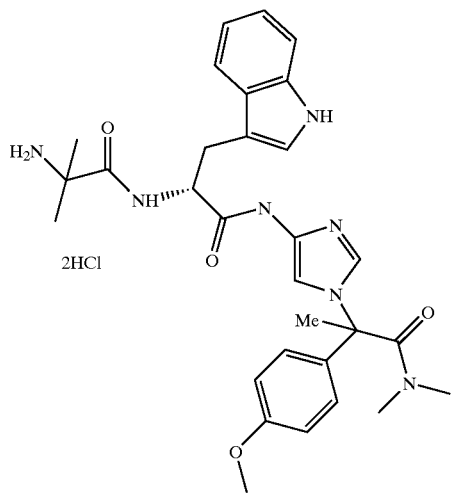

2HCl

Prepared as in Example 4 using the product of Preparation 46 (0.75 g, 1.13 mmol), trifluoroacetic acid (4.0 mL), anisole (0.4 mL), and dichloromethane (20 mL) to yield the desired product (0.62 g, 87%) as a pale yellow solid: $^1$H NMR (300 MHz, CDCl$_3$)—consistent with structure; Anal. calcd. for C$_{30}$H$_{37}$N$_7$O$_4$Cl$_2$; 56.96 C, 6.21 H, 15.50 N; found 55.48 C, 6.03 H, 14.63 N; ISMS (M+)—560.

Example 10

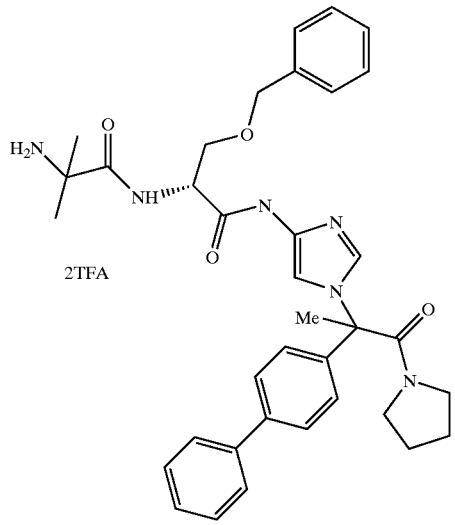

2TFA

Prepared as in Example 4 using the product of Preparation 47 (0.76 g, 1.05 mmol), trifluoroacetic acid (2.0 mL), anisole (0.2 mL), and dichloromethane (8.0 mL) to yield the desired product (0.76 g, 85% yield) as an off white solid: $^1$H NMR (300 MHz, CDCl$_3$)—consistent with structure; Anal. calcd. for C$_{40}$H$_{44}$N$_6$O$_8$F$_6$; 56.47 C, 5.21 H, 9.88 N; found 56.24 C, 5.32 H, 9.86 N; ISMS (M+)—623.

Example 9

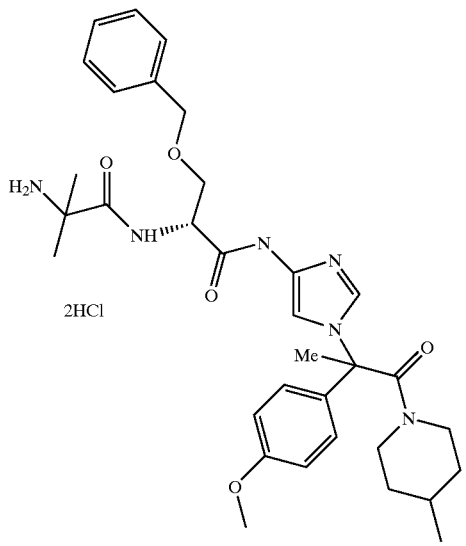

2HCl

Prepared as in Example 4 using the product of Preparation 43 (0.82 g, 1.16 mmol), trifluoroacetic acid (4.0 mL), anisole (0.4 mL), and dichloromethane (20 mL) to yield the desired product (0.71 g, 90%) as a pale yellow solid: $^1$H NMR (300 MHz, CDCl$_3$)—consistent with structure; Anal. calcd. for C$_{33}$H$_{46}$N$_6$O$_5$Cl$_2$; 58.49 C, 6.84 H, 12.40 N; found 55.40 C, 6.48 H, 11.80 N; ISMS (M+)—605.

Example 11

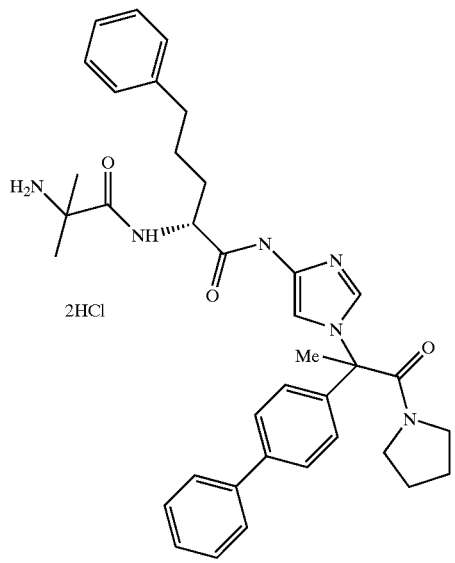

2HCl

Prepared as in Example 4 using the product of Preparation 48 (0.52 g, 0.72 mmol), trifluoroacetic acid (4.0 mL), anisole (0.4 mL), and dichloromethane (20 mL) to yield the desired product (0.47 g, 94%) as a pale yellow solid. $^1$H NMR (300 MHz, CDCl$_3$)—consistent with structure; Anal. calcd. for C$_{37}$H$_{46}$N$_6$O$_3$Cl$_2$; 64.06 C, 6.68 H, 12.11 N; found 62.18 C, 6.59 H, 11.78 N ISMS (M+)—621.

Example 12

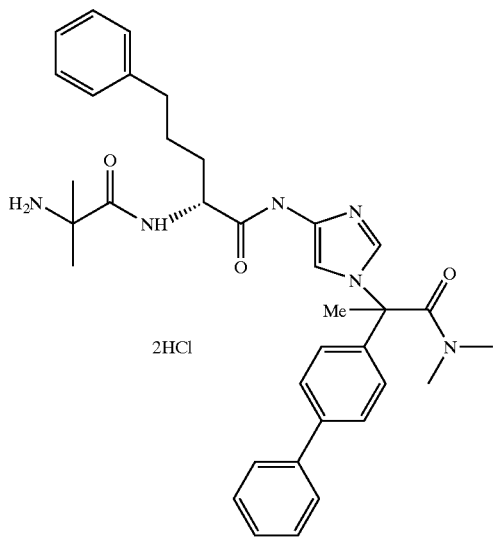

Prepared as in Example 4 using the product of Preparation 50 (0.32 g, mmol), trifluoroacetic acid (4.0 mL), anisole (0.4 mL), and dichloromethane (20 mL) to yield the desired product (0.26 g, %) an a pale yellow solid: $^1$H NMR (300 MHz, CDCl$_3$)—consistent with structure; Anal. calcd. for C$_{35}$H$_{44}$N$_6$O$_3$Cl$_2$; 62.96 C, 6.64 H, 12.59 N; found 60.05 C, 6.31 H, 11.98 N; FDMS (M+)—595.

Example 13

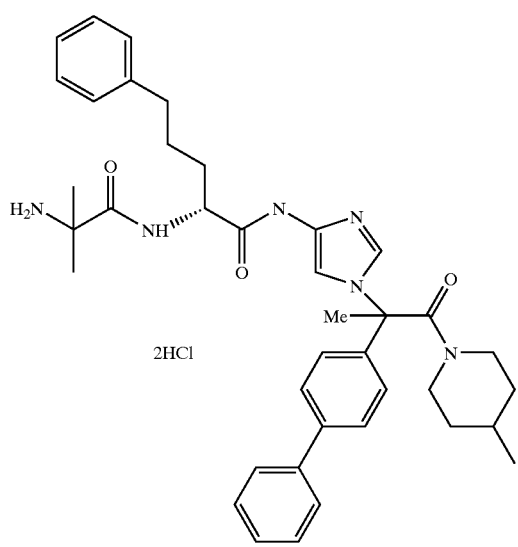

Prepared as in Example 4 using the product of Preparation 51 (0.22 g, 0.29 mmol), trifluoroacetic acid (4.0 mL), anisole (0.4 mL), and dichloromethane (20 mL) to yield the desired product (0.19 g, %) as a pale yellow solid: $^1$H NMR (300 MHz, CDCl$_3$)—consistent with structure; Anal. calcd. for C$_{39}$H$_{50}$N$_6$O$_3$Cl$_2$; 64.90 C, 6.98 H, 11.64 N; found 66.48 C, 7.24 H, 11.96 N; FDMS (M+)—649.

Example 14

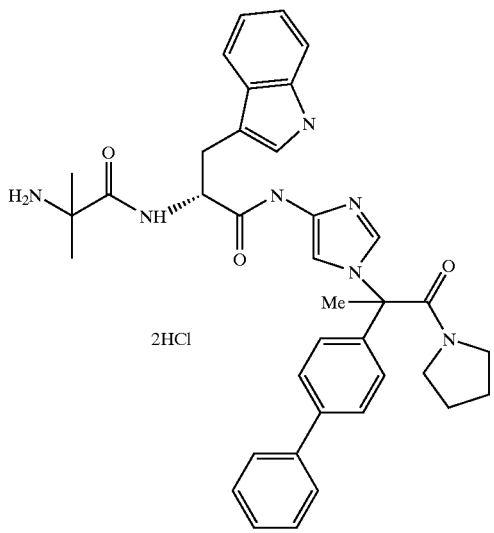

Prepared as in Example 4 using the product of Preparation 49 (0.96 g, 1.31 mmol), trifluoroacetic acid (4.0 mL), anisole (0.4 mL), and dichloromethane (20 mL) to yield the desired product (0.54 g, 59%) as a pale yellow solid: $^1$H NMR (300 MHz, CDCl$_3$)—consistent with structure; Anal. calcd. for C$_{37}$H$_{43}$N$_7$O$_3$Cl$_2$; 63.06 C, 6.15 H, 13.91 N; found 58.22 C, 5.48 H, 12.32 N; ISMS (M+)—632.

Example 15

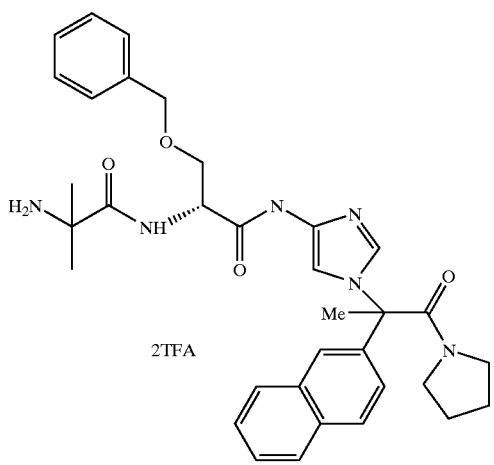

Prepared as in Example 1 using the product of Preparation 52 (0.41 g, 0.59 mmol), trifluoroacetic acid (2.0 mL), anisole (0.2 mL), and dichloromethane (8.0 mL) to yield the desired product (0.48 g, 99% yield) as an off white solid: $^1$H NMR (300 MHz, CDCl$_3$)—consistent with structure; Anal. calcd. for C$_{38}$H$_{42}$N$_6$O$_8$F$_6$; 55.34 C, 5.13 H, 10.19 N; found 55.60 C, 4.92 H, 9.89 N; ISMS (M+)—597.

EXAMPLES PART 4

Preparation 1

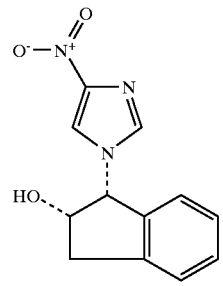

To a solution Preparation 306 from Examples Part 2 (1.58 g, 10 mmol) and (1R,2S)-(+)-cis-1-amino-2-indanol (1.49 g, 10 mmol) in methanol (10 mL) was added sodium bicarbonate (840 mg, 10 mmol) and water (5 mL). The resulting mixture was stirred at room temperature overnight. The solvent was removed in vacuo and the residue partitioned between ethyl acetate and brine. The organic phase was dried (MgSO$_4$) and concentrated in vacuo. The residue was purified by flash chromatography on silica eluting with 80% ethyl acetate/hexanes than 100% ethyl acetate, to give 1.65 g, 67% of the desired product as a tan foam. $^1$H NMR (CDCl$_3$) δ7.70 (s, 1H), 7.5–7.3 (m, 4H), 7.2 (d, J=9 Hz, 1H), 5.65 (d, J=5 Hz, 1H), 4.97 (m, 1H), 3.83 (br s, 1H), 3.35 (dd, J=6.5, 16 Hz, 1H), 3.12 (dd, J=4.16 Hz, 1H).

Preparation 2

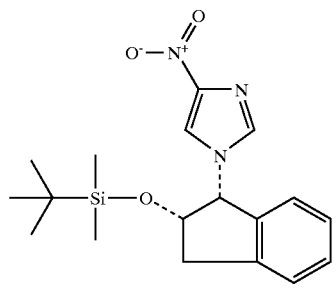

To a solution of Preparation 1 (490 mg, 2 mmol) in dry DMF (6 mL) was added t-butyldimethylsilyl chloride (300 mg, 2 mmol) and imidazole (136 mg, 2 mmol). The solution was stirred at room temperature for 24 h and an additional 50 mg of t-butyldimethylsilyl chloride was added. After stirring an additional 16 h the solvent was removed in vacuo. Flash chromatography of the residue, eluting with 50% ethyl acetate/hexanes gave 540 mg, 75% of the desired product as a white solid. $^1$H-NMR is consistent with the desired product. MS (ion spray) 360 (M+1). Anal. Calcd for C$_{18}$H$_{25}$N$_3$O$_3$Si, C: 60.14, H: 7.01, N: 11.69. Found: C: 60.40, H: 6.91, N: 11.58. [a]$_D$+51.6 (c=10).

Preparation 3

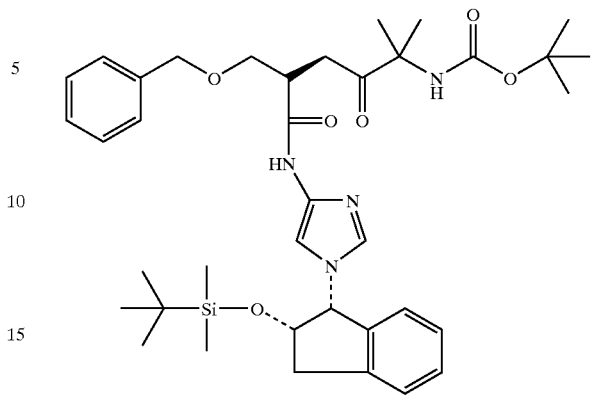

10% Pd on carbon (350 mg) was wet under nitrogen atmosphere with dry THF (5 mL). A solution of Preparation 2 (500 mg, 1.39 mmol) in dry THF (15 mL) was added and the mixture hydrogenated for 2 h under 40 psi hydrogen gas pressure. The catalyst was removed by filtration through celite and the filtrate concentrated in vacuo to approximately a volume of 10 mL. To this solution was added Preparation 4 of Examples Part 1 (532 mg, 1.4 mmol), HOBt hydrate (214 mg, 1.4 mmol), DCC (289 mg, 1.4 mmol), and the mixture stirred at room temperature overnight. The precipitated DCU was removed by filtration. The filtrate was diluted with ethyl acetate and the organic solution washed with 1N hydrochloric acid solution, saturated aqueous sodium bicarbonate solution, and brine then dried (MgSO$_4$) and concentrated in vacuo. Flash chromatography of the residue, eluting with 80% ethyl acetate/hexanes gave 570 mg, 59% of the desired product as a white foam. $^1$H-NMR is consistent with the desired product. MS (ion spray) 692 (M+1). IR 1709, 1669 cm$^{-1}$.

Example 1

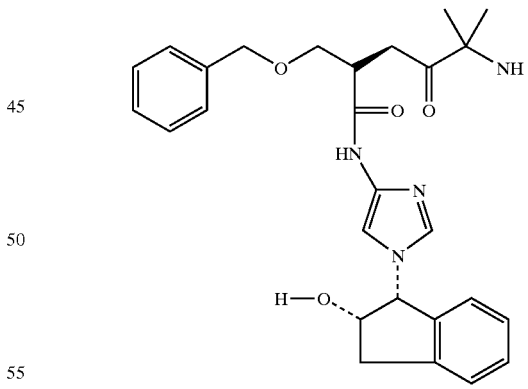

A compound of Preparation 3 (440 mg, 0.63 mmol) was dissolved in glacial acetic acid that had been previously saturated with dry hydrogen chloride gas (10 mL, approx. 3N in HCl). The mixture was stirred at room temperature for 30 min, then water (0.5 mL) was added and the mixture stirred an additional 1 h. The mixture was concentrated in vacuo, toluene was added and the solvent removed in vacuo to give a tan solid. This material was converted to the free base by partitioning between chloroform and saturated aqueous sodium bicarbonate solution. The organic phase was dried (MgSO$_4$) and concentrated in vacuo. Flash chromatography of the residue, eluting with 5% methanol/chloroform containing a trace of ammonium hydroxide gave two products. The more polar product, 80 mg, 23% yield was the desired compound. MS 478 (M+). The more polar product was reconverted to the bis hydrochloride salt by dissolving in chloroform and adding ethyl ether that had been previously saturated with dry hydrogen chloride gas. $^1$H NMR (DMSO-d$_6$) δ 11.25 (br s, 1H), 8.6 (d, J=7 Hz, (H), 8.4–8.1 (m, 5H), 7.4–7.15 (m, 10H), 7.02 (s, 1H), 5.75 (d, J=5 Hz, 1H), 4.70 (m, 1H), 4.56 (m, 1H), 4.45 (m, 2H), 3.65 (m, 2H), 3.12 (dd, J=6.5, 16 Hz, 1H)), 2.82 (dd, J=4, 16 Hz, 1H), 1.45 (s, 6H). The less polar product was identical to acetyl analog (the product from Example 172. Examples Part 2A) (160 mg, 48% yield).

Preparation 4

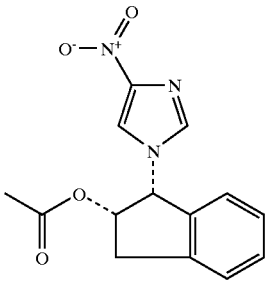

To a 0° C. solution of Preparation 1 (490 g, 0.2 mmol) in pyridine (10 mL) was added acetic anhydride (0.2 mL, 2 mmol). The mixture was allowed to warm to room temperature while stirring overnight. The solvent was removed in vacuo and the residue dissolved in ethyl acetate. The organic solution was washed with 1N hydrochloric acid solution, saturated aqueous sodium bicarbonate solution, and brine then dried (MgSO$_4$) and concentrated in vacuo. Flash chromatography of the residue on silica gel, eluting with 50% ethyl acetate hexanes gave 420 mg, 73% of the desired product as a colorless oil. $^1$H-NMR is consistent with the desired product. MS (ion spray) 288 (M+1). Anal. Calcd for C$_{14}$H$_{13}$N$_3$O$_4$, C: 58.53, H: 4.56, N: 14.63. Found: C: 58.30, H: 4.62, N: 14.41.

Racemic trans-1-amino-2-hydroxyindan was prepared from racemic indene oxide according to the method of D. R. Boyd, N. D. Sharma, N. I. Bowers, P. A. Goodrich, M. R. Groocock, A. J. Blacker, D. A. Clarke, T. Howard, H. Dalton. Tetrahedron Asymmetry 7, 1559–1562, 1996.

Preparation 5

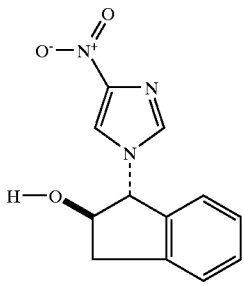

To a solution of Preparation 306 from Examples Part 2 (1.85 g, 11.67 mmol) and trans-1-amino-2-hydroxyindan (1.74 g, 11.76 mmol) in methanol (15 mL) was added sodium bicarbonate (1.0 g, 11.9 mmol) and water (8 mL). The resulting mixture was stirred at room temperature overnight. The solvent was removed in vacuo and the residue partitioned between ethyl acetate and brine. The organic phase was dried (MgSO$_4$) and concentrated in vacuo. The residue was purified by flash chromatography on silica gel eluting with 80% ethyl acetate/hexanes to give 1.73 g, 60% of the desired product as a tan foam. $^1$H-NMR is consistent with the desired product. MS (ion spray) 246 (M+1). Anal. Calcd for C$_{12}$H$_{11}$N$_3$O$_3$, C: 58.77, H: 4.52, N: 17.13. Found: C: 58.87, H: 4.65, N: 17.18.

Preparation 6

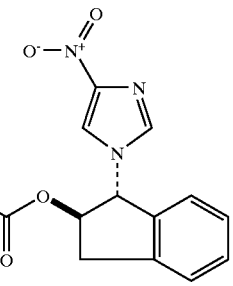

To a solution of Preparation 5 (290 mg, 1.18 mmol) in pyridine (10 mL) was added acetic anhydride (0.2 mL, 2 mmol). The mixture stirred at room temperature overnight. The solvent was removed in vacuo and the residue dissolved in ethyl acetate. The organic solution was washed with 1N hydrochloric acid solution, saturated aqueous sodium bicarbonate solution, and brine then dried (MgSO$_4$) and concentrated in vacuo to give 280 mg, 82% yield of the desired product as an off-white foam. $^1$H-NMR is consistent with the desired product. MS (ion spray) 288 (M+1). IR 1744, 1549 cm$^{-1}$ Preparation 7

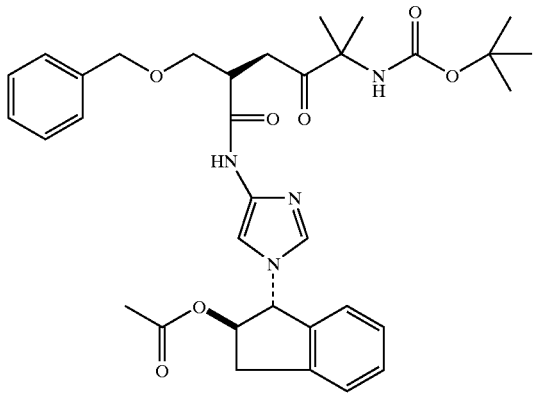

10% Pd on carbon (260 mg) was wet under a nitrogen atmosphere with dry THF (5 mL). A solution of Preparation 6 (275 mg, 0.95 mmol) in dry THF (7 mL) was added and the mixture hydrogenated for 1.5 h under 40 psi hydrogen gas pressure. The catalyst was removed by filtration through celite and the filtrate concentrated in vacuo to approximately a volume of 8 mL. To this solution was added Preparation 4 of Examples Part 1 (380 mg, 1.0 mmol), HOBt hydrate (153 mg, 1.0 mmol), DCC (206 mg, 1.0 mmol), and the mixture

497 stirred at room temperature for 60 h. The precipitated DCU was removed by filtration. The filtrate was diluted with ethyl acetate and the organic solution washed ah with 1N hydrochloric acid solution, saturated aqueous sodium bicarbonate solution, and brine then dried (MgSO$_4$) and concentrated in vacuo. Radial chromatography of the residue, eluting with 80% ethyl acetate/hexanes gave 310 mg, 52% of the desired product. $^1$H-NMR is consistent with the desired product. MS (ion spray) 620 (M+1). Anal. Calcd for C$_{33}$H$_{41}$N$_5$O$_7$, C: 63.96, H: 6.67, N: 11.30. Found: C: 63.30, H: 6.86, N: 11.13.

Example 2

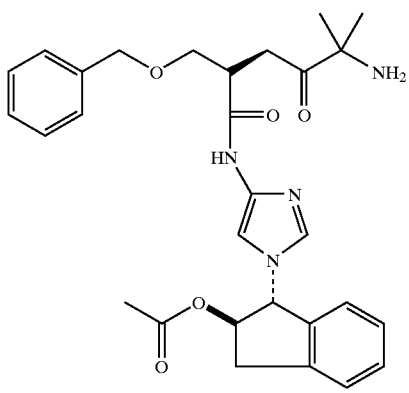

A compound of Preparation 7 (290 mg, 0.46 mmol) was dissolved in glacial acetic acid that had been previously saturated with dry hydrogen chloride gas (10 mL, approx. 3N in HCl). The mixture was stirred at room temperature for 20 min then concentrated in vacuo, toluene was added and the solvent removed in vacuo to give a yellow solid. This material was converted to the free base by partitioning between ethyl acetate and 0.1N aqueous sodium hydroxide solution. The organic phase was dried (MgSO$_4$) and concentrated in vacuo. Flash chromatography of the residue, eluting with 5% methanol/chloroform gave the desired product. The hydrochloride salt was reformed-by dissolving the product in glacial acetic acid that had been previously saturated with dry hydrogen chloride gas (5 mL, approx. 3N in HCl), then toluene was added and the solvent removed in vacuo to give 140 mg, 50% yield of the desired product a white solid. $^1$H NMR (DMSO-d$_6$) δ 11.05 (br s, 1H), 8.55 (d, J=8 Hz, 1H), 8.24 (br s, 2H), 8.10 (br s, 1H), 7.22–7.05 (m, 10H), 5.95 (d, J=7 Hz, 1H), 5.50 (m, 1H), 5.30 (br s, 2H), 4.78 (m, 1H), 4.52, (s, 2H), 3.73 (m, 2H), 3.52 (dm, J=16 Hz, 1H), 2.98 (dd, J=7, 16 Hz, 1H), 2.04 (s, 3H), 1.50 (s, 6H). MS (ion spray) 520 (M+1). Anal. Calcd for C$_{28}$H$_{35}$Cl$_2$N$_5$O$_5$+0.4H$_2$O. C: 56.02, H: 5.96, N: 11.67. Found: C: 56.33, H: 6.33, N: 11.27.

498

Preparation 8

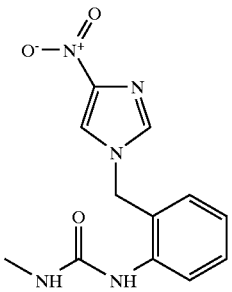

Preparation 391 of Examples Part 2A (950 mg, 4.35 mmol) was dissolved in THF (20 mL) and methyl isocyanate (0–3 mL, 5 mmol) was added. After 4 h of stirring there was no apparent change by TLC. An additional 10 mmol of methyl isocyanate was added along with triethyl amine (0.7 mL, 5 mmol) and the mixture was stirred an additional 60 h. The white precipitate that formed was collected by filtration and dried in vacuo to give 1.04 g, 87% of the desired urea. $^1$H-NMR is consistent with the desired product. MS (ion spray) 276 (M+1). Anal. Calcd for C$_{12}$H$_{13}$N$_5$O$_3$, C: 52.36, H: 4.76, N: 25.44. Found: C: 52.61, H: 4.74, N: 25.25.

Preparation 9

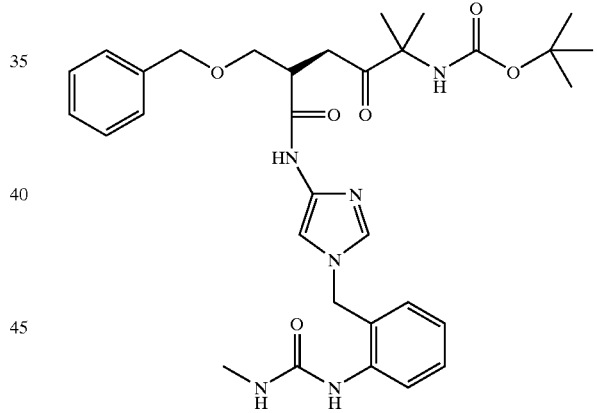

10% Pd on carbon (550 mg) was wet under a nitrogen atmosphere with ethyl acetate (5 mL). A slurry of Preparation 8 (550 mg, 2.0 mmol) in ethyl acetate (40 mL), methanol (40 mL) and acetic acid (1 mL) was added and the mixture hydrogenated for 2 h under 40 psi hydrogen gas pressure. The catalyst was removed by filtration through celite and the filtrate concentrated in vacuo. Toluene was added and the mixture reconcentrated in vacuo to give a purple solid. This solid was dissolved in THF (20 mL) and to this solution was added Preparation 4 of Examples Part 1 (760 mg, 2.0 mmol), HOBt hydrate (306 mg, 2.0 mmol), DCC (412 mg, 2.0 mmol), and triethyl amine (0.28 mL, 2.0 mmol). The mixture stirred at room temperature overnight. The precipitated DCU was removed by filtration. The filtrate was diluted with ethyl acetate and the organic solution washed with 1N hydrochloric acid solution, saturated aqueous sodium bicarbonate solution, and brine then dried (MgSO₄) and concentrated in vacuo. Flash chromatography of the residue, eluting with a step gradient of 2% methanol/ethyl acetate, to 5% methanol/ethyl acetate, to 5% methanol/1% acetic acid/ethyl acetate, to 10% methanol/1% acetic acid/ethyl acetate gave 240 mg, 19% of the desired product as an off-white solid. ¹H-NMR is consistent with the desired product. MS (ion spray) 608 (M+1).

Example 4

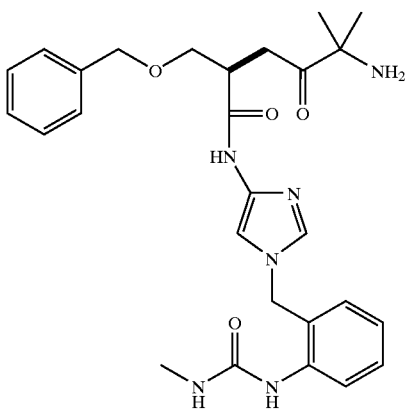

A compound of Preparation 9 (210 mg, 0.34 mmol) was dissolved in glacial acetic acid that had been previously saturated with dry hydrogen chloride gas (5 mL, approx. 3N in HCl). The mixture was stirred at room temperature for 1 h then concentrated in vacuo, toluene was added and the solvent removed in vacuo to give a gum. The residue was dissolved in methanol (2 mL), toluene was added and the solvents removed in vacuo to give 190 mg of the desired product as white powder. ¹H NMR (DMSO-d₆) d 11.20 (br 8, 1H), 8.71 (br s, 1H), 8.62 (d, J=7.5 Hz, 1H), 8.25 (br s, 2H), 7.72 (d, J=8.5 Hz, 1H), 7.34–7.12 (m, 9H), 7.04 (t, J=7.5 Hz, 1H), 6.86 (br s, 1H), 5.42 (ABq, J=14 Hz, 2H), 4.73 (q, J=7 Hz, 1H), 4.53 (s, 2H). 3.73 (m, 2H), 2.65 (s, 3H), 1.50 (s, 6H). MS (ion spray) 508 (M+1).

Preparation 10

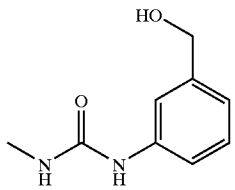

3-Aminobenzyl-alcohol (615 mg, 5 mmol) was dissolved in methylene chloride (10 mL) and methyl isocyanate (0.3 mL, 5 mmol) was added. The mixture was stirred at room temperature overnight. The white precipitate that formed was collected by filtration and dried in vacuo to give 775 mg, 86% of the desired urea. ¹H-NMR is consistent with the desired product. MS (inn spray) 181 (M+1). Anal. Calcd for C₉H₁₂N₂O₂, C: 59.99, H: 6.71, N: 15.55. Found: C: 60.23, H: 6.68, N: 15.37.

Preparation 11

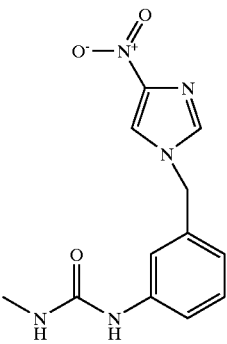

To a 0° C. solution of Preparation 10 (540 mg, 3 mmol) in THF (30 mL) was added triethyl amine (0.46 mL, 3.3 mmol) and methanesulfonyl chloride (0.255 mL, 3.3 mmol). The mixture was stirred at 0° C. for 1 h at which time TLC (EtOAc) indicated the alcohol had been consumed and a less polar product had formed. The solvent was removed in vacuo and the residue dissolved in dry DMF (10 mL). Potassium carbonate (966 mg, 7 mmol) and 4-nitro imidazole (339 mg, 3 mmol) were added, and the mixture was stirred at room temperature overnight. The DMF was removed in vacuo, the residue dissolved in chloroform/isopropanol (3/1), and washed with water, brine, then dried (MgSO₄) and concentrated to a solid. Flash chromatography on silica gel eluting with 3% methanol in ethyl acetate gave the desired product 410 mg 50%, contaminated with approximately 20% of the undesired 4-alkylated isomer (by NMR analysis). Anal. Calcd for C₁₂H₁₃N₅O₃, C: 52.36, H: 4.76, N: 25.44. Found: C: 52.66, H: 4.64, N: 25.31.

Preparation 12

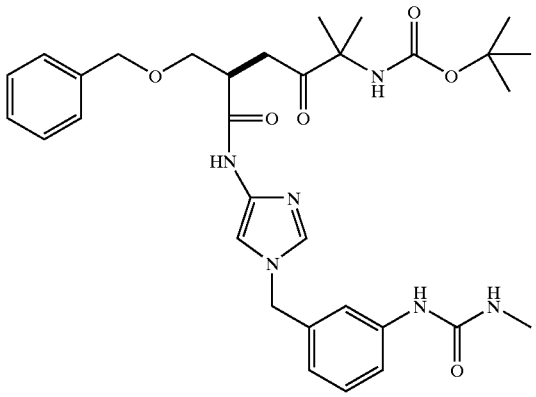

10% Pd on carbon (380 mg), was wet under a nitrogen atmosphere with ethyl acetate. (20 mL). A solution of Preparation 11 (380 mg, 1.4 mmol) in methanol (2.0 mL) was added and the mixture hydrogenated for 2 h under 40 psi hydrogen gas pressure. The catalyst was removed by filtration through celite and the filtrate concentrated in vacuo. THF was added and the mixture reconcentrated in vacuo to give a solid. This solid was dissolved in THF (10 mL) and to this solution was added Preparation 4 from Examples Part 1(532 mg, 1.4 mmol), HOBt hydrate (214 mg, 1.4 mmol), DCC (289 mg, 1.4 mmol). The mixture stirred at room temperature overnight. The precipitated DCU was removed by filtration. The filtrate was diluted with ethyl acetate and the organic solution washed with saturated aqueous sodium bicarbonate solution, and brine then dried (MgSO$_4$) and concentrated in vacuo. Flash chromatography of the residue eluting with a step gradient of 2% methanol/ethyl acetate, to 10% methanol/ethyl acetate gave 400 mg, of impure product as an off-white solid. Radial chromatography, 5% methanol/chloroform gave the desired product, 370 mg, 44% as a yellowish tinted foam. $^1$H-NMR is consistent with the desired product. MS (ion spray) 608 (M+1). Anal. Calcd for C$_{31}$H$_{41}$N$_7$O$_6$+0.2CHCl$_3$ C: 59.33, H: 6.58, N: 15.52. Found: C: 59.21, H: 6.65, N: 15.18.

Example 5

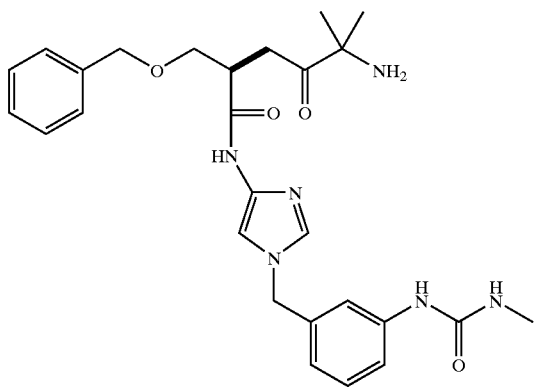

To a compound of Preparation 12 (0.3 g, 0.5 mmol) stirring in dichloromethane (6 mL) at room temperature was added trifluoroacetic acid (2 mL). After 2 h, the reaction mixture was concentrated to dryness. The residue was partitioned between ethyl acetate and saturated sodium bicarbonate and was then extracted with ethyl acetate. The combined organics were washed with brine, dried over sodium sulfate and concentrated to dryness. The residue was chromatographed over silica gel using ethanol/chloroform as eluant to yield 0.12 g (49%) of the desired product as a white foam. $^1$H-NMR is consistent with structure; MS (ion spray) 508.3 (M+1); Anal. Calc'd for C$_{26}$H$_{33}$N$_7$O$_4$.0.41CHCl$_3$: C, 57.00; H, 6.05; N, 17.62. Found: C, 57.17; H, 6.24; N, 17.22.

EXAMPLES PART 5

Preparation 1

Methyl 2R-{2-[(tert-butoxy)carbonylamino]-2-methylpropanoylamino}-2-phenylacetate To a solution of N-[(1,2-dimethylethoxy)carbonyl]-2-methylalanine (5.04 g, 24.79 mmol) and 2-chloro-4,6-dimethoxy-1,3,5-triazine (4.43 g, 24.79 mmol) in 100 mL of THF was added N-methylmorpholine (5.45 mL, 49.58 mmol). After 1 h, (R)-phenylglycine methyl ester hydrochloride (5.0 g, 24.79 mmol) was added in one portion, and the reaction mixture was stirred at room temperature for 16 h. The reaction was concentrated in vacuo, and the resulting residue was dissolved in 100 mL each of EtOAc and 10% (w/w) aqueous citric acid. The phases were separated and the organic layer was washed with saturated aqueous NaHCO$_3$ and saturated aqueous NaCl, dried over Na$_2$SO$_4$, filtered and concentrated in vacuo to give 8.51 g (98%) of a white solid. $^1$H NMR (DMSO, 300 MHz) d 8.05 (m, 1H), 7.40 (m, 5H), 6.90 (br s, 1H), 5.40 (d, 1H), 3.65 (s, 3H), 1.30 (m, 15H); $^{13}$C NMR (DMSO, 75 MHz) 174.2, 170.9, 154.3, 136.8, 128.4, 128.1, 128.0, 127.4, 78.2, 56.0, 52.3, 28.0, 25.2, 24.7 ppm; Anal. Calcd. for C$_{18}$H$_{26}$N$_2$O$_5$: C, 61.70; H, 7.48; N, 7.99. Found: C, 61.50; H, 7.36; N, 8.19.

Preparation 2

(R)-2-[(Tert-butoxy)carbonylamino]-2-methyl-N-({N-[1-(2-oxo-1-phenyl-2-pyrrolidinylethyl)imidazol-4-yl]carbamoyl}phenylmethyl)propanamide To a 0° C. solution of the methyl ester in Example 1, (1.0 g, 2.85 mmol) in dioxane (19 mL) and H$_2$O (9.5 mL) was added LiOH (0.682 g, 28.5 mmol). The reaction stirred for 40 min and was diluted with 50 mL of EtOAc. The pH was adjusted to 3 with conc. HCl and the phases were separated. The aqueous layer was extracted with EtOAc (2×25 mL). The combined organics were dried over Na$_2$SO$_4$, filtered and concentrated in vacuo to give 958 mg of the acid which was used as is in subsequent reactions.

N-methylmorpholine (0.25 mL, 2.27 mmol) was added to a suspension of 2-chloro-4,6-dimethoxy-1,3,5-triazine (405 mg, 2.27 mmol) and 2-{2-[(tert-butoxy) carbonylamino]-2-methylpropanoylamino}-2-phenylacetic acid (570 mg, 1.69 mmol) in CH$_2$Cl$_2$ (7 mL) and THF (2 mL) at 23° C. The mixture stirred for 2 h and 2-(4-aminoimidazolyl)-2-phenyl-1-pyrrolidinylethan-1-one dihydrochloride (779 mg, 2.27 mmol) was added in one portion. After 16 h, the reaction was diluted with EtOAc (50 mL) and 10% (w/w) aqueous citric acid. The phases were separated, and the organic layer was washed with 20 mL each of saturated aqueous NaHCO$_3$ and saturated aqueous NaCl, dried over Na$_2$SO$_4$, filtered and concentrated in vacuo. The residue was purified by flash chromatography (gradient 2/98 to 6/94 MeOH/CH$_2$Cl$_2$) to give 405 mg (40%) of the title compound. $^1$H NMR (CDCl$_3$, 300 MHz) d 10.61 (m, 1H), 7.75 (s, 1H), 7.45–7.15 (s, 12H), 5.95 (s, 1H), 5.80 (m, 1H), 3.60–3.38 (m, 3H), 3.10 (m, 1H), 2.15 (m, 1H), 1.98–1.65 (m, 3H), 1.50–1.05 (m, 15H); IR (CHCl$_3$) 3400, 3000, 1706, 1661, 1486, 1455, 1157 cm$^{-1}$; MS (electrospray) m/z 588 (M+H), 589 (M−H), 587.

Example 1

(R)-2-Amino-2-methyl-N-({N-[1-(2-oxo-1-phenyl-2-pyrrolidinylethyl)imidazol-4-yl]carbamoyl}phenylmethyl)propanamide), bis-trifluoroacetate Trifluoroacetic acid (1.4 mL, 18.3 mmol) was added to a solution of a compound of Example 2 (360 mg, 0.611 mmol), anisole (0.20 mL, 1.83 mmol) and CH$_2$Cl$_2$ (14 mL). After 4 h the solution was concentrated to an oil which was dissolved in CH$_2$Cl$_2$ (3.0 mL). This solution was added dropwise to Et$_2$O (25 mL) with vigorous stirring, and a white precipitate formed. After 12 h, the solid was filtered and washed with Et$_2$O (20 mL). The wet cake was dried at 40° C. in a vacuum oven for 12 h to yield 391 mg (91%). $^1$H NMR (DMSO-d$_6$, 300 MHz) d 10.70 (d, J=2.5 Hz, 1H), 8.66 (d, J=6.7 Hz, 1H), 8.02 (m, 3H), 7.54–7.10 (m, 12H), 6.39 (s, 1H), 5.58 (m, 1H), 3.60 (s, 1H), 3.30 (m, 2H), 2.90 (m, 1H) 1.80–1.55 (m, 4H), 1.07–0.70 (m, 6H); IR (KBr) 3064, 3035, 2980, 1672, 1575, 1539, 1497, 1201, 1133, 721, 700 cm$^{-1}$; MS (electrospray) m/z (freebase) 488; (freebase M+H), 489 (freebase M−H), 487.

Preparation 3

(R)-2-[(Tert-butoxy)carbonylamino]-2-methyl-N-[(N-{1-[2(4-methylpiperidyl)-2-oxo-1-phenylethyl]imidazol-4-yl}carbamoyl)phenylmethyl]propanamide N-methylmorpholine (0.16 mL, 1.49 mmol) was added to a suspension of 2-chloro-4,6-dimethoxy-1,3,5-triazine (268 mg, 1.53 mmol), 2-{2-[(tert-butoxy)carbonylamino]-2-methylpropanoylamino}-2-phenylacetic acid (502 mg, 1.49 mmol), CH$_2$Cl$_2$ (7 mL) and THF (2 mL) at 23° C. The heterogeneous reaction stirred for two hours and 2-(4-aminoimidazolyl)-1-(4-methylpiperidyl)-2-phenylethan-1-one dihydrochloride (613 mg, 1.65 mmol) was added. The mixture was stirred for 15.5 h, and EtOAc (40 mL) and 10% (w/w) aqueous citric acid (18 mL) were added. The layers were separated, and the organic layer was extracted with 15 mL each of saturated NaHCO$_3$ and saturated NaCl. The organic layer was dried (MgSO$_4$), concentrated in vacuo to 590 mg of solid, and purified by flash chromatography (10% i-PA/CHCl$_3$) to yield 440 mg (48%) of a foamy solid: $^1$H NMR (CDCl$_3$, 300 MHz) d 10.34 (m, 1H), 7.67 (s, 1H), 7.40–7.19 (m, 12H), 6.10 (m, 1H), 5.73 (m, 1H), 4.57 (m, 1H), 3.84 (m, 1H), 3.60 (m, 1H), 2.95 (m, 1H), 2.74–2.58 (m, 1H), 1.65–0.79 (m, 23H); $^{13}$C NMR (CDCl$_3$, 75 MHz) 174.0, 167.0, 165.3, 137.7, 136.7, 134.2, 133.5, 133.4, 129.4, 129.3, 129.2, 129.2, 128.7, 128.5, 128.5, 128.3, 128.2, 128.0, 127.2, 127.2, 108.1, 62.1, 62.0, 62.0, 61.9, 57.1, 56.6, 46.0, 46.0, 45.8, 42.9, 34.2, 33.6, 33.5, 30.8, 30.7, 28.2, 21.5, 21.4 ppm; IR (CHCl$_3$) 1456, 1487, 1560, 1661, 1707, 3010 cm$^{-1}$; MS (electrospray) m/z 617 (M+H), 438 & 615 (M–H), 436.

Example 2

(R)-2-Amino-2-methyl-N-[(N-{1-[2-(4-methylpiperidyl-2-oxo-1-phenylethyl]imidazol-4-yl}carbamoyl) phenylmethyl]propanamide bis-trifluoroacetate Trifluoroacetic acid (1.5 mL, 19.9 mmol) was added to a solution of a compound of Example 4 (410 mg, 0.66 mmol), anisole (0.22 mL, 2.0 mmol) and CH$_2$Cl$_2$ (16 mL). After 5 h the solution was concentrated to an oil which was dissolved in CH$_2$Cl$_2$ (3.5 mL). This solution was added dropwise to Et$_2$O (30 mL) with vigorous stirring, and a white precipitate formed. After 30 min the solid was filtered and washed with copious Et$_2$O. The wet cake was dried in a room temperature vacuum desiccator overnight to yield 283 mg (58%) of a white, hygroscopic powder: mp 182° C. (dec); $^1$H-NMR (DMSO-d$_6$; 300 MHz) d 10.79 (d, J=2.7 Hz, 1H), 8.72 (d, J=6.5 Hz, 1H), 8.15 (m, 2H), 7.54–7.20 (m, 11H), 7.19 (m, 1H), 6.73 (d, J=14.2 Hz, 1H), 5.61 (d, J=6.7 Hz, 1H), 4.36 (m, 1H), 3.72 (m, 1H), 2.69–2.48 (m, 2H), 1.59–1.24 (m, 9H), 1.07–0.70 (m, 5H); $^{13}$C NMR (DMSO-d$_6$, 75 MHz) 171.5, 171.4, 166.4, 165.6, 165.6, 165.4, 165.4, 158.3, 157.9, 137.2, 137.1, 137.0, 136.2, 136.1, 135.6, 135.5, 135.4, 133.2, 133.2, 133.1, 129.2, 128.9, 128.7, 128.4, 128.3, 128.3, 128.1, 128.0, 127.9, 127.6, 107.2, 107.2, 97.8, 60.3, 60.3, 60.0, 57.0, 56.9, 56.6, 45.2, 42.2, 42.0, 42.0, 34.0, 33.9, 33.3, 3.2, 33.0, 30.0, 23.2, 23.2, 21.5, 21.4 ppm; IR (KBr) 1137, 1201, 1540, 1576, 1670, 2955 cm$^{-1}$; MS (electrospray) 517 (freebase M+H), 438 & 515 (freebase M–H).

EXAMPLES PART 6

Example 1

Chromatographic Separation

Diastereomeric secretagogue compounds are separated on a 8×15 cm Prochrom® column packed with a Kromsil® CHI-DMB chiral phase. The chromatographic eluent consisted of 12% to 15% 3A alcohol, 0.2% dimethylethylamine in heptane. One to two gram loadings of mixtures of diastereomers have been separated by this technique. The active isomer has been demonstrated to be the second eluting component. Isolation of the desired isomer is completed by evaporation of the solvent by using a roto evaporator.

Since this is a chiral phase, enantiomers of the individual diastereomers are also resolved to yield compounds which are enantiomerically pure.

The procedure for packing the Prochrom® column, separation of the diastereomeric secretagogue SAR candidates, and analysis of the purified compounds is provided as follows:

Materials

Chemicals:

Kromasil® CHI-I, 10 m CSP Bulk 3A alcohol, QA 041N

Heptane, QD440N

Dimethylethylamine, Aldrich

Equipment:

8 cm Prochrom® column

Prochrom® LC-80 pumping system, fraction collector

Chromatography:

Column Preparation: Slurry 500 grams of Kromasil® CHI bulk packing in 400 ml of propanol. Pack in 8×16 cm Prochrom® column. Equilibrate with eluent consisting 13% 3A alcohol, 0.2% dimethylethylamine in heptane at a flow rate of 250 ml/min. Detector setting is 260 nm to 270 nm for the 200 mg loading per run. Change wavelength to 280 nm for 1.0 gram loadings.

Sample preparation: Dissolve approximately 1.0 grams of secretagogue mixture in small amount of 3A alcohol and dilute with approximately 5 ml of eluent.

Chromatographic separation: The first isomer from each series elutes in range of 6 to 8 minutes. The second isomer elutes in range of 8 to 10 minutes. Shave the front and back of isomer 1 to eliminate other isomeric impurities.

Fraction work up: Strip fractions to dryness using roto vap.

Sample Analysis Conditions:

a. Operating Conditions

Column: 0.46×25 cm Kromasil® CHI

Eluent: 15% ethanol, 0.2% dimethylethylamine in heptane

Flow Rate: 1.0 ml/min

Temperature: ambient uv: 250 nm

Injection: as needed b. System Suitability

I) isomer 1 elutes in 5 to 6 minutes, isomer 2 elutes in 8 to 10 minutes c. Analysis Procedure I) calculate the diastereomeric excess of each isolated isomer.

Both diastereomerically and optically pure secretagogue compounds are produced by this process.

Example 2

Chiral Synthesis of Nitroimidazole (L-isomer)

Preparation 2A

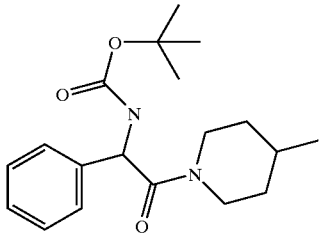

BOC-L-α-Phenylglycine (2.0 g, 9.12 mmol) was dissolved in 15 mL anhydrous THF and cooled to 0° C. DCC (1.97 g, 9.58 mmol) was added, followed by the addition of 4-methylpiperidine (1.08 mL, 9.12 mmol) and HOBt (1.29 g, 9.58 mmol). After stirring 30 min the ices bath was removed and stirring continued overnight at ambient temperature. The reaction was filtered, concentrated then diluted with EtOAc and washed with 10% aqueous sodium bicarbonate (1×50 mL), 0.1N HCl (1×50), and dried over sodium sulfate. Filtered, and concentrated to 3.2 g of a crude yellow oil. The oil was purified was radial chromatography eluting with 30:70 EtOAc:Hexanes. The appropriate fractions were concentrated to 2.5 g (83% yield) of a colorless foam. $^1$H-NMR (d, CDCl$_3$, 250 MHz, rotamers present) 0.60 (d, J=7.5 Hz, 1.5H), 0.77 (d, J=7.5 Hz, 1.5H), 1.00–1.50 (m, 5H), 1.25 (s, 9H), 2.45 (m, 1H), 2.80 (m, 1H), 3.62 (m, 1H), 4.43 (m, 1H), 5.43 (m, 1H), 6.02 (d, J=8 Hz, 1H), 7.10–7.30 (m, 5H); MS (ion spray) 333.5 (M+1); [α]$_D$=+95.9 (MeOH); Anal. Calc'd for C$_{19}$H$_{28}$N$_2$O$_3$: C, 68.65; H, 8.49; N, 8.43. Found: C, 69.04; H, 8.51; N, 8.91.

Preparation 2B

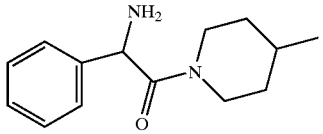

The Boc group was removed from the above compound (1.09 g, 3.28 mmol) by dissolving in 0.3 mL of methylene chloride and added 3 mL of trifluoroacetic acid. After stirring 1 h at room temperature the reaction was concentrated in vacuo (3×CH$_2$Cl$_2$). The compound was vacuum dried to 1.5 g (100%) of the ditrifluoroacetic acid salt. $^1$H-NMR (d, CDCl$_3$, 400 MHz, equal intensity rotamers present at room temperature) 0.01 (m, 0.5H), 0.70 (d, J=7.5 Hz, 1.5H), 0.83 (m, 0.5H), 0.88 (d, J=7.5 Hz, 1.5H), 1.00–1.60 (m, 4H), 2.55 (m, 1H), 2.90 (m, 1H), 3.52 (m, 1H), 4.35 (m, 1H), 5.42 (m, 1H), 7.32–7.43 (m, 5H), 8.18 (br s, 2H), 9.30 (br s, 2H); MS (ion spray) 233.1 (M+$^1$); [α]$_D$=+19.7 (1N HCl).

Preparation 2C

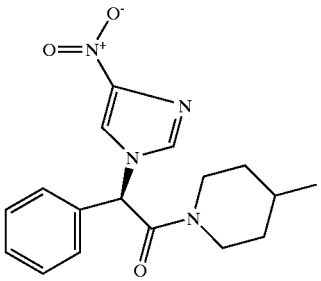

The above amine (1.5 g, 3.26 mmol) was dissolved in 10 mL methanol and 10 mL water and cooled to 0° C. Sodium bicarbonate (0.58 g, 6.85 mmol) was added and stirred 10 min followed by the addition of 1,4-dinitroimidazole. The solution quickly turned bright yellow and after stirring 30 min the ice bath was removed and stirring continued overnight at ambient temperature. The product was extracted into CH$_2$Cl$_2$, dried over sodium sulfate, filtered, and concentrated to 0.93 g of a crude white foam. A pure sample is obtained by crystallization from EtOAc (0.64 g, 60%). $^1$H-NMR (d, CDCl$_3$, 400 MHz, rotamers present) 0.05 (m, 0.5H), 0.59 (d, J=7.5 Hz, 1.5H), 0.72 (d, J=7.5 Hz, 1.5H), 0.79 (m, 0.5H), 0.93 (m, 0.5H), 1.14 (m, 0.5H), 1.23–1.56 (m, 3H), 2.44 (m, 1H), 2.82 (m, 1H), 3.36 (m, 1H), 4.37 (m, 1H), 5.88 (s, 0.5H), 5.90 (s, 0.5H), 7.02 (s, 1H), 7.10–7.30 (m, 5H), 7.52 (s, 1H); MS (ion spray) 329.3 (M+1); [α]$_D$=+177.6 (MeOH); 98% ee by chiral HPLC; Anal. Calc'd for C$_{17}$H$_{20}$N$_4$O$_3$: C, 62.18; H, 6.14; N, 17.06. Found: C, 62.25; H, 6.08; N, 17.09.

Example 3

Chiral Synthesis of Nitroimidazole D-Isomer

Preparation 3A

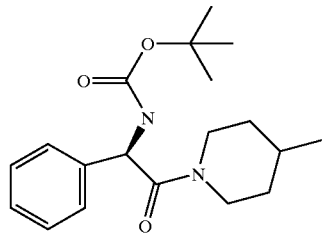

Boc-D-α-Phenylglycine (2.0 g, 9.12 mmol) was dissolved in 15 mL anhydrous THF and cooled to 0° C. DCC (1.97 g, 9.58 mmol) was added, followed by the addition of 4-methylpiperidine (1.08 mL, 9.12 mmol), and HOBt (1.29 g, 9.58 mmol). After stirring 30 min the ice bath was removed and stirring continued overnight at ambient temperature. The reaction was filtered, concentrated, then diluted with EtOAc and washed with 10% aqueous sodium bicarbonate (1×50 mL), 0.1N HCl (1×50 mL), and dried over sodium sulfate. Filtered, and concentrated to 3.1 g of a crude yellow oil. The oil was purified was radial chromatography eluting with 30:70 EtOAc:Hexanes. The appropriate fractions were concentrated to 2.2 g (73% yield) of a colorless foam. $^1$H-NMR (d, CDCl$_3$, 250 MHz, rotamers present) 0.60 (d, J=7.5 Hz, 1.5H), 0.77 (d, J=7.5 Hz, 1.5H), 1.00–1.50 (m, 5H), 1.25 (s, 9H), 2.45 (m, 1H), 2.80 (m, 1H), 3.62 (m, 1H), 4.43 (m, 1H), 5.43 (m, 1H), 6.02 (d, J=8 Hz, 1H), 7.10–7.30 (m, 5H); MS (ion spray) 333.5 (M+1); $[\alpha]_D$=−112.9 (MeOH) Anal. Calc'd for $C_{19}H_{28}N_2O_3$: C, 68.65; H, 8.49; N, 8.43. Found: C, 68.41; H, 8.11; N, 8.53.

Preparation 3B

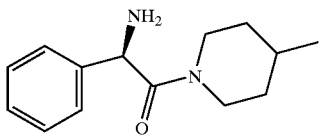

The Boc group was removed from the compound of Preparation 3A (1.0 g, 3.01 mmol) by dissolving in 2 mL of methylene chloride and added 2 mL of trifluoroacetic acid. After stirring 1 h at room temperature the reaction was concentrated in vacuo (3×CH$_2$Cl$_2$). The compound was vacuum dried to 1.4 g (100%) of the ditrifluoroacetic acid salt. $^1$H-NMR (d, CDCl$_3$, 400 MHz, equal intensity rotamers present at room temperature) 0.01 (m, 0.5H), 0.70 (d, J=7.5 Hz, 1.5H), 0.83 (m, 0.5H), 0.88 (d, J=7.5 Hz, 1.5H), 1.00–1.60 (m, 4H), 2.55 (m, 1H), 2.90 (m, 1H), 3.52 (m, 1H), 4.35 (m, 1H), 5.42 (m, 1H), 7.32–7.43 (m, 5H), 8.18 (br s, 2H), 9.30 (br s, 2H); MS (ion spray) 233.1 (M+1); $[\alpha]_D$=−38.1 (MeOH).

Preparation 3C

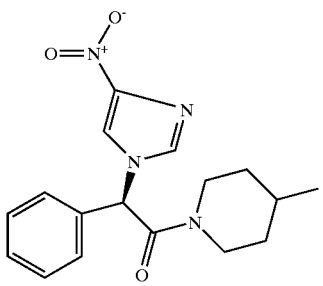

The amine from Preparation 3B (1.4 g, 3.04 mmol) was dissolved in 10 mL methanol and 10 mL water and cooled to 0° C. Sodium bicarbonate (0.51 g, 6.08 mmol) was added and stirred 10 min followed by the addition of 1,4-dinitroimidazole. The solution quickly turned bright yellow and after stirring 30 min the ice bath was removed and stirring continued overnight at ambient temperature. The product was extracted into CH$_2$Cl$_2$, dried over sodium sulfate, filtered, and concentrated to 0.93 g of a crude yellow foam. A pure sample is obtained by crystallization from EtOAc (0.60 g, 60%). $^1$H-NMR (d, CDCl$_3$, 400 MHz, rotamers present) 0.05 (m, 0.5H), 0.59 (d, J=7.5 Hz, 1.5H), 0.72 (d, J=7.5 Hz, 1.5H), 0.79 (m; 0.5H), 0.93 (m, 0.5H), 1.14 (m, 0.5H), 1.23–1.56 (m, 3H), 2.44 (m, 1H), 2.82 (m, 1H), 3.36 (m, 1H), 4.37 (m, 1H), 5.88 (s, 0.5H), 5.90 (s, 0.5H), 7.02 (s, 1H), 7.10–7.30 (m, 5H), 7.52 (s, 1H); MS (ion spray) 329.2 (M+1); $[\alpha]_D$=−175.7 (MeOH); 96% ee by chiral HPLC; Anal. Calc'd for $C_{17}H_{20}N_4O_3$: C, 62.18; H, 6.14; N, 17.06. Found: C, 62.93; H, 6.14; N, 17.21.

Example 4

Chiral Synthesis of Nitroimidazole (D-Isomer)

Preparation 4A

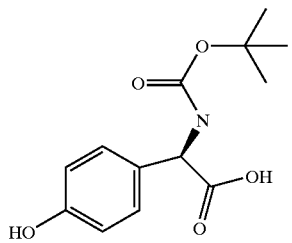

D-(p-hydroxyphenyl)glycine was Boc protected following the procedure of Salituro, JACS, 760 (1990).

Example 4B

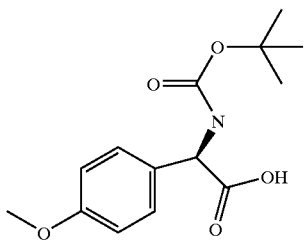

To a 0° C. solution of the phenol compound from Preparation 4A (3.0 g, 11.2 mmol) in 100 mL of DMF was added 1.03 g (60% dispersion, 25.8 mmol) NaH. The mixture was then sonicated at room temperature for 30 min and methyl iodide added (0.77 mL, 12.3 mmol). The reaction becomes near homogenous after an additional 30 min of sonication. An additional 0.2 mL of methyl iodide was added and the reaction stirred overnight at room temperature. The reaction was diluted with EtOAc and a few drops of water. The reaction was transferred to a separatory funnel and acidified with a 10% sodium bisulfate solution and brine. The organic layer was separated and dried with sodium sulfate to 3.4 g of a crude yellow oil. This oil was purified by radial chromatography eluting with 80/20/5 CH$_2$Cl$_2$/MeOH/NH$_4$OH. The appropriate fractions were taken up in EtOAc and washed with 10% sodium bisulfate/brine solution, dried over sodium sulfate, filtered and concentrated to 1.5 g (48%) of the desired ether. $^1$H-NMR (d, CDCl$_3$, 400 MHz, equal intensity rotamers present) 1.22 (s, 4.5H), 1.40 (s, 4.5H), 3.77 (s, 3H), 5.02 (d, J=5 Hz, 0.5H), 5.22 (d, J=5 Hz, 0.5H), 5.39 (d, J=5 Hz, 0.5H), 6.82 (m, 2H), 7.29 (m, 2H), 7.62 (m, 0.5H); MS (ion spray) 280.2 (M−1); $[\alpha]_D$=−134.1 (MeOH); Anal. Calc'd for $C_{14}H_{19}NO_5$: C, 59.78; H, 6.81; N, 4.98. Found: C, 60.07; H, 7.01; N, 4.99.

Preparation 4C

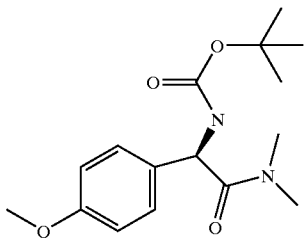

To a 0° C. solution of the acid from Preparation 4B (540 mg, 1.92 mmol) and dimethylamine hydrochloride (157 mg, 1.92 mmol) in 8 mL of anhydrous DMF was added diethylcyanophosphonate (DECP) 0.29 mL, 1.92 mmol) and triethylamine (0.27 mL, 1.92 mmol). After 30 min at 0° C. a second equivalent of dimethylamine hydrochloride, DECP, and triethylamine were added. After an additional 30 min the reaction was complete by TLC. The reaction was diluted with EtOAc, washed with 1:1 10% sodium bisulfate:brine, 1:1 10% sodium bicarbonate:brine, and brine. The organic layer was dried over sodium sulfate, filtered and concentrated to 0.90 g of a light yellow oil. This material was purified by radial chromatography eluting with 1:1 EtOAc:Hexanes. The appropriate fractions were vacuum dried to 0.50 g (85%) of a white solid. $^1$H-NMR (d, CDCl$_3$, 400 MHz) 1.40 (s, 9H), 2.85 (s, 3H), 2.95 (s, 3H), 3.79 (s, 3H), 5.50 (d, J=10 Hz, 1H), 5.96 (d, J=10 Hz, 1H), 6.83 (d, J=10 Hz, 2H), 7.29 (d, J=10 Hz, 2H); MS (ion spray) 309.3 (M+1); $[\alpha]_D$=−165.5 (MeOH).

Preparation 4D

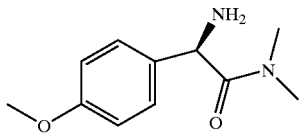

The Boc group was removed from the compound of Preparation 4C (450 mg, 1.46 mmol) by dissolving in 2 mL of methylene chloride and added 2 mL of trifluoroacetic acid. After stirring 90 min at room temperature the reaction was complete by TLC and HPLC and concentrated in vacuo (3×CH$_2$Cl$_2$). The compound was vacuum dried to 620 mg (97%) of the ditrifluoroacetic acid salt. This material was used without further characterization.

Preparation 4F

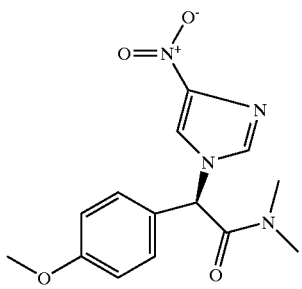

The amine from Preparation 4E (637 mg, 1.46 mmol) was dissolved in 10 mL methanol and 10 mL water and cooled to 0° C. Sodium bicarbonate (270 mg, 3.21 mmol) was added and stirred 10 min followed by the addition of 1,4-dinitroimidazole. The solution quickly turned bright yellow and after stirring 30 min the ice bath was removed and stirring continued 6 h. The product was extracted into CH$_2$Cl$_2$, washed with brine, dried over sodium sulfate, filtered, and concentrated to 450 mg of a crude yellow oil. The compound was purified by radial chromatography eluting with EtOAc. The appropriate fractions were dried to 410 mg (92%) of a light yellow solid. $^1$H-NMR (d, CDCl$_3$, 400 MHz) 2.88 (s, 3H), 3.01 (s, 3H), 3.80 (s, 3H), 6.01 (s, 1H), 6.94 (d, J=10 Hz, 2H), 7.29 (d, J=10 Hz, 2H), 7.37 (s, 1H), 7.68 (s, 1H); MS (ion spray) 305.2 (M+1); $[\alpha]_D$=−258.2 (MeOH); Anal. Calc'd for C$_{14}$H$_{16}$N$_4$O$_4$: C, 55.26; H, 5.30; N, 18.41. Found: C, 55.23; H, 5.27; N, 18.23.

Example 5

Alternate Chiral Synthesis of Nitroimidazole-D-isomer

Preparation 5A

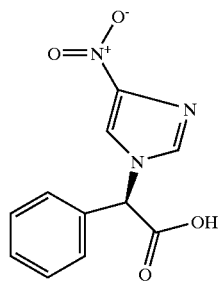

D-Phenylglycine (400 mg, 2.53 mmol) was suspended in 5 mL methanol and 5 mL water and cooled to 0° C. Sodium bicarbonate (400 mg, 5.06 mmol) was added and stirred 10 min followed by the addition of 1,4-dinitroimidazole. The solution quickly turned bright yellow and after stirring 30 min the ice bath was removed and stirring continued overnight at ambient temperature. The reaction was diluted with EtOAc and acidified with 0.2N HCl. The organic extract was washed with brine and dried over sodium sulfate. Filtered, and concentrated to 620 mg (99%) of a light yellow solid. $^1$H-NMR (d, DMSO, 400 MHz) 6.50 (s, 1H), 7.42 (m, 3H), 7.52 (m, 2H), 7.94 (s, 1H), 8.40 (s, 1H); MS (ion spray) 248.4 (M+1); $[\alpha]_D$=−146.2 (MeOH); Anal. Calc'd for C$_{11}$H$_9$N$_3$O$_4$·0.3H$_2$O: C, 52.30; H, 3.83; N, 16.63. Found: C, 52.17; H, 3.95; N, 16.79.

Preparation 5B

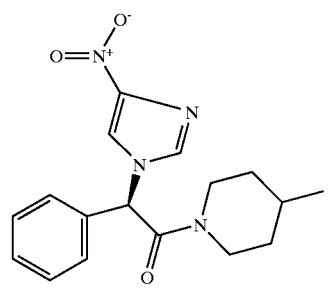

The acid from Preparation 5A (215 mg, 0.87 mmol) was dissolved in 10 mL anhydrous THF and cooled to 0° C.

Added 4-methylpiperidine (103 μL, 0.87 mmol) and diethylcyanophosphonate (DECP) (132 μL, 0.87 mmol). After 45 min a second equivalent of 4-methylpiperidine and DECP were added and stirring continued at 0° C. for an additional 45 min. Diluted the reaction with ethyl acetate (300 mL) and washed with aqueous 10% NaHSO$_4$/brine, 5% NaHCO$_3$/brine, brine (150 mL each) and dried over NaSO$_4$. Purified by radial chromatography eluting with EtOAc which gave 236 mg (83%) of the desired product as a yellow oil. An analytical sample was obtained by crystallization from EtOAc. $^1$H-NMR (d, DMSO, 400 MHz, rotamers present) −0.05 (m, 0.5H), 0.68 (d, J=7.5 Hz, 1.5H), 0.80 (m, 0.5H), 0.83 (d, J=7.5 Hz, 1.5H), 0.97 (m, 0.5H), 1.18 (m, 0.5H), 1.40–1.60 (m, 3H), 2.60 (m, 1H), 2.98 (m, 1H), 3.59 (m, 1H), 4.34 (m, 1H), 6.85 (s, 0.5H), 6.92 (s, 0.5H), 7.37–7.50 (m, 5H), 7.78 (s, 1H), 8.12 (s, 0.5H), 8.15 (s, 0.5H); MS (ion spray) 329.2 (M+1); [α]$_D$=−204.7 (MeOH); Anal. Calc'd for C$_{17}$H$_{20}$N$_4$O$_3$: C, 62.18; H, 6.14; N, 17.06. Found: C, 62.47; H, 6.21; N, 17.07.

EXAMPLES PART 7

Melting points were determined with a Thomas-Hoover capillary melting point apparatus and are uncorrected. Nuclear magnetic resonance studies were performed on a Bruker ARX 500 spectrometer. Merck silica gel 60 F254 plates (0.25 mm) were used for thin layer chromatography. Merck silica gel 60 230–400 mesh was used for flash chromatography. Biotage KP-SIL, 60A cartridges were used for Biotage Flash 40 purifications. HPLC conditions: Eluent: 0.1% trifluoroacetic acid in water:acetonitrile at 2 mL/min. Column: Zorbax RX-C8. Detection: 230 nm.

Preparation 1

Ethyl 2-(2-Naphthyl)acetate

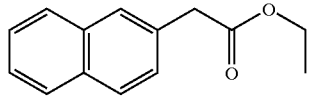

A steady stream of anhydrous hydrochloric acid was bubbled subsurface into a solution of 2-naphthylacetic acid (251.38 grams, 1.35 mmol) dissolved in ethanol (1760 mL) over a period of 10 minutes. The resulting solution was stirred at ambient temperature until complete as determined by hplc (2 hours). The reaction mixture was concentrated to dryness. The resulting oil was dissolved in ethyl acetate (200 mL) and filtered through silica gel (300 grams) eluting the product with ethyl acetate (1400 mL). The filtrate was concentrated to give 286.33 grams (99%) of ethyl 2-(2-naphthyl)acetate as a colorless oil. MS (FIA) m/z 215.3 [(M+H)$^+$]. $^1$H nmr (DMSO-d$_6$): δ 1.15–1.24 (t, 3H), 3.81–3.86 (d, 2H), 4.07–4.15 (q, 2H), 7.41–7.55 (m, 3H), 7.80–7.92 (m, 4H).

Preparation 2

Ethyl 2-Bromo-2-(2-naphthyl)acetate

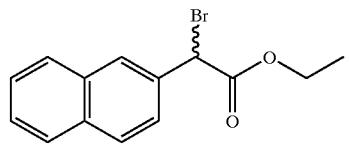

A solution consisting of ethyl 2-(2-naphthyl)acetate 1.07 grams, 5.0 mmol), N-bromosuccinimide (0.89 grams, 5.0 mmol), benzoyl peroxide (0.05 grams), and carbon tetrachloride (50 mL) was heated at reflux until complete as determined by hplc (3 hours). The reaction was cooled to ambient temperature, washed with water (2×25 mL), dried using sodium sulfate, and filtered. The filtrate was concentrated to dryness. The residue was purified using a Biotage Flash 40M system eluting with hexane:ethyl acetate (49:1) to give 1.20 grams (82%) of ethyl 2-bromo-2-(2-naphthyl) acetate, mp 80–82° C. MS (FIA) m/z 293.0 [(M+H)$^+$]. Anal. calcd. for C$_{14}$H$_{13}$O$_2$Br: C: 57.36; H: 4.47. Found: C: 57.62; H: 4.54. $^1$H nmr (CDCl$_3$): δ 1.27–1.33 (t, 3H), 4.18–4.36 (m, 2H), 5.56 (s, 1H), 7.52–7.55 (m, 2H), 7.71–7.76 (m, 1H), 7.82–7.92 (m, 3H), 7.97 (s, 1H).

Preparation 3

Ethyl 2-(2-Naphthyl)-2-(4-nitroimidazolyl)acetate

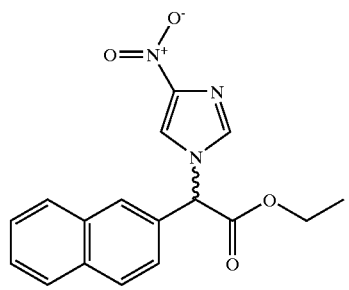

A yellow slurry consisting of ethyl 2-bromo-2-(2-naphthyl) acetate (384.04 grams, 1.31 mmol), 4-nitroimidazole (148.13 grams, 1.31 mmol), potassium carbonate (362.11 grams, 2.62 mmol), and dimethyl formamide (2500 mL) was stirred at ambient temperature until complete as determined by hplc (16 hours). The reaction mixture was diluted with water (2000 mL) and extracted with ethyl acetate (4×500 mL). The organic extracts were combined and washed with saturated sodium bicarbonate solution (2×500 mL), 10% citric acid solution (2×500 mL), saturated sodium chloride solution (2×500 mL), dried using sodium sulfate, and evaporated. A portion (50 grams) of the crude product was purified by column chromatography on silica gel eluting with dichloromethane:heptane (16:3) gradient to dichloromethane:heptane:methanol (16:3:0.2) giving 30.99 grams of ethyl 2-(2-naphthyl)-2-(4-nitroimidazolyl)acetate which was 90% pure by hplc. A 1 gram sample of the product was purified a second time using a Biotage Flash 40S system eluting with dichloromethane:heptane:methanol (16.9:3:0.1) to give 0.90 grams (46%) of ethyl 2-(2-naphthyl)-2-(4-nitroimidazolyl)acetate as a tan oil. MS (FIA) m/z 326.4 [(M+H)$^+$]. $^1$H nmr (CDCl$_3$): δ 1.25–1.31 (t, 3H), 4.28–4.39 (m, 2H), 6.16 (s, 1H), 7.36–7.44 (dd, 1H), 7.54–7.62 (m, 3H), 7.84–7.90 (m, 3H), 7.90–7.95 (m, 2H).

Preparation 3

Ethyl 2-[4-((2R)-2-{2-[(Tert-butoxy)carbonylamino]-2-methyl propanoylamino}-3-indol-3-ylpropanoylamino)imidazolyl]-2-(2-naphthyl)acetate

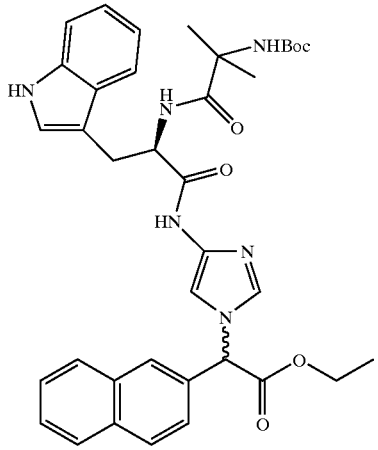

A mixture of ethyl 2-(2-naphthyl)-2-(4-nitroimidazolyl) acetate (2.04 grams, 6.27 mmol), tetrahydrofuran (20 mL), and 10% palladium on carbon (2.04 gram) was hydrogenated at ambient temperature and pressure until complete as determined by hplc (20 hours). The catalyst was removed by filtration and rinsed with tetrahydrofuran (10 mL). The filtrate was added to a slurry consisting of 1-[3-(dimethyl amino)propyl-3-ethylcarbodiimide hydrochloride (1.20 grams, 6.27 mmol), tetrahydrofuran (10 mL), and (2R)-2-{2-[(tert-butoxy)carbonylamino]-2-methylpropanoylamino}-3-indol-3-ylpropanoic acid (2.44 grams, 6.27 mmol) and stirred 16 hours at ambient temperature. The reaction mixture was partitioned between water (150 mL) and ethyl acetate (3×50 mL). The organic extracts were combined, washed with saturated sodium chloride solution, dried using sodium sulfate, and evaporated. The resulting crude oil was purified by column chromatography on silica gel with hexane:ethyl acetate:methanol (10:10:1) as an eluent giving 1.72 grams (41%) of ethyl 2-[4-((2R)-2-{2-[(tert-butoxy)carbonylamino]-2-methylpropanoylamino}-3-indol-3-ylpropanoyl amino)imidazolyl]-2-(2-naphthyl)acetate. A 0.2 gram sample was further purified using preparative reverse phase hplc to give 0.16 grams of ethyl 2-[4-((2R)-2-{2-[(tert-butoxy)carbonylamino]-2-methylpropanoylamino}-3-indol-3-ylpropanoyl amino)imidazolyl]-2-(2-naphthyl)acetate for analytical study. MS (FIA) m/z 667.4 [(M+H)$^+$]. Anal. calcd. exact mass for $C_{37}H_{43}N_6O_6$ [(M+H)$^+$]=667.3244. Exact mass found by mass spectrometry: $C_{37}H_{43}N_6O_6$ [(M+H)$^+$]=667.3254. $^1$H nmr (CDCl$_3$): 1.25–1.42 (m, 19H), 3.24–3.33 (m, 2H), 4.28–4.33 (m, 2H), 4.98–5.01 (m, 1H), 5.94 (s, 1H), 6.85–7.01 (m, 3H), 7.18–7.21 (m, 2H), 7.35–7.39 (m, 2H), 7.49–7.58 (m, 4H), 7.78–7.84 (m, 4H), 8.69 (s, 1H), 10.65 (s, broad, 1H).

Preparation 4

Ethyl 2-[4-((2R)-2-{2-[(Tert-butoxy)carbonylamino]-2-methyl propanoylamino}-3-indol-3-ylpropanoylamino)imidazolyl]-2-phenylacetate

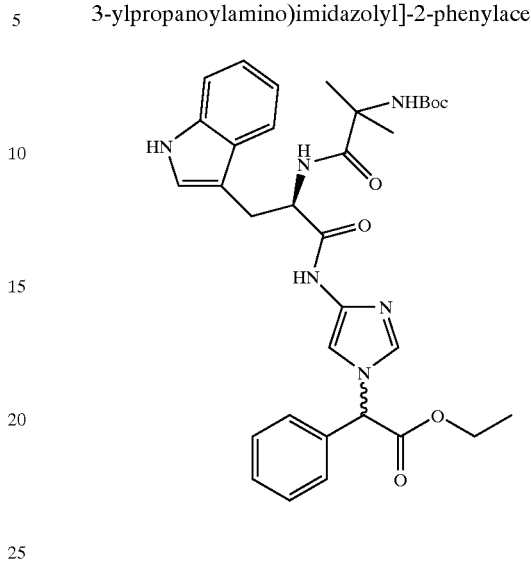

This compound was obtained from the reduction of ethyl 2-(4-nitroimidazolyl)-2-phenylacetate and subsequent reaction with (2R)-{2-(2-[(tert-butoxy) carbonylamino]-2-methyl propanoylamino}-3-indole-3-ylpropanoic acid as a yellow foam in 73% yield after purification by flash chromatography using dichloromethane:methanol (19:1) as the eluent. MS (FIA) m/z 617.5 [(M+H)$^+$]. $^1$H nmr (CDCl$_3$): δ 1.19–1.32 (m, 18H), 3.10–3.12 (m, 1H), 3.16–3.17 (m, 1H), 3.32 (s, 1H), 4.22–4.27 (m, 2H), 4.69 (s, broad, 1H), 6.44 (s, 1H), 6.85–6.91 (m, 2H), 7.00 (t, 1H), 7.07–7.08 (m, 1H), 7.38–7.40 (m, 1H), 7.42–7.45 (m, 6H), 7.55–7.56 (m, 2H), 10.16 (s, broad, 1H), 10.75 (s, 1H).

Preparation 5

Ethyl 2-[4-((2R)-2-{2-[(Tert-butoxy)carbonylamino]-2-methylpropanoylamino}-3-cyclohexylpropanoylamino) imidazolyl]-2-phenylacetate

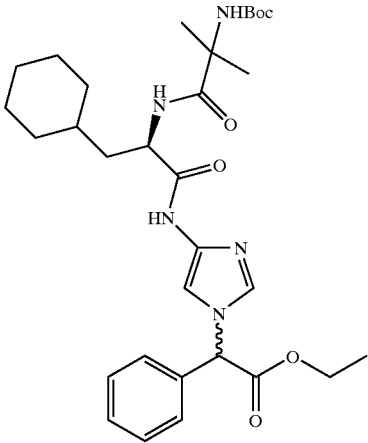

This compound was obtained from the reduction of ethyl 2-(4-nitroimidazolyl)-2-phenylacetate and subsequent reaction with (2R)-2-{2-[(tert-butoxy) carbonylamino]-2-methyl propanoylamino}-3-cyclohexylpropanoic acid as a yellow foam in 45% yield after after purification by flash chromatography using dichloromethane:methanol (29:1) as the eluent. $^1$H nmr (CDCl$_3$): δ 0.77–0.99 (m, 4H), 1.00–1.21 (m, 5H), 1.22–1.27 (m, 7H), 1.33–1.45 (m, 8H), 1.48–1.74 (m, 6H), 4.19–4.30 (m, 2H), 4.70–4.75 (m, 1H), 5.10 (s, broad, 1H), 5.84–5.86 (t, 1H), 6.92 (s, broad, 1H), 7.25–7.41 (m, 7H), 7.51 (m, 1H), 10.5 (s, broad, 1H).

Preparation 6

Ethyl 2-[4-((2R)-2-{2-[(Tert-butoxy)carbonylamino]-2-methylpropanoylamino}pentanoylamino) imidazolyl]-2-phenylacetate

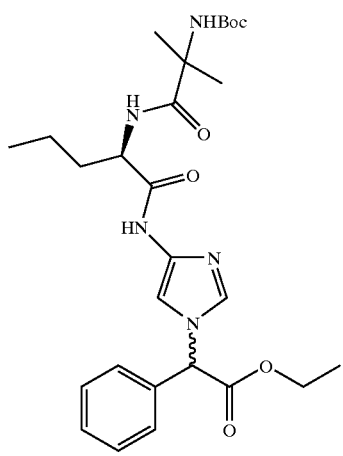

This compound was obtained from the reduction of ethyl 2-(4-nitroimidazolyl)-2-phenylacetate and subsequent reaction with (2R)-2-{2-[(tert-butoxy)carbonylamino]-2-methyl propanoylamino}pentanoic acid as a yellow foam in 61% yield after purification using preparative reverse phase hplc. MS (FD+) m/z 529 (M$^+$). $^1$H nmr (CDCl$_3$): δ 0.82–0.84 (m, 3H), 1.25–1.46 (m, 20H), 1.60–1.75 (m, 1H), 1.77–1.83 (m, 1H), 4.24–4.32 (m, 2H), 4.76–4.78 (m, 1H), 5.25 (s, broad, 1H), 5.93–5.96 (m, 1H), 7.15–7.30 (m, 1H), 7.36–7.39 (m, 5H), 7.48–7.49 (m, 1H), 7.61–7.64 (d, 1H), 11.10–11.20 (m, 1H).

Preparation 7
Ethyl 2-[4-((2R)-2-{2-[(Tert-butoxy)carbonylamino]-2-methylpropanoylamino}hexanoylamino)imidazolyl]-2-phenylacetate

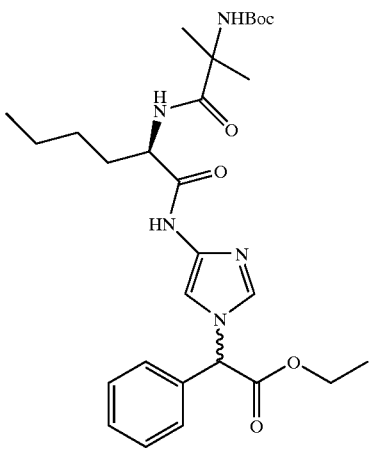

This compound was obtained from the reduction of ethyl 2-(4-nitroimidazolyl)-2-phenylacetate and subsequent reaction with (2R)-2-{2-[(tert-butoxy) carbonylamino]-2-methyl propanoylamino}hexanoic acid as a yellow foam in 74% yield after purification by flash chromatography using dichloromethane:methanol (19:1) as the eluent. $^1$H nmr (CDCl$_3$): δ 0.87–0.88 (d, 3H), 1.28–1.32 (m, 7H), 1.44–1.46 (m, 8H), 1.51 (s, 6H), 1.66–1.68 (m, 3H), 1.95 (s, broad, 1H), 4.28–4.34 (m, 2H), 4.60–4.62 (m, 1H), 5.05 (s, broad, 1H), 5.85 (s, 1H), 6.90–7.00 (m, 1H), 7.36–7.46 (m, 6H), 9.65 (s, broad, 1H).

Preparation 8
Ethyl 2-[4-((2R)-2-{2-[(Tert-butoxy)carbonylamino]-2-methylpropanoylamino}-3-(3-thienyl)propanoylamino) imidazolyl]-2-phenylacetate

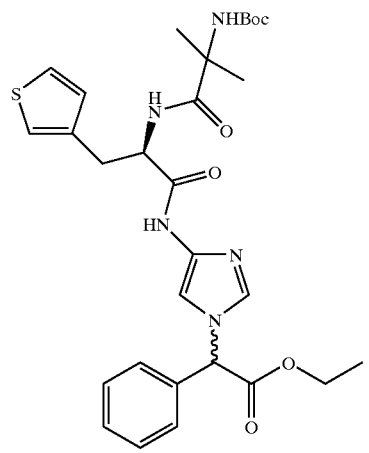

This compound was obtained from the reduction of ethyl 2-(4-nitroimidazolyl)-2-phenylacetate and subsequent reaction with (2R)-2-{2-[(tert-butoxy)carbonylamino]-2-methyl propanoylamino}-3-(3-thienyl)propanoic acid as a yellow foam in 53% yield after purification using preparative reverse phase hplc. MS (FD+) m/z 583 (M+). Anal. calcd. for C29H37N5O6·½H2O: C: 58.77; H: 6.46; N: 11.82. Found: C: 58.83; H: 6.03; N: 11.83. $^1$H nmr (CDCl$_3$): δ 1.20–1.23 (m, 3H), 1.33 (s, 9H), 1.40 (s, 6H), 3.29–3.30 (d, 2H), 4.18–4.27 (m, 2H), 5.04 (s, broad, 1H), 5.40 (s, broad, 1H), 5.94 (s, broad, 1H), 6.72–6.76 (m, 2H), 6.96–6.98 (t, 1H), 7.34 (s, 5H), 7.48 (s, 2H), 7.54–7.62 (m, 1H), 11.38 (m, 1H).

Preparation 9

Ethyl 2-[4-((2R)-3-Benzo[b]thiophen-3-yl-2-{2-[(tert-butoxy) carbonylamino]-2-methylpropanoylamino}propanoylamino) imidazolyl]-2-phenylacetate

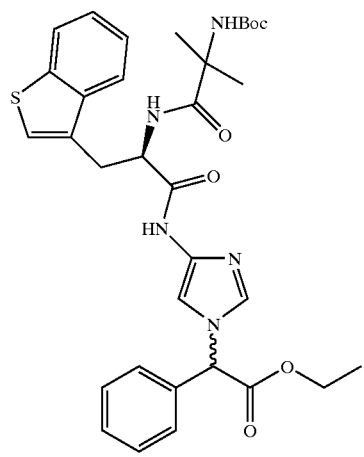

This compound was obtained from the reduction of ethyl 2-(4-nitroimidazolyl)-2-phenylacetate and subsequent reaction with (2R)-3-benzo[b]thiophen-3-yl-2-{2-[(tert-butoxy) carbonylamino]-2-methylpropanoylamino}propanoic acid as a yellow foam in 82% yield. $^1$H nmr (CDCl$_3$): δ 1.26–1.46 (m, 18H), 3.34–3.35 (m, 1H), 3.55–3.56 (m, 1H), 4.26–4.33 (m, 2H), 5.15 (s, broad, 2H), 5.82–5.84 (t, 1H), 7.20–7.47 (m, 10H), 7.60–7.65 (m 0.5H), 7.72–7.73 (m, 1H), 8.11–8.12 (m, 0.5H), 11.10 (m, broad, 1H). $^{13}$C nmr (CDCl$_3$): δ 14.46, 14.60, 19.34, 21.42, 25.69, 28.62, 36.64, 53.29, 54.39, 57.01, 60.77, 62.67, 64.05, 108.00, 122.26, 124.23, 124.34, 124.51, 125.58, 125.60, 125.87, 126.37, 127.92, 128.18, 128.24, 128.28, 128.35, 128.94, 129.58, 129.64, 129.68, 134.11, 134.53, 137.61, 140.55, 168.81, 168.86, 171.51, 174.81.

Preparation 10

2-[4-((2R)-2-{2-[(Tert-butoxy)carbonylamino]-2-methylpropanoylamino}-3-indol-3-ylpropanoylamino) imidazolyl]-2-(2-naphthyl)acetic Acid

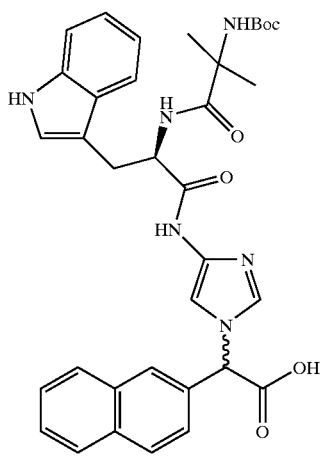

A solution consisting of ethyl 2-[4-((2R)-2-{2-[(tert-butoxy)carbonylamino]-2-methylpropanoylamino}-3-indol-3-ylpropanoylamino)imidazolyl]-2-(2-naphthyl)acetate (1.52 grams, 2.28 mmol), lithium hydroxide (0.11 grams, 4.56 mmol), dioxane (10 mL), and water (10 mL) was stirred at ambient temperature until complete as determined by hplc (30 minutes). The reaction mixture was concentrated to dryness and the residue was dissolved in water (20 mL). The aqueous solution was adjusted to a pH of 3 using a 10% sodium bisulfate solution and extracted with ethyl acetate (3×25 mL). The organic layers were combined, dried using sodium sulfate, filtered, and concentrated to give 1.34 grams (92%) of 2-[4-((2R)-2-{2-[(tert-butoxy)carbonylamino]-2-methyl propanoylamino}-3-indol-3-ylpropanoylamino) imidazolyl]-2-(2-naphthyl)acetic acid.

Preparation 11

2-[4-(2R)-2-{2-[(Tert-butoxy)carbonylamino]-2-methyl propanoylamino}-3-cyclohexylpropanoylamino)imidazolyl]-2-phenylacetic Acid

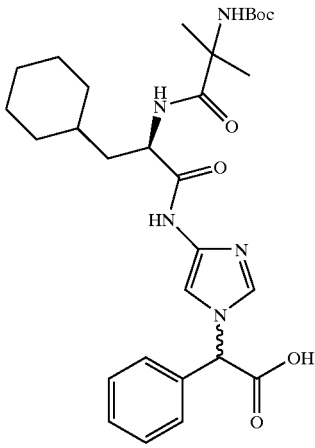

This compound was obtained from the hydrolysis of ethyl 2-[4-((2R)-2-{2-[(tert-butoxy) carbonylamino]-2-methyl propanoylamino}-3-cyclohexylpropanoylamino)imidazolyl]-2-phenylacetate as a white powder in 69% yield. $^1$H nmr (DMSO-d$_6$): δ 0.64–0.92 (m, 3H), 0.93–1.15 (m, 3H), 1.16–1.41 (m, 7H), 1.42–1.73 (m, 4H), 4.36 (s, broad, 1H), 6.08 (s, 1H), 6.98 (s, 1H), 7.15 (s, 1H), 7.31 (s, 5H), 7.49 (s, 2H), 10.0 (d, broad, 1H).

Preparation 12

2-[4-((2R)-2-{2-[(Tert-butoxy)carbonylamino]-2-methyl propanoylamino}-3-(2-naphthyl)propanoylamino)imidazolyl]-2-phenylacetic Acid

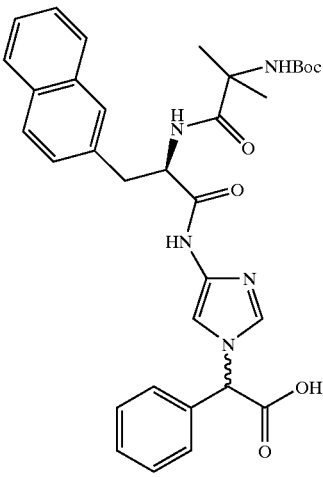

This compound was obtained from the reduction of ethyl 2-(4-nitroimidazolyl)-2-phenylacetate and subsequent reaction with (2R)-2-{2-[(tert-butoxy)carbonylamino]-2-methyl propanoylamino}-3-(2-naphthyl)propanoic acid followed by hydrolysis to give a white solid in 76% yield. $^1$H nmr (DMSO-d$_6$): δ 1.02–1.13 (t, 7H), 1.27 (s, 8H), 3.24 (m, 3H), 3.50 (m, 1H), 4.58–4.78 (m, 1H), 6.24 (s, 1H), 7.00 (s, broad, 1H), 7.13–7.56 (m, 9H), 7.73 (d, 1.5H), 7.84 (d, 1.5H), 8.16 (m, 1H), 9.98 (s, broad, 0.5H), 10.11 (s, broad, 0.5H), 13.51 (s, broad, 1H).

Preparation 13

N-[(1R)-2-Indol-3-yl-1-(N-{1-[2-(4-methylpiperidinyl)-1-(2-naphthyl)-2-oxoethyl]imidazol-4-yl}carbamoyl)ethyl]-2-[(tert-butoxy)carbonylamino]-2-methylpropanamide

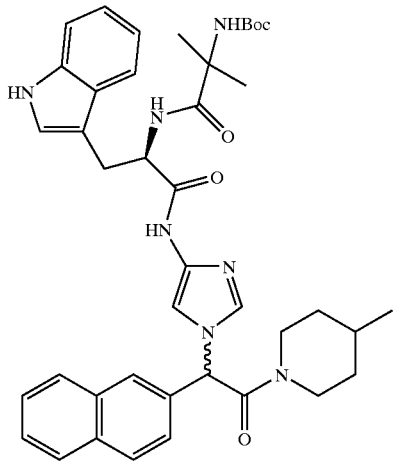

A solution consisting of 2-[4-((2R)-2-{2-[(tert-butoxy)carbonylamino]-2-methylpropanoylamino}-3-indol-3-yl propanoylamino)imidazolyl]-2-(2-naphthyl)acetic acid (0.55 grams, 0.861 mmol), 4-methylpiperidine (0.085 grams, 0.861 mmol), 1,3-dicyclohexylcarbodiimide (0.195 grams, 0.947 mmol), 1-hydroxybenzotriazole hydrate (0.116 grams, 0.861 mmol) and dimethyl formamide (5 mL) was stirred at ambient temperature until complete as determined by hplc (7 hours). The reaction mixture was diluted with water (40 mL) and extracted with ethyl acetate (4×25 mL). The organic extracts were combined, washed with saturated sodium chloride solution (2×35 mL), dried using sodium sulfate, and concentrated to an oil. The crude product was purified using preparative reverse phase hplc to give 0.32 grams (52%) of N-[(1R)-2-indol-3-yl-1-(N-{1-[2-(4-methyl piperidyl)-1-(2-naphthyl)-2-oxoethyl]imidazol-4-yl}carbamoyl)ethyl]-2-[(tert-butoxy)carbonylamino]-2-methylpropanamide. $^1$H nmr (CDCl$_3$): 0.76–0.77 (d, 2H), 0.91–0.95 (m, 2H), 1.23–1.36 (m, 18H), 1.54 (m, 1H), 1.67 (m, 1H), 2.70–2.72 (m, 2H), 3.25–3.29 (m, 2H), 3.68 (m, 1H), 4.55–4.70 (m, 1H), 4.98 (m, 1H), 6.24 (m, 1H), 6.81–6.83 (d, 1H), 6.92 (m, 1H), 7.00–7.01 (m, 1H), 7.18–7.28 (m, 3H), 7.37–7.55 (m, 5H), 7.76–7.83 (m, 4H), 8.80 (s, broad; 1H), 10.38 (s, broad, 1H). $^{13}$C nmr (CDCl$_3$): δ 14.60, 19.32, 19.47, 21.41, 21.83, 21.90, 25.39, 25.55, 26.04, 28.56, 28.63, 28.84, 31.05, 31.16, 31.21, 33.98, 34.08, 34.29, 34.69, 43.42, 46.28, 46.52, 49.38, 54.55, 56.99, 60.77, 62.31, 69.97, 71.02, 108.80, 110.24, 111.79, 119.02, 119.36, 121.86, 124.10, 125.99, 127.12, 127.36, 127.97, 128.08, 128.10, 128.16, 128.33, 128.63, 128.71, 129.77, 132.26, 133.63, 133.75, 134.02, 136.58, 137.29, 155.16, 157.65, 166.07, 166.18, 166.22, 166.34, 169.40, 171.52, 175.12.

Preparation 14

N-[(1R)-2-Indol-3-yl-1-(N-{1-[2-(4-methylpiperidyl)-2-oxo-1-phenylethyl]imidazol-4-yl}carbamoyl)ethyl]-2-[(tert-butoxy)carbonylamino]-2-methylpropanamide

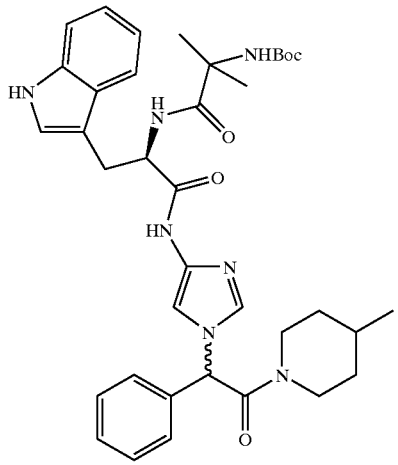

This compound was obtained from the hydrolysis of ethyl 2-[4-((2R)-2-{2-[(tert-butoxy) carbonylamino]-2-methyl propanoylamino}-3-indol-3-ylpropanoylamino)imidazolyl]-2-phenylacetate and subsequent reaction with 4-methyl piperidine in 84% yield after Biotage Flash 40M purification using dichloromethane:methanol (24:1) as the eluent. MS (FIA) m/z 670.5 [(M+H)⁺]. ¹H nmr (CDCl₃) δ 0.74–0.75 (d, 2H), 0.89–0.90 (d, 2H), 1.17–1.32 (m, 18H), 1.53–1.63 (m, 3H), 2.66–2.70 (m, 1H), 3.05 (t, 1H), 3.15–3.20 (m, 1H), 3.69–3.83 (m, 1H), 4.36–4.49 (m, 1H), 4.67 (s, broad, 1H), 6.90–6.93 (m, 2H), 7.01–7.04 (m, 2H), 7.11 (s, 1H), 7.26–7.32 (m, 2H), 7.40–7.54 (m, 5H), 7.67 (s, broad, 1H), 8.16 (m, broad, 1H), 10.49 (s, broad, 1H), 10.84 (s, 1H).

Preparation 15

N-((1R)-2-Indol-3-yl-1-{N-[1-(2-oxo-1-phenyl-2-pyrrolidinylethyl)imidazol-4-yl]carbamoyl}ethyl)-2-[(tert-butoxy)carbonylamino]-2-methylpropanamide

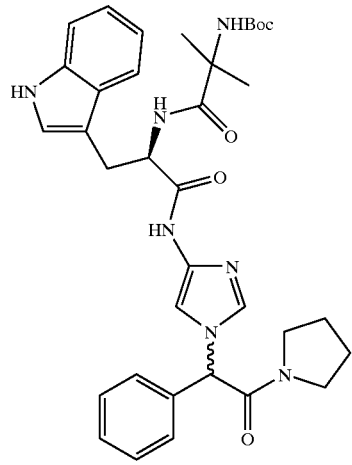

This compound was obtained from the hydrolysis of ethyl 2-[4-((2R)-2-{2-[(tert-butoxy) carbonylamino]-2-methyl propanoylamino}-3-indol-3-ylpropanoylamino)imidazolyl]-2-phenylacetate and subsequent reaction with pyrrolidine in 80% yield after purification by flash chromatography using dichloromethane:methanol (19:1) as the eluent. ¹H nmr (CDCl₃): δ 1.10–1.40 (m, 15H), 1.67–1.92 (m, 3H), 2.92–3.60 (m, 5H), 4.90 (s, broad, 1H), 5.33 (s, broad, 1H), 5.85 (d, 1H), 6.80–7.05 (m, 3H), 7.13–7.39 (m, 10H), 7.44–7.80 (m, 2H), 8.96 (s, broad, 1H), 10.20 (s, broad, 1H), ¹³C nmr (CDCl₃): δ 14.25, 21.11, 24.02, 25.63, 26.08, 28.24, 33.87, 46.39, 46.64, 54.28, 56.67, 60.46, 63.07, 63.09, 108.33, 109.73, 110.69, 111.47, 118.36, 118.56, 119.05, 121.57, 123.77, 125.01, 126.42, 127.60, 128.51, 129.38, 133.14, 133.85, 136.23, 136.45, 136.49, 165.7.9, 165.85, 169.17, 174.87.

Preparation 16

N-((1R)-2-Cyclohexyl-1-{N-[1-(2-oxo-1-phenyl-2-pyrrolidinylethyl)imidazol-4-yl]carbamoyl}ethyl)-2-[(tert-butoxy)carbonylamino]-2-methylpropanamide

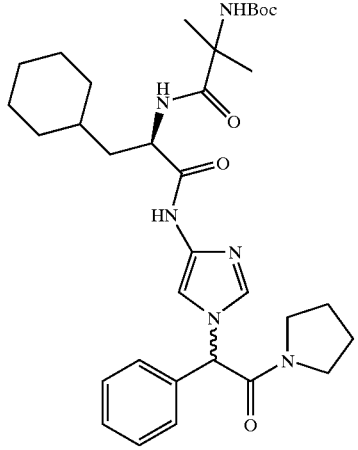

This compound was obtained from the reaction of 2-[4-((2R)-2-{2-[(tert-butoxy) carbonylamino]-2-methylpropanoylamino}-3-cyclohexylpropanoylamino)imidazolyl]-2-phenylacetic acid and pyrrolidine in 99% yield after purification by flash chromatography using dichloromethane:methanol (19:1) as the eluent. ¹H nmr (CDCl₃): δ 0.71–1.00 (m, 2H), 1.00–1.16 (m, 2H), 1.17–2.18 (m, 28H), 3.07–3.20 (s, broad, 1H), 3.38–3.64 (m, 3H), 4.62–4.77 (m, 1H), 5.91 (t, 1H), 7.38 (m, 7H), 9.93 (s, broad, 1H), 10.60 (s, broad, 1H).

Preparation 17

Methyl 1-{2-[4-((2R)-2-{2-[(Tert-butoxy)carbonylamino]-2-methylpropanoylamino}-3-cyclohexylpropanoylamino) imidazolyl]-2-phenylacetyl}(2S)pyrrolidine-2-carboxylate

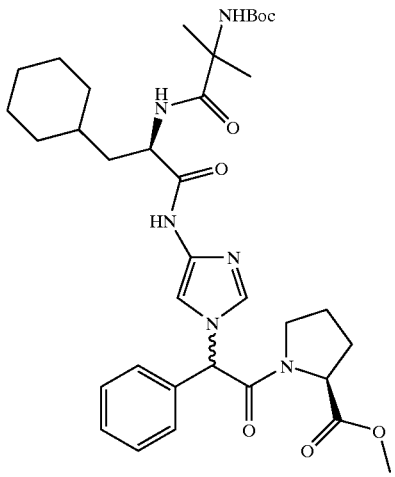

This compound was obtained from the reaction of 2-[4-((2R)-2-{2-[(tert-butoxy)carbonylamino]-2-methylpropanoylamino}-3-cyclohexylpropanoylamino) imidazolyl]-2-phenylacetic acid and L-proline methyl ester in 88% yield after purification by flash chromatography using dichloromethane:methanol (19:1) as the eluent. $^1$H nmr (CDCl$_3$): δ 0.75–0.98 (m, 4H), 0.98–1.21 (m, 4H), 1.21–1.50 (m, 12H), 1.50–1.80 (m, 5H), 1.80–2.07 (m, 3H), 2.07–2.28 (m, 1H), 3.19–3.36 (m, 1H), 3.37–3.72 (m, 2H), 3.72 (s, 3H), 4.03–4.61 (m, 1H), 4.61–4.75 (m, 1H), 5.11 (s, broad, 1H), 5.92–6.00 (m, 1H), 7.00 (s, broad, 1H), 7.21–7.49 (m, 7H), 8.00 (s, 1H), 9.60 (s, broad, 1H).

Preparation 18

(2R)-2-{2-[(Tert-butoxy)carbonylamino]-2-methylpropanoyl amino}-N-[1-(2-oxo-1-phenyl-2-pyrrolidinylethyl)imidazol-4-yl]pentanamide

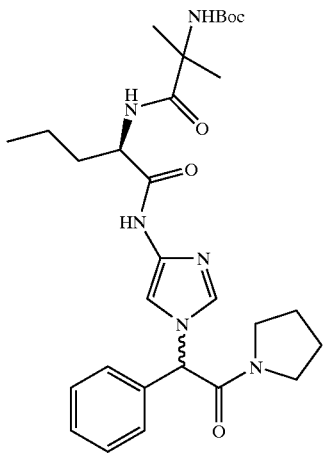

This compound was obtained from the hydrolysis of ethyl 2-[4-((2R)-2-(2-[(tert-butoxy)carbonylamino]-2-methyl propanoylamino)pentanoylamino)imidazolyl]-2-phenylacetate and subsequent reaction with pyrrolidine in 87% yield after purification by preparative reverse phase hplc. $^1$H nmr (CDCl$_3$): δ 0.72–0.75 (m, 3H), 1.18–1.41 (m, 17H), 1.75–1.79 (m, 4H), 1.80–1.92 (m, 1H), 3.00 (s, broad, 1H), 3.09–3.11 (m, 1H), 3.44–3.52 (m, 3H), 4.74 (m, 1H), 5.45 (s, broad, 1H), 6.09–6.10 (d, 1H), 7.28–7.52 (m, 8H), 10.98–11.07 (m, 1H). $^{13}$C nmr (CDCl$_3$): δ 14.14, 14.54, 18.95, 21.36, 24.35, 24.88, 26.43, 26.49, 26.54, 28.65, 35.62, 35.68, 46.72, 46.86, 53.55, 56.85, 60.70, 63.31, 108.46, 128.86, 129.46, 129.59, 133.70, 134.69, 134.74, 137.31, 166.20, 166.26, 170.06, 171.46, 175.02.

Preparation 19

(2R)-2-{2-[(Tert-butoxy)carbonylamino]-2-methylpropanoyl amino)}-N-{1-[2-(4-methylpiperidyl)-2-oxo-1-phenylethyl]imidazol-4-yl}pentanamide

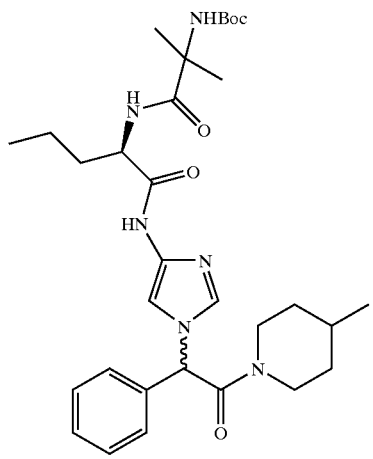

This compound was obtained from the hydrolysis of ethyl 2-[4-((2R)-2-{2-[(tert-butoxy)carbonylamino]-2-methyl propanoylamino}pentanoylamino)imidazolyl]-2-phenylacetate and subsequent reaction with 4-methylpiperidine in 72% yield after purification by preparative reverse phase hplc. $^1$H nmr (CDCl$_3$): δ 0.30–0.40 (m, 0.5H), 0.77–0.80 (m, 4H), 0.91–0.92 (d, 1H), 1.05–1.20 (m, 0.5H), 1.23–1.56 (m, 23H), 1.62–1.67 (m, 1H), 1.76 (s, broad, 1H), 2.59–2.72 (m, 1.5H), 3.00 (t, 0.5H), 3.71 (m, 1H), 4.53–4.61 (dd, 1H), 4.73 (s, broad, 1H), 5.40 (s, broad, 1H), 6.26–6.32 (m, 1H), 7.29–7.45 (m, 7H), 10.89–10.93 (m, 1H). $^{13}$C nmr (CDCl$_3$): δ 14.15, 14.16, 14.56, 18.97, 21.82, 21.93, 24.90, 25.39, 26.01, 26.50, 26.55, 28.69, 31.12, 31.20, 33.93, 34.25, 34.70, 35.53, 35.64, 43.35, 46.31, 46.42, 53.63, 53.85, 56.90, 60.74, 62.23, 62.32, 108.61, 128.65, 128.93, 129.47, 129.60, 129.70, 134.01, 134.97, 137.16, 137.24, 165.99, 166.06, 166.12, 166.21, 170.04, 175.05.

Preparation 20

(2R)-2-{2-[(Tert-butoxy)carbonylamino]-2-methylpropanoyl amino}-N-[1-(2-oxo-1-phenyl-2-pyrrolidinylethyl)imidazol-4-yl]hexanamide

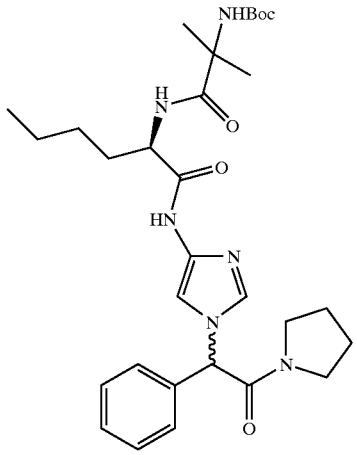

This compound was obtained from the hydrolysis of ethyl 2-[4-((2R)-2-{2-[(tert-butoxy) carbonylamino]-2-methyl propanoylamino}hexanoylamino)imidazolyl]-2-phenylacetate and subsequent reaction with pyrrolidine in 63% yield after purification by preparative reverse phase hplc. $^1$H nmr (CDCl$_3$): δ 0.68–0.71 (m, 3H), 1.20–1.22 (m, 5H), 1.33 (s, 11H), 1.41 (s, 3H), 1.68 (m, 1H), 1.74–1.78 (m, 4H), 1.86–1.88 (m, 1H), 3.08–3.09 (m, 1H), 3.44–3.51 (m, 3H), 4.74 (s, broad, 1H), 5.50 (s, broad, 1H), 6.09–6.10 (d, 1H), 7.27–7.33 (m, 3H), 7.37–7.39 (m, 2H), 7.45–7.57 (m, 3H), 11.05–11.06 (m, 1H). $^{13}$C nmr (CDCl$_3$): δ 14.11, 19.35, 22.73, 24.35, 26.42, 26.46, 26.51, 27.65, 28.68, 31.15, 33.22, 33.30, 46.72, 46.84, 53.72, 56.84, 63.27, 69.71, 108.47, 128.84, 129.43, 129.57, 133.68, 133.76, 134.74, 134.80, 137.30, 166.19, 166.26, 170.11, 175.01.

Preparation 21

(2R)-2-{2-[(Tert-butoxy)carbonylamino]-2-methylpropanoyl amino}-N-1-[2-{4-methylpiperidyl)-2-oxo-1-phenylethyl]imidazol-4-yl}hexanamide

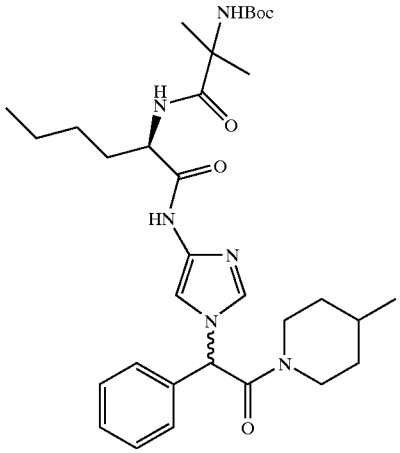

This compound was obtained from the hydrolysis of ethyl 2-[4-((2R)-2-{2-[(tert-butoxy) carbonylamino]-2-methyl propanoylamino}hexanoylamino)imdazolyl]-2-phenylacetate and subsequent reaction with 4-methylpiperidine in 66% yield after purification by preparative reverse phase hplc. $^1$H nmr (CDCl$_3$): δ 0.73–0.74 (m, 3H), 0.89–0.91 (m, 1H), 1.21–1.66 (m, 28H), 1.75–1.87 (m, 1H), 2.57–2.63 (q, 1H), 2.72 (t, 0.5H), 2.99 (t, 0.5H), 3.70–3.72 (m, 1H), 4.53–4.61 (dd, 1H), 4.73 (s, broad, 1H), 5.43 (s, broad, 1H), 6.28–6.31 (d, 1H), 7.33–7.50 (m, 7H), 11.01–11.03 (m, 1H). $^{13}$C nmr (CDCl$_3$): δ 14.15, 14.55, 19.34, 21.39, 21.83, 21.93, 22.76, 25.40, 26.49, 26.56, 27.63, 26.70, 28.73, 31.12, 31.21, 33.24, 33.33, 33.94, 34.24, 34.70, 43.32, 46.30, 46.41, 53.72, 56.88, 60.72, 62.10, 62.17, 62.26, 108.57, 128.64, 128.92, 129.42, 129.56, 129.67, 133.84, 135.00, 135.04, 135.07, 137.20, 131.25, 137.28, 137.32, 165.97, 166.02, 166.12, 166.18, 170.00, 174.95.

Preparation 22

N-[(1R)-1-(N-{1-[2-(4-Methylpiperidyl)-2-oxo-1-phenylethyl]imidazol-4-yl}carbamoyl)-2-(3-thienyl)ethyl]-2-[(tert-butoxy)carbonylamino]-2-methylpropanamide

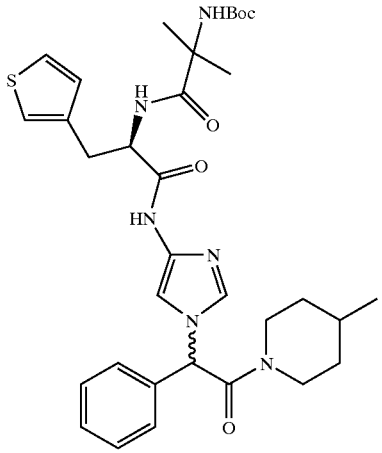

This compound was obtained from the hydrolysis of ethyl 2-[4-((2R)-2-{2-[(tert-butoxy) carbonylamino]-2-methyl propanoylamino}-3-(3-thienyl)propanoylamino) imidazolyl]-2-phenylacetate and subsequent reaction with 4-methyl piperidine in 70% yield after purification by preparative reverse phase hplc. $^1$H nmr (CDCl$_3$): δ 0.79–0.80 (d, 2H), 0.91–0.92 (m, 2H), 0.93–1.15 (m, 3H), 1.32–1.40 (m, 15H), 1.45–1.55 (m, 1H), 1.64 (m, 1H), 2.60–2.62 (m, 1H), 2.75 (t, 0.5H), 2.98 (t, 0.5H), 3.32–3.35 (d, 2H), 3.70 (m, 1H), 4.50–4.67 (dd, 1H), 5.00 (m, 1H), 5.50 (s, broad, 1H), 6.23–6.24 (m, 1H), 6.73–6.76 (m, 2H), 6.97–6.98 (m, 1H), 7.32–7.45 (m, 6H), 7.56 (s, broad, 1H), 10.94 (s, broad, 1H). $^{13}$C nmr (CDCl$_3$) : δ 14.58, 19.45, 21.40, 21.95, 25.58, 25.62, 25.69, 28.75, 31.12, 33.15, 33.94, 33.98, 34.26, 43.36, 46.32, 46.45, 49.28, 54.74, 56.97, 60.74, 62.17, 62.28, 69.84, 108.79, 124.54, 126.95, 127.23, 128.60, 128.93, 129.60, 129.70, 134.03, 135.01, 135.14, 137.05, 137.19, 138.80, 157.69, 165.97, 168.51, 171.49, 175.14.

Preparation 23

N-((1R)-1-{N-[1-(2-Oxo-1-phenyl-2-pyrrolidinylethyl) imidazol-4-yl]carbamoyl}-2-(3-thienyl)ethyl)-2-[(tert-butoxy)carbonylamino]-2-methylpropanamide

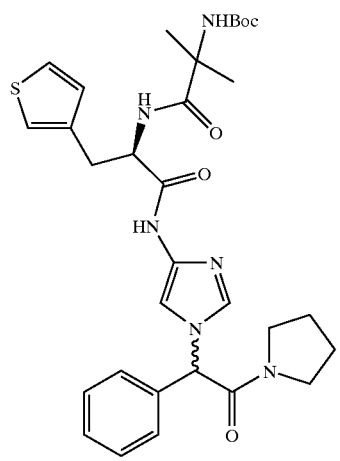

This compound was obtained from the hydrolysis of ethyl 2-[4-((2R)-2-{2-[(tert-butoxy) carbonylamino]-2-methyl propanoylamino}-3-(3-thienyl)propanoylamino) imdazolyl]-2-phenylacetate and subsequent reaction with pyrrolidine in 71% yield after purification by preparative reverse phase hplc. $^1$H nmr (CDCl$_3$): δ 1.32–1.39 (m, 15H), 1.77–1.81 (m, 3H), 1.90 (m, 1H), 3.13 (m, broad, 1H), 3.35 (s, 2H), 3.48–3.54 (m, 3H), 4.97–5.08 (m, 1H), 5.50 (s, broad, 1H), 6.03–6.05 (m, 1H), 6.73–6–6.76 (m, 2H), 6.98–6.99 (m, 1H), 7.34–7.40 (m, 5H), 7.45–7.48 (m, 2H), 10.91 (s, broad, 1H). $^{13}$C nmr (CDCl$_3$): δ 14.58, 19.37, 21.41, 24.39, 25.55, 25.60, 25.66, 26.46, 28.73, 31.19, 33.15, 46.76, 46.91, 54.73, 56.98, 60.74, 63.36, 69.84, 108.56, 108.63, 124.56, 126.94, 127.24, 128.79, 128.82, 128.87, 129.53, 129.65, 133.82, 134.70, 134.83, 134.87, 137.14, 137.19, 137.24, 138.79, 166.11, 168.52, 171.50, 175.08.

Preparation 24

N-[(1R)-2-Benzo[b]thiophen-3-yl-1-{N-[1-(2-oxo-1-phenyl-2-pyrrolidinylethyl)imidazol-4-yl] carbamoyl}ethyl)-2-[(tert-butoxy)carbonylamino]-2-methylpropanamide

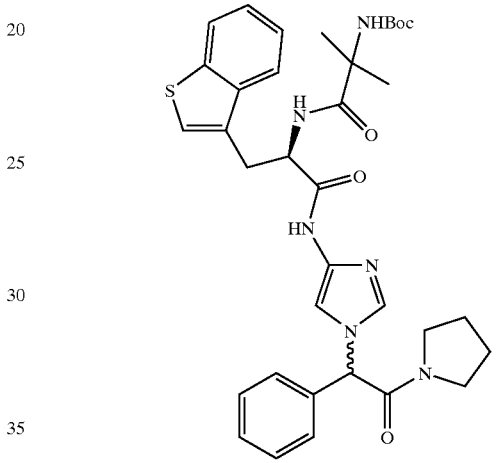

This compound was obtained from the hydrolysis of ethyl 2-[4-((2R)-3-benzo[b]-thiophen-3-yl-2-{2-[(tert-butoxy) carbonylamino]-2-methylpropanoylamino}propanoyl-amino)imidazolyl]-2-phenylacetate and subsequent reaction with pyrrolidine in 68% yield after purification by preparative reverse phase hplc. $^1$H nmr (CDCl$_3$): δ 1.21–1.34 (m, 15H), 1.76–1.87 (m, 3H), 3.00–3.10 (m, 1H), 3.34–3.38 (m, 2H), 3.48–3.57 (m, 3H), 5.17 (s, 1H), 5.40 (s, broad, 1H), 5.92 (s, 1H), 7.16–7.30 (m, 1H), 7.34 (s, 10H), 7.39–7.46 (m, 1H), 7.57–7.59 (m, 0.5H), 7.68–7.69 (m, 1H), 8.06–8.07 (d, 0.5H), 10.85 (s, broad; 1H). $^{13}$C nmr (CDCl$_3$): 14.58, 19.38, 21.41, 24.38, 25.54, 25.64, 25.70, 26.03, 26.43, 28.58, 31.20, 34.26, 36.36, 46.70, 46.90, 49.27, 53.40, 54.44, 56.93, 60.75, 63.23, 69.80, 108.47, 108.61, 122.87, 124.29, 124.35, 124.44, 125.64, 125.84, 126.45, 127.78, 128.17, 128.75, 128.79, 128.83, 129.51, 129.61, 132.48, 133.42, 134.04, 134.78, 137.14, 139.34, 140.45, 157.71, 166.11, 168.93, 171.51, 175.01, 175.13.

Preparation 25

N-[(1R)-2-Benzo[b]thiophen-3-yl-1-(N-{1-[2-(4-methyl piperidyl)-2-oxo-1-phenylethyl]imidazol-4-yl}carbamoyl) ethyl]-2-[(tert-butoxy) carbonylamino]-2-methylpropanamide

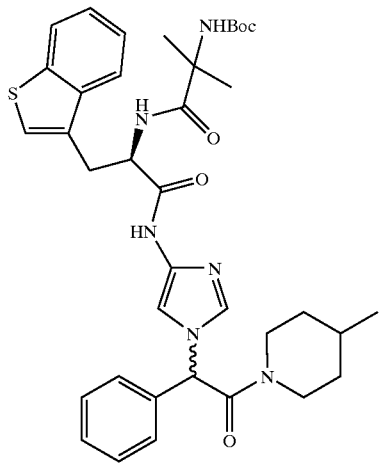

This compound was obtained from the hydrolysis of ethyl 2-[4-((2R)-3-benzo[b]-thiophen-3-yl-2-{2-[(tert-butoxy) carbonylamino]-2-methylpropanoylamino}propanoylamino) imidazolyl]-2-phenylacetate and subsequent reaction with 4-methylpiperidine in 71% yield after purification by preparative reverse phase hplc. $^1$H nmr (CDCl$_3$): δ 0.78–0.79 (d, 1H), 0.90–1.00 (d, 1H), 1.12–1.33 (n, 20H), 1.51 (m, 1H), 1.64 (m, 1H), 2.61–2.67 (m, 1.5H), 2.90 (m, 1H), 3.32–3.33 (m, 1H), 3.51–3.62 (m, 2.5H), 4.57–4.68 (m, 1H), 5.45 (s, 1H), 6.11–6.14 (s, broad, 1H), 7.19–7.45 (m, 10H), 7.57–7.59 (m, 0.5H), 7.67–7.69 (m, 1H), 8.06 (s, broad, 0.5H), 11.00 (s, broad, 1H). $^{13}$C nmr (CDCl$_3$): δ 14.59, 19.41, 21.41, 21.86, 21.88, 21.98, 25.45, 25.69, 25.79, 26.04, 28.71, 31.15, 32.10, 33.97, 34.26, 34.68, 36.40, 43.27, 46.27, 46.40, 49.24, 53.42, 54.44, 56.90, 60.75, 62.13, 108.68, 108.81, 122.87, 124.28, 124.35, 124.41, 125.64, 125.84, 126.45, 127.78, 128.20, 128.61, 128.85, 129.47, 129.57, 129.66, 132.50, 133.40, 134.03, 135.05, 135.15, 139.38, 140.44, 157.75, 165.86, 66.05, 169.02, 171.50, 174.98, 175.14.

Example 1

N-[(1R)-2-Indol-3-yl-1-(N-{1-[2-(4-methylpiperidyl)-1-(2-naphthyl)-2-oxoethyl]imidazol-4-yl}carbamoyl)ethyl]-2-amino-2-methylpropanamide Dihydrochloride A solution consisting of N-[(1R)-2-indol-3-yl-1-(N-(1-[2-(4-methylpiperidyl)-1-(2-naphthyl)-2-oxoethyl]imidazol-4-yl)carbamoyl)ethyl]-2-[(tert-butoxy)carbonylamino]-2-methyl propanamide (0.32 grams, 0.445 mmol) and anisole (0.25 mL) dissolved in methylene chloride (20 mL) was added trifluoroacetic acid (2.5 mL). The resulting reaction mixture was stirred at ambient temperature until complete as determined by hplc (2.5 hours). The reaction mixture was concentrated to dryness. The residue was dissolved in methanol (5 mL) and applied to a Varian Mega Bond Elut SCX ion exchange column (5 gram). The column was washed with methanol (50 mL). The product was eluted from the column with 2N ammonia in methanol (30 mL). The eluent was concentrated to dryness to give the free base (0.28 grams). A 1.95 M solution of anhydrous HCl in ethyl acetate (0.456 mL, 0.89 mmol) was added to the free base which was dissolved in ethyl acetate (10 mL). The resulting precipitate was collected by filtration and dried in vacuum to give 0.27 grams (87%) of N-[(1R)-2-indol-3-yl-1-(N-{1-[2-(4-methylpiperidyl)-1-(2-naphthyl)-2-oxoethyl]imidazol-4-yl}carbamoyl)ethyl]-2-amino-2-methylpropanamide dihydrochloride. MS (FIA) m/z 620.7 [(M+H)$^+$]. Anal. calcd. for $C_{36}H_{41}N_7O_3 \cdot 2HCl \cdot \frac{1}{2}H_2O$: C: 61.62; H: 6.32; N: 13.97. Found: C: 61.42; H: 6.18; N: 13.62. Anal. calcd. exact mass for $C_{36}H_{42}N_7O_3$ [(M+H)$^+$]=620.3349. Exact mass found by mass spectrometry: $C_{36}H_{42}N_7O_3$ [(M+H)$^+$]=620.3355. $^1$H nmr (DMSO-d$_6$): 0.65–0.67 (d, 2H), 0.89–0.90 (d, 2H), 1.16–1.24 (m, 2H), 1.35–1.36 (d, 4H), 1.51–1.53 (d, 4H), 1.63–1.65 (m, 1H), 2.68–2.74 (m, 1.5H), 3.08 (t, 0.5H), 3.17–3.19 (m, 1H), 3.26–3.27 (m, 1H), 3.71–3.82 (m, 1H), 4.40–4.55 (m, 1H), 4.71–4.72 (t, 1H), 6.90–7.00 (m, 1H), 7.02–7.04 (m, 1H), 7.26–7.33 (m, 3H), 7.52 (m, 1H), 7.59–7.62 (m, 3H), 7.74 (m, 1H), 7.98–8.09 (m, 4H), 8.31–8.32 (d, 3H), 8.49–8.61 (m, 1H), 8.66–8.68 (d, 1H), 10.94 (s, 1H), 11.35 (s, 1H).

Example 2

N-[(1R)-2-Indol-3-yl-1-(N-{1-[2-(4-methylpiperidyl)-2-oxo-1-phenylethyl]imidazol-4-yl}carbamoyl)ethyl]-2-amino-2-methyl propanamide Dihydrochloride

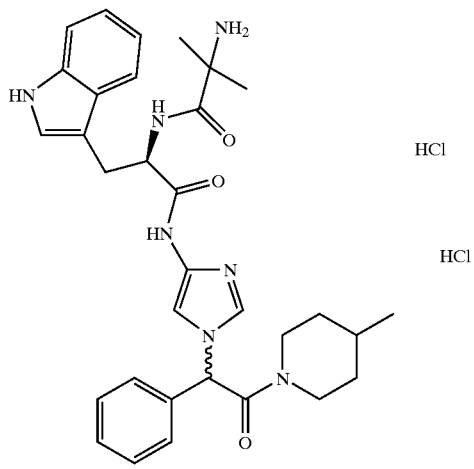

This compound was obtained from N-[(1R)-2-indol-3-yl-1-(N-{1-[2-(4-methylpiperidyl)-2-oxo-1-phenylethyl]imidazol-4-yl}carbamoyl)ethyl]-2-[(tert-butoxy)carbonylamino]-2-methyl propanamide as a red foam in 100% yield. MS (FIA) m/z 570.5 [(M+H)$^+$]. $^1$H nmr (d-MeOH): δ 0.81–0.82 (d, 2H), 0.98–0.99 (d, 2H), 1.18–1.21 (m, 2H), 1.34–1.37 (m, 1H), 1.43 (s, 3H), 1.61 (s, 6H), 1.71 (t, 1H), 2.73–2.76 (m, 1.5H), 3.14 (t, 0.5H), 3.27–3.33 (m, 1H), 3.40–3.44 (m, 1H), 3.61–3.65 (m, 1H), 3.75–3.77 (d, 1H), 4.45–4.60 (m, 1H), 4.81 (s, broad, 4H), 6.94–6.99 (m, 1.5H), 7.06–7.07 (m, 1.5H), 7.19 (s, 1H), 7.31–7.35 (m, 2H), 7.52–7.61 (m, 6H), 8.62–8.65 (d, 1H).

Example 3

N-((1R)-2-Indol-3-yl-1-{N-[1-(2-oxo-1-phenyl-2-pyrrolidinyl ethyl)imidazol-4-yl]carbamoyl}ethyl)-2-amino-2-methyl propanamide Bistrifluoroacetic Acid

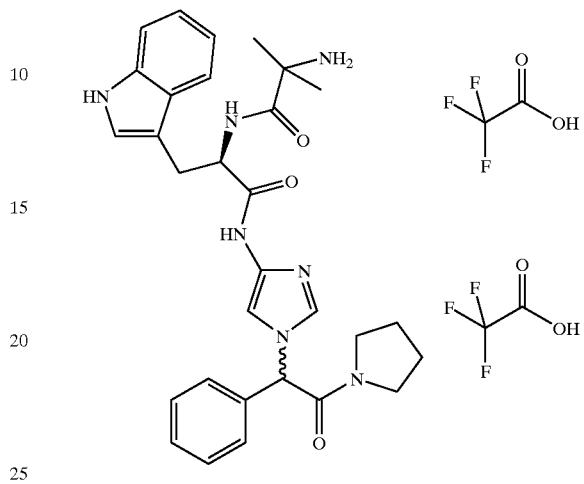

This compound was obtained from N-((1R)-2-indol-3-yl-1-{N-[1-(2-oxo-1-phenyl-2-pyrrolidinylethyl)imidazol-4-yl]carbamyl}ethyl)-2-[(tert-butoxy)carbonylamino]-2-methylpropanamide as a white solid in 50% yield. MS (FD+) m/z 541 (M$^+$). Anal. calcd. for $C_{30}H_{35}N_7O_3 \cdot 2C_2HF_3O_2$: C: 53.06; H: 4.85; N: 12.74. Found: C: 52.93; H: 4.88; N: 12.55. $^1$H nmr (DMSO-d$_6$): δ 1.29 (s, 3H), 1.46–1.48 (d, 3H), 1.72–1.88 (m, 4H), 2.94 (m, 1H), 3.06–3.07 (m, 1H), 3.19–3.20 (m, 1H), 3.40–3.41 (d, 2H), 3.67–3.69 (m, 1H), 4.78 (s, broad, 1H), 6.53 (s, 1H), 6.93–6.97 (m, 1H), 7.06 (m, 1H), 7.20 (d, 1H), 7.31–7.36 (m, 2H), 7.42–7.42 (m, 4H), 7.73–7.80 (m, 2H), 8.01 (s, broad, 2H), 8.36–8.38 (d, 1H), 10.82–10.85 (d, 2H).

Example 4

N-((1R)-2-Cyclohexyl-1-{N-[1-(2-oxo-1-phenyl-2-pyrrolidinyl ethyl)imidazol-4-yl]carbamoyl}ethyl)-2-amino-2-methyl propanamide Bistrifluoroacetic Acid

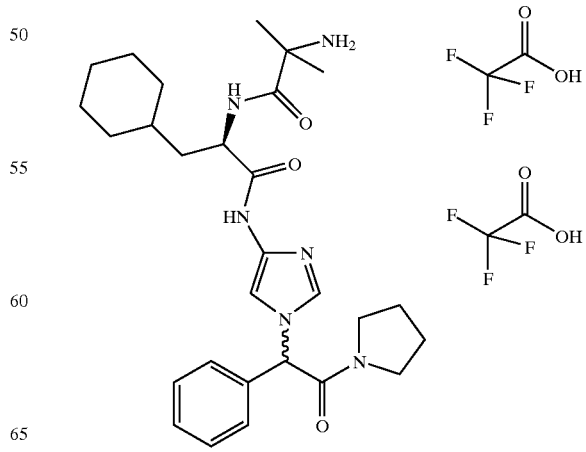

533

This compound was obtained from N-((1R)-2-cyclohexyl-1-{N-[1-(2-oxo-1-phenyl-2-pyrrolidinylethyl)imidazol-4-yl]carbamoyl}ethyl)-2-[(tert-butoxy)carbonylamino]-2-methyl propanamide as a white solid in 81% yield. MS (FD+) m/z 508.2 (M+) Anal. calcd. for $C_{28}H_{40}N_6O_3.2C_2HF_3O_2$: C: 52.17; H: 5.75; N: 11.41. Found: C: 52.11; H: 5.81; N: 11.40. $^1$H nmr (DMSO-$d_6$): δ 0.91 (m, 2H), 1.11–1.13 (m, 3H), 1.31 (s, broad, 1H), 1.48–1.79 (m, 18H), 2.91–2.93 (m, 1H), 3.38 (m, 2H), 3.65–3.68 (m, 1H), 4.53–4.54 (m, 1H), 6.52 (s, 1H), 7.30 (s, 1H), 7.41–7.48 (m, 5H), 7.77–7.81 (d, 1H), 8.13–8.14 (d, 3H), 8.30–8.31 (d, 1H), 10.68 (s, 1H).

Example 5

Methyl 1-(2-{4-[(2R)-2-(2-Amino-2-methylpropanoylamino)-3-cyclohexylpropanoylamino]imidazolyl}-2-phenylacetyl) (2S)pyrrolidine-2-carboxylate Bistrifluoroacetic Acid

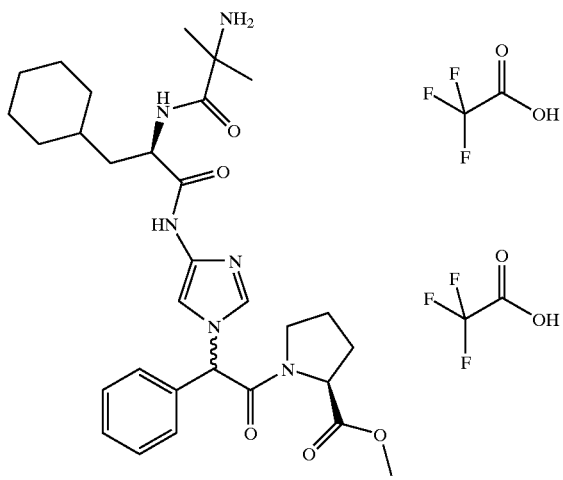

This compound was obtained from methyl 1-{2-[4-((2R)-2-{2-[(tert-butoxy)carbonylamino]-2-methylpropanoyl-amino}-3-cyclohexylpropanoylamino)imidazolyl]-2-phenylacetyl}(2S) pyrrolidine-2-carboxylate as an off white solid in 53% yield. MS (FD+) m/z 566.2 (M+). Anal. calcd. for $C_{30}H_{42}N_6O_5.2C_2HF_3O_2$: C: 51.38; H: 5.58; N: 10.57. Found: C: 51.44; H: 5.59; N: 10.66. $^1$H nmr (DMSO-$d_6$): δ 0.91 (m, 2H), 1.12–1.16 (m, 3H), 1.30 (s, broad, 1H), 1.47–1.67 (m, 13H), 1.81–1.87 (m, 3H), 2.10–2.30 (m, 1H), 2.95–3.15 (m, 1H) 3.64 (s, 1H), 3.68 (s, 2H), 3.72–3.75 (m, 1H), 4.41–4.43 (t, 1H), 4.53–4.54 (m, 1H), 6.59–6.62 (m, 1H), 7.17–7.19 (d, 0.5H), 7.37–7.47 (m, 6.5H), 7.57–7.62 (d, 1H), 8.11 (s, broad, 3H), 8.25–8.28 (m, 1H), 10.55 (s, 1H).

Example 6

(2R)-2-(2-Amino-2-methylpropanoylamino)-N-[1-(2-oxo-1-phenyl-2-pyrrolidinylethyl)imidazol-4-yl] pentanamide Bistrifluoroacetic Acid

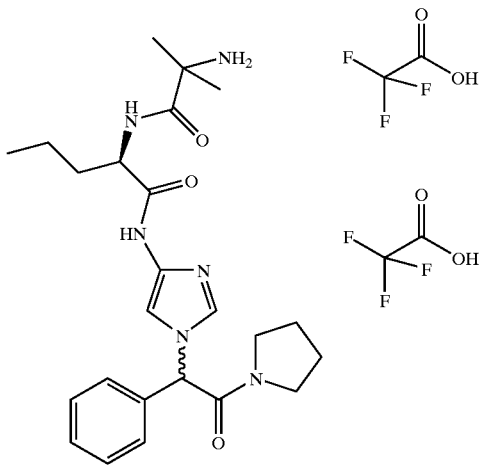

This compound was obtained from (2R)-2-{2-[(tert-butoxy) carbonylamino]-2-methylpropanoylamino}-N-[1-(2-oxo-1-phenyl-2-pyrrolidinylethyl)imidazol-4-yl] pentanamide as an off white solid in 82% yield. MS (FD+) m/z 454 (M+). Anal. calcd. for $C_{24}H_{34}N_6O_3.2C_2HF_3O_2$: C: 49.27; H: 5.32; N: 12.31. Found: C: 49.19; H: 5.29; N: 12.25. $^1$H nmr (DMSO-$d_6$): δ 0.88–0.90 (m, 3H), 1.20–1.30 (m, 1H), 1.30–1.39 (m, 1H), 1.50–1.51 (m, 6H), 1.68–1.85 (m, 7H), 2.89–2.90 (m, 1H), 3.40 (s, broad, 2H), 3.67 (s, broad, 1H), 4.41–4.42 (m, 1H), 6.59 (s, 1H), 7.35 (s, 1H), 7.44–7.46 (m, 5H), 7.96–8.00 (d, 1H), 8.19–8.20 (m, 3H), 8.33–8.35 (d, 1H), 10.85 (s, 1H).

Example 7

(2R)-2-(2-Amino-2-methylpropanoylamino)-N-{1-[2-(4-methylpiperidyl)-2-oxo-1-phenylethyl]imidazol-4-yl}pentanamide Bistrifluoroacetic Acid

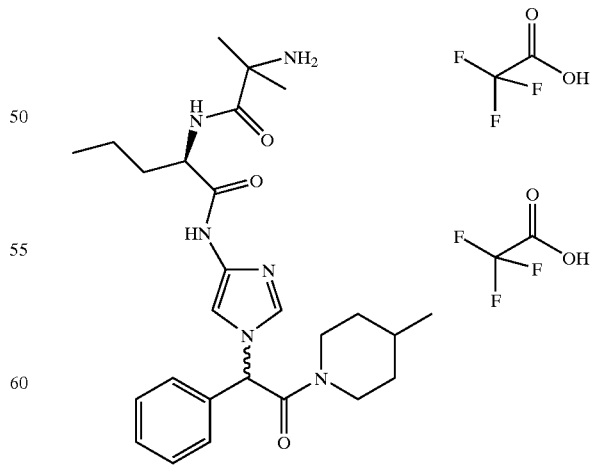

This compound was obtained from (2R)-2-{2-[(tert-butoxy) carbonylamino]-2-methylpropanoylamino}-N-{1-

[2-(4-methyl piperidyl)-2-oxo-1-phenylethyl]imidazol-4-yl}pentanamide as an off white solid in 85% yield. MS (FD+) m/z 482 (M+). Anal. calcd. for $C_{26}H_{38}N_6O_3\cdot 2C_2HF_3O_2\cdot \frac{1}{2}H_2O$: C: 50.07; H: 5.74; N: 11.68. Found: C: 49.94; H: 5.53; N: 11.51. $^1$H nmr (DMSO-$d_6$): δ 0.73–0.74 (d, 2H), 0.86–0.89 (m, 7H), 0.95–1.69 (m, 12H), 2.61–2.68 (m, 2H), 3.02 (t, 1H), 3.69–3.76 (t, 1H), 4.36–4.41 (m, 2H), 6.82–6.87 (d, 1H), 7.29 (s, 1H), 7.37–7.49 (m, 5H), 7.86–7.91 (m, 1H), 8.17–8.19 (d, 3H), 8.32–8.33 (d, 1H), 10.79 (s, 1H).

Example 8

(2R)-2-(2-Amino-2-methylpropanoylamino)-N-{1-[2-(4-methylpiperidyl)-2-oxo-1-phenylethyl]imidazol-4-yl}hexanamide Bistrifluoroacetic Acid

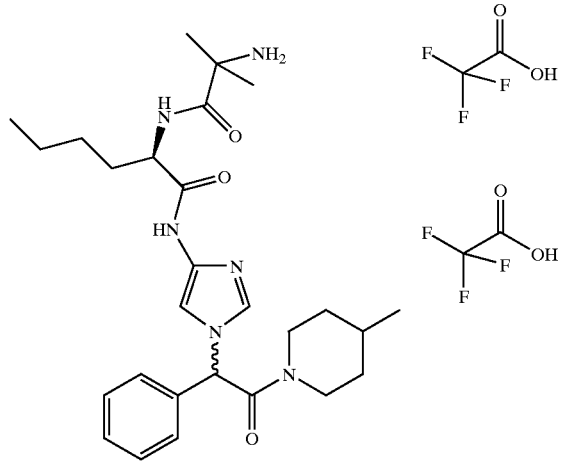

This compound was obtained from (2R)-2-{2-[(tert-butoxy) carbonylamino]-2-methylpropanoylamino}-N-{1-[2-(4-methyl piperidyl)-2-oxo-1-phenylethyl]imidazol-4-yl}hexanamide as an off white solid in 90% yield. MS (FD+) m/z 496.3 (M+). Anal. calcd. for $C_{27}H_{40}N_6O_3\cdot 2C_2HF_3O_2$: C: 51.38; H: 5.84; N: 11.60. Found: C: 51.38; H: 5.83; N: 11.59. $^1$H nmr (DMSO-$d_6$): δ 0.73–0.74 (d, 2H), 0.84–0.89 (m, 5H), 1.00–1.28 (m, 1H), 1.28–1.30 (m, 5H), 1.49–1.69 (m, 11H), 2.64–2.66 (m, 1.5H), 3.02 (t, 0.5H), 3.69–3.72 (t, 1H), 4.39–4.43 (m, 2H), 6.82–6.84 (m, 1H), 7.28–7.30 (m, 1H), 7.38–7.49 (m, 5H), 7.87–7.90 (m, 1H), 8.16–8.17 (d, 3H), 8.32–8.33 (d, 1H), 10.80 (s, 1H).

Example 9

(2R)-2-(2-Amino-2-methylpropanoylamino)-N-[1-(2-oxo-1-phenyl-2-pyrrolidinylethyl)imidazol-4-yl]hexanamide Bistrifluoroacetic Acid

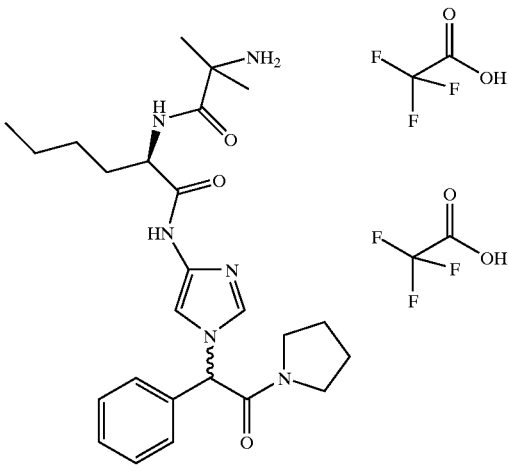

This compound was obtained from (2R)-2-{2-[(tert-butoxy) carbonylamino]-2-methylpropanoylamino}-N-[1-(2-oxo-1-phenyl-2-pyrrolidinylethyl)imidazol-4-yl]hexanamide as an off white solid in 92% yield. MS (FD+) m/z 468.2 (M+). Anal. calcd. for $C_{25}H_{36}N_6O_3\cdot 2C_2HF_3O_2$: C: 50.00; H: 5.50; N: 12.06. Found: C: 49.79; H: 5.55; N: 12.07. $^1$H nmr (DMSO-$d_6$): δ 0.84–0.88 (m, 3H), 1.28–1.30 (m, 4H), 1.50–1.52 (d, 6H), 1.71–1.78 (m, 6H), 2.87–2.89 (m, 1H), 3.39–3.40 (m, 2H), 3.67–3.69 (m, 1H), 4.37–4.40 (m, 1H), 6.62 (s, 1H), 7.38 (s, 1H), 7.42–7.49 (m, 5H), 8.09–8.13 (d, 1H), 8.20–8.21 (m, 3H), 8.37–8.38 (d, 1H), 10.98 (s, 1H), 11.69 (s, broad, 1H).

Example 10

N-((1R)-{N-[1-(2-Oxo-1-phenyl-2-pyrrolidinylethyl)imidazol-4-yl]carbamoyl}-2-(3-thienyl)ethyl)-2-amino-2-methylpropanamide Bistrifluoroacetic Acid

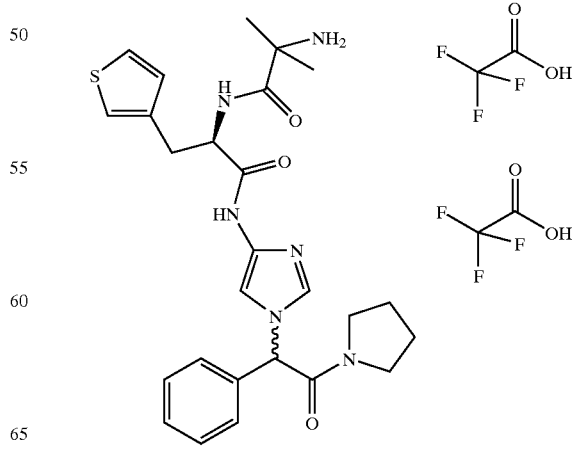

This compound was obtained from N-((1R)-1-{N-[1-(2-oxo-1-phenyl-2-pyrrolidinylethyl)imidazol-4-yl]carbamoyl}-2-(3-thienyl)ethyl)-2-[(tert-butoxy)carbonylamino]-2-methyl propanamide as an off white solid in 90% yield. MS (FD+) m/z 508.2 (M+). Anal. calcd. for $C_{26}H_{32}N_6O_3S \cdot 2C_2HF_3O_2$: C: 48.91; H: 4.65; N: 10.99 11.41. Found: C: 48.68; H: 4.53; N: 11.26. $^1$H nmr. (DMSO-$d_6$): δ 1.40 (s, 3H), 1.50–1.52 (d, 3H), 1.72–1.85 (m, 4H), 2.92–2.93 (m, 1H), 3.22 (m, 1H), 3.32 (m, 1H), 3.39–3.42 (m, 2H), 3.67–3.69 (m, 1H), 4.70–4.74 (m, 1H), 6.59 (s, 1H), 6.93–6.98 (d, 2H), 7.32–7.33 (d, 1H), 7.39–7.49 (m, 6H), 7.92–7.96 (d, 1H), 8.15–8.16 (d, 3H), 8.57–8.58 (d, 1H), 8.70 (s, broad, 1H), 10.99 (s, 1H).

Example 11

N-[(1R)-1-(N-{1-[2-(4-Methylpiperidyl)-2-oxo-1-phenylethyl]imidazol-4-yl}carbamoyl)-2-(3-thienyl)ethyl]2-amino-2-methyl propanamide Bistrifluoroacetic Acid

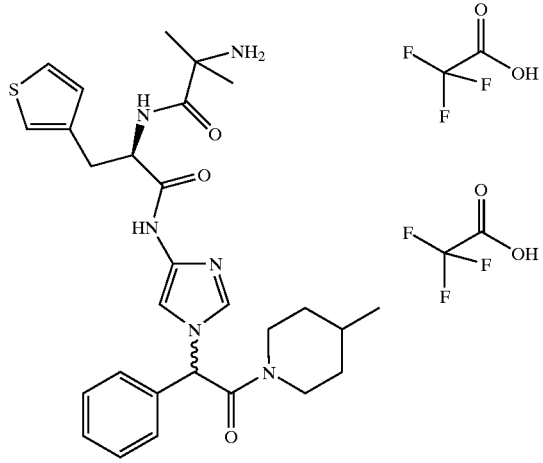

This compound was obtained from N-[(1R)-1-(N-{1-[2-(4-methylpiperidyl)-2-oxo-1-phenylethyl]imidazol-4-yl}carbamoyl]-2-(3-thienyl)ethyl)-2-[(tert-butoxy) carbonylamino]-2-methylpropanamide an off white solid in 84% yield. MS (FD+) m/z 536.2 (M+). Anal. calcd. for $C_{29}H_{36}N_6O_3S \cdot 2C_2HF_3O_2$: C: 50.26; H: 5.01; N: 10.99. Found: C: 50.06; H: 4.89; N: 11.00. $^1$H nmr (DMSO-$d_6$): δ 0.73–0.74 (d, 2H), 0.89–0.90 (d, 2H), 0.95–1.20 (m, 1H), 128–1.52 (m, 8H), 1.60–1.63 (m, 1H), 2.64–2.69 (m, 1.5H), 3.03 (t, 0.5H), 3.19–3.22 (t, 1H), 3.30–3.34 (t, 1H), 3.71–375 (m, 1H), 4.40–4.44 (m, 1H), 4.71 (m, 1H), 6.85–6.98 (m, 3H), 7.32–7.48 (m, 7H), 7.92–7.97 (m, 1H), 8.16–8.17 (d, 3H), 8.57–8.58 (d, 1H), 11.02 (s, 1H), 11.3 (s, broad, 1H).

Example 12

N-((1R)-2-Benzo[b]thiophen-3-yl-1-{N-[1-(2-oxo-1-phenyl-2-pyrrolidinylethyl)imidazol-4-yl]carbamoyl}ethyl)-2-amino-2-methylpropanamide Bistrifluoroacetic Acid

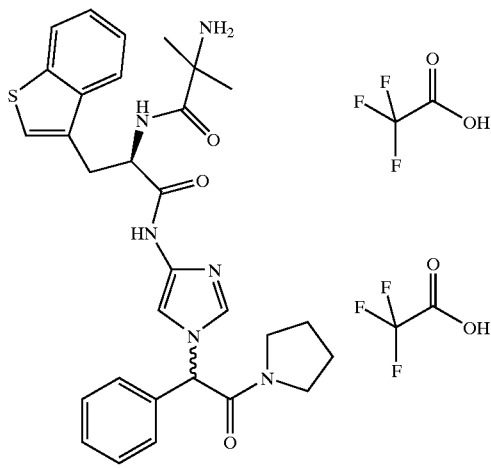

This compound was obtained from N-((1R)-2-benzo[b]thiophen-3-yl-1-{N-[1-(2-oxo-1-phenyl-2-pyrrolidinylethyl)imidazol-4-yl]carbamoyl}ethyl)-2-[(tert-butoxy)carbonylamino]-2-methyl propanamide as an off white solid in 89% yield. MS (FD+) m/z 557.9 (M+). $^1$H nmr (DMSO-$d_6$): δ 1.21–1.22 (d, 2H), 1.28–1.29 (d, 1H), 1.46–1.49 (m, 3H), 1.75–1.87 (m, 4H), 2.93–2.95 (m, 1H), 3.36–3.42 (m, 3.5H), 3.68–3.69 (m, 1.5H), 4.95–4.98 (m, 1H), 6.57 (s, 1H), 7.39–7.54 (m, 9H), 7.79–8.05 (m, 6H), 8.15 (m, 0.5H), 8.30 (m, 0.5H), 8.55–8.56 (m, 1H), 10.95–11.05 (d, 1H).

Example 13

N-[(1R)-2-Benzo[b]thiophen-3-yl-1-(N-{1-[2-(4-methyl piperidyl)-2-oxo-1-phenylethyl]imidazol-4-yl}carbamoyl) ethyl]-2-amino-2-methylpropanamide Bistrifluoroacetic Acid

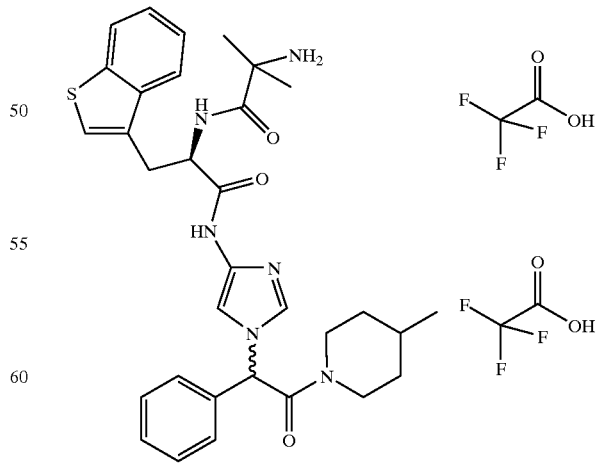

This compound was obtained from N-[(1R)-2-benzo[b]thiophen-3-yl-1-(N-{1-[2-(4-methylpiperidyl)-2-oxo-1- phenylethyl]imidazol-4-yl}carbamoyl)ethyl]-2-[(tert-butoxy)carbonyl amino]-2-methylpropanamide as an off white solid in 72% yield. MS (FIA) m/z 586.7 [(M+H)$^+$]. $^1$H nmr (DMSO-d$_6$); δ 0.74–0.76 (d, 2H), 0.89–0.90 (d, 2H), 1.0–1.64 (m, 10H), 2.65–2.70 (m, 1.5H), 3.04 (t, 0.5H), 3.15–3.35 (m, 1.5H), 3.62–3.75 (m, 1H), 4.42–4.45 (m, 1H), 4.97 (m, 1H), 6.84–6.89 (d, 1H), 7.39–7.57 (m, 10H), 7.79–8.20 (m, 6H), 8.36 (t, 0.5H), 8.53–8.57 (m, 1H), 10.97–11.06 (d, 1H).

Example 14

N-[(1R)-1-(N-{1-[(N,N-Dimethylcarbamoyl)-2-naphthylmethyl}imidazol-4-yl}carbamoyl)-2-indol-3-ylethyl]-2-amino-2-methyl propanamide Dihydrochloride

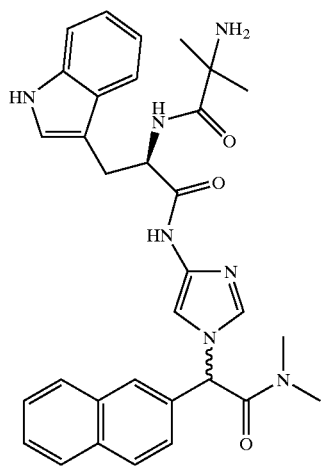

This compound was obtained from the reaction of 2-[4-((2R)-2-{2-[(tert-butoxy)carbonylamino]-2-methylpropanoylamino}-3-indol-3-ylpropanoylamino)imidazolyl]-2-(2-naphthyl)acetic acid and dimethylamine followed by deprotection according to the general procedure as an off white solid in 90% yield. MS (FIA) m/z 566.6 [(M+H)$^+$]. $^1$H nmr (DMSO-d$_6$); δ 1.36–1.37 (d, 3H), 1.51–1.53 (d, 3H), 2.92 (s, 3H), 2.99 (s, 3H), 3.19–3.22 (m, 1H), 3.27–3.31 (m, 1H), 4.68–4.73 (m, 1H), 6.90–6.94 (m, 1H), 6.97–7.03 (m, 1H), 7.29–7.33 (m, 2H), 7.38 (s, 1H), 7.55 (s, 1H), 7.60–7.62 (t, 3H), 7.73 (t, 1H), 7.98–8.06 (m, 4H), 8.36–8.37 (d, 3H), 8.72–8.74 (d, 2H), 10.97 (s, 1H), 11.49 (s, 1H).

Example 15

N-((1R)-2-(2-Naphthyl)-1-{N-[1-(2-oxo-1-phenyl-2-pyrrolidinylethyl)imidazol-4-yl]carbamoyl}ethyl)-2-amino-2-methylpropanamide

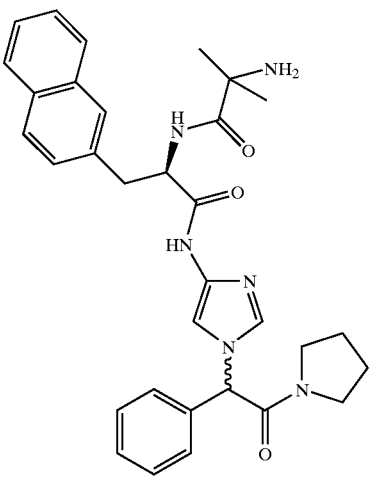

This compound was obtained from 2-[4-((2R)-2-{2-[(tert-butoxy)carbonylamino]-2-methylpropanoylamino}-3-(2-naphthyl) propanoylamino)imidazolyl]-2-phenylacetic acid and pyrrolidine followed by deprotection according to the general procedure to give a tan foam in 53% yield. MS (FD$^+$) m/z 552 (M$^+$). $^1$H nmr (CDCl$_3$): δ 1.06–1.25 (m, 9H), 1.81–1.92 (m, 3H), 3.12–3.13 (m, 1H), 3.44–3.61 (m, 4H), 5.03–5.05 (m, 1H), 5.88 (s, 1H), 7.26–7.44 (m, 13H), 7.6 (m, 0.5H), 7.75–7.76 (m, 1H), 8.15 (m, 0.5H), 8.24 (m, 1H), 10.5 (m, 1H).

Example 16

Methyl 1-(2-{4-[(2R)-2-(2-Amino-2-methylpropanoylamino)-3-(2-naphthyl)propanoylamino]imidazolyl}-2-phenylacetyl)(2S) pyrrolidine-2-carboxylate Bistrifluoroacetic Acid

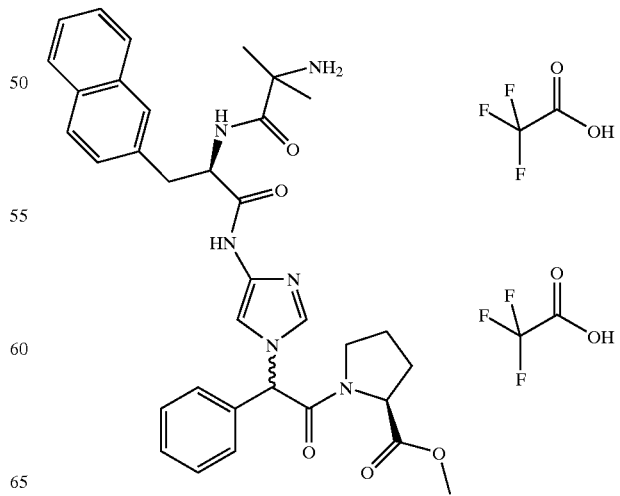

This compound was obtained from 2-[4-((2R)-2-{2-[(tert-butoxy)carbonylamino]-2-methylpropanoylamino}-3-(2-naphthyl) propanoylamino)imidazolyl]-2-phenylacetic acid and L-proline methyl ester followed by deprotection according to the general procedure to give a white solid in 76% yield. MS (FD⁺) m/z 610.0 (M⁺). IR (KBr): 1744.15, 1669.60, 1535.15, 1437.31, 1201.83, 1136.77, 721.83.

EXAMPLES PART 8

Preparation 1

2-(4-Nitroimidazolyl)-2-phenylacetic acid

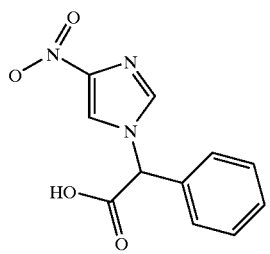

1

Lithium hydroxide (18.1 g, 750 mm, 2 eq) was added to a stirred slurry of ethyl 2-(4-nitroimidazoyl)-2-phenylacetate (Preparation 11 from Examples Part 1) (104 g, 379 mm) in 250 mL of ethanol. Deionized water was added to the resulting mixture and the stirring was continued for 4 hours. The ethanol was removed under vacuum and the resulting aqueous solution was washed with 100 mL of diethyl ether. The aqueous layer was diluted with 100 mL of deionized water and the pH was adjusted to 1.8 with concentrated HCl after cooling to 12° C. The resulting slurry was stirred for 30 minutes at less than 5 degrees and filtered. The wet cake was washed with 100 mL of deionized water and dried under a stream of air on the filter overnight to yield 90.34 g (96%) of a brown solid. The product may be recrystallized from isopropyl alcohol to give 72.31 g (80% recovery, 77% overall yield) of a tan solid. Elemental analysis: Calculated: % C 53.45, % H 3.67. % N 16.97; Found: % C 53.67, % H 3.79, % N 16.65. MS: 247 (M⁺): IR (cm⁻¹) 1719; H¹ nmr (d⁶ DMSO): d 6.51 (s, 1H), 7.43–7.55 (m, 5H), 7.95 (s, 1H), 8.40 (s, 1H)

Preparation 2

1-(4-Methylpiperidinyl)-2-(4-nitroimidazolyl)-2-phenylethan-1-one

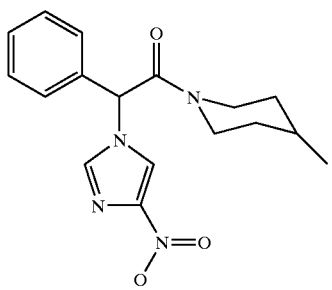

2

N-Methyl morpholine (2.22 ml, 1.0 eq) was added to a stirred solution of 2-(4-nitroimidazolyl)-2-phenylacetic acid (1) (5.0 g, 20.2 mm) and 2-chloro-4,6-dimethoxy-1,3,5-triazine (3.61 g, 20.2 mm 1.0 eq) in 50 ml of anhydrous tetrahydrofuran at 25° C. After stirring the reaction mixture at ambient temperature for 1 h, 4-methylpiperidine (2.39 mL, 24.14 mm, 1.1 eq) was added and stirring continued for 50 min. The reaction mixture was quenched by the addition of 1M HCl. The layers were separated and the organic layer was washed with saturated NaHCO3. The resulting emulsion was broken and all the solids dissolved by the addition of deionized water. The layers were separated and the organic layer washed with brine; dried over MgSO₄ and filtered. The volatiles were removed under vacuum to give a tan foam (6.08 g, 91% yield). The foam was slurried in hexane overnight to achieve partial crystallization of the product. This was filtered to give a cream colored solid (1.29 g, 19%) which assayed 97% by HPLC. Analytical data are under PX026948. The gummy residue was treated with refluxing methyl t-butyl ether to facilitate crystallization. After refluxing, the slurry was cooled and filtered to give a cream colored product (3.02 g, 45%). Elemental analysis: Calculated: % C 62.18, % H 6.14, % N 17.06; Found: % C 62.05, % H 3.79, % N 16.65 MS: 328 (M⁺) IR (cm⁻¹) 1659; H¹ nmr: d (d⁶ DMSO): 0.5 (m, 0.4H) 0.70 (d, J+6 Hz, 1.5H), 0.87 (d, J=6 Hz, 1.5H), 0.75–1.65 (m, 4.6H), 2.50–2.70 (m, 2.5H), 2.9–3.1 (m, 0.5H), 3.5–3.7 (m, 1H), 4.28–4.45 (m, 1H), 6.89 (s, 0.5H), 6.94 (s, 0.5H), 7.4–7.5 (m, 5H), 7.79 (s, 1H), 8.18 (s, 1H)

Preparation 3

2-(4-nitroimidazolyl)-2-phenyl-1-pyrrolidinylethane-1-one

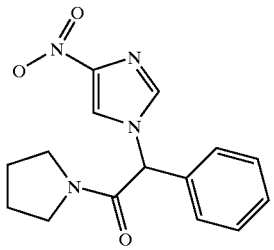

3

N-Methyl morpholine (22.25 ml, 2 eq) was added to a stirred solution of 2-(4-nitroimidazolyl)-2-phenylacetic acid (1) (25.03 g, 101.2 mm) and 2-chloro-4,6-dimethoxy-1,3,5-triazine (18.1 g, 101.2 mm, 1.0 eq) in 50 ml of anhydrous tetrahydrofuran at 25° C. After stirring the reaction mixture at ambient temperature for 1 h 7.2 mL (101.2 mm, 1.0 eq) of pyrrolidine was added dropwise. The reaction was stirred at room temperature for 2 hours. The reaction mixture was quenched by the addition of 200 mL of ethyl acetate and 200 mL of 1M HCl. The layers were separated and the organic layer was washed with 100 ml of saturated sodium bicarbonate solution. The mixture resulting from the bicarbonate wash was diluted 1:1 with deionized water to dissolve the resulting solids and the layers were separated. The organic layer was washed with brine, dried over magnesium sulfate, filtered and the volatiles were removed under vacuum to give a brown foam. This foam was dissolved in methanol, diethyl ether and methylene chloride. Evaporation of the solvents overnight yielded a brown solid which was slurried in 200 mL of diethyl ether for 4 hours. The resulting slurry was filtered and the cake was washed with diethyl ether. The solids were dried under vacuum overnight to give a cream colored product (21.68 g, 71%) d (d⁶ DMSO): 1.69–1.84 (m, 3H), 2.80–2.85 (m, 0.7H), 3.32–3.41 (m, 3.6H), 3.64–3.67 (m, 0.7H), 6.65 (s, 1H), 7.42–7.50 (m, 5H), 7.83 (s, 1H), 8.22 (s, 1H)

Preparation 4

Methyl (2S)-1-[2-(4-nitroimidazolyl)-2-phenylacetyl]pyrrolidine-2-carboxylate

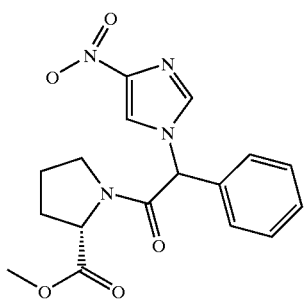

4

N-Methyl morpholine (17.79 ml, 2 eq) was added to a stirred solution of 2-(4-nitroimidazolyl)-2-phenylacetic acid (1) (20 g, 80.9 mm) and 2-chloro-4,6-dimethoxy-1,3,5-triazine (14.45 g, 80.1 mm, 1.0 eq) in 175 ml of anhydrous tetrahydrofuran at 25° C. After stirring the reaction mixture at ambient temperature for 1.5 h, 14.45 g (80.9 mm, 1.0 eq) of proline methyl ester hydrochloride was added. The reaction was stirred overnight at room temperature and the solvent was evaporated under a stream of nitrogen. The residue was partitioned between 200 Ml of 1M HCl and 200 mL of deionized water. The layers were separated and the organic layer was washed with saturated sodium bicarbonate solution. A quantity of water sufficient to dissolve the resulting solids was added. The organic layer was washed with brine, dried over magnesium sulfate, filtered and the volatiles were removed under vacuum to give a brown foam. The foam was dissolved in methyl t-butyl ether, methylene chloride and methanol to effect crystallization. The resulting slurry was filtered and dried under vacuum to give 17.45 g (60%) of a cream colored product MS: 358 (M⁺) IR (cm⁻¹): 1744, 1668; H¹ nmr d (d⁶ DMSO): 1.42–1.46 (m, 3H), 1.6–1.9 (m, 1H), 2.42–2.63 (m, 1H), 3.21 (s, 1.5H), 3.25 (s, 1.5H), 3.30–3.36 (m, 1H), 4.01–4.06 (m, 1H), 6.36 (s, 0.5H), 6.43 (s, 0.5 h), 7.0–7.2 (m, 5H), 7.38 (s, 0.5H), 7.41 (s, 0.5H), 7.75 (s, 0.5H), 7.83 (s, 0.5H)

Preparation 5

Methyl (2S)-1-[2-(4-aminoimidazolyl)-2-phenylacetyl]pyrrolidine-2-carboxylate, dihydrochloride

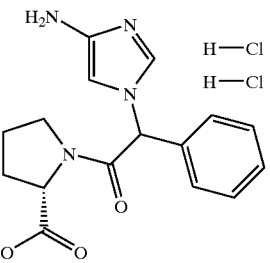

5

Ethanol (12 mL) was added to a mixture of methyl (2S)-1-[2-(4-nitroimidazolyl)-2-phenylacetyl]pyrrolidine-2-carboxylate (4) (148 mg, 0.4 mm) and 10% Pd on carbon (15 mg) in a Bradley hydrogenation apparatus. The stirred reaction mixture was subjected to a 60 psi H₂ atmosphere and warmed to 60° C. After 2 hours, the reaction mixture was cooled to room temperature and the catalyst was removed by filtration. Anhydrous HCl gas was added to the filtered solution until saturation. The volatiles were then removed under vacuum to give 0.15 g (100%) of a yellow solid mixed with a brown gum.

Preparation 6

2-(4-aminoimidazolyl)-2-phenyl-1-pyrrolidinylethan-1-one, dihydrochloride

6

Ethanol (200 ml) was added to a mixture of 2-(4-nitroimidazolyl)-2-phenyl-1-pyrrolidinylethan-1-one (3) (0.752 g, 2.8 mm) and 10% Pd on carbon (75 mg) in a Bradley hydrogenation apparatus. The stirred reaction mixture was subjected to a 60 psi H₂ atmosphere and warmed to 60° C. After 2 hours, the reaction mixture was cooled to room temperature and the catalyst was removed by filtration. Anhydrous HCl gas was added to the filtered solution until saturation. The volatiles were then removed under vacuum to give a light yellow foam. Diethyl ether and methylene chloride (25:1) were added to the foam and the-resulting mixture was stirred overnight to achieve crystallization. The resulting slurry was filtered and the cake was washed with diethyl ether. The cake was dried under vacuum to give 0.659 g (93%) of a yellow solid. LGD 208.

Preparation 7

2-(4-aminoimidazolyl)-1-(4-methylpiperidinyl)-2-phenylethan-1-one, dihydrochloride

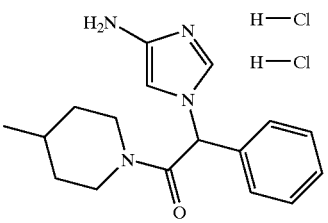

Methanol (140 mL) was added to a mixture of 1-(4-methylpiperidyl)-2-(4-nitroimidazolyl)-2-phenylethan-1-one (2) (2.16 g, 6.5 mm) and 0.214 g of 10% palladium on carbon in a Bradley hydrogenation apparatus. The stirred reaction mixture was subjected to a 60 psi $H_2$ atmosphere and warmed to 60° C. After 2 hours, the reaction mixture was cooled to room temperature and the catalyst was removed by filtration. Anhydrous HCl gas was added to the filtered solution until saturation. The volatiles were then removed under vacuum and the residue was crystallized from methylene chloride:methyl t-butyl ether 1:3. The resulting slurry was filtered and the wet cake was washed with methyl t-butyl ether and dried under vacuum to give 2.23 (93%)g of a yellow solid. MS: 298 (M+1$^+$); IR (cm$^{-1}$): 1648; $H^1$ nmr d (d$^6$ DMSO): 0.11–0.21 (m, 0.5H), 0.725 (d, J=4.9 Hz, 1.5H), 1.11–1.21 (m, 0.5H), 1.25–1.40 (m, 1H), 1.59–1.80 (m, 2H), 2.72–2.81 (m, 1H) 3.08–3.15 (m, 0.5H) 3.32 (s, 0.5H), 3.32 (s, 0.5H), 3.32 (s, 0.5H) 3.75 (d, J=8 Hz, 1H), 4.50–4.57 (dd, J=7.3 Hz, 1H). 4.95 (s, 1H), 6.8 (s, 0.5H), 6.9 (s, 0.5H), 7.39–7.60 (m, 5H), 8.29 (s, 0.5H), 8.45 (s, 0.5H)

Example 1

N-((1R)-2-indol-3-yl-1-[N-[1-(2-oxo-1-phenyl]-2-pyrrolidinylethyl)imidazol-4-yl]carbamoyl)ethyl)-2-[(tert-butoxy)carbonylamino]-2-methylpropanamide

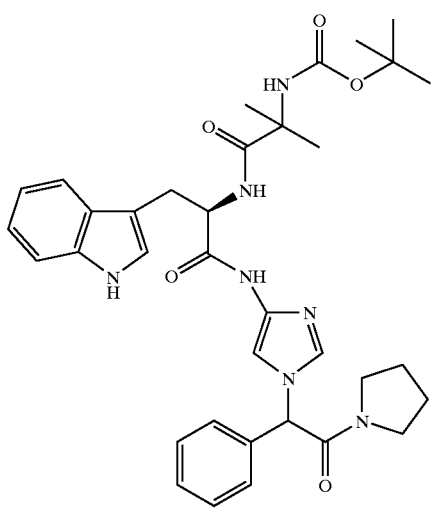

N-Methyl morpholine (0.28 mL, 8.32 mm, 1 eq) was added to a stirred slurry of 2-chloro-4,6-dimethoxy-1,3,5-triazine (0.46 g, 2.57 mm, 1 eq) and (2R)-2-{2-[(tert-butoxycarbonylamino]-2-methylpropanoylamino}-3-indol-3-ylpropanoic acid (1 g, 2.57 mm) in 10 mL of anhydrous tetrahydrofuran cooled to less than 0° C. After 1.5 hours, 2-(4-aminoimidazolyl)-2-phenyl-1-pyrrolidinylethan-1-one, hydrochloride (0.97 g, 2.82 mm, 1.1 eq) was added and stirring was continued at ice bath temperatures. The reaction was stirred for 4 hours and quenched by the addition of 15 mL of deionized water and ethyl acetate. The ethyl acetate layer was washed with a saturated sodium bicarbonate solution, dried over magnesium sulfate and the volatiles were removed under vacuum to give the crude product as a light purple foam (1.4 g, 84%) The crude product was purified by preparative chromatography to provide 0.52 g (31.5%) of the product as a foam. $^1$H nmr (CDCl$_3$): δ 1.10–1.40 (m, 15H), 1.67–1.92 (m, 3H), 2.92–3.60 (m, % H), 4.90 (s, broad, 1H), 5.33 (s, broad, 1H), 5.85 (d, 1H), 6.80–7.05 (m, 3H), 7.13–7.39 (m, 10H), 7.44–7.80 (m, 2H), 8.96 (s, broad, 1H), 10.20 (s, broad, 1H).

Example 2

N-((1R)-2-indol-3-yl-1-{N-[1-(2-oxo-1-phenyl-2-pyrrolidinylethyl)imidazol-4-yl]carbamoyl)}ethyl)-2-amino-2-methylpropanamide, 2,2,2-trifluoroacetic acid, 2,2,2-trifluoroacetic acid salt

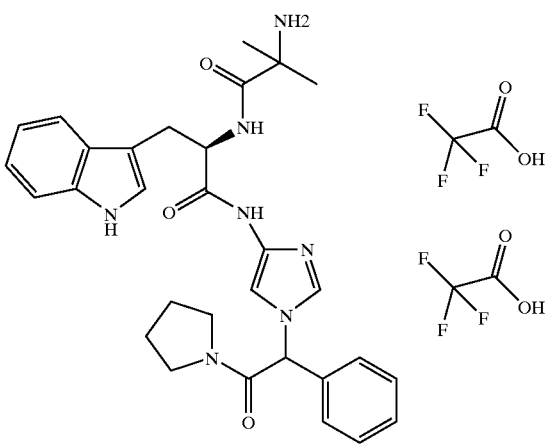

Trifluoroacetic acid (0.57 mL, 7.4 mm, 33 eq) was added to a stirred solution of N-((1R)-2-indol-3-yl-1-{N-[1-(2-oxo-1-phenyl-2-pyrrolidinylethyl)imidazol-4-yl]carbamoyl}ethyl)-2-[(tert-butoxy)carbonylamino]-2-methylpropanamide (8) (0.152 g, 0.22 mm) in 5 mL of methylene chloride. After stirring at room temperature for 3 hours, the reaction mixture was diluted with 50 mL of diethyl ether. The resulting solids were isolated by centrifugation and washed with diethyl ether. The solids were dried under vacuum to give the product as a cream colored solid (0.084 g, 48%) MS (FD+) m/z 541 (M$^+$) Anal. calcd. for $C_{30}H_{35}N_7O_3 \cdot 2C_2HF_3O_2$: C: 53.06; H: 4.85; N: 12.74. Found: C: 52.93; H: 4.88; N: 12.55. $^1$H nmr (DMSO-d$_6$): δ 1.29 (s, 3H), 1.46–1.48 (d, 3H), 1.72–1.88 (m, 4H), 2.94 (m, 1H), 3.06–3.07 (m, 1H), 3.19–3.20 (m, 1H), 3.40–3.41 (d, 2H), 3.67–3.69 (m, 1H), 4.78 (s, broad, 1H), 6.53 (s, 1H), 6.93–6.97 (m, 1H), 7.06 (m, 1H), 7.20 (d, 1H), 7.31–7.36 (m, 2H), 7–42–7.42 (m, 4H), 7.73–7.80 (m, 2H), 8.01 (s, broad, 2H), 8.36–8.38 (d, 1H), 10.82–10.85 (d, 2H).

Example 3

Methyl 1-{2-[4-((2R)-2-{2-[(tert-butoxy)carbonylamino]-2-methylpropanoylamino}-3-indol-3-ylpropanoylamino)imidazolyl]-2-phenylacetyl}pyrrolidine-2-carboxylate

10

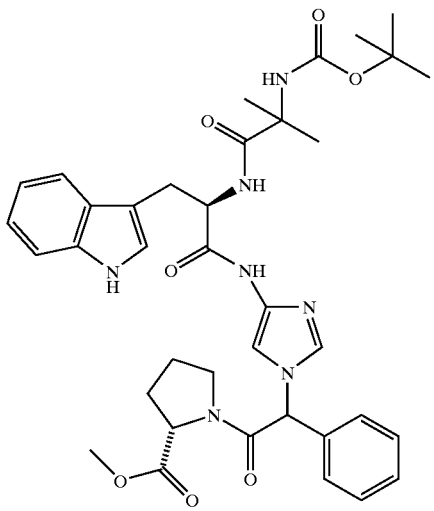

NMR data support the assigned structure. MS: 699.9

Example 4

Methyl 1-(2-{4-[(2R)-2-(2-amino-2-methylpropanoylamino)-3-indol-3-ylpropanoylamino]imidazolyl-2-phenylacetyl}pyrrolidine-2-carboxylate, dihydrochloride

12

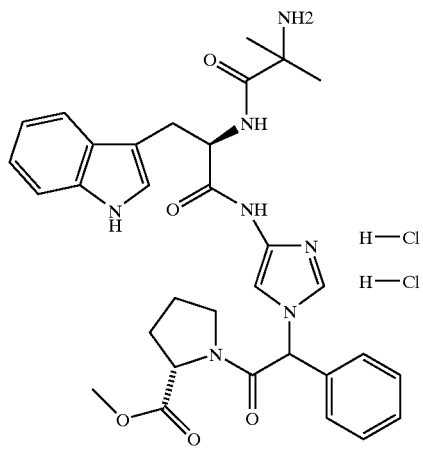

NMR data support the assigned structure. MS: 599

Example 5

N-((1R)-2-(2-naphthyl)-1-{N-[1-(2-oxo-1-phenyl-2-pyrrolidinylethyl)imidazol-4-yl]carbamoyl}ethyl)-2-[(tert-butoxy)carbonylamino]-2-methylpropanamide

12

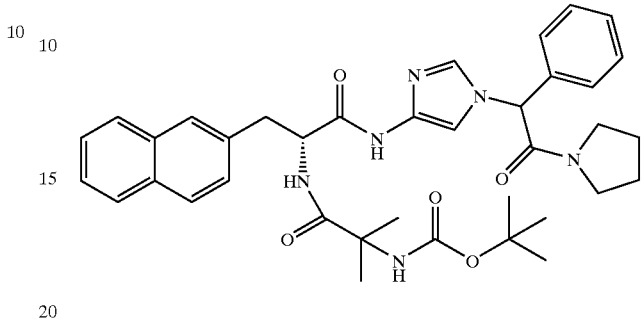

NMR data support the assigned structure. MS: 652

Example 6

N-((1R)-2-(2-napthyl)-1-{N-[1-(2-oxo-1-phenyl-2-pyrrolidinylethyl)imidazol-4-yl]carbamoyl}ethyl)-2-amino-2-methylpropanamide, dihydrochloride

13

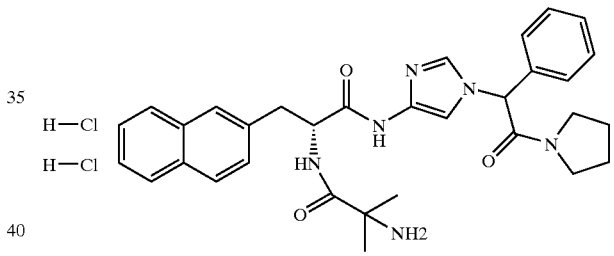

NMR data support the assigned structure. MS: 552

Example 7

N-[(1R)-1-(N-{1-[2-(4-methylpiperidyl)-2-oxo-1-phenylethyl]imidazol-4-yl}carbamoyl)-2-(2-naphthyl)ethyl]-2-[(tert-butoxy)carbonylamino]-2-methylpropanamide

14

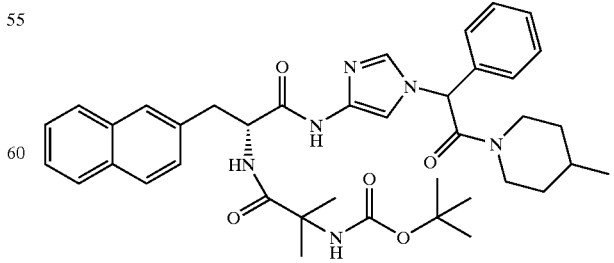

NMR data support the assigned structure. MS: 680

Example 8

N-[(1R)-1-(N-{1-[2-(4-methylpiperidyl)-2-oxo-1-phenylethyl]imidazol-4-yl}carbamoyl)-2-(2-naphthyl)ethyl]-2-amino-2-methylpropanamide dihydrochloride

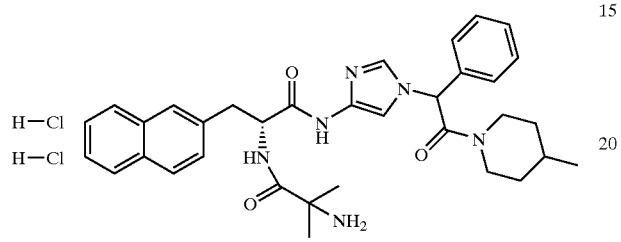

NMR data support the assigned structure. MS: 581 (M+1⁺)

Example 9

N-((1R)-1-{N-[1-(2-oxo-1-phenyl-2-pyrrolidinylethyl)imidazol-4-yl]carbamoyl}-2-phenylethyl)-2-[(tert-butoxy)carbonylamino]-2-methylpropanamide

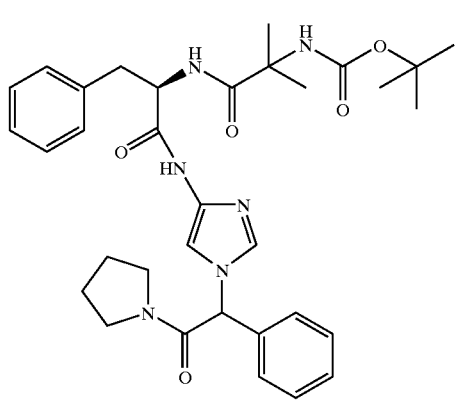

NMR data support the assigned structure. MS: 602

Example 10

N-((1R)-1-{N-[1-(2-oxo-1-phenyl-2-pyrrolidinylethyl)imidazol-4-yl]carbamoyl}-2-phenylethyl)-2-amino-2-methylpropanamide, dihydrochloride

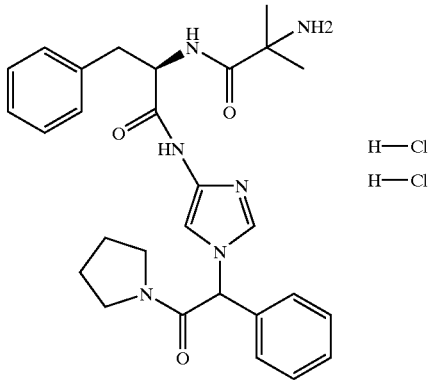

NMR data support the assigned structure. MS: 502

Example 11

N-[(1R)-1-(N-{1-[2-(4-methylpiperidyl)-2-oxo-1-phenylethyl]imidazol-4-yl}carbamoyl)-2-phenylethyl]-2-[(tert-butoxy)carbonylamino]-2-methylpropanamide

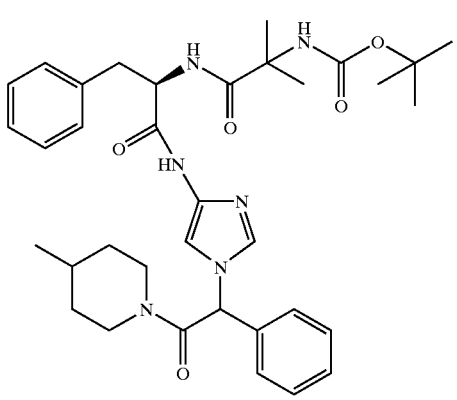

NMR data support the assigned structure. MS: 630

Example 12

N-[(1R)-1-(N-{1-[2-(4-methylpiperidyl)-2-oxo-1-phenylethyl]imidazol-4-yl}carbamoyl)-2-phenlethyl]-2-amino-2-methylpropanamide, dihydrochloride

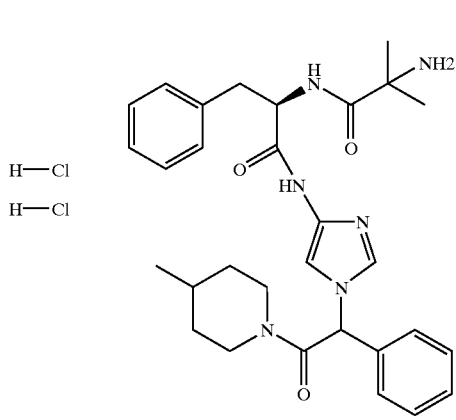

NMR data support the assigned structure. MS: 530

Example 13

(2R)-2-({2-[(tert-butoxy)carboylamino]-2-methylpropanoylamino}-N-[1-(2-oxo-1-phenyl-2-pyrrolidinylethyl)imidazol-4-yl]-4-phenylbutanamide

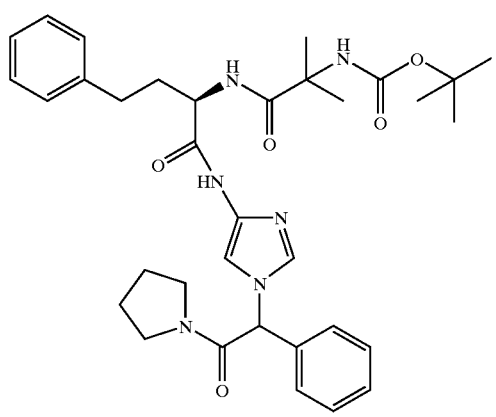

NMR data support the assigned structure. MS: 616

Example 14

(2R)-2-(2-amino-2-methylpropanoylamino)-N-[1-(2-oxo-1-phenyl-2-pyrrolidinylethyl)imidazol-4-yl]-4-phenylbutanamide, dihydrochloride

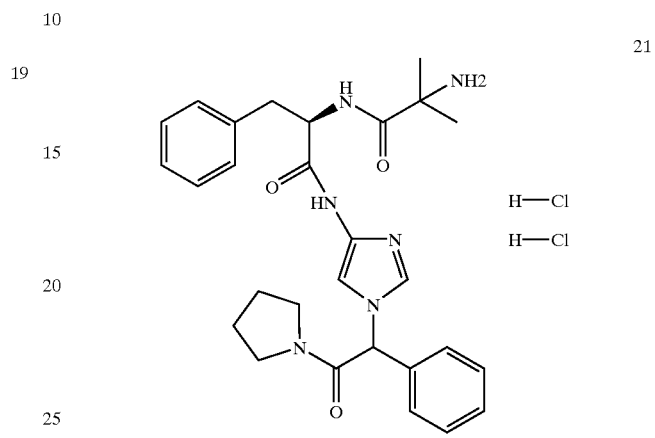

NMR data support the assigned structure. MS: 517 (m+1⁺)

Example 15

(2R)-2-{2-[(tert-butoxy)carbonylamino]-2-methylpropanoylamino}-N-{1-[2-(4-methylpiperidinyl)-2-oxo-1-phenylethyl]imidazol-4-yl}-4-phenylbutanamide

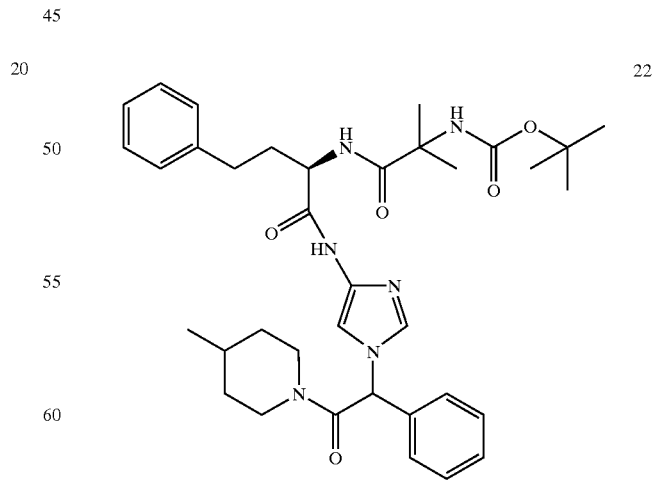

NMR data support the assigned structure.

Example 16

(2R)-2-(2-amino-2-methylpropanoylamino)-N-{1-[2-(4-methylpiperidinyl)-2-oxo-1-phenylethyl]imidazol-4-yl}-4-phenylbutanamide, dihydrochloride

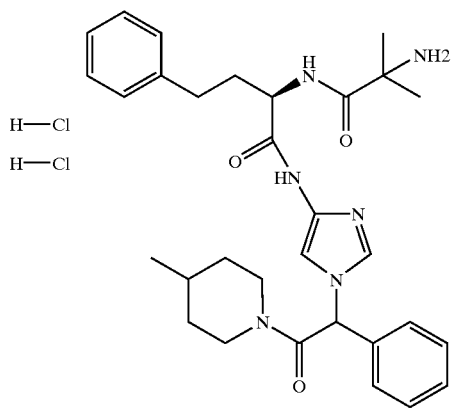

NMR data support the assigned structure. MS: 544

Example 17

Methyl 1-(2-[4-((2R)-2-{2-[(tert-butoxy)carbonylamino]-2-methylpropanoylamino}-4-phenylbutanoylamino)imidazolyl]-2-phenylacetyl)pyrrolidine-2-carboxylate

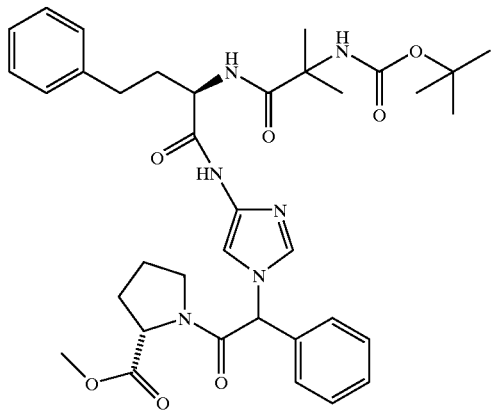

NMR data support the assigned structure.

Example 18

Methyl 1-(2-{4-[(2R)-2-(2-amino-2-methylpropanoylamino)-4-phenylbutanoylamino]imidazolyl}-2-phenylacetyl)pyrrolidine-2-carboxylate, dihydrochloride

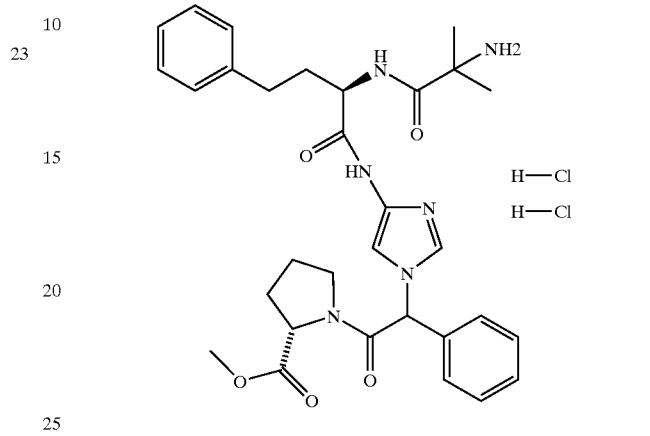

NMR data support the assigned structure. MS:575 (m+1$^+$)

EXAMPLES PART 9

Example 1

Pituitary Cell Culture Assay for Growth Hormone Secretion

Thirty-two 250 g male Sprague-Dawley rats were used for each assay. The animals were killed by decapitation and anterior pituitaries were removed and placed into ice cold culture medium. The pituitaries were sectioned into eighths and enzymatically digested using trypsin (Sigma Chemical) to weaken connective tissue. Pituitary cells were dispersed by mechanical agitation, collected, pooled and then seeded into 24-well plates (300,000 cells/well). After 4 days of culture, the cells formed an even monolayer. Cells were then washed with medium and challenged to secrete GH by the addition of GH secretagogues to the medium. After 15 min at 37° C., the medium was removed and stored frozen until radioimmunoassays for rat GH were performed. Doses of secretagogue were added in quadruplicate. Representative Data is provided in Table 1 below. Compounds disclosed herein are active in the assay as described. Both $EC_{50}$ and efficacy values were calculated by the 4-parameter logistic equation. Such values were pooled and represented as mean+/−standard error, when appropriate.

TABLE 1

| EXAMPLES PART 1 Example # | GH secretion $EC_{50}$ (mM) |
|---|---|
| 6 | 5.53 |
| 8 | 2.39 |

We claim:
1. A compound of formula I

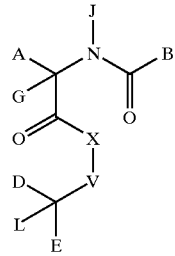

I wherein:
A is $C_1$–$C_6$alkyl, aryl, $C_1$–$C_6$alkylaryl, $C_1$–$C_6$alkyl(O) $C_1$–$C_6$alkylaryl, $C_1$–$C_6$alkyl(S)$C_1$–$C_6$alkylaryl, indolyl, indolinyl, thienyl, ($C_1$–$C_6$alkyl)thienyl, benzothienyl, benzofuranyl, naphthanyl, cyclohexyl, ($C_1$–$C_6$alkyl)indolyl, ($C_1$–$C_6$alkyl)benzothienyl, ($C_1$–$C_6$alkyl)naphthanyl, ($C_1$–$C_6$alkyl)benzofuranyl, and ($C_1$–$C_6$alkyl)cyclohexyl;

B is $NH_2$, $NHR_1$, $C_1$–$C_6$alkyl$NH_2$, $C_1$–$C_6$alkyl$NHR_1$, $C_1$–$C_6$alkylaryl$NH_2$, $C_1$–$C_6$alkylaryl$NHR_1$, $C_1$–$C_6$alkylcyclohexyl$NH_2$, $C_1$–$C_6$alkylcyclohexyl-$NHR_1$, $R_1$-piperidin-3-yl($C_1$–$C_6$alkyl), $R_1$-piperidin-2-yl($C_1$–$C_6$alkyl), $R_1$-piperidin-4-yl($C_1$–$C_6$alkyl), $R_1$-quinolin-2-yl($C_1$–$C_6$alkyl), $R_1$-(2,4-dihydroquinolin-2-yl($C_1$–$C_6$alkyl), $R_1$-isoquinolin-2-yl($C_1$–$C_6$alkyl), and $R_1$-(2,4-dihydroisoquinolin-2-yl ($C_1$–$C_6$alkyl);

$R_1$ is hydrogen, $C_1$–$C_6$alkyl, $C_1$–$C_6$alkyl(OH), or $C_1$–$C_6$alkylidenyl(OH)$R_2$;

$R_2$ is $C_1$–$C_6$alkyl, $C_1$–$C_6$alkenyl, $C_1$–$C_6$alkyl(O)$C_1$–$C_6$ alkyl, C(O)O—$C_1$–$C_6$ alkyl, aryl, or $C_1$–$C_6$alkylaryl;

X is $C_1$–$C_6$alkylidenyl, O, S, NH, or N($C_1$–$C_6$alkyl);
V is

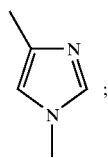

;

D is hydrogen, $C_1$–$C_6$alkyl, $C_1$–$C_6$alkyl(O)(CO) $C_1$–$C_6$alkyl, $C_1$–$C_6$alkyl(O)(CO)N($C_1$–$C_6$alkyl)$_2$, C(O)$R_6$, $C_1$–$C_6$alkyl(O)$R_6$, $C_1$–$C_6$alkyl(OH), $C_1$–$C_6$ alkylC(O)$R_6$, $C_1$–$C_6$alkyl$R_6$, ($C_1$–$C_6$alkyl)NHSO$_2$ ($C_1$–$C_6$alkyl), $R_6$ is H, $C_1$–$C_6$alkyl, naphthyl, acetyl, $NH_2$, NH($C_1$–$C_6$alkyl), NH($C_1$–$C_6$alkyl)O($C_1$–$C_6$alkyl), NH($C_1$–$C_6$alkyl)S($C_1$–$C_6$alkyl), NH($C_1$–$C_6$alkylidenyl)OCH$_3$, NH($C_3$–$C_6$ cycloalkyl), NH($C_1$–$C_6$alkyl) C(O)($C_1$–$C_6$alkyl), NH($C_1$–$C_6$alkyl)NH($C_1$–$C_6$alkyl), NH($C_1$–$C_6$alkyl)C(O)O($C_1$–$C_6$alkyl), N($C_1$–$C_6$alkyl)$_2$, O($C_1$–$C_6$alkyl), E is hydrogen, $C_1$–$C_6$alkyl, C(O)$C_1$–$C_6$alkyl, aryl, (aryl) C(O)N$R_6$, (aryl)($C_1$–$C_6$alkyl)C(O)$R_6$, $C_1$–$C_6$alkylaryl, C(O)aryl, $C_1$–$C_6$alkylC(O)aryl, naphthyl, $C_1$–$C_6$alkylnaphthyl, C(O)naphthyl, $C_1$–$C_6$alkylC(O) naphthyl, heteroaryl, $C_1$–$C_6$alkylheteroaryl, C(O) heteroaryl, $C_1$–$C_6$alkylC(O)heteroaryl, indanyl, $C_1$–$C_6$alkylindanyl, C(O)indanyl, $C_1$–$C_6$alkylC(O) indanyl, cycloalkyl;

G is hydrogen, $C_1$–$C_6$alkyl, aryl, $C_1$–$C_6$alkylaryl, and $C_1$–$C_6$alkenyl;

J is hydrogen, $C_1$–$C_6$alkyl, aryl, and $C_1$–$C_6$alkylaryl;

L is $C_1$–$C_6$alkyl;

or a pharmaceutically acceptable salt or solvate thereof.

2. A compound according to claim 1 wherein A is selected from the group consisting of

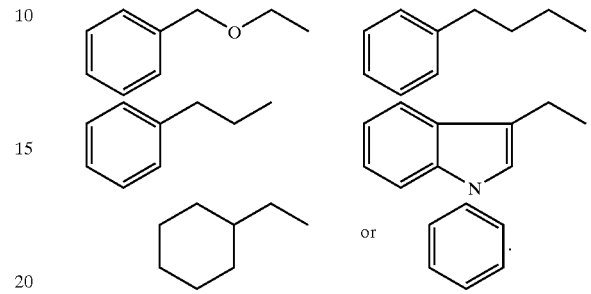

3. A compound according to claim 1 wherein B is

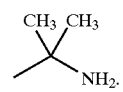

4. A compound according to claim 1 wherein X is NH.
5. A compound according to claim 1 wherein E is

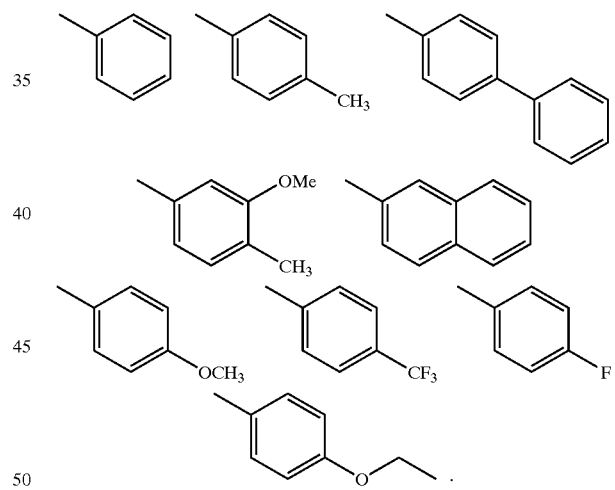

6. A compound according to claim 1 wherein G is H.
7. A compound according to claim 1 wherein J is H.
8. A compound according to claim 1 wherein L is $CH_3$.
9. A compound according to claim 1 wherein A is

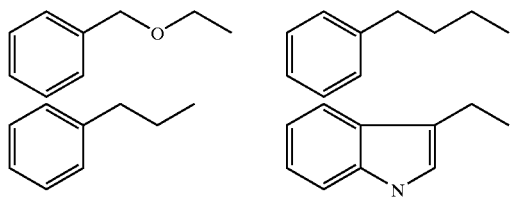

557

-continued

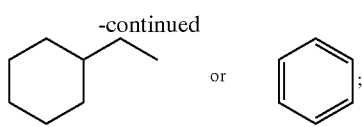

B is

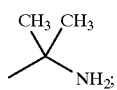

J is H;
G is H;
X is NH;
E is

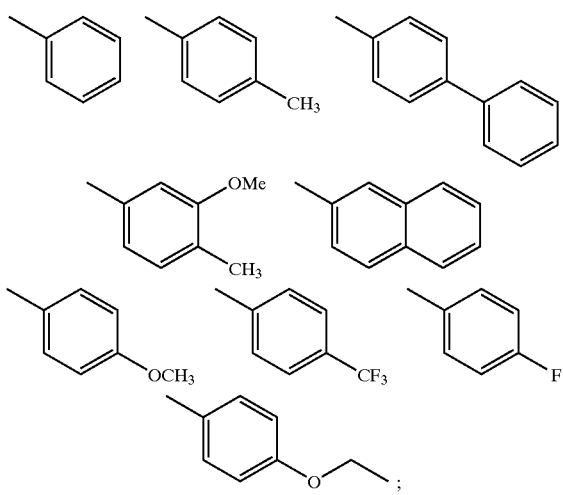

and L is CH₃;

or a pharmaceutically acceptable salt thereof.

10. A compound of claim 1 wherein said compound is

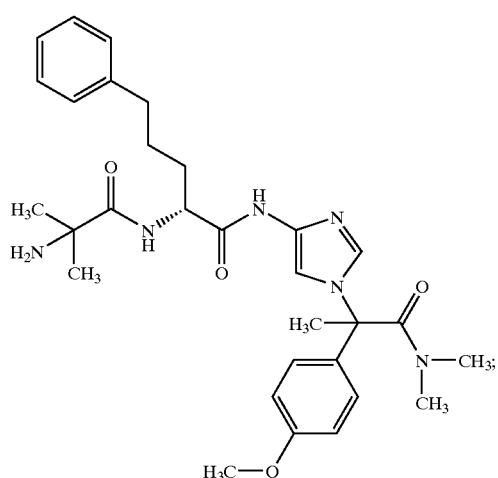

or a pharmaceutically acceptable salt thereof.

558

11. A compound of claim 1 wherein said compound is

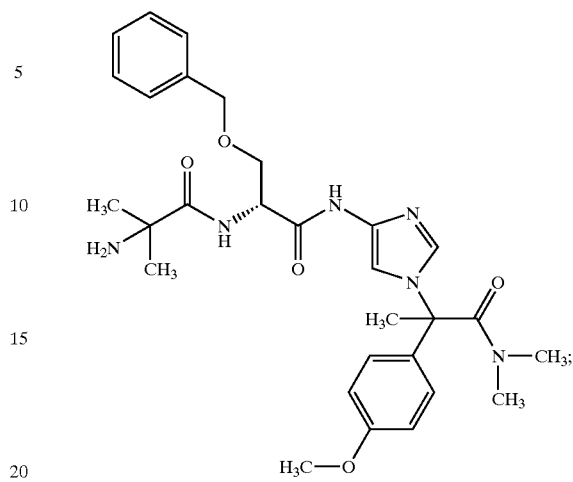

or a pharmaceutically acceptable salt thereof.

12. A compound of claim 1 wherein said compound is

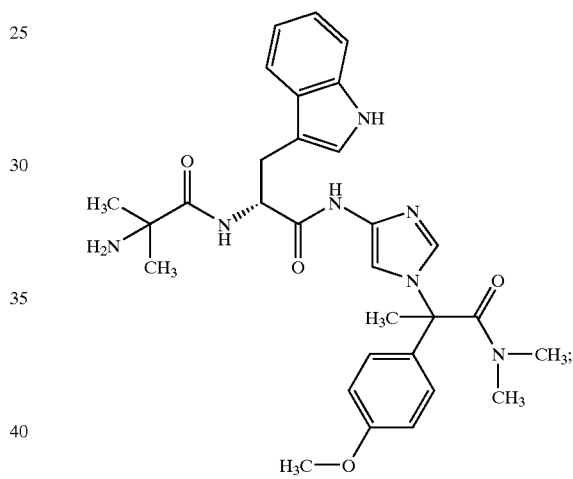

or a pharmaceutically acceptable salt thereof.

13. A compound of claim 1 wherein said compound is

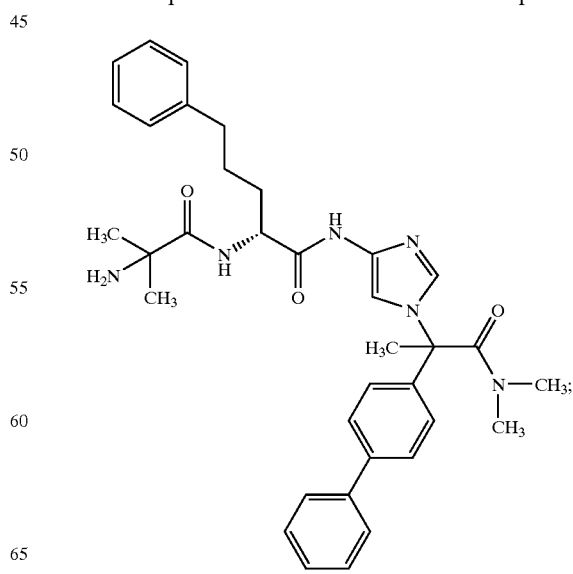

or a pharmaceutically acceptable salt thereof.

14. A pharmaceutical formulation which comprises as an active ingredient a compound of claim 1, or a pharmaceutically acceptable salt or solvate thereof, associated with one or more pharmaceutically acceptable carriers, diluents, or excipients.

15. A method for increasing the level of endogenous growth hormone in a human or an animal which comprises administering to said human or animal an effective amount of a compound of claim 1.

* * * * *